(12) United States Patent
Sette et al.

(10) Patent No.: US 7,888,472 B2
(45) Date of Patent: Feb. 15, 2011

(54) OPTIMIZED MULTI-EPITOPE CONSTRUCTS AND USES THEREOF

(75) Inventors: Alessandro Sette, La Jolla, CA (US); Robert Chesnut, Cardiff-by-the-Sea, CA (US); Mark J. Newman, Carlsbad, CA (US); Brian D. Livingston, San Diego, CA (US); Lilia Maria Babe, Emerald Hills, CA (US); Yiyou Chen, San Jose, CA (US); Lawrence M. Deyoung, Montara, CA (US); Manley T. F. Huang, Palo Alto, CA (US); Scott D. Power, San Bruno, CA (US)

(73) Assignees: Epimmune Inc., San Diego, CA (US); GENimmune N.V., Zwijnaarde (BE)

( * ) Notice: Subject to any disclaimer, the term of this patent is extended or adjusted under 35 U.S.C. 154(b) by 0 days.

(21) Appl. No.: 12/408,472

(22) Filed: Mar. 20, 2009

(65) Prior Publication Data

US 2010/0068218 A1    Mar. 18, 2010

Related U.S. Application Data

(62) Division of application No. 10/677,754, filed on Oct. 3, 2003, now Pat. No. 7,507,803.

(60) Provisional application No. 60/415,463, filed on Oct. 3, 2002, provisional application No. 60/419,973, filed on Oct. 22, 2002.

(51) Int. Cl.
  *C07K 14/00*  (2006.01)
  *A61K 39/00*  (2006.01)
(52) U.S. Cl. .................. 530/350; 424/184.1; 424/225.1
(58) Field of Classification Search ........................ None
  See application file for complete search history.

(56) References Cited

U.S. PATENT DOCUMENTS

| 7,507,803 B2 | 3/2009 | Sette et al. |
| 2002/0119127 A1 | 8/2002 | Sette et al. |

FOREIGN PATENT DOCUMENTS

| WO | WO 99/58658 A2 | 11/1999 |
| WO | WO 01/21189 A1 | 3/2001 |
| WO | WO 01/47541 A1 | 7/2001 |
| WO | WO 02/19986 A1 | 3/2002 |
| WO | WO 2005/033265 A2 | 4/2005 |

OTHER PUBLICATIONS

Livingston, B., et al., "Optimization of epitope processing enhances immunogenicity of multiepitiope DNA vaccines," *Vaccine* 19:4652-4660, Elsevier Science Ltd., The Netherlands (2001).
Oseroff, C., et al., "Pools of lipidated HTL-CTL constructs prime for multiple HBV and HCV CTL epitope responses," *Vaccine* 16:823-833, Elsevier Science, The Netherlands (1998).
Sobao, Y., et al., "Identification of hepatitis B virus-specific CTL epitopes presented by HLA-A*2402, the most common HLA class I allele in East Asia," *J. Hepatol.* 34:922-929, Elsevier Science B.V., The Netherlands (2001).
International Search Report for International Application No. PCT/US03/31303, United States Patent and Trademark Office, mailed Jul. 22, 2004.
Office Action dated Nov. 28, 2007, in U.S. Appl. No. 10/677,754, Sette, A. et al., filed Oct. 3, 2003.

*Primary Examiner*—Zachariah Lucas
*Assistant Examiner*—Nicole Kinsey White
(74) *Attorney, Agent, or Firm*—Sterne, Kessler, Goldstein & Fox P.L.L.C.

(57) ABSTRACT

The invention relates to the field of biology. In particular, it relates to multi-epitope nucleic acid and peptide vaccines and methods of designing such vaccines to provide increased immunogenicity.

6 Claims, 90 Drawing Sheets

FIG. 1

Synthetic polypeptides encoding HIV-derived HTL epitopes

HTL polyepitope: | HIV pol 711 | HIV gag 171 | HIV pol 335 | HIV pol

HIV-FT

| signal | A*0201 Pol 448 | A*0201 Pol 774 | A*1101 Pol 347 | A*1101 Pol 98 | A*0201 Vpr 62 | A*1101 Pol 930 | A*1101 B*0701 Pol 893 | A*1101 Env 61 | A*0201 Pol 498 | A*1101 Pol 929 |
|---|---|---|---|---|---|---|---|---|---|---|
| | 60 | 62 | 10 | 28 | 19 | 20 | 458 | 27 | 192 | 8 |

| A*1101 Pol 931 | B*0701 Env 250 | A*1101 Pol 971 | A*0201 Nef 221 | A*1101 Nef 100 | A*0201 Gag 271 | A*1101 Env 46 | A*0201 Gag 386 | B*0701 Env 259 | A*0201 Env 134 |
|---|---|---|---|---|---|---|---|---|---|
| 3 | 100 | 28 | 36 | 9 | 167 | 3 | 67 | 423 | 102 |

FIG.3A

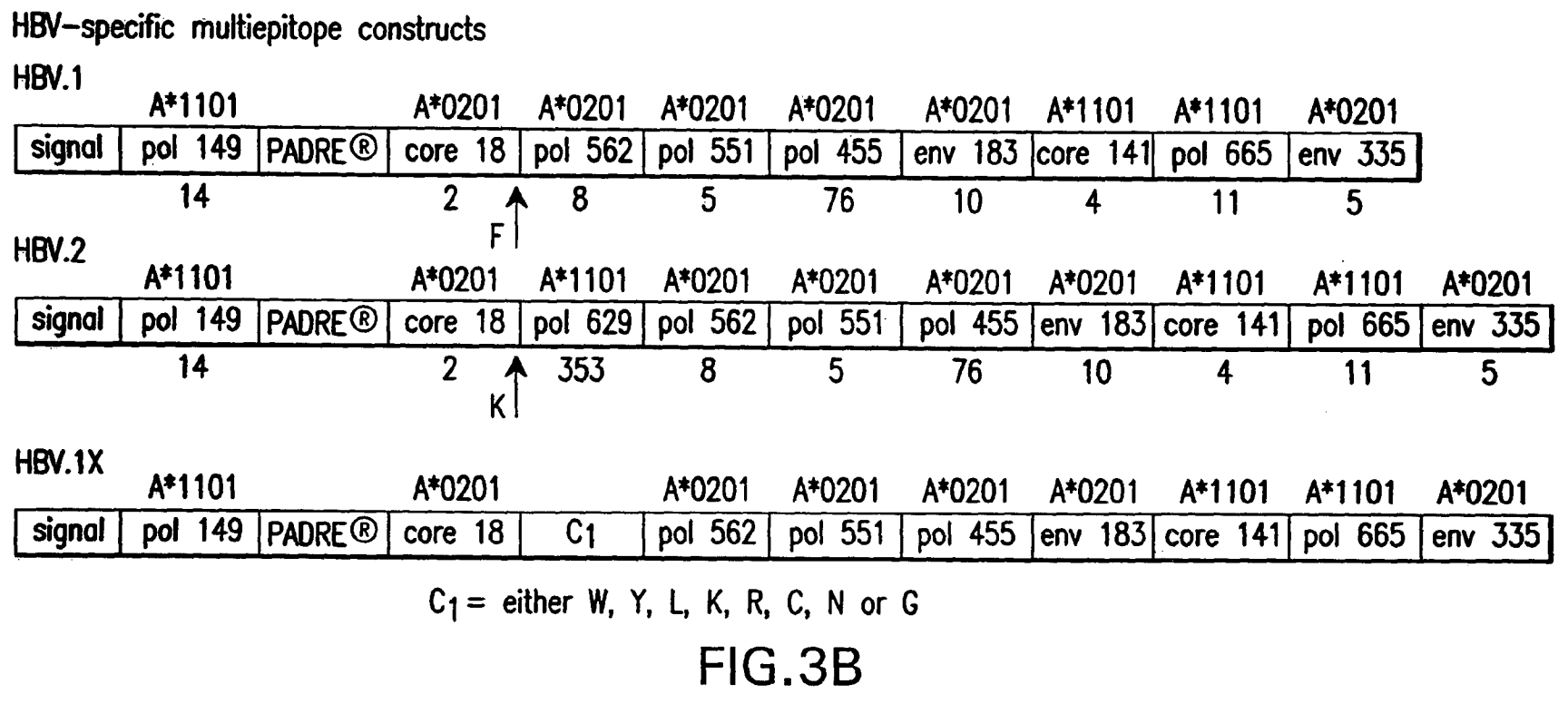

HBV-specific multiepitope constructs

HBV.1

| signal | A*1101 pol 149 | P

HIV-CPT

| B*0702 | | A*1101 | | A*1101 | | A*1101 | | B*0702 | | A*1101 | | A*0201 | | A*1101 |
|---|---|---|---|---|---|---|---|---|---|---|---|---|---|---|
| signal | env 259 | KAA | pol 971 | KAA | pol 98 | K | PADRE | K | rev 75 | K | pol 347 | – | env 134 | GA | pol 929 | GA |

| A*1101 | | B*0702 | | A*0201 | | A*0201 | | A*0201 | | A*0201 | | A*1101 | | B*0702 | | A*1101 |
|---|---|---|---|---|---|---|---|---|---|---|---|---|---|---|---|---|
| pol 722 | NA | pol 893 | KA | pol 498 | GAAA | nef 221 | NA | gag 386 | N | vpr 62 | N | env 47 | K | env 250 | NAAA | KAA |

| B*0702 | | B*0702 | | A*1101 | | A*1101 | | B*0702 | | A*0201 |
|---|---|---|---|---|---|---|---|---|---|---|---|
| gag 237 | NAAA | gag 545 | NAAA | env 61 | N | pol 448 | NAAA | nef 94 | N | gag 271 |

FIG.9B

HIV-TC

| A*2402 | A*1101 | A*1101 | B*0702 | A*1101 | A*0201 | A*0201 | A*0101 |
|---|---|---|---|---|---|---|---|
| signal | Pol 597 | K | Pol 347 | — | Pol 722 | NAA | Env 250 | K | Gag 237 | N | Nef 221 | N | Pol 132 | K | Gag 317 | KAAA |

| A*0201 | A*1101 | A*1101 | A*0201 | A*2402 | A*1101 | A*0101 | A*2402 |
| Vpr 62 | N | Env 61 | N | Gag 162 | GA | Pol 448 | GAAA | Vpr 46 | KAA | Nef 100 | GAAA | Pol 295 | NAAA | Env 671 | N |

| A*0201 | A*2402 | A*2402 | B*0702 | B*0702 | A*0201 | A*0201 | B*0702 |
| Pol 183 | N | Gag 271 | NA | Pol 244 | KAAA | Rev 75 | KAAA | Pol 893 | KA | Env 651 | GAA | Pol 498 | NAAA | Pol 186 | K |

| A*2402 | A*1101 | A*2402 | A*0201 | A*0201 | A*0201 | A*0101 | A*0101 |
| Env 55 | KAAA | Pol 98 | K | Pol 533 | KAAA | Gag 386 | N | Pol 163 | GAAA | Pol 684 | KAAA | Env 259 | KA | Pol 368 | KAAA |

| A*1101 | A*2402 | A*2402 | A*1101 | A*2402 | A*1101 | A*0201 | A*0201 |
| Pol 929 | NAA | Pol 530 | K | Vpr 14 | KA | Pol 971 | KA | Nef 94 | GAAA | Env 681 | K | Vif 7 | NAA | Pol 879 | K | PADRE® | — |

| A*0201 | A*0201 | A*0201 | A*1101 | A*0201 | B*0702 |
| Env 134 | NAA | Pol 774 | K | Env 163 | N | Env 47 | KAAA | Vpr 59 | K | Pol 772 | NAAA | Gag 545 |

FIG. 9C

| Sequence | Length | Code |
|---|---|---|
| VLAEAMSQV | 9 | A |
| ILKEPVHGV | 9 | B |
| TLNFPISPI | 9 | C |
| SLLNATDIAV | 10 | D |
| QMAVFIHNFK | 10 | E |
| VTVYYGVPVWK | 11 | F |
| FPVRPQVPL | 9 | G |
| YPLASLRSLF | 10 | H |
| VIYQYMDDLY | 10 | I |
| IYQEPFKNL | 9 | J |
| IWGCSGKLI | 9 | K |

— 202

| AA | C+1 ranking | N-1 ranking |
|---|---|---|
| K | 2.20 | 0.64 |
| C | 2.00 | 1.00 |
| N | 2.00 | 0.00 |
| G | 1.80 | 1.33 |
| T | 1.50 | 0.00 |
| A | 1.33 | 1.21 |
| F | 1.33 | 1.00 |
| S | 1.33 | 0.00 |
| W | 1.20 | 0.00 |
| Q | 1.20 | 0.00 |
| R | 1.17 | 1.57 |
| M | 1.00 | 0.00 |
| Y | 1.00 | 0.75 |
| I | 0.86 | 0.50 |
| L | 0.75 | 2.20 |
| V | 0.00 | 1.19 |
| D | 0.00 | 0.00 |
| H | 0.00 | 0.00 |
| E | 0.00 | 0.00 |
| P | 0.00 | 0.00 |

— 204

Motif Specification

XXXX(FY)XX(LIMV)
XXXX(FY)XXX(LIMV)
XXXXNXXX(LIMV)
XXXXNXXXX(LIMV)
X(LM)XXXXXXV
X(LM)XXXXXXXV
X(LMVT)XXXXXX(KRY)
X(LMVT)XXXXXXX(KRY)
XPXXXXXX(LIMVF)
XPXXXXXXX(LIMVF)

MaxInsertions={enter value here} 208

OutputToScreen=yes/no   210

OutputToFile=yes/no   212

MinimumAccepted={enter value here}   214

MaxDuplicateFunctionValues={enter value here}   216

MaxSearchTime (min.)={enter value here}   218

Exhaustive=yes/no   220

NumStochasticProbes={enter value here}   222

MaxHitsPerProbe={enter value here}   224

RandomProbeStart=yes/no   226

FIG.11B

Junctional Analyzer run on Saturday, February 26, 2000 09:06:23 pm.
The following non-zero AA weights will be used.

| AA | N-1 ranking | C+1 ranking |
|---|---|---|
| A | 1.21 | 1.33 |
| C | 1.00 | 2.00 |
| F | 1.00 | 1.33 |
| G | 1.33 | 1.80 |
| I | 0.50 | 0.86 |
| K | 0.64 | 2.20 |
| L | 2.20 | 0.75 |
| M | 0.00 | 1.00 |
| N | 0.00 | 2.00 |
| Q | 0.00 | 1.20 |
| R | 1.57 | 1.17 |
| S | 0.00 | 1.33 |
| T | 0.00 | 1.50 |
| V | 1.19 | 0.00 |
| W | 0.00 | 1.20 |
| Y | 0.75 | 1.00 |

⎬ 204

The following 10 motif specifications will be used to search for junctionals.

| Count | Motif Specification |
|---|---|
| 1 | XXXX(FY)XX(LIMV) |
| 2 | XXXX(FY)XXX(LIMV) |
| 3 | XXXXNXXX(LIMV) |
| 4 | XXXXNXXXX(LIMV) |
| 5 | X(LM)XXXXXXV |
| 6 | X(LM)XXXXXXV |
| 7 | X(LMVT)XXXXX(KRY) |
| 8 | X(LMVT)XXXXXX(KRY) |
| 9 | XPXXXXXX(LIMVF) |
| 10 | XPXXXXXXX(LIMVF) |

⎬ 206

| Code | Peptide | Length |
|---|---|---|
| A | VLAEAMSQV | 9 |
| B | ILKEPVHGV | 9 |
| C | TLNFPISPI | 9 |
| D | SLLNATDIAV | 10 |
| E | QMAVFIHNFK | 10 |
| F | VTVYYGVPVWK | 11 |
| G | FPVRPQVPL | 9 |
| H | YPLASLRSLF | 10 |
| I | VIYQYMDDLY | 10 |
| J | IYQEPFKNL | 9 |
| K | IWGCSGKLI | 9 |

⎬ 202

MaxInsertions = 4 (208)

FIG. 13A

OutputToScreen = No

OutputToFile = Yes

MinimumValueAccepted = 0

MaxDuplicateFunctionValues = 50

SearchTime = 5

NumStochasticProbes = 10

MaxHitsPerProbe = 25

RandomProbeStart = Yes

| Col. 1<br>Code 1 | Col. 2<br>I1 | Col. 3<br>I2 | Col. 4<br>I3 | Col. 5<br>I4 | Col. 6<br>Code 2 | Col. 7<br>C | Col. 8<br>N | Col. 9<br>C+N | Col. 10<br>J | Col. 11<br>MaxFunc. |
|---|---|---|---|---|---|---|---|---|---|---|
| A | C | A |   |   | L | B | 2.00 | 2.20 | 4.40 | 0 | 8.80 |
| A | C |   |   |   | L | C | 2.00 | 2.20 | 4.40 | 0 | 8.80 |
| A | C |   |   |   | L | D | 2.00 | 2.20 | 4.40 | 0 | 8.80 |
| A | C |   |   |   | L | E | 2.00 | 2.20 | 4.40 | 0 | 8.80 |
| A | C |   |   |   | R | F | 2.00 | 1.57 | 3.14 | 2 | 1.57 |
| A | C |   |   |   | R | G | 2.00 | 1.57 | 3.14 | 1 | 3.14 |
| A | C |   |   |   | R | H | 2.00 | 1.57 | 3.14 | 0 | 6.28 |
| A | C |   |   |   |   | I | 1.80 | 1.33 | 2.39 | 1 | 2.39 |
| A | C |   |   |   | G | J | 2.00 | 1.33 | 2.66 | 0 | 5.32 |
| A | C | A | A |   | R | K | 2.00 | 1.57 | 3.14 | 0 | 6.28 |
| B | C | A | A |   | G | A | 2.00 | 1.33 | 2.66 | 0 | 5.32 |
| B | C | A |   |   | R | C | 2.00 | 1.57 | 3.14 | 0 | 6.28 |
| B | C | A |   |   | R | D | 2.00 | 1.57 | 3.14 | 0 | 6.28 |
| B | C | A |   |   | R | E | 2.00 | 1.57 | 3.14 | 0 | 6.28 |
| B | C | A | A |   | G | F | 2.00 | 1.33 | 2.66 | 1 | 2.66 |
| B | C |   |   |   | R | G | 2.00 | 1.57 | 3.14 | 1 | 3.14 |
| B | C |   |   |   | R | H | 2.00 | 1.57 | 3.14 | 0 | 6.28 |
| B | C | A | A |   | G | I | 2.00 | 1.33 | 2.66 | 1 | 2.66 |
| B | C | A | A |   | G | J | 2.00 | 1.33 | 2.66 | 0 | 5.32 |
| B | C | A | A |   | G | K | 2.00 | 1.33 | 2.66 | 0 | 5.32 |
| C | C | A |   |   | R | A | 2.00 | 1.57 | 3.14 | 1 | 3.14 |
| C | C |   |   |   | R | B | 2.00 | 1.57 | 3.14 | 1 | 3.14 |
| C | C |   |   |   | L | D | 2.00 | 2.20 | 4.40 | 1 | 4.40 |
| C | C | A |   |   | R | E | 2.00 | 1.57 | 3.14 | 1 | 3.14 |
| C | C |   |   |   | R | F | 2.00 | 1.57 | 3.14 | 1 | 3.14 |
| C | C |   |   |   | R | G | 2.00 | 1.57 | 3.14 | 1 | 3.14 |
| C | C |   |   |   | R | H | 2.00 | 1.57 | 3.14 | 0 | 6.28 |
| C | C | A |   |   | R | I | 2.00 | 1.57 | 3.14 | 1 | 3.14 |
| C | C | A | A |   | R | J | 2.00 | 1.57 | 3.14 | 0 | 6.28 |
| C | C | A | A |   | R | K | 2.00 | 1.57 | 3.14 | 0 | 6.28 |

FIG. 13B

| Code 1 | I1 | I2 | I3 | I4 | Code 2 | C | N | C+N | J | MaxFunc |
|---|---|---|---|---|---|---|---|---|---|---|
| D | C | | | L | A | 2.00 | 2.20 | 4.40 | 0 | 8.80 |
| D | C | | | L | B | 2.00 | 2.20 | 4.40 | 0 | 8.80 |
| D | C | | | L | C | 2.00 | 2.20 | 4.40 | 0 | 8.80 |
| D | C | | | L | E | 2.00 | 2.20 | 4.40 | 0 | 8.80 |
| D | C | | | R | F | 1.80 | 1.33 | 2.39 | 0 | 4.79 |
| D | C | | | G | G | 2.00 | 1.57 | 3.14 | 0 | 6.28 |
| D | C | A | A | L | H | 2.00 | 1.33 | 2.66 | 0 | 5.32 |
| D | C | | | G | I | 2.00 | 2.20 | 4.40 | 1 | 4.40 |
| D | C | A | | R | J | 2.00 | 1.33 | 2.66 | 0 | 5.32 |
| D | C | | | L | K | 2.00 | 1.57 | 3.14 | 0 | 6.28 |
| E | C | A | A | L | A | 2.00 | 2.20 | 4.40 | 0 | 8.80 |
| E | C | A | A | L | B | 2.00 | 2.20 | 4.40 | 0 | 8.80 |
| E | C | A | A | L | C | 2.00 | 2.20 | 4.40 | 0 | 8.80 |
| E | C | A | A | L | D | 2.00 | 2.20 | 4.40 | 0 | 8.80 |
| E | C | A | | R | F | 2.00 | 1.57 | 3.14 | 0 | 6.28 |
| E | C | A | | R | G | 2.00 | 1.57 | 3.14 | 0 | 6.28 |
| E | C | A | | R | H | 2.00 | 1.57 | 3.14 | 0 | 6.28 |
| E | C | A | A | L | I | 2.00 | 2.20 | 4.40 | 0 | 8.80 |
| E | C | A | | R | J | 2.00 | 1.57 | 3.14 | 0 | 6.28 |
| E | C | A | | R | K | 2.00 | 1.57 | 3.14 | 0 | 6.28 |
| F | K | A | A | L | A | 2.20 | 2.20 | 4.84 | 1 | 4.84 |
| F | K | A | A | G | B | 2.20 | 1.33 | 2.93 | 1 | 2.93 |
| F | K | A | A | G | C | 2.20 | 1.33 | 2.93 | 0 | 5.85 |
| F | K | A | A | G | D | 2.20 | 1.33 | 2.93 | 0 | 5.85 |
| F | K | A | A | G | E | 2.20 | 1.33 | 2.93 | 0 | 5.85 |
| F | K | A | A | G | G | 2.20 | 1.33 | 2.93 | 1 | 2.93 |
| F | K | A | A | G | H | 2.20 | 1.33 | 2.93 | 1 | 2.93 |
| F | K | A | A | G | I | 2.20 | 1.33 | 2.93 | 1 | 2.93 |
| F | K | A | | R | J | 2.20 | 1.57 | 3.45 | 1 | 3.45 |
| F | K | A | | R | K | 2.20 | 1.57 | 3.45 | 0 | 6.91 |
| G | C | | | R | A | 2.00 | 1.57 | 3.14 | 1 | 3.14 |
| G | C | A | | R | B | 2.00 | 1.57 | 3.14 | 2 | 1.57 |
| G | C | A | | R | C | 2.00 | 1.57 | 3.14 | 1 | 3.14 |
| G | C | | | L | D | 2.00 | 2.20 | 4.40 | 1 | 4.40 |
| G | C | A | | R | E | 2.00 | 1.57 | 3.14 | 2 | 1.57 |
| G | C | | | L | F | 2.00 | 2.20 | 4.40 | 4 | 1.10 |
| G | C | | | G | H | 2.00 | 1.33 | 2.66 | 0 | 5.32 |
| G | C | A | A | R | I | 2.00 | 1.57 | 3.14 | 2 | 1.57 |
| G | C | A | A | R | J | 2.00 | 1.57 | 3.14 | 1 | 3.14 |
| G | C | A | A | R | K | 2.00 | 1.57 | 3.14 | 0 | 6.28 |
| H | C | A | A | G | A | 2.00 | 1.33 | 2.66 | 0 | 5.32 |
| H | C | A | A | G | B | 2.00 | 1.33 | 2.66 | 1 | 2.66 |
| H | C | A | A | G | C | 2.00 | 1.33 | 2.66 | 0 | 5.32 |
| H | C | A | A | G | D | 2.00 | 1.33 | 2.66 | 0 | 5.32 |
| H | C | A | A | G | E | 2.00 | 1.33 | 2.66 | 0 | 5.32 |
| H | C | A | A | G | F | 2.00 | 1.33 | 2.66 | 1 | 2.66 |
| H | C | | | G | G | 2.00 | 1.57 | 3.14 | 1 | 3.14 |
| H | C | A | A | G | I | 2.00 | 1.33 | 2.66 | 1 | 2.66 |
| H | C | A | A | G | J | 2.00 | 1.33 | 2.66 | 1 | 2.66 |
| H | C | A | A | G | K | 2.00 | 1.33 | 2.66 | 0 | 5.32 |

FIG.13C

| Code 1 | I1 | I2 | I3 | I4 | Code 2 | C | N | C+N | J | MaxFunc |
|---|---|---|---|---|---|---|---|---|---|---|
| I | K | A | A | G | A | 2.20 | 1.33 | 2.93 | 0 | 5.85 |
| I | K | A | A | G | B | 2.20 | 1.33 | 2.93 | 1 | 2.93 |
| I | K | A |   | G | C | 2.20 | 1.33 | 2.93 | 0 | 5.85 |
| I | K | A |   | G | D | 2.20 | 1.33 | 2.93 | 0 | 5.85 |
| I | K |   | A | G | E | 2.20 | 1.33 | 2.93 | 0 | 5.85 |
| I | K | A | A | G | F | 2.20 | 1.33 | 2.93 | 1 | 2.93 |
| I | K |   |   | R | G | 2.20 | 1.57 | 3.45 | 1 | 3.45 |
| I | K | A | A | G | H | 2.20 | 1.33 | 2.93 | 0 | 5.85 |
| I | K |   |   | G | J | 2.20 | 1.33 | 2.93 | 1 | 2.93 |
| I | K | A | A | G | K | 2.20 | 1.33 | 2.93 | 0 | 5.85 |
| J | K | A | A | R | A | 2.20 | 1.57 | 3.45 | 0 | 6.91 |
| J | K | A | A | R | B | 2.20 | 1.57 | 3.45 | 1 | 3.45 |
| J | K | A |   | R | C | 2.20 | 1.57 | 3.45 | 0 | 6.91 |
| J | K | A |   | R | D | 2.20 | 1.57 | 3.45 | 0 | 6.91 |
| J | K | A |   | R | E | 2.20 | 1.57 | 3.45 | 1 | 3.45 |
| J | K |   | A | R | F | 2.20 | 1.57 | 3.45 | 2 | 1.73 |
| J | K |   |   | R | G | 2.20 | 1.57 | 3.45 | 1 | 3.45 |
| J | K |   |   | R | H | 2.20 | 1.57 | 3.45 | 0 | 6.91 |
| J | K | A | A | R | I | 2.20 | 1.57 | 3.45 | 1 | 3.45 |
| J | K | A | A | R | K | 2.20 | 1.57 | 3.45 | 0 | 6.91 |
| K | K |   |   | L | A | 2.20 | 2.20 | 4.84 | 0 | 9.68 |
| K | K |   |   | L | B | 2.20 | 2.20 | 4.84 | 0 | 9.68 |
| K | K |   |   | L | C | 2.20 | 2.20 | 4.84 | 0 | 9.68 |
| K | K |   |   | L | D | 2.20 | 2.20 | 4.84 | 0 | 9.68 |
| K | K | A | A | L | E | 2.20 | 2.20 | 4.84 | 0 | 9.68 |
| K | K | A | A | R | F | 2.20 | 1.57 | 3.45 | 1 | 3.45 |
| K | G |   |   |   | G | 1.80 | 1.33 | 2.39 | 0 | 4.79 |
| K | K |   |   | R | H | 2.20 | 1.57 | 3.45 | 0 | 6.91 |
| K | K |   |   | L | I | 2.20 | 2.20 | 4.84 | 1 | 4.84 |
| K | K |   |   | R | J | 2.20 | 1.57 | 3.45 | 0 | 6.91 |

Junctional Analyzer took 142.77 seconds.

EP-HIV-1090
MGMQVQIQSLFLLLLWVPGSRGKLVGKLNWAGAAILKEPVHGVNAACPKVSFEPIKIPIHYCAPAKAKFVAAW
TLKAAAKAFPVRPQVPLGAAKLTPLCVTLGAAAVLAEAMSQVKVYLAWVPAHKGAAAAIFQSSMTKKTTLFCA
SDAKNIPYNPQSQGVVKHPVHAGPIANVTVYYGVPVWKKAAAQMAVFIHNFKNAAAYPLASLRSLFNLTFGWC
FKLNRILQQLLFINAKIQNFRVYYRKAAVTIKIGGQLKKVPLQLPPLKAMTNNPPIPV

ATGGGAATGCAGGTGCAGATCCAGAGCCTGTTTCTGCTCCTCCTGTGGGTGCCCGGATCCAGAGGAAAGCTGG
TGGGCAAACTCAACTGGGCCGGAGCTGCAATCCTGAAGGAGCCCGTCCACGGGGTGAATGCCGCTTGCCCTAA
AGTCAGCTTCGAACCAATTAAGATCCCCATTCATTACTGTGCACCTGCCAAAGCTAAGTTTGTGGCCGCTTGG
ACCCTCAAGGCCGCTGCAAAAGCCTTCCCAGTGAGGCCCCAGGTGCCTCTGGGCGCCGCTAAACTCACACCAC
TGTGCGTCACTCTGGGAGCCGCTGCAGTGCTGGCAGAGGCCATGTCCCAAGTGAAGGTGTATCTGGCTTGGGT
GCCCGCCCACAAGGGGGCCGCTGCAGCCATCTTTCAGTCTAGCATGACCAAGAAAACAACTCTGTTCTGTGCC
TCCGACGCTAAGAACATCCCTTATAATCCACAGTCTCAGGGCGTGGTCAAGCATCCCGTGCACGCCGGACCTA
TTGCTAACGTGACCGTGTACTATGGGGTCCCAGTGTGGAAGAAAGCCGCTGCACAGATGGCCGTGTTTATTCA
CAATTTCAAAAACGCCGCTGCATACCCCCTCGCCAGCCTGAGATCCCTCTTCAACCTGACATTCGGCTGGTGC
TTTAAGCTGAACCGGATCCTGCAGCAACTGCTCTTTATCAATGCTAAAATCCAGAACTTCCGCGTCTACTATA
GGAAGGCTGCAGTGACTATCAAAATTGGCGGACAACTGAAGAAAGTGCCTCTCCAGCTGCCCCCTCTCAAGGC
AATGACCAACAATCCCCCTATCCCAGTCTGA

HIV-CPT
MGMQVQIQSLFLLLLWVPGSRGIPIHYCAPAKAAKIQNFRVYYRKAAVTIKIGGQLKKAKFVAAWTLKAAAKV
PLQLPPLKAIFQSSMTKKLTPLCVTLGAQMAVFIHNFKGAKVYLAWVPAHKNAIPYNPQSQGVVKAILKEPVH
GVGAAALTFGWCFKLNAVLAEAMSQVNRILQQLLFINAAACPKVSFEPIKVTVYYGVPVWKKAAHPVHAGPIA
NAAAYPLASLRSLFNAAATTLFCASDAKNKLVGKLNWANAAAFPVRPQVPLNMTNNPPIPV

ATGGGGATGCAGGTGCAGATCCAGAGCCTGTTTCTGCTCCTCCTGTGGGTGCCCGGATCCAGAGGAATCCCCA
TTCACTACTGCGCCCCTGCTAAGGCAGCCAAAATCCAGAACTTCAGGGTGTATTACAGAAAGGCTGCAGTCAC
CATTAAAATCGGCGGACAACTGAAGAAAGCCAAGTTTGTGGCCGCTTGGACACTCAAGGCCGCTGCAAAGGTC
CCACTGCAGCTCCCCCCTCTGAAGGCCATCTTCCAGAGCTCCATGACTAAGAAACTGACCCCACTGTGTGTGA
CACTCGGGGCCCAGATGGCTGTGTTCATCCATAATTTTAAAGGCGCCAAGGTCTACCTGGCTTGGGTGCCCGC
ACACAAGAACGCCATTCCTTACAATCCACAGTCTCAAGGAGTGGTCAAAGCTATTCTGAAGGAGCCCGTGCAC
GGGGTGGGCGCCGCTGCACTCACTTTCGGATGGTGCTTTAAACTGAACGCCGTGCTGGCTGAAGCCATGAGCC
AGGTCAATCGGATCCTGCAGCAACTGCTCTTCATTAACGCCGCTGCATGTCCTAAGGTGTCCTTCGAGCCAAT
CAAAGTGACCGTGTATTACGGGGTCCCCGTGTGGAAGAAAGCCGCTCATCCTGTCCACGCAGGCCCAATCGCC
AACGCCGCTGCATATCCCCTCGCCTCTCTGCGCAGCCTGTTTAACGCCGCTGCAACAACCCTCTTTTGCGCCT
CCGACGCTAAGAATAAACTGGTGGGAAAGCTGAACTGGGCCAACGCAGCTGCATTCCCTGTGAGGCCACAGGT
CCCCCTCAATATGACTAACAATCCCCCTATCCCAGTGTGA

FIG.18A

HIV-FT
MQVQIQSLFLLLLWVPGSRGKLVGKLNWAMASDFNLPPVAIFQSSMTKVTIKIGGQLKRILQQLLFIMAVFIH
NFKIPYNPQSQGVVTTLFCASDAKILKEPVHGVQMAVFIHNFKGAAVFIHNFKRCPKVSFEPIKIQNFRVYYR
LTFGWCFKLQVPLRPMTYKMTNNPPIPVTVYYGVPVWKVLAEAMSQVIPIHYCAPAKLTPLCVTL

ATGCAGGTGCAGATCCAGAGCCTGTTTCTGCTCCTCCTGTGGGTGCCCGGATCCAGAGGAAAGCTGGTGGGGA
AGCTGAACTGGGCCATGGCCAGCGATTTCAACCTGCCCCCCGTGGCCATCTTCCAGAGCAGCATGACCAAGGT
GACCATCAAGATCGGGGGGCAGCTGAAGAGGATCCTGCAGCAGCTGCTGTTCATCATGGCCGTGTTCATCCAC
AACTTCAAGATCCCCTACAACCCCCAGAGCCAGGGGGTGGTGACCACCCTGTTCTGCGCCAGCGATGCCAAGA
TCCTGAAGGAGCCCGTGCACGGGGTGCAGATGGCCGTGTTCATCCACAACTTCAAGGGCGCCGCCGTGTTCAT
CCACAACTTCAAGAGGTGCCCCAAGGTGAGCTTCGAGCCCATCAAGATCCAGAACTTCAGGGTGTACTACAGG
CTGACCTTCGGGTGGTGCTTCAAGCTGCAGGTGCCCCTGAGGCCCATGACCTACAAGATGACCAACAACCCCC
CCATCCCCGTGACCGTGTACTACGGGGTGCCCGTGTGGAAGGTGCTGGCCGAGGCCATGAGCCAGGTGATCCC
CATCCACTACTGCGCCCCCGCCAAGCTGACCCCCCTGTGCGTGACCCTG

FIG.18B

HIV-TC
MGMQVQIQSLFLLLLWVPGSRGYWQATWIPEWKAIFQSSMTKKVYLAWVPAHKNAACPKVSFEPIKHPVHAGP
IANLTFGWCFKLNKMIGGIGGFIKFRDYVDRFYKAAARILQQLLFINTTLFCASDAKNQMVHQAISPRGAKLV
GKLNWAGAAAIYETYGDTWKAAQVPLRPMTYKGAAAVTVLDVGDAYNAAARYLKDQQLLNTLNFPISPINMTN
NPPIPVNAPYNTPVFAIKAAAVPLQLPPLKAAIPYNPQSQGVVKALLQLTVWGIGAAILKEPVHGVNAAAFPI
SPIETVKVWKEATTTLFKAAAVTIKIGGQLKKIYQEPFKNLKAAAVLAEAMSQVNLVGPTPVNIGAAAEVNIV
TDSQYKAAAIPIHYCAPAKAVIYQYMDDLYKAAAQMAVFIHNFKNAATYQIYQEPFKPYNEWTLELKAKIQNF
RVYYRKAFPVRPQVPLGAAAIWGCSGKLIKVMIVWQVDRNAAKAACWWAGIKAKFVAAWTLKAAAKLTPLCVT
LNAAMASDFNLPPVKSLLNATDIAVNVTVYYGVPVWKKAAAAIIRILQQLKRAMASDFNLNAAAYPLASLRSL
F

ATGGGGATGCAGGTGCAGATCCAGAGCCTGTTTCTGCTCCTCCTGTGGGTGCCCGGATCTAGAGGATACTGGC
AAGCTACTTGGATTCCAGAATGGAAAGCTATCTTTCAATCCTCAATGACGAAGAAGGTATACCTGGCATGGGT
CCCAGCACACAAGAACGCCGCTTGCCCAAAGGTGTCCTTTGAACCCATTAAACACCCAGTGCACGCAGGGCCA
ATAGCGAATTTGACATTCGGGTGGTGCTTCAAACTAAACAAAATGATCGGCGGCATTGGAGGCTTTATCAAGT
TTAGAGATTACGTGGACCGATTCTATAAAGCCGCTGCCCGTATACTCCAGCAGCTACTATTCATCAACACCAC
TCTCTTCTGCGCTTCAGACGCTAAGAACCAAATGGTACACCAAGCCATAAGCCCTAGAGGAGCCAAGCTCGTA
GGGAAATTAAATTGGGCGGGTGCAGCAGCAATCTACGAGACTTACGGCGATACCTGGAAAGCAGCCCAGGTTC
CGTTACGCCCAATGACCTATAAAGGCGCAGCAGCAGTAACAGTTCTAGATGTAGGAGACGCTTACAACGCTGC
CGCAAGATACCTAAAAGATCAGCAGTTACTCAACACACTAAATTTCCCAATTAGCCCGATAAACATGACAAAT
AACCCACCAATTCCCGTCAATGCTCCCTACAACACTCCAGTATTCGCAATCAAAGCCGCTGCTGTCCCCCTGC
AGCTCCCTCCTCTGAAAGCTGCGATACCTTACAACCCACAGAGCCAAGGTGTTGTCAAAGCACTGCTTCAGCT
AACAGTTTGGGGAATTGGTGCTGCAATTCTAAAAGAGCCAGTTCATGGGGTTAACGCCGCCGCCTTCCCAATC
AGTCCTATTGAGACTGTGAAAGTATGGAAAGAAGCCACAACCACACTTTTTAAGGCAGCCGCAGTTACAATTA
AAATAGGGGGCCAACTTAAGAAAATATACCAGGAACCTTTCAAGAATCTCAAAGCCGCTGCAGTGCTCGCCGA
GGCTATGTCACAGGTGAATTTGGTCGGACCAACACCCGTAAACATCGGAGCCGCAGCCGAAGTGAACATAGTC
ACCGACTCACAGTACAAAGCCGCTGCAATACCCATACATTATTGTGCTCCCGCAAAGGCCGTGATCTATCAAT
ATATGGACGACCTGTATAAGGCCGCCGCGCAGATGGCAGTCTTTATCCACAACTTTAAAAACGCAGCTACTTA
TCAGATCTACCAGGAACCATTCAAACCGTACAATGAGTGGACCTTGGAACTAAAGGCCAAAATTCAGAACTTC
AGGGTATATTATAGAAAAGCATTTCCAGTGAGGCCCCAGGTGCCTCTGGGTGCCGCAGCAATATGGGGATGTT
CTGGAAAACTGATCAAGGTGATGATTGTATGGCAAGTGGACAGAAATGCAGCTAAGGCAGCCTGTTGGTGGGC
AGGTATAAAAGCAAAGTTCGTGGCAGCATGGACGCTTAAAGCAGCCGCAAAACTCACTCCTCTCTGCGTGACA
CTTAATGCAGCCATGGCCTCTGATTTCAACCTTCCCCCTGTAAAATCCCTGCTTAATGCGACAGATATCGCAG
TCAACGTAACAGTATATTATGGCGTGCCAGTCTGGAAAAAAGCCGCCGCGGCCATAATTCGGATACTGCAGCA
GCTGAAAAGAGCTATGGCGAGTGACTTCAACCTGAATGCGGCCGCCTACCCCTTGGCATCGTTAAGGTCACTA
TTTTGA

FIG.18C

HCV.1
MGMQVQIQSLFLLLLWVPGSRGLLFNILGGWVDLMGYIPLVYLVAYQATVILAGYGAGVRLIVFPDLGVHMWNFISGI
YLLPRRGPRLYLVTRHADVVLVGGVLAALLFLLLADAFLLLADARVWMNRLIAFACTCGSSDLYLSAFSLHSYGVAGA
LVAFKLPGCSFSIFKTSERSQPRLIFCHSKKKFWAKHMWNFIPFYGKAIRMYVGGVEHRQLFTFSPRRRLGVRATRKV
GIYLLPNRAKFVAAWTLKAAA*

GAATTCGCCGCCACCATGCAGGTGCAGATCCAGAGCCTGTTTCTGCTCCTCCTGTGGGTGCCCGGATCCAGAGGACTG
CTGTTCAACATCCTGGGGGGGTGGGTGGATCTGATGGGGTACATCCCCCTGGTGTACCTGGTGGCCTACCAGGCCACC
GTGATCCTGGCCGGGTACGGGGCCGGGGTGAGGCTGATCGTGTTCCCCGATCTGGGGGTGCACATGTGGAACTTCATC
AGCGGGATCTACCTGCTGCCCAGGAGAGGACCTAGACTGTACCTGGTGACTAGACACGCTGATGTGGTGCTGGTGGGA
GGAGTGCTGGCTGCTCTGCTGTTTCTGCTGCTGGCTGATGCTTTCCTGCTGCTGGCTGATGCTAGAGTGTGGATGAAC
AGACTGATCGCTTTCGCTTGTACATGTGGAAGCTCCGATCTGTATCTGAGCGCTTTCAGCCTGCACAGCTACGGAGTG
GCTGGAGCTCTGGTGGCTTTTAAGCTGCCTGGATGTAGCTTTAGCATCTTTAAGACCAGCGAAAGAAGCCAGCCTAGA
CTGATCTTTTGTCACAGCAAGAAGAAGTTTTGGGCTAAGCACATGTGGAATTTTATCCCTTTCTATGGAAAGGCTATC
AGAATGTATGTGGGAGGAGTGGAACACAGACAGCTGTTTACATTTAGCCCTAGAAGGAGACTGGGAGTGAGAGCTACA
AGAAAGGTGGGAATCTATCTGCTGCCTAATAGATGAAAGCTTGGG*

HCV.2
MGMQVQIQSLFLLLLWVPGSRGDLMGYIPLVAKFVAAWTLKAAALLFLLLADALIFCHSKKKQLFTFSPRRYLVTRHA
DVYLLPRRGPRLCTCGSSDLYHMWNFISGIFWAKHMWNFAKFVAAWTLKAAAILAGYGAGVYLVAYQATVGVAGALVA
FKIPFYGKAIRMYVGGVEHRVLVGGVLAAFLLLADARVLPGCSFSIFAKFVAAWTLKAAAKTSERSQPRRLGVRATRK
RLIVFPDLGVWMNRLIAFALSAFSLHSYLLFNILGGWVVGIYLLPNR*

GAATTCGCCGCCACCATGGGAATGCAGGTGCAGATCCAGAGCCTGTTTCTGCTCCTCCTGTGGGTGCCCGGATCCAGA
GGAGATCTGATGGGATATATCCCTCTGGTGGCTAAGTTTGTGGCTGCTTGGACACTGAAGGCTGCTGCTCTGCTGTTT
CTGCTGCTGGCTGATGCTCTGATCTTCTGTCACAGCAAGAAGAAGCAGCTGTTTACATTTAGCCCAAGAAGATATCTG
GTGACAAGACACGCTGATGTGTATCTGCTGCCTAGACGCGGACCTAGACTGTGTACATGTGGAAGCTCCGATCTGTAT
CACATGTGGAACTTTATCAGCGGAATCTTTTGGGCTAAGCACATGTGGAATTTTCATCCTGGCTGGATATGGAGCTGGA
GTGTATCTGGTGGCTTATCAGGCTACAGTGGGAGTGGCTGGAGCTCTGGTGGCTTTCAAGATCCCATTCTATGGAAAG
GCTATCAGAATGTATGTGGGAGGAGTGGAACACAGAGTGCTGGTGGGAGGAGTGCTGGCTGCTTTCCTGCTGCTGGCT
GATGCTAGAGTGCTGCCAGGATGTAGCTTTAGCATCTTCAAGACTTCCGAACGCTCCCAGCCTAGAAGACTGGGAGTG
AGAGCTACAAGGAAGAGACTGATCGTGTTTCCAGATCTGGGAGTGTGGATGAATAGACTGATCGCTTTCGCTCTGAGC
GCTTTCAGCCTGCACAGCTATCTGCTGTTCAACATCCTGGGAGGATGGGTGGTGGGAATCTATCTGCTGCCAAACAGA
TGAAAGCTT

HCV.3s1
MGMQVQIQSLFLLLLWVPGSRGYLVAYQATVAKFVAAWTLKAAALLFLLLADALIFCHSKKKYLVTRHADVLGFGAYM
SKCTCGSSDLYHMWNFISGIFWAKHMWNF*

GAATTCGCCGCCACCATGGGAATGCAGGTGCAGATCCAAAGCCTGTTTCTGCTCCTCCTGTGGGTGCCCGGATCCAGA
GGATACCTCGTCGCCTACCAGGCCACTGTGGCTAAATTCGTGGCAGCCTGGACACTGAAAGCTGCAGCTCTGCTCTTC
CTGCTCCTGGCCGATGCACTCATCTTCTGCCATTCCAAGAAAAAGTATCTGGTCACCAGACATGCTGACGTGCTGGGG
TTTGGCGCCTACATGAGCAAGTGCACCTGTGGCAGCTCCGACCTGTATCACATGTGGAACTTTATTTCTGGAATCTTT
TGGGCCAAGCACATGTGGAATTTCTGAAAGCTT

FIG.18D

HCV.3s2
MGMQVQIQSLFLLLLWVPGSRGVLVGGVLAAAKFVAAWTLKAAAFLLLADARVLSAFSLHSYILAGYGAGVWM
NRLIAFAIPFYGKAIVAGALVAFKVGIYLLPNR*

GAATTCGCCGCCACCATGGGAATGCAGGTGCAGATCCAAAGCCTGTTTCTGCTCCTCCTGTGGGTGCCCGGAT
CCAGAGGAGTCCTGGTGGGCGGCGTCCTGGCCGCTGCTAAGTTTGTCGCTGCTTGGACACTGAAGGCAGCCGC
TTTCCTGCTCCTGGCAGACGCCAGGGTGCTGTCTGCCTTCAGCCTCCACTCCTACATCCTCGCAGGGTATGGC
GCAGGCGTGTGGATGAATCGGCTGATCGCCTTTGCCATTCCATTCTATGGGAAAGCCATTGTGGCTGGCGCCC
TGGTGGCATTCAAGGTCGGGATCTACCTCCTGCCTAACCGCTGAAAGCTT

HCV.3s2(-3)
MGMQVQIQSLFLLLLWVPGSRGVLVGGVLAAAKFVAAWTLKAAAFLLLADARVLSAFSLHSYILAGYGAGVWM
NRLIAFA*

GAATTCGCCGCCACCATGGGAATGCAGGTGCAGATCCAAAGCCTGTTTCTGCTCCTCCTGTGGGTGCCCGGAT
CCAGAGGAGTCCTGGTGGGCGGCGTCCTGGCCGCTGCTAAGTTTGTCGCTGCTTGGACACTGAAGGCAGCCGC
TTTCCTGCTCCTGGCAGACGCCAGGGTGCTGTCTGCCTTCAGCCTCCACTCCTACATCCTCGCAGGGTATGGC
GCAGGCGTGTGGATGAATCGGCTGATCGCCTTTGCCTGAGGATCC

HCV.3s3
MGMQVQIQSLFLLLLWVPGSRGDLMGYIPLVAKFVAAWTLKAAARLGVRATRKLLFNILGGWVRMYVGGVEHR
RLIVFPDLGVGVAGALVAFKLPGCSFSIFKTSERSQPRQLFTFSPRRYLLPRRGPRL

GAATTCGCCGCCACCATGGGAATGCAGGTGCAGATCCAAAGCCTGTTTCTGCTCCTCCTGTGGGTGCCCGGAT
CCAGAGGAGACCTGATGGGCTACATCCCTCTCGTGGCCAAGTTTGTGGCAGCTTGGACCCTGAAGGCCGCTGC
CAGACTGGGAGTGCGCGCTACACGGAAACTCCTGTTTAACATCCTGGGAGGGTGGGTGCGGATGTACGTCGGA
GGCGTCGAGCACAGAAGGCTCATTGTCTTTCCAGATCTCGGCGTGGGCGTCGCAGGCGCACTCGTGGCCTTCA
AACTGCCAGGGTGCAGCTTCAGCATTTTCAAGACCTCCGAACGCTCCCAACCCAGACAGCTGTTCACTTTCTC
TCCTCGGAGGTATCTGCTGCCCAGACGCGGACCCAGGCTGTGAAAGCTT

HCV.PC3
MGMQVQIQSLFLLLLWVPGSRGLLFNILGGWVKAKFVAAWTLKAAALADGGCSGGAYRLIVFPDLGVKFWAKH
MWNFIGVAGALVAFKKQLFTFSPRR*

GAATTCGCCGCCACCATGGGAATGCAGGTGCAGATCCAAAGCCTGTTTCTGCTCCTCCTGTGGGTGCCCGGAT
CCAGAGGACTGCTCTTCAACATCCTGGGCGGATGGGTGAAGGCCAAGTTCGTGGCTGCCTGGACCCTGAAGGC
TGCCGCTCTGGCCGACGGGGGATGCAGCGGCGGAGCTTACAGGCTCATTGTCTTTCCCGATCTCGGAGTCAAA
TTTTGGGCAAAGCACATGTGGAATTTCATCGGGGTGGCCGGAGCCCTGGTCGCTTTTAAAAAGCAGCTCTTCA
CCTTCTCCCCAAGACGGTGAGGTACC

FIG.18E

HCV.PC4
MGMQVQIQSLFLLLLWVPGSRGRLGVRATRKKAKFVAAWTLKAAAKTSERSQPRNLPGCSFSIFNDLMGYIPL
VKYLLPRRGPRLNTLCGFADLMGYRMYVGGVEHR*

GAATTCGCCGCCACCATGGGAATGCAGGTGCAGATCCAAAGCCTGTTTCTGCTCCTCCTGTGGGTGCCCGGAT
CCAGAGGAAGGCTGGGCGTGAGAGCCACCCGGAAGAAGGCCAAGTTCGTGGCTGCCTGGACCCTGAAGGCTGC
CGCTAAAACAAGCGAGCGCTCCCAGCCCAGGAACCTGCCTGGATGCTCTTTCAGCATCTTTAATGACCTCATG
GGGTACATTCCACTGGTGAAGTATCTGCTCCCCAGACGGGGCCCTCGCCTGAACACTCTCTGTGGATTTGCTG
ATCTGATGGGGTACAGGATGTATGTCGGCGGAGTCGAACACAGATGAGGTACC

HCV.2431(1P)
MGMQVQIQSLFLLLLWVPGSRGVLVGGVLAAAFLLLADARVLSAFSLHSYILAGYGAGVWMNRLIAFAGAAAR
LGVRATRKKAAAKTSERSQPRNLPGCSFSIFNDLMGYIPLVKYLLPRRGPRLNTLCGFADLMGYRMYVGGVEH
RKLLFNILGGWVKAAALADGGCSGGAYRLIVFPDLGVKFWAKHMWNFIGVAGALVAFKKQLFTFSPRRNGYLV
AYQATVAAALLFLLLADALIFCHSKKKYLVTRHADVLGFGAYMSKCTCGSSDLYHMWNFISGIFWAKHMWNFK
AAAAKFVAAWTLKAAA

GAATTCGCCGCCACCATGGGAATGCAGGTGCAGATCCAAAGCCTGTTTCTGCTCCTCCTGTGGGTGCCCGGCT
CCAGAGGAGTCCTGGTGGGCGGCGTCCTGGCAGCCGCTTTCCTGCTCCTGGCAGACGCCAGGGTGCTGTCTGC
CTTCAGCCTCCACTCCTACATCCTCGCAGGGTATGGCGCAGGCGTGTGGATGAATCGGCTGATCGCCTTTGCC
GGCGCTGCCGCAAGGCTGGGCGTGAGAGCCACCCGGAAGAAGGCTGCCGCTAAAACAAGCGAGCGCTCCCAGC
CCAGGAACCTGCCTGGATGCTCTTTCAGCATCTTTAATGACCTCATGGGGTACATTCCACTGGTGAAGTATCT
GCTCCCCAGACGGGGCCCTCGCCTGAACACTCTCTGTGGATTTGCTGATCTGATGGGGTACAGGATGTATGTC
GGCGGAGTCGAACACAGAAAACTGCTCTTCAACATCCTGGGCGGATGGGTGAAGGCTGCCGCTCTGGCCGACG
GGGGATGCAGCGGCGGAGCTTACAGGCTCATTGTCTTTCCCGATCTCGGAGTCAAATTTTGGGCAAAGCACAT
GTGGAATTTCATCGGGGTGGCCGGAGCCCTGGTCGCTTTTAAAAAGCAGCTCTTCACCTTCTCCCCAAGACGG
AACGGATACCTCGTCGCCTACCAGGCCACTGTGGCTGCAGCTCTGCTCTTCCTGCTCCTGGCCGATGCACTCA
TCTTCTGCCATTCCAAGAAAAAGTATCTGGTCACCAGACATGCTGACGTGCTGGGGTTTGGCGCCTACATGAG
CAAGTGCACCTGTGGCAGCTCCGACCTGTATCACATGTGGAACTTTATTTCTGGAATCTTTTGGGCCAAGCAC
ATGTGGAATTTTAAGGCCGCAGCAGCTAAATTCGTGGCAGCCTGGACACTGAAAGCAGCTGCATGAGGATCC

FIG. 18F

HCV.4312(1P)
MGMQVQIQSLFLLLLWVPGSRGRLGVRATRKKAAAKTSERSQPRNLPGCSFSIFNDLMGYIPLVKYLLPRRGPRLNTLC
GFADLMGYRMYVGGVEHRKLLFNILGGWVKAAALADGGCSGGAYRLIVFPDLGVKFWAKHMWNFIGVAGALVAFKKQLF
TFSPRRNGYLVAYQATVAAALLFLLLADALIFCHSKKKYLVTRHADVLGFGAYMSKCTCGSSDLYHMWNFISGIFWAKH
MWNFKKAAAVLVGGVLAAAFLLLADARVLSAFSLHSYILAGYGAGVWMNRLIAFANAAAKFVAAWTLKAAA*

GAATTCGCCGCCACCATGGGAATGCAGGTGCAGATCCAAAGCCTGTTTCTGCTCCTCCTGTGGGTGCCCGGCTCCAGAG
GAAGGCTGGGCGTGAGAGCCACCCGGAAGAAGGCTGCCGCTAAAACAAGCGAGCGCTCCCAGCCCAGGAACCTGCCTGG
ATGCTCTTTCAGCATCTTTAATGACCTCATGGGGTACATTCCACTGGTGAAGTATCTGCTCCCCAGACGGGGCCCTCGC
CTGAACACTCTCTGTGGATTTGCTGATCTGATGGGGTACAGGATGTATGTCGGCGGAGTCGAACACAGAAAACTGCTCT
TCAACATCCTGGGCGGATGGGTGAAGGCTGCCGCTCTGGCCGACGGGGGATGCAGCGGCGGAGCTTACAGGCTCATTGT
CTTTCCCGATCTCGGAGTCAAATTTTGGGCAAAGCACATGTGGAATTTTCATCGGGGTGGCCGGAGCCCTGGTCGCTTTT
AAAAAGCAGCTCTTCACCTTCTCCCCAAGACGGAACGGATACCTCGTCGCCTACCAGGCCACTGTGGCTGCAGCTCTGC
TCTTCCTGCTCCTGGCCGATGCACTCATCTTCTGCCATTCCAAGAAAAAGTATCTGGTCACCAGACATGCTGACGTGCT
GGGGTTTGGCGCCTACATGAGCAAGTGCACCTGTGGCAGCTCCGACCTGTATCACATGTGGAACTTTATTTCTGGAATC
TTTTGGGCCAAGCACATGTGGAATTTTAAGAAAGCCGCTGCAGTCCTGGTGGGCGGCGTCCTGGCAGCCGCTTTCCTGC
TCCTGGCAGACGCCAGGGTGCTGTCTGCCTTCAGCCTCCACTCCTACATCCTCGCAGGGTATGGCGCAGGCGTGTGGAT
GAATCGGCTGATCGCCTTTGCCAATGCTGCAGCTAAATTCGTGGCAGCCTGGACACTGAAAGCAGCTGCATGAGGATCC

AOSI.K
MGMQVQIQSLFLLLLWVPGSRGHTLWKAGILYKAKFVAAWTLKAAAFLPSDFFPSVKFLLSLGIHLYMDDVVLGVGLSR
YVARLFLLTRILTISTLPETTVVRRQAFTFSPTYKWLSLLVPFV

ATGGGAATGCAGGTGCAGATCCAGAGCCTGTTTCTGCTCCTCCTGTGGGTGCCCGGGTCCAGAGGACACACCCTGTGGA
AGGCCGGAATCCTGTATAAGGCCAAGTTCGTGGCTGCCTGGACCCTGAAGGCTGCCGCTTTTCCTGCCTAGCGATTTCTT
TCCTAGCGTGAAGTTCCTGCTGTCCCTGGGAATCCACCTGTATATGGATGACGTGGTGCTGGGAGTGGGACTGTCCAGG
TACGTGGCTAGGCTGTTCCTGCTGACCAGAATCCTGACCATCTCCACCCTGCCAGAGACCACCGTGGTGAGGAGGCAGG
CCTTCACCTTTAGCCCCTACCTATAAGTGGCTGAGCCTGCTGGTGCCCTTTGTGTGA

HBV.1
MGMQVQIQSLFLLLLWVPGSRGHTLWKAGILYKAKFVAAWTLKAAAFLPSDFFPSVFLLSLGIHLYMDDVVLGVGLSRY
VARLFLLTRILTISTLPETTVVRRQAFTFSPTYKWLSLLVPFVIPIPSSWAFTPARVTGGVFKVGNFTGLYLPSDFFPS
VTLWKAGILYKNVSIPWTHKLVVDFSQFSRSAICSVVRRALMPLYACI

ATGGGAATGCAGGTGCAGATCCAGAGCCTGTTTCTGCTCCTCCTGTGGGTGCCCGGGTCCAGAGGACACACCCTGTGGA
AGGCCGGAATCCTGTATAAGGCCAAGTTCGTGGCTGCCTGGACCCTGAAGGCTGCCGCTTTTCCTGCCTAGCGATTTCTT
TCCTAGCGTGTTCCTGCTGTCCCTGGGAATCCACCTGTATATGGATGACGTGGTGCTGGGAGTGGGACTGTCCAGGTAC
GTGGCTAGGCTGTTCCTGCTGACCAGAATCCTGACCATCTCCACCCTGCCAGAGACCACCGTGGTGAGGAGGCAGGCCT
TCACCTTTAGCCCCTACCTATAAGTGGCTGAGCCTGCTGGTGCCCTTTGTGATCCCTATCCCTAGCTCCTGGGCTTTCAC
CCCAGCCAGGGTGACCGGAGGAGTGTTTAAGGTGGGAAACTTCACCGGCCTGTATCTGCCCAGCGATTTCTTTCCTAGC
GTGACCCTGTGGAAGGCCGGGATCCTGTACAAGAATGTGTCCATCCCTTGGACCCACAAGCTGGTGGTGGACTTTTCCC
AGTTCAGCAGATCCGCTATCTGCTCCGTGGTGAGGAGAGCTCTGATGCCACTGTATGCCTGTATCTGA

FIG.18G

HBV.2

MGMQVQIQSLFLLLLWVPGSRGHTLWKAGILYKAKFVAAWTLKAAAFLPSDFFPSVNFLLSLGIHLYMDDVVLGVGLSR
YVARLFLLTRILTISTLPETTVVRRQAFTFSPTYKGAAAWLSLLVPFVNIPIPSSWAFKTPARVTGGVFKVGNFTGLYN
LPSDFFPSVKTLWKAGILYKNVSIPWTHKGAALVVDFSQFSRNSAICSVVRRALMPLYACI

ATGGGAATGCAGGTGCAGATCCAGAGCCTGTTTCTGCTCCTCCTGTGGGTGCCCGGGTCCAGAGGACACACCCTGTGGA
AGGCCGGAATCCTGTATAAGGCCAAGTTCGTGGCTGCCTGGACCCTGAAGGCTGCCGCTTTCCTGCCTAGCGATTTCTT
TCCTAGCGTGAACTTCCTGCTGTCCCTGGGAATCCACCTGTATATGGATGACGTGGTGCTGGGAGTGGGACTGTCCAGG
TACGTGGCTAGGCTGTTCCTGCTGACCAGAATCCTGACCATCTCCACCCTGCCAGAGACCACCGTGGTGAGGAGGCAGG
CCTTCACCTTTAGCCCTACCTATAAGGGAGCCGCTGCCTGGCTGAGCCTGCTGGTGCCCTTTGTGAATATCCCTATCCC
TAGCTCCTGGGCTTTCAAGACCCCAGCCAGGGTGACCGGAGGAGTGTTTAAGGTGGGAAACTTCACCGGCCTGTATAAC
CTGCCCAGCGATTTCTTTCCTAGCGTGAAGACCCTGTGGAAGGCCGGAATCCTGTACAAGAATGTGTCCATCCCTTGGA
CCCACAAGGGAGCCGCTCTGGTGGTGGACTTTTCCCAGTTCAGCAGAAATTCCGCTATCTGCTCCGTGGTGAGGAGAGC
TCTGATGCCACTGTATGCCTGTATCTGA

PfCTL.1

MQVQIQSLFLLLLWVPGSRGILSVSSFLFVNAAAQTNFKSLLRNLPSENERGYKAAALLACAGLAYKKAAAAKFVAAWT
LKAAAKAFMKAVCVEVNAAASFLFVEALFNATPYAGEPAPFKAAAKYKLATSVLKAGVSENIFLKNAAAYFILVNLLIK
AGLLGVVSTV

ATGGGAATGCAGGTGCAGATCCAGAGCCTGTTTCTGCTCCTCCTGTGGGTGCCCGGATCCAGAGGAATCCTGAGCGTGT
CCTCTTTCCTGTTTGTCAACGCCGCTGCACAGACCAATTTCAAGAGCCTCCTGAGGAACCTCCCCTCCGAGAACGAAAG
AGGCTACAAAGCCGCTGCACTGCTCGCCTGCGCTGGACTGGCCTATAAGAAAGCCGCTGCAGCCAAGTTCGTGGCCGCT
TGGACACTGAAGGCCGCTGCAAAAGCCTTTATGAAGGCTGTCTGTGTGGAGGTCAATGCCGCTGCATCTTTCCTGTTTG
TGGAGGCCCTCTTTAACGCTACTCCTTACGCAGGGGAACCAGCCCCCTTCAAGGCCGCTGCAAAATATAAGCTGGCAAC
CAGCGTGCTGAAGGCTGGCGTGTCCGAGAATATTTTTCTGAAAAACGCCGCTGCATACTTCATCCTGGTGAATCTGCTC
ATTAAGGCCGGACTCCTGGGGGTGGTCTCTACAGTGTGA

PfCTL.2

MQVQIQSLFLLLLWVPGSRGFVEALFQEYNAAAKYLVIVFLINALACAGLAYKKFYFILVNLLKAALFFIIFNKNAAAK
FVAAWTLKAAAKFILVNLLIFHNFQDEENIGIYKLPYGRTNLKAAAVLLGGVGLVLNFLIFFDLFLVKAVLAGLLGVV

ATGGGAATGCAGGTGCAGATCCAGAGCCTGTTTCTGCTCCTCCTGTGGGTGCCCGGATCCAGAGGATTCGTGGAGGCCC
TGTTTCAGGAATACAACGCCGCTGCAAAGTATCTCGTCATCGTGTTCCTGATCAATGCTCTGGCATGCGCCGGCCTCGC
TTACAAAAAGTTTTACTTCATTCTGGTCAACCTGCTCAAGGCCGCTCTGTTCTTTATCATTTTCAATAAAAACGCCGCA
GCTAAGTTTGTGGCCGCATGGACCCTGAAGGCCGCTGCAAAATTCATCCTCGTGAATCTGCTCATTTTTCACAACTTCC
AAGACGAGGAAAATATCGGAATTTATAAGCTGCCCTACGGGAGGACAAACCTGAAAGCCGCTGCAGTCCTGCTCGGCGG
AGTGGGGCTGGTGCTCAATTTTCTGATCTTCTTTGATCTGTTCCTGGTGAAGGCCGTCCTGGCCGGCCTGCTCGGAGTC
GTGTGA

FIG.18H

PfCTL.3
MQVQIQSLFLLLLWVPGSRGVFLIFFDLFLNAAAPSDGKCNLYKAAAVTCGNGIQVRKLFHIFDGDNEIKAHVLSHNSY
EKNYYGKQENWYSLKKILSVFFLANAAAKFIKSLFHIFKAAALYISFYFIKAKFVAAWTLKAAAKAAAYYIPHQSSLKA
AAGLIMVLSFL

ATGGGAATGCAGGTGCAGATCCAGAGCCTGTTTCTGCTCCTCCTGTGGGTGCCCGGATCCAGAGGAGTGTTCCTGATCT
TCTTTGACCTGTTCCTGAACGCCGCTGCACCCAGCGATGGCAAGTGCAATCTCTACAAGGCCGCTGCAGTGACCTGTGG
AAACGGGATTCAGGTCAGGAAACTCTTTCACATCTTCGACGGCGATAACGAGATCAAGGCCCATGTGCTGTCCCACAAT
TCTTATGAAAAAAACTACTATGGAAAGCAAGAGAATTGGTACAGCCTGAAGAAAATTCTGTCCGTGTTCTTTCTCGCCA
ACGCCGCTGCAAAGTTTATCAAGTCTCTGTTCCATATTTTCAAGGCCGCTGCACTCTACATCAGCTTCTATTTTATTAA
AGCCAAATTTGTGGCCGCTTGGACACTGAAGGCCGCTGCAAAAGCCGCTGCATACTATATCCCTCACCAGAGCTCCCTG
AAGGCCGCTGCAGGGCTGATCATGGTGCTCTCTTTCCTGTGA

PfCTL/HTL(N)
MQVQIQSLFLLLLWVPGSRGSSVFNVVNSSIGLIMVLSFLGPGPGLYISFYFILVNLLIFHINGKIIKNSEGPGPGPDS
IQDSLKESRKLSGPGPGVLAGLLGVVSTVLLGGVGLVLGPGPGLPSENERGYYIPHQSSLGPGPGQTNFKSLLRNLGVS
ENIFLKGPGPGFQDEENIGIYGPGPGKYLVIVFLIFFDLFLVGPGPGKFIKSLFHIFDGDNEIGPGPGKSKYKLATSVL
AGLLGPGPGLPYGKTNLGPGPGRHNWVNHAVPLAMKLIGPGPGMRKLAILSVSSFLFVEALFQEYGPGPGVTCGNGIQV
RGPGPGMNYYGKQENWYSLKKGPGPGPSDGKCNLYADSAWENVKNVIGPFMKAVCVEVGPGPGKILSVFFLALFFIIFN
KGPGPGHVLSHNSYEKGPGPGKYKIAGGIAGGLALLACAGLAYKFVVPGAATPYAGEPAPF

ATGGGAATGCAGGTGCAGATCCAGAGCCTGTTTCTGCTCCTCCTGTGGGTGCCCGGATCCAGAGGAAGTAGTGTGTTCA
ATGTTGTGAACTCATCAATTGGTCTGATCATGGTGCTGAGCTTTCTCG
GGCCAGGGCCAGGATTATATATTTCTTTCTACTTCATCCTTGTCAACCTGTTAATATTCCACATTAACGGCAAAATAAT
AAAGAACAGTGAAGGCCCTGGGCCTGGGCCTGACTCGATCCAGGATTCTCTAAAAGAATCGAGGAAGCTCTCCGGACCA
GGCCCTGGTGTACTCGCCGGGTTGCTGGGAGTAGTTAGCACAGTGCTGTTAGGAGGCGTCGGCCTCGTCTTAGGACCTG
GACCAGGTCTGCCGTCCGAAAACGAAAGAGGATACTACATACCTCACCAGAGCAGCCTCGGCCCAGGCCCCGGACAAAC
CAATTTCAAATCCCTCTTGCGAAATCTAGGAGTGAGCGAGAACATATTTCTTAAAGGACCCGGTCCCGGCTTTCAGGAC
GAGGAGAATATAGGTATTTACGGTCCAGGACCTGGAAAATACCTAGTGATCGTATTCCTAATTTTTTTTGACCTATTTC
TGGTGGGCCCAGGTCCCGGAAAGTTCATTAAATCACTCTTCCACATTTTTGACGGAGATAACGAGATAGGACCCGGTCC
CGGGAAATCAAAGTACAAACTAGCCACTTCAGTGCTGGCCGGCCTTCTAGGGCCGGGCCCAGGGCTCCCCTATGGAAAG
ACAAATCTTGGCCCCGGTCCAGGACGGCACAACTGGGTGAATCATGCGGTTCCATTGGCCATGAAACTAATCGGGCCCG
GTCCAGGCATGCGCAAACTTGCAATTCTAAGCGTAAGTTCATTTCTGTTCGTAGAGGCACTGTTTCAAGAATATGGCCC
AGGACCTGGCGTCACATGTGGGAATGGGATCCAGGTGAGAGGACCGGGACCTGGTATGAACTATTACGGTAAACAGGAA
AATTGGTACTCCCTGAAAAAGGGTCCAGGCCCCGGCCCCTCAGATGGTAAGTGCAACCTGTATGCTGACTCAGCATGGG
AGAACGTAAAAAATGTAATAGGCCCATTCATGAAGGCAGTTTGTGTCGAAGTCGGACCAGGCCCAGGAAAAATACTTTC
TGTCTTCTTCCTAGCTCTCTTCTTCATCATCTTCAACAAGGGACCAGGGCCAGGTCACGTGTTATCCCATAACTCTTAT
GAAAAAGGGCCAGGACCTGGGAAATACAAAATCGCAGGAGGGATCGCCGGCGGGCTAGCGCTCCTTGCCTGCGCAGGCT
TGGCTTACAAATTCGTTGTACCAGGAGCTGCAACACCCTATGCAGGAGAACCTGCCCCATTTTGAAGATCTGC

FIG.18I

Pf33
MGMQVQIQSLFLLLLWVPGSRGFMKAVCVEVNVTCGNGIQVRKGLIMVLSFLNAALFHIFDGDNEIKAALLACAGLAYK
KSFLFVEALFNAAPSDGKCNLYKAAQTNFKSLLRNLPSENERGYKAAGVSENIFLKNAAAYFILVNLLIKAAAILSVSS
FLFVNTPYAGEPAPFKAAAKYKLATSVLKAAVFLIFFDLFLNYYIPHQSSLKAAGLLGNVSTVGAVLLGGVGLVLNLAC
AGLAYKKAKFIKSLFHIFKAAFYFILVNLLKAFLIFFDLFLVKALFFIIFNKNYYGKQENWYSLKFVEALFQEYNAAAK
FVAAWTLKAAAKILSVFFLANAVLAGLLGNVNFQDEENIGIYKAAALYISFYFIKAFILVNLLIFHNAALPYGRTNLKA
AHVLSHNSYEKNAAAKYLVIVFLI

GCCGCCACCATGGGAATGCAGGTGCAGATCCAGAGCCTGTTTCTGCTCCTCCTGTGGGTGCCCGGATCCAGAGGATTTA
TGAAAGCTGTCTGTGTAGAGGTGAATGTAACATGCGGTAACGGAATTCAGGTGAGAAAGGGACTCATCATGGTACTCAG
CTTTCTGAACGCAGCCCTGTTCCACATCTTTGACGGAGACAATGAAATCAAAGCCGCATTGCTCGCCTGTGCCGGACTA
GCCTATAAAAAGAGTTTCCTTTTCGTTGAAGCACTATTTAACGCAGCACCCAGTGACGGTAAATGCAACCTATATAAAG
CAGCTCAGACTAATTTTCAAAAGCCTGTTAAGAAATCTGCCCTCAGAGAATGAAAGGGGTTACAAAGCCGCCGGCGTGTC
CGAGAATATTTTCCTGAAGAACGCCGCTGCTTATTTTATACTCGTGAATCTACTCATAAAGGCAGCCGCAATCCTTTCA
GTGTCCAGCTTTCTGTTTGTTAACACACCATATGCGGGCGAGCCGGCTCCTTTCAAGGCTGCAGCAAAATACAAGCTTG
CCACATCAGTATTGAAAGCAGCTGTGTTTTTGATATTCTTTGATCTTTTTTTAAACTACTACATACCTCATCAGTCTAG
TCTTAAAAGCAGCCGGGCTACTGGGGAACGTCTCTACTGTGGGGGCCGTCTTACTTGGAGGAGTTGGCCTCGTGTTGAAC
CTCGCGTGCGCAGGTCTGGCCTACAAAAAAGCGAAATTCATCAAGTCTCTGTTCCACATTTTTAAAGCCGCATTCTATT
TCATACTAGTGAACCTTCTCAAAGCTTTCCTGATCTTCTTCGATCTATTCCTCGTAAAAGCGCTATTCTTCATTATCTT
TAACAAAAATTATTACGGCAAGCAAGAAAATTGGTACTCACTCAAGTTTGTAGAAGCTCTGTTCCAGGAATACAACGCC
GCTGCTAAATTCGTTGCAGCTTGGACCCTGAAAGCAGCTGCAAAGATCCTATCGGTCTTCTTTCTCGCTAATGCCGTAT
TAGCAGGACTTCTAGGCAACGTGAACTTTCAAGACGAAGAGAATATAGGCATCTACAAAGCCGCAGCACTGTACATTTC
ATTCTACTTCATCAAGGCCTTCATACTGGTCAACCTTCTGATATTTCATAATGCAGCACTGCCATATGGGAGAACCAAC
TTGAAAGCGGCCCACGTGTTGAGCCACAACTCCTACGAGAAGAACGCCGCCGCGAAATATCTCGTCATTGTCTTCCTGA
TTTGA

TB.1
MQVQIQSLFLLLLWVPGSRGRMSRVTTFTVKALVLLMLPVVNLMIGTAAAVVKALVLLMLPVGAGLMTAVYLVGAAAMA
LLRLPVKRMFAANLGVNSLYFGGICVGRLPLVLPAVNAAAAKFVAAWTLKAAAKAAARLMIGTAAAGFVVALIPLVNAM
TYAAPLFVGAAAAMALLRLPLV

ATGCAGGTGCAGATCCAGAGCCTGTTTCTGCTCCTCCTGTGGGTGCCCGGATCCAGAGGAAGGATGAGCAGAGTGACCA
CATTCACTGTCAAGGCCCTGGTGCTCCTGATGCTCCCCGTCGTGAACCTGATGATCGGCACCGCTGCAGCCGTCGTGAA
AGCTCTCGTCCTGCTCATGCTCCCTGTGGGAGCAGGGCTGATGACAGCCGTGTACCTGGTCGGCGCTGCAGCCATGGCC
CTCCTGCGGCTGCCAGTGAAGCGCATGTTTGCTGCAAATCTGGGAGTCAACTCCCTCTATTTCGGGGGCATTTGCGTGG
GAAGGCTGCCCCTCGTGCTGCCTGCTGTGAATGCAGCCGCTGCCAAATTTGTCGCCGCTTGGACTCTGAAGGCAGCCGC
TAAGGCCGCTGCAAGACTGATGATCGGGACCGCCGCTGCCGGCTTCGTGGTCGCCCTGATTCCCCTGGTGAACGCCATG
ACATACGCAGCTCCTCTGTTTGTGGGAGCCGCTGCAGCCATGGCTCTCCTGCGGCTGCCACTGGTGTGA

FIG.18J

BCL A2 #90
MQVQIQSLFLLLLWVPGSRGIMIGHLVGVNRLLQETELVNAKVAEIVHFLNAKVFGSLAFVNAYLSGANLNVG
AAYLQLVFGIEVNAAAKFVAAWTLKAAAKAAAVVLGVVFGINSMPPPGTRVNAAAATVGIMIGVNAKLCPVQL
WV

ATGCAGGTGCAGATCCAGAGCCTGTTTCTGCTCCTCCTGTGGGTGCCCGGGTCCAGAGGAATTATGATCGGCC
ATCTGGTGGGCGTCAACAGACTGCTGCAGGAAACCGAGCTGGTGAATGCCAAGGTGGCCGAAATTGTGCACTT
TCTCAACGCAAAGGTGTTTGGTTCCCTGGCTTTTGTCAATGCCTATCTGAGCGGCGCTAACCTCAACGTCGGA
GCCGCCTACCTCCAGCTGGTCTTCGGCATCGAGGTCAACGCTGCTGCAAAATTCGTGGCAGCTTGGACCCTCA
AGGCTGCAGCAAAGGCTGCCGCCGTCGTGCTCGGAGTGGTGTTCGGGATCAACTCTATGCCACCTCCCGGGAC
TAGGGTCAATGCTGCCGCCGCAACAGTGGGAATCATGATTGGGGTGAATGCCAAACTGTGCCCAGTGCAACTG
TGGGTGTGA

BCL A2 #88
MQVQIQSLFLLLLWVPGSRGVVLGVVFGINAAAAKFVAAWTLKAAAKVAEIVHFLNAYLSGANLNVGAAYLQL
VFGIEVNIMIGHLVGVNRLLQETELVNAKVFGSLAFVNAKLCPVQLWVNAAAATVGIMIGVNSMPPPGTRV

ATGCAGGTGCAGATCCAGAGCCTGTTTCTGCTCCTCCTGTGGGTGCCCGGGTCCAGAGGAGTCGTGCTGGGAG
TCGTCTTCGGCATTAATGCCGCCGCTGCAAAGTTCGTGGCTGCCTGGACCCTGAAGGCCGCAGCTAAAGTGGC
AGAGATCGTGCACTTTCTGAACGCCTACCTGAGCGGAGCAAATCTGAACGTCGGCGCTGCCTATCTGCAGCTC
GTGTTTGGAATTGAAGTGAACATCATGATTGGACATCTGGTGGGCGTGAACAGGCTGCTCCAGGAAACTGAGC
TGGTCAACGCTAAAGTGTTCGGGTCTCTCGCCTTTGTGAACGCTAAGCTCTGCCCCGTCCAACTCTGGGTCAA
TGCCGCAGCCGCTACAGTGGGGATCATGATCGGCGTGAACTCCATGCCTCCACCAGGGACCAGAGTGTGA

BCL A2 #63
MQVQIQSLFLLLLWVPGSRGKLCPVQLWVNAAAATVGIMIGVNIMIGHLVGVNRLLQETELVNAKVAEIVHFL
NAKVFGSLAFVNAYLSGANLNVGAAYLQLVFGIEVNAAAKFVAAWTLKAAAKAAAVVLGVVFGINSMPPPGTR
V

ATGCAGGTGCAGATCCAGAGCCTGTTTCTGCTCCTCCTGTGGGTGCCCGGGTCCAGAGGAAAGCTCTGCCCCG
TGCAACTGTGGGTCAACGCCGCCGCCGCAACCGTCGGCATTATGATCGGGGTGAACATCATGATCGGACACCT
GGTCGGCGTGAACAGGCTGCTGCAGGAGACAGAACTGGTCAATGCCAAGGTGGCTGAAATTGTCCATTTCCTG
AATGCCAAAGTGTTCGGCTCTCTCGCTTTCGTGAACGCTTATCTGAGCGGAGCTAACCTCAACGTGGGGGCCG
CATACCTCCAGCTCGTCTTTGGGATTGAGGTGAATGCCGCAGCTAAATTTGTCGCTGCCTGGACCCTGAAGGC
AGCAGCCAAGGCTGCCGCAGTGGTGCTGGGAGTGGTGTTTGGAATCAATTCCATGCCTCCACCAGGCACTAGA
GTGTGAGGATCC

FIG.18K

Prostate 1

LTFFWLDRSVKAAAVLVHPQWVLTVKAAALLQERGVAYIKAALLLSIALSVNPLVCNGVLQGVKAAIMYSAHD
TTVKAAAFLTPKKLQCVNAMMNDQLMFLNAGLPSIPVHPVKAAALGTTCYVGAAILLWQPIPVNFLRPRSLQC
VKAFLTLSVTWIGVNALLYSLVHNLGAATLMSAMTNL

ATGCAGGTGCAGATCCAGAGCCTGTTTCTGCTCCTCCTGTGGGTGCCCGGGTCCAGAGGATTGACATTTTTT
GGCTGGATAGATCGGTTAAGGCTGCAGCCGTGCTTGTTCATCCCCAGTGGGTCTTGACCGTAAAGGCTGCCG
CTGCTACAAGAAAGAGGGGTCGCATACATCAAAGCTGCTCTCCTCTTGAGTATTGCGCTAAGTGTAAACCCG
CTAGTTTGTAATGGGGTGTTACAAGGTGTGAAAGCGGCGATTATGTACAGTGCCCACGACACTACCGTAAAAG
CAGCCGCTTTCCTGACCCCAAAAAAACTCCAATGCGTGAACGCAATGATGAATGATCAGCTGATGTTTTTAAA
CGCTGGCTTACCTTCTATACCGGTTCATCCAGTCAAGGCCGCGGCATTGGGTACGACGTGTTATGTTGGAGCA
GCGATACTTCTTTGGCAGCCCATACCAGTAAATTTTTTAAGACCTAGATCCTTACAATGCGTCAAAGCATTCC
TTACACTCTCAGTAACTTGGATCGGAGTCAATGCTCTGCTATATAGCCTCGTACACAACTTGGGCGCGGCCAC
ACTTATGAGTGCAATGACGAATTTAGCTAAGTTCGTGGCGGCCTGGACTCTAAAGGCCGCAGCA

HIV-1043

MEKVYLAWVPAHKGIGGGPGPGQKQITKIQNFRVYYRGPGPGWEFVNTPPLVKLWYQGPGPGYRKILRQRKID
RLIDGPGPGQHLLQLTVWGIKQLQGPGPGGEIYKRWIILGLNKIVRMYGPGPGQGQMVHQAISPRTLNGPGPG
IKQFINMWQEVGKAMYGPGPGWAGIKQEFGIPYNPQGPGPGKTAVQMAVFIHNFKRGPGPGSPAIFQSSMTKI
LEPGPGPGEVNIVTDSQYALGIIGPGPGHSNWRAMASDFNLPPGPGPGAETFYVDGAANRETKGPGPGGAVVI
QDNSDIKVVPGPGPGFRKYTAFTIPSINNE

ATGGAGAAGGTGTACCTGGCCTGGGTTCCAGCCCACAAAGGCATCGGGGGAGGGCCCGGACCTGGGCAGAAAC
AGATCACCAAGATCCAGAACTTCCGGGTATACTACCGGGGACCTGGTCCAGGTTGGGAGTTTGTGAACACACC
ACCCTTAGTAAAGCTCTGGTACCAGGGCCCCGGTCCCGGATACCGTAAAATCCTGAGGCAAAGAAAGATAGAT
CGCCTCATTGATGGCCCGGGCCCAGGCCAGCACCTTCTGCAGCTTACAGTGTGGGGAATTAAACAGCTGCAGG
GGCCGGGCCCCGGGGGGGAAATTTATAAAAGGTGGATCATTCTGGGTCTGAACAAGATCGTCCGCATGTATGG
CCCTGGACCCGGACAGGGGCAGATGGTCCACCAAGCAATCAGCCCTCGAACCTTGAATGGACCGGGCCCAGGA
ATCAAGCAATTCATTAACATGTGGCAAGAAGTTGGTAAGGCTATGTACGGTCCCGGCCCTGGATGGGCAGGGA
TAAAACAGGAGTTTGGAATCCCTTACAATCCCCAGGGTCCTGGGCCAGGTAAAACGGCAGTGCAGATGGCCGT
GTTCATTCATAATTTTAAGCGGGGCCCTGGACCTGGCAGCCCAGCTATATTTCAAAGTTCGATGACCAAAATC
TTGGAGCCCGGCCCAGGGCCGGGCGAAGTGAACATTGTCACAGATTCTCAGTATGCCCTCGGCATCATAGGGC
CCGGACCAGGGCATTCCAATTGGCGCGCCATGGCGTCTGACTTTAATCTACCTCCTGGGCCAGGCCCTGGCGC
GGAAACTTTCTATGTGGACGGCGCTGCAAACAGGGAGACTAAGGGACCCGGACCCGGCGGCGCTGTAGTCATT
CAGGACAACTCAGACATCAAGGTGGTTCCCGGTCCAGGCCCCGGGTTCAGAAAGTATACCGCCTTCACTATTC
CGTCCATCAACAATGAGTGA

FIG.18L

HIV-1043 PADRE
MEKVYLAWVPAHKGIGGGPGPGQKQITKIQNFRVYYRGPGPGWEFVNTPPLVKLWYQGPGPGYRKILRQRKID
RLIDGPGPGQHLLQLTVWGIKQLQGPGPGGEIYKRWIILGLNKIVRMYGPGPGQGQMVHQAISPRTLNGPGPG
IKQFINMWQEVGKAMYGPGPGWAGIKQEFGIPYNPQGPGPGKTAVQMAVFIHNFKRGPGPGSPAIFQSSMTKI
LEPGPGPGEVNIVTDSQYALGIIGPGPGHSNWRAMASDFNLPPGPGPGAETFYVDGAANRETKGPGPGGAVVI
QDNSDIKVVPGPGPGFRKYTAFTIPSINNEGPGPGAKFVAAWTLKAAA

ATGGAGAAGGTGTACCTGGCCTGGGTTCCAGCCCACAAAGGCATCGGGGGAGGGCCCGGACCTGGGCAGAAAC
AGATCACCAAGATCCAGAACTTCCGGGTATACTACCGGGGACCTGGTCCAGGTTGGGAGTTTGTGAACACACC
ACCCTTAGTAAAGCTCTGGTACCAGGGCCCCGGTCCCGGATACCGTAAAATCCTGAGGCAAAGAAAGATAGAT
CGCCTCATTGATGGCCCGGGCCCAGGCCAGCACCTTCTGCAGCTTACAGTGTGGGGAATTAAACAGCTGCAGG
GGCCGGGCCCCGGGGGGGAAATTTATAAAAGGTGGATCATTCTGGGTCTGAACAAGATCGTCCGCATGTATGG
CCCTGGACCCGGACAGGGGCAGATGGTCCACCAAGCAATCAGCCCTCGAACCTTGAATGGACCGGGCCCAGGA
ATCAAGCAATTCATTAACATGTGGCAAGAAGTTGGTAAGGCTATGTACGGTCCCGGCCCTGGATGGGCAGGGA
TAAAACAGGAGTTTGGAATCCCTTACAATCCCCAGGGTCCTGGGCCAGGTAAAACGGCAGTGCAGATGGCCGT
GTTCATTCATAATTTTAAGCGGGGCCCTGGACCTGGCAGCCCAGCTATATTTCAAAGTTCGATGACCAAAATC
TTGGAGCCCGGCCCAGGGCCGGGCGAAGTGAACATTGTCACAGATTCTCAGTATGCCCTCGGCATCATAGGGC
CCGGACCAGGGCATTCCAATTGGCGCGCCATGGCGTCTGACTTTAATCTACCTCCTGGGCCAGGCCCTGGCGC
GGAAACTTTCTATGTGGACGGCGCTGCAAACAGGGAGACTAAGGGACCCGGACCCGGCGGCGCTGTAGTCATT
CAGGACAACTCAGACATCAAGGTGGTTCCCGGTCCAGGCCCCGGGTTCAGAAAGTATACCGCCTTCACTATTC
CGTCCATCAACAATGAGGGCCCCGGCCCAGGTGCCAAGTTCGTGGCTGCCTGGACCCTGAAGGCTGCCGCTTG
A

HIV 75mer
EKVYLAWVPAHKGIGGPGPGQGQMVHQAISPRTLNGPGPGSPAIFQSSMTKILEPGPGPGFRKYTAFTIPSIN
NE GAGAAGGTGTACCTGGCCTGGGTGCCTGCCCACAAGGGAATCGGAGGACCTGGCCCTGGACAGGGACAGATGG
TGCACCAGGCCATCAGCCCTAGGACCCTGAACGGACCTGGACCTGGAAGCCCTGCCATCTTCCAGAGCAGCAT
GACCAAGATCCTGGAGCCCGGACCTGGACCTGGATTCAGGAAGTACACCGCCTTCACCATCCCCAGCATCAAC
AACGAGTGA

FIG.18M

PfHTL
MQVQIQSLFLLLLWVPGSRGRHNWVNHAVPLAMKLIGPGPGKCNLYADSAWENVKNGPGPGKSKYKLATSVL
AGLLGPGPGQTNFKSLLRNLGVSEGPGPGSSVFNVVNSSIGLIMGPGPGVKNVIGPFMKAVCVEGPGPGMNY
YGKQENWYSLKKGPGPGGLAYKFVVPGAATPYGPGPGPDSIQDSLKESRKLNGPGPGLLIFHINGKIIKNSE
GPGPGAGLLGNVSTVLLGGVGPGPGKYKIAGGIAGGLALLGPGPGMRKLAILSVSSFLFV

ATGGGAATGCAGGTGCAGATCCAGAGCCTGTTTCTGCTCCTCCTGTGGGTGCCCGGATCCAGAGGAAGGCAC
AACTGGGTGAATCATGCTGTGCCCCTGGCTATGAAGCTGATCGGCCCTGGACCAGGGAAATGCAACCTCTAC
GCAGACAGCGCCTGGGAGAACGTCAAGAATGGCCCCGGACCTGGGAAATCCAAGTATAAGCTCGCTACCTCT
GTGCTGGCAGGCCTGCTCGGACCAGGCCCCGGACAGACAAATTTCAAAAGCCTGCTCAGAAACCTGGGAGTG
TCCGAGGGGCCTGGCCCAGGATCTAGCGTCTTTAATGTGGTCAACTCCTCTATTGGGCTCATCATGGGACCC
GGACCTGGGGTGAAAAATGTCATTGGCCCATTCATGAAGGCCGTGTGTGTCGAAGGACCCGGGCCTGGCATG
AACTACTATGGAAAGCAAGAAAATTGGTACAGCCTGAAGAAAGGCCCTGGGCCAGGCGGACTGGCTTACAAG
TTTGTGGTCCCAGGGGCAGCCACTCCCTATGGGCCTGGGCCAGGCCCCGATTCCATCCAGGACTCTCTCAAA
GAGAGCCGGAAACTGAACGGACCCGGGCCTGGACTGCTCATTTTCCACATCAATGGCAAAATTATCAAGAAC
AGCGAGGGACCTGGGCCAGGCGCCGGACTGCTGGGGAACGTGTCCACCGTCCTGCTCGGCGGAGTGGGGCCC
GGCCCTGGGAAGTACAAGATCGCTGGAGGGATCGCAGGCGGACTGGCCCTCCTGGGCCCAGGACCAGGGATG
CGCAAACTGGCTATTCTCTCTGTCTCCAGCTTTCTGTTTGTGTGA

FIG.18N

| Protein | Sequence | Restriction |
|---|---|---|
| HIV gag 386 | VLAEAMSQV | HLA-A2 |
| HIV gag 271 | MTNNPPIPV | HLA-A2 |
| HIV pol 774 | MASDFNLPPV | HLA-A2 |
| HIV pol 448 | KLVGKLNWA | HLA-A2 |
| HIV pol 163 | LVGPTPVNI | HLA-A2 |
| HIV pol 498 | ILKEPVHGV | HLA-A2 |
| HIV pol 879 | KAACWWAGI | HLA-A2 |
| HIV pol 132 | KMIGGIGGFI | HLA-A2 |
| HIV pol 772 | RAMASDFNL | HLA-A2 |
| HIV pol 183 | TLNFPISPI | HLA-A2 |
| HIV env 134 | KLTPLCVTL | HLA-A2 |
| HIV env 651 | LLQLTVWGI | HLA-A2 |
| HIV env 163 | SLLNATDIAV | HLA-A2 |
| HIV nef 221 | LTFGWCFKL | HLA-A2 |
| HIV vpr 59 | AIIRILQQL | HLA-A2 |
| HIV vpr 62 | RILQQLLFI | HLA-A2 |
| HIV pol 929 | QMAVFIHNFK | HLA-A3 |
| HIV pol 722 | KVYLAWVPAHK | HLA-A3 |
| HIV pol 971 | KIQNFRVYYR | HLA-A3 |
| HIV pol 347 | AIFQSSMTK | HLA-A3 |
| HIV pol 98 | VTIKIGGQLK | HLA-A3 |
| HIV env 61 | TTLFCASDAK | HLA-A3 |
| HIV env 47 | VTVYYGVPVWK | HLA-A3 |
| HIV nef 100 | QVPLRPMTYK | HLA-A3 |
| HIV vif 7 | VMIVWQVDR | HLA-A3 |
| HIV gag 162 | QMVHQAISPR | HLA-A3 |
| HIV gag 545 | YPLASLRSLF | HLA-B7 |
| HIV gag 237 | HPVHAGPIA | HLA-B7 |
| HIV pol 186 | FPISPIETV | HLA-B7 |
| HIV pol 893 | IPYNPQSQGVV | HLA-B7 |
| HIV env 259 | IPIHYCAPA | HLA-B7 |
| HIV env 250 | CPKVSFEPI | HLA-B7 |
| HIV nef 94 | FPVRPQVPL | HLA-B7 |
| HIV rev 75 | VPLQLPPL | HLA-B7 |
| HIV pol 684 | EVNIVTDSQY | HLA-A1 |
| HIV gag 317 | FRDYVDRFY | HLA-A1 |
| HIV pol 368 | VIYQYMDDLY | HLA-A1 |
| HIV pol 295 | VTVLDVGDAY | HLA-A1 |
| HIV pol 533 | IYQEPFKNL | HLA-A24 |
| HIV pol 244 | PYNTPVFAI | HLA-A24 |
| HIV pol 530 | TYQIYQEPF | HLA-A24 |
| HIV pol 597 | YWQATWIPEW | HLA-A24 |
| HIV env 681 | IWGCSGKLI | HLA-A24 |
| HIV env 671 | RYLKDQQLL | HLA-A24 |

FIG. 19A

| Protein | Sequence | Restriction |
|---|---|---|
| HIV env 55 | VWKEATTTLF | HLA-A24 |
| HIV vpr 46 | IYETYGDTW | HLA-A24 |
| HIV vpr 14 | PYNEWTLEL | HLA-A24 |
| HIV gag 298 | KRWIILGLNKIVRMY | HLA-DR |
| HIV pol 596 | WEFVNTPPLVKLWYQ | HLA-DR |
| HIV pol 956 | QKQITKIQNFRVYYR | HLA-DR |
| HIV pol 712 | KVYLAWVPAHKGIGG | HLA-DR |
| HIV gag 294 | GEIYKRWIILGLNKI | HLA-DR |
| HIV pol 711 | EKVYLAWVPAHKGIG | HLA-DR |
| HIV env 729 | QHLLQLTVWGIKQLQ | HLA-DR |
| HIV gag 171 | QGQMVHQAISPRTLN | HLA-DR |
| HIV pol 335 | SPAIFQSSMTKILEP | HLA-DR |
| HIV env 566 | IKQFINMWQEVGKAMY | HLA-DR |
| HIV pol 303 | FRKYTAFTIPSINNE | HLA-DR |
| HIV pol 758 | HSNWRAMASDFNLPP | HLA-DR |
| HIV pol 915 | KTAVQMAVFIHNFKR | HLA-DR |
| HIV vpu 31 | YRKILRQRKIDRLID | HLA-DR3 |
| HIV pol 874 | WAGIKQEFGIPYNPQ | HLA-DR3 |
| HIV pol 674 | EVNIVTDSQYALGII | HLA-DR3 |
| HIV pol 619 | AETFYVDGAANRETK | HLA-DR3 |
| HIV pol 989 | GAVVIQDNSDIKVVP | HLA-DR3 |
| HCV NS4 1812 | LLFNILGGWV | HLA-A2 |
| HCV NS1/E2 728 | FLLLADARV | HLA-A2 |
| HCV NS4 1590 | YLVAYQATV | HLA-A2 |
| HCV NS5 2611 | RLIVFPDLGV | HLA-A2 |
| HCV CORE 132 | DLMGYIPLV | HLA-A2 |
| HCV NS4 1920 | WMNRLIAFA | HLA-A2 |
| HCV NS4 1666 | VLVGGVLAA | HLA-A2 |
| HCV NS4 1769 | HMWNFISGI | HLA-A2 |
| HCV NS4 1851 | ILAGYGAGV | HLA-A2 |
| HCV CORE 35 | YLLPRRGPRL | HLA-A2 |
| HCV NS1/E2 726 | LLFLLLADA | HLA-A2 |
| HCV LORF 1131 | YLVTRHADV | HLA-A2 |
| HCV CORE 51 | KTSERSQPR | HLA-A3 |
| HCV CORE 43 | RLGVRATRK | HLA-A3 |
| HCV ENV1 290 | QLFTFSPRR | HLA-A3 |
| HCV NS1/E2 632 | RMYVGGVEHR | HLA-A3 |
| HCV NS3 1396 | LIFCHSKKK | HLA-A3 |
| HCV NS4 1863 | GVAGALVAFK | HLA-A3 |
| HCV NS4 1864 | VAGALVAFK | HLA-A3 |
| HCV NS3 1262 | LGFGAYMSK | HLA-A3 |
| HCV Core 169 | LPGCSFSIF | HLA-B7 |
| HCV NS5 2922 | LSAFSLHSY | HLA-A1 |
| HCV NS3 1128 | CTCGSSDLY | HLA-A1 |
| HCV NS5 2180 | LTDPSHITA | HLA-A1 |

FIG. 19B

| Protein | Sequence | Restriction |
|---|---|---|
| HCV Core 126 | LTCGFADLMGY | HLA-A1 |
| HCV NS3 1305 | LADGGCSGGAY | HLA-A1 |
| HCV NS4 1765 | FWAKHMWNF | HLA-A24 |
| HCV NS5 2875 | RMILMTHFF | HLA-A24 |
| HCV NS5 2639 | VMGSSYGF | HLA-A24 |
| HCV NS4 1765 | FWAKHMWNFI | HLA-A24 |
| P. falciparum SSP2-230 | FMKAVCVEV | HLA-A2 |
| P. falciparum EXP1-83 | GLLGVVSTV | HLA-A2 |
| P. falciparum CSP-7 | ILSVSSFLFV | HLA-A2 |
| P. falciparum LSA1-94 | QTNFKSLLR | HLA-A3 |
| P. falciparum LSA1-105 | GVSENIFLK | HLA-A3 |
| P. falciparum SSP2-522 | LLACAGLAYK | HLA-A3 |
| P. falciparum SSP2-539 | TPYAGEPAPF | HLA-B7 |
| P. falciparum LSA1-1663 | LPSENERGY | HLA-A1 |
| P. falciparum EXP1-73 | KYKLATSVL | HLA-A24 |
| P. falciparum CSP-12 | SFLFVEALF | HLA-A24 |
| P. falciparum LSA1-10 | YFILVNLLI | HLA-A24 |
| P. falciparum SSP2-14 | FLIFFDLFLV | HLA-A2 |
| P. falciparum EXP1-80 | VLAGLLGVV | HLA-A2 |
| P. falciparum EXP1-91 | VLLGGVGLVL | HLA-A2 |
| P. falciparum SSP2-523 | LACAGLAYK | HLA-A3 |
| P. falciparum EXP1-10 | ALFFIIFNK | HLA-A3 |
| P. falciparum LSA1-11 | FILVNLLIFH | HLA-A3 |
| P. falciparum SSP2-126 | LPYGRTNL | HLA-B7 |
| P. falciparum CSP-15 | FVEALFQEY | HLA-A1 |
| P. falciparum LSA1-1794 | FQDEENIGIY | HLA-A1 |
| P. falciparum LSA1-9 | FYFILVNLL | HLA-A24 |
| P. falciparum SSP2-8 | KYLVIVFLI | HLA-A24 |
| P. falciparum CSP-394 | GLIMVLSFL | HLA-A2 |
| P. falciparum EXP1-2 | KILSVFFLA | HLA-A2 |
| P. falciparum CSP-344 | VTCGNGIQVR | HLA-A3 |
| P. falciparum LSA1-59 | HVLSHNSYEK | HLA-A3 |
| P. falciparum SSP2-207 | PSDGKCNLY | HLA-A1 |
| P. falciparum LSA1-1671 | YYIPHQSSL | HLA-A24 |
| P. falciparum LSA1-1876 | KFIKSLFHIF | HLA-A24 |
| P. falciparum SSP2-13 | VFLIFFDLFL | HLA-A24 |
| P. falciparum LSA1-1881 | LFHIFDGDNEI | HLA-A24 |
| P. falciparum CSP-55 | YYGKQENWYSL | HLA-A24 |
| P. falciparum LSA1-5 | LYISFYFI | HLA-A24 |
| P. falciparum CSP-2 | MRKLAILSVSSFLFV | HLA-DR |
| P. falciparum CSP-53 | MNYYGKQENWYSLKK | HLA-DR |
| P. falciparum CSP-375 | SSVFNVVNSSIGLIM | HLA-DR |
| P. falciparum SSP2-61 | RHNWVNHAVPLAMKLI | HLA-DR |
| P. falciparum SSP2-165 | PDSIQDSLKESRKLN | HLA-DR3 |
| P. falciparum SSP2-211 | KCNLYADSAWENVKN | HLA-DR3 |

FIG. 19C

| Protein | Sequence | Restriction |
|---|---|---|
| P. falciparum SSP2-223 | VKNVIGPFMKAVCVE | HLA-DR |
| P. falciparum SSP2-509 | KYKIAGGIAGGLALL | HLA-DR |
| P. falciparum SSP2-527 | GLAYKFVVPGAATPY | HLA-DR |
| P. falciparum EXP1-71 | KSKYKLATSVLAGLL | HLA-DR |
| P. falciparum EXP1-82 | AGLLGNVSTVLLGGV | HLA-DR |
| P. falciparum LSA1-16 | LLIFHINGKIIKNSE | HLA-DR |
| P. falciparum LSA1-94 | QTNFKSLLRNLGVSE | HLA-DR |
| HBV core 18 | FLPSDFFPSV | HLA-A2 |
| HBV env 183 | FLLTRILTI | HLA-A2 |
| HBV env 335 | WLSLLVPFV | HLA-A2 |
| HBV pol 455 | GLSRYVARL | HLA-A2 |
| HBV pol 538 | YMDDVVLGV | HLA-A2/A1 |
| HBV pol 773 | ILRGTSFVYV | HLA-A2 |
| HBV pol 562 | FLLSLGIHL | HLA-A2 |
| HBV pol 642 | ALMPLYACI | HLA-A2 |
| HBV env 338 | GLSPTVWLSV | HLA-A2 |
| HBV core 141 | STLPETTVVRR | HLA-A3 |
| HBV pol 149 | HTLWKAGILYK | HLA-A3/A1 |
| HBV pol 150 | TLWKAGILYK | HLA-A3 |
| HBV pol 388 | LVVDFSQFSR | HLA-A3 |
| HBV pol 47 | NVSIPWTHK | HLA-A3 |
| HBV pol 531 | SAICSVVRR | HLA-A3 |
| HBV pol 629 | KVGNFTGLY | HLA-A3/A1 |
| HBV pol 665 | QAFTFSPTYK | HLA-A3 |
| HBV core 19 | LPSDFFPSV | HLA-B7 |
| HBV env 313 | IPIPSSWAF | HLA-B7 |
| HBV pol 354 | TPARVTGGVF | HLA-B7 |
| TB | RMSRVTTFTV | HLA-A2 |
| TB | ALVLLMLPVV | HLA-A2 |
| TB | LMIGTAAAVV | HLA-A2 |
| TB | ALVLLMLPV | HLA-A2 |
| TB | GLMTAVYLV | HLA-A2 |
| TB | MALLRLPV | HLA-A2 |
| TB | RMFAANLGV | HLA-A2 |
| TB | SLYFGGICV | HLA-A2 |
| TB | RLPLVLPAV | HLA-A2 |
| TB | RLMIGTAAA | HLA-A2 |
| TB | FVVALIPLV | HLA-A2 |
| TB | MTYAAPLFV | HLA-A2 |
| TB | AMALLRLPLV | HLA-A2 |
| p53 139 | KLCPVQLWV | HLA-A2 |
| CEA 687 | ATVGIMIGV | HLA-A2 |
| CEA 691 | IMIGHLVGV | HLA-A2 |
| Her2/neu 689 | RLLQETELV | HLA-A2 |
| MAGE3 112 | KVAEIVHFL | HLA-A2 |

FIG.19D

| Protein | Sequence | Restriction |
|---|---|---|
| Her2/neu 665 | VVLGVVFGI | HLA-A2 |
| p53 149 | SMPPPGTRV | HLA-A2 |
| PAP.21.T2 | LTFFWLDRSV | HLA-A2 |
| PAP.112 | TLMSAMTNL | HLA-A2 |
| PAP.284 | IMYSAHDTTV | HLA-A2 |
| PSM.288.V10 | GLPSIPVHPV | HLA-A2 |
| PSM.441 | LLQERGVAYI | HLA-A2 |
| PSM.469L2 | LLYSLVHNL | HLA-A2 |
| PSM.663 | MMNDQLMFL | HLA-A2 |
| PSA.3.V11 | FLTLSVTWIGV | HLA-A2 |
| PSA.143.V8 | ALGTTCYV | HLA-A2 |
| PSA.161 | FLTPKKLQCV | HLA-A2 |
| HuK2.4.L2 | LLLSIALSV | HLA-A2 |
| HuK2.53.V11 | VLVHPQWVLTV | HLA-A2 |
| HuK2.165 | FLRPRSLQCV | HLA-A2 |
| HuK2.216.V11 | PLVCNGVLQGV | HLA-A2 |

FIG. 19E

| ID# | Epitope | Sequence | Conservation | HLA restriction | Prototype Binding | XRN[1] |
|---|---|---|---|---|---|---|
| 924.07 | core 18 | FLPSDFFPSV | 45 | A2 | 3.5 | 5 |
| 777.03 | env 183 | FLLTRILTI | 80 | A2 | 9.8 | 4 |
| 1013.01 | env 335 | WLSLLVPFV | 100 | A2 | 5.4 | 4 |
| 1168.02 | pol 455 | GLSRYVARL | 55 | A2 | 55.9 | 3 |
| 1090.77 | pol 538 | YMDDVVLGV | 90 | A2/A1 | 6.4 | 5 |
| 927.11 | pol 562 | FLLSLGIHL | 95 | A2 | 7.8 | 3 |
| 927.15 | pol 642 | ALMPLYACI | 95 | A2 | 12.9 | 4 |
| 1083.01 | core 141 | STLPETTVVRR | 95 | A3/A11 | 735/4.5 | 4 |
| 1147.16 | pol 149 | HTLWKAGILYK | 100 | A3/A1 | 15.4/15.6 | 5 |
| 1069.15 | pol 150 | TLWKAGILYK | 100 | A3/A11 | 2.1/33 | 2 |
| 1069.20 | pol 388 | LVVDFSQFSR | 100 | A3/A11 | 6875/17 | 3 |
| 1069.16 | pol 47 | NVSIPWTHK | 100 | A3/A11 | 174/117 | 3 |
| 1090.11 | pol 531 | SAICSVVRR | 95 | A3/A11 | 2189/29 | 3 |
| 1142.05 | pol 629 | KVGNFTGLY | 95 | A3/A1 | 58/365 | 2 |
| 1090.10 | pol 665 | QAFTFSPTYK | 95 | A3/A11 | 249/8 | 3 |
| 988.05 | core 19 | LPSDFFPSV | 45 | B7 | 3026.8 | 4 |
| 1145.04 | env 313 | IPIPSSWAF | 100 | B7 | 42.3 | 4 |
| 1147.04 | pol 354 | TPARVTGGVF | 90 | B7 | 13.2 | 2 |
| 1147.02 | pol 429 | HPAAMPHLL | 100 | B7 | 56.6 | 4 |
| 1039.06 | env 359 | WMMWYWGPSLY | 85 | A1 | 16.3 | 3 |
| 1448.01 | core 419 | DLLDTASALY | 75 | A1 | 2.3 | 3 |
| 1373.88 | core 137 | LTFGRETVLEY | 75 | A1 | 80.0 | 3 |
| 1090.07 | pol 415 | LSLDVSAAFY | 95 | A1 | 6.0 | 3 |
| 20.0271 | pol 392 | SWPKFAVPNL | 95 | A24 | 2.1 | 2 |
| 1373.56 | env 332 | RFSWLSLLVPF | 100 | A24 | 12.0 | 2 |
| 1373.07 | core 117 | EYLVSFGVW | 90 | A24 | 16.0 | 2 |
| 1069.23 | pol 745 | KYTSFPWLL | 85 | A24 | 1.0 | 3 |

[1] XRN = Cross binding, number of HLA types in the superType panel of 5 for which significant binding as detected

FIG.20A

HBV2 EpiGene

| HBV 2A | signal | Pol 149 | PADRE® | Core 18 | Pol 562 | Pol 538 | Pol 455 | Env 183 | Core 141 | Pol 665 | Env 335 | Env 313 | Pol 354 | Pol 629 | Core 19 | Pol 150 | Pol 47 | Pol 388

HBV-2

MGMQVQIQSLFLLLLWVPGSRGHTLWKAGILYKAKFVAAWTLKAAAFLPSDFFPSVNFLLSLGIHLYMDDVVLGVGLS
RYVARLFLLTRILTISTLPETTVVRRQAFTFSPTYKGAAAWLSLLVPFVNIPIPSSWAFKTPARVTGGVFKVGNFTGL
YNLPSDFFPSVKTLWKAGILYKNVSIPWTHKGAALVVDFSQFSRNSAICSVVRRALMPLYACI

ATGGGAATGCAGGTGCAGATCCAGAGCCTGTTTCTGCTCCTCCTGTGGGTGCCCGGGTCCAGAGGACACACCCTGTGG
AAGGCCGGAATCCTGTATAAGGCCAAGTTCGTGGCTGCCTGGACCCTGAAGGCTGCCGCTTTCCTGCCTAGCGATTTC
TTTCCTAGCGTGAACTTCCTGCTGTCCCTGGGAATCCACCTGTATATGGATGACGTGGTGCTGGGAGTGGGACTGTCC
AGGTACGTGGCTAGGCTGTTCCTGCTGACCAGAATCCTGACCATCTCCACCCTGCCAGAGACCACCGTGGTGAGGAGG
CAGGCCTTCACCTTTAGCCCTACCTATAAGGGAGCCGCTGCCTGGCTGAGCCTGCTGGTGCCCTTTGTGAATATCCCT
ATCCCTAGCTCCTGGGCTTTTCAAGACCCCAGCCAGGGTGACCGGAGGAGTGTTTAAGGTGGGAAACTTCACCGGCCTG
TATAACCTGCCCAGCGATTTCTTTCCTAGCGTGAAGACCCTGTGGAAGGCCGGAATCCTGTACAAGAATGTGTCCATC
CCTTGGACCCACAAGGGAGCCGCTCTGGTGGTGGACTTTTCCCAGTTCAGCAGAAATTCCGCTATCTGCTCCGTGGTG
AGGAGAGCTCTGATGCCACTGTATGCCTGTATCTGA

FIG. 20D

HBV-2A

MGMQVQIQSLFLLLLWVPGSRGHTLWKAGILYKAKFVAAWTLKAAAFLPSDFFPSVNFLLSLGIHLYMDDVVLGVGLS
RYVARLFLLTRILTISTLPETTVVRRQAFTFSPTYKGAAAWLSLLVPFVNIPIPSSWAFKTPARVTGGVFKVGNFTGL
YNLPSDFFPSVKTLWKAGILYKNVSIPWTHKGAALVVDFSQFSRNSAICSVVRRKAWMMWYWGPSLYKKYTSFPWLLN
AHPAAMPHLLKAAADLLDTASALYNAAARFSWLSLLVPFNAASWPKFAVPNLKLTFGRETVLEYKALSLDVSAAFYGA
AEYLVSFGVWGAALMPLYACI

ATGGGAATGCAGGTGCAGATCCAGAGCCTGTTTCTGCTCCTCCTGTGGGTGCCCGGGTCCAGAGGACACACCCTGTGG
AAGGCCGGAATCCTGTATAAGGCCAAGTTCGTGGCTGCCTGGACCCTGAAGGCTGCCGCTTTCCTGCCTAGCGATTTC
TTTCCTAGCGTGAACTTCCTGCTGTCCCTGGGAATCCACCTGTATATGGATGACGTGGTGCTGGGAGTGGGACTGTCC
AGGTACGTGGCTAGGCTGTTCCTGCTGACCAGAATCCTGACCATCTCCACCCTGCCAGAGACCACCGTGGTGAGGAGG
CAGGCCTTCACCTTTAGCCCTACCTATAAGGGAGCCGCTGCCTGGCTGAGCCTGCTGGTGCCCTTTGTGAATATCCCT
ATCCCTAGCTCCTGGGCTTTTCAAGACCCCAGCCAGGGTGACCGGAGGAGTGTTTAAGGTGGGAAACTTCACCGGCCTG
TATAACCTGCCCAGCGATTTCTTTCCTAGCGTGAAGACCCTGTGGAAGGCCGGAATCCTGTACAAGAATGTGTCCATC
CCTTGGACCCACAAGGGAGCCGCTCTGGTGGTGGACTTTTCCCAGTTCAGCAGAAATAGCGCCATCTGTTCGGTCGTG
AGAAGGAAAGCCTGGATGATGTGGTACTGGGGTCCTAGTCTGTATAAGAAGTACACCTCATTCCCATGGCTCTTGAAT
GCCCATCCCGCTGCAATGCCACACCTGCTTAAAGCTGCGGCGGATCTGCTGGACACAGCCTCAGCTTTATATAATGCT
GCAGCAAGATTCTCCTGGTTGTCTCTCTTAGTGCCCTTCAACGCAGCTTCCTGGCCAAAATTTGCCGTTCCGAACCTG
AAGCTCACTTTTGGAAGAGAGACAGTACTTGAATACAAAGCACTAAGCCTTGACGTGTCAGCAGCCTTCTACGGAGCA
GCAGAATATCTAGTATCTTTTGGGGTCTGGGGCGCAGCCCTCATGCCTCTATACGCCTGCATTTGA

FIG. 20E

HBV-2B

MGMQVQIQSLFLLLLWVPGSRGHTLWKAGILYKAKFVAAWTLKAAAFLPSDFFPSVNFLLSLGIHLYMDDVVL
GVGLSRYVARLFLLTRILTISTLPETTVVRRQAFTFSPTYKGAAAWLSLLVPFVNIPIPSSWAFKTPARVTGG
VFKVGNFTGLYNLPSDFFPSVKTLWKAGILYKNVSIPWTHKGAALVVDFSQFSRNSAICSVVRRKEYLVSFGV
WGLSLDVSAAFYNAAAKYTSFPWLLNAHPAAMPHLLKAAADLLDTASALYNSWPKFAVPNLKLTFGRETVLEY
KAAWMMWYWGPSLYKAAARFSWLSLLVPFGAAALMPLYACI

ATGGGAATGCAGGTGCAGATCCAGAGCCTGTTTCTGCTCCTCCTGTGGGTGCCCGGGTCCAGAGGACACACCC
TGTGGAAGGCCGGAATCCTGTATAAGGCCAAGTTCGTGGCTGCCTGGACCCTGAAGGCTGCCGCTTTCCTGCC
TAGCGATTTCTTTCCTAGCGTGAACTTCCTGCTGTCCCTGGGAATCCACCTGTATATGGATGACGTGGTGCTG
GGAGTGGGACTGTCCAGGTACGTGGCTAGGCTGTTCCTGCTGACCAGAATCCTGACCATCTCCACCCTGCCAG
AGACCACCGTGGTGAGGAGGCAGGCCTTCACCTTTAGCCCTACCTATAAGGGAGCCGCTGCCTGGCTGAGCCT
GCTGGTGCCCTTTGTGAATATCCCTATCCCTAGCTCCTGGGCTTTCAAGACCCCAGCCAGGGTGACCGGAGGA
GTGTTTAAGGTGGGAAACTTCACCGGCCTGTATAACCTGCCCAGCGATTTCTTTCCTAGCGTGAAGACCCTGT
GGAAGGCCGGAATCCTGTACAAGAATGTGTCCATCCCTTGGACCCACAAGGGAGCCGCTCTGGTGGTGGACTT
TTCCCAGTTCAGCAGAAATTCAGCAATTTGTTCGGTGGTGAGAAGAAAGGAATATCTTGTTTCATTTGGCGTC
TGGGGGCTGTCACTGGATGTAAGTGCGGCATTTTACAATGCCGCCGCAAAATATACAAGCTTCCCATGGCTCC
TAAACGCACACCCAGCTGCAATGCCGCATCTACTGAAAGCAGCCGCTGACCTCTTAGACACTGCCTCCGCTCT
GTACAACTCTTGGCCCAAGTTTGCCGTGCCTAATCTCAAGTTGACCTTCGGTAGAGAGACAGTCTTAGAATAC
AAAGCGGCCTGGATGATGTGGTACTGGGGACCCTCTCTGTATAAAGCCGCTGCAAGGTTCTCCTGGCTTAGCC
TTCTCGTACCATTCGGAGCAGCTGCCCTAATGCCTTTGTACGCATGCATCTGA

FIG.20F

| ID# | Epitope | Sequence | Conservation | HLA restriction | Prototype Binding | XRN |
|---|---|---|---|---|---|---|
| 924.07 | core 18 | FLPSDFFPSV | 45 | A2 | 3.5 | 5 |
| 777.03 | env 183 | FLLTRILTI | 80 | A2 | 9.8 | 4 |
| 1013.01 | env 335 | WLSLLVPFV | 100 | A2 | 5.4 | 4 |
| 927.11 | pol 562 | FLLSLGIHL | 95 | A2 | 7.8 | 3 |
| 1090.77 | pol 538 | YMDDVVLGV | 90 | A2/A1 | 6.4 | 5 |
| 1083.01 | core 141 | STLPETTVVRR | 95 | A3/A11 | 735/4.5 | 4 |
| 1147.16 | pol 149 | HTLWKAGILYK | 100 | A3/A1 | 15.4/15.6 | 5 |
| 1090.11 | pol 531 | SAICSVVRR | 95 | A3/A11 | 2189/29 | 3 |
| 1090.10 | pol 665 | QAFTFSPTYK | 95 | A3/A11 | 249/8 | 3 |
| 1145.04 | env 313 | IPIPSSWAF | 100 | B7 | 42.3 | 4 |
| 1147.04 | pol 354 | TPARVTGGVF | 90 | B7 | 13.2 | 2 |
| 1147.02 | pol 429 | HPAAMPHLL | 100 | B7 | 56.6 | 4 |
| 1147.05 | pol 530 | FPHCLAFSYM | 95 | B7 | 58.5 | 5 |
| 1039.06 | env 359 | WMMWYWGPSLY | 85 | A1 | 16.3 | 3 |
| 1448.01 | core 419 | DLLDTASALY | 75 | A1 | 2.3 | 3 |
| 1373.56 | env 137 | LTFGRETVLEY | 75 | A1 | 80.0 | 3 |
| 1090.07 | pol 415 | LSLDVSAAFY | 95 | A1 | 6.0 | 3 |
| 20.0271 | pol 392 | SWPKFAVPNL | 95 | A24 | 2.1 | 2 |
| 1373.56 | env 332 | RFSWLSLLVPF | 100 | A24 | 12.0 | 2 |
| 1373.07 | core 117 | EYLVSFGVW | 90 | A24 | 16.0 | 2 |
| 1069.23 | pol 745 | KYTSFPWLL | 85 | A24 | 1.0 | 3 |

FIG.21A

HBV 21A

| signal | Pol 392 | ®PADRE | Core 141 | Pol 429 | Pol 149 | Env 183 | Pol 415 | Pol 745 | Env 332 | Pol 354 | Core 117 | Pol 538 | Core 419 | Pol 530 | Env 359 | Pol 531 | Pol 562 | Env 313 | Env 335 | Core 18 | Core 137 | Pol 665 |
|---|---|---|---|---|---|---|---|---|---|---|---|---|---|---|---|---|---|---|---|---|---|---|
| | A24 | | A3 | B7 | A3 | A2 | A1 | A24 | A24 | B7 | A24 | A2 | A1 | B7 | A1 | A3 | A2 | B7 | A2 | A2 | A1 | A3 |

HBV 21B

| signal | Pol 538 | Core 117 | Core 419 | Pol 149 | Core 18 | Pol 530 | Env 332 | Pol 392 | Pol 665 | Pol 531 | Env 183 | Env 313 | Env 359 | Pol 354 | Pol 562 | Core 137 | Core 141 | Pol 429 | ®PADRE | Pol 415 | Env 335 | Pol 745 |
|---|---|---|---|---|---|---|---|---|---|---|---|---|---|---|---|---|---|---|---|---|---|---|
| | A2 | A24 | A1 | A3 | A2 | B7 | A24 | A24 | A3 | A3 | A2 | B7 | A1 | B7 | A2 | A1 | A3 | B7 | | A1 | A2 | A24 |

FIG.21B

HBV-21A

MGMQVQIQSLFLLLLWVPGSRGSWPKFAVPNLKAAAAKFVAAWTLKAAAKSTLPETTVVRRKHPAAMPHLLKAAAHTL
WKAGILYKKAFLLTRILTIGALSLDVSAAFYNAAAKYTSFPWLLNAAARFSWLSLLVPFNAATPARVTGGVFKAAEYL
VSFGVWGAAAYMDDVVLGVNDLLDTASALYNAAAFPHCLAFSYMKAAAWMMWYWGPSLYKAASAICSVVRRKNFLLSL
GIHLNIPIPSSWAFKAAWLSLLVPFVNAFLPSDFFPSVKLTFGRETVLEYKQAFTFSPTYK

ATGGGAATGCAGGTGCAGATCCAGAGCCTGTTTCTGCTCCTCCTGTGGGTGCCCGGGTCCAGAGGATCTTGGCCTAAA
TTCGCAGTGCCAAACCTTAAAGCCGCGGCTGCTAAGTTCGTAGCTGCCTGGACACTAAAGGCCGCCGCTAAGAGCACA
CTGCCAGAGACCACCGTGGTCCGGCGAAAGCATCCAGCCGCAATGCCCCACTTGCTCAAAGCAGCCGCCCACACTCTT
TGGAAGGCTGGGATATTGTACAAGAAAGCCTTCCTTCTGACCAGGATATTAACTATCGGAGCTCTGTCACTCGACGTT
TCTGCTGCCTTCTACAACGCGGCGGCAAAATACACTAGCTTTCCATGGCTACTCAACGCAGCCGCCAGATTTTCTTGG
CTATCACTACTGGTGCCATTTAATGCAGCAACACCTGCTAGAGTGACTGGCGGCGTCTTTAAAGCAGCCGAGTACTTG
GTGAGCTTTGGCGTCTGGGGTGCAGCGGCATATATGGATGATGTAGTGTTAGGGGTGAACGACCTCCTGGACACAGCC
AGTGCGCTGTACAATGCAGCTGCATTCCCGCATTGCCTAGCCTTCAGTTATATGAAAGCAGCAGCCTGGATGATGTGG
TACTGGGGACCGTCCCTTTATAAAGCAGCTTCAGCAATCTGTTCCGTTGTGAGGAGAAAAAACTTTTTACTCTCCCTC
GGTATTCACCTGAACATTCCCATCCCTTCCTCATGGGCATTCAAAGCCGCTTGGCTGAGTCTACTCGTACCTTTCGTT
AATGCATTTCTGCCCAGCGACTTTTTTCCCCTCGGTAAAACTGACATTCGGACGCGAAACAGTCCTTGAATATAAGCAG
GCCTTCACGTTCTCACCAACCTATAAATGA

FIG.21D

HBV-21B

MGMQVQIQSLFLLLLWVPGSRGYMDDVVLGVNAAAEYLVSFGVWNDLLDTASALYGAAHTLWKAGILYKKAFLPSDFF
PSVKAFPHCLAFSYMKAARFSWLSLLVPFNAASWPKFAVPNLKAAAQAFTFSPTYKNAAASAICSVVRRKAFLLTRIL
TINIPIPSSWAFKAAWMMWYWGPSLYKAAATPARVTGGVFKAANFLLSLGIHLNLTFGRETVLEYKHPAAMPHLLKAA
STLPETTVVRRKWLSLLVPFVNAAAAKFVAAWTLKAAAKLSLDVSAAFYNAAAKYTSFPWLL

ATGGGAATGCAGGTGCAGATCCAGAGCCTGTTTCTGCTCCTCCTGTGGGTGCCCGGGTCCAGAGGATACATGGATGAC
GTTGTGTTAGGCGTTAATGCAGCCGCAGAATATCTCGTGTCATTCGGCGTCTGGAACGACCTGTTGGACACTGCATCT
GCTCTGTACGGTGCAGCCCATACCCTGTGGAAGGCCGGAATCCTCTACAAAAAGGCATTCCTACCTAGCGACTTTTTT
CCTTCAGTGAAAGCCTTCCCCACATTGCCTAGCATTCTCGTATATGAAAGCGGCTAGGTTCTCATGGCTTAGTCTTCTA
GTACCTTTCAATGCCGCCTCCTGGCCCAAATTCGCCGTACCAAATCTAAAAGCGGCCGCGCAGGCCTTTACATTCTCT
CCGACTTATAAAAATGCAGCAGCCTCCGCTATTTGTAGCGTCGTGCGCCGAAAGGCCTTCCTGCTAACCCGGATTTTG
ACGATAAACATCCCCATCCCTTCTAGCTGGGCTTTCAAAGCAGCATGGATGATGTGGTACTGGGGTCCCAGCTTATAC
AAAGCTGCGGCAACCCCAGCAAGAGTGACAGGGGGCGTGTTTAAGGCCGCCAACTTCCTCCTGAGTCTCGGAATACAC
CTGAACTTAACCTTTGGGAGAGAGACAGTACTGGAGTATAAACACCCAGCAGCTATGCCGCACCTACTCAAAGCCGCT
TCAACACTCCCAGAAACAACTGTAGTGAGGAGAAAATGGCTCTCCCTGCTTGTCCCATTTGTCAACGCCGCCGCCGCT
AAGTTTGTGGCCGCTTGGACACTTAAGGCTGCAGCAAAGTTGTCACTTGATGTTAGTGCAGCGTTCTATAACGCAGCT
GCAAAATACACTTCCTTTCCCTGGCTGCTGTGA

FIG.21E

| ID# | Epitope | Sequence | Conservation | HLA restriction | Prototype Binding | XRN |
|---|---|---|---|---|---|---|
| 924.07 | core 18 | FLPSDFFPSV | 45 | A2 | 3.5 | 5 |
| 777.03 | env 183 | FLLTRILTI | 80 | A2 | 9.8 | 4 |
| 1013.01 | env 335 | WLSLLVPFV | 100 | A2 | 5.4 | 4 |
| 1168.02 | pol 455 | GLSRYVARL | 55 | A2 | 55.9 | 3 |
| 1090.77 | pol 538 | YMDDVVLGV | 90 | A2/A1 | 6.4 | 5 |
| 927.11 | pol 562 | FLLSLGIHL | 95 | A2 | 7.8 | 3 |
| 1083.01 | core 141 | STLPETTVVRR | 95 | A3/A11 | 735/4.5 | 4 |
| 1147.16 | pol 149 | HTLWKAGILYK | 100 | A3/A1 | 15.4/15.6 | 5 |
| 1069.20 | pol 388 | LVVDFSQFSR | 100 | A3/A11 | 6875/17 | 3 |
| 1069.16 | pol 47 | NVSIPWTHK | 100 | A3/A11 | 174/117 | 3 |
| 1090.11 | pol 531 | SAICSVVRR | 95 | A3/A11 | 2189/29 | 3 |
| 1090.10 | pol 665 | QAFTFSPTYK | 95 | A3/A11 | 249/8 | 3 |
| 988.05 | core 19 | LPSDFFPSV | 45 | B7 | 3026.8 | 4 |
| 1145.04 | env 313 | IPIPSSWAF | 100 | B7 | 42.3 | 4 |
| 1147.04 | pol 354 | TPARVTGGVF | 90 | B7 | 13.2 | 2 |
| 1147.02 | pol 429 | HPAAMPHLL | 100 | B7 | 56.6 | 4 |
| 1147.05 | pol 530 | FPHCLAFSYM | 95 | B7 | 58.5 | 5 |
| 1359.01 | pol 640 | YPALMPLYACI | 95 | B7 | 1393.4 | 3 |
| 1039.06 | env 359 | WMWYWGPSLY | 85 | A1 | 16.3 | 3 |
| 1448.01 | core 419 | DLLDTASALY | 75 | A1 | 2.3 | 3 |
| 1373.88 | core 137 | LTFGRETVLEY | 75 | A1 | 80.0 | 3 |
| 1373.78 | pol 166 | ASFCGSPY | 100 | A1 | 247.0 | 3 |
| 1090.07 | pol 415 | LSLDVSAAFY | 95 | A1 | 6.0 | 3 |
| 1069.08 | env 249 | ILLLCLIFLL | 100 | A1 | 192.0 | 1 |
| 20.0269 | env 236 | RWMCLRRFII | 95 | A24 | 11.0 | 3 |
| 20.0271 | pol 392 | SWPKFAVPNL | 95 | A24 | 2.1 | 2 |
| 1373.56 | env 332 | RFSWLSLLVPF | 100 | A24 | 12.0 | 2 |
| 1373.38 | core 101 | LWFHISCLTF | 85 | A24 | 6.7 | 3 |
| 1373.07 | core 117 | EYLVSFGVW | 90 | A24 | 16.0 | 2 |
| 1069.23 | pol 745 | KYTSFPWLL | 85 | A24 | 1.0 | 3 |

HBV-30B

MGMQVQIQSLFLLLLWVPGSRGFLLTRILTINAAASWPKFAVPNLKAAAHTLWKAGILYKKADLLDTASALYNQAFTFS
PTYKGAAANVSIPWTHKGAAAFLLSLGIHLNIPIPSSWAFKAAALWFHISCLTFKAAAILLLCLIFLLNAAAYPALMPL
YACINAHPAAMPHLLKAAASFCGSPYKAAGLSRYVARLNKYTSFPWLLNFLPSDFFPSVKAFPHCLAFSYMKAEYLVSF
GVWNAALTFGRETVLEYKAAALPSDFFPSVKAYMDDVVLGVNLVVDFSQFSRNAAARWMCLRRFIINAARFSWLSLLVP
FNAATPARVTGGVFKAAWLSLLVPFVNSAICSVVRRKAKFVAAWTLKAAAKWMMWYWGPSLYKAASTLPETTVVRRKLS
LDVSAAFY

ATGGGAATGCAGGTCCAGATACAGAGCTTGTTCCTCCTCCTGCTTTGGGTCCCCGGATCAAGGGGTTTCCTCCTAACCC
GCATCCTGACAATTAACGCCGCAGCCTCCTGGCCAAAATTTGCCGTGCCAAATCTCAAGGCAGCTGCACACACACTATG
GAAAGCAGGGATACTGTACAAGAAAGCCGATCTGCTAGACACAGCGTCTGCGTTGTACAACCAGGCTTTTACTTTCTCT
CCTACATATAAAGGCGCAGCTGCAAACGTGAGTATCCCTTGGACGCACAAAGGAGCCGCTGCCAACTTCTTACTGTCCC
TGGGCATCCATCTAAATATCCCTATTCCTTCATCCTGGGCATTTAAAGCAGCCGCCTTATGGTTCCACATAAGTTGTCT
GACCTTCAAAGCCGCAGCAATCCTGCTCCTTTGCCTCATTTTCTTACTAAACGCCGCTGCCTATCCAGCTCTTATGCCA
TTGTACGCATGTATCAACGCCCACCCCGCAGCAATGCCCCACCTCCTTAAAGCTGCCGCCAGTTTCTGCGGTTCTCCTT
ATAAAGCAGCAGGGCTGTCCAGATACGTAGCTAGGCTAAACAAGTATACCAGCTTCCCCTGGTTACTTAATTTCCTGCC
GTCAGATTTCTTTCCATCAGTTAAGGCCTTCCCTCATTGTCTGGCCTTTAGCTACATGAAGGCTGAATATTTGGTATCC
TTCGGCGTGTGGAATGCGGCACTGACATTTGGAAGGGAGACAGTGCTCGAGTACAAAGCCGCCGCACTACCCTCGGACT
TCTTCCCATCGGTCAAAGCTTACATGGACGATGTAGTCCTCGGCGTTAACTTAGTAGTGGACTTTTCTCAATTTTCCAG
AAACGCAGCGGCCAGATGGATGTGCCTTCGGCGTTTTATAATAAACGCCGCTCGATTCAGCTGGCTATCACTCCTAGTT
CCATTTAATGCAGCTACACCCGCACGGGTGACAGGTGGAGTTTTCAAGGCAGCGTGGCTTTCACTGCTTGTGCCATTTG
TGAACTCAGCTATTTGCTCAGTAGTGAGAAGGAAGGCAAAATTCGTCGCTGCCTGGACTCTCAAAGCTGCCGCAAAGTG
GATGATGTGGTATTGGGGACCGAGCTTGTACAAAGCGGCCTCTACTCTGCCAGAAACTACCGTAGTGAGAAGAAAACTG
AGCCTGGACGTCAGCGCGGCATTCTACTGA

FIG.22D

HBV-30C

MGMQVQIQSLFLLLLWVPGSRGFLLSLGIHLNAAAKYTSFPWLLNAAAARFSWLSLLVPFNAAFPHCLAFSYMKAALVVD
FSQFSRGAILLLCLIFLLNAAAHTLWKAGILYKKAWMMWYWGPSLYKAYPALMPLYACIGAAAWLSLLVPFVNFLLTRI
LTINIPIPSSWAFKAAAEYLVSFGVWNLPSDFFPSVKFLPSDFFPSVKDLLDTASALYNSWPKFAVPNLKAAASAICSV
VRRKLSLDVSAAFYNAAAKFVAAWTLKAAAKAANVSIPWTHKGAAGLSRYVARLNAAASTLPETTVVRRKHPAAMPHLL
KAAARWMCLRRFIINASFCGSPYKAAYMDDVVLGVNALWFHISCLTFKAAATPARVTGGVFKAAALTFGRETVLEYKQA
FTFSPTYK

ATGGGAATGCAGGTGCAAATACAGTCTCTCTTCCTTTTGCTTCTCTGGGTTCCAGGATCACGGGGCTTCTTGCTTAGCT
TGGGCATCCACCTAAATGCTGCTGCAAAATACACATCTTTTCCTTGGCTCCTTAATGCCGCCGCTAGGTTTTCATGGCT
GAGTCTGCTAGTACCTTTCAATGCGGCTTTCCCACATTGCCTAGCTTTTAGCTATATGAAAGCTGCTTTAGTCGTGGAC
TTTTCACAGTTTAGCAGAGGAGCAATCCTGCTGCTATGTCTGATATTCCTTCTAAACGCAGCAGCCCACACACTCTGGA
AAGCTGGTATCCTTTACAAGAAAGCCTGGATGATGTGGTATTGGGGACCCAGCCTCTACAAAGCATACCCTGCCCTGAT
GCCACTATACGCATGCATTGGCGCGGCAGCCTGGTTATCCCTTTTAGTACCGTTTGTCAACTTTCTATTAACCAGAATC
CTGACGATTAATATTCCGATCCCAAGTTCCTGGGCATTCAAAGCAGCCGCGGAGTATCTGGTTTCATTTGGCGTATGGA
ACCTGCCAAGCGACTTCTTTCCTTCTGTTAAGTTCCTCCCCTCCGATTTCTTTCCATCGGTGAAAGACCTCCTTGATAC
CGCGAGCGCTCTGTACAACTCGTGGCCAAAATTCGCAGTTCCAAACCTAAAAGCCGCCGCCAGTGCCATTTGTTCCGTG
GTAAGGAGAAAATTATCACTCGACGTGTCCGCAGCATTTTATAACGCTGCTGCAAAGTTTGTCGCAGCATGGACATTGA
AGGCTGCAGCGAAAGCAGCAAATGTATCAATACCCTGGACCCACAAGGGTGCAGCCGGGCTGTCTAGGTATGTGGCGAG
GCTAAACGCCGCCGCCCTCAACACTGCCTGAGACTACTGTCGTGAGACGCAAACACCCTGCCGCAATGCCCCACCTGCTG
AAAGCAGCCGCACGATGGATGTGCCTCAGAAGATTCATAATAAACGCTTCTTTCTGTGGGTCACCCTACAAAGCCGCTT
ACATGGACGATGTGGTCCTCGGAGTGAATGCCCTCTGGTTCCATATCAGCTGCCTGACATTCAAGGCAGCCGCCACCCC
CGCTCGTGTGACAGGAGGTGTCTTCAAAGCCGCGGCACTGACTTTCGGTCGGGAAACTGTATTGGAATATAAGCAGGCC
TTCACATTCTCCCCAACATACAAGTGA

FIG.22E

HBV-CL

MQVQIQSLFLLLLWVPGSRGFLLSLGIHLNAAAKYTSFPWLLNAAARFSWLSLLVPFNAAFPHCLAFSYMKA
ALVVDFSQFSRGAILLLCLIFLLNAAAHTLWKAGILYKKAWMMWYWGPSLYKAYPALMPLYACIGAAAWLSL
LVPFVNFLLTRILTINAAAIPIPSSWAFKAAAEYLVSFGVWNLPSDFFPSVKAAAFLPSDFFPSVKAAADLL
DTASALYNSWPKFAVPNLKAAASAICSVVRRKLSLDVSAAFYNAAAKFVAAWTLKAAAKAANVSIPWTHKGA
AGLSRYVARLNAAASTLPETTVVRRKHPAAMPHLLKAAARWMCLRRFIINASFCGSPYKAAYMDDVVLGVNA
LWFHISCLTFKAAATPARVTGGVFKAAALTFGRETVLEYKQAFTFSPTYK

ATGGGAATGCAGGTGCAAATACAGTCTCTCTTCCTTTTGCTTCTCTGGGTTCCAGGATCACGGGGCTTCTTG
CTTAGCTTGGGCATCCACCTAAATGCTGCTGCAAAATACACATCTTTTCCTTGGCTCCTTAATGCCGCCGCT
AGGTTTTCATGGCTGAGTCTGCTAGTACCTTTCAATGCGGCTTTCCCACATTGCCTAGCTTTTAGCTATATG
AAAGCTGCTTTAGTCGTGGACTTTTCACAGTTTAGCAGAGGAGCAATCCTGCTGCTATGTCTGATATTCCTT
CTAAACGCAGCAGCCCACACACTCTGGAAAGCTGGTATCCTTTACAAGAAAGCCTGGATGATGTGGTATTGG
GGACCCAGCCTCTACAAAGCATACCCTGCCCTGATGCCACTATACGCATGCATTGGCGCGGCAGCCTGGTTA
TCCCTTTTAGTACCGTTTGTCAACTTTCTATTAACCAGAATCCTGACGATTAATGCTGCCGCCATTCCGATC
CCAAGTTCCTGGGCATTCAAAGCAGCCGCGGAGTATCTGGTTTCATTTGGCGTATGGAACCTGCCAAGCGAC
TTCTTTCCTTCTGTTAAGGCCGCTGCTTTCCTCCCCTCCGATTTCTTTCCATCGGTGAAAGCCGCTGCCGAC
CTCCTTGATACCGCGAGCGCTCTGTACAACTCGTGGCCAAAATTCGCAGTTCCAAACCTAAAAGCCGCCGCC
AGTGCCATTTGTTCCGTGGTAAGGAGAAAATTATCACTCGACGTGTCCGCAGCATTTTATAACGCTGCTGCA
AAGTTTGTCGCAGCATGGACATTGAAGGCTGCAGCGAAAGCAGCAAATGTATCAATACCCTGGACCCACAAG
GGTGCAGCCGGGCTGTCTAGGTATGTGGCGAGGCTAAACGCCGCCGCCTCAACACTGCCTGAGACTACTGTC
GTGAGACGCAAACACCCTGCCGCAATGCCCCACCTGCTGAAAGCAGCCGCACGATGGATGTGCCTCAGAAGA
TTCATAATAAACGCTTCTTTCTGTGGGTCACCCTACAAAGCCGCTTACATGGACGATGTGGTCCTCGGAGTG
AATGCCCTCTGGTTCCATATCAGCTGCCTGACATTCAAGGCAGCCGCCACCCCCGCTCGTGTGACAGGAGGT
GTCTTCAAAGCCGCGGCACTGACTTTCGGTCGGGAAACTGTATTGGAATATAAGCAGGCCTTCACATTCTCC
CCAACATACAAGTGA

FIG.23C

| Supertype | Epitope | # DR Bound | HLA-DR Binding Capacity (IC50 nM) | | | | | | | | | | | | | | |
|---|---|---|---|---|---|---|---|---|---|---|---|---|---|---|---|---|---|
| | | | DRB1*0101 | DRB1*1501 | DRB1*0301 | DRB1*0401 | DRB1*0405 | DRB1*1101 | DRB1*1201 | DRB1*1302 | DRB1*0701 | DRB1*0802 | DRB1*0901 | DRB5*0101 | DRB3*0101 | DRB4*0101 |
| DR | pol 412 | 10 | 2.0 | 21 | - | 10.0 | 47 | 303 | 397 | 143 | 173 | 598 | 791 | 1067 | 1837 | 4179 |
| | pol 664 | 11 | 10 | 41 | - | 88 | 181 | 82 | - | 190 | 90 | 416 | 142 | 144 | 4848 | 322 |
| | env 180 | 10 | 1 | 217 | - | 9 | 258 | 6 | 4229 | 9 | 8 | 189 | 56 | 1158 | 4374 | 696 |
| | pol 774 | 9 | 15 | 748 | - | 119 | 94 | 443 | - | - | 94 | 818 | 220 | 400 | - | - |
| | core 120 | 8 | 27 | 43 | - | 58 | 220 | 11 | 817 | 565 | 78 | 76 | 1773 | 7 | 6454 | 395 |
| | pol 145 | 10 | 17 | 4.0 | - | 2271 | 1499 | 42 | 149 | 766 | 61 | 36 | 133 | 35 | - | 782 |
| | env 339 | 9 | 408 | 14 | - | 315 | 28 | 54 | 452 | 2330 | 2744 | 60 | 31 | 1516 | 1661 | 22 |
| | pol 501 | 8 | 248 | 558 | - | 77 | 244 | 492 | 9462 | - | - | 800 | 1551 | 560 | - | 102 |
| | pol 523 | 7 | 27 | 359 | - | 560 | 246 | 1749 | - | 59 | 328 | 940 | 1373 | 4764 | - | 1347 |
| | pol 618 | 6 | 3.0 | 4370 | - | 40 | 34 | 1617 | - | 821 | 62 | 872 | 5175 | 1246 | - | 3060 |
| | pol 767 | 8 | 55 | 386 | - | 966 | 1634 | 1520 | 802 | 143 | 44 | 214 | 299 | 3276 | - | 6553 |
| | core 50 | 7 | 810 | 8.0 | - | 326 | - | 458 | - | - | 676 | 210 | 952 | 124 | 575 | 48 |
| DR3 | pol 694 | 2 | 7470 | 5009 | 67 | 490 | 1203 | - | - | 2022 | - | - | - | - | 1808 | 1044 |
| | pol 385 | 3 | 7372 | 1368 | 36 | 208 | 251 | - | - | 946 | - | - | - | - | 2525 | 8711 |
| | pol 96 | 1 | 8415 | 4153 | 43 | 3916 | 1908 | 6666 | - | 4461 | 5063 | 5354 | - | 4330 | - | 8121 |
| | pol 420 | 4 | 38 | 3089 | 62 | 168 | 17 | 4923 | 1859 | 36 | - | 1065 | 7126 | - | 5 | 7 |

FIG.24A

HBV-HTL

MGTSFVYVPSALNPADGPGPGLCQVFADATPTGWGLGPGPGRHYLHTLWKAGILYKGPGPGPHHTALRQAILC
WGELMTLAGPGPGESRLVVDFSQFSRGNGPGPGPFLLAQFTSAICSVVGPGPGLVPFVQWFVGLSPTVGPGPG
LHLYSHPIILGFRKIGPGPGSSNLSWLSLDVSAAFGPGPGLQSLTNLLSSNLSWLGPGPGAGFFLLTRILTIP
QSGPGPGVSFGVWIRTPPAYRPPNAPIGPGPGVGPLTVNEKRRLKLIGPGPGKQCFRKLPVNRPIDWGPGPGA
ANWILRGTSFVYVPGPGPGKQAFTFSPTYKAFLCGPGPGAKFVAAWTLKAAA

ATGGGAACTTCTTTTGTGTATGTCCCTTCCGCTCTGAACCCAGCAGACGGACCCGGGCCTGGCCTGTGCCAGG
TCTTCGCCGACGCAACTCCCACAGGGTGGGGGCTGGGGCCAGGACCAGGCAGGCACTACCTGCATACTCTGTG
GAAGGCAGGAATCCTCTATAAAGGGCCCGGCCCAGGCCCTCACCACACCGCCCTGAGGCAGGCCATCCTGTGC
TGGGGGGAGCTCATGACCCTGGCCGGACCTGGACCCGGGGAGAGCAGACTGGTGGTGGATTTCAGCCAATTCA
GCAGAGGAAACGGACCCGGCCCTGGGCCTTTTCTGCTGGCTCAGTTTACATCTGCTATTTGTTCTGTGGTCGG
CCCCGGGCCCGGACTCGTGCCTTTCGTGCAGTGGTTCGTGGGACTGTCCCCTACAGTCGGGCCCGGCCCAGGG
CTGCATCTGTACTCCCACCCAATCATCCTCGGCTTCCGCAAGATTGGACCCGGCCCAGGCTCCAGCAATCTCT
CCTGGCTCTCTCTGGACGTGTCTGCCGCCTTTGGCCCTGGACCAGGCCTGCAAAGCCTGACTAATCTGCTCAG
CAGCAACCTGTCCTGGCTGGGACCTGGCCCAGGGGCTGGCTTCTTTCTGCTCACCCGGATTCTCACAATTCCC
CAGTCCGGACCAGGACCAGGAGTCAGTTTCGGGGTGTGGATCAGGACCCCTCCTGCTTATAGACCACCCAATG
CTCCAATCGGCCCCGGCCCTGGCGTCGGGCCACTGACCGTGAATGAGAAGCGCCGGCTGAAGCTGATCGGCCC
TGGCCCTGGCAAGCAGTGCTTTCGCAAACTGCCCGTGAACAGACCTATTGATTGGGGCCCCGGCCCTGGAGCA
GCCAACTGGATTCTCAGGGGAACAAGCTTCGTCTACGTGCCCGGGCCCGGACCAGGGAAGCAGGCTTTTACCT
TCTCTCCCACTTACAAGGCCTTCCTCTGTGGGCCAGGCCCCGGCGCCAAGTTTGTGGCAGCATGGACCCTCAA
AGCCGCTGCCTGA

FIG.24C

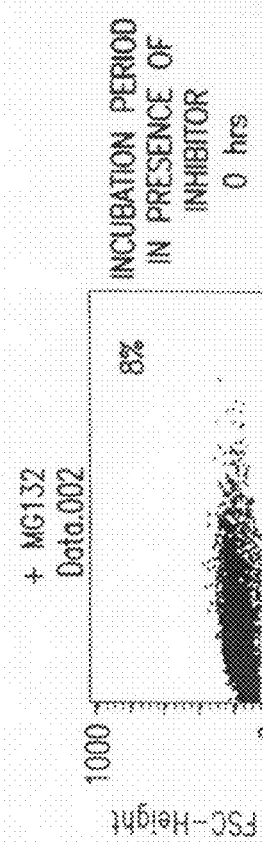
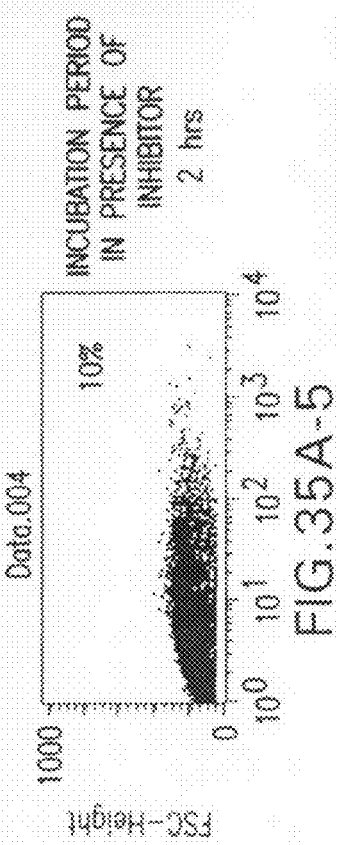
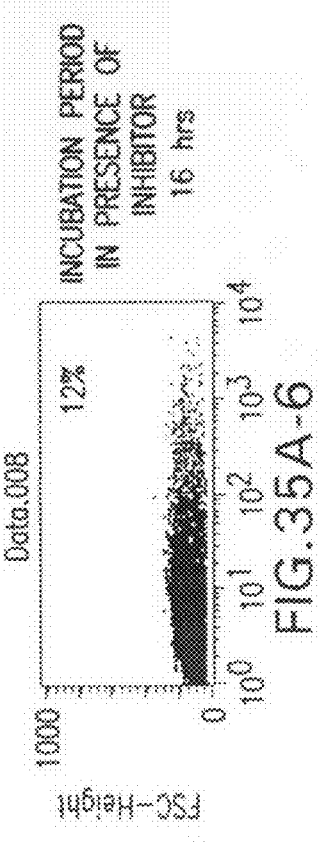
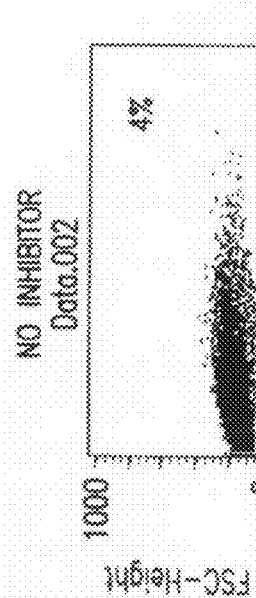
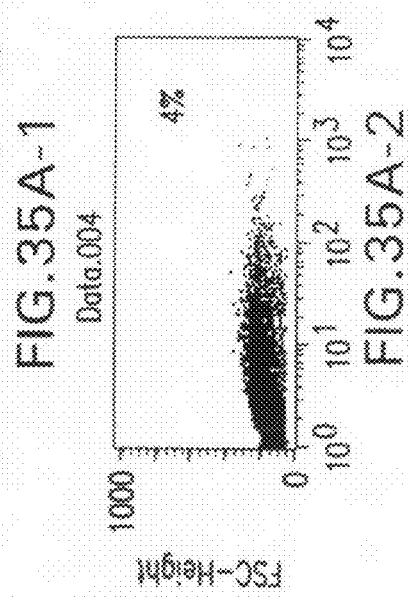
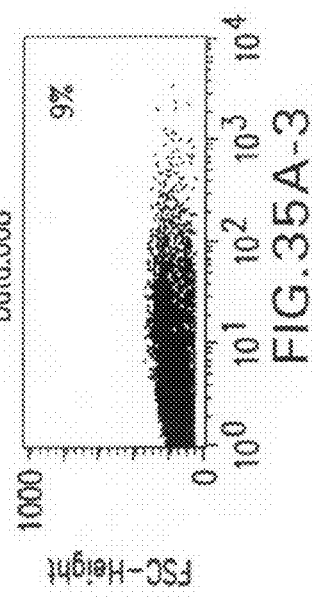
FIG.35A-1  FIG.35A-2  FIG.35A-3  FIG.35A-4  FIG.35A-5  FIG.35A-6

| plasmid | No inhibitor | with inhibitor | Fold Increase (aver.) |
|---|---|---|---|
| Fluorescent Protein (no epitopes control) | 30%<br>34% | 35%<br>33% | 1.1 |
| HBV AOSIb fusion | 5%<br>4.4 | 12%<br>8% | 2.1 |
| HBV AOSIb2 fusion | 2%<br>1.2% | 10%<br>6.6 | 5.3 |

FIG.35E

GCR-3697 Immunogenicity Data

| | | CTL response (SU) | | | | | |
|---|---|---|---|---|---|---|---|
| | | 2 x PVP Immunization | | | CT Pre-treatment | | |
| HLA Supertype | Epitope | Freq. | GeoMean | X/÷ | Freq. | GeoMean | X/÷ |
| HLA-A2 | core 18 | 12/12 | 199.3 | 2.1 | 4/4 | 288.9 | 1.3 |
| | env 183 | 12/12 | 171.2 | 2.8 | 4/4 | 401.2 | 1.4 |
| | env 335 | 12/12 | 86.4 | 2.3 | 4/4 | 153.6 | 1.7 |
| | pol 455 | 12/12 | 120.4 | 1.8 | 4/4 | 411.3 | 1.8 |
| | pol 538 | 12/12 | 149.9 | 3.2 | 4/4 | 148.1 | 2.2 |
| | pol 562 | 12/12 | 266.2 | 2 | 4/4 | 353.3 | 1.5 |
| HLA-A3 | core 141 | 6/6 | 94.4 | 1.4 | 12/12 | 167.6 | 1.4 |
| | pol 149 | 6/6 | 103 | 2.2 | 12/12 | 386.7 | 1.5 |
| | pol 655 | 5/6 | 10.1 | 2.3 | 12/12 | 108 | 3.6 |
| | pol 388 | 0/6 | | | 0/12 | | |
| | pol 47 | 0/6 | | | 3/12 | 3.2 | 1.1 |
| | pol 531 | 1/6 | 3.9 | | 2/12 | 5.5 | 1 |
| HLA-A24 | env 236 | 1/6 | 22.6 | | 2/11 | 23.4 | 1.2 |
| | pol 392 | 5/6 | 78.1 | 1.5 | 10/11 | 54.8 | 2.2 |
| | env 332 | 2/6 | 16.7 | 1.1 | 3/11 | 25.6 | 1.6 |
| | core 101 | 1/6 | 37 | | 0/11 | | |
| | core 117 | 3/6 | 34.4 | 1.9 | 2/11 | 27.4 | 3 |
| | pol 745 | 2/6 | 51.2 | 1.3 | 1/11 | 32.6 | |
| HLA-B7 | pol 530 | 6/6 | 292.4 | 3.1 | 3/6 | 177 | 1.3 |
| | pol 640 | 4/6 | 76.5 | 1.7 | 5/7 | 104.6 | 1.8 |
| | core 19 | 3/6 | 12 | 2.5 | 2/7 | 8.8 | 1.6 |
| | env 313 | 0/6 | 0 | 0 | 6/6 | 323.1 | 2.9 |
| | pol 354 | 0/6 | 0 | 0 | 4/6 | 351.5 | 3.2 |
| | pol 429 | 2/6 | 13.7 | 1.1 | 1/6 | 1.4 | |

OPTIMIZED MULTI-EPITOPE CONSTRUCTS AND USES THEREOF

CROSS-REFERENCE TO RELATED APPLICATIONS

This application is a divisional of U.S. patent application Ser. No. 10/677,754, filed Oct. 3, 2003, now U.S. Pat. No. 7,507,803, which claims the benefit of U.S. Provisional Application 60/415,463 filed Oct. 3, 2002, and to U.S. Provisional Application 60/419,973, filed Oct. 22, 2002, which are herein incorporated by reference.

STATEMENT REGARDING FEDERALLY-SPONSORED RESEARCH

Part of the work performed during development of this invention utilized U.S. Government funds. The U.S. Government has certain rights in this invention.

FIELD OF THE INVENTION

This present invention relates to the field of biology. In particular, it relates to multi-epitope nucleic acid vaccines and methods of designing such vaccines to provide increased immunogenicity.

BACKGROUND

The technology relevant to multi-epitope ("minigene" e.g., "epigene" vaccines is developing. Several independent studies have established that induction of simultaneous immune responses against multiple epitopes can be achieved. For example, responses against a large number of T cell specificities can be induced and detected. In natural situations, Doolan et al (*Immunity*, Vol. 7(1):97-112 (1997)) simultaneously detected recall T cell responses, against as many as 17 different *P. falciparum* epitopes using PBMC from a single donor. Similarly, Bertoni and colleagues (*J Clin Invest*, Vol. 100(3): 503-13 (1997)) detected simultaneous CTL responses against 12 different HBV-derived epitopes in a single donor. In terms of immunization with multi-epitope nucleic acid vaccines, several examples have been reported where multiple T cell responses were induced. For example, minigene vaccines composed of approximately ten MHC Class I epitopes in which all epitopes were immunogenic and/or antigenic have been reported. Specifically, minigene vaccines composed of 9 EBV (Thomson et al., *Proc Natl Acad Sci USA*, Vol. 92(13): 5845-9 (1995)), 7 HIV (Woodberry et al., *J Virol*, Vol. 73(7): 5320-5 (1999)), 10 murine (Thomson et al., *J Immunol*, Vol. 160(4):1717-23 (1998)) and 10 tumor-derived (Mateo et al., *J Immunol*, Vol. 163(7):4058-63 (1999)) epitopes have been shown to be active. It has also been shown that a multi-epitope DNA plasmid encoding nine different HLA-A2.1- and A11-restricted epitopes derived from HBV and HIV induced CTL against all epitopes (Ishioka et al., *J Immunol*, Vol. 162(7): 3915-25 (1999)).

Thus, minigene vaccines containing multiple MHC Class I and Class II (i.e., CTL and HTL) epitopes can be designed, and presentation and recognition can be obtained for all epitopes. However, the immunogenicity of multi-epitope constructs appears to be strongly influenced by a number of variables, a number of which have heretofore been unknown. For example, the immunogenicity (or antigenicity) of the same epitope expressed in the context of different vaccine constructs can vary over several orders of magnitude. Thus, there exists a need to identify strategies to optimize multi-epitope vaccine constructs. Such optimization is important in terms of induction of potent immune responses and ultimately, for clinical efficacy. Accordingly, the present invention provides strategies to optimize antigenicity and immunogenicity of multi-epitope vaccines encompassing a large number of epitopes, and optimized multi-epitope vaccines, particularly minigene vaccines, generated in accordance with these strategies.

The following paragraphs provide a brief review of some of the main variables potentially influencing minigene immunogenicity, epitope processing, and presentation on antigen presenting cells (APCs) in association with Class I and Class II MHC molecules.

Immunodominance

Of the many thousand possible peptides that are encoded by a complex foreign pathogen, only a small fraction ends up in a peptide form capable of binding to MHC Class I antigens and thus of being recognized by T cells. This phenomenon, of obvious potential impact on the development of a multi-epitope vaccine, is known as immunodominance (Yewdell et al., *Annu Rev Immunol*, 17:51-88 (1999)). Several major variables contribute to immunodominance. Herein, we describe variables affecting the generation of the appropriate peptides, both in qualitative and quantitative terms, as a result of intracellular processing.

Junctional Epitopes

A junctional epitope is defined as an epitope created due to the juxtaposition of two other epitopes. The new epitope is composed of a C-terminal section derived from a first epitope, and an N-terminal section derived from a second epitope. Creation of junctional epitopes is a potential problem in the design of multi-epitope minigene vaccines, for both Class I and Class II restricted epitopes for the following reasons. Firstly, when developing a minigene composed of, or containing, human epitopes, which are typically tested for immunogenicity in HLA transgenic laboratory animals, the creation of murine epitopes could create undesired immunodominance effects. Secondly, the creation of new, unintended epitopes for human HLA Class I or Class II molecules could elicit in vaccine recipients, new T cell specificities that are not expressed by infected cells or tumors that are targets of induced T cell responses. These responses are by definition irrelevant and ineffective and could even be counterproductive, by creating undesired immunodominance effects.

The existence of junctional epitopes has been documented in a variety of different experimental situations. Gefter and collaborators first demonstrated the effect in a system in which two different Class II restricted epitopes were juxtaposed and colinearly synthesized (Perkins et al., *J Immunol*, Vol. 146(7):2137-44 (1991)). The effect was so marked that the immune system recognition of the epitopes could be completely "silenced" by these new junctional epitopes (Wang et al., *Cell Immunol*, Vol. 143(2):284-97 (1992)). Helper T cells directed against junctional epitopes were also observed in humans as a result of immunization with a synthetic lipopeptide, which was composed of an HLA-A2-restricted HBV-derived immunodominant CTL epitope, and a universal Tetanus Toxoid-derived HTL epitope (Livingston et al, *J Immunol*, Vol. 159(3):1383-92 (1997)). Thus, the creation of junctional epitopes is a major consideration in the design of multi-epitope constructs.

The present invention provides methods of addressing this problem and avoiding or minimizing the occurrence of junctional epitopes.

Flanking Regions

Class I restricted epitopes are generated by a complex process (Yewdell et al., *Annu Rev Immunol*, 17:51-88 (1999)). Limited proteolysis involving endoproteases and potential trimming by exoproteases is followed by translocation across the endoplasmic reticulum (ER) membrane by transporters associated with antigen processing (TAP) molecules. The major cytosolic protease complex involved in generation of antigenic peptides, and their precursors, is the proteasome (Niedermann et al., *Immunity*, Vol. 2(3):289-99 (1995)), although ER trimming of CTL precursors has also been demonstrated (Paz et al., *Immunity* Vol. 11(2):241-51 (1999)). It has long been debated whether or not the residues immediately flanking the C and N terminus of the epitope, have an influence on the efficiency of epitope generation.

The yield and availability of processed epitope has been implicated as a major variable in determining immunogenicity and could thus clearly have a major impact on overall minigene potency in that the magnitude of immune response can be directly proportional to the amount of epitope bound by MHC and displayed for T cell recognition. Several studies have provided evidence that this is indeed the case. For example, induction of virus-specific CTL that is essentially proportional to epitope density (Wherry et al., *J Immunol*, Vol. 163(7):3735-45 (1999)) has been observed. Further, recombinant minigenes, which encode a preprocessed optimal epitope, have been used to induce higher levels of epitope expression than naturally observed with full-length protein (Anton et al., *J Immunol*, Vol. 158(6):2535-42 (1997)). In general, minigene priming has been shown to be more effective than priming with the whole antigen (Restifo et al., *J Immunol*, Vol. 154(9):4414-22 (1995); Ishioka et al., *J Immunol*, Vol. 162(7):3915-25 (1999)), even though some exceptions have been noted (Iwasaki et al., *Vaccine*, Vol. 17(15-16): 2081-8 (1999)).

Early studies concluded that residues within the epitope (Hahn et al., *J Exp Med*, Vol. 176(5):1335-41 (1992)) primarily regulate immunogenicity. Similar conclusions were reached by other studies, mostly based on grafting an epitope in an unrelated gene, or in the same gene, but in a different location (Chimini et al., *J Exp Med*, Vol. 169(1):297-302 (1989); Hahn et al., *J Exp Med*, Vol. 174(3):733-6 (1991)). Other experiments however (Del Val et al., *Cell*, Vol. 66(6): 1145-53 (1991); Hahn et al., *J Exp Med*, Vol. 176(5):1335-41 (1992)), suggested that residues localized directly adjacent to the CTL epitope can directly influence recognition (Couillin et al., *J Exp Med*, Vol. 180(3):1129-34 (1994); Bergmann et al., *J Virol*. Vol. 68(8):5306-10 (1994)). In the context of minigene vaccines, the controversy has been renewed. Shastri and coworkers (Shastri et al., *J Immunol*, Vol. 155(9):4339-46 (1995)) found that T cell responses were not significantly affected by varying the N-terminal flanking residue but were inhibited by the addition of a single C-terminal flanking residue. The most dramatic inhibition was observed with isoleucine, leucine, cysteine, and proline as the C-terminal flanking residues. In contrast, Gileadi (Gileadi et al., *Eur J Immunol*, Vol. 29(7):2213-22 (1999)) reported profound effects as a function of the residues located at the N terminus of mouse influenza virus epitopes. Bergmann and coworkers found that aromatic, basic and alanine residues supported efficient epitope recognition, while G and P residues were strongly inhibitory (Bergmann et al., *J Immunol*, Vol. 157(8):3242-9 (1996)). In contrast, Lippolis (Lippolis et al., *J Virol*, Vol. 69(5):3134-46 (1995)) concluded that substituting flanking residues did not effect recognition. However, only rather conservative substitutions that are unlikely to affect proteasome specificity were tested.

It appears that the specificity of these effects, and in general of natural epitopes, roughly correlates with proteasome specificity. For example, proteasome specificity is partly trypsin-like (Niedermann et al., *Immunity*, Vol. 2(3):289-99 (1995)), with cleavage following basic amino acids. Nevertheless, efficient cleavage of the carboxyl side of hydrophobic and acidic residues is also possible. Consistent with these specificities are the studies of Sherman and collaborators, which found that an R to H mutation at the position following the C-terminus of a p53 epitope affects proteasome-mediated processing of the protein (Theobald et al., *J Exp Med*, Vol. 188(6):1017-28 (1998)). Several other studies (Hanke et al., *J Gen Virol*, Vol. 79 (Pt 1):83-90 (1998); Thomson et al., *Proc Natl Acad Sci USA*, Vol. 92(13):5845-9 (1995)) indicated that minigenes can be constructed utilizing minimal epitopes, and that these flanking sequences appear not be required, although the potential for further optimization by the use of flanking regions was also acknowledged.

In sum, for HLA Class I epitopes, the effects of flanking regions on processing and presentation of CTL epitopes is as yet undefined. A systematic analysis of the effect of modulation of flanking regions has not been performed for minigene vaccines. Thus, analysis utilizing minigene vaccines encoding epitopes restricted by human Class I in general is needed. The present invention provides such an analysis and accordingly, provides multi-epitope vaccine constructs optimized for immunogenicity and antigenicity, and methods of designing such constructs.

HLA Class II peptide complexes are also generated as a result of a complex series of events that is distinct from HLA Class I processing. The processing pathway involves association with Invariant chain (Ii), its transport to specialized compartments, the degradation of Ii to CLIP, and HLA-DM catalyzed removal of CLIP (see (Blum et al., *Crit Rev Immunol*, Vol. 17(5-6):411-7 (1997); Arndt et al., *Immunol Res*, Vol. 16(3):261-72 (1997)) for review. Moreover, there is a potentially crucial role of various cathepsins in general, and cathepsin S and L in particular, in Ii degradation (Nakagawa et al., *Immunity*, Vol. 10(2):207-17 (1999)). In terms of generation of functional epitopes however, the process appears to be somewhat less selective (Chapman H. A., *Curr Opin Immunol*, Vol. 10(1):93-102 (1998)), and peptides of many sizes can bind to MHC Class II (Hunt et al., *Science*, Vol. 256 (5065):1817-20 (1992)). Most or all of the possible peptides appear to be generated (Moudgil et al., *J Immunol*, Vol. 159 (6):2574-9 (1997); and Thomson et al., *J Virol*, Vol. 72(3): 2246-52 (1998)). Thus, as compared to the issue of flanking regions, the creation of junctional epitopes can be a more serious concern in particular embodiments.

SUMMARY OF THE INVENTION

The invention provides multi-epitope nucleic acid constructs encoding a plurality of CTL and/or HTL epitopes and polypeptide constructs comprising a plurality of CTL and/or HTL epitopes (preferably encoded by the nucleic acid constructs), as well as cells comprising such nucleic acid constructs and/or polypeptide constructs, compositions comprising such nucleic acid constructs and/or polypeptide constructs and/or such cells, and methods for stimulating an immune response (e.g. therapeutic methods) utilizing such nucleic acid constructs and/or polypeptide constructs and/or compositions and/or cells.

In some embodiments, the invention provides a polynucleotide comprising or alternatively consisting of:

(a) a multi-epitope construct (e.g., minigene) comprising nucleic acids encoding the hepatitis B virus (HBV) cytotoxic T lymphocyte (CTL) epitopes pol 562, pol 745, env 332, pol 530, pol 388, env 249, env 359, pol 640, env 335, env 183, env 313, core 117, core 19, core 18, core 419, pol 392, pol 531, pol 415, pol 47, pol 455, core 141, pol 429, env 236, pol 166, pol 538, core 101, pol 354 and core 137 (i.e., the HBV CTL epitope each consisting of the relevant sequence in Table 7), wherein the nucleic acids are directly or indirectly joined to one another in the same reading frame;

(b) the multi-epitope construct of (a), which further comprises a nucleic acid encoding the HBV CTL epitope pol 665 (i.e. the pol 665 epitope in Table 7), directly or indirectly joined in the same reading frame to CTL epitope nucleic acids of (a);

(c) a multi-epitope construct comprising nucleic acids encoding the hepatitis B virus (HBV) cytotoxic T lymphocyte (CTL) epitopes pol 149, core 18, pol 562, pol 538, pol 455, env 183, core 141, pol 665, env 335, env 313, pol 354, pol 629, core 19, pol 150, pol 47, pol 388, pol 531 and pol 642, wherein the nucleic acids are directly or indirectly joined to one another in the same reading frame;

(d) the multi-epitope construct of (a) or (b) or (c), which further comprises one or a plurality of spacer nucleic acids, directly or indirectly joined in the same reading frame to the CTL epitope nucleic acids;

(e) the multi-epitope construct of (d), wherein the one or plurality of spacer nucleic acids are positioned between the CTL epitope nucleic acids of (a), between the CTL epitope nucleic acids of (a) and (b), between the CTL epitope nucleic acids of (a) and (b) and of (a) and of (c), or between the CTL epitope nucleic acids of (c);

(f) the multi-epitope construct of (d) or (e), wherein the spacer nucleic acids encode an amino acid sequence 1 to 8 residues in length;

(g) the multi-epitope construct of any of (d) to (f), wherein two or more of the spacer nucleic acids encode different (i.e., non-identical) amino acid sequences;

(h) the multi-epitope construct of any of (d) to (g), wherein two or more of the spacer nucleic acids encode an amino acid sequence different from the amino acid sequence encoded by other spacer nucleic acids;

(i) the multi-epitope construct of any of (d) to (h), wherein two or more of the spacer nucleic acids encodes the identical amino acid sequence;

(j) the multi-epitope construct of any of (d) to (i), wherein one or more of the spacer nucleic acids encode an amino acid sequence comprising or consisting of three consecutive alanine (Ala) residues;

(k) the multi-epitope construct of any of (a) to (j), which further comprises one or a plurality of nucleic acids encoding a HTL epitope, directly or indirectly joined in the same reading frame to the CTL epitope nucleic acids and/or the spacer nucleic acids;

(l) the multi-epitope construct of (k), wherein the HTL epitope is a PADRE® epitope;

(m) the multi-epitope construct of (k), wherein the HTL epitope is an HBV HTL epitope;

(n) the multi-epitope construct of (m), wherein the HBV HTL epitope is selected from the group consisting of pol 774, pol 694, pol 145, core 50, pol 385, pol 523, env 339, pol 501, pol 420, pol 412, env 180, core 120, pol 96, pol 618, pol 767, and pol 664 (i.e., the HBV HTL epitope each consisting of the relevant sequence in Table 11);

(o) the multi-epitope construct of any of (k) to (n), which further comprises one or a plurality of spacer nucleic acids between a CTL epitope and an HTL epitope or between HTL epitopes;

(p) the multi-epitope construct of any of (a) to (o), which further comprises one or more MHC Class I and/or MHC Class II targeting nucleic acid;

(q) the multi-epitope construct of (p), wherein the targeting nucleic acid encodes a targeting sequence selected from the group consisting of: Ig kappa signal sequence, tissue plasminogen activator signal sequence, insulin signal sequence, endoplasmic reticulum signal sequence, LAMP-1 lysosomal targeting sequence, LAMP-2 lysosomal targeting sequence, HLA-DM lysosomal targeting sequence, HLA-DM-association sequences of HLA-DO, Ig-α cytoplasmic domain, Ig-β cytoplasmic domain, Ii protein, influenza matrix protein, HBV surface antigen, HBV core antigen, and yeast Ty protein;

(r) the multi-epitope construct of any of (a) to (q), which is optimized for CTL and/or HTL epitope processing;

(s) the multi-epitope construct of any of (a) to (r), wherein the CTL nucleic acids are sorted to minimize the number of CTL and/or HTL junctional epitopes;

(t) the multi-epitope construct of any of (k) to (s), wherein the HTL nucleic acids are sorted to minimize the number of CTL and/or HTL junctional epitopes;

(u) the multi-epitope construct of any of (a) to (t), which comprises one or more nucleic acids encoding one or more flanking amino acid residues;

(v) the multi-epitope construct of (u), wherein the one or more flanking amino acid residues is selected from the group consisting of: K, R, N, Q, G, A, S, C, and T at a C+1 position of a CTL epitope nucleic acid;

(w) the multi-epitope construct of any of (a) to (v), wherein the HBV CTL nucleic acids are joined in the order shown in FIG. 27A;

(x) the multi-epitope construct of any of (n) to (w), wherein the HBV HTL nucleic acids are joined in the order shown in FIG. 28A;

(y) the multi-epitope construct of any of (c) to (v) or (x), wherein the HBV CTL nucleic acids are joined in the order shown in FIG. 34.

(z) the multi-epitope construct of any of (a) to (x), which encodes a peptide comprising or consisting of an amino acid sequence shown in FIG. 24B, or Table 13, 14, 18 or 19;

(aa) the multi-epitope construct of (z), which comprises a nucleic acid sequence selected from the group consisting of: nucleotides +1 to 1248 of the nucleotide sequence in Table 13, nucleotides +1 to 1032 of the nucleotide sequence in Table 14, the nucleotide sequence in FIG. 24C, nucleotides +1 to 2292 of the nucleotide sequence in Table 18, and nucleotides +1 to 2232 of the nucleotide sequence in Table 19;

(bb) the multi-epitope construct of any of (c) to (v) or (x) or (y) or (z), which encodes a peptide comprising or consisting of an amino acid sequence shown in Table 23 or 24;

(cc) the multi-epitope construct of (bb), which comprises a nucleic acid sequence selected from the group consisting of: nucleotides +1 to 618 of the nucleotide sequence in Table 23, or nucleotides +1 to 657 of the nucleotide sequence in Table 24;

(dd) the multi-epitope construct of any of (a) to (cc), and one or more regulatory sequences;

(ee) the multi-epitope construct of any of (a) to (dd), and one or more IRESs;

(ff) the multi-epitope construct of any of (a) to (ee), and one or more promoters;

(gg) the multi-epitope construct of any of (a) to (ff), and one or more CMV promoters;

(hh) the multi-epitope construct of any of (a) to (gg), and two or more CMV promoters;

(ii) the multi-epitope construct of any of (a) to (hh), and a vector;

(jj) the multi-epitope construct of (ii), wherein the vector is an expression vector;

(kk) the multi-epitope construct of any of (a) to (jj), which has the structure of a multi-epitope construct shown in FIG. 29A(i), (ii), or (iii).

In some embodiments, the polynucleotide of (a) to (kk) has the structure of a vector shown in FIG. 29A(i), (ii), or (iii).

In some embodiments, the invention provides a polynucleotide comprising two multi-epitope constructs, the first comprising the HBV multi-epitope construct in any of (a) to (kk), above, and the second comprising HBV HTL epitopes such as those in (n), wherein the first and second multi-epitope constructs are not directly joined, and/or are not joined in the same frame. Each first and second multi-epitope construct may be operably linked to a regulatory sequence such as a promoter or an IRES. The polynucleotide comprising the first and second multi-epitope constructs may comprise, e.g., at least one promoter and at least one IRES, one promoter and one IRES, two promoters, or two or more promoters and/or IRESs. The promoter may be a CMV promoter or other promoter described herein or known in the art. In preferred embodiments, the two multi-epitope constructs have the structure shown in FIG. 29A(i) or (ii). The second multi-epitope construct may encode a peptide comprising or consisting of an amino acid sequence shown in FIG. 24C or Table 14. The second multi-epitope construct may comprises a nucleic acid sequence selected from the nucleotide sequence in FIG. 24C, and nucleotides +1 to 1032 of the nucleotide sequence in Table 14.

In other embodiments the invention provides peptides encoded by the polynucleotides described above, for example, a peptide comprising or alternatively consisting of:

(a) a multi-epitope construct (e.g., minigene) comprising the hepatitis B virus (HBV) cytotoxic T lymphocyte (CTL) epitopes pol 562, pol 745, env 332, pol 530, pol 388, env 249, env 359, pol 640, env 335, env 183, env 313, core 117, core 19, core 18, core 419, pol 392, pol 531, pol 415, pol 47, pol 455, core 141, pol 429, env 236, pol 166, pol 538, core 101, pol 354 and core 137 (i.e., CTL epitopes of FIG. 27A, consisting of the sequences in Table 7), directly or indirectly joined to one another;

(b) the multi-epitope construct of (a), which further comprises the HBV CTL epitope pol 665, directly or indirectly joined to the CTL epitopes of (a);

(c) a multi-epitope construct comprising the hepatitis B virus (HBV) cytotoxic T lymphocyte (CTL) epitopes pol 149, core 18, pol 562, pol 538, pol 455, env 183, core 141, pol 665, env 335, env 313, pol 354, pol 629, core 19, pol 150, pol 47, pol 388, pol 531 and pol 642, directly or indirectly joined to one another;

(d) the multi-epitope construct of (a) or (b) or (c), which further comprises one or a plurality of spacers, directly or indirectly joined to the CTL epitopes;

(e) the multi-epitope construct of (d), wherein the one or plurality of spacers are positioned between the CTL epitopes of (a), between the CTL epitopes of (a) and (b), between the CTL epitopes of (a) and (b) and of (a) and of (c), or between the CTL epitopes of (c);

(f) the multi-epitope construct of (d) or (e), wherein the spacers are 1 to 8 amino acid residues in length;

(g) the multi-epitope construct of any of (d) to (f), wherein two or more of the spacers comprise or consist of different (i.e., non-identical) amino acid sequences;

(h) the multi-epitope construct of any of (d) to (g), wherein two or more of the spacers comprise or consist of an amino acid sequence different from the amino acid sequence of the other spacers;

(i) the multi-epitope construct of any of (d) to (h), wherein two or more of the spacers comprise or consist of the identical amino acid sequence;

(j) the multi-epitope construct of any of (d) to (i), wherein one or more of the spacers comprises or consists of three consecutive alanine (Ala) residues;

(k) the multi-epitope construct of any of (a) to (j), which further comprises one or a plurality of HTL epitopes, directly or indirectly joined to the CTL epitopes and/or the spacers;

(l) the multi-epitope construct of (k), wherein the one or plurality of HTL epitopes is a PADRE® epitope;

(m) the multi-epitope construct of (k), wherein the one or plurality of HTL epitopes is an HBV HTL epitope;

(n) the multi-epitope construct of (m), wherein the one or plurality of HTL epitopes is selected from the group consisting of pol 774, pol 694, pol 145, core 50, pol 385, env 339, pol 501, pol 420, pol 412, env 180, core 120, pol 96, pol 618, pol 767, and pol 664;

(o) the multi-epitope construct of any of (k) to (n), which further comprises one or a plurality of spacers between a CTL epitope and an HTL epitope or between HTL epitopes;

(p) the multi-epitope construct of any of (a) to (o), which further comprises one or more MHC Class I and/or MHC Class II targeting sequences;

(q) the multi-epitope construct of (p), wherein the one or more targeting sequence is selected from the group consisting of: Ig kappa signal sequence, tissue plasminogen activator signal sequence, insulin signal sequence, and endoplasmic reticulum signal sequence, LAMP-1 lysosomal targeting sequence, LAMP-2 lysosomal targeting sequence, HLA-DM lysosomal targeting sequence, HLA-DM-association sequences of HLA-DO, Ig-α cytoplasmic domain, Ig-β cytoplasmic domain, Ii protein, influenza matrix protein, HBV surface antigen, HBV core antigen, and yeast Ty protein;

(r) the multi-epitope construct of any of (a) to (q), which is optimized for CTL and/or HTL epitope processing;

(s) the multi-epitope construct of any of (a) to (r), wherein the CTL epitopes are sorted to minimize the number of CTL and/or HTL junctional epitopes;

(t) the multi-epitope construct of any of (k) to (s), wherein the HTL epitopes are sorted to minimize the number of CTL and/or HTL junctional epitopes;

(u) the multi-epitope construct of any of (a) to (t), which comprises one or more flanking amino acid residues;

(v) the multi-epitope construct of (u), wherein one or more the flanking amino acid residues is selected from the group consisting of K, R, N, Q, G, A, S, C, and T at a C+1 position of a CTL epitope;

(w) the multi-epitope construct of any of (a) to (v), wherein the HBV CTL epitopes are joined in the order shown in FIG. 27A;

(x) the multi-epitope construct of any of (n) to (w), wherein the HBV HTL epitopes are joined in the order shown in FIG. 28A;

(y) the multi-epitope construct of any of (c) to (v) or (x), wherein the HBV CTL epitopes are joined in the order shown in FIG. 34;

(z) the multi-epitope construct of any of (a) to (x), which comprises or consists of an amino acid sequence shown in FIG. 24B, or Table 13, 14, 18 or 19;

(aa) the multi-epitope construct of (z), which is encoded by a nucleic acid sequence selected from the group consisting of: nucleotides +1 to 1248 of the nucleotide sequence in Table 13, nucleotides +1 to 1032 of the nucleotide sequence in Table 14, the nucleotide sequence in FIG. 24C, nucleotides +1 to 2292 of the nucleotide sequence in Table 18, and nucleotides +1 to 2232 of the nucleotide sequence in Table 19;

(bb) the multi-epitope construct of any of (c) to (v), or (x) or (y), which comprises or consists of an amino acid sequence shown in Table 23 or 24;

(cc) the multi-epitope construct of (bb), which is encoded by a nucleic acid sequence selected from the group consisting of: nucleotides +1 to 618 of the nucleotide sequence in Table 23 and nucleotides +1 to 657 of the nucleotide sequence in Table 24.

In other embodiments, the invention provides cells comprising the polynucleotides and/or polypeptides above; compositions comprising the polynucleotides and/or polypeptides and/or cells; methods for making these polynucleotides, polypeptides, cells and compositions; and methods for stimulating an immune response (e.g. therapeutic and/or prophylactic methods) utilizing these polynucleotides and/or polypeptides and/or cells and/or compositions. The invention is described in further detail below.

DEFINITIONS

The following definitions are provided to enable one of ordinary skill in the art to understand some of the preferred embodiments of invention disclosed herein. It is understood, however, that these definitions are exemplary only and should not be used to limit the scope of the invention as set forth in the claims. Those of ordinary skill in the art will be able to construct slight modifications to the definitions below and utilize such modified definitions to understand and practice the invention disclosed herein. Such modifications, which would be obvious to one of ordinary skill in the art, as they may be applicable to the claims set forth below, are considered to be within the scope of the present invention.

Throughout this disclosure, "binding data" results are often expressed in terms of "$IC_{50}$'s." $IC_{50}$ is the concentration of peptide in a binding assay at which 50% inhibition of binding of a reference peptide is observed. Given the conditions in which the assays are run (i.e., limiting HLA proteins and labeled peptide concentrations), these values approximate $K_D$ values. Assays for determining binding are described in detail, e.g., in PCT publications WO 94/20127 and WO 94/03205. It should be noted that $IC_{50}$ values can change, often dramatically, if the assay conditions are varied, and depending on the particular reagents used (e.g., HLA preparation, etc.). For example, excessive concentrations of HLA molecules will increase the apparent measured $IC_{50}$ of a given ligand. Alternatively, binding is expressed relative to a reference peptide. Although as a particular assay becomes more, or less, sensitive, the $IC_{50}$'s of the peptides tested may change somewhat, the binding relative to the reference peptide will not significantly change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good, intermediate, weak, or negative binder is generally based on its $IC_{50}$, relative to the $IC_{50}$ of a standard peptide. Binding may also be determined using other assay systems including those using: live cells (e.g., Ceppellini et al., *Nature* 339:392, 1989; Christnick et al., *Nature* 352:67, 1991; Busch et al., *Int. Immunol.* 2:443, 19990; Hill et al., *J. Immunol.* 147:189, 1991; del Guercio et al., *J. Immunol.* 154:685, 1995), cell free systems using detergent lysates (e.g., Cerundolo et al., *J. Immunol.* 21:2069, 1991), immobilized purified MHC (e.g., Hill et al., *J. Immunol.* 152, 2890, 1994; Marshall et al., *J. Immunol.* 152:4946, 1994), ELISA systems (e.g., Reay et al., *EMBO J.* 11:2829, 1992), surface plasmon resonance (e.g., Khilko et al., *J. Biol. Chem.* 268:15425, 1993); high flux soluble phase assays (Hammer et al., *J. Exp. Med.* 180:2353, 1994), and measurement of class I MHC stabilization or assembly (e.g., Ljunggren et al., *Nature* 346:476, 1990; Schumacher et al., *Cell* 62:563, 1990; Townsend et al., *Cell* 62:285, 1990; Parker et al., *J. Immunol.* 149:1896, 1992).

The designation of a residue position in an epitope as the "carboxyl terminus" or the "carboxyl terminal position" refers to the residue position at the end of the epitope that is nearest to the carboxyl terminus of a peptide, which is designated using conventional nomenclature as defined below. "C+1" refers to the residue or position immediately following the C-terminal residue of the epitope, i.e., refers to the residue flanking the C-terminus of the epitope. The "carboxyl terminal position" of the epitope occurring at the carboxyl end of the multi-epitope construct may or may not actually correspond to the carboxyl terminal end of polypeptide. In preferred embodiments, the epitopes employed in the optimized multi-epitope constructs are motif-bearing epitopes and the carboxyl terminus of the epitope is defined with respect to primary anchor residues corresponding to a particular motif.

The designation of a residue position in an epitope as "amino terminus" or "amino-terminal position" refers to the residue position at the end of the epitope which is nearest to the amino terminus of a peptide, which is designated using conventional nomenclature as defined below. "N−1" refers to the residue or position immediately adjacent to the epitope at the amino terminal end (position number 1) of an eptiope. The "amino terminal position" of the epitope occurring at the amino terminal end of the multi-epitope construct may or may not actually corresponds to the amino terminal end of the polypeptide. In preferred embodiments, the epitopes employed in the optimized multi-epitope constructs are motif-bearing epitopes and the amino terminus of the epitope is defined with respect to primary anchor residues corresponding to a particular motif.

A "computer" or "computer system" generally includes: a processor; at least one information storage/retrieval apparatus such as, for example, a hard drive, a disk drive or a tape drive; at least one input apparatus such as, for example, a keyboard, a mouse, a touch screen, or a microphone; and display structure. Additionally, the computer may include a communication channel in communication with a network such that remote users may communicate with the computer via the network to perform multi-epitope construct optimization functions disclosed herein. Such a computer may include more or less than what is listed above. The network may be a local area network (LAN), wide area network (WAN) or a global network such as the world wide web (e.g., the internet).

A "construct" as used herein generally denotes a composition that does not occur in nature. A construct may be a "polynucleotide construct" or a "polypeptide construct." A construct can be produced by synthetic technologies, e.g., recombinant DNA preparation and expression or chemical synthetic techniques for nucleic acids and amino acids and peptides and polypeptides. A construct can also be produced by the addition or affiliation of one material with another such that the result is not found in nature in that form.

The term "multi-epitope construct" when referring to nucleic acids and polynucleotides can be used interchangeably with the terms "minigene" and "multi-epitope nucleic acid vaccine," and other equivalent phrases, and comprises multiple epitope nucleic acids that encode peptide epitopes of any length that can bind to a molecule functioning in the immune system, preferably a class I HLA and a T-cell receptor or a class II HLA and a T-cell receptor. The epitope nucleic acids in a multi-epitope construct can encode class I HLA epitopes and/or class II HLA epitopes. Class I HLA-encoding epitope nucleic acids are referred to as CTL epitope nucleic acids, and class II HLA-encoding epitope nucleic acids are referred to as HTL epitope nucleic acids. Some multi-epitope constructs can have a subset of the multi-epitope nucleic acids encoding class I HLA epitopes and another subset of the multi-epitope nucleic acids encoding class II HLA epitopes. The CTL epitope nucleic acids preferably encode an epitope peptide of less than about 15 residues in length, or less than about 13 amino acids in length, or less than about 11 amino acids in length, preferably about 8 to about 13 amino acids in length, more preferably about 8 to about 11 amino acids in length (e.g. 8, 9, 10, or 11), and most preferably about 9 or 10 amino acids in length. The HTL epitope nucleic acids can encode an epitope peptide of less than about 50 residues in length, and usually consist of about 6 to about 30 residues, more usually between about 12 to 25, and often about 15 to 20, and preferably about 7 to about 23, preferably about 7 to about 17, more preferably about 11 to about 15 (e.g. 11, 12, 13, 14, or 15), and most preferably about 13 amino acids in length. The multi-epitope constructs described herein preferably include 5 or more, 10 or more, 15 or more, 20 or more, or 25 or more epitope nucleic acids. All of the epitope nucleic acids in a multi-epitope construct may be from one organism (e.g., the nucleotide sequence of every epitope nucleic acid may be present in HBV or HIV strains), or the multi-epitope construct may include epitope nucleic acids sequences present in two or more different organisms (e.g., the nucleotide sequence of some epitope encoding nucleic acid sequences from HBV and some from HIV and/or some from HCV). The term "epigene" is used herein to refer to certain multi-epitope constructs. As described hereafter, one or more epitope nucleic acids in the multi-epitope construct may be flanked by a spacer nucleic acid, and/or other nucleic acids also described herein or otherwise known in the art.

The term "multi-epitope construct," when referring to polypeptides, can be used interchangeably with the terms "minigene construct," "multi-epitope vaccine," and other equivalent phrases, and comprises multiple peptide epitopes of any length that can bind to a molecule functioning in the immune system, preferably a class I HLA and a T-cell receptor or a class II HLA and a T-cell receptor. The epitopes in a multi-epitope construct can be class I HLA epitopes and/or class II HLA epitopes. Class I HLA epitopes are referred to as CTL epitopes, and class II HLA epitopes are referred to as HTL epitopes. Some multi-epitope constructs can have a subset of class I HLA epitopes and another subset of class II HLA epitopes. The CTL epitopes preferably are less than about 15 residues in length, or less than about 13 residues in length, or less than about 11 residues in length, and preferably encode an epitope peptide of about 8 to about 13 amino acids in length, more preferably about 8 to about 11 amino acids in length (e.g. 8, 9, 10, or 11), and most preferably about 9 amino acids in length. The HTL epitopes are less than about 50 residues in length and usually consist of about 6 to about 30 residues, more usually between about 12 to 25, and often about 15 to 20 residues, and preferably about 7 to about 23, preferably about 7 to about 17, more preferably about 11 to about 15 (e.g. 11, 12, 13, 14, or 15), and most preferably about 13 amino acids in length. The multi-epitope constructs described herein preferably include 5 or more, 10 or more, 15 or more, 20 or more, or 25 or more epitopes. All of the epitopes in a multi-epitope construct may be from one organism (e.g., every epitope may be present in HBV or HIV strains), or the multi-epitope construct may include epitopes present in two or more different organisms (e.g., some epitopes from HBV and some from HIV and/or some from HCV). The term "epigene" is used herein to refer to certain multi-epitope constructs. As described hereafter, one or more epitopes in the multi-epitope construct may be flanked by a spacer sequences, and/or other sequences also described herein or otherwise known in the art.

A "multi-epitope vaccine," which is synonymous with a "polyepitopic vaccine," is a vaccine comprising multiple epitopes.

"Cross-reactive binding" indicates that a peptide is bound by more than one HLA molecule; a synonym is "degenerate binding."

A "cryptic epitope" elicits a response by immunization with an isolated peptide, but the response is not cross-reactive in vitro when intact whole protein that comprises the epitope is used as an antigen.

A "dominant epitope" is an epitope that induces an immune response upon immunization with a whole native antigen (see, e.g., Sercarz, et al., *Annu. Rev. Immunol.* 11:729-766, 1993). Such a response is cross-reactive in vitro with an isolated peptide epitope.

With regard to a particular amino acid sequence, an "epitope" is a set of amino acid residues that is involved in recognition by a particular immunoglobulin, or in the context of T cells, those residues necessary for recognition by T cell receptor proteins and/or Major Histocompatibility Complex (MHC) receptors. In an immune system setting, in vitro or in vivo, an epitope is the collective features of a molecule, such as primary, secondary and tertiary peptide structure, and charge, that together form a site recognized by an immunoglobulin, T cell receptor or HLA molecule. Throughout this disclosure epitope and peptide are often used interchangeably. It is to be appreciated, however, that isolated or purified protein or peptide molecules larger than and comprising an epitope of the invention are still within the bounds of the invention.

A "flanking residue" is a residue that is positioned next to an epitope. A flanking residue can be introduced or inserted at a position adjacent to the N-terminus or the C-terminus of an epitope.

An "immunogenic peptide" or "peptide epitope" is a peptide that comprises an allele-specific motif or supermotif such that the peptide will bind an HLA molecule and induce a CTL and/or HTL response. Thus, immunogenic peptides of the invention are capable of binding to an appropriate HLA molecule and thereafter inducing a cytotoxic T cell response, or a helper T cell response, to the antigen from which the immunogenic peptide is derived.

"Heteroclitic analogs" are defined herein as a peptide with increased potency for a specific T cell, as measured by increased responses to a given dose, or by a requirement of lesser amounts to achieve the same response. Advantages of heteroclitic analogs include that the epitopes can be more potent, or more economical (since a lower amount is required to achieve the same effect). In addition, modified epitopes might overcome antigen-specific T cell unresponsiveness (T cell tolerance).

"Human Leukocyte Antigen" or "HLA" is a human class I or class II Major Histocompatibility Complex (MHC) protein (see, e.g., Stites, et al., IMMUNOLOGY, 8$^{TH}$ ED., Lange Publishing, Los Altos, Calif. (1994)).

An "HLA supertype or HLA family," as used herein, describes sets of HLA molecules grouped based on shared peptide-binding specificities. HLA class I molecules that share similar binding affinity for peptides bearing certain amino acid motifs are grouped into such HLA supertypes. The terms HLA superfamily, HLA supertype family, HLA family, and HLA xx-like molecules (where xx denotes a particular HLA type), are synonyms.

As used herein, "high affinity" with respect to HLA class I molecules is defined as binding with an $IC_{50}$, or $K_D$ value, of 50 nM or less; "intermediate affinity" with respect to HLA class I molecules is defined as binding with an $IC_{50}$ or $K_D$ value of between about 50 and about 500 nM. "High affinity" with respect to binding to HLA class II molecules is defined as binding with an $IC_{50}$ or $K_D$ value of 100 nM or less; "intermediate affinity" with respect to binding to HLA class II molecules is defined as binding with an $IC_{50}$ or $K_D$ value of between about 100 and about 1000 nM.

An "$IC_{50}$" is the concentration of peptide in a binding assay at which 50% inhibition of binding of a reference peptide is observed. Depending on the conditions in which the assays are run (i.e., limiting HLA proteins and labeled peptide concentrations), these values may approximate $K_D$ values.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithm or by manual alignment and visual inspection.

"Introducing" an amino acid residue at a particular position in a multi-epitope construct, e.g., adjacent, at the C-terminal side, to the C-terminus of the epitope, encompasses configuring multiple epitopes such that a desired residue is at a particular position, e.g., adjacent to the epitope, or such that a deleterious residue is not adjacent to the C-terminus of the epitope. The term also includes inserting an amino acid residue, preferably a preferred or intermediate amino acid residue, at a particular position. An amino acid residue can also be introduced into a sequence by substituting one amino acid residue for another. Preferably, such a substitution is made in accordance with analoging principles set forth, e.g., in co-pending U.S. Ser. No. 09/260,714 filed Mar. 1, 1999 and PCT application number PCT/US00/19774.

The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment.

"Link" or "join" refers to any method known in the art for functionally connecting peptides, including, without limitation, recombinant fusion, covalent bonding, disulfide bonding, ionic bonding, hydrogen bonding, and electrostatic bonding.

"Major Histocompatibility Complex" or "MHC" is a cluster of genes that plays a role in control of the cellular interactions responsible for physiologic immune responses. In humans, the MHC complex is also known as the HLA complex. For a detailed description of the MHC and HLA complexes, see, Paul, FUNDAMENTAL IMMUNOLOGY, 3$^{RD}$ ED., Raven Press, New York, 1993).

As used herein, "middle of the peptide" is a position in a peptide that is neither amino or carboxyl terminal.

A "minimal number of junctional epitopes" as used herein refers to a number of junctional epitopes that is lower than what would be created using a random selection criterium.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "negative binding residue" or "deleterious residue" is an amino acid that if present at certain positions (typically not a primary anchor position) in a peptide epitope, results in decreased binding affinity of the peptide for the peptide's corresponding HLA molecule.

The phrase "operably linked" refers to a linkage in which a nucleotide sequence is connected to another nucleotide sequence (or sequences) in such a way as to be capable of altering the functioning of the sequence (or sequences). For example, a nucleic acid or multi-epitope nucleic acid construct that is operably linked to a regulatory sequence, such as a promoter/operator, places expression of the nucleic acid or construct under the influence or control of the regulatory sequence. Two nucleotide sequences (such as a protein encoding sequence and a promoter region sequence linked to the 5' end of the encoding sequence) are said to be operably linked if induction of promoter function results in the transcription of the protein encoding sequence mRNA and if the nature of the linkage between the two nucleotide sequences does not (1) result in the introduction of a frame-shift mutation nor (2) prevent the expression regulatory sequences to direct the expression of the mRNA or protein. Thus, a promoter region would be operably linked to a nucleotide sequence if the promoter were capable of effecting transcription of that nucleotide sequence.

"Optimizing" refers to increasing the immunogenicity or antigenicity of a multi-epitope construct having at least one epitope pair by sorting epitopes to minimize the occurrence of junctional epitopes, inserting flanking residues that flank the C-terminus or N-terminus of an epitope, and inserting spacer residue to further prevent the occurrence of junctional epitopes or to provide a flanking residue. An increase in immunogenicity or antigenicity of an optimized multi-epitope construct is measured relative to a multi-epitope construct that has not been constructed based on the optimization parameters and is using assays known to those of skill in the art, e.g., assessment of immunogenicity in HLA transgenic mice, ELISPOT, inteferon-gamma release assays, tetramer staining, chromium release assays, and presentation on dendritic cells.

The term "peptide" is used interchangeably with "oligopeptide" in the present specification to designate a series of residues, typically L-amino acids, connected one to the other, typically by peptide bonds between the α-amino and carboxyl groups of adjacent amino acids. The CTL-inducing peptides of the invention are less than about 15 residues in length, preferably 13 residues or less in length and preferably are about 8 to about 13 amino acids in length, more preferably about 8 to about 11 amino acids in length (e.g. 8, 9, 10, or 11), and most preferably about 9 amino acids in length. The preferred HTL-inducing oligopeptides are less than about 50 residues in length and usually consist of about 6 to about 30 residues, more usually between about 12 to 25, and often about 15 to 20 residues, and can encode an epitope peptide of about 7 to about 23, preferably about 7 to about 17, more preferably about 11 to about 15 (e.g. 11, 12, 13, 14, or 15), and most preferably about 13 amino acids in length. The multi-epitope constructs described herein preferably include 5 or more, 10 or more, 15 or more, 20 or more, or 25 or more epitope nucleic acids.

The nomenclature used to describe peptide, polypeptide, and protein compounds follows the conventional practice wherein the amino group is presented to the left (the N-terminus) and the carboxyl group to the right (the C-terminus) of each amino acid residue. When amino acid residue positions are referred to, they are numbered in an amino to carboxyl direction with position one being the position closest to the amino terminal end of the epitope, or the peptide, polypeptide or protein of which it may be a part. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three-letter or single-letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G. Symbols for the amino acids are shown below.

| Single Letter Symbol | Three Letter Symbol | Amino Acids |
| --- | --- | --- |
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Amino acid "chemical characteristics" are defined as: Aromatic (F, W, Y); Aliphatic-hydrophobic (L, I, V, M); Small polar (S, T, C); Large polar (Q, N); Acidic (D, E); Basic (R, H, K); Proline; Alanine; and Glycine.

The terms "PanDR binding peptide," "PanDR binding epitope," "PADRE® peptide," and "PADRE® epitope," refer to a type of HTL peptide which is a member of a family of molecules that binds more than one HLA class II DR molecule. PADRE® peptides bind to most HLA-DR molecules and stimulate in vitro and in vivo human helper T lymphocyte (HTL) responses. The pattern that defines the PADRE® family of molecules can be thought of as an HLA Class II super-motif. For example, a PADRE® peptide may comprise the formula: aKXVAAWTLKAAa (SEQ ID NO:1), where "X" is either cyclohexylalanine, phenylalanine or tyrosine, and "a" is either D-alanine or L-alanine, has been found to bind to most HLA-DR alleles, and to stimulate the response of T helper lymphocytes from most individuals, regardless of their HLA type. An alternative of a PADRE® epitope comprises all "L" natural amino acids which can be provided in peptide/polypeptide form and in the form of nucleic acids that encode the epitope, e.g., in multi-epitope constructs. Specific examples of PADRE® peptides are also disclosed herein.

"Pharmaceutically acceptable" refers to a generally non-toxic, inert, and/or physiologically compatible composition.

"Presented to an HLA Class I processing pathway" means that the multi-epitope constructs are introduced into a cell such that they are largely processed by an HLA Class I processing pathway. Typically, multi-epitope constructs are introduced into the cells using expression vectors that encode the multi-epitope constructs. HLA Class II epitopes that are encoded by such a multi-epitope construct are also presented on Class II molecules, although the mechanism of entry of the epitopes into the Class II processing pathway is not defined.

A "primary anchor residue" or a "primary MHC anchor" is an amino acid at a specific position along a peptide sequence that is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding grooves of an HLA molecule, with their side chains buried in specific pockets of the binding grooves themselves. In one embodiment, for example, the primary anchor residues of an HLA class I epitope are located at position 2 (from the amino terminal position) and at the carboxyl terminal position of a 9-residue peptide epitope in accordance with the invention. The primary anchor positions for each motif and supermotif are described, for example, in Tables I and III of PCT/US00/27766, or PCT/US00/19774. Preferred amino acids that can serve as in the anchors for most Class II epitopes consist of M and F in position one and V, M, S, T, A and C in position six. Tolerated amino acids that can occupy these positions for most Class II epitopes consist of L, I, V, W, and Y in position one and P, L and I in position six. The presence of these amino acids in positions one and six in Class II epitopes defines the HLA-DR1, 4, 7 supermotif. The HLA-DR3 binding motif is defined by preferred amino acids from the group of L, I, V, M, F, Y and A in position one and D, E, N, Q, S and T in position four and K, R and H in position six. Other amino acids may be tolerated in these positions but they are not preferred.

Furthermore, analog peptides can be created by altering the presence or absence of, i.e. replacing, a particular residue in these primary anchor positions. Such analogs are used to modulate the binding affinity of a peptide comprising a particular motif or supermotif.

"Promiscuous recognition" occurs where a distinct peptide is recognized by the same T cell clone in the context of various HLA molecules. Promiscuous recognition or binding is synonymous with cross-reactive binding.

A "protective immune response" or "therapeutic immune response" refers to a CTL and/or an HTL response to an antigen derived from an infectious agent or a tumor antigen, which in some way prevents or at least partially arrests disease symptoms, side effects or progression. The immune response may also include an antibody response that has been facilitated by the stimulation of helper T cells.

By "regulatory sequence" is meant a polynucleotide sequence that contributes to or is necessary for the expression of an operably associated nucleic acid or nucleic acid construct in a particular host organism. The regulatory sequences that are suitable for prokaryotes, for example, include a promoter, optionally an operator sequence, and an internal ribosome binding site (IRES). Eukaryotic cells are known to utilize promoters, polyadenylation signals, and enhancers. Promoter may be a CMV promoter or other promoter described herein or known in the art. Regulatory sequences include IRESs. Other specific examples of regulatory sequences are described herein and otherwise known in the art.

The term "residue" refers to an amino acid or amino acid mimetic incorporated into a peptide or protein by an amide bond or amide bond mimetic.

A "secondary anchor residue" is an amino acid at a position other than a primary anchor position in a peptide that may influence peptide binding. A secondary anchor residue occurs at a significantly higher frequency amongst bound peptides than would be expected by random distribution of amino acids at one position. The secondary anchor residues are said to occur at "secondary anchor positions." A secondary anchor residue can be identified as a residue that is present at a higher frequency among high or intermediate affinity binding peptides, or a residue otherwise associated with high or intermediate affinity binding. For example, analog peptides can be created by altering the presence or absence of, i.e. replacing, a particular residue in these secondary anchor positions. Such analogs are used to finely modulate the binding affinity of a peptide comprising a particular motif or supermotif. The terminology "fixed peptide" is sometimes used to refer to an analog peptide.

"Sorting epitopes" refers to determining or designing an order of the epitopes in a multi-epitope construct.

A "spacer" refers to a sequence that is inserted between two epitopes in a multi-epitope construct to prevent the occurrence of junctional epitopes and/or to increase the efficiency of processing. A multi-epitope construct may have one or more spacer nucleic acids. A spacer nucleic acid may flank each epitope nucleic acid in a construct, or the spacer nucleic acid to epitope nucleic acid ratio may be about 2 to 10, about 5 to 10, about 6 to 10, about 7 to 10, about 8 to 10, or about 9 to 10, where a ratio of about 8 to 10 has been determined to yield favorable results for some constructs.

The spacer nucleic acid may encode one or more amino acids. A spacer nucleic acid flanking a class I HLA epitope in a multi-epitope construct is preferably between one and about eight amino acids in length. A spacer nucleic acid flanking a class II HLA epitope in a multi-epitope construct is preferably greater than five, six, seven, or more amino acids in length, and more preferably five or six amino acids in length.

The number of spacers in a construct, the number of amino acids in a spacer, and the amino acid composition of a spacer can be selected to optimize epitope processing and/or minimize junctional epitopes. It is preferred that spacers are selected by concomitantly optimizing epitope processing and junctional motifs. Suitable amino acids for optimizing epitope processing are described herein. Also, the suitable amino acid spacing for minimizing the number of junctional epitopes in a construct is described herein for class I and class II HLAs. For example, spacers flanking class II HLA epitopes preferably include G, P, and/or N residues as these are not generally known to be primary anchor residues (see, e.g., PCT/US00/19774). A particularly preferred spacer for flanking a class II HLA epitope includes alternating G and P residues, for example, $(GP)_n$, $(PG)_n$, $(GP)_nG$, $(PG)_nP$, and so forth, where n is an integer between one and ten, preferably two or about two, and where a specific example of such a spacer is GPGPG (SEQ ID NO:2). A preferred spacer, particularly for class I HLA epitopes, comprises one, two, three or more consecutive alanine (A) residues (see, for example, FIG. 23A, which depicts a spacer having three consecutive alanine residues).

In some multi-epitope constructs, it is sufficient that each spacer nucleic acid encodes the same amino acid sequence. In multi-epitope constructs having two spacer nucleic acids encoding the same amino acid sequence, the spacer nucleic acids encoding those spacers may have the same or different nucleotide sequences, where different nucleotide sequences may be preferred to decrease the likelihood of unintended recombination events when the multi-epitope construct is inserted into cells.

In other multi-epitope constructs, one or more of the spacer nucleic acids may encode different amino acid sequences. While many of the spacer nucleic acids may encode the same amino acid sequence in a multi-epitope construct, one, two, three, four, five or more spacer nucleic acids may encode different amino acid sequences, and it is possible that all of the spacer nucleic acids in a multi-epitope construct encode different amino acid sequences. Spacer nucleic acids may be optimized with respect to the epitope nucleic acids they flank by determining whether a spacer sequence will maximize epitope processing and/or minimize junctional epitopes, as described herein.

Multi-epitope constructs may be distinguished from one another according to whether the spacers in one construct optimize epitope processing or minimize junctional epitopes over another construct, and preferably, constructs may be distinguished where one construct is concomitantly optimized for epitope processing and junctional epitopes over the other. Computer assisted methods and in vitro and in vivo laboratory methods for determining whether a construct is optimized for epitope processing and junctional motifs are described herein.

A "subdominant epitope" is an epitope that evokes little or no response upon immunization with whole antigens which comprise the epitope, but for which a response can be obtained by immunization with an isolated epitope, and this response (unlike the case of cryptic epitopes) is detected when whole protein is used to recall the response in vitro or in vivo.

A "supermotif" is an amino acid sequence for a peptide that provides binding specificity shared by HLA molecules encoded by two or more HLA alleles. Preferably, a supermotif-bearing peptide is recognized with high or intermediate affinity (as defined herein) by two or more HLA antigens.

"Synthetic peptide" refers to a peptide that is not naturally occurring, but is man-made using such methods as chemical synthesis or recombinant DNA technology.

A "TCR contact residue" or "T cell receptor contact residue" is an amino acid residue in an epitope that is understood to be bound by a T cell receptor; these are defined herein as not being a primary MHC anchor. T cell receptor contact residues are defined as the position/positions in the peptide where all analogs tested induce T-cell recognition relative to that induced with a wildtype peptide.

The term "homology," as used herein, refers to a degree of complementarity between two nucleotide sequences. The word "identity" may substitute for the word "homology" when a nucleic acid has the same nucleotide sequence as another nucleic acid. Sequence homology and sequence identity can also be determined by hybridization studies under high stringency and/or low stringency, and disclosed herein are nucleic acids that hybridize to the multi-epitope constructs under low stringency or under high stringency. Also, sequence homology and sequence identity can be determined by analyzing sequences using algorithms and computer programs known in the art. Such methods be used to assess whether a nucleic acid is identical or homologous to the multi-epitope constructs disclosed herein. The invention pertains in part to nucleotide sequences having 80% or more, 85% or more, 90% or more, 95% or more, 97% or more, 98% or more, or 99% or more identity to the nucleotide sequence of a multi-epitope construct disclosed herein.

As used herein, the term "stringent conditions" refers to conditions that permit hybridization between nucleotide sequences and the nucleotide sequences of the disclosed multi-epitope constructs. Suitable stringent conditions can be defined by, for example, the concentrations of salt or formamide in the prehybridization and hybridization solutions, or by the hybridization temperature, and are well known in the art. In particular, stringency can be increased by: reducing the concentration of salt, increasing the concentration of formamide, or raising the hybridization temperature. For example, hybridization under high stringency conditions could occur in about 50% formamide at about 37° C. to 42° C. In particular, hybridization could occur under high stringency conditions at 42° C. in 50% formamide, 5×SSPE, 0.3% SDS, and 200 µg/ml sheared and denatured salmon sperm DNA or at 42° C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. Hybridization could occur under reduced stringency conditions in about 35% to 25% formamide at about 30° C. to 35° C. For example, reduced stringency conditions could occur at 35° C. in 35% formamide, 5×SSPE, 0.3% SDS, and 200 µg/ml sheared and denatured salmon sperm DNA. The temperature range corresponding to a particular level of stringency can be further narrowed by calculating the purine:pyrimidine ratio of the nucleic acid of interest, and adjusting the temperature accordingly. Variations on the above ranges and conditions are well known in the art.

In addition to utilizing hybridization studies to assess sequence identity or sequence homology, known computer programs may be used to determine whether a particular nucleic acid is homologous to a multi-epitope construct disclosed herein. An example of such a program is the Bestfit program (Wisconsin Sequence Analysis Package, Version 8 for Unix, Genetics Computer Group, University Research Park, 575 Science Drive, Madison, Wis. 53711), and other sequence alignment programs are known in the art and may be utilized for determining whether two or more nucleotide sequences are homologous. Bestfit uses the local homology algorithm of Smith and Waterman, Advances in Applied Mathematics 2: 482-489 (1981), to find the best segment of homology between two sequences. When using Bestfit or any other sequence alignment program to determine whether a particular sequence is, for instance, 95% identical to a reference sequence, the parameters may be set such that the percentage of identity is calculated over the full length of the reference nucleotide sequence and that gaps in homology of up to 5% of the total number of nucleotides in the reference sequence are allowed.

| Acronyms used herein are as follows: | |
|---|---|
| APC: | Antigen presenting cell |
| CD3: | Pan T cell marker |
| CD4: | Helper T lymphocyte marker |

-continued

| Acronyms used herein are as follows: | |
|---|---|
| CD8: | Cytotoxic T lymphocyte marker |
| CEA: | Carcinoembryonic antigen |
| CFA: | Complete Freund's Adjuvant |
| CMV: | Human Cytomegalovirus |
| CTL: | Cytotoxic T lymphocytes |
| Cardiotoxin: | A natural 60 amino acid peptide that causes local muscle destruction (a protein kinase C inhibitor) |
| DC: | Dendritic cells. DC functioned as potent antigen presenting cells by stimulating cytokine release from CTL lines that were specific for a model peptide derived from hepatitis B virus (HBV). In vitro experiments using DC pulsed ex vivo with an HBV peptide epitope have stimulated CTL immune responses in vitro following delivery to naïve mice. |
| DMSO: | Dimethylsulfoxide |
| DNA: | Deoxyribonucleic acid |
| EBV: | Epstein Barr Virus |
| ELISA: | Enzyme-linked immunosorbant assay |
| ELISPOT: | ELISA-like procedure that detects individual cells secreting probed cytokine as a distinct spot on a culture membrane |
| Epigene: | Multi-epitope DNA constructs |
| E:T: | Effector:target ratio |
| FACS: | Flourescence-activated cell sorter |
| FCS: | Fetal calf serum |
| G-CSF: | Granulocyte colony-stimulating factor |
| GM-CSF: | Granulocyte-macrophage (monocyte)-colony stimulating factor |
| HBV: | Hepatitis B virus |
| HER2/Neu: | c-erbB-2 |
| HIV: | Human Immunodeficiency Virus |
| HLA: | Human leukocyte antigen |
| HLA-DR: | Human leukocyte antigen class II |
| HPLC: | High Performance Liquid Chromatography |
| HTC: | Helper T cells |
| HTL: | Helper T Lymphocyte |
| ID: | Identity |
| IFA: | Incomplete Freund's Adjuvant |
| IFNγ: | Interferon gamma |
| IL-4: | Interleukin-4 cytokine |
| IRES: | Internal ribosome entry site |
| IV: | Intravenous |
| LU$_{30\%}$: | Cytotoxic activity required to achieve 30% lysis at a 100:1 (E:T) ratio |
| MAb: | Monoclonal antibody |
| MAGE: | Melanoma antigen |
| MHC: | Major Histocompatibility Complex |
| MLR: | Mixed lymphocyte reaction |
| MNC: | Mononuclear cells |
| PADRE ™: | a PanDR binding peptide |
| PATR: | Pan Troglodytes |
| PB: | Peripheral blood |
| PBL: | Peripheral blood lymphocyte |
| PBMC: | Peripheral blood mononuclear cell |
| SC: | Subcutaneous |
| SDS: | Sodium dodecyl sulfate |
| S.E.M.: | Standard error of the mean |
| SU: | Secretory units |
| QD: | Once a day dosing |
| TAA: | Tumor associated antigen |
| TCR: | T cell receptor |
| TNF: | Tumor necrosis factor |
| WBC: | White blood cells |

This application may be relevant to U.S. Ser. No. 09/189, 702 filed Nov. 10, 1998, which is a CIP of U.S. Ser. No. 08/205,713 filed Mar. 4, 1994, which is a CIP of Ser. No. 08/159,184 filed Nov. 29, 1993 and now abandoned, which is a CIP of Ser. No. 08/073,205 filed Jun. 4, 1993 and now abandoned, which is a CIP of Ser. No. 08/027,146 filed Mar. 5, 1993 and now abandoned. The present application is also related to U.S. Ser. No. 09/226,775, which is a CIP of U.S. Ser. No. 08/815,396, which claims the benefit of U.S. Ser. No. 60/013,113, now abandoned. Furthermore, the present application is related to U.S. Ser. No. 09/017,735, which is a CIP of abandoned U.S. Ser. No. 08/589,108; U.S. Ser. No. 08/753, 622, U.S. Ser. No. 08/822,382, abandoned U.S. Ser. No. 60/013,980, U.S. Ser. No. 08/454,033, U.S. Ser. No. 09/116,424, and U.S. Ser. No. 08/349,177. The present application is also related to U.S. Ser. No. 09/017,524, U.S. Ser. No. 08/821,739, abandoned U.S. Ser. No. 60/013,833, U.S. Ser. No. 08/758,409, U.S. Ser. No. 08/589,107, U.S. Ser. No. 08/451,913, U.S. Ser. No. 08/186,266, U.S. Ser. No. 09/116,061, and U.S. Ser. No. 08/347,610, which is a CIP of U.S. Ser. No. 08/159,339, which is a CIP of abandoned U.S. Ser. No. 08/103,396, which is a CIP of abandoned U.S. Ser. No. 08/027,746, which is a CIP of abandoned U.S. Ser. No. 07/926,666. The present application may also be relevant to U.S. Ser. No. 09/017,743, U.S. Ser. No. 08/753,615; U.S. Ser. No. 08/590,298, U.S. Ser. No. 09/115,400, and U.S. Ser. No. 08/452,843, which is a CIP of U.S. Ser. No. 08/344,824, which is a CIP of abandoned U.S. Ser. No. 08/278,634. The present application may also be related to provisional U.S. Ser. No. 60/087,192 and U.S. Ser. No. 09/009,953, which is a CIP of abandoned U.S. Ser. No. 60/036,713 and abandoned U.S. Ser. No. 60/037,432. In addition, the present application may be relevant to U.S. Ser. No. 09/098,584, and U.S. Ser. No. 09/239,043. The present application may also be relevant to co-pending U.S. Ser. No. 09/583,200 filed May 30, 2000, U.S. Ser. No. 09/260,714 filed Mar. 1, 1999, and U.S. Provisional Application No. 60/239,008, filed Oct. 6, 2000, and U.S. Provisional Application No. 60/166,529, filed Nov. 18, 1999. In addition, the present application may also be relevant to U.S. Provisional Application No. 60/239,008, filed Oct. 6, 2000, now abandoned; co-pending U.S. application Ser. No. 10/130,548, which is the U.S. Natl. Phase Application of PCT/US00/31856, filed Nov. 20, 2000 and published as WO 01/36452 on May 25, 2001; and co-pending U.S. application Ser. No. 10/116,118, filed Apr. 5, 2002. All of the above applications are incorporated herein by reference.

BRIEF DESCRIPTION OF THE DRAWINGS

FIGS. 11A-B illustrate an exemplary input text file containing user input parameters used for executing a Junctional Analyzer program, in accordance with one embodiment of the invention.

FIGS. 13A-D illustrate an exemplary output text file containing output results of a Junctional Analyzer program, in accordance with one embodiment of the invention.

Figure 17:
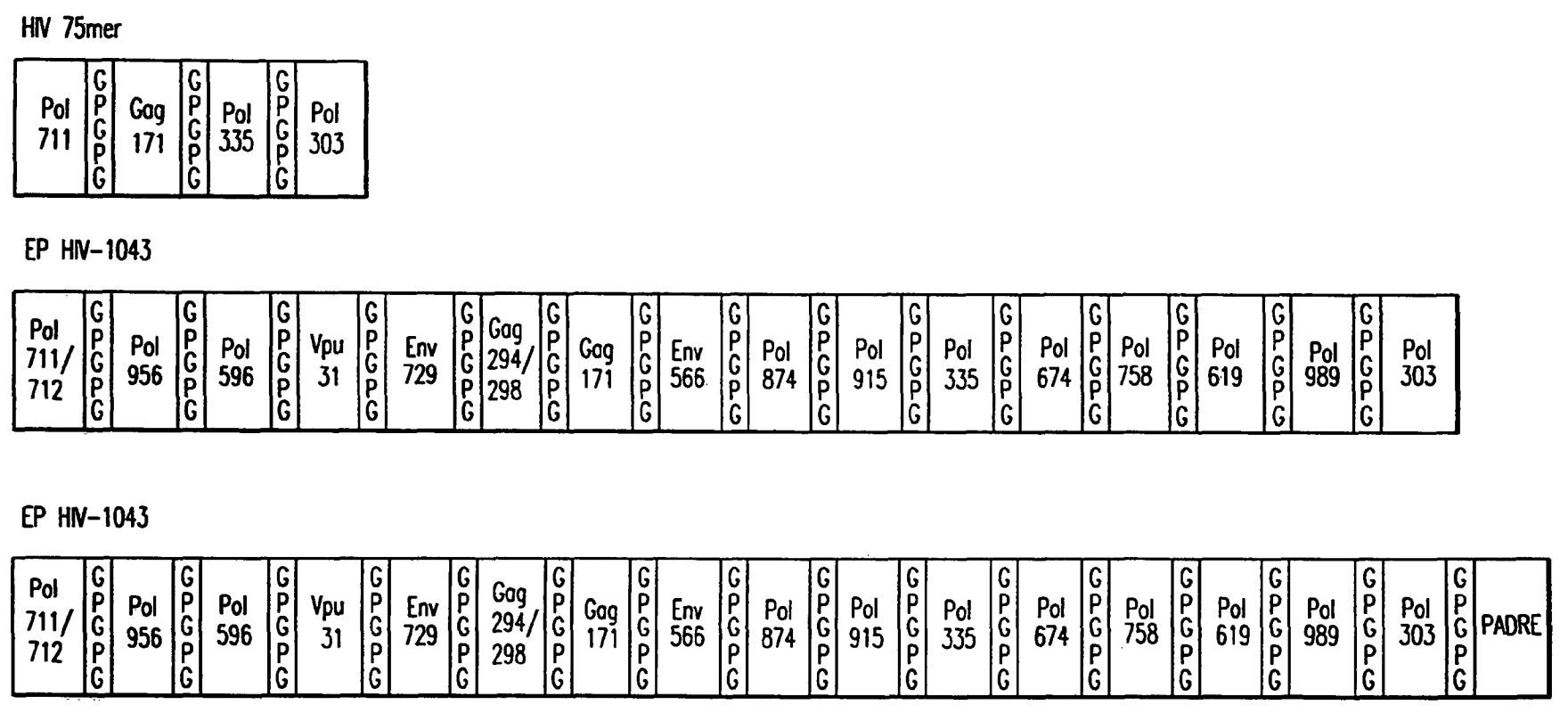

FIG. 17 is a schematic depicting the epitopes present in HIV 75 mer, EP-HIV-1043, and the EP-HIV-1043-PADRE® construct.

FIGS. 18A-N show the amino acid sequences and nucleic acid sequences of certain multi-epitope constructs.

FIGS. 19A-E show the amino acid sequences and nucleic acid sequences of certain multi-epitope constructs.

FIGS. 20A-20F show the HBV CTL epitopes used to construct three related epigene constructs, HBV-2, HBV-2A and HBV-2B, the order of epitopes in the epigene constructs, the immune responses induced in HLA-A2 or HLA-A3/11 transgenic mice and the amino acid and nucleic acid sequences of the epigene constructs. In FIG. 20B, the signal sequence in HBV-2, HBV-2A and HBV-2B is the Ig kappa consensus signal sequence, although other signal sequences could be utilized.

FIGS. 21A-21E show the HBV CTL epitopes used to construct two 21 CTL epitope epigene constructs, HBV-21A and HBV-21B, the order of epitopes in the epigene constructs, the immune responses induced in HLA-A2 or HLA-A3/11 transgenic mice and the amino acid and nucleic acid sequences of the epigene constructs.

Figure 22B:
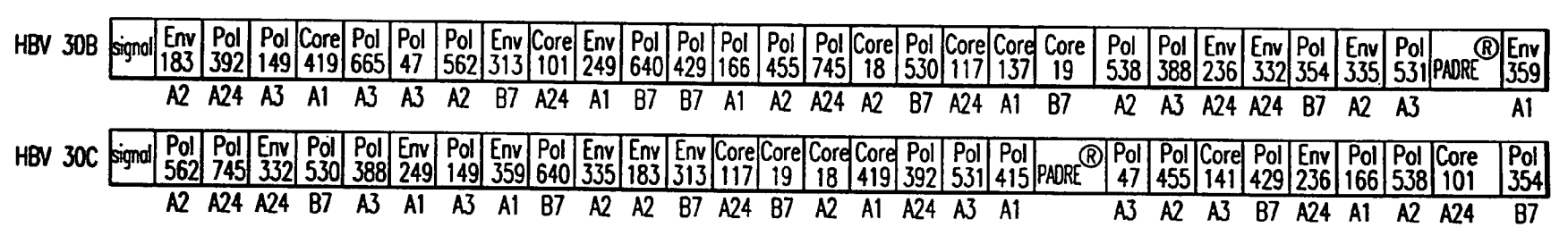

FIGS. 22A-22E show the HBV CTL epitopes used to construct two 30 CTL epitope epigene constructs, HBV-30B and HBV-30C, the order of epitopes in the epigene constructs, the immune responses induced in HLA-A2 or HLA-A3/11 transgenic mice and the amino acid and nucleic acid sequences of the epigene constructs.

FIGS. 23A-23C show the modifications made to spacers flanking two HLA-A2 restricted CTL epitopes in the HBV-30C epigene construct. Modifications were designed to increase the efficiency of processing and subsequent presentation and thus, increase immunogenicity of the epitopes. Immunogenicity was measured using HLA-A2 or HLA-A3/11 transgenic mice, and the amino acid and nucleic acid sequences of the epigene construct are noted. In FIG. 23A, the lysine (K) spacer flanking the Core 18 epitope in HBV-30C were modified to include three alanine residues (AAA) in HBV-30CL. Also, one asparagine (N) spacer flanking env 183 epitope in HBV-30C was modified to include three alanine residues (AAA) in HBV-30CL.

FIGS. 24A-24C show HTL epitopes, and their binding affinity to selected HLA-DR alleles, used to construct a multi-epitope vaccine comprising HTL epitopes separated by GPGPG (SEQ ID NO:2) amino acid spacers. The nucleic acid sequence of the multi-epitope vaccine and the amino acid sequence encoded by the nucleic acid are shown in FIG. 24C.

FIGS. 25A-B show the population coverage for CTL epitopes contained in GCR-5835. FIG. 25A. Percentage of individuals projected to present the indicated number of HLA-A/B-epitope combinations in a composite population derived from gene frequencies in Asian, Black, European Caucasian, and North American Caucasian populations (Black bars). Also shown on the right axis is the cumulative plot of percent population coverage (Open circles). FIG. 25B. Summary of the cumulative percent projected population coverage in Asian, Black, European Caucasian, and North American Caucasian populations as a function of the number of epitopes bound by HLA alleles.

FIGS. 26A-26B show population coverages for epitopes contained in a list. FIG. 26A. Percentage of individuals projected to present the indicated number of HLA-DR-epitope combinations in a composite population derived from gene frequencies in Asian, Black, European Caucasian, and North American Caucasian populations (black bars). Also shown on the right axis is the cumulative plot of percent population coverage (open circles). FIG. 26B. Summary of the cumulative percent projected population coverage in Asian, Black, European Caucasian, and North American Caucasian populations as a function of the number of epitopes bound by HLA alleles.

FIGS. 27A-27B show (A) a schematic of HBV30K and (B) the HLA supertype restriction of the component epitopes. Immunogenicity of a vaccine 30 epitope epigene construct. HLA-A2 or -A11 transgenic mice were immunized intramuscularly with 100 μg of the vaccine HBV epigene plasmid HBV30K or the prototype HBV vaccine HBV2. Eleven days after the immunization splenocytes were stimulated in vitro with the epitopes encoded in the vaccine. After six days in culture the epitope-specific CTL responses were measured using an in situ IFN-γ ELISA assay.

FIGS. 28A-28B show a schematic of the HBV HTL vaccine construct and its immunogenicity. FIG. 26A. GPGPG (SEQ ID NO:2) spacers introduced between epitopes are indicated. FIG. 28B. $H2^{bxd}$ mice were immunized intramuscularly with 100 μg of a vaccine HBV HTL epigene construct or the individual peptides emulsified in CFA. Eleven days after the immunization CD4 T cells were purified from splenocytes and HTL responses were measured using a primary IFN-γ ELISPOT assay.

FIGS. 29A-29B show HBV vaccine plasmid configurations and their relative immunogenicity. FIG. 29A. Schematic (i) dual CMV promoter plasmid; (ii) IRES containing plasmid; (iii) CTL+HTL epigene construct fusion. FIG. 29B. Relative immunogenicity of different vaccine configurations. HLA-A2-transgenic mice were immunized intramuscularly with 100 μg of HBV30K (CTL epigene construct control), HBV30K.H1 (dual CMV promoter plasmid), HBV30K.H3 (IRES containing plasmid) or HBV30K/HTL (GCR-5835; CTL+HTL epigene construct fusion). Eleven days after the immunization splenocytes were stimulated in vitro with the epitopes encoded in the vaccine. After six days in culture the epitope-specific CTL responses were measured using an in situ IFN-γ ELISA assay.

FIG. 30 shows the relative immunogenicity of GCR-5835 and GCR-3697. HLA-A2 transgenic mice were immunized intramuscularly with either 50 μg or 5 μg of the GCR-5835 or GCR-3697. Eleven days after the immunization CD8+ cells were isolated from splenocytes and epitope-specific CTL responses were measured using an IFN-γ ELISPOT assay.

FIG. 31 shows a comparison of PVP formulated, naked, and CT GCR-5835. HLA-A2. $1/K^b$ transgenic mice were immunized a single time with 100 μg of GCR 5835 formulated in PVP, naked, or naked in cardiotoxin (CT) pre-treated animals. After eleven days in vivo, splenocytes were restimulated in vitro with the indicated peptides. After six days, IFN-γ was measured in response to peptide in an in situ ELISA assay. Data are presented as the geometric mean of the secretory units (SU) for positive cultures, x/, standard deviation. The frequency of positive cultures/total cultures tested is indicated above each bar.

FIG. 32 shows a comparison of GCR-5835 and the lipopeptide vaccine. HLA-A2.$1/K^b$ transgenic mice were immunized with either 100 μg of GCR-5835 in cardiotoxin (CT) pre-treated animals or 100 μg of the lipopeptide vaccine. After eleven days in vivo, $CD8^+$ splenocytes were isolated, and IFN-γ was measured in response to the indicated peptide in an ELISPOT assay (A). Data are presented as the average spot forming cells (SFC) per $10^6$ splenocytes plated. Alternatively, splenocytes were restimulated in vitro with the indicated peptides. After six days, IFN-γ was measure in response to peptide in an in situ ELISA assay (B). Data are presented as the geometric mean of the secretory units (SU) for positive cultures, ±standard deviation.

FIGS. 33A-33B show a summary of immunogenicity data from individual mice. HLA-A2.$1/K^b$ transgenic mice were either not immunized, or immunized with 100 μg of PVP-formulated GCR-5835 in a single immunization (A), or immunized twice at a 7 day interval (B). Eleven days after the final immunization, splenocytes from each mouse were restimulated in vitro with a pool of the indicated peptides. After six days, IFN-γ was measured in response to the individual peptides as well as a pool of all peptides in an ELISPOT assay. Data are presented as the average spot forming cells (SFC) per $10^6$ splenocytes plated.

Figure 34:
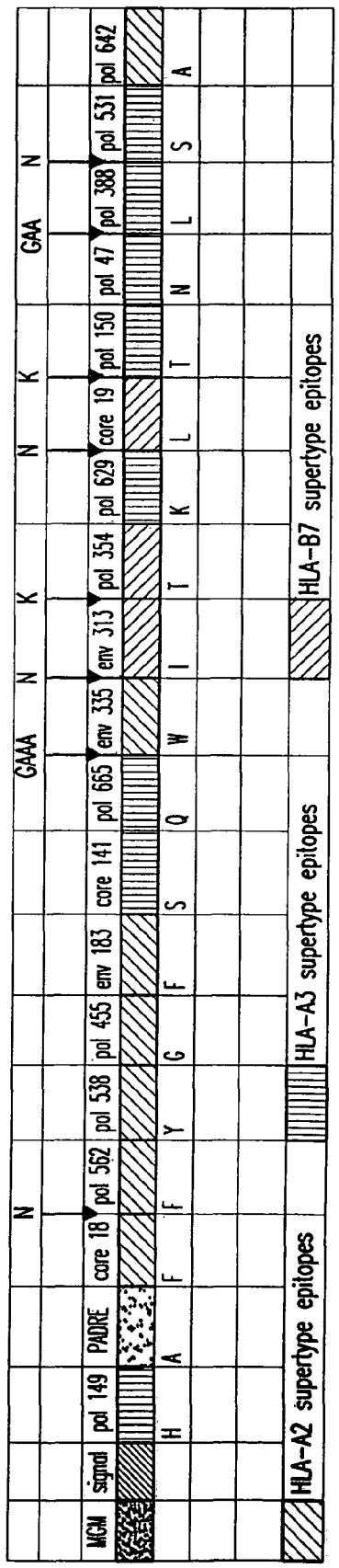
Figures 1, 35B:
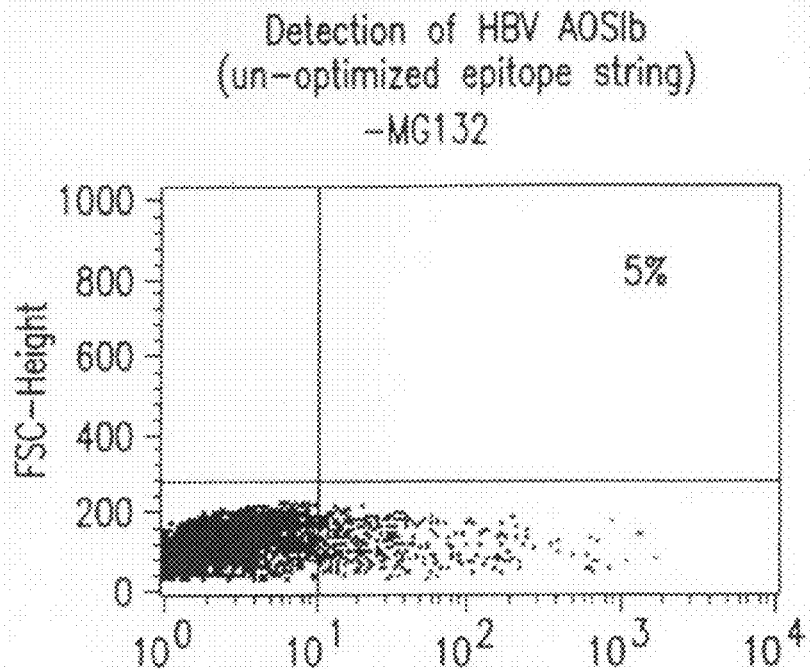
Figures 2, 35B:
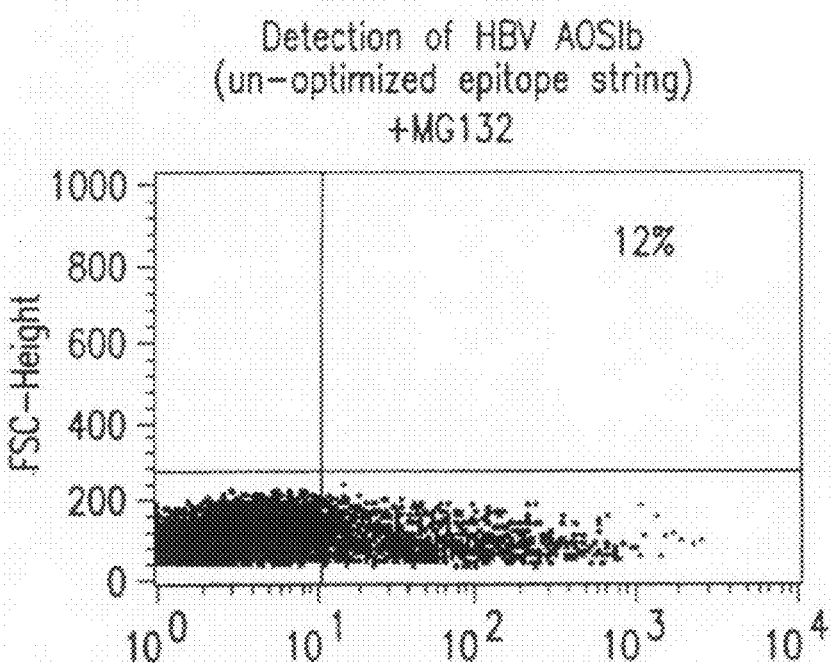
Figures 1, 35C:
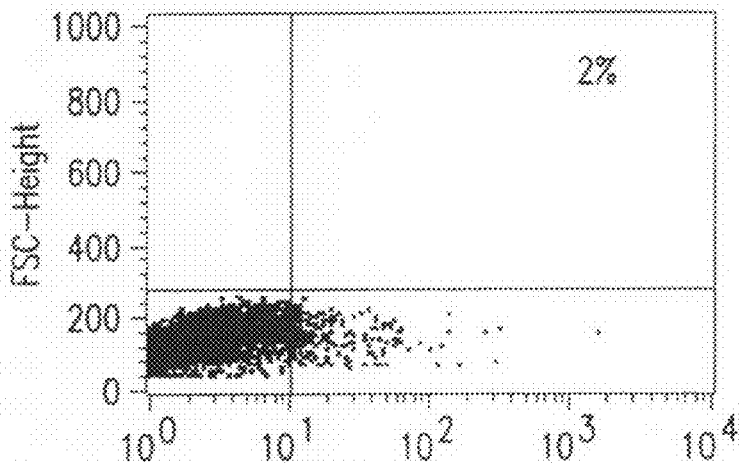
Figures 2, 35C:
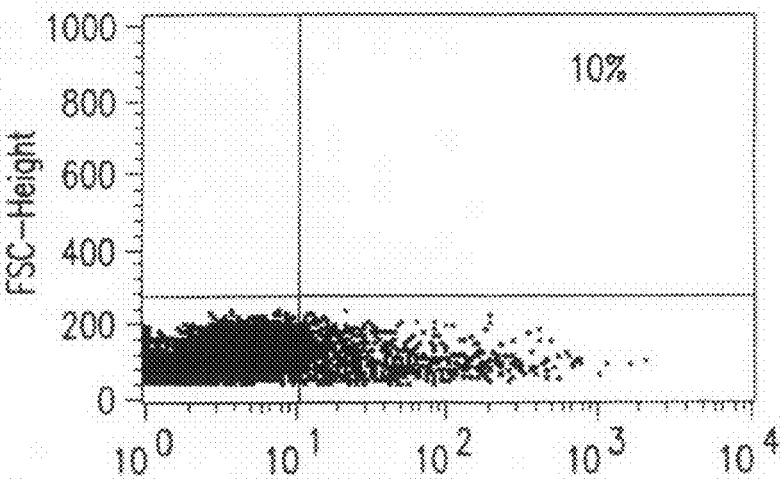
Figure 35D:
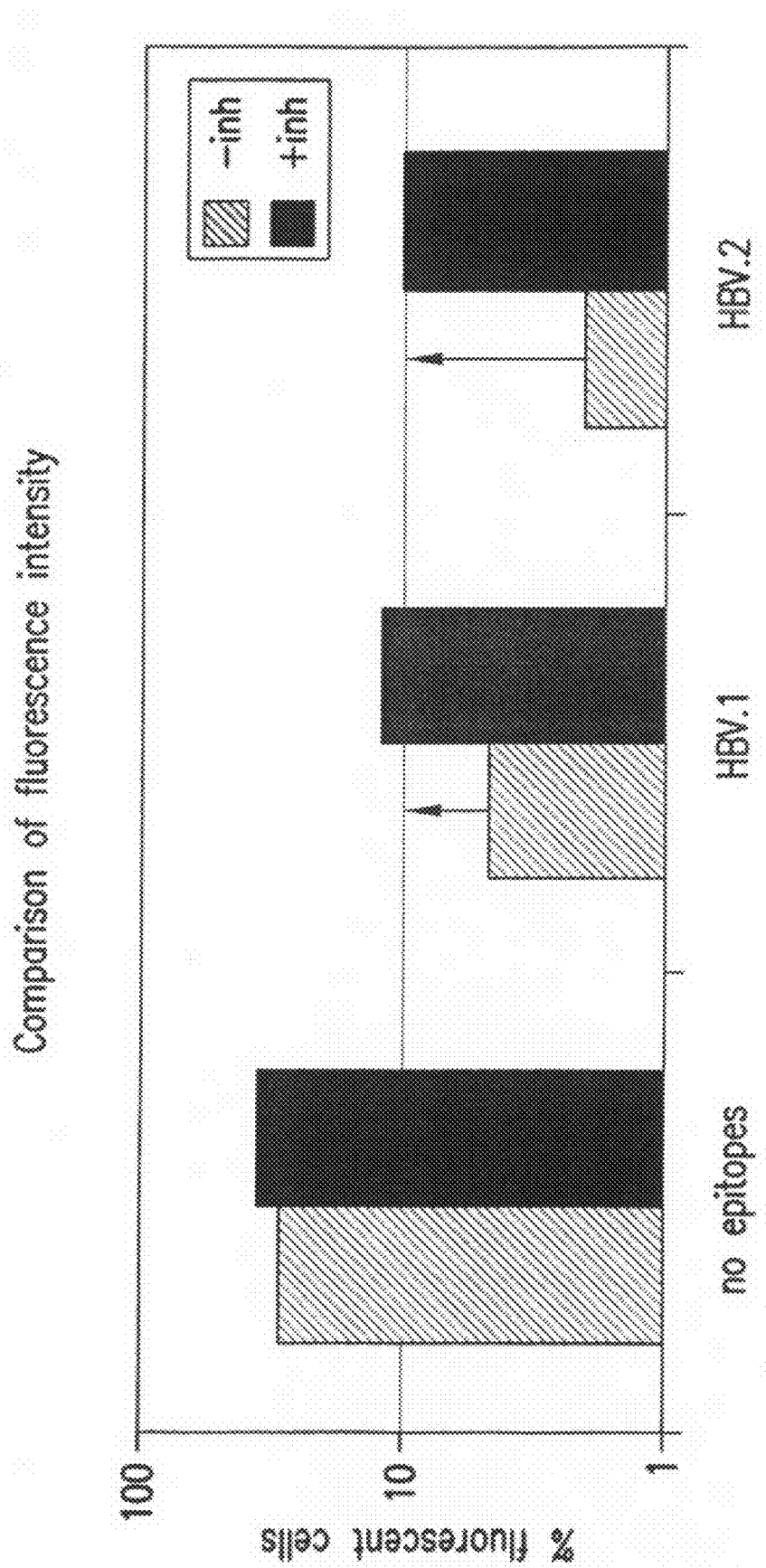

FIG. 34 shows a schematic of the HBV AOSIb and HBV AOSIb2 constructs. The HBV AOSIb2 construct has additional amino acids added (indicated with arrows above the schematic) to enhance proteasomal processing while the HBV AOSIb construct has no added residues.

FIGS. 35A-35E show the results after transient transfection of human 293 cells in the presence or absence of the proteasome inhibitor MG132. The proteasome inhibitor MG132 was added at 5 µM 24 hours post-transfection. Flourescence in live cells was detected by flow cytometry and fluorescence microscopy 24 hours after addition of the proteasome inhibitor (unless otherwise noted). (A) Flow cytometry (FACS) results for a time-course of cells transfected with plasmid AOSIb. (B) Flow cytometry (FACS) results at 24 hours for cells transfected with plasmid HBV AOSIb. (C) Flow cytometry (FACS) results at 24 hours for cells transfected with plasmid HBV AOSIb2. (D) Data are presented graphically as a comparison of fluorescence intensity. (E) The relative increase in fluorescence intensity is compared between control plasmid, HBV AOSIb, and HBV AOSIb2 for the above experiments.

Figure 36:
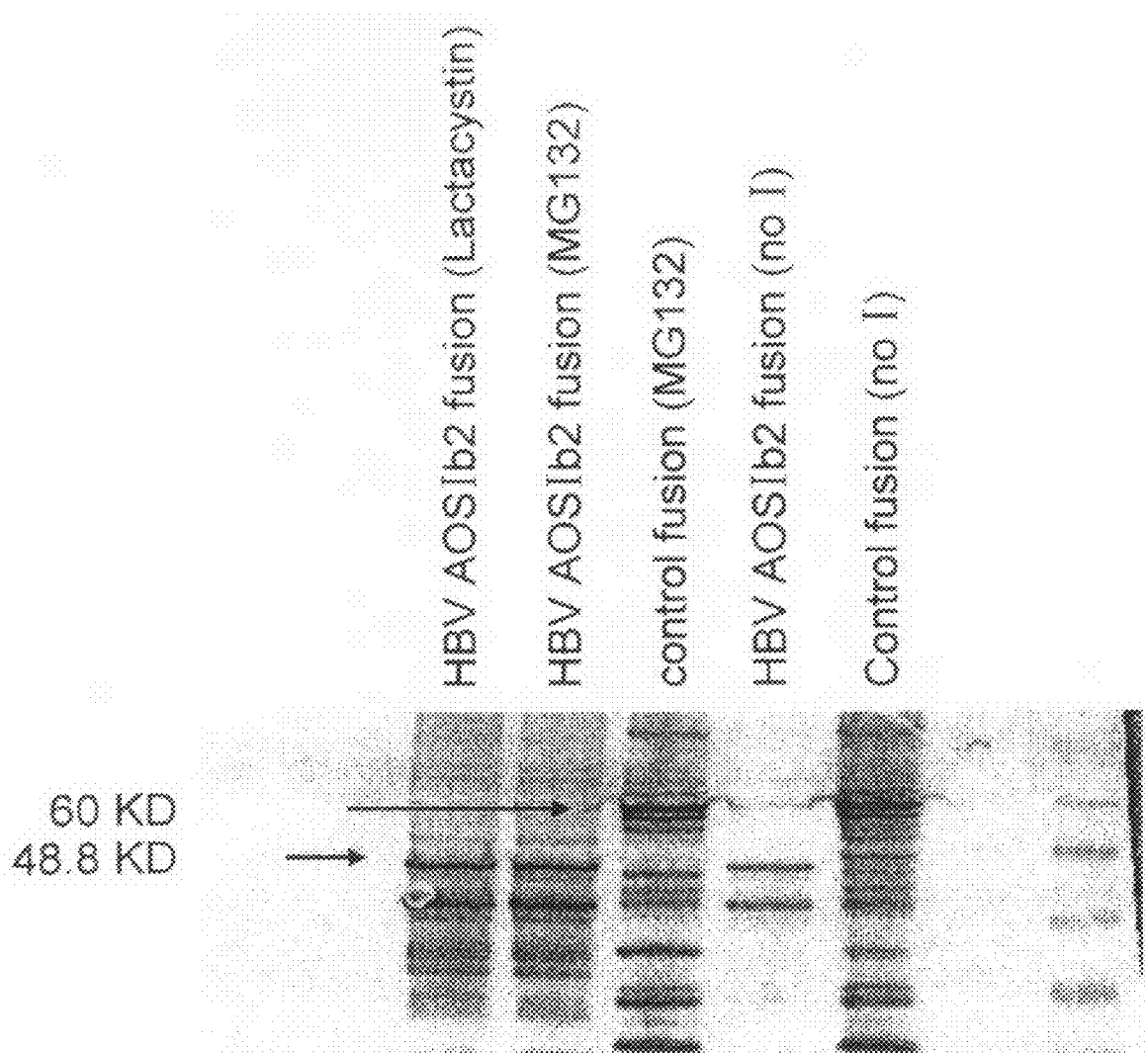

FIG. 36 shows the amount of proteins detectable upon addition of the proteasome inhibitors lactacystin (25 uM) or MG132 (5 uM). Whole cell lysates were prepared from transfected cells and transferred to a blotting membrane. Proteins were detected using an antibody against the fusion partner protein. Arrows indicate the predicted size of the full-length fusion proteins.

Figure 37A:
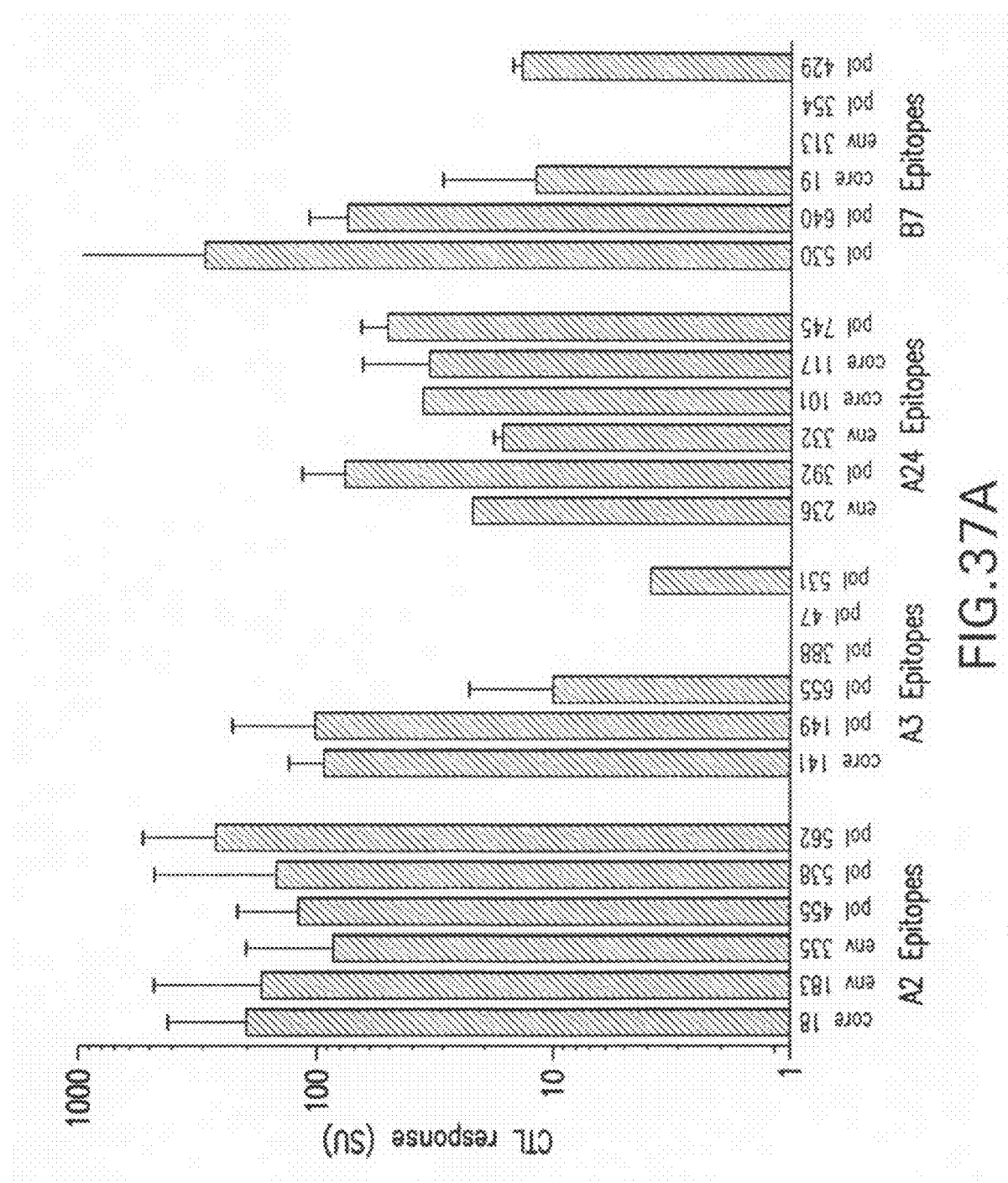

FIGS. 37A-37B show epitope-specific T cell responses measured in HLA transgenic mice immunized with GCR-3697 using splenic lymphocytes obtained 11-14 days following immunization. Groups of 6-9 HLA-transgenic mice were immunized bilaterally with 100 µg of DNA in the tibialis anterior muscle. DNA was delivered in either PBS or PVP formulations; in the case of PBS formulations the injection site was pre-treated by cardiotoxin injection.

Figure 38:
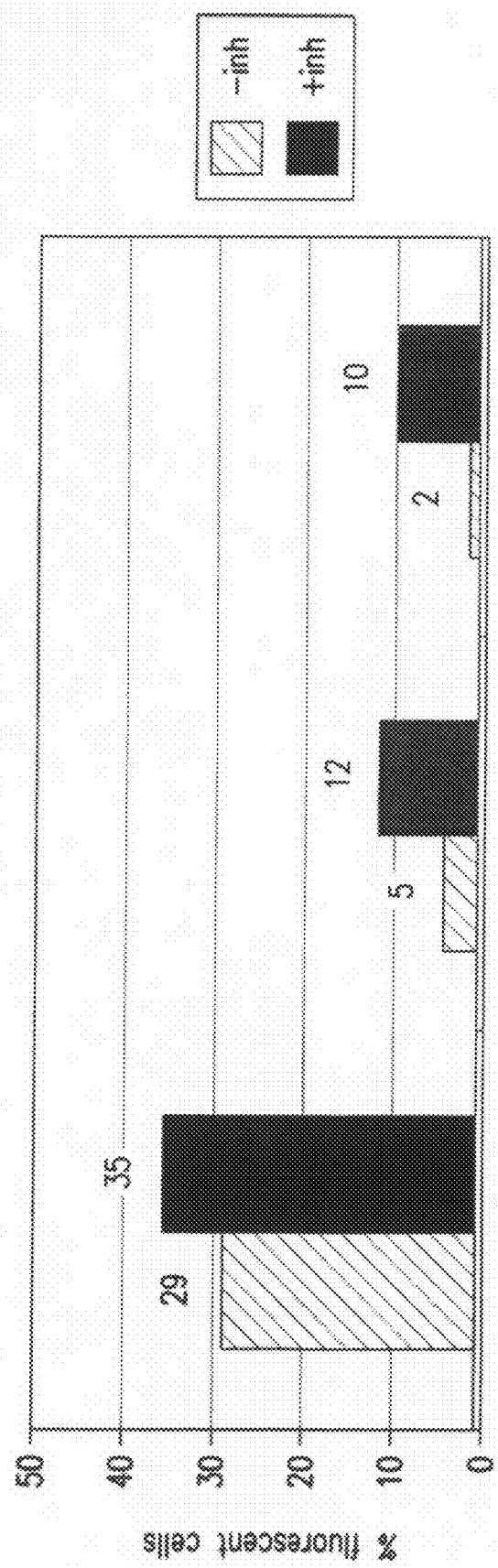

FIG. 38 shows a comparison of fluorescence intensity measured by FACS analysis for the 3 plasmids: no epitope construct (fluorescent protein only), fluorescent conjugated polyepitope HBV AOSIb, or fluorescent conjugated polyepitope HBV AOSIb2. Human 293 cells were transfected with plasmid and the proteasome inhibitor MG132 was added at 5 µM 24 hours post-transfection. Flourescence in live cells was detected by FACS 24 hours after addition of the proteasome inhibitor.

Figure 39:
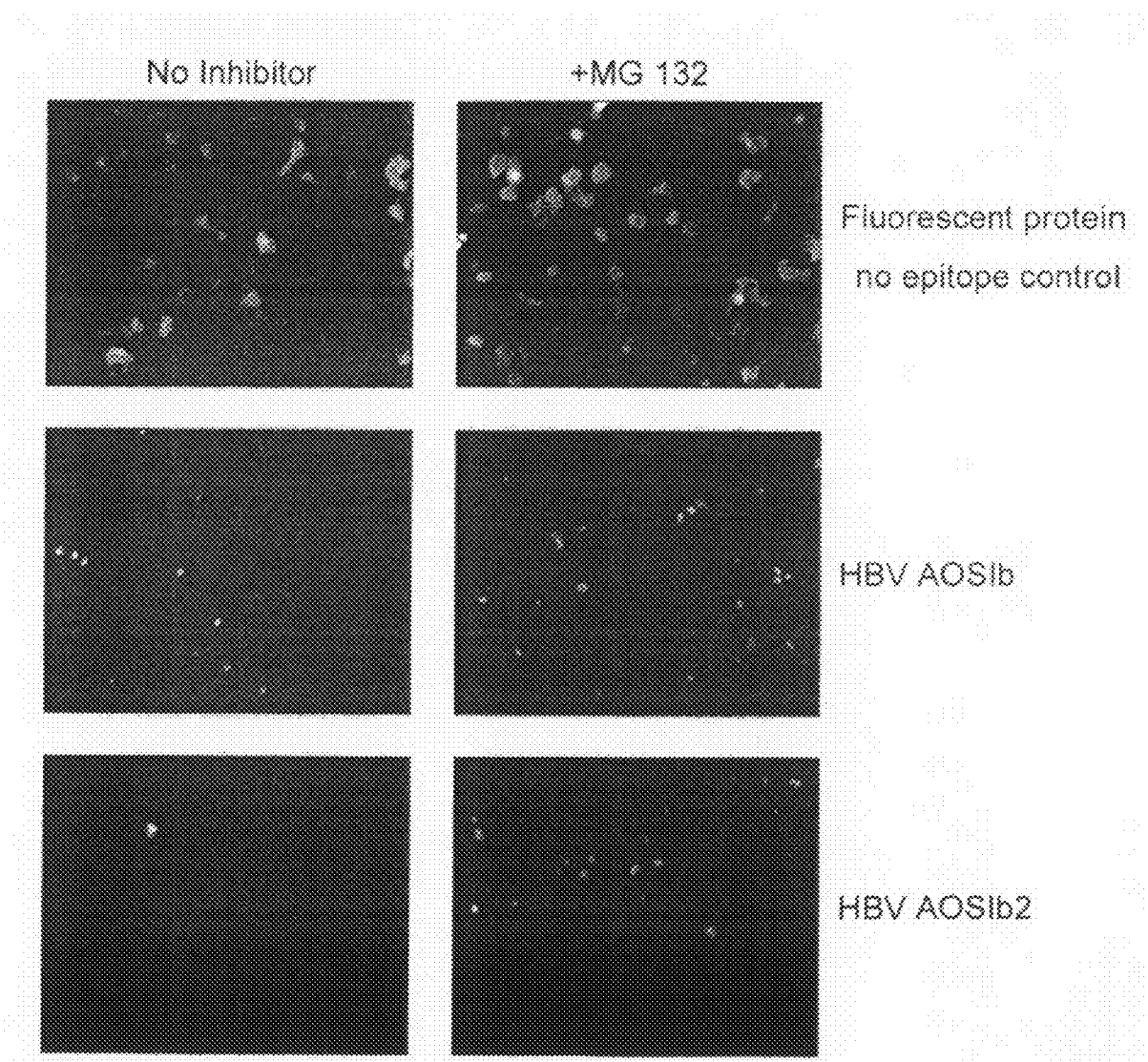

FIG. 39 shows fluorescence microscopy images for cells cultured with: no epitope construct (fluorescent protein only), fluorescent conjugated polyepitope HBV AOSIb, or fluorescent conjugated polyepitope HBV AOSIb2. Human 293 cells were transfected with plasmid and the proteasome inhibitor MG132 was added at 5 µM 24 hours post-transfection. Flourescence in live cells was detected by fluorescence microscopy 24 hours after addition of the proteasome inhibitor.

DETAILED DESCRIPTION OF THE INVENTION

The invention is described in detail below with reference to the figures wherein like elements are referenced with like numerals throughout.

The invention provides a method and system for optimizing the efficacy of multi-epitope vaccines, preferably to minimize the number of junctional epitopes and maximize, or at least increase, the immunogenicity and/or antigenicity of multi-epitope vaccines. The present invention also provides multi-epitope nucleic acid constructs encoding a plurality of CTL and/or HTL epitopes and polypeptides encoded by such constructs, as well as cells comprising such constructs and/or polypeptides, compositions comprising such constructs, polypeptides, and/or cells, and methods for stimulating an immune response (e.g. therapeutic methods) utilizing such constructs and/or polypeptides and cells.

In one embodiment of the invention, a computerized method for designing a multi-epitope construct having multiple epitopes includes the steps of: storing a plurality of input parameters in a memory of a computer system, the input parameters including a plurality of epitopes, at least one motif for identifying junctional epitopes, a plurality of amino acid insertions and at least one enhancement weight value for each insertion; generating a list of epitope pairs from the plurality of epitopes; determining for each epitope pair at least one optimum combination of amino acid insertions based on the at least one motif, the plurality of insertions and the at least one enhancement weight value for each insertion; and identifying at least one optimum arrangement of the plurality of epitopes, wherein a respective one of the at least one optimum combination of amino acid insertions is inserted at a respective junction of two epitopes, so as to provide an optimized multi-epitope construct. In a preferred embodiment, the step of identifying at least one optimum arrangement of epitopes may be accomplished by performing either an exhaustive search wherein all permutations of arrangements of the plurality of epitopes are evaluated or a stochastic search wherein only a subset of all permutations of arrangements of the plurality of epitopes are evaluated.

In a further embodiment, the method determines for each epitope pair at least one optimum combination of amino acid insertions by calculating a function value (F) for each possible combination of insertions for each epitope pair, wherein the number of insertions in a combination may range from 0 to a maximum number of insertions (MaxInsertions) value input by a user, and the function value is calculated in accordance with the equation $F=(C+N)/J$, when $J>0$, and $F=2(C+N)$, when $J=0$, wherein C equals the enhancement weight value of a C+1 flanking amino acid, N equals the enhancement weight value of an N−1 flanking amino acid, and J equals the number of junctional epitopes detected for each respective combination of insertions in an epitope pair based on said at least one motif.

In another embodiment of the invention, a computer system for designing a multi-epitope construct having multiple epitopes, includes: a memory for storing a plurality of input parameters such as a plurality of epitopes, at least one motif for identifying junctional epitopes, a plurality of amino acid insertions and at least one enhancement weight value for each insertion; a processor for retrieving the input parameters from memory and generating a list of epitope pairs from the plurality of epitopes; wherein the processor further determines for each epitope pair at least one optimum combination of amino acid insertions, based on the at least one motif, the plurality of insertions and the at least one enhancement weight value for each insertion. The processor further identifies at least one optimum arrangement of the plurality of epitopes, wherein a respective one of the optimum combinations of amino acid insertions are inserted at a respective junction of two epitopes, to provide an optimized multi-epitope construct; and a display monitor, coupled to the processor, for displaying at least one optimum arrangement of the plurality of epitopes to a user.

In a further embodiment, the invention provides a data storage device storing a computer program for designing a multi-epitope construct having multiple epitopes, the computer program, when executed by a computer system, performing a process that includes the steps of: retrieving a plurality of input parameters from a memory of a computer system, the input parameters including, for example, a plurality of epitopes, at least one motif for identifying junctional epitopes, a plurality of amino acid insertions and at least one enhancement weight value for each insertion; generating a list of epitope pairs from the plurality of epitopes; determining for each epitope pair at least one optimum combination of amino acid insertions based on the at least one motif, the plurality of insertions and the at least one enhancement weight value for each insertion; and identifying at least one optimum arrangement of the plurality of epitopes, wherein a respective one of the at least one optimum combination of amino acid insertions is inserted at a respective junction of two epitopes, so as to provide an optimized multi-epitope construct.

In another embodiment, the invention provides a method and system for designing a multi-epitope construct that comprises multiple epitopes. The method comprising steps of: (i) sorting the multiple epitopes to minimize the number of junctional epitopes; (ii) introducing a flanking amino acid residue at a C+1 position of an epitope to be included within the multi-epitope construct; (iii) introducing one or more amino acid spacer residues between two epitopes of the multi-epitope construct, wherein the spacer prevents the occurrence of a junctional epitope; and, (iv) selecting one or more multi-epitope constructs that have a minimal number of junctional epitopes, a minimal number of amino acid spacer residues, and a maximum number of flanking amino acid residues at a C+1 position relative to each epitope. In some embodiments, the spacer residues are independently selected from residues that are not known HLA Class II primary anchor residues. In particular embodiments, introducing the spacer residues prevents the occurrence of an HTL epitope. Such a spacer often comprises at least 5 amino acid residues independently selected from the group consisting of G, P, and N. In some embodiments the spacer is GPGPG (SEQ ID NO:2).

In some embodiments, introducing the spacer residues prevents the occurrence of a CTL epitope and further, wherein the spacer is 1, 2, 3, 4, 5, 6, 7, or 8 amino acid residues independently selected from the group consisting of A and G. Often, the flanking residue is introduced at the C+1 position of a CTL epitope and is selected from the group consisting of K, R, N, G, and A. In some embodiments, the flanking residue is adjacent to the spacer sequence. The method of the invention can also include substituting an N-terminal residue of an epitope that is adjacent to a C-terminus of an adjacent epitope within the multi-epitope construct with a residue selected from the group consisting of K, R, N, G, and A.

In some embodiments, the method of the invention can also comprise a step of predicting a structure of the multi-epitope construct, and further, selecting one or more constructs that have a maximal structure, i.e., that are processed by an HLA processing pathway to produce all of the epitopes comprised by the construct. In some embodiments, the multi-epitope construct encodes EP-HIV-1090 as set out in FIG. 9, HIV-CPT as set out in FIG. 9, or HIV-TC as set out in FIG. 9.

In another embodiment of the invention, a system for optimizing multi-epitope constructs include a computer system having a processor (e.g., central processing unit) and at least one memory coupled to the processor for storing instructions executed by the processor and data to be manipulated (i.e., processed) by the processor. The computer system further includes an input device (e.g., keyboard) coupled to the processor and the at least one memory for allowing a user to input desired parameters and information to be accessed by the processor. The processor may be a single CPU or a plurality of different processing devices/circuits integrated onto a single integrated circuit chip. Alternatively, the processor may be a collection of discrete processing devices/circuits selectively coupled to one another via either direct wire/conductor connections or via a data bus. Similarly, the at least one memory may be one large memory device (e.g., EPROM), or a collection of a plurality of discrete memory devices (e.g., EEPROM, EPROM, RAM, DRAM, SDRAM, Flash, etc.) selectively coupled to one another for selectively storing data and/or program information (i.e., instructions executed by the processor). Those of ordinary skill in the art would easily be able to implement the desired computer system architecture to perform the operations and functions disclosed herein.

In one embodiment, the computer system includes a display monitor for displaying information, instructions, images, graphics, etc. The computer system receives user inputs via a keyboard. These user input parameters may include, for example, the number of insertions (i.e., flanking residues and spacer residues), the peptides to be processed, the C+1 and N−1 weighting values for each amino acid, and the motifs to use for searching for junctional epitopes. Based on these input values/parameters, the computer system executes a "Junctional Analyzer" software program that automatically determines the number of junctional epitope for each peptide pair and also calculates an "enhancement" value for each combination of flanking residues and spacers that may be inserted at the junction of each peptide pair. The results of the junctional analyzer program are then used in either an exhaustive or stochastic search program which determines the "optimal" combination or linkage of the entire set of peptides to create a multi-epitope polypeptide, or nucleic acids, having a minimal number of junctional epitopes and a maximum functional (e.g., immunogenicity) value.

In one embodiment, if the number of peptides to be processed by the computer system is less than fourteen, an exhaustive search program is executed by the computer system which examines all permutations of the peptides making up the polypeptide to find the permutation with the "best" or "optimal" function value. In one embodiment, the function value is calculated using the equation (Ce+Ne)/J when J is greater than zero and 2*(Ce+Ne) when J is equal to zero, where Ce is the enhancement "weight" value of an amino acid at the C+1 position of a peptide, Ne is the enhancement "weight" value of an amino acid at the N−1 position of a peptide, and J is the number of junctional epitopes contained in the polypeptide encoded by multi-epitope nucleic acid sequence. Thus, maximizing this function value will identify the peptide pairs having the least number of junctional epitopes and the maximum enhancement weight value for flanking residues. If the number of peptides to be processed is fourteen or more, the computer system executes a stochastic search program that uses a "Monte Carlo" technique to examine many regions of the permutation space to find the best estimate of the optimum arrangement of peptides (e.g., having the maximum function value).

In a further embodiment, the computer system allows a user to input parameter values which format or limit the output results of the exhaustive or stochastic search program. For example, a user may input the maximum number of results having the same function value ("MaxDuplicateFunctionValue=X") to limit the number of permutations that are generated as a result of the search. Since it is possible for the search programs to find many arrangements that give the same function value, it may be desirable to prevent the output file from being filled by a large number of equivalent solutions. Once this limit is reached no more results are reported until a larger or "better" function value is found. As another example, the user may input the maximum number of "hits" per probe during a stochastic search process. This parameter prevents the stochastic search program from generating too much output on a single probe. In a preferred embodiment, the number of permutations examined in a single probe is limited by several factors: the amount of time set for each probe in the input text file; the speed of the computer, and the values of the parameters "MaxHitsPerProbe" and "MaxDuplicateFunctionValues." The algorithms used to generate and select permutations for analysis may be in accordance with well-known recursive algorithms found in many computer science textbooks. For example, six permutations of three things taken three at a time would be generated in the following sequence: ABC; ACB; BAC; BCA; CBA; CAB. As a further example of an input parameter, a user may input how the stochastic search is performed, e.g., randomly, statistically or other methodology; the maximum time allowed for each probe (e.g., 5 minutes); and the number of probes to perform.

Also disclosed herein are multi-epitope constructs designed by the methods described above and hereafter. The multi-epitope constructs include spacer nucleic acids between a subset of the epitope nucleic acids or all of the epitope nucleic acids. One or more of the spacer nucleic acids may encode amino acid sequences different from amino acid sequences encoded by other spacer nucleic acids to optimize epitope processing and to minimize the presence of junctional epitopes.

The invention relates to a method and system of designing multi-epitope vaccines with optimized immunogenicity. In preferred embodiments, the vaccine comprises CTL and HTL epitopes. Vaccines in accordance with the invention allow for significant, non-ethnically biased population coverage, and can preferably focus on epitopes conserved amongst different viral or other antigenic isolates. Through the method and system disclosed herein, vaccines can be optimized with regard to the magnitude and breadth of responses, and can allow for the simplest epitope configuration. Finally, general methods are provided to evaluate immunogenicity of a multi-epitope vaccine in humans.

The method of the invention comprises designing a multi-epitope construct based on principles identified herein. In one aspect, the invention provides for simultaneous induction of responses against specific CTL and HTL epitopes, using single promoter multi-epitope constructs. Such constructs can contain many different epitopes, preferably greater than 10, often greater than 20, 25, 30, 25, 40, 45, 50, 55, 60, 65, 70, or more.

In a preferred embodiment, a computer system identifies one or more optimal multi-epitope constructs by performing the following functions and/or analyses:

(i) the epitopes to be incorporated into the multi-epitope construct are sorted to provide an order that minimizes the number of junctional epitopes formed. A more detailed discussion of this sorting procedure is provided below with reference to FIGS. 11 and 12. Preferably, as a secondary consideration in ordering epitopes, epitopes are positioned such that residues at the N-terminus of an epitope that promote CTL immunogenicity are juxtaposed to the C-terminus of another CTL epitope.

(ii) flanking residues that enhance immunogenicity may be inserted at the flanking positions of epitopes. In particular embodiments, flanking residues are inserted at the C+1 position of CTL epitopes.

(iii) spacer sequences may be inserted between epitopes to prevent occurrence of junctional epitopes. In particular embodiments, the spacer sequences can also include a residue that promotes immunogenicity at the N-terminus of the linker such that the residue flanks the C-terminus of a CTL epitope.

In particular embodiments to prevent HTL junctional epitopes, a spacer composed of amino acid residues that do not correspond to any known HLA Class II anchor residue, are used, e.g., alternating G and P residues (a GP spacer) is included between two HTL epitopes.

Another aspect of the invention, (consideration (ii) above) involves the introduction or substitution of particular amino acid residues at positions that flank epitopes, e.g., a position immediately adjacent to the C-terminus of the epitope, thereby generating multi-epitope constructs with enhanced antigenicity and immunogenicity compared to constructs that do not contain the particular residue introduced or substituted at that site, i.e., non-optimized multi-epitope constructs. The methods of optimizing multi-epitope constructs comprise a step of introducing a flanking residue, preferably K, N, G, R, or A at the C+1 position of the epitope, i.e., the position immediately adjacent to the C-terminus of the epitope. In an alternative embodiment, residues that contribute to decreased immunogenicity, i.e., negatively charged residues, e.g., D, aliphatic residues (I, L, M, V) or aromatic non-trytophan residues, are replaced. The flanking residue can be introduced by positioning appropriate epitopes to provide the favorable flanking residue, or by inserting a specific residue.

As noted in the background section, multi-epitope constructs (minigenes) encoding up to 10 epitopes have been used to induce responses against a number of different epitopes. The data relating to an experimental multi-epitope construct, pMin.1 has been published (Ishioka et al., *J Immunol*, Vol. 162(7):3915-25 (1999)). Disclosed herein, are parameters for designing and evaluating multi-epitope constructs with optimized immunogenicity that address myriad disease indications of interest.

Figure 14A:
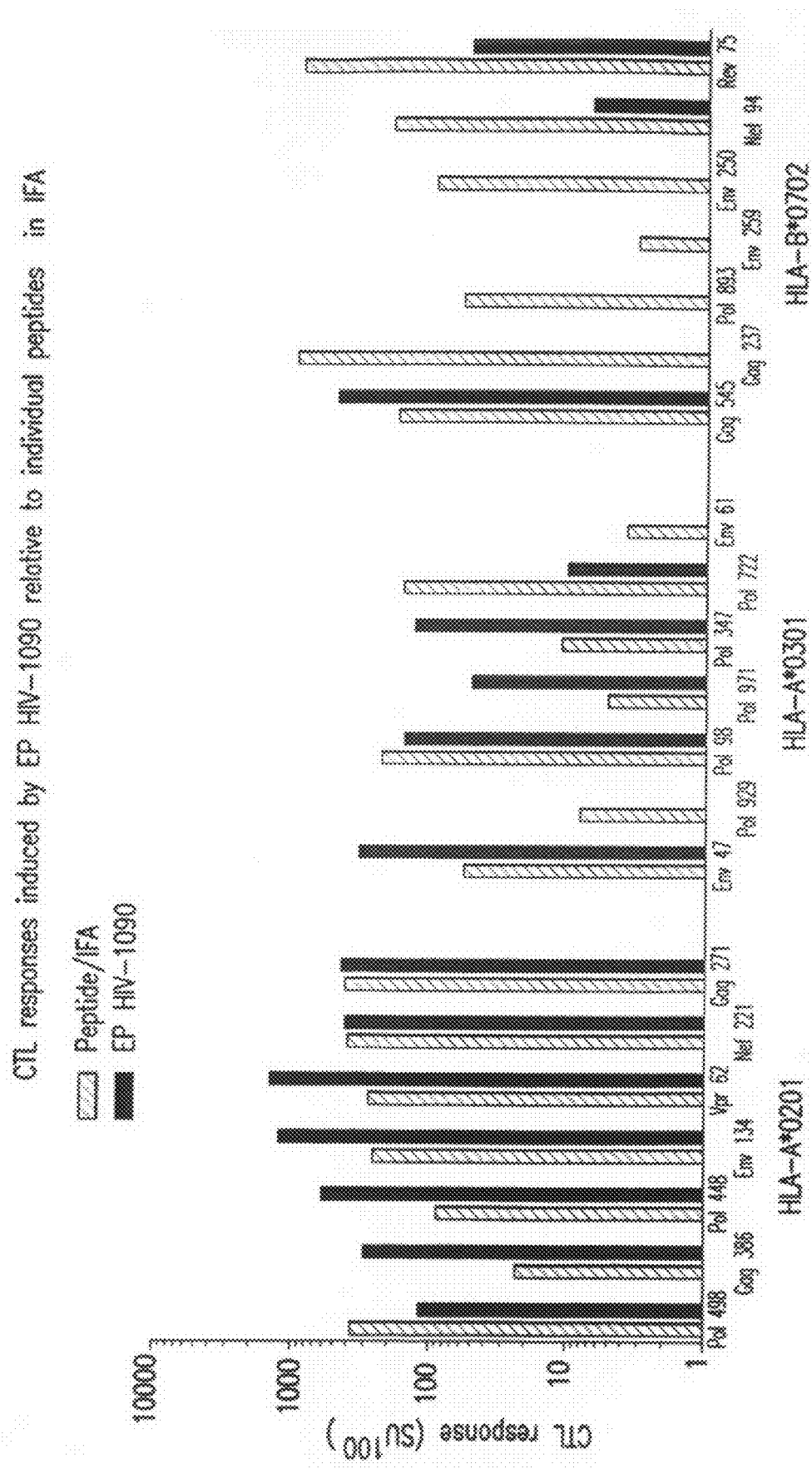
FIG. 14A depicts CTL responses induced by EP-HIV-90 relative to individual peptides in IFA.
Figures 1, 14B:
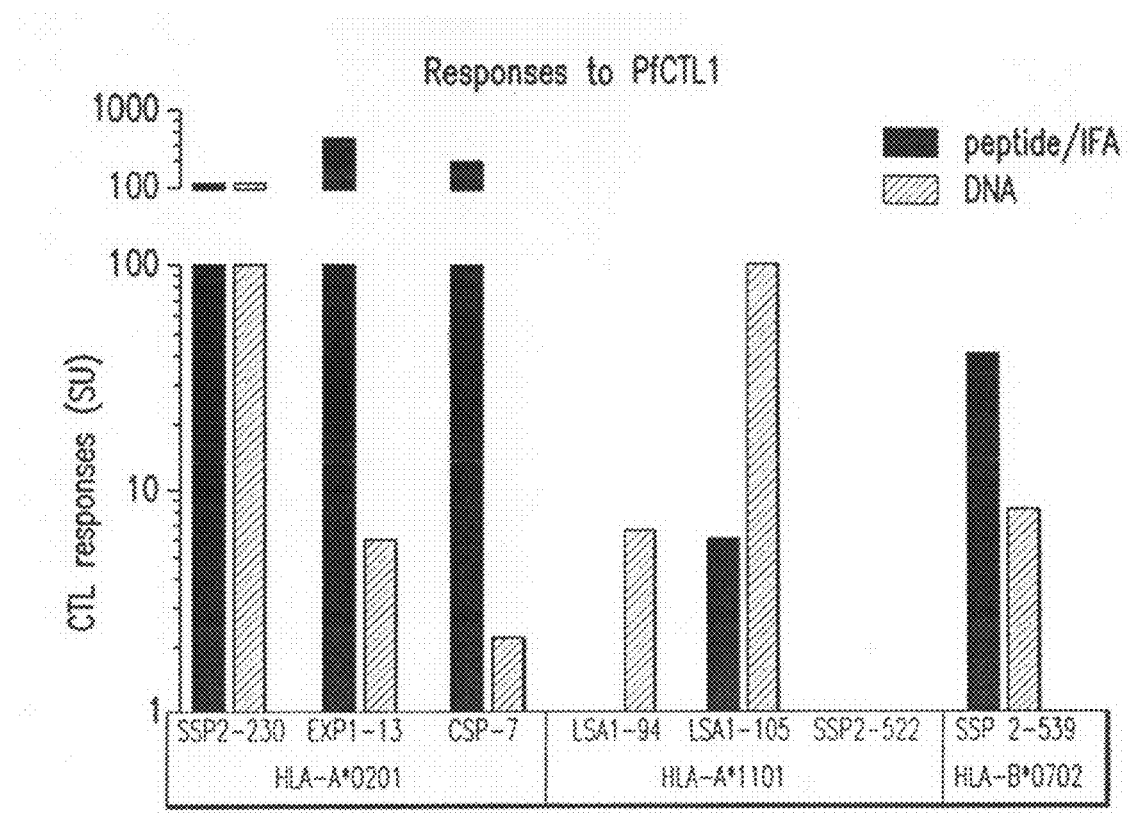
FIG. 1 illustrates data on three different multi-epitope constructs, incorporating 20 to 25 different CTL epitopes each.
FIG. 14B depicts CTL responses induced by PfCTL.1, PfCTL.2, and PfCTL.3 relative to individual peptides.
Figures 2, 14B:
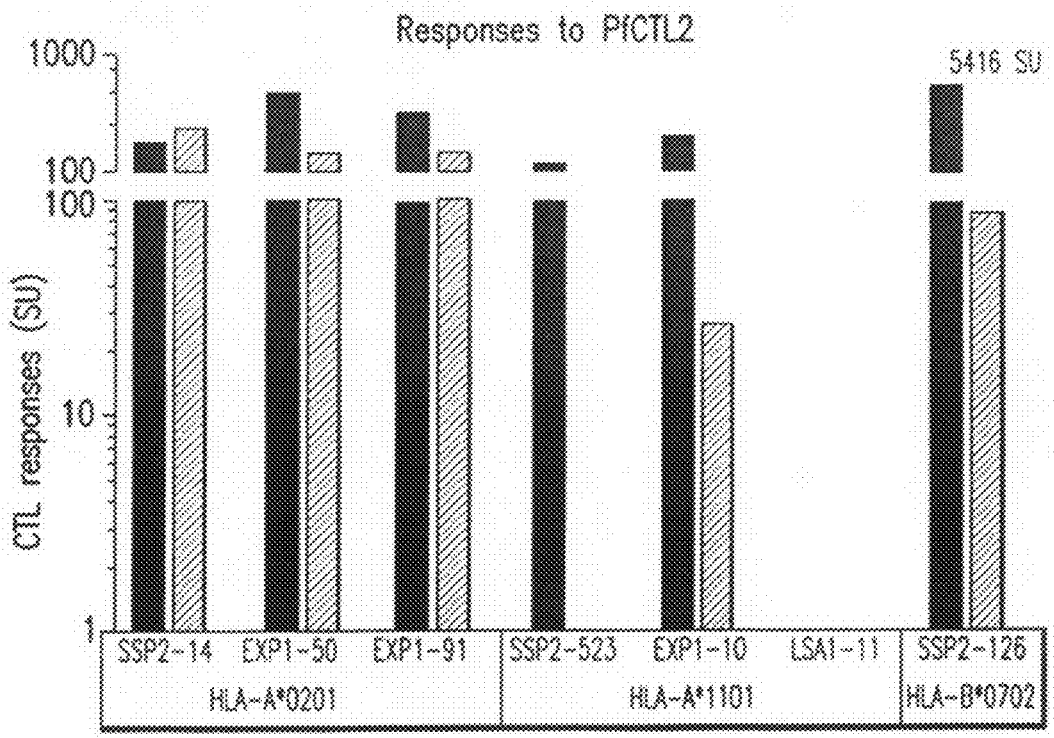
FIG. 2 illustrates two different synthetic polypeptides (FIG. 2a) where the first construct incorporates four different epitopes linearly cosynthetized, and the second construct incorporates a GPGPG (SEQ ID NO:2) spacer.

Design parameters were identified based on a number of studies. In a preliminary evaluation of multi-epitope constructs, data on three different multi-epitope constructs, incorporating 20 to 25 different CTL epitopes each, are presented (FIG. 1). One construct is based on HIV-derived epitopes, (HIV-1), while the other two incorporate HCV-derived epitopes (HCV1 and HCV2, respectively). The immunogenicity of these different multi-epitope constructs has been measured in either A2 or A11 HLA transgenic mice (A1, A24 and B7 restricted epitopes were not evaluated).

Thus, eleven days after a single i.m. DNA vaccine injection, responses against 8 to 14 different representative epitopes were evaluated following a single six day in vitro restimulation, utilizing assays to measure CTL activity (either chromium release or in situ IFN production, as described herein). Priming of epitope specific CTL could be demonstrated for 6/8 (75%), 10/14 (72%) and 13/14 (93%) of the epitopes tested in the case of HIV-1, HCV1 and HCV2, respectively. Thus, multi-epitope constructs, capable of simultaneously priming CTL responses against a large number of epitopes, can be readily designed. However, it should be emphasized that CTL priming for some epitopes was not detected and, in several of the 36 cases considered, responses were infrequent, or varied significantly in magnitude over at least three orders of magnitude (1000-fold). These results strongly suggested that a more careful analysis and optimization of the multi-epitope constructs was required.

The possibility that the suboptimal performance of priming for certain epitopes might be related to multi-epitope construct size was also examined. In fact, most of the published reports describe multi-epitope construct of up to ten epitopes, and in the few instances in which 20-epitope constructs have been reported, activity directed against only two or three epitopes was measured. To address this possibility, two smaller epigene constructs (HIV-1.1 and HIV-1.2) each encompassing ten epitopes, and corresponding to one half of the HIV-1 epigene construct, were synthesized and tested. Responses against four representative epitopes were measured.

the program can be run for any desired length of time. In either case, the computer system of the present invention identifies and provides at least one configuration having a minimum number of junctional epitopes.

An example of the results of this type of approach is presented in Table 2. The number of junctional motifs in ten

TABLE 1

Immunogenicity appears to be independent of epigene construct size.

| | CTL response to different epigene constructs | | | | | |
|---|---|---|---|---|---|---|
| CTL | HIV 1 (20 mer) | | HIV 1.1 (10 mer) | | HIV 1.2 (10 mer) | |
| Epitope | Frequency[1] | Magnitude[2] | Frequency | Magnitude | Frequency | Magnitude |
| Pol 774 | 0/8 | * | 0/4 | * | NA[3] | NA |
| Pol 498 | 18/19 | 46.7 | 4/4 | 16.4 | NA | NA |
| Gag 271 | 4/13 | 4.0 | NA | NA | 0/4 | * |
| Env 134 | 5/8 | 16.1 | NA | NA | 4/4 | 14.8 |

[1]Represents the fraction of independent cultures yielding positive responses
[2]Lytic Units (LU)
[3]Not Applicable It was found that the responses induced by the smaller epigene constructs were comparable, and if anything, lower than those induced by the twenty-epitope construct (Table 1). Accordingly, factors relating to epigene construct size are unlikely explanations for the observed suboptimal priming to certain epitopes and thus other parameters, disclosed herein, are used to design efficacious multi-epitope constructs.

The Minimization of Junctional Motifs

One of the considerations in designing multi-epitope constructs is the inadvertent creation of junctional epitopes when placing epitopes adjacent to each other. The presence of such epitopes in a multi-epitope construct could significantly affect performance. Strategies to guard against this undesired effect are disclosed herein for application to the development of multi-epitope vaccines. Junctional epitopes can first be minimized by sorting the epitopes to identify an order in which the numbers of junctional epitopes is minimized. Such a sorting procedure can be performed using a computer or by eye, if necessary, or depending on the number of epitopes to be included in the multi-epitope construct.

For example, a computer program that finds patterns, e.g., Panorama, manufactured by ProVUE Development, Huntington Beach, Calif., U.S.A., can be used in accordance with one embodiment of the invention. A very large number of different epitope arrangements can be considered in designing a particular multi-epitope construct. A computer program accepts as input, the particular set of epitopes considered, and the motifs to be scanned in order to evaluate whether there are any junctional epitopes bearing these motifs. For example, a program can simulate building a multi-epitope construct, and in an heuristic computational algorithm, examine epitope pairs to avoid or minimize the occurrence of junctional motifs. The program can for example, evaluate $6 \times 10^5$ (about half a million) multi-epitope construct configurations/second.

A complete analysis of a 10-epitope construct using a computer program as described in the preceding paragraph requires examining 10 factorial $\cong 3.6 \times 10^6$ combinations and can be completed in six seconds. A fourteen-epitope construct can be completely analyzed in a couple of days. Thus, analysis time goes up very rapidly as larger constructs are considered. However, a complete analysis is not always required and different random assortments of the same epitopes contained in the HCV1 epigene, which incorporates 25 epitopes, and is the result of a two-day computer analysis, is presented in this Table. In the non-optimized assortments, a large number of HLA-A2, A11 and $K^b$ motifs were found, approximately 25 to 38, with an average of 31. By comparison, only two such junctional motifs are present in the HCV1 epigene construct assortment. In conclusion, a computer program can be utilized to effectively minimize the number of junctional motifs present in multi-epitope constructs.

TABLE 2

Occurrence of junctional epitopes.

| epigene construct | selection criteria | junctional motifs |
|---|---|---|
| HCV.a | random | 33 |
| HCV.b | random | 26 |
| HCV.c | random | 28 |
| HCV.d | random | 27 |
| HCV.e | random | 30 |
| HCV.f | random | 26 |
| HCV.g | random | 38 |
| HCV.h | random | 33 |
| HCV.i | random | 33 |
| HCV.j | random | 34 |
| HCV.l | minimized | 2 |

Eliminating Class II Junctional Epitopes and Testing for Class II Restricted Responses In Vivo As a further element in eliminating junctional epitopes, spacer sequences can be inserted between two epitopes that create a junctional epitope when juxtaposed.

In one embodiment, to correct the problem of junctional epitopes for HTL epitopes, a spacer of, for example, five amino acids in length is inserted between the two epitopes. The amino acid residues incorporated into such a spacer are preferably those amino acid residues that are not known to be primary anchor residues for any of the HLA Class II binding motifs. Such residues include G, P, and N. In a preferred embodiment, a spacer with the sequence GPGPG (SEQ ID NO:2) is inserted between two epitopes. Previous work has demonstrated that the GP spacer is particularly effective in disrupting Class II binding interactions (Sette et al., *J. Immu-* nol., 143:1268-73 (1989)). All known human Class II binding motifs and the mouse IA$^b$ (the Class II expressed by HLA transgenic mice) do not tolerate either G or P at the main anchor positions, which are spaced four residues apart. This approach virtually guarantees that no Class II restricted epitopes can be formed as junctional epitopes.

Figure 2B:
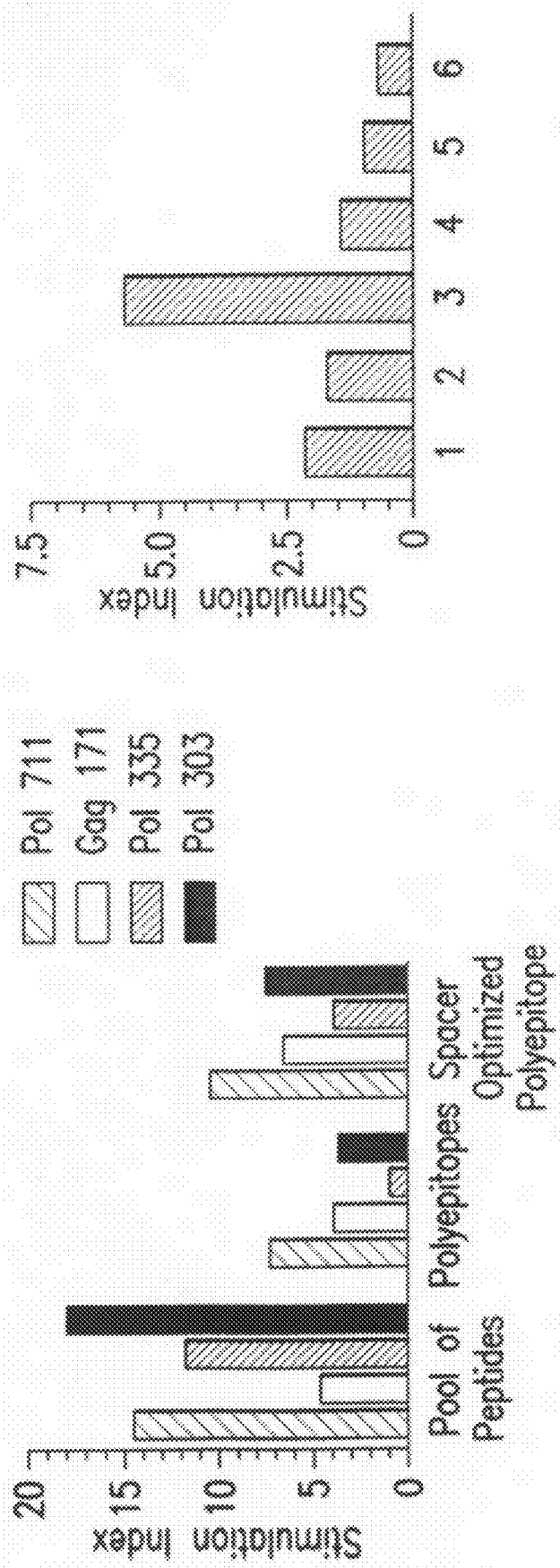
FIG. 2b illustrates the capacity of 2 nanomoles of these different constructs to prime for proliferative responses to the various epitopes in $IA^b$ positive mice, compared to the responses induced by equimolar amounts of a pool of the same peptides (3 micrograms of each peptide).

In an example validating this design consideration, we synthesized polypeptides incorporating HIV-derived HTL epitopes. These epitopes are broadly cross-reactive HLA DR binding epitopes. It was then determined that these epitopes also efficiently bind the murine IA$^b$ Class II molecule. A diagram illustrating the two different synthetic polypeptides considered is shown in FIG. 2a.

The first construct incorporates four different epitopes linearly arranged, while the second construct incorporates the GPGPG (SEQ ID NO:2) spacer. Synthetic peptides corresponding to the three potential junctional epitopes were also synthesized.

The capacity of 2 nanomoles of these different constructs to prime for proliferative responses to the various epitopes in IA$^b$ positive mice was tested, and compared to the responses induced by equimolar amounts of a pool of the same peptides (3 micrograms of each peptide). Specifically, groups of 3 mice were injected with peptides in CFA emulsions, 11 days after injection their lymph node cells were cultured in vitro for an additional 3 days, and thymidine incorporation was measured in the last 24 hours of culture. It was found (FIG. 2b) that, as predicted on the basis of their high affinity IA$^b$ binding capacity, all four epitopes induced good proliferation responses. Stimulation index (SI) values in the range of 4.9 to 17.9 were observed when these peptides were injected in a pool. However, when the linear polypeptide incorporating the same epitopes was tested, the response directed against Pol 335 was lost. This was associated with appearance of a response directed against a junctional epitope spanning Gag 171 and Pol 335. The use of the GPGPG (SEQ ED NO:2) spacer eliminated this problem, presumably by destroying the junctional epitope, and the Pol 335 response was regained. The responses observed were of magnitude similar to those observed with the pool of isolated peptides.

These results demonstrate that responses against multiple HIV-derived Class II epitopes can be simultaneously induced, and also illustrate how IA$^b$/DR crossreactivity can be utilized to investigate the immunogenicity of various constructs incorporating HTL epitopes. Finally, they demonstrate that appropriate spacers can be employed to effectively disrupt Class II junctional epitopes that would otherwise interfere with effective vaccine immunogenicity.

In the case of Class I restricted responses, one case of a naturally occurring junctional epitope and the consequent inhibition of epitope specific responses has been presented by McMichael and coworkers (Tussey et al., *Immunity*, Vol. 3(1): 65-77 (1995)). To address the problem of junctional epitopes for Class I, similar analyses can be performed. For example, a specific computer program is employed to identify potential Class I restricted junctional epitopes, by screening for selected murine motifs and for the most common human Class I HLA A and B motifs.

Spacer sequences can also similarly be employed to prevent CTL junctional epitopes. Often, very small residues such as A or G are preferred spacer residues. G also occurs relatively infrequently as a preferred primary anchor residue (see, e.g., PCT/US00/24802) of an HLA Class I binding motif. These spacers can vary in length, e.g., spacer sequences can typically be 1, 2, 3, 4, 5, 6, 7, or 8 amino acid residues in length and are sometimes longer. Smaller lengths are often preferred because of physical constraints in producing the multi-epitope construct.

The Influence of Flanking Regions on CTL Multi-Epitope Construct Immunogenicity

Another factor to be considered in designing multi-epitope constructs is to insert residues that favor immunogenicity at the position flanking the C-terminus of a CTL epitope.

Disclosed herein are studies that identify residues that increase immunogenicity and, accordingly, residues that are inserted in multi-epitope constructs to optimize immunogenicity.

The molecular context in which an epitope was expressed often dramatically influenced the frequency and/or magnitude of priming of CTL specific for that epitope in HLA transgenic mice. Two examples are shown in Table 3.

TABLE 3

Differences in effectiveness of T cell priming for specific epitopes in different epigene constructs.

| Epitope Identity | Epigene Construct | SEQ ID NO: | Flanking Sequence (N terminus) | Epitope Sequence | Flanking Sequence (C-terminus) | Immune Response Frequency | Immune Response Magnitude[1] |
|---|---|---|---|---|---|---|---|
| Core 18 | HBV.1 | 3 | TLKAAA | FLPSDFFPSV | FLLSLG | 6/6 | 5.5 |
|  | pMin1 | 4 | TLKAAA | FLPSDFFPSV | KLTPLC | 6/6 | 1074.5 |
| Core 132 | HCV1 | 5 | ILGGWV | DLMGYIPLV | YLVAYQ | 2/12 | 107.7 |
|  | HCV2 | 6 | VPGSRG | DLMGYIPLV | AKFVA | 17/18 | 929.2 |

[1] IFNγ secretory units

The immunogenicity of the HBV Core 18 epitope expressed in the pMin5 epigene construct was approximately 200-fold lower in magnitude than that observed in the case of the pMin1 epigene construct. Similarly, the immunogenicity of the HCV Core 132 epitope expressed in the context of the HCV1 epigene construct was marginal, with significant T cell priming demonstrable in only 2 of 12 different independent CTL experiments/cultures performed. These two positive experiments yielded responses of approximately 100 SU of IFNγ. However, when the same epitope was expressed in the context of the HCV2 epigene construct, positive responses were observed in 17/18 cases, and with average magnitudes approximately five-fold higher.

Immunogenicity of HIV-FT in HLA-A*0201/Kb Transgenic Mice

Figures 3, 14B:
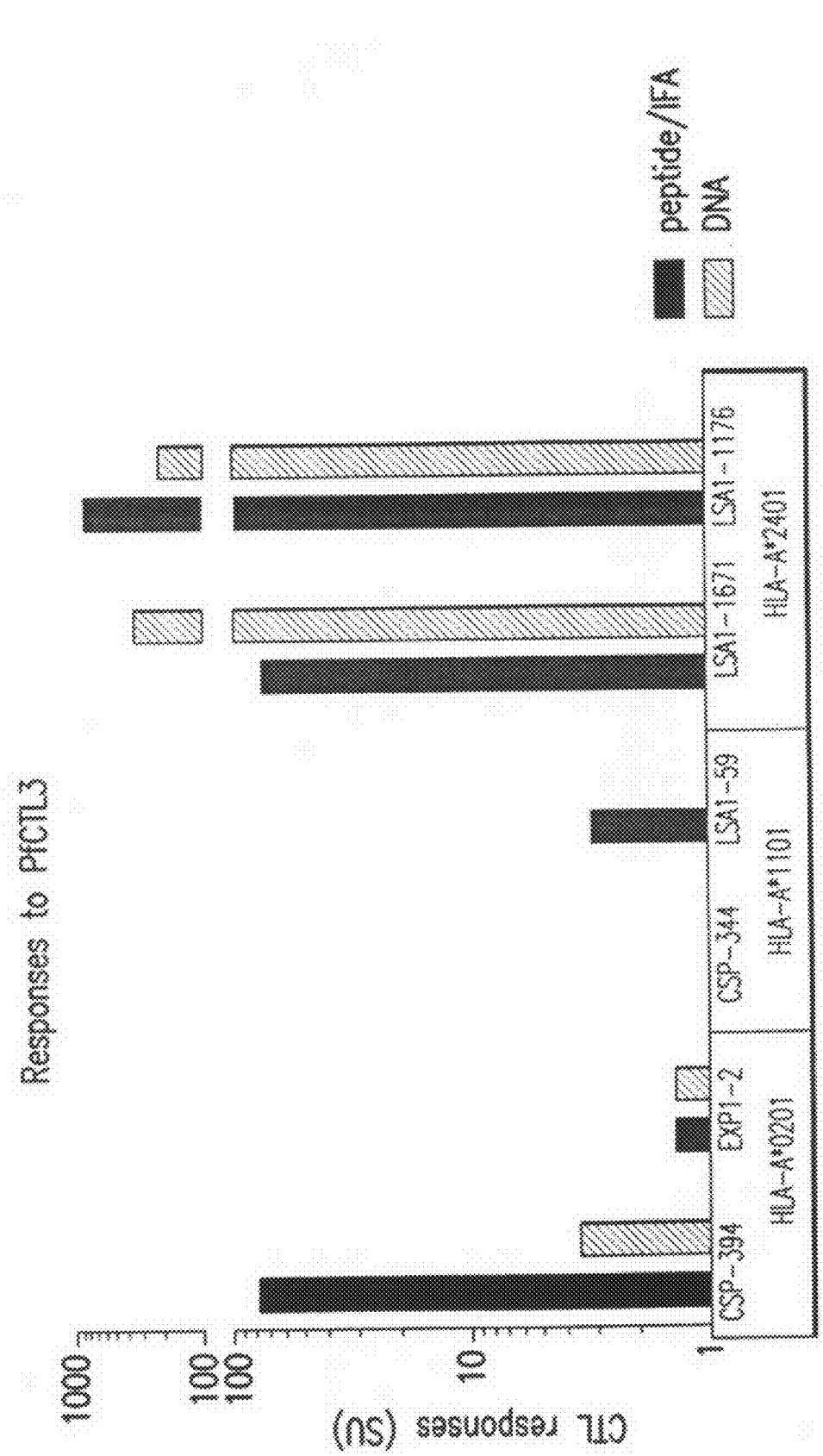
FIG. 3 depicts the structure of multi-epitope DNA constructs. The HLA restriction is shown above each epitope, the A*0201 epitopes are bolded. The HLA binding affinity ($IC_{50}$ nM) is provided below each epitope. (a) Schematic of HIV-FT illustrating order of the encoded epitopes. (b) Schematics of the of the HBV-specific constructs. The C+1 amino acid relative to Core 18 is indicated with an arrow. The HBV-specific constructs with single amino acid insertions at the $C_1$ position of Core 18 are illustrated as HBV.1X.

An HIV multi-epitope DNA vaccine, HIV-FT (FIG. 3a) encodes 20 HIV-derived CTL epitopes. Of these 20 epitopes, eight are restricted by HLA-A*0201, nine by HLA-A*1101 and three by HLA-B*0702. All epitopes bound their relevant restriction element with high or moderate affinity. All of the HLA-A*0201 restricted epitopes bound purified HLA-A*0201 molecules with roughly similar affinities, with $IC_{50}$ values in the 19-192 nM range (FIG. 3a). The HLA-A*0201 epitopes chosen for inclusion in HIV-FT are recognized in HIV-1 infected individuals and were also highly effective in priming for recall CTL responses when emulsified with IFA and utilized to prime HLA-A*0201/$K^b$ transgenic mice. The construct was designed to encode the epitopes sequentially without any intervening spacer sequences between them and a consensus Igκ signal sequence was fused to the 5' end of the construct to facilitate transport of the encoded antigen into the endoplasmic reticulum (Ishioka et al., *J. Immunol.* 162:3915-3925, 1999).

Figure 4A:
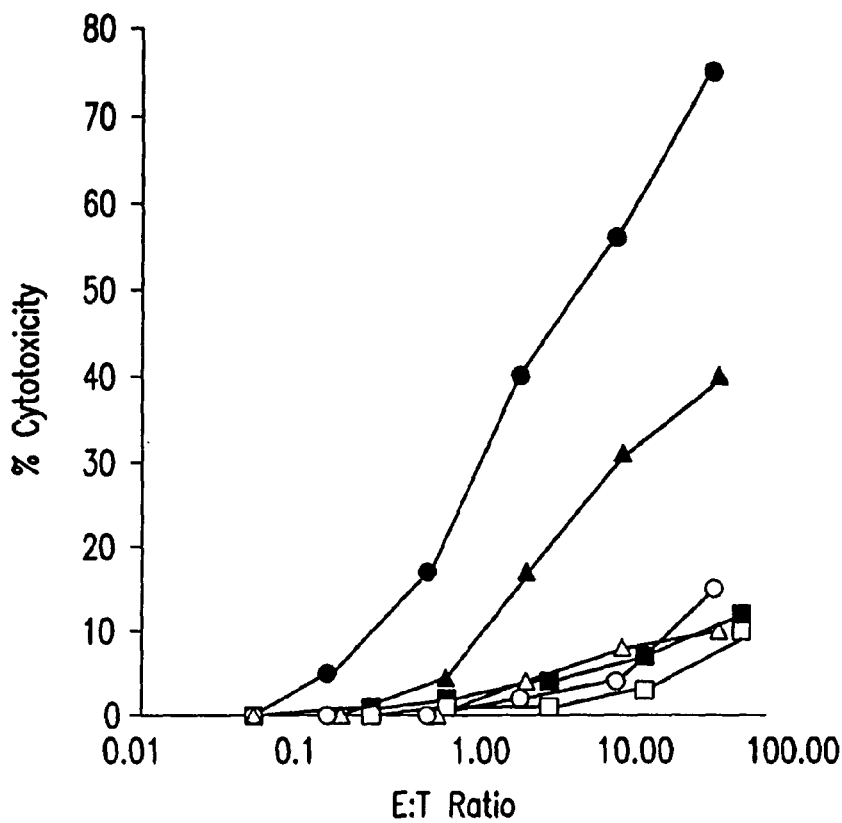
FIG. 4 illustrates the immunogenicity of the HLA-A*0201 epitopes in HIV-FT in HLA-A*0201/$K^b$ transgenic mice. (a) Representative CTL responses against epitopes Pol 498 (circles), Vpr 62 (triangle), Gag 386 (squares). Cytotoxicity was assayed in a $^{51}$Cr release assay against Jurkat-HLA-A*0201/$K^b$ target cells in the presence (filled symbols) or absence (open symbols) of each peptide. (b) Summary of CTL responses of immunogenicity of HIV-FT in HLA-A*0201/$K^b$ transgenic mice. Bars indicate the geometric mean CTL response of positive cultures. The frequency of positive CTL cultures is also indicated.
Figure 4B:
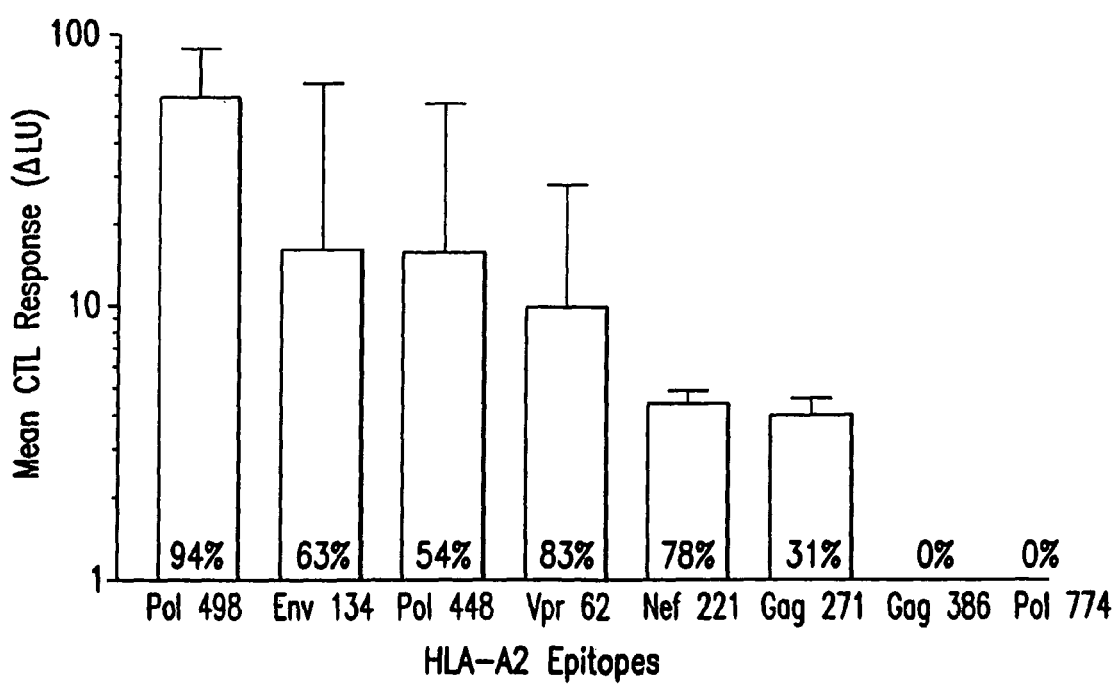

The ability of HIV-FT to prime recall CTL responses in vivo was evaluated by intramuscular immunization of HLA-A*0201/$K^b$ transgenic mice. Splenocytes from animals immunized with 100 μg of HIV-FT plasmid DNA were stimulated with each of the HLA-A*0201 epitopes encoded in HIV-FT and assayed for peptide-specific CTL activity after six days of culture. Representative CTL responses against three of the epitopes in HIV-FT are shown in FIG. 4a. To more conveniently compile results from different experiments the percent cytotoxicity values for each splenocyte culture were expressed in lytic units (Vitiello, et al., *J. Clin. Invest* 95:341-349, 1995). Of the eight HLA-A*0201 restricted epitopes encoded in HIV-FT, Pol 498, Env 134, Pol 448, Vpr 62, Nef 221, and Gag 271, primed for CTL responses following DNA immunization, (FIG. 4b). The magnitude of the CTL responses varied over greater than a 10-fold range, from as high as nearly 50 LU against Pol 498, too as little as 4 LU against Nef 221 and Gag 271. Similarly, the frequency of recall CTL responses varied between epitopes, with the Pol 498 epitope inducing responses in 94% of the experiments while CTL responses to Gag 271 were detected in only 31% of the experiments. In conclusion, DNA immunization with HIV-FT, which sequentially encodes the epitopes without any spacer amino acids, induced recall CTL responses against the majority of the epitopes analyzed. However, the magnitude and the frequency of the responses varied greatly between epitopes.

Correlation Between Epitope Immunogenicity and Levels of HIV-FT Epitope Presentation in Transfected Cell Lines The differential immunogenicity of the HLA-A*0201 epitopes in HIV-FT was then assessed. Differential MHC binding affinity could be excluded as all of the epitopes bind HLA-A*0201 with high affinity (FIG. 3a). In addition, lack of a suitable repertoire of TCR specificities in HLA-A*0201/$K^b$ transgenic mice could be excluded since all epitopes yielded comparable CTL responses following immunization of HLA transgenic mice with the optimal preprocessed peptide emulsified in IFA. Variations in the relative amounts of each epitope presented for T cell recognition may account for the differences in epitope immunogenicity.

To test this, Jurkat cells, a human T cell line, expressing the HLA-A*0201/$K^b$ gene (Vitiello et al., *J. Exp. Med.* 173, 1007-1015, 1991) were transfected with the HIV-FT expressed in an episomal vector. A human cell line was selected for use to eliminate any possible artifacts that may be associated with potential differences in the processing capabilities between humans and mice. This transfected cell line matches the human MHC presentation with human antigen processing capabilities and provides support for the subsequent development of CTL epitope-based DNA vaccines for use in humans.

Peptide-specific CTL lines detected presentation in the transfected targets of four of the HLA-A*0201 epitopes encoded in the HIV-FT, Pol 498, Env 134, Pol 448 and Nef 221. To quantitate the level at which each of these epitopes was produced and presented, the CTL lines specific for the various epitopes were incubated with untransfected targets and variable amounts of each epitope or peptides. These CTL dose response curves were utilized as standard curves to determine the peptide concentration inducing levels of IFNγ secretion equivalent to those observed in response to the HIV-FT transfected target cells. This value is referred to as a "peptide equivalent dose" and taken as a relative measure of the amount of epitope presented on the transfected cell.

Table 4 summarizes the findings of this analysis for eight of the HLA-A*0201 epitopes encoded in the HIV-FT. Peptide equivalent doses varied from a high of 33.3 ng/ml for Nef 221 to less than 0.4 ng/ml peptide equivalents for epitopes Gag 271, Gag 386 and Pol 774. Cumulatively these results indicate that in human cells lines transfected with HIV-FT there is at least a 100-fold variation exists in the levels of presentation of the different HLA-A*0201 restricted epitopes. All of the epitopes that were presented at detectable levels in antigenicity assays were also immunogenic in vivo. The only epitope that was immunogenic and not antigenic was Gag 271. In this case, immunization of HLA-A*0201/Kb transgenic mice with HIV-FT induced a weak CTL response in less than a third of the cultures tested. The other two epitopes, which were presented below the limit of sensitivity for the antigenicity analysis, Gag 386 and Pol 774, were non-immunogenic. In conclusion these results suggest that the heterogeneity in CTL responses induced by HIV-FT immunization can at least in part be attributed to suboptimal epitope presentation.

TABLE 4

Comparison of HIV-FT immunogenicity and antigenicity

| Epitope | HIV-FT Immunogenicity | | HIV-FT Antigenicity | |
|---|---|---|---|---|
| | magnitude[1] | frequency[2] | Peptide Equivalents[3] | n[4] |
| Pol 498 | 58.8 (2.2) | 94% (16/17) | 23.8 (2.0) | 4 |
| Env 134 | 16.1 (5.0) | 63% (5/8) | 6.2 (1.2) | 3 |
| Pol 448 | 15.7 (2.6) | 54% (7/13) | 24.7 (3.9) | 3 |
| Vpr 62 | 9.9 (1.9) | 83% (10.12) | ND | — |
| Nef 221 | 4.4 (1.3) | 78% (7/9) | 33.3 (6.0) | 3 |
| Gag 271 | 4.0 (1.4) | 31% (4/13) | <0.4 | 6 |
| Gag 386 | 0 | 0% (0/17) | <0.4 | 3 |
| Pol 774 | 0 | 0% (0/8) | <0.4 | 1 |

[1] magnitude expressed as LU (ref); the correlation coefficient relative to peptide equivalents R + 0.44
[2] frequency of positive cultures (number cultures >2LU/total tested); the correlation coefficient relative to peptide equivalents R + 0.8.
[3] magnitude expressed in ng/ml
[4] number of independent experiments Flanking Amino Acids Influence CTL Epitope Immunogenicity In Vivo Following Vaccination As described herein, the particular amino acids flanking individual CTL epitopes is one factor that influences or enhances the efficiency with which an epitope is processed by altering the susceptibility of the antigen to proteolytic cleavage. To examine the influence of flanking amino acids on epitope immunogenicity, immunogenicity data was obtained from HLA-A*0201, -A*1101 and -B*0701 transgenic mice immunized with a number of unrelated experimental multi-epitope DNA constructs encoding minimal CTL epitopes without intervening sequences. A database representing 94 different epitope/flanking residue combinations was compiled to determine the possible influence the immediately flanking amino acids on epitope immunogenicity. A given epitope and flanking amino acid combination was included only once to prevent artificial skewing of the analysis because of redundancies. Epitope immunogenicity in HLA transgenic was considered optimal if greater than 100 SU or 20 LU in at least 30% of the cultures measured. CTL responses were typically scored in one of four categories: (+++), outstanding-more than 200 LU or 1000 SU; (++), good-20-200 LU or 100-1000 SU; (+), intermediate-2 to 20 LU or 10 to 100 SU; and (+/−), weak or negative-less than 2 LU or 10 SU. The numbers of optimal versus sub-optimal responses were categorized based on the chemical type of amino acid in the flanking positions and the significance of differences were determined using a chi-square test.

Figure 5:
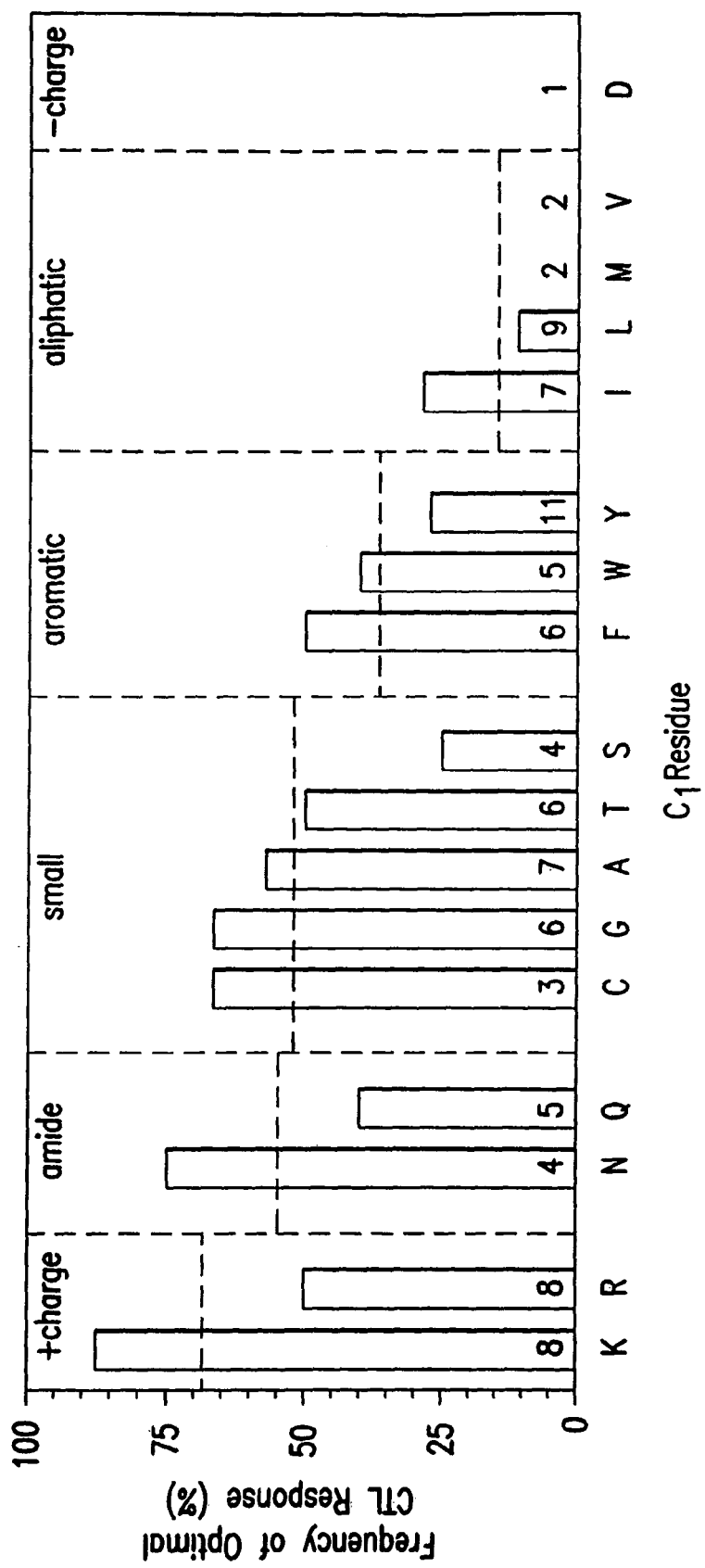
FIG. 5 shows the influence of the C+1 amino acid on epitope immunogenicity. A database incorporating CTL responses from a variety of multi-epitope constructs representing 94 epitope/C+1 amino acid combinations was analyzed to determine the frequency (%) of instances in which a particular combination was associated with an optimal CTL response. CTL responses were considered optimal if greater than 100 SU or 20 LU in at least 30% of the cultures measured. The number of times a given epitope/C+1 amino acid combination was observed is also provided.

This analysis did not find any associations between the type of amino acids present at the amino-terminus of an epitope and immunogenicity. However, significant effects of the carboxyl-terminus flanking residue, the C+1 residue, were identified. Positively charged amino acids, K or R were most frequently associated with optimal CTL responses, a frequency of 68% (FIG. 5). The presence of amino acids N and Q at the C+1 residue was also associated with strong CTL responses in 55.5% of the cases examined; when epitopes were flanked at the C+1 position by N, they induced optimal CTL responses in ¾ cases. In general, small residues such as C, G, A, T, and S promoted intermediate CTL responses inducing strong responses in 54% of the combinations available for analysis. Conversely, epitopes flanked by aromatic and aliphatic amino acids induced optimal in vivo responses in only 36% and 17% of the cases, respectively. The negatively charged residue, D, yielded a suboptimal CTL response. The influence of C+1 amino acid on epitope immunogenicity was found to be statistically significant using a chi-square test ($P<0.03$). No significant influence on epitope immunogenicity was noted when similar analysis was performed for C-terminal residues more distal than the C+1 position.

Direct Evaluation of the Effect of the C1 Residue on Epitope Immunogenicity

To directly evaluate the effect of preferred versus deleterious types of amino acids in the C+1 flanking position, two multi-epitope constructs, referred to as HBV.1 and HBV.2 (FIG. 3b) were evaluated. As with HIV-FT, these HBV constructs encode the epitopes sequentially without intervening spacers. The HBV.1 and HBV.2 epigenes were generated by replacing the HIV-1 epitopes in pMin1 (an experimental multi-epitope construct previously characterized (Ishioka, supra) with similar HBV-derived epitopes).

Figure 6A:
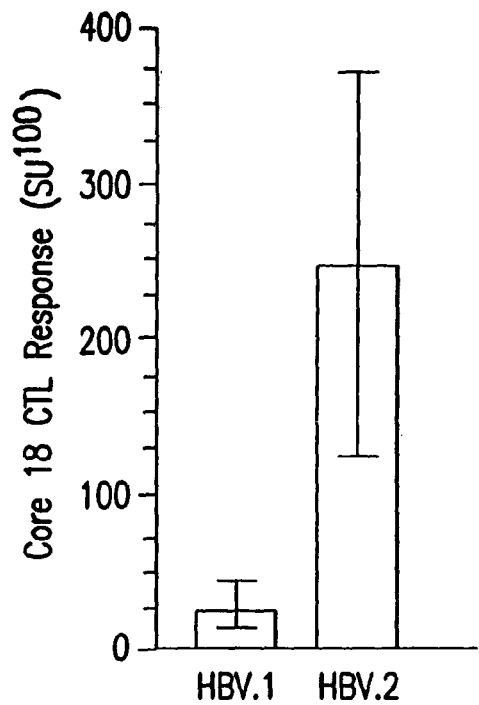
FIG. 6 shows CTL responses to HBV-specific constructs (a) CTL responses to Core 18 epitope following DNA immunization of HLA-A*0201/$K^b$ transgenic mice. (b) CTL responses to HBV Core 18 following DNA immunization of HLA-A*0201/$K^b$ transgenic mice with constructs which vary by a single amino acid insertion at the C+1 position of Core 18.

For HBV.1, the HIV-1 epitope directly following the highly immunogenic HBV Core 18 epitope was replaced with the HBV Pol 562 epitope. This altered the C+1 residue from a K to an F. The second construct, HBV.2, was produced by the insertion of an additional epitope, HBV Pol 629, between the HBV Core 18 and Pol 562 epitopes; a change that replaced the C+1 amino acid with a K residue. When the immunogenicity of the Core 18 epitope presented in these different contexts was evaluated in HLA-A*0201/$K^b$ transgenic mice, it was determined that the Core 18 was virtually non-immunogenic in HBV.1 but strongly immunogenic in HBV.2 (FIG. 6a). The reduction of in vivo immunogenicity for this epitope was as would be predicted by our previous analysis.

Figure 6B:
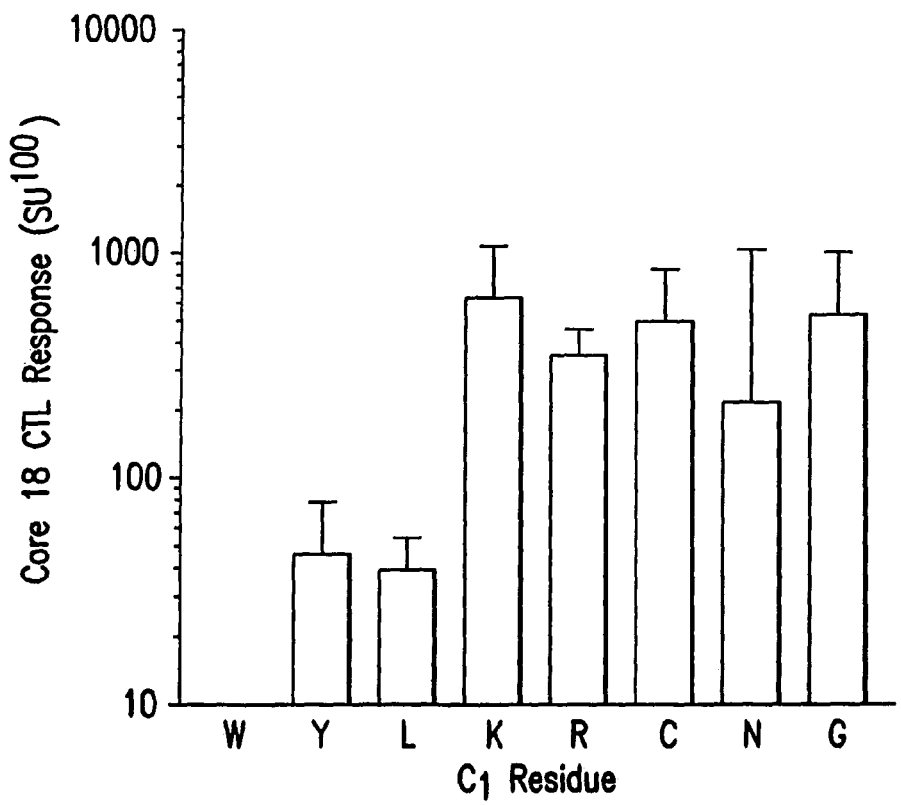

To further test the effects of the C+1 flanking amino acid on CTL epitope immunogenicity, a set of constructs that differ from HBV.1 by the insertion of single amino acids at the C+1 position relative to the Core 18 epitope (FIG. 3b) was evaluated. Little or no CTL response was observed against the Core 18 epitope when flanked at the C+1 position by W, Y, or L (FIG. 6b). In contrast, insertion of a single K residue dramatically increased the CTL response to Core 18. The responses were comparable to those observed in HBV.2, where the Core 18 epitope is flanked by Pol 629 epitope (Pol 629 has a K at the N-terminus). Enhancement of the Core 18 CTL response was also observed to insertion of R, C, N, or G. The effect of these insertions is specific, as the immunogenicity of other epitopes within these constructs did not exhibit significant changes in CTL responses (data not shown). In conclusion, these data indicate that the C+1 amino acid can dramatically influence epitope immunogenicity.

Figure 7:
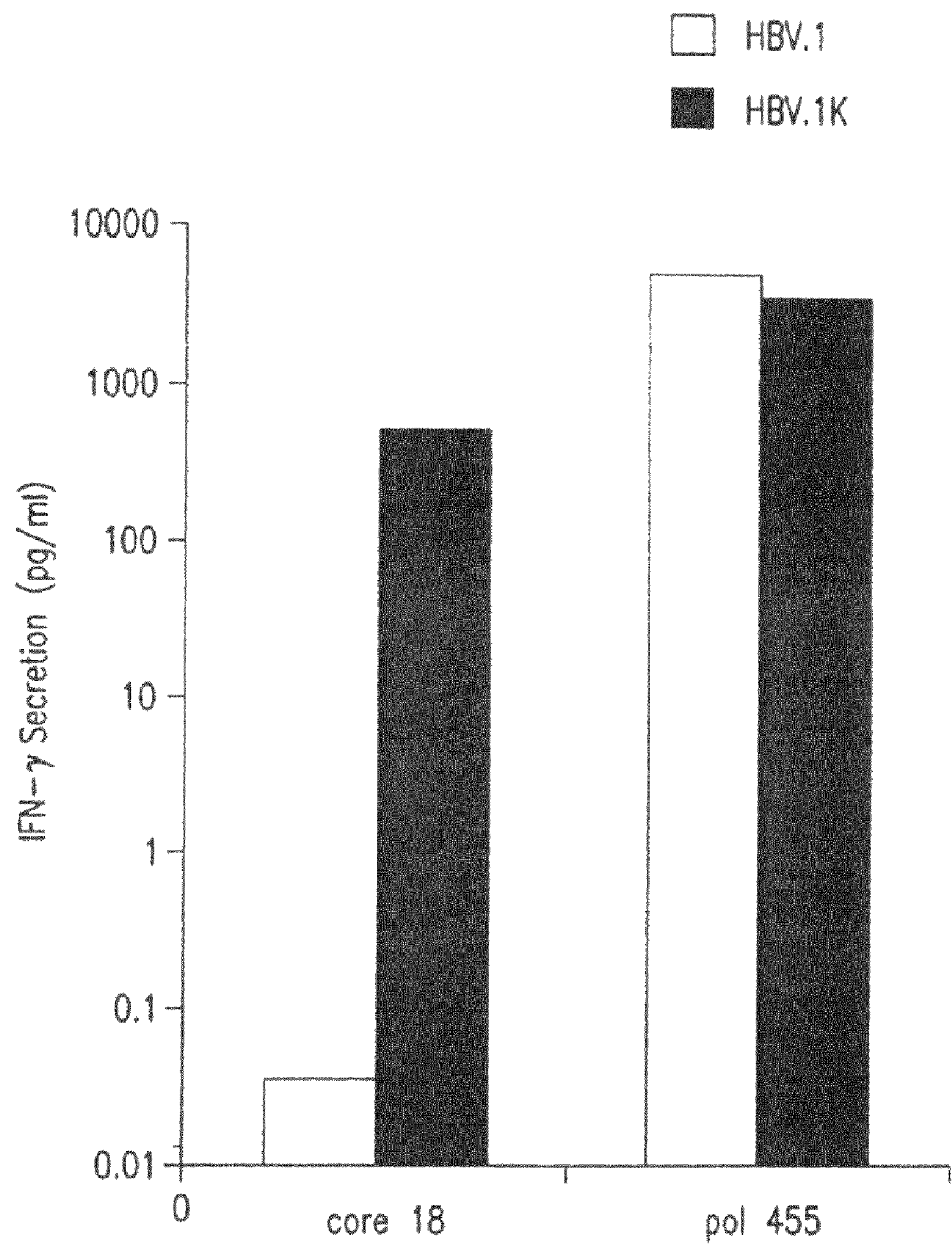
FIG. 7 shows levels of HBV Core 18 presentation in HBV.1 (shaded bars) and HBV.1K (hatched bars) transfected cell lines. Epitope presentation was quantified using peptide-specific CTL lines. Presentation of HBV Pol 455 is shown for comparative purposes.

Variations in CTL Epitope Immunogenicity are Correlated with the Amount Presented If the variation of the immunogenicity of Core 18 associated with different C+1 residues was the result of differential sensitivity to proteolytic cleavage then large differences in the levels of epitope presentation should be detectable in different constructs. To test this, Jurkat cells, expressing the same HLA-A*0201/$K^b$ gene expressed in the transgenic mice, were transfected with an episomal vector expressing either HBV.1 or HBV.1K. The Core 18 epitope was presented at >$10^5$ higher levels when a K was in the C+1 position, compared to the presence of an F in the same position (FIG. 7). It is unlikely that this difference in Core 18 presentation is attributed to differences in gene expression between target cell lines since presentation of Pol 455 varied by less than ten-fold. These data demonstrate the striking effect that amino acids at the C+1 position can exert on efficiency of epitope presentation in multi-epitope DNA vaccines. Thus, these data show that the immunogenicity of CTL epitopes in a DNA vaccine can be optimized through design considerations that affect the level of epitope presentation. This type of optimization is applicable to epitope-based vaccines delivered using other formats, such as viral vectors as well as other expression vectors known to those of skill in the art, since the effects are exerted after the antigen is transcribed and translated.

In summary, for flanking residues, it was found that either very small residues such as A, C or G, or large residues such as Q, W, K, or R were generally associated with good or outstanding responses. The absence of a C+1 residue because of a stop codon in the multi-epitope construct, or the presence of intermediate size residues such as S or T was associated with a more intermediate response pattern. Finally, in the case of a negatively charged residue, D; aliphatic (V, I, L, M) or aromatic non-tryptophan residues (Y, F), relatively poor responses were observed. These results show that the particular residue flanking the epitope's C-terminus can dramatically influence the response frequency and magnitude. Flanking residues at the C+1 position can also be introduced in combination with spacer sequences. Thus, a residue that favors immunogenicity, preferably, K, R, N, A, or G, is included as a flanking residue of a spacer.

Sorting and Optimization of Multi-Epitope Constructs

To develop multi-epitope constructs using the invention, the epitopes for inclusion in the multi-epitope construct are sorted and optimized using the parameters defined herein.

Sorting and optimization can be performed using a computer or, for fewer numbers of epitopes, not using a computer.

Figure 10:
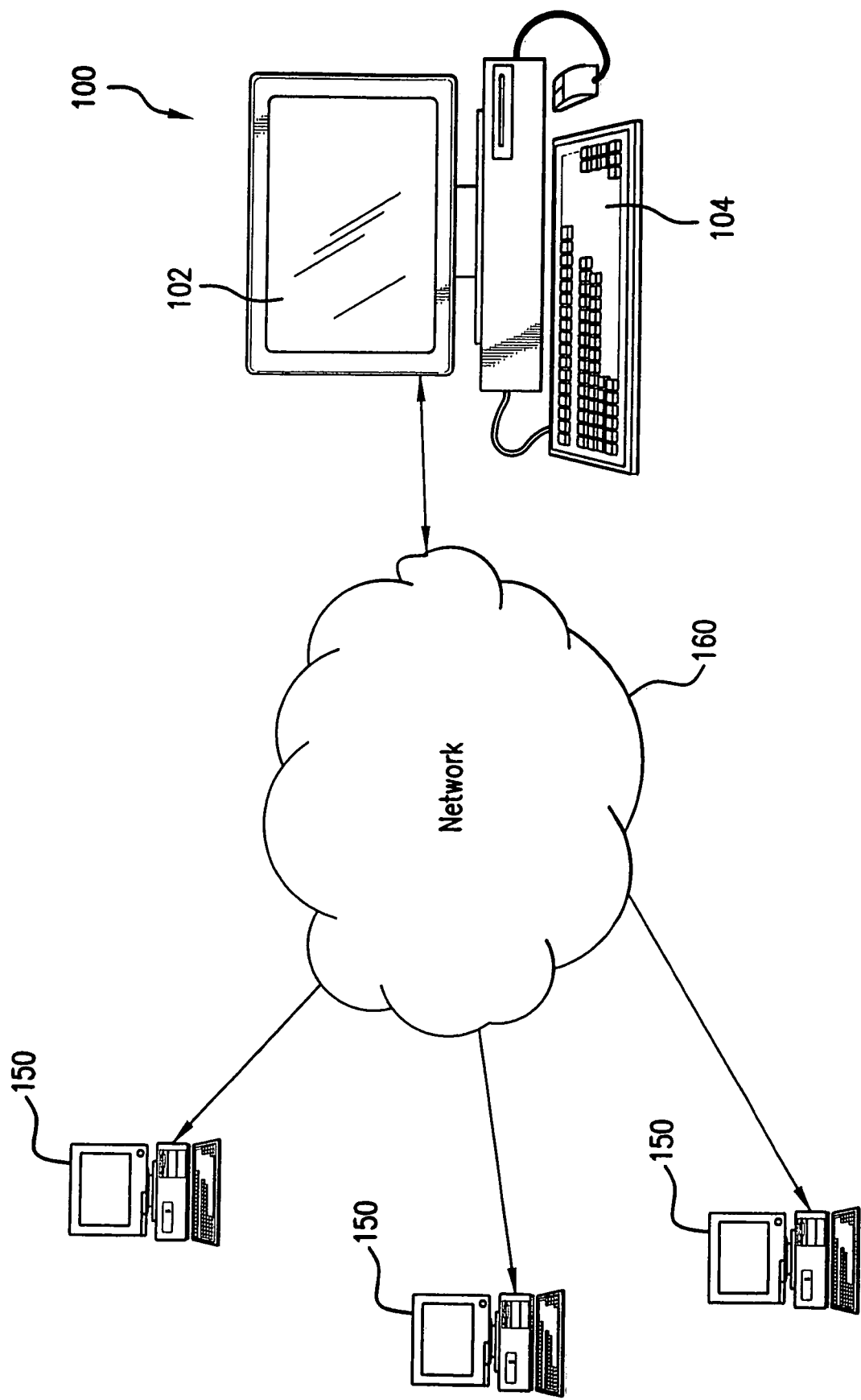
FIG. 10 illustrates a computer system for performing automatic optimization of multi-epitope constructs in accordance with one embodiment of the invention.

Computerized optimization can typically be performed as follows. The following provides an example of a computerized system that identifies and optimizes, e.g., provides for a minimal number of junctional epitopes and a maximal number of flanking residues, epitope combinations. FIG. 10 illustrates a computer system 100 for performing the optimization of multi-epitope constructs, in accordance with one embodiment of the invention. The computer system 100 may be a conventional-type computer which includes processing circuitry, e.g., a central processing unit (CPU), memory, e.g., a hard disk drive (ROM), a random access memory (RAM), cache, and other components, devices and circuitry (not shown) typically found in computers today. In a preferred embodiment, the computer system 100 includes, among other components and devices, a Macintosh G3 333 MHz processor, a six Gigabyte (GB) hard drive, 96 Megabytes of RAM, and 512 Kilobytes (KB) of cache memory, capable of searching 600,000 to 700,000 permutations per second. The computer system 100 further includes a monitor 102 for displaying text, graphics and other information to a user and a keyboard 104 for allowing a user to input data, commands, and other information to the computer system 100.

As shown in FIG. 10, in one embodiment, the computer system 100 may communicate with one or more remote computers 150 through a computer network 160 such that registered users at remote locations can perform the junctional analyses and multi-epitope construct optimization procedures described herein by logging on at the remote computers 150 and supplying a required password or user identification. The computer network 160 may be a local area network (LAN), a wide area network (WAN), or the world-wide web (i.e., Internet). These types of networks are well-known in the art and, therefore, a discussion of these networks and their communication protocols is not provided herein.

In a preferred embodiment, the computer system 100 stores a software program, e.g., object code, in the hard drive memory of the computer system 100. This object code is executed by the CPU for performing the functions described herein. One component, or module, of the software program carries out the function of analyzing and identifying junctional epitopes at the peptide junctions of the polypeptide encoded by a multi-epitope nucleic acid construct as well as evaluating combinations of spacer and flanking residues at these junctions. This software module is referred to herein as the "Junctional Analyzer" module or program. In a preferred embodiment, the Junctional Analyzer analyzes and processes peptides entered by a user in accordance with other criteria, data and operating parameters described below.

FIGS. 11A-B (hereinafter FIG. 11) illustrate an exemplary input text file 200 containing user input data and parameters which is used by the Junctional Analyzer program, in accordance with one embodiment of the invention. As shown in FIG. 11, various types of input data are provided to the program. First, a user may enter a set of peptides or epitopes 202 for processing. A set of weights 204 for each amino acid, when it appears in a C+1 and N−1 position, is also entered into the text file by the user. In one embodiment, the weight values are determined by statistical or empirical analysis of experimental results reflecting the immunogenicity or antigenicity "enhancement" effects of each amino acid when it is placed at the C+1 or N−1 positions of a polypeptide. However, the assignment of weight values for each amino acid may be performed by any number of methodologies, including in vitro and in vivo studies, which would be apparent to those of ordinary skill in the art, depending on the desired criteria used to determine the weight values. Some examples of such experiments or studies are described in further detail below.

In a preferred embodiment, a database containing different epitope/flanking residue combinations is stratified on the basis of epitope immunogenicity and the number of optimal versus suboptimal responses is sorted to rank the amino acids and assign enhancement weight values. The text file also contains a set of motifs 206 to use in detecting junctional epitopes. In a preferred embodiment, the user may also enter a maximum number of amino acids (spacers and flanking) to insert between each pair of peptides (MaxInsertions) 208 to function as spacers and/or flanking residues. Other parameters, values or commands (collectively referred to herein as "parameters") to control the operation of the program may also be entered such as, for example: "OutputToScreen (Y/N)" 210; "OutputToFile (Y/N)" 212; the minimum function value to accept as a valid result ("MinimumAccepted") 214; the maximum number of results having the same function value ("MaxDuplicateFunctionValue") 216; the maximum time allowed for a search in minutes ("SearchTime") 218; whether an Exhaustive Search is desired ("Exhaustive=Y/N") 220; the number of Stochastic search probes ("NumStochasticProbes") 222; the maximum number of hits allowed per single probe during a stochastic search ("MaxHitsPerProbe") 224; and whether the start of each probe should be random or other ("RandomProbeStart(Y/N)") 226. These parameters are provided for purposes of illustration only. Other parameters to control the operation and output format of the program may be entered as would be obvious to those of ordinary skill in the art.

The motifs 206 in the text file 200 provide a "mask" or structural model for identifying junctional epitopes. For example the first motif 206a shown in FIG. 11, XXXX(F or Y)XX(L, I, M or V), defines an epitope that is eight amino acids in length. The value "X" indicates that any amino acid may be at that position of the epitope. The value "(F or Y)" indicates that either an F amino acid or a Y amino acid may be in the fifth position of the epitope. Similarly, "(L, I, M or V)" indicates that any one of the listed amino acids, L, I, M or V, may be in the eighth position of the epitope. Therefore if a sequence of eight amino acids spanning a junction of two peptides satisfies the above motif criteria, it is identified as a junctional epitope.

Figure 12:
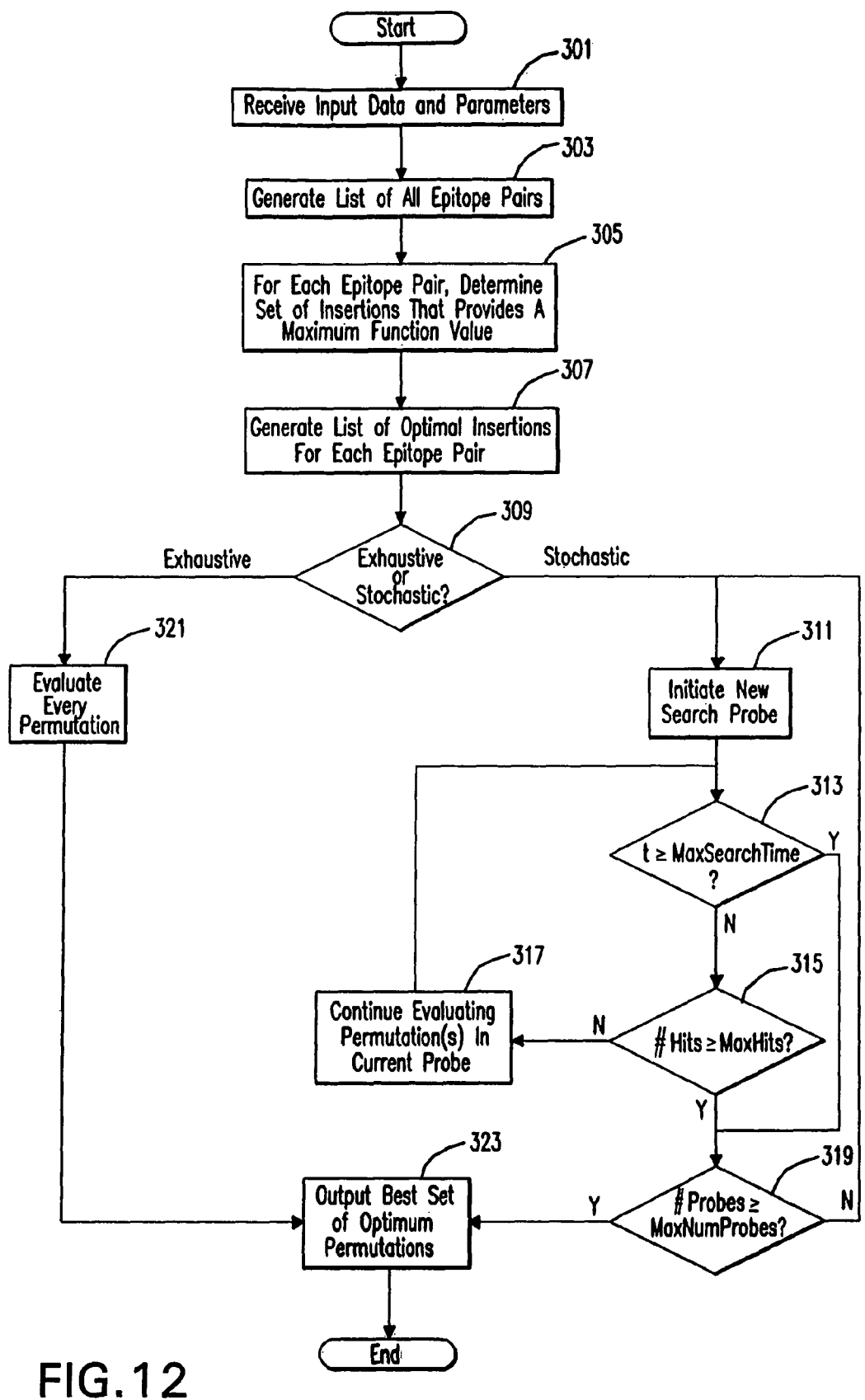
FIG. 12 illustrates a flow chart diagram of a software program for identifying optimal multi-epitope constructs, in accordance with one embodiment of the invention.

FIG. 12 illustrates a flow chart diagram of one embodiment of the Junctional Analyzer program. At step 301, the program receives user inputs and instructions for performing the junctional analysis operation. In a preferred embodiment, the program uses an input text file 200 as shown in FIG. 11 to input parameters 202-226. As is well-known in the art, such a text file may be derived, for example, from a Microsoft Excel™ spreadsheet file or document, to specify desired input parameters (e.g., epitopes, motifs, flanking residue weight values, maximum number of hits, maximum search time, etc.) for its operation. At step 303, the Junctional Analyzer program generates a list of all epitope pairs. For example, if ten epitope sequences are entered by the user, there will be a total of ninety (10×9) epitope (peptide) pairs. Next, at step 305, for each pair of peptides or epitopes, the program determines the set of insertions that results in the minimum number of junctional epitopes and/or the maximum effect from the C+1 and N−1 contribution of spacing residues. To make this determination, the program calculates a function value for each possible combination of spacers for each peptide pair, where the number of spacers can range from 0 to MaxInsertions 208 (FIG. 11) and any arrangement of known or prespecified amino acids may be considered. In a preferred embodiment, the function value is calculated using the following equation: F=(C+N)/J, where C is the enhancement weight value for a flanking amino acid located at the C+1 position of an epitope, N is the enhancement weight value for a flanking amino acid located at the N−1 position of an epitope, and J is the number of junctional epitopes present. Since multiple motifs may be satisfied at one junction of a peptide pair, J may be a number greater than one. When J=0, F=2(C+N). This second equation was chosen because for a fixed value of (C+N), the function value F will double when J changes from two to one, and will double again when J changes from one to zero. It is understood, however, that the above equations are exemplary only and that other equations for evaluating peptide pairs can be easily added to the program at any time. Modifications or changes to the above equations, depending on the desired criteria for emphasis or evaluation, would be readily apparent to those of ordinary skill in the art. At step 307, the program outputs the optimum combination of insertions (spacing and/or flanking residues) for each pair of peptides and the maximum function value for each pair of peptides. In a preferred embodiment, at step 307, the output from this program is generated as an output text file that lists, for each pair of peptides, the insertion that yields the maximum function result.

FIGS. 13A-D (hereinafter FIG. 13) illustrate an exemplary output text file 400 that lists, for each peptide pair, the spacer combination having the maximum function value. In the example shown in FIG. 13, eleven peptides, labeled A-K 202 (FIG. 11), were processed, the Motifs 206 were used to detect junctional epitopes, the enhancement weight values for each potential flanking residue 204 were used, and MaxInsertions 208 was set to four. Other parameters for controlling the operation and format of the Junctional Analyzer program were set as illustrated by the parameter settings 402. For purposes of convenience, in a preferred embodiment, these input parameters are repeated in the output text file 400. The output text file 400 includes an output table 404 which contain the results of steps 305 (FIG. 12). The first column (Col. 1) of the output table 404 indicates the first peptide of a pair. The second column (Col. 2) of the output table lists the first amino acid insertions that function both as a spacer and the C+1 flanking amino acid. The third column lists a second spacer amino acid. The fourth column lists a third spacer amino acid. The fifth column lists a fourth spacer amino acid that is also the N−1 flanking amino acid for the second peptide of the pair which is listed in column six. The seventh column lists the enhancement weight value of the C+1 flanking amino acid listed in column two. The eighth column lists the enhancement weight value of the N−1 flanking amino acid listed in column six 412. The ninth column lists the sum of the C+1 and N−1 enhancement weight values. The tenth column lists the number of junctional epitopes found in the peptide pair and the eleventh column lists the maximum function value for the peptide pair based on the equations listed above. For example, the first row of the output table 404 shows that for the peptide pair A-B, corresponding to the peptides VLAE-AMSQV (SEQ ID NO:7)-ILKEPVHGV (SEQ ID NO:8), the spacer combination of three amino acids, CAL, eliminates all junctional epitopes and provides a maximum function value of 8.80. It is understood, however, that other output options may be implemented in accordance with the invention. For example, the output table 404 may show the top 32 results for each pair of peptides, or show every result for all possible insertions in the order evaluated, or trace the motif search process to generate large output files, depending on the level of detail and/or analysis desired by the user.

In a preferred embodiment, the information contained in the output table 404 is used to perform either an "Exhaustive J Search" or a "Stochastic J Search" to identify a polypeptide construct linking all eleven peptides, including optimum spacer combinations. For eleven peptides, for example, there will be ten junctions. Therefore, the permutation that yields the largest sum of function values taking into account all ten junctions is identified as the "optimum" permutation(s) of the multi-epitope constructs. In one embodiment, for the convenience of the user, the output text file 400 will also contain the original list of peptides/epitopes 202, the weight values used 204, the motifs used 206, and MaxInsertion value 208, and other parameter settings 402 entered into the input text file 200 of FIG. 11.

The "Exhaustive J Search" looks at all permutations of the peptides and selects the ones that have the largest function sum. However, due to the factorial nature of permutations, as the number of peptides to be processed increases, the time required to complete an "Exhaustive J Search" increases almost exponentially. For example, using a standard Macintosh 333 MHz computer, the estimated running time for 13 peptides is approximately 2.9 hours and would be approximately 40 hours for 14 peptides. The "Stochastic J Search" is designed to search many areas of the permutation sequence, rather than the entire permutation space, and report the best function sum that it finds. By reporting only permutations that meet or exceed the current maximum function total, it is possible to search a much broader area of the permutation sequence. This technique has been successful with as many as 20 peptides. The time to perform an exhaustive search of 20 peptides is estimated to be on the order of $1.3\times10^5$ years.

Referring again to FIG. 12, at step 309, the program determines whether to perform an "Exhaustive J Search" or a "Stochastic J Search" of the possible permutations of polypeptides from the output text file 400. In a preferred embodiment, the determination at step 309 is made by the user who inputs whether the search will be Exhaustive or Stochastic as indicated by the input parameter, Exhaustive (Y/N) 220 (FIG. 11). In other embodiments, the program may automatically select either a Stochastic or Exhaustive search depending on the number of peptides to be processed. For example, if less than 14 epitopes are to be included, an "Exhaustive J Search" routine is automatically selected by the program. The Exhaustive search program examines all permutations of the epitopes making up the multi-epitope construct to find the one(s) with the best value for the sum of the optimizing function for all pairs of epitopes. This is guaranteed to find the "best" permutation(s) since all are examined. If 14 or more epitopes are to be included in the multi-epitope construct, a "Stochastic J Search" is used. In a preferred embodiment, the "Stochastic J Search" uses a Monte Carlo technique, known to those of skill in the art, to examine many regions of the permutation space to find the best estimate of the optimum arrangement of the peptides. However, other methods of Stochastic searching may be implemented in accordance with the invention. For example, rather than randomly picking a starting permutation for each stochastic probe, the program may require that each probe begin with a permutation beginning with a different one of the peptides entered by the user. For example, if there were just three peptides, A, B and C, the three probes would begin with, for example, ABC, BAC and CBA. This method provides a fairly uniform coverage of the possible permutations.

If a "Stochastic J Search" has been selected, next, at step 311, the program begins the Stochastic search by initiating a probe. Next, at step 313, the program determines if the maximum search time per probe has been exceeded. If the maximum search time has not been reached, next, at step 315, the program determines whether a single probe has reached or exceeded the maximum number of "hits" per probe. In one embodiment, a probe hit is registered when a permutation's function value sum is the same as or greater than the largest function sum previously registered for one or more previously analyzed permutations. If the maximum number of hits per probe has not been reached, then, at step 317, the current stochastic probe evaluates the next permutation or set of permutations and the process returns step 313. If at step 315 it is determined that the maximum number of hits per probe has been reached or exceeded, then, the program proceeds to step 319, where the program determines whether a maximum number of probes have already been executed. Also, if at step 313, it is determined that the maximum time limit per probe has been reached or exceeded, the program proceeds to step 319 to determine if the maximum number of probes have been completed. If, at step 319, it is determined that the maximum number of probes has not been reached, the program returns to step 311 and a new search probe is initiated. If at step 319 it is determined that the maximum number of probes have been executed, the program then proceeds to step 323 where it outputs the best set of optimum permutations identified up to that point. This "best set" may consist of only those permutations having the highest function sum or, alternatively, may consist of the permutations having the top three highest function sums, for example, or any other output criteria desired by the user.

In one preferred embodiment, if a probe has received a maximum number of hits specified per probe, any unused time for that probe is divided by the remaining probes to decide how much time should be allocated to each of the remaining probes. In other words, if a probe terminates early because of finding too many hits then the remaining probes are allocated more time. This functionality can be easily implemented by those of ordinary skill in the computer programming arts.

If at step 309, an Exhaustive search has been selected, then, at step 321, an exhaustive search is initiated which analyzes every permutation, as described above. At the completion of the Exhaustive analysis, the program proceeds to step 323 where it outputs the "best set" of optimum permutations found. As mentioned above, this "best set" may include those permutations with the highest sum function values, or the top three highest sum function values, or permutations meeting any desired criteria specified by the user (e.g., top 30 permutations with the highest function values).

For each of the decision steps or determination steps discussed above (e.g., steps 313, 315 and 319), the program may be set to perform a query at periodic intervals (e.g., every five seconds) or, alternatively, the program may be set to perform a query after a specified number of permutations (e.g., five) have been analyzed or after every permutation has been analyzed. Any one of these operation and timing protocols is easily implemented and adjusted by those of ordinary skill in the art.

Figure 9A:
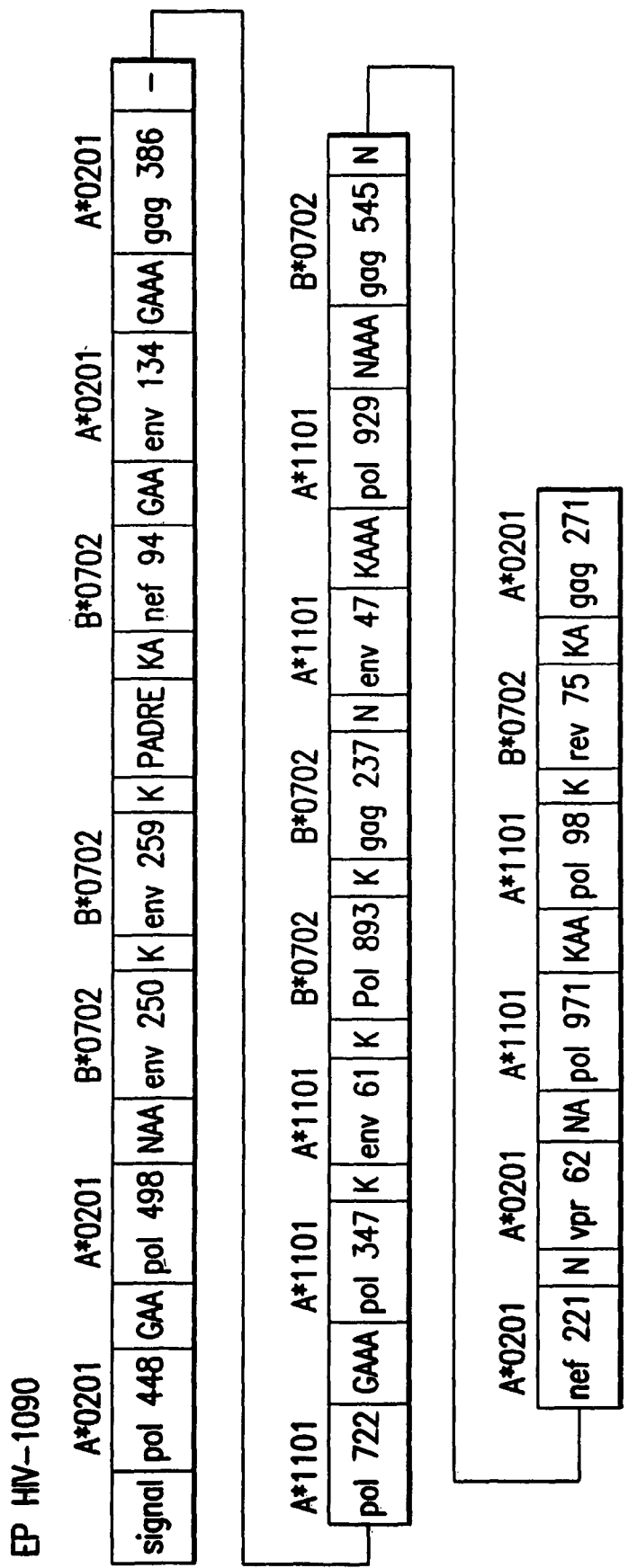
FIG. 9 shows HIV multi-epitope constructs optimized using the methods of the present invention

The Program output provides a list of the best arrangements of the epitopes. Since many permutations may have the same value of the evaluation function, several are generated so that other factors can be considered in choosing the optimum arrangement. Examples of multi-epitope constructs generated using the above-described computerized techniques are illustrated in FIG. 9. An exemplary process flow implemented by the method and system of the invention is provided above. As would be readily apparent to those of ordinary skill, other factors such as charge distribution, hydrophobic/hydrophilic region analysis, or folding prediction could also be incorporated into the evaluation function to further optimize the multi-epitope constructs. In addition, the multi-epitope construct may be further optimized by processing a multi-epitope construct already optimized by the process through the same or similar process one or more additional times. In the subsequent rounds of processing one or more parameters may be modified as compared to the parameters used in the first round of optimization. An example of a multi-epitope construct that was optimized in two rounds is the HBV-30CL construct.

Multi-epitope constructs can also be optimized by considering the resulting macromolecular structure. Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures, within a polypeptide. These structures are commonly known as domains. Domains are portions of a polypeptide that form a compact functional unit of the polypeptide. Typical domains are formed by combinations of secondary structure (e.g., β-sheets and α-helices). "Tertiary structure" refers to the complete three-dimensional structure of a polypeptide monomer. "Quaternary structure" refers to the three dimensional structure formed by the noncovalent association of independent tertiary units.

Structural predictions such as charge distribution, hydrophobic/hydrophilic region analysis, or folding predictions can be performed using sequence analysis programs known to those of skill in the art, for example, hydrophobic and hydrophilic domains can be identified (see, e.g., Kyte & Doolittle, *J. Mol. Biol.* 157:105-132 (1982) and Stryer, *Biochemistry* ($3^{rd}$ ed. 1988); see also any of a number of Internet based sequence analysis programs, such as those found at dot.imgen.bcm.tmc.edu.

A three-dimensional structural model of a multi-epitope construct can also be generated. This is generally performed by entering amino acid sequence to be analyzed into a predictive computer system that can generate a model. The amino acid sequence represents the primary sequence or subsequence of the protein, which encodes the structural information of the protein. The three-dimensional structural model of the protein is then generated by the interaction of the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model. The tertiary structure of the protein encoded by the secondary structure is then formed on the basis of the energy terms of the secondary structure. The user can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like. Those multi-epitope constructs that are most readily accessible to the HLA processing apparatus are then selected.

Assessment of Immunogenicity of Multi-Epitope Vaccines

The development of multi-epitope constructs represents a unique challenge, because the species-specificity of the peptide binding to MHC. Different MHC types from different species tend to bind different sets of peptides (Rammensee et al., *Immunogenetics*, Vol. 41(4):178-228 (1995)). As a result, it is not possible to test in regular laboratory animals a construct composed of human epitopes. Alternatives to overcome this limitation are generally available. They include: 1) testing analogous constructs incorporating epitopes restricted by non-human MHC; 2) reliance on control epitopes restricted by non human MHC; 3) reliance on crossreactivity between human and non-human MHC; 4) the use of HLA transgenic animals; and 5) antigenicity assays utilizing human cells in vivo. The following is a brief overview of the development of the technology for analyzing antigenicity and immunogenicity.

Class I HLA Transgenic Mice

The utility of HLA transgenic mice for the purpose of epitope identification (Sette et al., *J Immunol*, Vol. 153(12): 5586-92 (1994); Wentworth et al., *Int Immunol*, Vol. 8(5): 651-9 (1996); Engelhard et al., *J Immunol*, Vol. 146(4):1226-32 (1991); Man et al., *Int Immunol*, Vol. 7(4):597-605 (1995); Shirai et al., *J Immunol*, Vol. 154(6):2733-42 (1995)), and vaccine development (Ishioka et al., *J Immunol*, Vol. 162(7): 3915-25 (1999)) has been established. Most of the published reports have investigated the use of HLA A2.1/$K^b$ mice but it should be noted that B*27, and B*3501 mice are also available. Furthermore, HLA A*11/$K^b$ mice (Alexander et al., *J Immunol*, Vol. 159(10):4753-61 (1997)), and HLA B7/$K^b$ and HLA A1/$K^b$ mice have also been generated.

Data from 38 different potential epitopes was analyzed to determine the level of overlap between the A2.1-restricted CTL repertoire of A2.1/$K^b$-transgenic mice and A2.1+ humans (Wentworth et al., *Eur J Immunol*, Vol. 26(1):97-101 (1996)). In both humans and mice, an MHC peptide binding affinity threshold of approximately 500 nM correlates with the capacity of a peptide to elicit a CTL response in vivo. A high level of concordance between the human data in vivo and mouse data in vivo was observed for 85% of the high-binding peptides, 58% of the intermediate binders, and 83% of the low/negative binders. Similar results were also obtained with HLA A11 and HLA B7 transgenic mice (Alexander et al., *J Immunol*, Vol. 159(10):4753-61 (1997)). Thus, because of the extensive overlap that exists between T cell receptor repertoires of HLA transgenic mouse and human CTLs, transgenic mice are valuable for assessing immunogenicity of the multi-epitope constructs described herein.

The different specificities of TAP transport as it relates to HLA A11 mice does not prevent the use of HLA-A11 transgenic mice of evaluation of immunogenicity. While both murine and human TAP efficiently transport peptides with an hydrophobic end, only human TAP has been reported to efficiently transport peptides with positively charged C terminal ends, such as the ones bound by A3, A11 and other members of the A3 supertype. This concern does not apply to A2, A1 or B7 because both murine and human TAP should be equally capable of transporting peptides bound by A2, B7 or A1. Consistent with this understanding, Vitiello (Vitiello et al., *J Exp Med*, Vol. 173(4):1007-15 (1991)) and Rotzschke (Rotzschke O, Falk K., *Curr Opin Immunol*, Vol. 6(1):45-51 (1994)) suggested that processing is similar in mouse and human cells, while Cerundolo (Rotzschke O, Falk K., *Curr Opin Immunol*, Vol. 6(1):45-51 (1994)) suggested differences in murine versus human cells, both expressing HLA A3 molecules. However, using HLA A11 transgenics, expression of HLA molecules on T and B cells in vivo has been observed, suggesting that the reported unfavorable specificity of murine TAP did not prevent stabilization and transport of A11/$K^b$ molecules in vivo (Alexander et al., *J Immunol*, Vol. 159(10): 4753-61 (1997)). These data are in agreement with the previous observation that peptides with a charged C-termini could be eluted from murine cells transfected with A11 molecules (Maier et al., *Immunogenetics*; Vol. 40(4):306-8 (1994)). Responses in HLA A11 mice to complex antigens, such as influenza, and most importantly to A11 restricted epitopes encoded by multi-epitope constructs (Ishioka et al., *J Immunol*, Vol. 162(7):3915-25 (1999)) has also been detected. Thus, the TAP issue appears to be of minor concern with transgenic mice.

Another issue of potential relevance in the use of HLA transgenic mice is the possible influence of $\beta 2$ microglobulin on HLA expression and binding specificity. It is well known that human $\beta 2$ binds both human and mouse MHC with higher affinity and stability than mouse $\beta 2$ microglobulin (Shields et al., *Mol Immunol* Vol. 35(14-15):919-28 (1998)). It is also well known that more stable complexes of MHC heavy chain and $\beta 2$ facilitate exogenous loading of MHC Class I (Vitiello et al., *Science*, Vol. 250(4986):1423-6 (1990)). We have examined the potential effect of this variable by generating mice that are double transgenics for HLA/$K^b$ and human $\beta 2$. Expression of human $\beta 2$ was beneficial in the case HLA B7/$K^b$ mice, and was absolutely essential to achieve good expression levels in the case of HLA A1 transgenic mice. Accordingly, HLA/$K^b$ and $\beta 2$ double transgenic mice are currently and routinely bred and utilized by the present inventors. Thus, HLA transgenic mice can be used to model HLA-restricted recognition of four major HLA specificities (namely A2, A11, B7 and A1) and transgenic mice for other HLA specificities can be developed as suitable models for evaluation of immunogenicity.

Antigenicity Testing for Class I Epitopes

Several independent lines of experimentation indicate that the density of Class I/peptide complexes on the cell surface may correlate with the level of T cell priming. Thus, measuring the levels at which an epitope is generated and presented on an APC's surface provides an avenue to indirectly evaluate the potency of multi-epitope nucleic acid vaccines in human cells in vitro. As a complement to the use of HLA Class I transgenic mice, this approach has the advantage of examining processing in human cells. (Ishioka et al., *J Immunol*, Vol. 162(7):3915-25 (1999))

Several possible approaches to experimentally quantitate processed peptides are available. The amount of peptide on the cell surface can be quantitated by measuring the amount of peptide eluted from the APC surface (Sijts et al., *J Immunol*, Vol. 156(2):683-92 (1996); Demotz et al., *Nature*, Vol. 342(6250):682-4 (1989)). Alternatively, the number of peptide-MHC complexes can be estimated by measuring the amount of lysis or lymphokine release induced by infected or transfected target cells, and then determining the concentration of peptide necessary to obtain equivalent levels of lysis or lymphokine release (Kageyama et al., *J Immunol*, Vol. 154 (2):567-76 (1995)).

A similar approach has also been used to measure epitope presentation in multi-epitope nucleic acid-transfected cell lines. Specifically, multi-epitope constructs that are immunogenic in HLA transgenic mice are also processed into optimal epitopes by human cells transfected with the same constructs, and the magnitude of the response observed in transgenic mice correlates with the antigenicity observed with the transfected human target cells (Ishioka et al., *J Immunol*, Vol. 162(7):3915-25 (1999)).

Using antigenicity assays, a number of related constructs differing in epitope order or flanking residues can be transfected into APCs, and the impact of the aforementioned variables on epitope presentation can be evaluated. This can be a preferred system for testing where a relatively large number of different constructs need to be evaluated. Although it requires large numbers of epitope-specific CTLs, protocols that allow for the generation of highly sensitive CTL lines (Alexander-Miller et al., *Proc Natl Acad Sci USA*, Vol. 93(9): 4102-7 (1996)) and also for their expansion to large numbers (Greenberg P. D., Riddell S. R., *Science*, Vol. 285(5427):546-51 (1999)) have been developed to address this potential problem.

It should also be kept in mind that, if the cell selected for the transfection is not reflective of the cell performing APC function in vivo, misleading results could be obtained. Cells of the B cell lineage, which are known "professional" APCs, are typically employed as transfection recipients. The use of transfected B cells of this type is an accepted practice in the field. Furthermore, a good correlation has already been noted between in vitro data utilizing transfected human B cells and in vivo results utilizing HLA transgenic mice, as described in more detail herein.

Measuring HTL Responses

In preferred embodiments, vaccine constructs are optimized to induce Class II restricted immune responses. One method of evaluating multi-epitope constructs including Class II epitopes, is to use HLA-DR transgenic mice. Several groups have produced and characterized HLA-DR transgenic mice (Taneja V., David C. S., *Immunol Rev*, Vol. 169:67-79 (1999)).

An alternative also exists which relies on crossreactivity between certain human MHC molecules and particular MHC molecules expressed by laboratory animals. Bertoni and colleagues (Bertoni et al., *J Immunol*, Vol. 161(8):4447-55 (1998)) have noted that appreciable crossreactivity can be demonstrated between certain HLA Class I supertypes and certain PATR molecules expressed by chimpanzees. Crossreactivity between human and macaques at the level of Class II (Geluk et al., *J Exp Med*, Vol. 177(4):979-87 (1993)) and Class I molecules (Dzuris, et al., *J Immunol.*, July 1999) has also been noted. Finally, it can also be noted that the motif recognized by human HLA B7 supertype is essentially the same as the one recognized by the murine Class I $L^d$ (Rammensee et al., *Immunogenetics*, Vol. 41(4):178-228 (1995)). Of relevance to testing HLA DR restricted epitopes in mice, it has been shown by Wall, et al (Wall et al., *J. Immunol.*, 152:4526-36 (1994)) that similarities exist in the motif of DR1 and $IA^b$. We routinely breed our transgenic mice to take advantage of this fortuitous similarity. Furthermore, we have also shown that most of our peptides bind to $IA^b$, so that we use these mice for the study of CTL and HTL immunogenicity.

Measuring and Quantitating Immune Responses from Clinical Samples

A crucial element to assess vaccine performance is to evaluate its capacity to induce immune responses in vivo. Analyses of CTL and HTL responses against the immunogen, as well as against common recall antigens are commonly used and are known in the art. Assays employed included chromium release, lymphokine secretion and lymphoproliferation assays.

More sensitive techniques such as the ELISPOT assay, intracellular cytokine staining, and tetramer staining have become available in the art. It is estimated that these newer methods are 10- to 100-fold more sensitive than the common CTL and HTL assays (Murali-Krishna et al., *Immunity*, Vol. 8(2):177-87 (1998)), because the traditional methods measure only the subset of T cells that can proliferate in vitro, and may, in fact, be representative of only a fraction of the memory T cell compartment (Ogg G. S., McMichael A. J., *Curr Opin Immunol*, Vol. 10(4):393-6 (1998)). Specifically in the case of HIV, these techniques have been used to measure antigen-specific CTL responses from patients that would have been undetectable with previous techniques (Ogg et al., *Science*, Vol. 279(5359):2103-6 (1998); Gray et al., *J Immunol*, Vol. 162(3):1780-8 (1999); Ogg et al., *J Virol*, Vol. 73(11):9153-60 (1999); Kalams et al., *J Virol*, Vol. 73(8): 6721-8 (1999); Larsson et al., *AIDS*, Vol. 13(7):767-77 (1999); Corne et al., *J Acquir Immune Defic Syndr Hum Retrovirol*, Vol. 20(5):442-7 (1999)).

With relatively few exceptions, direct activity of freshly isolated cells has been difficult to demonstrate by the means of traditional assays (Ogg G. S., McMichael A. J., *Curr Opin Immunol*, Vol. 10(4):393-6 (1998)). However, the increased sensitivity of the newer techniques has allowed investigators to detect responses from cells freshly isolated from infected humans or experimental animals (Murali-Krishna et al., *Immunity*, Vol. 8(2):177-87 (1998); Ogg G. S., McMichael A. J., *Curr Opin Immunol*, Vol. 10(4):393-6 (1998)). The availability of these sensitive assays, which do not depend on an in vitro restimulation step, has greatly facilitated the study of CTL function in natural infection and cancer. In contrast, assays utilized as an endpoint to judge effectiveness of experimental vaccines are usually performed in conjunction with one or more in vitro restimulation steps (Ogg G. S., McMichael A. J., *Curr Opin Immunol*, Vol. 10(4):393-6 (1998)). In fact, with few exceptions (Hanke et al., *Vaccine*, Vol. 16(4):426-35 (1998)), freshly isolated Class I-restricted CD8+ T cells have been difficult to demonstrate in response to immunization with experimental vaccines designed to elicit CTL responses. The use of sensitive assays, such as ELISPOT or in situ IFNγ ELISA, have been combined with a restimulation step to achieve maximum sensitivity; MHC tetramers are also used for this purpose.

MHC tetramers were first described in 1996 by Altman and colleagues. They produced soluble HLA-A2 Class I molecules that were folded with HIV-specific peptides containing a CTL epitope complexed together into tetramers tagged with fluorescent markers. These are used to label populations of T cells from HIV-infected individuals that recognize the epitope (Ogg G. S., McMichael A. J., *Curr Opin Immunol*, Vol. 10(4):393-6 (1998)). These cells were then quantified by flow cytometry, providing a frequency measurement for the T cells that are specific for the epitope. This technique has become very popular in HIV research as well as in other infectious diseases (Ogg G. S., McMichael A. J., *Curr Opin Immunol*, Vol. 10(4):393-6 (1998); Ogg et al., *Science*, Vol. 279(5359):2103-6 (1998); Gray et al., *J Immunol*, Vol. 162 (3):1780-8 (1999); Ogg et al., *J Virol*, Vol. 73(11):9153-60 (1999); Kalams et al., *J Virol*, Vol. 73(8):6721-8 (1999)). However, HLA polymorphism can limit the general applicability of this technique, in that the tetramer technology relies on defined HLA/peptide combinations. However, it has been shown that a variety of peptides, including HIV-derived peptides, are recognized by peptide-specific CTL lines in the context of different members of the A2, A3 and B7 supertypes (Threlkeld et al., *J Immunol*, Vol. 159(4):1648-57 (1997); Bertoni et al., *J Clin Invest*, Vol. 100(3):503-13 (1997)). Taken together these observations demonstrate that a T cell receptor (TCR) for a given MHC/peptide combination can have detectable affinity for the same peptide presented by a different MHC molecule from the same supertype.

In circumstances in which efficacy of a prophylactic vaccine is primarily correlated with the induction of a long-lasting memory response, restimulation assays can be the most appropriate and sensitive measures to monitor vaccine-induced immunological responses. Conversely, in the case of therapeutic vaccines, the main immunological correlate of activity can be the induction of effector T cell function, most aptly measured by primary assays. Thus, the use of sensitive assays allows for the most appropriate testing strategy for immunological monitoring of vaccine efficacy.

Antigenicity of Multi-Epitope Constructs in Transfected Human APC's

Antigenicity assays are performed to evaluate epitope processing and presentation in human cells. An episomal vector to efficiently transfect human target cells with multi-epitope nucleic acid vaccines is used to perform such an analysis.

Figure 8:
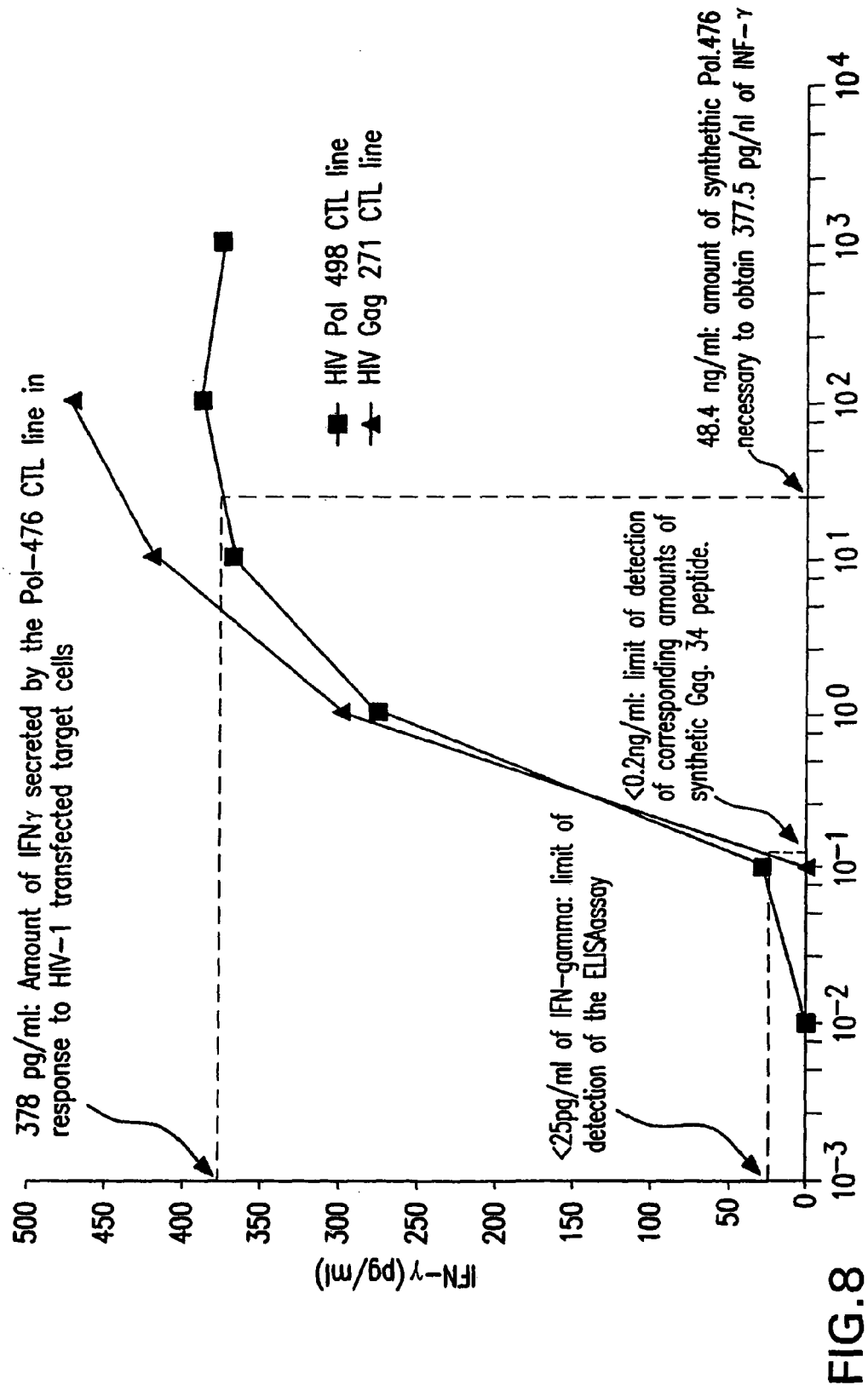
FIG. 8 depicts data for 221A2$K^b$ target cells transfected with the HIV-FT epigene construct. These transfected cells were assayed for their capacity to present epitopes to CTL lines derived from HLA transgenic mice and specific for various HIV-derived CTL epitopes. To correct for differences in antigen sensitivity of different CTL lines, peptide dose titrations, using untransfected cells as APC, were run in parallel.

For example, 221 A2K$^b$ target cells were transfected with an HIV-1 epigene vaccine. The 221 A2K$^b$ target cell expresses the A2K$^b$ gene that is expressed in HLA transgenic mice, but expresses no endogenous Class I (Shimizu Y, DeMars R., *J Immunol*, Vol. 142(9):3320-8 (1989)). These transfected cells were assayed for their capacity to present antigen to CTL lines derived from HLA transgenic mice and specific for various HIV-derived CTL epitopes. To correct for differences in antigen sensitivity of different CTL lines, peptide dose titrations, using untransfected cells as APC, were run in parallel. Representative data is presented in FIG. 8. In the case of HIV Pol 498-specific CTL, the transfected target cells induced the release of 378 pg/ml of IFNγ. Inspection of the peptide dose responses reveals that, 48 ng/ml of exogenously added peptide was necessary to achieve similar levels of IFNγ release. These results demonstrate that relatively large amounts of Pol 498 epitope are presented by the transfected cells, equivalent to 48 ng/ml of exogenously added peptide.

TABLE 5

Comparison between antigenicity in transfected human cells and immunogenicity in HLA transgenic mice of the HIV-1 minigene

| Epitope | Antigenicity | | Immunogenicity | |
|---|---|---|---|---|
| | Peptide Equivalents[1] | n[2] | % response[3] | Magnitude[4] |
| HIV Pol 498 | 30.5 | (6) | 95% | 46.7 |
| HIV Env 134 | 6.2 | (3) | 62% | 16.1 |
| HIV Nef 221 | 2.1 | (5) | 82% | 3.8 |
| HIV Gag 271 | <0.2 | (6) | 31% | 4 |

[1]ng/ml;
[2]number of independent experiments;
[3]% of CTL cultures yielding positive results;
[4]Lytic Units By comparison, less than 25 pg/ml IFNγ was detected utilizing the CTL specific for the Gag 271 epitope. The control peptide titration with untransfected target cells revealed that this negative result could not be ascribed to poor sensitivity of the particular CTL line utilized, because as little as 0.2 pg/ml of "peptide equivalents" (PE) could be detected. Thus, it appears that the Gag 271 epitope is not efficiently processed and presented in the HIV-1 transfected target cells. Utilizing the "peptide equivalents" figure as an approximate quantitation of the efficiency of processing, it can be estimated that at least 200-fold less Gag 271 is presented by the transfected targets, compared to the Pol 498 epitope.

The results of various independent determinations for four different epitopes contained within HIV-FT are compiled in Table 5. The amount of each epitope produced from the HIV-FT transfected cells ranged from 30.5 PE for Pol 498, to a low of less than 0.2 PE for Gag 271. The two epitopes Env 134 and Nef 221 were associated with intermediate values, of 6.1 and 2.1 PE, respectively.

These results were next correlated with the in vivo immunogenicity values observed for each epitope after immunization with the HIV-FT construct. The Pol 498 epitope was also the most immunogenic, as would be predicted. The Env 134 and Nef 221 epitopes, for which intermediate immunogenicity was observed in vivo, were also processed in vitro with intermediate efficiency by the transfected human cells. Finally, the Gag 271, for which no detectable in vitro processing was observed, was also associated with in vivo immunogenicity suboptimal in both frequency and magnitude.

These data have several important implications. First, they suggest that different epitopes contained within a given construct may be processed and presented with differential efficiency. Second, they suggest that immunogenicity is proportional to the amount of processed epitope generated. Finally, these results provide an important validation of the use of transgenic mice for the purpose of optimization of multi-epitope vaccines destined for human use.

III. Preparation of Multi-Epitope Constructs

Epitopes for inclusion in the multi-epitope constructs typically bear HLA Class I or Class II binding motifs, as described for example in PCT applications PCT/US00/27766, or PCT/US00/19774. Multi-epitope constructs can be prepared according to the methods set forth in Ishioka, et al., *J. Immunol.* (1999) 162(7):3915-3925, for example.

Multiple HLA class II or class I epitopes present in a multi-epitope construct can be derived from the same antigen, or from different antigens. For example, a multi-epitope construct can contain one or more HLA epitopes that can be derived from two different antigens of the same virus or from two different antigens of different viruses. Epitopes for inclusion in a multi-epitope construct can be selected by one of skill in the art, e.g., by using a computer to select epitopes that contain HLA allele-specific motifs or supermotifs. The multi-epitope constructs of the invention can also encode one or more broadly cross-reactive binding, or universal, HLA class II epitopes, e.g., PADRE® epitope (Epimmune, San Diego, Calif.), (described, for example, in U.S. Pat. Nos. 5,736,142; 6,413,935; and 5,679,640) or a PADRE® family molecule.

Universal HLA Class II epitopes can be advantageously combined with other HLA Class I and Class II epitopes to increase the number of cells that are activated in response to a given antigen and provide broader population coverage of HLA-reactive alleles. Thus, the multi-epitope constructs of the invention can include HLA epitopes specific for an antigen, universal HLA class II epitopes, or a combination of specific HLA epitopes and at least one universal HLA class II epitope.

HLA Class I epitopes are generally less than about 15 residues in length, preferably 13 residues or less in length and preferably are about 8 to about 13 amino acids in length, more preferably about 8 to about 11 amino acids in length (e.g. 8, 9, 10, or 11), and most preferably about 9 amino acids in length. HLA Class II epitopes are generally less than about 50 residues in length and usually consist of about 6 to about 30 residues, more usually between about 12 to 25, and often about 15 to 20 residues, and can encode an epitope peptide of about 7 to about 23, preferably about 7 to about 17, more preferably about 11 to about 15 (e.g. 11, 12, 13, 14, or 15), and most preferably about 13 amino acids in length. An HLA Class I or II epitope can be derived from any desired antigen of interest. The antigen of interest can be a viral antigen, surface receptor, tumor antigen, oncogene, enzyme, or any pathogen, cell or molecule for which an immune response is desired. Epitopes can be selected based on their ability to bind one or multiple HLA alleles. Epitopes that are analogs of naturally occurring sequences can also be included in the multi-epitope constructs described herein. Such analog peptides are described, for example, in PCT applications PCT/US97/03778, PCT/US00/19774, and co-pending U.S. Ser. No. 09/260,714 filed Mar. 1, 1999.

Figure 20C:
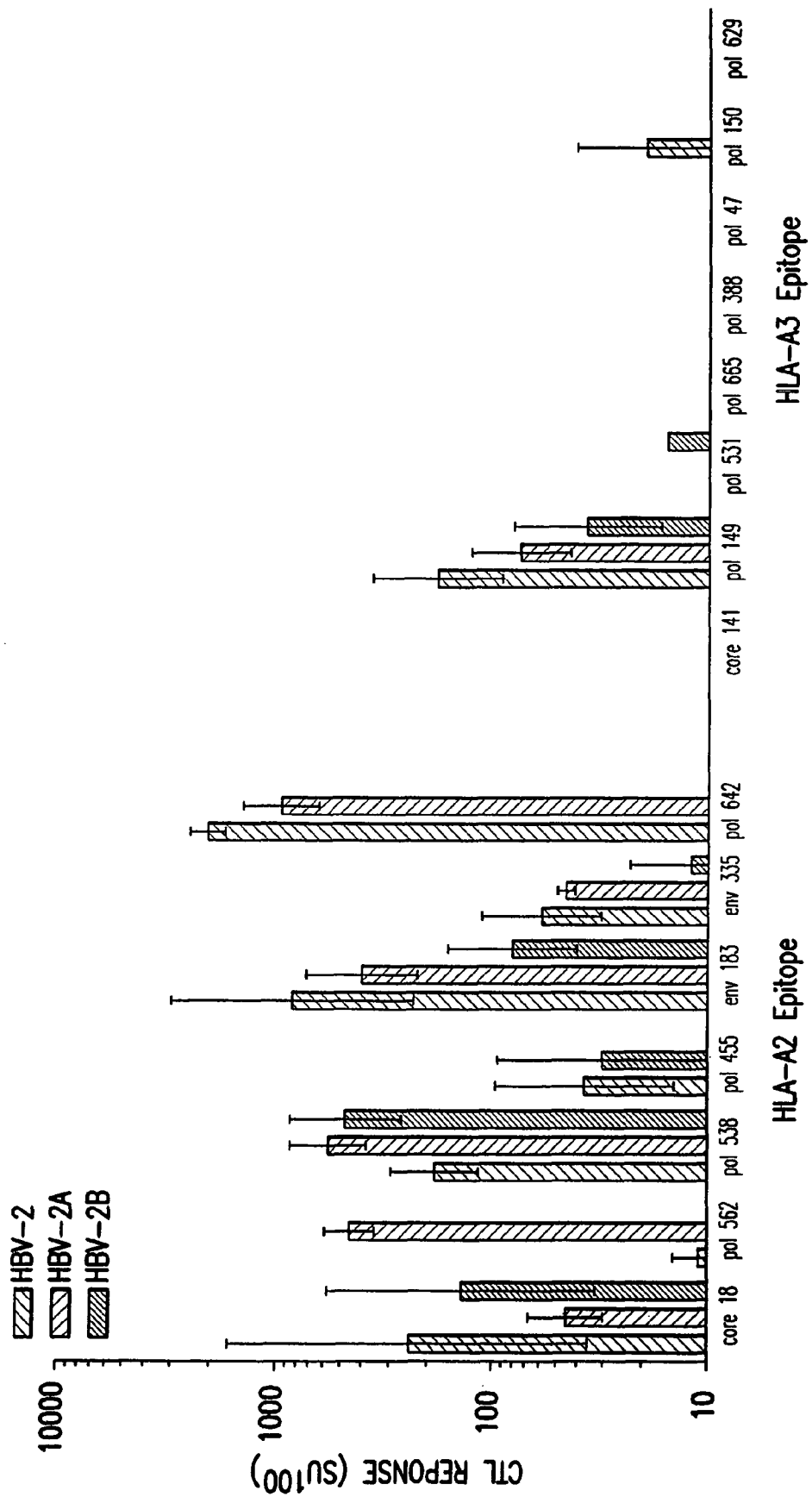
Figure 21C:
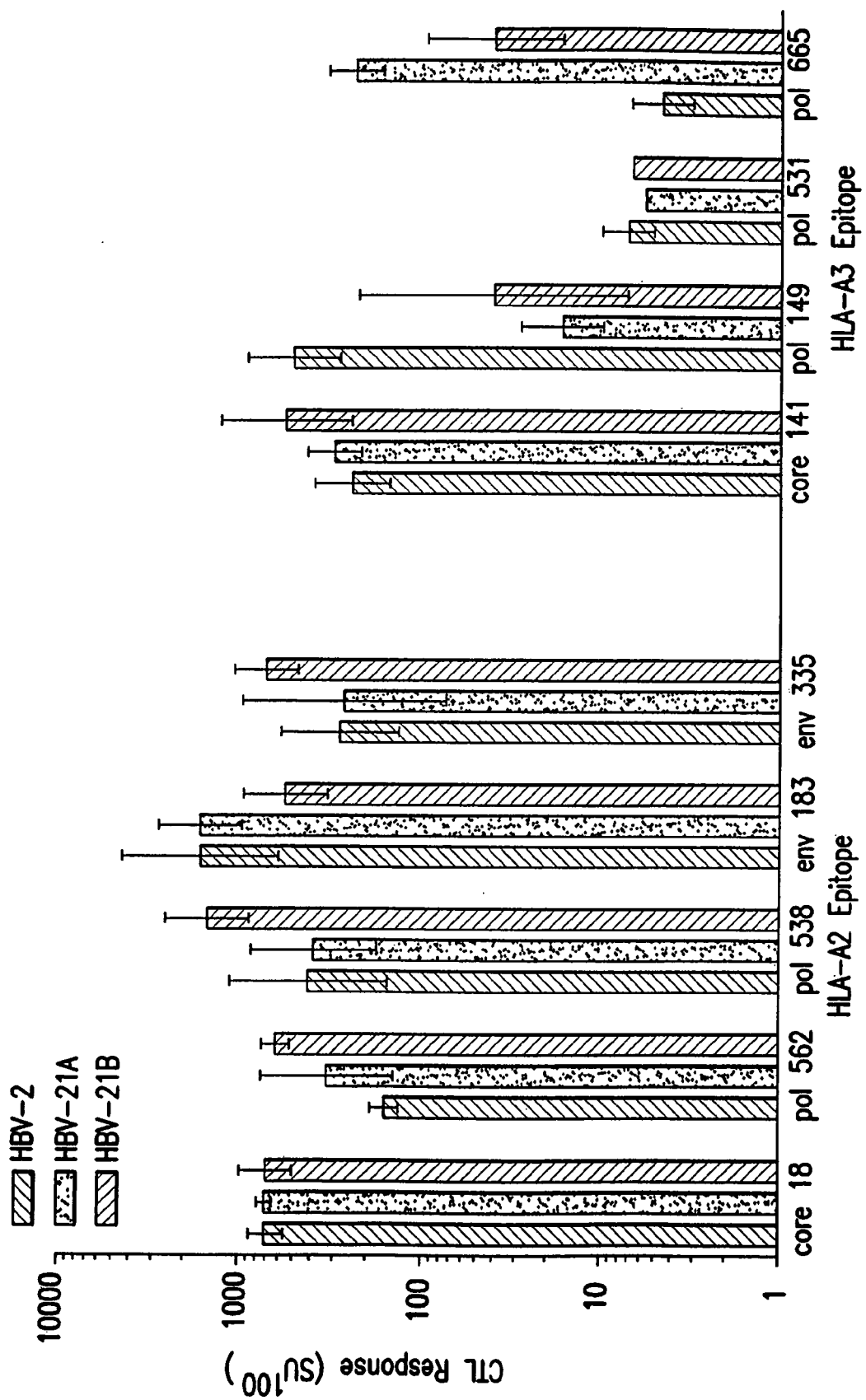
Figure 22C:
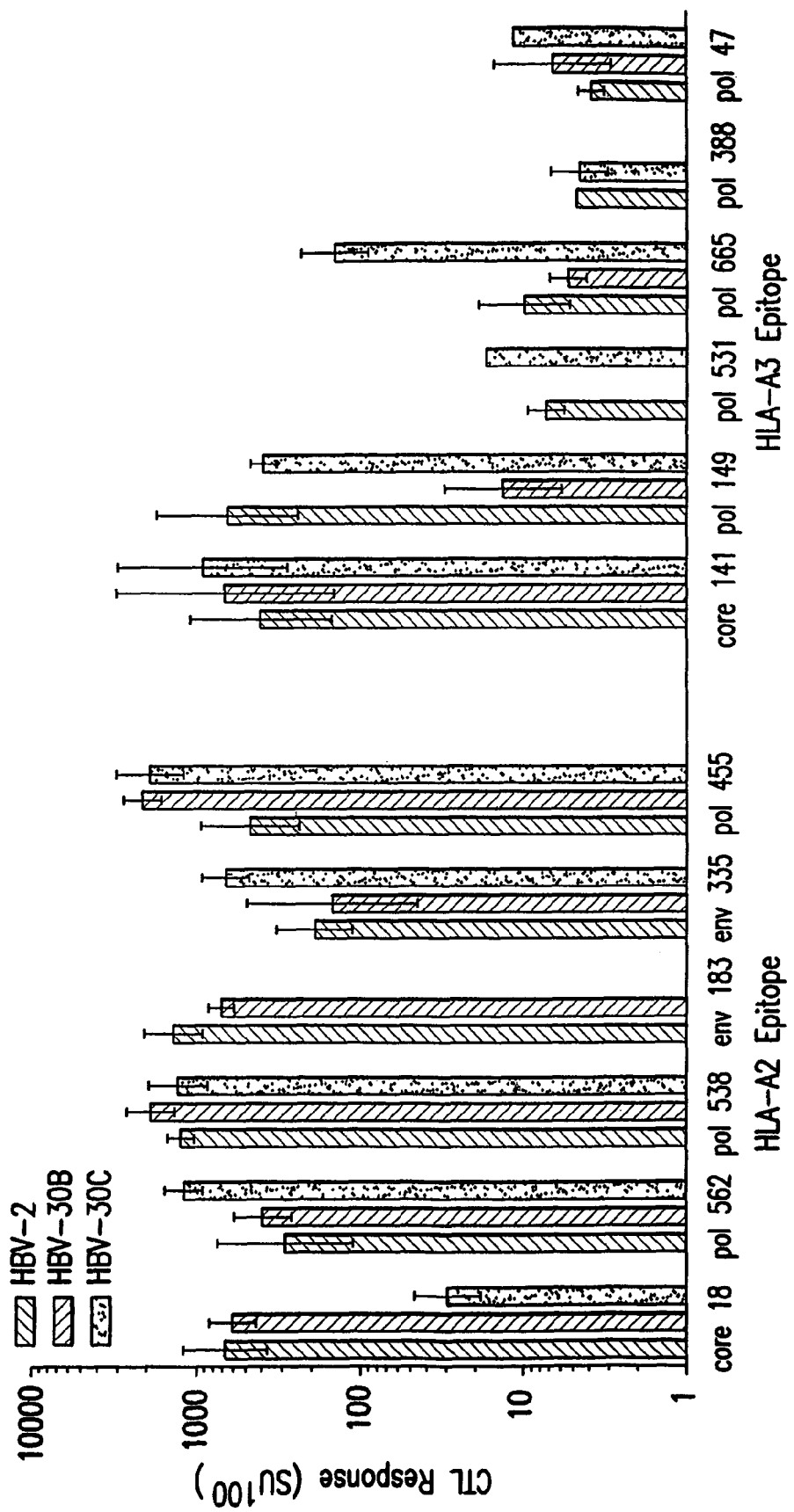
Figure 23A:
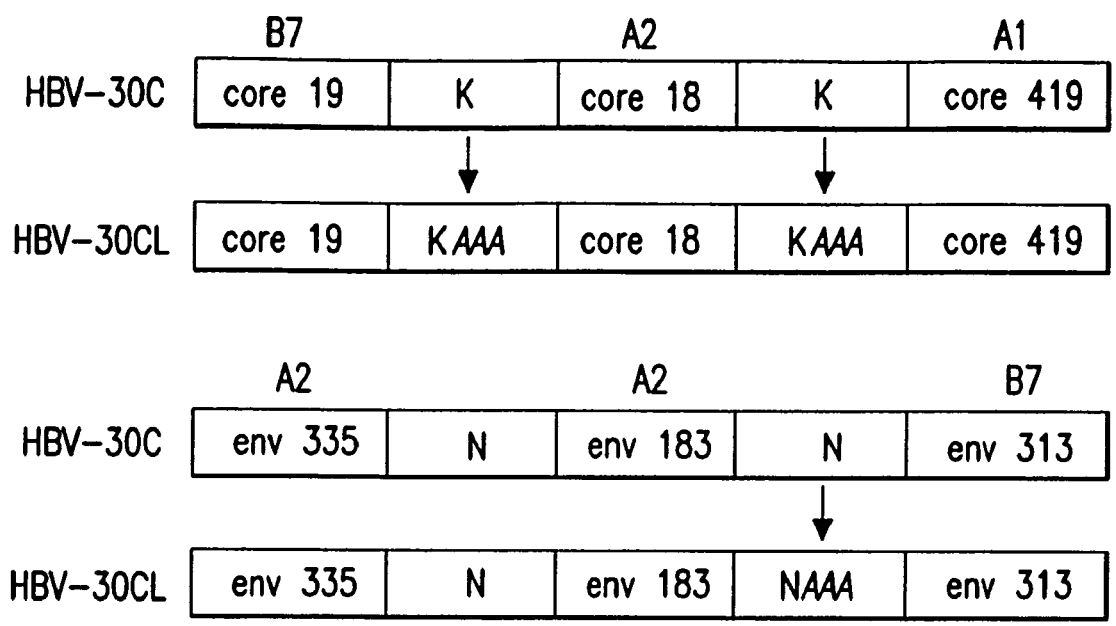
Figure 23B:
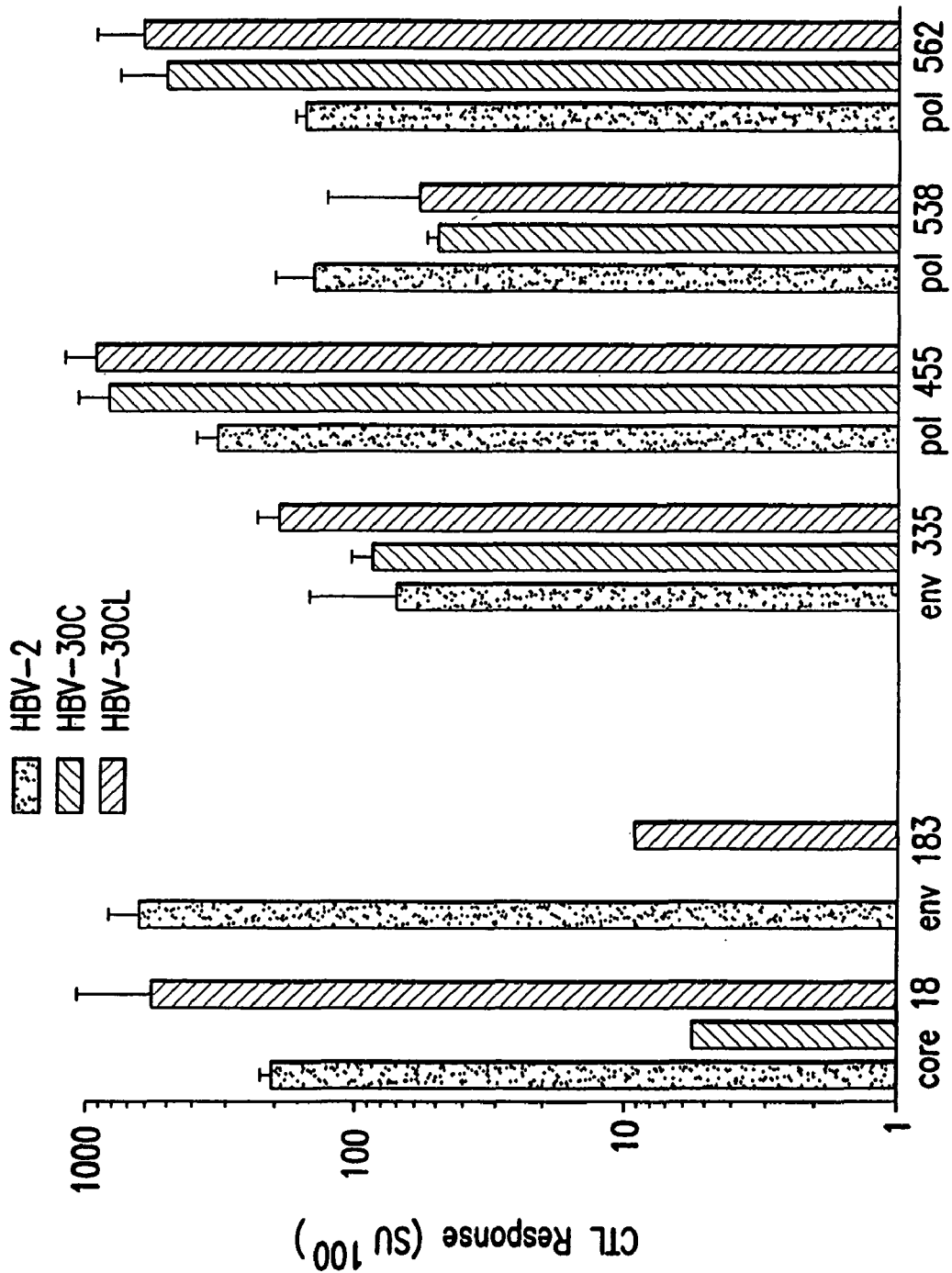
Figure 24B:
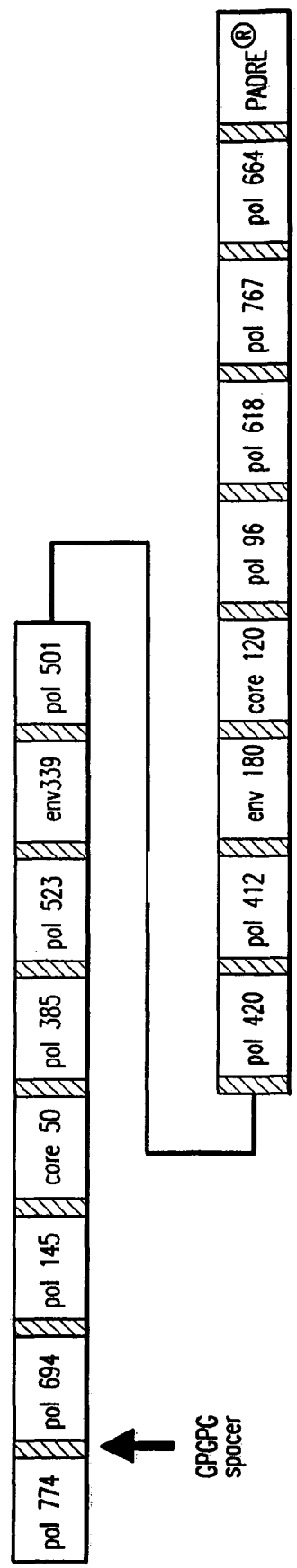

Given the methods described herein for optimizing epitope configuration and spacers between the epitopes, the skilled artisan may include any HLA epitopes into the multi-epitope constructs described herein. FIGS. 2, 3, 9, 17, 18A-18N, 27A, 28A, 29A, and Tables 13, 14, 18, and 19 depict exemplary multi-epitope constructs using epitopes listed in FIGS. 19A-19E. Exemplary constructs are also set forth in FIGS. 20B, 20D, 20E, and 20F (epitopes are listed in FIG. 20A); FIGS. 21B, 21D, and 21E (epitopes are listed in FIG. 21A); FIGS. 22B, 22D, and 22E (epitopes are listed in 22A); FIG. 23C; and FIGS. 24B and 24C (epitopes are listed in FIG. 24A). Multi-epitope constructs may include five or more, or six, seven, eight, nine, ten, eleven, twelve, thirteen, fourteen, fifteen, twenty, twenty-five, or thirty or more of the epitopes set forth in FIGS. 19A-19E, 20A, 21A, 22A, and 24A. Multi-epitope constructs that include any combinations of these epitopes can be optimized using the procedures set forth herein, and spacers can be optimized as well.

Multi-epitope constructs can be generated using methodology well known in the art. For example, polypeptides comprising the multi-epitope constructs can be synthesized and linked. Typically, multi-epitope constructs are constructed using recombinant DNA technology.

IV. Expression Vectors and Construction of a Multi-Epitope Constructs

The multi-epitope constructs of the invention are typically provided as an expression vector comprising a nucleic acid encoding the multi-epitope polypeptide. Construction of such expression vectors is described, for example in PCT/US99/10646. The expression vectors contain at least one promoter element that is capable of expressing a transcription unit encoding the nucleic acid in the appropriate cells of an organism so that the antigen is expressed and targeted to the appropriate HLA molecule. For example, for administration to a human, a promoter element that functions in a human cell is incorporated into the expression vector.

In preferred embodiments, the invention utilizes routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994); *Oligonucleotide Synthesis: A Practical Approach* (Gait, ed., 1984); Kuijpers, *Nucleic Acids Research* 18(17):5197 (1994); Dueholm, *J. Org. Chem.* 59:5767-5773 (1994); *Methods in Molecular Biology*, volume 20 (Agrawal, ed.); and Tijssen, *Laboratory Techniques in Biochemistry and Molecular Biology—Hybridization with Nucleic Acid Probes*, e.g., Part I, chapter 2 "Overview of principles of hybridization and the strategy of nucleic acid probe assays" (1993)).

The nucleic acids encoding the epitopes are assembled in a construct according to standard techniques. In general, the nucleic acid sequences encoding multi-epitope polypeptides are isolated using amplification techniques with oligonucleotide primers, or are chemically synthesized. Recombinant cloning techniques can also be used when appropriate. Oligonucleotide sequences are selected which either amplify (when using PCR to assemble the construct) or encode (when using synthetic oligonucleotides to assemble the construct) the desired epitopes.

Amplification techniques using primers are typically used to amplify and isolate sequences encoding the epitopes of choice from DNA or RNA (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify epitope nucleic acid sequences directly from mRNA, from cDNA, from genomic libraries or cDNA libraries. Restriction endonuclease sites can be incorporated into the primers. Multi-epitope constructs amplified by the PCR reaction can be purified from agarose gels and cloned into an appropriate vector.

Synthetic oligonucleotides can also be used to construct multi-epitope constructs. This method is performed using a series of overlapping oligonucleotides, representing both the sense and non-sense strands of the gene. These DNA fragments are then annealed, ligated and cloned. Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The epitopes of the multi-epitope constructs are typically subcloned into an expression vector that contains a strong promoter to direct transcription, as well as other regulatory sequences such as enhancers and polyadenylation sites. Suitable promoters are well known in the art and described, e.g., in Sambrook et al. and Ausubel et al. Eukaryotic expression systems for mammalian cells are well known in the art and are commercially available. Such promoter elements include, for example, cytomegalovirus (CMV), Rous sarcoma virus long terminal repeats (RSV LTR) and Simian Virus 40 (SV40).

The expression vector typically contains a transcription unit or expression cassette that contains all the additional elements required for the expression of the multi-epitope construct in host cells. A typical expression cassette thus contains a promoter operably linked to the multi-epitope construct and signals required for efficient polyadenylation of the transcript. Additional elements of the cassette may include enhancers and introns with functional splice donor and acceptor sites.

In addition to a promoter sequence, the expression cassette can also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic cells may be used. Expression vectors containing regulatory elements from eukaryotic viruses are typically used as eukaryotic expression vectors, e.g., SV40 vectors, CMV vectors, papilloma virus vectors, and vectors derived from Epstein Bar virus.

The multi-epitope constructs of the invention can be expressed from a variety of vectors including plasmid vectors as well as viral or bacterial vectors. Examples of viral expression vectors include attenuated viral hosts, such as vaccinia or fowlpox. As an example of this approach, vaccinia virus is used as a vector to express nucleotide sequences that encode the peptides of the invention. Upon introduction into a host bearing a tumor, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848.

A wide variety of other vectors useful for therapeutic administration or immunization, e.g. adeno and adeno-associated virus vectors, retroviral vectors, non-viral vectors such as BCG (*Bacille Calmette Guerin*), *Salmonella typhi* vectors, detoxified anthrax toxin vectors, and the like, will be apparent to those skilled in the art.

Immunogenicity and antigenicity of the multi-epitope constructs are evaluated as described herein.

Targeting Sequences

The expression vectors of the invention may encode one or more MHC epitopes operably linked to a MHC targeting sequence, and are referred to herein as "targeting nucleic acids" or "targeting sequences." The use of a MHC targeting sequence enhances the immune response to an antigen, relative to delivery of antigen alone, by directing the peptide epitope to the site of MHC molecule assembly and transport to the cell surface, thereby providing an increased number of MHC molecule-peptide epitope complexes available for binding to and activation of T cells.

MHC Class I targeting sequences can be used in the present invention, e.g., those sequences that target an MHC Class I epitope peptide to a cytosolic pathway or to the endoplasmic reticulum (see, e.g., Rammensee et al., *Immunogenetics* 41:178-228 (1995)). For example, the cytosolic pathway processes endogenous antigens that are expressed inside the cell. Although not wishing to be bound by any particular theory, cytosolic proteins are thought to be at least partially degraded by an endopeptidase activity of a proteasome and then transported to the endoplasmic reticulum by the TAP molecule (transporter associated with processing). In the endoplasmic reticulum, the antigen binds to MHC Class I molecules. Endoplasmic reticulum signal sequences bypass the cytosolic processing pathway and directly target endogenous antigens to the endoplasmic reticulum, where proteolytic degradation into peptide fragments occurs. Such MHC Class I targeting sequences are well known in the art, and include, e.g., signal sequences such as those from Ig kappa, tissue plasminogen activator or insulin. A preferred signal peptide is the human Ig kappa chain sequence. Endoplasmic reticulum signal sequences can also be used to target MHC Class II epitopes to the endoplasmic reticulum, the site of MHC Class I molecule assembly. MHC Class II targeting sequences can also be used in the invention, e.g., those that target a peptide to the endocytic pathway. These targeting sequences typically direct extracellular antigens to enter the endocytic pathway, which results in the antigen being transferred to the lysosomal compartment where the antigen is proteolytically cleaved into antigen peptides for binding to MHC Class II molecules. As with the normal processing of exogenous antigen, a sequence that directs a MHC Class II epitope to the endosomes of the endocytic pathway and/or subsequently to lysosomes, where the MHC Class II epitope can bind to a MHC Class II molecule, is a MHC Class II targeting sequence. For example, a group of MHC Class II targeting sequences useful in the invention are lysosomal targeting sequences, which localize polypeptides to lysosomes. Since MHC Class II molecules typically bind to antigen peptides derived from proteolytic processing of endocytosed antigens in lysosomes, a lysosomal targeting sequence can function as a MHC Class II targeting sequence. Lysosomal targeting sequences are well known in the art and include sequences found in the lysosomal proteins LAMP-1 and LAMP-2 as described by August et al. (U.S. Pat. No. 5,633,234, issued May 27, 1997), which is incorporated herein by reference.

Other lysosomal proteins that contain lysosomal targeting sequences include HLA-DM. HLA-DM is an endosomal/lysosomal protein that functions in facilitating binding of antigen peptides to MHC Class II molecules. Since it is located in the lysosome, HLA-DM has a lysosomal targeting sequence that can function as a MHC Class II molecule targeting sequence (Copier et al., *J. Immunol.* 157:1017-1027 (1996), which is incorporated herein by reference).

The resident lysosomal protein HLA-DO can also function as a lysosomal targeting sequence. In contrast to the resident lysosomal proteins LAMP-1 and HLA-DM, which encode specific Tyr-containing motifs that target proteins to lysosomes, HLA-DO is targeted to lysosomes by association with HLA-DM (Liljedahl et al., *EMBO J.* 15:4817-4824 (1996)), which is incorporated herein by reference. Therefore, the sequences of HLA-DO that cause association with HLA-DM and, consequently, translocation of HLA-DO to lysosomes can be used as MHC Class II targeting sequences. Similarly, the murine homolog of HLA-DO, H2-DO, can be used to derive a MHC Class II targeting sequence. A MHC Class II epitope can be fused to HLA-DO or H2-DO and targeted to lysosomes.

In another example, the cytoplasmic domains of B cell receptor subunits Ig-α and Ig-β mediate antigen internalization and increase the efficiency of antigen presentation as described in, for example, Bonnerot et al., *Immunity* 3:335-347 (1995). Therefore, the cytoplasmic domains of the Ig-α and Ig-β proteins can function as MHC Class II targeting sequences that target a MHC Class II epitope to the endocytic pathway for processing and binding to MHC Class II molecules.

Another example of a MHC Class II targeting sequence that directs MHC Class II epitopes to the endocytic pathway is a sequence that directs polypeptides to be secreted, where the polypeptide can enter the endosomal pathway. These MHC Class II targeting sequences that direct polypeptides to be secreted mimic the normal pathway by which exogenous, extracellular antigens are processed into peptides that bind to MHC Class II molecules. Any signal sequence that functions to direct a polypeptide through the endoplasmic reticulum and ultimately to be secreted can function as a MHC Class II targeting sequence so long as the secreted polypeptide can enter the endosomal/lysosomal pathway and be cleaved into peptides that can bind to MHC Class II molecules.

In another example, the Ii protein binds to MHC Class II molecules in the endoplasmic reticulum, where it functions to prevent peptides present in the endoplasmic reticulum from binding to the MHC Class II molecules. Therefore, fusion of a MHC Class II epitope to the Ii protein targets the MHC Class II epitope to the endoplasmic reticulum and a MHC Class II molecule. For example, the CLIP sequence of the Ii protein can be removed and replaced with a MHC Class II epitope sequence so that the MHC Class II epitope is directed to the endoplasmic reticulum, where the epitope binds to a MHC Class II molecule.

In some cases, antigens themselves can serve as MHC Class II or I targeting sequences and can be fused to a universal MHC Class II epitope to stimulate an immune response. Although cytoplasmic viral antigens are generally processed and presented as complexes with MHC Class I molecules, long-lived cytoplasmic proteins such as the influenza matrix protein can enter the MHC Class II molecule processing pathway as described in, for example, Guéguen & Long, *Proc. Natl. Acad. Sci. USA* 93:14692-14697 (1996). Therefore, long-lived cytoplasmic proteins can function as a MHC Class I and/or MHC Class II targeting sequence. For example, an expression vector encoding influenza matrix protein fused to a universal MHC Class II epitope can be advantageously used to target influenza antigen and the universal MHC Class II epitope to the MHC Class I and MHC Class II pathway for stimulating an immune response to influenza.

Other examples of antigens functioning as MHC Class II targeting sequences include polypeptides that spontaneously form particles. The polypeptides are secreted from the cell that produces them and spontaneously form particles, which are taken up into an antigen-presenting cell by endocytosis such as receptor-mediated endocytosis or are engulfed by phagocytosis. The particles are proteolytically cleaved into antigen peptides after entering the endosomal/lysosomal pathway.

One such polypeptide that spontaneously forms particles is HBV surface antigen (HBV-S) as described in, for example, Diminsky et al., *Vaccine* 15:637-647 (1997) or Le Borgne et al., *Virology* 240:304-315 (1998). Another polypeptide that spontaneously forms particles is HBV core antigen as described in, for example, Kuhröber et al., *International Immunol.* 9:1203-1212 (1997). Still another polypeptide that spontaneously forms particles is the yeast Ty protein as described in, for example, Weber et al., *Vaccine* 13:831-834 (1995). For example, an expression vector containing HBV-S antigen fused to a universal MHC Class II epitope can be advantageously used to target HBV-S antigen and the universal MHC Class II epitope to the MHC Class II pathway for stimulating an immune response to HBV.

Administration In Vivo

The invention also provides methods for stimulating an immune response by administering an expression vector of the invention to an individual. Administration of an expression vector of the invention for stimulating an immune response is advantageous because the expression vectors of the invention target MHC epitopes to MHC molecules, thus increasing the number of CTL and HTL activated by the antigens encoded by the expression vector.

Initially, the expression vectors of the invention are screened in mouse to determine the expression vectors having optimal activity in stimulating a desired immune response. Initial studies are therefore carried out, where possible, with mouse genes of the MHC targeting sequences. Methods of determining the activity of the expression vectors of the invention are well known in the art and include, for example, the uptake of $^3$H-thymidine to measure T cell activation and the release of $^{51}$Cr to measure CTL activity as described below in Examples II and III. Experiments similar to those described in Example IV are performed to determine the expression vectors having activity at stimulating an immune response. The expression vectors having activity are further tested in human. To circumvent potential adverse immunological responses to encoded mouse sequences, the expression vectors having activity are modified so that the MHC Class I or MHC Class II targeting sequences are derived from human genes. For example, substitution of the analogous regions of the human homologs of genes containing various MHC Class I or MHC Class II targeting sequences are substituted into the expression vectors of the invention. Expression vectors containing human MHC Class I or MHC Class II targeting sequences, such as those described in Example I below, are tested for activity at stimulating an immune response in human.

The invention also relates to pharmaceutical compositions comprising a pharmaceutically acceptable carrier and an expression vector of the invention. Pharmaceutically acceptable carriers are well known in the art and include aqueous or non-aqueous solutions, suspensions and emulsions, including physiologically buffered saline, alcohol/aqueous solutions or other solvents or vehicles such as glycols, glycerol, oils such as olive oil or injectable organic esters.

A pharmaceutically acceptable carrier can contain physiologically acceptable compounds that act, for example, to stabilize the expression vector or increase the absorption of the expression vector. Such physiologically acceptable compounds include, for example, carbohydrates, such as glucose, sucrose or dextrans, antioxidants such as ascorbic acid or glutathione, chelating agents, low molecular weight polypeptides, antimicrobial agents, inert gases or other stabilizers or excipients. Expression vectors can additionally be complexed with other components such as peptides, polypeptides and carbohydrates. Expression vectors can also be complexed to particles or beads that can be administered to an individual, for example, using a vaccine gun. One skilled in the art would know that the choice of a pharmaceutically acceptable carrier, including a physiologically acceptable compound, depends, for example, on the route of administration of the expression vector.

The invention further relates to methods of administering a pharmaceutical composition comprising an expression vector of the invention to stimulate an immune response. The expression vectors are administered by methods well known in the art as described in, for example, Donnelly et al. (*Ann. Rev. Immunol.* 15:617-648 (1997)); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997). In one embodiment, the multi-epitope construct is administered as naked nucleic acid.

A pharmaceutical composition comprising an expression vector of the invention can be administered to stimulate an immune response in a subject by various routes including, for example, orally, intravaginally, rectally, or parenterally, such as intravenously, intramuscularly, subcutaneously, intraorbitally, intracapsularly, intraperitoneally, intracisternally or by passive or facilitated absorption through the skin using, for example, a skin patch or transdermal iontophoresis, respectively. Furthermore, the composition can be administered by injection, intubation or topically, the latter of which can be passive, for example, by direct application of an ointment or powder, or active, for example, using a nasal spray or inhalant. An expression vector also can be administered as a topical spray, in which case one component of the composition is an appropriate propellant. The pharmaceutical composition also can be incorporated, if desired, into liposomes, microspheres or other polymer matrices as described in, for example, Felgner et al., U.S. Pat. No. 5,703,055; Gregoriadis, *Liposome Technology*, Vols. I to III (2nd ed. 1993). Liposomes, for example, which consist of phospholipids or other lipids, are nontoxic, physiologically acceptable and metabolizable carriers that are relatively simple to make and administer.

The expression vectors of the invention can be delivered to the interstitial spaces of tissues of an animal body as described in, for example, Felgner et al., U.S. Pat. Nos. 5,580,859 and 5,703,055. Administration of expression vectors of the invention to muscle is a particularly effective method of administration, including intradermal and subcutaneous injections and transdermal administration. Transdermal administration, such as by iontophoresis, is also an effective method to deliver expression vectors of the invention to muscle. Epidermal administration of expression vectors of the invention can also be employed. Epidermal administration involves mechanically or chemically irritating the outermost layer of epidermis to stimulate an immune response to the irritant (Carson et al., U.S. Pat. No. 5,679,647).

Other effective methods of administering an expression vector of the invention to stimulate an immune response include mucosal administration as described in, for example, Carson et al., U.S. Pat. No. 5,679,647. For mucosal administration, the most effective method of administration includes intranasal administration of an appropriate aerosol containing the expression vector and a pharmaceutical composition. Suppositories and topical preparations are also effective for delivery of expression vectors to mucosal tissues of genital, vaginal and ocular sites. Additionally, expression vectors can be complexed to particles and administered by a vaccine gun.

The dosage to be administered is dependent on the method of administration and will generally be between about 0.1 μg up to about 200 μg. For example, the dosage can be from about 0.05 μg/kg to about 50 mg/kg, in particular about 0.005-5 mg/kg. An effective dose can be determined, for example, by measuring the immune response after administration of an expression vector. For example, the production of antibodies specific for the MHC Class II epitopes or MHC Class I epitopes encoded by the expression vector can be measured by methods well known in the art, including ELISA or other immunological assays. In addition, the activation of T helper cells or a CTL response can be measured by methods well known in the art including, for example, the uptake of $^3$H-thymidine to measure T cell activation and the release of $^{51}$Cr to measure CTL activity (see Examples II and III below).

The pharmaceutical compositions comprising an expression vector of the invention can be administered to mammals, particularly humans, for prophylactic or therapeutic purposes. Examples of diseases that can be treated or prevented using the expression vectors of the invention include infection with HBV, HCV, HIV and CMV as well as prostate cancer, renal carcinoma, cervical carcinoma, lymphoma, condyloma acuminatum and acquired immunodeficiency syndrome (AIDS).

In therapeutic applications, the expression vectors of the invention are administered to an individual already suffering from cancer, autoimmune disease or infected with a virus. Those in the incubation phase or acute phase of the disease can be treated with expression vectors of the invention, including those expressing all universal MHC Class II epitopes, separately or in conjunction with other treatments, as appropriate.

In therapeutic and prophylactic applications, pharmaceutical compositions comprising expression vectors of the invention are administered to a patient in an amount sufficient to elicit an effective immune response to an antigen and to ameliorate the signs or symptoms of a disease. The amount of expression vector to administer that is sufficient to ameliorate the signs or symptoms of a disease is termed a therapeutically effective dose. The amount of expression vector sufficient to achieve a therapeutically effective dose will depend on the pharmaceutical composition comprising an expression vector of the invention, the manner of administration, the state and severity of the disease being treated, the weight and general state of health of the patient and the judgment of the prescribing physician.

EXAMPLES

The following examples are offered to illustrate, but not to limit the claimed invention. It is understood that the examples and embodiments described herein are for illustrative purposes only and that various modifications or changes in light thereof are suggested to persons skilled in the art and are to be included within the spirit and purview of this application and scope of the appended claims.

Examples 1-9 provide examples of assays for evaluating the immunogenicity and antigenicity of multi-epitope constructs.

Example 1

Antigenicity Assays

High-affinity peptide-specific CTL lines can be generated from splenocytes of transgenic mice that have been primed with DNA, peptide/IFA, or lipopeptide. Briefly, splenocytes from transgenic mice are stimulated 0.1 μg/ml peptide and LPS blasts. Ten days after the initial stimulation, and weekly thereafter, cells are restimulated with LPS blasts pulsed for 1 hour with 0.1 μg/ml peptide. CTL lines are assayed 5 days following restimulation in an in situ IFNγ ELISA as described above. Alternatively, CTL lines that are derived from, e.g., patients infected with the targeted pathogen or who have the targeted disease, e.g., cancer, can be used. Specific CTL lines that are not available either from transgenic mice or from patients are generated from PBMC of normal donors, drawing on the expertise in the art.

Target cells to be used in these assays are Jurkat or 0.221 cells transfected with A2.1/$K^b$, A11/$K^b$, A1/$K^b$, or B7/$K^b$ for CTL lines derived from transgenic mice. All these cell lines are currently available to us (Epimmune Inc., San Diego, Calif.). In the case of human CTL lines, 0.221 cells transfected with the appropriate human HLA allele are utilized. We currently have 0.221 cells transfected with A2 and A1, and are generating A11, A24 and B7 transfectants. In an alternative embodiment, if unforeseen problems arise in respect to target cells, LPS blasts and EBV-transformed lines are utilized for murine and human CTL lines, respectively.

To assay for antigenicity, serially diluted CTLs are incubated with $10^5$ target cells and multiple peptide concentrations ranging from 1 to $10^{-6}$ μg/ml. In addition, CTLs are also incubated with target cells transfected with an episomal vector containing a multi-epitope construct of interest. Episomal vectors are known in the art.

The relative amount of peptide generated by natural processing within the multi-epitope nucleic acid-transfected APCs is quantitated as follows. The amount of IFNγ generated by the CTL lines upon recognition of the transfected target cells are recorded. The amount of synthetic peptide necessary to yield the same amount of IFNγ are interpolated from a standard curve generated when the same CTL line is incubated in parallel with known concentrations of peptide.

Example 2

Mice, Immunizations and Cell Cultures

The derivation of the HLA-A2.1/$K^b$ (Vitiello et al., *J Exp Med*, Vol. 173(4):1007-15 (1991)) and A11/$K^b$ (Alexander et al., *J Immunol*, Vol. 159(10):4753-61 (1997)) transgenic mice used in this study has been described. HLA B7 $K^b$ transgenic mice are available in house (Epimmune Inc., San Diego, Calif.). HLA DR2, DR3 and DR4 transgenic mice are obtained from C. David (Mayo Clinic). Non-transgenic H-$2^b$ mice are purchased from Charles River Laboratories or other commercial vendors. Immunizations are performed as described in (Ishioka et al., *J Immunol*, Vol. 162(7):3915-25 (1999)). All cells are grown in culture medium consisting of RPMI 1640 medium with HEPES (Gibco Life Technologies) supplemented with 10% FBS, 4 mM L-glutamine, 50 μM 2-ME, 0.5 mM sodium pyruvate, 100 μg/ml streptomycin and 100 U/ml penicillin.

HLA transgenic mice and antigenicity assays are used for the purpose of testing and optimization CTL responses. The natural crossreactivity between HLA-DR and $IA^b$ can also be exploited to test HTL responses. This evaluation provides an assessment of the antigenicity and immunogenicity of multi-epitope constructs.

Example 3

Proliferation Assays

To assess the ability of HTL epitopes to induce an immune response, assays such as proliferation assays are often performed. For example, mouse CD4 T lymphocytes are immunomagnetically isolated from splenic single cell suspensions using DynaBeads Mouse CD4 (L3T4) (Dynal). Briefly, $2\times10^7$ spleen cells are incubated with $5.6\times10^7$ magnetic beads for 40 minutes at 4° C., and then washed 3 times. Magnetic beads are detached using DetachaBead Mouse CD4 (Dynal). Isolated CD4 T lymphocytes ($2\times10^5$ cells/well) are cultured with $5\times10^5$ irradiated (3500 rad) syngeneic spleen cells in triplicate in flat-bottom 96-well microtiter plates. Purified peptides are added to wells at a final concentration of 20, 1, 0.05 and 0 μg/ml and cells are cultured for a total of 4 days. Approximately 14 hour before harvesting, 1 μCi of $^3$H-thymidine (ICN) is added to each well. The wells are harvested onto Unifilter GF/B plates (Packard) using the Filtermate Harvester (Packard). $^3$H-Thymidine incorporation is determined by liquid scintillation counting using the TopCount™ microplate scintillation counter (Packard).

Example 4

$^{51}$Chromium Release Assay

This assay to measure CTL activity is well known in the art. The assay quantifies the lytic activity of the T cell population by measuring the percent $^{51}$Cr released from a $^{51}$Cr-labeled target population (Brunner et al., *Immunology*, Vol. 14(2): 181-96 (1968)). Data derived from the chromium release assay is usually expressed either as a CTL frequency/$10^6$ cell (limiting dilution analysis, LDA; (*Current Protocols in Immunology*, Vol 1, John Wiley & Sons, Inc., USA 1991 Chapter 3; *Manual of Clinical Laboratory Immunology*, Fifth edition, ASM Press, 1997 Section R), or by a less cumbersome quantitative assessment of bulk CTL activity (lytic Units; LU assay). In a LU assay, the standard E:T ratio versus percent cytotoxicity data curves generated in a $^{51}$Cr-release assay are converted into lytic units (LU) per $10^6$ effector cells, with 1 LU defined as the lytic activity required to achieve 30% lysis of target cells (Wunderlick, J., Shearer, G., and Livingston, A. In: J. Coligan, A. Kruisbeek, D. Margulies, E. Shevach, and W. Strober (Eds.), *Current Protocols in Immunology*, Vol 1, "Assays for T cell function: induction and measurement of cytotoxic T lymphocyte activity." John Wiley & Sons, Inc., USA, p. 3.11.18). The LU calculation allows quantifying responses and thus readily comparing different experimental values.

Example 5

In Situ IFNγ ELISA

An in situ IFNγ ELISA assay has been developed and optimized for both freshly isolated and peptide-restimulated splenocytes (see, e.g., McKinney et al., *J. Immunol. Meth.* 237 (1-2):105-117 (2000)). This assay is based on the ELISPOT assay, but utilizes a soluble chromagen, making it readily adaptable to high-throughput analysis. In both the primary and restimulation assays, this technique is more sensitive than either a traditional supernatant ELISA or the $^{51}$Cr-release assay, in that responses are observed in the in situ ELISA that are not detectable in these other assays. On a per cell basis, the sensitivity of the in situ ELISA is approximately one IFNγ secreting cell/$10^4$ plated cells.

96-well ELISA plates are coated with anti-IFNγ (rat anti-mouse IFNα MAb, Clone R4-6A2, Pharmingen) overnight at 4° C., and then blocked for 2 hours at room temperature with 10% FBS in PBS. Serially diluted primary splenocytes or CTLs are cultured for 20 hours with peptide and $10^5$ Jurkat A2.1/$K^b$ cells/well at 37° C. with 5% $CO_2$. The following day, the cells are washed out and the amount of IFNγ that had been secreted into the wells is detected in a sandwich ELISA, using biotinylated α-IFNγ (rat anti-mouse IFNγ mAb, Clone XMG1.2, Pharmingen) to detect the secreted IFNγ. HRP-coupled strepavidin (Zymed) and TMB (ImmunoPure® TMB Substrate Kit, Pierce) are used according to the manufacturer's directions for color development. The absorbance is read at 450 nm on a Labsystems Multiskan RC ELISA plate reader. In situ IFNγ ELISA data is evaluated in secretory units (SU), based on the number of cells that secrete 100 pg of IFNγ in response to a particular peptide, corrected for the background amount of IFN in the absence of peptide.

Example 6

ELISPOT Assay

The ELISPOT assay quantifies the frequency of T cells specific for a given peptide by measuring the capacity of individual cells to be induced to produce and release specific lymphokines, usually IFNγ. The increased sensitivity of the ELISPOT assay has allowed investigators to detect responses from cells freshly isolated from infected humans or experimental animals (Murali-Krishna et al., *Immunity*, Vol. 8(2): 177-87 (1998); Ogg et al., *Science*, Vol. 279(5359):2103-6 (1998)). The ELISPOT assays are conducted as described above for the IFNγ ELISA until the final steps, where ExtrAvidin-AP (Sigma, 1:500 dilution) is used in place HRP-strepavidin. Color is developed using the substrate 5-BCIP (Bio-Rad) according to the manufacturer's directions. Spots are counted using a phase contrast microscope. Alternatively, spots are counted utilizing the Zeiss KS ELISPOT reader. In this case the BCIP/NBT (Zymed) substrate is used.

The ELISPOT assay is routinely utilized to quantitate immune responses. The spots can be manually counted, however, in a preferred mode, a KS ELISPOT reader from Zeiss, a microscope-based system with software specifically designed to recognize and count spots is used.

Example 7

Tetramer Staining

Tetramer staining is a flow cytometric technique that detects epitope-specific human $CD8^+$ T-lymphocytes based on the interaction between the peptide epitope, class I antigen and the T-cell receptor specific for the epitope. This assay allows for the rapid quantitation of epitope specific human $CD8^+$ T-lymphocytes in freshly isolated blood samples. MHC tetramers for various HIV peptide/HLA combinations can be obtained from, e.g., the NIH repository (Tetramer Core Facility: http://www.miaid.nih.gov/reposit/tetramer/index.html). To label epitope-specific cells, $1 \times 10^6$ PBMC in a 100 µl volume are incubated in the dark for 40 minutes with 5 µg/ml of the appropriate tetramer plus monoclonal antibodies that recognize human CD3 and CD8 (available in different fluorochrome-conjugated forms from commercial sources including PharMingen, San Diego, Calif. or BioSource, Camarillo, Calif.). The cells are washed and paraformaldehyde fixed prior to analysis using a FACSan or FACSCalibur flow cytometer (Becton Dickinson Immunocytometry Systems, San Jose, Calif.). Sample data are analyzed using CellQuest software.

Example 8

Assays from Clinical Samples

Various assays to evaluate the specific $CD8^+$ CTL activity in frozen PBMC samples from patients or volunteers can be used. ELISPOT, chromium release, in situ IFNγ release, proliferation and tetramer assays are all useful to evaluate responses from various experimental models, e.g., those of murine and/or primate origin.

Experimental methods for the murine version of these assays are described above, and these are adapted to human systems as described (Livingston et al, *J Immunol*, Vol. 159 (3):1383-92 (1997); Heathcote et al., *Hepatology*, Vol. 30(2): 531-6 (1999); Livingston et al., *J Immunol*, Vol. 162(5):3088-95 (1999)) and can be further adapted a recognized by one of ordinary skill in the art. Calculations on the amounts of frozen PBMC samples necessary to complete the assays are also described greater detail in Example 14.

Example 9

Transgenic Animals

Transgenic mice (HLA-A2.1/$K^b$ $H2^b$; HLA-A11/$K^b$; HLA-B7/$K^b$) are immunized intramuscularly in the anterior tibialis muscle or subcutaneously in the base of the tail with doses up to 100 µg of DNA or peptide in 10-100 µl volumes. DNA is formulated in saline, and peptides in IFA. 11-21 days later, the animals are sacrificed using $CO_2$ asphyxiation, their spleens removed and used as the source of cells for in vitro determination of CTL function. Typically, 3-6 mice per experimental group are used. In addition, spleens from non-immunized mice are used as a source of APC for restimulation of CTL cultures. Both males and females of 8-12 weeks of age are used.

Example 10

Demonstration of Simultaneous Induction of Responses Against Multiple CTL and HTL Epitopes Construction and Testing of CTL Epitope Strings:

This example provides an example of testing multiple CTL and HTL epitopes. For example, epitope strings encompassing 10-12 different CTL epitopes under the control of a single promoter are synthesized and incorporated in a standard plasmid, pcDNA 3.1 (Invitrogen, San Diego). These constructs include a standard signal sequence and a universal HTL epitope, PADRE® epitope. Each set of epitopes is chosen to allow balanced population coverage. To facilitate testing and optimization, a balanced representation of epitopes that have been shown to be immunogenic in transgenic mice, and/or antigenic in humans are included.

The specific order of these CTL epitopes is chosen to minimize Class I junctional motifs by the use of the computer program, as described herein. If, despite best efforts regarding order optimization, potential junctional epitopes are still present in a construct in accordance with the invention, corresponding peptides are synthesized to monitor for CTL responses against such epitopes in HLA transgenic mice. Generally, minimization of junctional motifs is successful and adequate. However, if responses against any junctional epitopes are detected, these junctional epitopes are disrupted by the use of short one to two residue spacers, such as K, AK, KA, KK, or A, compatible with expected proteolytic cleavage preferences discussed in the previous sections.

Since the ultimate use of optimized constructs is a human vaccine, optimized human codons are utilized. Similarly, if such constructs were to be expressed in bacteria or S19 cells, the codon utilization could be modified to provide expression in these systems. However, to facilitate the optimization process in HLA transgenic mice, care is applied to select, whenever possible, human codons that are also optimal for mice. Human and murine codon usage is very similar. See, for example, Tables 21 and 22.

Human cells transfected with the various multi-epitope nucleic acid vaccine constructs can be used in antigenicity assays, conducted in parallel with in vivo testing in HLA transgenic mice. Any potential discrepancy between multi-epitope vaccine efficacy, due to the differential codon usage, is addressed by the availability of these two different assay systems.

Typically, antigenicity and immunogenicity testing of plasmid constructs is conducted in parallel. In vivo testing in transgenic mice are performed for A2, A11, and B7 HLA transgenic mice. Following a protocol well established in our laboratory, cardiotoxin pretreated mice are injected i.m. with 100 µg of each plasmid and responses evaluated eleven days later (Ishioka et al., *J Immunol*, Vol. 162(7):3915-25 (1999)). Assays will include ELISPOT from freshly isolated cells, as well as interferon gamma release and cytotoxicity chromium release assays from restimulated cell cultures. All of the above mentioned techniques are well established in the art. The simultaneous measurement of responses against epitopes is not problematic, as large colonies of transgenic mice are already established "in house" for these HLA types. Groups of four to six mice are adequate to measure responses against six to ten different epitopes, in multiple readout assays. Testing of HLA A2-restricted, HIV-derived epitopes in HLA A2 transgenic mice is typically employed. However, should problems be encountered, antigenicity testing using human APC can be used as an alternative strategy, or, can be used to complement the transgenic mice studies.

For the purpose of extending the correlation between immunogenicity in transgenic animals and antigenicity, as noted in the studies reported herein, antigenicity testing is utilized to evaluate responses against epitopes such as Pol 498, Env 134, Nef 221, Gag 271, for which high affinity CTL lines are already available in house. For the purpose of generating additional suitable CTL lines, direct immunization of HLA transgenic mice with peptides emulsified in adjuvant, or lipopeptides are utilized, as described herein, and routinely applied in our laboratory, to generate lines for use in antigenicity assays.

Antigenicity assays are also used, as a primary readout for epitopes for which in vivo optimization experiments are not feasible. These epitopes include A24 and possibly A1 restricted epitopes, as well as any epitope which is non-immunogenic in HLA transgenic mice. In any such cases, we use human CTL lines, generated from pathogen-exposed individuals. Alternatively, we generate CTL lines for in vitro CTL induction, using GMCSF/IL4-induced dendritic cells and peripheral blood lymphocytes (Celis et al., *Proc Natl Acad Sci USA*, Vol. 91(6):2105-9 (1994)).

Episomal vectors encoding the multi-epitope constructs are generated and transfected into appropriate human cell lines to generate target cells. For example, the human T cell line Jurkat can be used, but lymphoblastoid cell lines have also been successfully utilized. For experiments utilizing CTL lines of human origin, well-characterized HLA-matched, homozygous, EBV cell lines are commonly used as a source of purified-MHC and as target cells and are used as recipients of the multi-epitope nucleic acid transfections. For experiments utilizing CTL lines derived from HLA transgenic mice, a collection of Class I negative, EBV-transformed, mutant cell lines 0.221 (Shimizu Y, DeMars R, *J Immunol*, Vol. 142(9):3320-8 (1989)) transfected with matching HLA/$K^b$ chimeric constructs are used as the recipient of the multi-epitope nucleic acid transfections. Such cells effectively present peptide antigens to CTL lines (Celis et al., *Proc Natl Acad Sci USA*, Vol. 91(6):2105-9 (1994)).

Construction and Testing of HTL Epitope Strings

Epitope strings encompassing 3-20 different HTL epitopes under the control of a single promoter are synthesized and incorporated into a standard plasmid, pcDNA 3.1 (Invitrogen, San Diego). To facilitate testing and optimization, each set of epitopes for a given construct is chosen to provide a balanced representation of epitopes which are already known to be immunogenic in $IA^b$ mice. In addition, all the peptides corresponding to junctions are synthesized and tested for binding to $IA^b$ and, most importantly, for binding to a panel of fourteen different DR molecules, representative of the most common DR alleles worldwide (Southwood et al., *J Immunol*, Vol. 160(7):3363-73 (1998)). Thus, HTL epitopes that are not directed to an antigen of interest are not created within these plasmids. However, should junctional regions with good DR binding potential (and hence, potential DR restricted immunogenicity in vivo) be detected, a spacer such as GPGPG (SEQ ID NO:2) is introduced to eliminate them. In all constructs, the number of Class I junctional motifs will also be minimized, as described herein.

Experimental vaccine plasmids are tested for immunogenicity using HLA DR transgenic mice and/or mice of the H2b haplotype. Proliferation and/or cytokine production are measured (IL5, IFNγ). In a typical protocol, cardiotoxin treated mice are injected i.m. with 100 μg of each plasmid, and immune responses evaluated eleven days later (Ishioka et al., *J Immunol*, Vol. 162(7):3915-25 (1999)).

Testing for Interactions Between CTL and HTL Epitopes

The activities described above yield small, functional blocks of epitopes, which are utilized to demonstrate simultaneous responses/antigenicity against all epitopes analyzable. These blocks are the subject to further optimization, as described in the next example. Using these same constructs, immunodominance is assessed. Specifically, all the CTL epitope constructs are mixed together, or all the HTL epitope constructs are mixed together. The results obtained with the pool of constructs are then compared with the results obtained with the same construct, injected separately.

These constructs are also used to determine the effects of HTL epitopes on responses to CTL epitopes. Specifically, HTL and CTL containing plasmids are pooled and injected in mice, and CTL and HTL responses to selected epitopes are measured as described herein. Often, it is determined whether the presence, e.g., of HTL epitopes derived from the target antigen enhances CTL responses beyond the level of response attained using a plasmid-containing a pan DR binding epitope, e.g., PADRE® peptide or a PADRE® family molecule, in the CTL epitope constructs. Typically, it is also determined whether PADRE® peptide inhibits or augments responses to target antigen-derived HTL epitopes or conversely, if HTL epitopes derived from the antigen of interest inhibit or augment responses to PADRE® peptide.

Responses to a large number of epitopes are attainable using this methodology. It is possible that the pooling of constructs may inhibit responses against some of the weaker epitopes. In this case, the pooling experiments are repeated after optimization.

Example 11

Optimization of CTL and HTL Multi-Epitope Constructs

This example describes the optimization the CTL and HTL constructs described in Example 10. The potential influence of flanking residues on antigenicity and immunogenicity is also assessed in optimizing minigen constructs. These studies involve the inclusion of flanking residues, a synonym for which is "spacers," which have been designed to facilitate effective processing.

Such an analysis can be performed as follows. First, the results of testing of the CTL multi-epitope constructs described in Example 10 are analyzed for trends and correlations between activity and the presence of specific residues at the 3 residues flanking the epitope's N- and C-termini. Epitopes for which suboptimal CTL priming is noted, that are suboptimal with respect to magnitude of response, are the targets for flanking region optimization. For each of the CTL multi-epitope nucleic acid vaccines, encoding 10-12 different CTL epitopes, 'second generation' multi-epitope nucleic acid vaccines, with optimized configuration, are produced.

In one embodiment, the first optimization design is to introduce either an Alanine (A) or Lysine (K) residue at position C+1 for all epitopes associated with suboptimal performance. A second optimization design is to introduce in the C+1 position, the residue naturally occurring in the target antigen, e.g., HIV, that are associated with antigenicity.

For selected epitopes, additional modifications are also introduced. Specifically, the effect of introducing other residue spacers at the epitope C- and N-termini are also investigated. Depending on the results of the analysis of the multiepitope nucleic acid vaccines described in Example 10, residues investigated may further include, for example, G, Q, W, S and T. If junctional epitopes are created by these modifications, then alternative epitope orders are rationally designed as described herein on order to eliminate the junctional epitopes. All second-generation constructs are tested for antigenicity and immunogenicity, as described herein.

As a result of these modifications, variations in activity that correspond to specific modifications of the multi-epitope constructs are identified. Certain modifications are found that have general, beneficial effects. To confirm this, generation and testing of additional multi-epitope nucleic acid vaccines in which all epitopes (also the ones which displayed acceptable antigenicity and immunogenicity) are subject to the same modification are conducted. In some instances, increased activity is noted for some epitopes but not others, or less desirably that certain modifications increase the activity of some, but decrease the activity of other epitopes. In such cases, additional multi-epitope nucleic acid vaccines are designed and tested, to retain the beneficial modifications, while excluding those alterations that proved to be detrimental or have no effect.

These multi-epitope nucleic acid vaccines are designated so that: a) a minimum of predicted junctional epitopes are present; and b) the epitopes which were not functional in the previous multi-epitope nucleic acid vaccines are now in a more efficacious context.

For HTL multi-epitope constructs, the data obtained from the "first generation" constructs are inspected for trends, in terms of junctional epitopes, and epitope position within the constructs, and proximity to spacers, e.g. GPGPG (SEQ ID NO:2) spacers. If specific trends are detected, second generation constructs are designed based on these trends. Alternatively, in case of multi-epitope constructs yielding suboptimal activity, the potential effectiveness of other targeting strategies, such as the ones based on Ii and LAMP are reevaluated, and compared to no targeting and simple, leader sequence targeting.

When large variations in activity of either the CTL or HTL multi-epitope constructs described in this section are detected, the results are consistent with influences such as conformational or "long-range" effects impacting construct activity. These variables can be analyzed by means of current molecular and cellular biology techniques. For example, cell lines transfected with the various multi-epitope constructs could be analyzed for mRNA expression levels, and stability by Northern analysis or primer extension assays (*Current Protocols in Molecular Biology*, Vol 3, John Wiley & Sons, Inc. USA 1999).

In all multi-epitope nucleic acid vaccines, an antibody tag such as MYC/his can also be included. This tag allows for testing of protein expression levels. The inclusion of MYC/his tag (Manstein et al., *Gene*, Vol. 162(1):129-34 (1995)) also allows determination of the stability of the expressed products, by pulse-chase experiments. The results of these assays can then be compared with the results of the antigenicity and immunogenicity experiments. The results are inspected for the presence of trends and general rules, and correlation between the different variables examined.

Example 12

Determination of the Simplest Plasmid Configuration Capable of Effective Delivery of Selected Epitopes The experiments described in Examples 11 and 12 are designed to address variables concerning multi-epitope nucleic acid vaccine design. Ideally, a vector that can be used in humans is used through the entire program, but one DNA vaccine plasmid for the vaccine epitope optimization studies can be used and then switched to a vector suitable for human use. Actual vector selection is dependent on several variables. For example, the availability of vectors, suitable for human use, through a reliable source, such as the National Gene Vector Laboratory (University of Michigan) is a factor.

In this example, the optimized constructs are also ligated to form larger blocks of epitopes. All constructs are preferably designed to incorporate PADRE® peptides and leader sequence targeting in the case of CTL multi-epitope constructs. Specifically, two pairs of the 10-12 CTL epitope constructs are ligated to generate two 20-24 CTL epitope constructs. In a situation where ligation of epitopes yields suboptimal (decreased) activity compared to the smaller constructs, alternative combinations and orders of ligation are investigated. The specific pair of 20-24 CTL epitope constructs yielding optimal activity are then ligated and the resulting construct encompassing all CTL epitopes evaluated for activity. Once again up to two alternative orientations are investigated. Because of the relatively large size of this construct, the specific effect of targeting sequences are confirmed, since it is possible that leader sequence targeting are more effective on small size constructs, while larger size constructs may be most effectively targeted by ubiquitin signals. Specifically, one construct without any specific targeting sequences is generated and compared to a construct that is targeted for degradation by the addition of a ubiquitin molecule.

A similar strategy is used for HTL. Two pairs of the 3-5 HTL epitope constructs are ligated to generate two 7-9 HTL epitope constructs. Once again, in a situation where ligation of these epitopes yields suboptimal (decreased) activity, alternative combinations and order of ligation are investigated. The specific pair of 7-9 CTL epitope constructs yielding optimal activity are ligated and the resulting construct, encompassing all HTL epitopes, is evaluated for activity. Once again, up to two alternative orientations are investigated.

Based on these results an optimized plasmid configuration capable of effective delivery of a panel, e.g., of HIV epitopes, is selected for clinical trial evaluation. Of course, epitopes from any antigen of interest (infectious or disease-associated) can be used alone or in combination. This configuration will entail one or more HTL epitope constructs and one or more CTL epitope constructs. A combination of one long CTL and one long HTL epitope construct capable of effectively delivering all encoded epitopes, is most preferable, as it simplifies further clinical development of the vaccine. In case undesirable interactions between the two constructs are observed when co-injected, injection of the different plasmids in the same animals, but in different injection sites, or at different points in time can be examined. Alternatively, if a single CTL construct and HTL construct encoding all the desired epitopes is not identified, pools of constructs are considered for further development.

Example 13

Evaluation and Characterization of CD8+ Lymphocyte Responses Induce Following Immunization with Multi-Epitope Vaccine CD8+ lymphocyte responses were measured mostly relying on the ELISPOT technique. The ELISPOT assay is known in the art, and is regularly used in our laboratory. An automated Zeiss ELISPOT reader is also used as set forth herein. The assays utilized to measure CD8+ responses are primarily the IFNγ ELISPOT assay on freshly isolated cells as well as cells restimulated in vitro with peptide. In addition, in selected instances, chromium release assays are utilized. The results were correlated with the ones observed in the case of the ELISPOT assays. Tetramer staining on selected peptide/MHC combinations was also performed.

The clinical assay was developed and validated. The timing of this activity coincides with the period of time that follows selection of a clinical vaccine epigene construct, and precedes the availability of actual samples from individuals enrolled in the clinical trial. Assays for CTL evaluation can be established based on experience in the art, for example, experience in establishing assays for CTL evaluations in the Phase I and II trials of an experimental HBV vaccine (Livingston et al, *J Immunol*, Vol. 159(3):1383-92 (1997); Heathcote et al., *Hepatology*, Vol. 30(2):531-6 (1999); Livingston et al., *J Immunol*, Vol. 162(5):3088-95 (1999)). Specifically, Ficoll-purified PBMC derived from normal subjects, as well from, e.g., unvaccinated volunteers can be used. As noted previously, other antigenic target(s) can be used in accordance with the invention.

Example 14

Design of Optimized Multi-Epitope DNA-Based Vaccine Constructs

Optimized constructs were designed with the aid of the computer-assisted methods described above which simultaneously minimize the formation of junctional epitopes and optimize C+1 processing efficiency. The following motifs were utilized for junctional minimization: murine $K^b$ (XXXX(F or Y)$X_{2-3}$(L, I, M or V)); $D^b$ (XXXXN$X_{2-3}$L, I, M or V)); human A2 (X(L or M)$X_{6-7}$V); human A3/A11 (X(L, I, M or V)$X_{6-7}$(K, R or Y)); and human B7 (XP$X_{6-7}$(L, I, M, V or F)). The C+1 propensity values were calculated from the data presented in FIG. 6 and are as follows: K=2.2; N=2; G=1.8; T=1.5; A,F,S=1.33; W,Q=1.2; R=1.7; M,Y=1; I=0.86; L=0.76; V,D,H,E,P=0. Insertion of up to four amino acids was permitted. Examples of constructs designed by this procedure and other procedures set forth herein are depicted in FIG. 18. A number of these constructs were characterized in vitro and in vivo immunogenicity studies, which are set forth hereafter. FIG. 19 lists amino acid epitope sequences encoded by certain nucleic acid sequences in the multi-epitope constructs.

Example 15

Immunogenicity Testing of Multi-Epitope CTL Constructs and Influence of Flanking Amino Acids HLA transgenic mice were used for immunogenicity testing of different multi-epitope constructs. One group of mice were pretreated by injecting 50 μl of 10 μM cardiotoxin bilaterally into the tibialis anterior muscle, and then four or five days later, 100 μg of a DNA construct diluted in PBS was administered to the same muscle. In another group, each mouse was injected with a peptide emulsified in CFA, wherein the peptide corresponds to an epitope within the DNA construct administered to mice in the DNA injection group. Eleven to fourteen days after immunization, splenocytes from DNA vaccinated animals and peptide vaccinated animals were recovered and CTL activity was measured in one of several assays, including a standard $^{51}$Cr-release assay, an ELISPOT assay that measured γ-IFN production by purified CD8+ T-lymphocytes without peptide epitope-specific restimulation, and an in situ ELISA, which included an in vitro epitope-specific restimulation step with a peptide epitope. Examples of CTL activity induced by the EP-HIV-1090 construct upon stimulation with peptide epitopes are shown in FIG. 14A, and CTL activity induced by the PfCTL.1, PfCTL.2, and PFCTL.3 constructs upon stimulation with peptide epitopes are shown in FIG. 14B.

The effect of different amino acids in the C+1 flanking position was directly evaluated by inserting different amino acids at the C+1 position relative to the Core 18 epitope in the HBV.1 construct. The immunogenicity data clearly demonstrate reduced immunogenicity of the Core 18 epitope when it was flanked at the C+1 position by W, Y, or L (FIG. 6b). In contrast, insertion of a single K residue dramatically increased the CTL response to Core 18. Enhancement of CTL responses was also observed using R, C, N, or G at the C+1 position. These data clearly demonstrate that C+1 processing optimization can improve multi-epitope construct design.

Example 16

Figure 15:
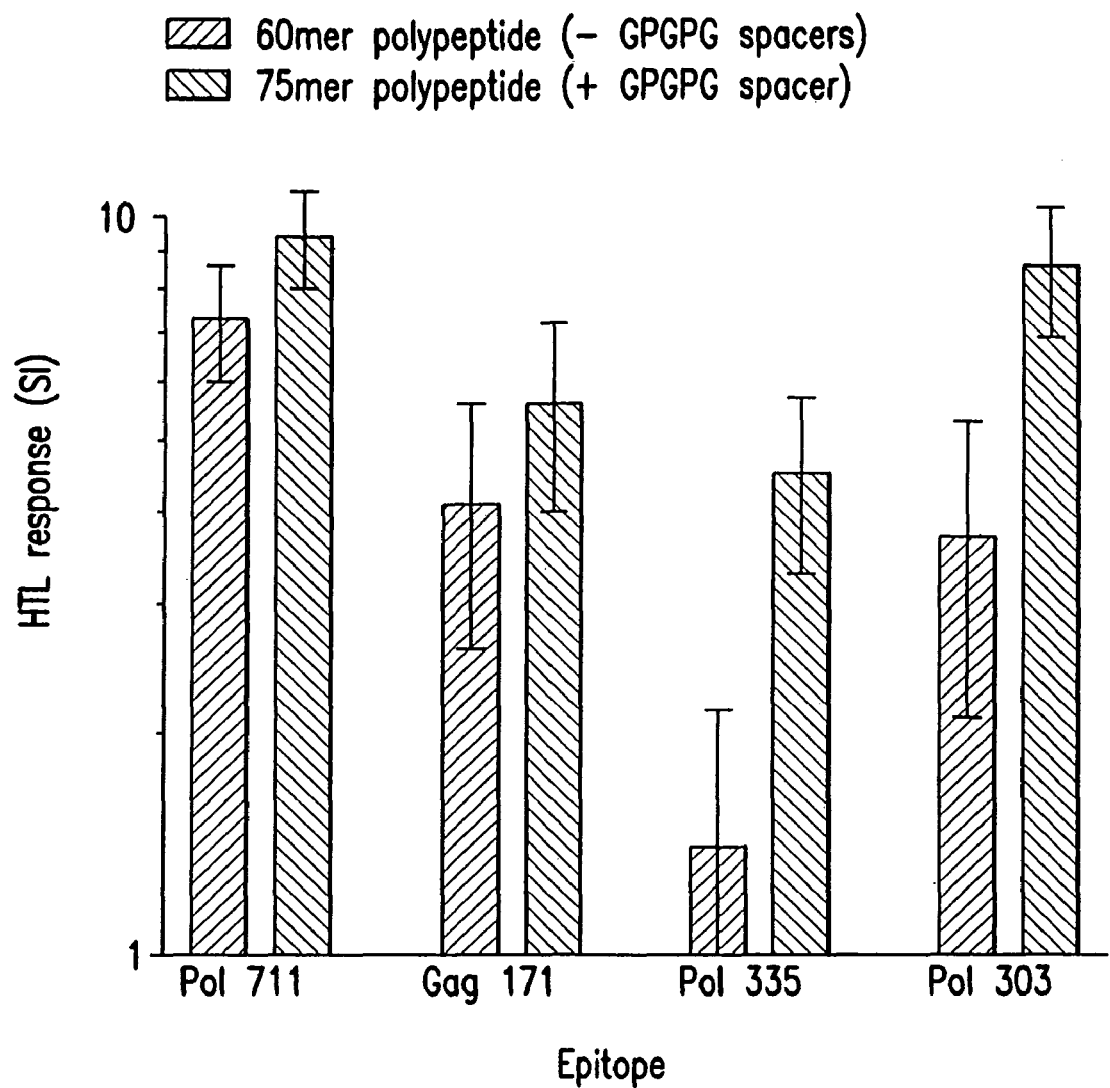
FIG. 15 shows the effect of GPGPG (SEQ ID NO:2) spacers in class II epitope constructs HIV 75 mer and HIV 60 mer on HTL responses to particular epitopes.

Immunogenicity Testing of Multi-Epitope HTL Constructs and Influence of Spacer Sequences A universal spacer consisting of GPGPG (SEQ ID NO:2) was developed to separate HTL epitopes, thus disrupting junctional epitopes. The logic behind the design of this spacer is that neither G nor P are used as primary anchors, positions 1 and 6 in the core region of an HTL peptide epitope, by any known murine or human MHC Class I or MHC Class II molecule. The gap of five amino acids introduced by this spacer separates adjacent epitopes so the amino acids of two epitopes cannot physically serve as anchors in the 1 and 6 positions. The utility of the GPGPG (SEQ ID NO:2) spacer was tested using synthetic peptides composed of four HIV-1 epitopes, one having three spacers and the other lacking spacers, known to bind mouse $IA^b$. HIV 75 mer was the construct having three GPGPG (SEQ ID NO:2) spacers and HIV 60 mer was the construct lacking the three spacers. Immunization of CB6F1 mice with the peptide in CFA induced HTL responses against 3 of 4 of the epitopes in the absence of the spacer but all epitopes were immunogenic when the spacer was present (FIG. 15). This evidence demonstrates that spacers can improve the performance of multi-epitope constructs.

Figure 16:
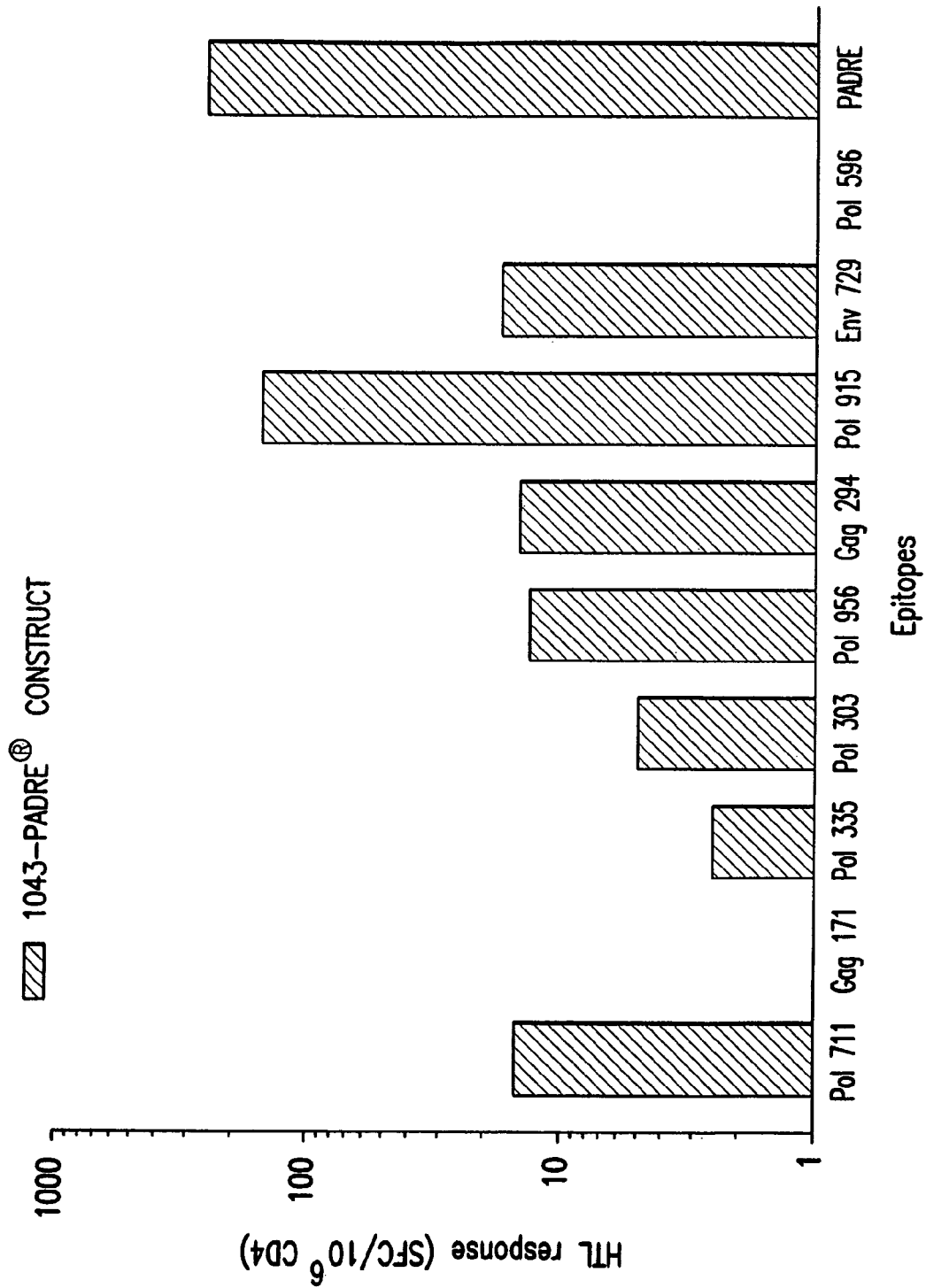
FIG. 16 depicts HTL responses to particular epitopes present in the EP-HIV-1043-PADRE® construct.

The ability of multi-epitope HTL DNA-based constructs to induce an HTL response in vivo was evaluated by intramuscular immunization of $H2^{bxd}$ mice with an EP-HIV-1043-PADRE® construct. The EP-HIV-1043-PADRE® construct is set forth in FIG. 18, and the difference between the EP-HIV-1043-PADRE® construct and EP-HIV-1043 is that the former includes a C-terminal GPGPG (SEQ ID NO:2) spacer followed by the PADRE® sequence AKXVAAWTL-KAAA (SEQ ID NO:1). Eleven days after immunization, no booster immunizations were administered, CD4 T cells were purified from the spleen, and peptide specific HTL responses were measured in a primary γ-IFN ELISPOT assay. Examples of HTL activity induced by constructs encoding HIV epitopes are shown in FIG. 16. Overall, the HTL responses induced by DNA immunization with the multi-epitope HIV HTL construct were generally of equal or greater magnitude than the responses induced by peptide immunization.

Example 17

Development of an Epitope-Based HBV Immunotherapeutic Vaccine

1. Introduction

Natural Correlates of Viral Clearance

The cellular immune response associated with the natural clearance of acute HBV infection is broad and multi-specific. This response includes both CTL and HTL directed against epitopes from multiple viral gene products (Chisari, F. V. and Ferrari, C. Annu. Rev. Immunol. 13:29-60 (1995)). Chronic HBV infection is rarely resolved by the immune system, but when this happens, viral clearance is associated with increases in CTL activity, ALT flares and reductions in viral load (Guidotti, L. G. and Chisari, F. V., Annu. Rev. Immunol. 19:65-91 (2001)). Viral clearance can also be induced in a significant fraction (10-15%) of individuals receiving IFN-α treatment and, similar to spontaneous clearance, the effect is correlated with increased cellular immune responses.

The magnitude of cellular immune responses associated with control of HBV infection was investigated in several studies. For comparative purposes, the following values (mean and range) represent the number of antigen-specific cells per million CD8+ cells. Lohr and coworkers utilized ELISPOT assays to quantitate HBV-specific responses detected in peripheral blood lymphocytes (PBL) during the acute phase of infection (Lohr, H. F. et al., Liver 18:405-413 (1998)). They reported a range of 400-2800 Spot Forming Cells (SFC) (mean 1400) responding to HBV core 18-27. Maini et al. used tetramer staining, which is reported to be approximately four-fold more sensitive than ELISPOT assays (Tan, L. C. et al., J. Immunol. 162:1827-1835 (1999)), and determined a range of 80-14,000 tetramer-positive cells for the core 18-27 epitope, with a mean of 4,000 (Maini, M. K. et al., Gastroenterology 117:1386-1396 (1999)). Taking into account the differential sensitivity of the assays, this translates to an estimated range of 20 to 3500 ELISPOT-positive cells, with a mean of a 1000 specific cells.

Using the same assay, Webster et al., reported 7000 tetramer-positive cells for the core 18-27 epitope (1750 ELISPOT-positive cells), 200 cells for the env 335 (50 ELISPOT-positive cells) and 1200 for the pol 562 epitope (300 ELISPOT-positive cells) (Webster, G. J. et al., Hepatology. 32:1117-1124 (2000)). In the case of two other epitopes analyzed, a mean of 200 tetramer-positive cells (80-6000 range) for env 335, and a mean of 220 cells for the pol 562 epitope (80-3200 range) were observed (Maini, M. K. et al., Gastroenterology 117:1386-1396 (1999)). Rough estimates of these responses in terms of ELISPOT cells are a mean of 50 SFC for env 335 (20-1500 range) and a mean of 55 SFC for pol 562 (20-800 range). These data are comparable to data obtained utilizing the LDA assay, which is approximately 40-50-fold less sensitive than the ELISPOT assay (Murali-Krishna, K. et al., Adv. Exp. Med. Biol. 452:123-142 (1998)). For example, Rehermann and colleagues estimated 15 cells were specific for env 335, and 18 cells were specific for pol 445 (Rehermann, B. et al., J. Clin. Invest. 97:1655-1665 (1996)). Assuming a 45-fold differential sensitivity of the assays, these values correspond to 675 and 810 epitope-specific ELISPOT positive cells, respectively. Additional data comes from Lohr et al. who used ELISPOT assays to quantitate HBV-specific responses in patients that responded to IFN-α treatment that resulted in viral clearance (Lohr H. F. et al., Liver 18:4-5-413 (1998)). In this study, a mean of 600 SFC (range 200-1300) specific for HBV core 18-27 was reported.

In summary, CTL specific for various HBV epitopes are detected in PBL during clearance of the HBV virus. The frequency of functional cells detected by ELISPOT ranged from 20-400 cells/million CD8+ cells (low) to 820-3500 SFC/million CD8+ cells (high), with an average response between 50-1000 SFC/million CD8+ cells.

The importance of HBV-specific CTL was demonstrated directly using HBV-transgenic mice. Specifically, adoptive transfer of cloned CTL specific for different viral antigens, including the env, core and pol antigens, and restricted by murine MHC molecules, led to the elimination of the expression of viral antigens (Tsui, L. V. et al., Proc. Natl. Acad. Sci. USA. 92:12398-12402 (1995); Guidotti, L. G. et al., Immunity. 4:25-36 (1996)). These data clearly document the importance of CTL responses to the control of HBV infection The magnitude of HTL responses during HBV infection is generally lower than for CTL. Utilizing whole antigens and ELISPOT assays, Lohr et al. observed overall frequencies of 47±5.2 SFC per million CD4+ cells in patients responding to IFN-α treatment and 42±12 SFC per million CD4+ cells during acute infection. (Lohr, H. F. et al., Liver 18:405-413 (1998)) Webster et al. reported that 2,900 tetramer-positive cells per million CD4+ cells were detected against core antigen in a patient 10 weeks post-infection (Webster, G. J. et al., Hepatology. 32:1117-1124 (2000)).

In conclusion, these data provide a means of establishing a level of immunogenicity for therapeutic HBV vaccines designed to induce CTL responses.

B. Immune Tolerance is Associated with Chronic HBV Infection

HBV epitope-specific immune tolerance is associated with chronic HBV infection (Chisari, F. V. and Ferrari, C. Annu. Rev. Immunol. 13:29-60 (1995); Alexander, J. et al., Immunol. Res. 18:79-92 (1998); Milich, D. R., Can. J. Gastroenterol. 14:781-787 (2000); Hilleman, M. R. et al., Vaccine. 19:1837-1848 (2001); Jung, M. C. et al., Lancet Infect. Dis. 2:43-50 (2002)). In the infected individual, high levels of viremia are believed to be responsible for this immune tolerant status. Although this effect can be so pronounced that it leads to a generalized Th1/Th2 imbalance and general peripheral tolerance, it does not result in deletion of HBV-specific CTL precursors (Rossol, S. et al., B. J. Clin. Invest. 99:3025-3033 (1997); Chen et al, Immunity 12: 83-93 (2000); Sette, A. D. et al., J. Immunol. 166:1389-1397 (2001)). Indeed, studies in HBV-transgenic mice were used to demonstrate that tolerance can be "broken" by the use of epitope-based vaccines and non-pathogen derived, optimized HTL epitopes (Livingston, B. D. et al., J. Immunol. 159:1383-1392 (1997); Alexander, J. et al., Immunol. Res. 18:79-92 (1998); Sette, A. D. et al., J. Immunol. 166:1389-1397 (2001)). The data generated using patient samples obtained during spontaneous resolution of HBV infection and during response to IFN-α treatment also suggests that this defect is reversible. Additional data to support this hypothesis was derived in studies utilizing the antiviral drug, lamivudine, as discussed below.

Previous HBV Immunotherapy Clinical Trials

Clinical studies using a lipopeptide vaccine composed of a promiscuous HTL epitope and the HBV core 18 CTL epitope, provided data to document immunogenicity of individual epitopes in normal volunteers (Livingston, B. D. et al., *Hum. Immunol.* 60:1013-1017 (1999); Livingston, B. D. et al., *J. Immunol.* 159:1383-1392 (1997); Vitiello, A. et al., *J. Clin. Invest.* 95:341-349 (1995)). The levels of CTL induced in healthy subjects were comparable to those measured in acutely infected individuals who clear the virus, either spontaneously or as a result of IFN-α treatment. Subsequent trials in chronic HBV patients were, however, disappointing: The levels of CTL induced in these patients were significantly lower than the levels observed in normal subjects and no reductions in viral loads were observed. Importantly, at the time of these clinical trials, antiviral drug therapy was not available. Thus, there was no way to reduce the viremia associated with immune tolerance.

D. Effects of Antiviral Drug Therapy on HBV Replication, Integration and Immune System Tolerance Chronic HBV infection is associated with high levels of viremia averaging about $2.2 \times 10^{11}$ viral particles per 3 liters of serum, which is equivalent to the average total body burden (Nowak, M. A. et al., *Proc. Natl. Acad. Sci. USA.* 93:4398-4402 (1996)). The presence of high numbers of viral particles in the serum is thought to be responsible, at least in part, for the immune tolerance detected in chronic HBV patients (Schlaak, J. F. et al., *J. Hepatology* 30:353-358 (1999)). The nucleoside analog lamivudine (Epivir-HBV) (GlaxoSmith-Kline, Research Triangle Park, N.C. 27709) is a reverse transcriptase inhibitor originally developed for the treatment of HIV. It was also approved for the treatment of chronic HBV infection, is known to have potent inhibitory effects on HBV replication, and rapidly reduces the production of new infectious virus particles in patients (Nowak, M. A. et al., *Proc. Natl. Acad. Sci. USA.* 93:4398-4402 (1996)). In multiple studies, HBV DNA becomes undetectable during lamivudine treatment in the majority of patients (Dienstag, J. L. et al., *Hepatology* 30:1082-1087 (1999); Boni, C. et al., *Hepatology.* 33:963-971 (2001)). Within the first six months of treatment there is a major decline in the level of viremia, which continues with longer-term treatment. HBsAg and HBeAg levels decline over time in most patients although the rate and magnitude are less than that observed for viral particles. Liver enzymes also fall to near normal levels in the majority of patients with 6 months or more of lamivudine therapy (Dienstag, J. L. et al., *Hepatology* 30:1082-1087 (1999); Boni, C. et al., *Hepatology.* 33:963-971 (2001)). Lamivudine does not totally suppress viral protein production because covalently closed-circular DNA (cccDNA) and integrated HBV DNA will support the production of some viral proteins over a prolonged period of time.

In addition, the hypo-responsiveness of HBV-specific CTL and HTL, typical of chronic HBV infection, appears to be overcome or at least decreased by lamivudine treatment (Boni, C. et al., *B. J. Clin. Invest.* 102:968-975 (1998); Boni, C. et al., *Hepatology.* 33:963-971 (2001)). Interestingly, the rebound in T-cell activity appears as early as one month after initiation of lamivudine therapy following the initial sharp decline in viremia. However, when lamivudine treatment is suspended, viral replication rebounds in as little as one week, depending on the duration of treatment (Dienstag, J. L. et al., *N. Eng. J. Med.* 333:1657-1661 (1995); Dienstag, J. L. et al., *Hepatology* 30:1082-1087 (1999)). Also, there has been reported a rapid emergence of drug-resistant HBV mutants. Thus, lamivudine alone is limited in usefulness as a therapy for chronic HBV infection.

E. Immunotherapeutic Vaccine Design

The design and evaluation of therapeutic vaccines capable of inducing cellular immune responses of the magnitude needed to control HBV replication and ultimately, mediate viral clearance is of great clinical importance. Vaccines are designed to induce both HBV-specific CTL and HTL responses, and are tested clinically in both healthy volunteers and chronically-infected patients. In the latter group, patients are restricted to those treated successfully with lamivudine or similar antiviral for a minimum of six months.

Epitope Selection

CTL Epitopes from the HLA-A2, -A3 and -B7 Supertype Families

The majority of HLA class I molecules can be classified into relatively few major HLA class I supertypes when grouped by the characteristics of their overlapping, yet independent, peptide binding repertoires (Table 6A-B). By selecting epitopes capable of binding most, or all, of the HLA molecules in a given supertype, it is possible to limit the numbers of epitopes needed to produce an effective multi-epitope vaccine. Selection of the most common HLA supertypes facilitates design of a vaccine for treatment of individuals with HBV infection (Bertoni, R., J. et al., *J. Clin. Invest.* 100:503-513 (1997); Sette, A. et al., *Immunogenetics.* 50:201-212 (1999); Sette, A. et al., *Curr. Opin. Immunol.* 10:478-482 (1998)).

TABLE 6A

Phenotypic frequencies of HLA Class I

| | | Phenotypic Frequency (%) | | | |
|---|---|---|---|---|---|
| Supertype | HLA allele | Asian | Black | E Cauc | NA Cauc |
| A2 | A*0201 | 15.8 | 19.6 | 45.1 | 32.0 |
| | A*0202 | 0.2 | 8.7 | 1.5 | 3.7 |
| | A*0203 | 8.7 | 0.2 | 0.2 | 4.1 |
| | A*0206 | 10.8 | 0.6 | 0.2 | 7.8 |
| | A*6802 | 0.2 | 9.6 | 1.3 | 2.2 |
| A3 | A*0301 | 13 | 14.6 | 26.8 | 25.9 |
| | A*1101 | 35.3 | 1.1 | 11.5 | 12.4 |
| | A*3101 | 8.2 | 1.3 | 5.1 | 4.5 |
| | A*3301 | 5.2 | 4.0 | 1.8 | 1.6 |
| | A*6801 | 0.5 | 7.0 | 6.0 | 5.0 |
| A1 | A*0101 | 1.5 | 7.0 | 30.7 | 29.4 |
| | A*2902 | 0.5 | 5.1 | 6.3 | 5.7 |
| | A*3002 | 2.2 | 30.7 | 4.7 | 4.9 |
| A24 | A*2402 | 49.5 | 4.2 | 16.5 | 15.6 |
| | A*2301 | 0.2 | 17.9 | 3.2 | 4.5 |
| | A*2902 | 0.5 | 5.1 | 6.3 | 5.7 |
| | A*3002 | 2.2 | 30.7 | 4.7 | 4.9 |
| B7 | B*0702 | 5.6 | 13.8 | 24.9 | 25.6 |
| | B*3501 | 9.3 | 9.0 | 16.0 | 17.4 |
| | B*5101 | 12.2 | 4.6 | 10.7 | 9.3 |
| | B*5301 | 0.2 | 19.4 | 0.6 | 1.2 |
| | B*5401 | 8.6 | 0.1 | 0.1 | 0.1 |

TABLE 6B

Phenotypic frequencies of HLA Class II

| | Phenotypic frequency (%) | | | |
|---|---|---|---|---|
| Antigen | Asian | Black | E Cauc | NA Cauc |
| DR1 | 6.0 | 13.1 | 19.3 | 22.5 |
| DR2w2 B1 | 34.7 | 29.2 | 27.6 | 27.3 |
| DR3 | 5.2 | 22.4 | 24.7 | 21.0 |

TABLE 6B-continued

Phenotypic frequencies of HLA Class II

| Antigen | Phenotypic frequency (%) | | | |
|---|---|---|---|---|
| | Asian | Black | E Cauc | NA Cauc |
| DR4w4 | 0.9 | 3.3 | 14.3 | 14.8 |
| DR4w14 | 1.7 | 0.7 | 4.3 | 7.5 |
| DR4w15 | 16.0 | 1.0 | 1.5 | 1.7 |
| DR5w11 | 7.7 | 23.1 | 18.2 | 18.5 |
| DR6w19 | 10.5 | 39.9 | 21.6 | 22.0 |
| DR7 | 4.2 | 14.8 | 25.5 | 23.4 |
| DR8w2 | 18.6 | 10.7 | 5.4 | 6.7 |
| DR9 | 23.5 | 3.9 | 2.0 | 2.0 |
| DR5w12 | 15.3 | 9.6 | 3.4 | 2.2 |

A set of HBV-derived CTL epitopes that bind to multiple HLA supertype alleles has been identified (Table 7).

TABLE 7

| HBV Vaccine HLA-A2, -A3 & -B7 CTL Epitopes | | | | | | | | |
|---|---|---|---|---|---|---|---|---|
| HLA | | | SEQ ID | | Prototype Allele | | Immunogenicity | |
| Supertype | Epitope | Sequence | NO: | Conservation (%)[1] | Binding ($IC_{50}$ nM)[2] | XRN[3] | Human[4] | Mice[5] |
| A2 | core 18 | FLPSDFFPSV | 9 | 45 | 3.5 | 5 | + | + |
| A2 | env 183 | FLLTRILTI | 10 | 80 | 9.8 | 4 | + | + |
| A2 | env 335 | WLSLLVPFV | 11 | 100 | 5.4 | 4 | + | + |
| A2 | env 338 | LLVPFVQWFV | 12 | 95 | 5.7 | 5 | | |
| A2 | env 378 | LLPIFFCLWV | 13 | 100 | 158.9 | 1 | | |
| A2 | pol 455 | GLSRYVARL | 14 | 55 | 55.9 | 3 | + | + |
| A2 | pol 538 | YMDDVVLGV | 15 | 90 | 6.4 | 5 | + | + |
| A2 | pol 773 | ILRGTSFVYV | 16 | | | | | |
| A2 | pol 562 | FLLSLGIHL | 17 | 95 | 7.8 | 3 | + | + |
| A2 | pol 642 | ALMPLYACI | 18 | 95 | 12.9 | 4 | | |
| A2 | env 338 | GLSPTVWLSV | 19 | | | | | |
| A3 | core 141 | STLPETTVVRR | 20 | 95 | 735/4.5* | 4 | + | + |
| A3 | pol 149 | HTLWKAGILYK | 21 | 100 | 15.4/15.6 | 5 | + | + |
| A3 | pol 150 | TLWKAGILYK | 22 | 100 | 2.1/33 | 2 | | |
| A3 | pol 388 | LVVDFSQFSR | 23 | 100 | 6875/17 | 3 | + | + |
| A3 | pol 47 | NVSIPWTHK | 24 | 100 | 174/117 | 3 | + | + |
| A3 | pol 531 | SAICSVVRR | 25 | 95 | 2189/29 | 3 | + | + |
| A3/A1 | pol 629 | KVGNFTGLY | 26 | 95 | 58/365 | 2 | | |
| A3 | pol 655 | QAFTFSPTYK | 27 | 95 | 249/8 | 3 | + | + |
| B7 | core 19 | LPSDFFPSV | 28 | 45 | 3026.8 | 4 | + | − |
| B7 | env 313 | IPIPSSWAF | 29 | 100 | 42.3 | 4 | + | + |
| B7 | pol 354 | TPARVTGGVF | 30 | 90 | 13.2 | 2 | + | − |
| B7 | pol 429 | HPAAMPHLL | 31 | 100 | 56.6 | 4 | − | + |
| B7 | pol 640 | YPALMPLYA | 32 | | | | | |
| B7 | pol 541 | FPHCLAFSY | 33 | | | | | |
| B7 | pol 530 | FPHCLAFSYM | 34 | 95 | 58.5 | 5 | − | + |

TABLE 7-continued HBV Vaccine HLA-A2, -A3 & -B7 CTL Epitopes

| HLA Supertype | Epitope | Sequence | SEQ ID NO: | Conservation (%)[1] | Prototype Allele Binding (IC$_{50}$ nM)[2] | XRN[3] | Immunogenicity Human[4] | Mice[5] |
|---|---|---|---|---|---|---|---|---|
| B7 | pol 640 | YPALMPLY | 35 | | | | | |
| B7 | pol 640 | YPALMPLYACI | 36 | 95 | 1393.4 | 3 | − | + |

[1]Sequence identity in 20 strains of HBV including adr, adw, ayr, and ayw isolates.
[2]Prototype alleles for the respective supertypes are A2: A*0201, A3: A*0301/A*1101, B7: B*0702.
[3]Number of supertype alleles bound ≦500 nM.
[4]Recall CTL responses in patients with chronic or active HBV infection.
[5]CTL responses induced in HLA-transgenic mice after immunization with a peptide emulsified in IFA.
*Binding to HLA-A*0301 and -A*1101 respectively.

Six each of the HLA-A2, -A3 and -B7 supertype epitopes were selected for use in vaccine development. The cutoff for binding affinity considered was 500 nM, since this level of binding affinity correlates with CTL immunogenicity and antigenicity (Sette, A. et al., *J. Immunol.* 153:5586-5592 (1994)). All of these epitopes are conserved in the most prevalent HBV strains. The core 18 epitope is conserved in a relatively modest 45% of the HBV sequences examined but the majority of the sequences that do not contain this particular epitope encode a variant which contains a conserved substitution (isoleucine for leucine) at the C-terminus of the epitope. All but one of the 18 selected epitopes bind at least three of the five the most common members of a given supertype. These epitopes were derived from the env, pol and core antigens, consistent with our goal to generate immune responses directed against multiple viral antigens, thus mimicking what the natural clearance of HBV.

Human immune system recognition of these epitopes was demonstrated using recall CTL assays and PBL from individuals with either acute or chronic infection (Bertoni, R., J. et al., *J. Clin. Invest.* 100:503-513 (1997)). Immune recognition of these epitopes by PBL demonstrates that the epitopes were produced in the course of natural HBV infection and that the appropriate TCR are present in the human repertoire. With the exception of three HLA-B7-restricted epitopes, the entire set of vaccine epitopes were recognized by CD8+ T-lymphocytes obtained from HBV patients (Table 7).

The HLA-A2, -A3 and -B7 epitopes were also tested for immunogenicity using HLA-transgenic animals. Following immunization with synthetic peptides emulsified IFA, CTL responses were measured using an in situ IFN-γ ELISA assay (Vitiello, A. et al., *J. Clin. Invest.* 95:341-349 (1995)). Data obtained in this assay was converted to secretory units (SU) for evaluation (McKinney, D. M. et al., *J. Immunol. Methods.* 237:105-117 (2000)). A SU is the number of cells that secrete 100 pg of IFN-γ in response to a particular peptide, corrected for the background amount of IFN-γ produced in the absence of peptide. The data shown in the last column of Table 7 summarizes the findings of these experiments. The fact that most of these epitopes are immunogenic in HLA-transgenic mice is of relevance, as it offers a means of evaluating the potency of multi-epitope vaccines using a small animal model.

In conclusion, a set of epitopes suitable for inclusion in an epitope-based vaccine and restricted by three common HLA class I supertypes can be untilized for vaccine development.

CTL Epitopes from the HLA-A1 and -A24 Supertypes

Epitopes binding to multiple members of the HLA-A1 and -A24 supertypes were identified for the purpose of treating patients afforded by the vaccine and to increase the multiplicity of determinants contained in our epitope package (Table 8).

TABLE 8

HBV Vaccine HLA-A1 & -A24 CTL Epitopes

| HLA Supertype | Epitope | Sequence | SEQ ID NO: | Conservation (%)[1] | Prototype Allele Binding (IC$_{50}$ nM)[2] | XRN[3] |
|---|---|---|---|---|---|---|
| A1 | env 359 | WMMWYWGPSLY | 37 | 85 | 16.3 | 3 |
| A1 | core 419 | DLLDTASALY | 38 | 75 | 2.3 | 3 |
| A1 | core 137 | LTFGRETVLEY | 39 | 75 | 80.0 | 3 |
| A1 | pol 149 | HTLWKAGILY | 40 | 100 | 381.0 | 3 |
| A1 | pol 166 | ASFCGSPY | 41 | 100 | 247.0 | 3 |
| A1 | pol 415 | LSLDVSAAFY | 42 | 95 | 6.0 | 3 |
| A1 | pol 580 | YSLNFMGY | 43 | 85 | 382.0 | 3 |
| A1 | env 249 | ILLLCLIFLL | 44 | 100 | 192.0 | 1 |
| A24 | env 236 | RWMCLRRFII | 45 | 95 | 11.0 | 3 |

TABLE 8-continued

HBV Vaccine HLA-A1 & -A24 CTL Epitopes

| HLA Supertype | Epitope | Sequence | SEQ ID NO: | Conservation (%)[1] | Prototype Allele Binding (IC$_{50}$ nM)[2] | XRN[3] |
|---|---|---|---|---|---|---|
| A24 | pol 392 | SWPKFAVPNL | 46 | 95 | 2.1 | 2 |
| A24 | env 332 | RFSWLSLLVPF | 47 | 100 | 12.0 | 2 |
| A24 | env 332 | RFSWLSLLVPF | 47 | 100 | 12.0 | 2 |
| A24 | core 101 | LWFHISCLTF | 48 | 85 | 6.7 | 3 |
| A24 | core 117 | EYLVSFGVW | 49 | 90 | 16.0 | 2 |
| A24 | pol 167 | SFCGSPYSW | 50 | 100 | 146.0 | 3 |
| A24 | pol 529 | AFPHCLAF | 51 | 95 | 78.0 | 3 |
| A24 | pol 639 | GYPALMPLY | 52 | 95 | 280.0 | 2 |
| A24 | pol 745 | KYTSFPWLL | 53 | 85 | 1.0 | 3 |

[1]Sequence identity in 20 strains of HBV including adr, adw, ayr, and ayw isolates.
[2]Prototype alleles for the respective supertypes are A1: A*0101, A24: A*2402.
[3]Number of supertype alleles bound ≦500 nM.

Of the over one hundred motif-positive peptides identified, 24 peptides were selected for further study based on their binding characteristics to purified HLA-A1 or -A24, and related supertype molecules and six each restricted to HLA-A1 or HLA-A24 were selected as vaccines; three related alleles were used to define the HLA-A1 and -A24 supertype families. Of these epitopes, core 117 and pol 745 were independently reported as being recognized by CTL from HBV-infected individuals (Sobao, Y. et al., J. Hepatol. 34:922-929 (2001)).

To provide additional evidence showing that the selected epitopes could be recognized by human CD8+ T-lymphocytes, we induced primary CTL responses using PBL obtained from non-infected normal donors. This in-vitro primary CTL induction assay utilizes PBL obtained by leukapheresis from HLA-A1 or -A24 positive, male and female donors. The PBL were used as the source of dendritic cells (DC), antigen-presenting cells and CD8+ T-lymphocytes (Keogh, E. et al., J. Immunol. 167:787-796 (2001)). To induce the expansion of precursor CTL to mature cells, purified CD8+ cells were co-cultured with cytokine-generated, peptide-pulsed DC in the presence of 10 ng/ml of recombinant human IL-7. This culture step induced the activation and initial maturation of precursor CTL, but restimulation and extended culture was needed to expand their numbers for testing. The restimulation was done on days 7 and 14 using adherent monocytes pulsed with peptide. Seven days after the second restimulation, the cultures were assayed for CTL activity, using either the in situ ELISA or the ELISPOT assays. A culture was considered positive if the measured response is at least twice the background level of expression, determined using an irrelevant peptide, and ≧50 pg/well. A positive response demonstrates the presence of the appropriate TCR in humans.

A compilation of the data obtained using the HLA-A1 and -A24 epitopes is provided in Table 9.

TABLE 9

Primary Immunogenicity of HLA-A1 & -A24 HBV CTL Epitopes

| HLA Supertype | Epitope | Sequence | SEQ ID NO: | Donors+/ Total Tested[1] | +Wells/Total Tested[2] | Avg. SI[3] | Net IFN-γ (pg/well)[4] |
|---|---|---|---|---|---|---|---|
| A1 | env 359 | WMMWYWGPSLY | 37 | 1/4 | 1/192 | 23.0 | 175 |
| A1 | core 419 | DLLDTASALY | 38 | 1/3 | 3/144 | 29.0 | 67 |
| A1 | core 137 | LTFGRETVLEY | 39 | 3/3 | 3/144 | 27.3 | 100 |
| A1 | pol 166 | ASFCGSPY | 41 | 2/4 | 3/192 | 41.2 | 60 |
| A1 | pol 415 | LSLDVSAAFY | 42 | 1/4 | 1/192 | 57.0 | 56 |
| A1 | env 249 | ILLLCLIFLL | 44 | 3/3 | 7/144 | 21.0 | 93 |
| A24 | env 236 | RWMCLRRFIIF | 45 | 0/2 | 0/96 | | |
| A24 | env 332 | RFSWLSLLVPF | 47 | 1/2 | 1/96 | 2.5 | 186 |
| A24 | core 101 | LWFHISCLTF | 48 | 1/2 | 2/96 | 2.8 | 248 |

TABLE 9-continued

Primary Immunogenicity of HLA-A1 & -A24 HBV CTL Epitopes

| HLA Supertype | Epitope | Sequence | SEQ ID NO: | Donors+/ Total Tested[1] | +Wells/Total Tested[2] | Avg. SI[3] | Net IFN-γ (pg/well)[4] |
|---|---|---|---|---|---|---|---|
| A24 | core 117 | EYLVSFGVWI | 49 | 1/2 | 1/96 | 2.3 | 158 |
| A24 | pol 392 | SWPKFAVPNL | 46 | 0/3 | 0/144 | | |
| A24 | pol 745 | KYTSFPWLL | 53 | 2/2 | 10/96 | 108.0 | 144 |

[1] Number of donors with positive CTL response of total number of donors tested.
[2] Number of cultures with positive CTL response of total cultures tested.
[3] Average stimulation index of CTL responses calculated as: IFN-γ secretion with peptide/IFN-γ secretion without peptide.
[4] Net IFN-γ production adjusted for control irrelevant peptide.

The data is expressed as the number of positive wells out of the total wells tested, the average stimulation index of the positive cultures and the net IFN-γ release of the positive cultures. Significant CTL responses were induced for all of the HLA-A1 restricted epitopes and for 4/6 of the HLA-A24 epitopes included in the current HBV vaccine studies.

HLA-A1 and -A24 transgenic mice are not currently available. However, a significant degree of similarity exists between the binding motifs of HLA-A24 epitopes and the murine class I $K^d$. We therefore tested four of the vaccine HLA-A24 epitopes for their capacity to bind purified $K^d$ molecules in vitro and assessed immunogenicity. We found that one of these epitopes was immunogenic in the $H2^{bxd}$ mice (Table 10). Two other epitopes were not tested for binding but proved to be immunogenic when tested in $H2^{bxd}$ mice following immunization with peptide/IFA emulsions. IFN-γ responses after in vitro restimulation ranged from 158.7 to 339.6 SU. This level of activity was similar to the levels observed with a known control $K^d$-restricted epitope (Romero, et al., Nature 341: 323. (1989)). Thus, the $H2^{bxd}$ can be used in the absence of HLA-A24 transgenic mice.

TABLE 10

Cross Reactivity of HLA-A24 Epitopes with $K^d$

| Epitope | Sequence | SEQ ID NO: | Conservation (%)[1] | $K^d$ Binding (IC$_{50}$ nM) | Murine Immunogenicity[2] (SU) |
|---|---|---|---|---|---|
| env 236 | RWMCLRRFII | 45 | 95 | NT | 339.6 |
| pol 392 | SWPKFAVPNL | 46 | 95 | NT | 261.0 |
| env 332 | RFSWLSLLVPF | 47 | 100 | | |
| env 332 | RFSWLSLLVPF | 47 | 100 | — | 0.0 |
| core 101 | LWFHISCLTF | 48 | 85 | — | 0.0 |
| core 117 | EYLVSFGVW | 49 | 90 | — | 0.0 |
| pol 167 | SFCGSPYSW | 50 | 100 | | |
| pol 529 | AFPHCLAF | 51 | 95 | | |
| pol 639 | GYPALMPLY | 52 | 95 | | |
| pol 745 | KYTSFPWLL | 53 | 85 | 77.5 | 158.7 |
| CS 252[3] | SYIPSAEKI | 54 | NA | 9.2 | 49.2 |

[1] Sequence identity in 20 strains of HBV including adr, adw, ayr, and ayw isolates.
[2] CTL response, measured in an in situ ELISA assay, (McKinney et al. 2000) after peptide/IFA immunization of $H2^{bxd}$ mice.
[3] Control A24 epitope (Romero et al. 1991).
NT: not tested
NA: not applicable C. Projected Population Coverage of Vaccines Composed of CTL Epitopes The population coverage of vaccines composed of the selected epitopes was determined based on the phenotypic frequencies of HLA types defined by the HLA workshop and on the binding characteristics of the epitopes (Gjerston, D. W. and Terasaki, P. I. HLA. American society for Histocompatibility and Immunogenetics. Lenexa, Kans. (1998)).

Figure 25A:
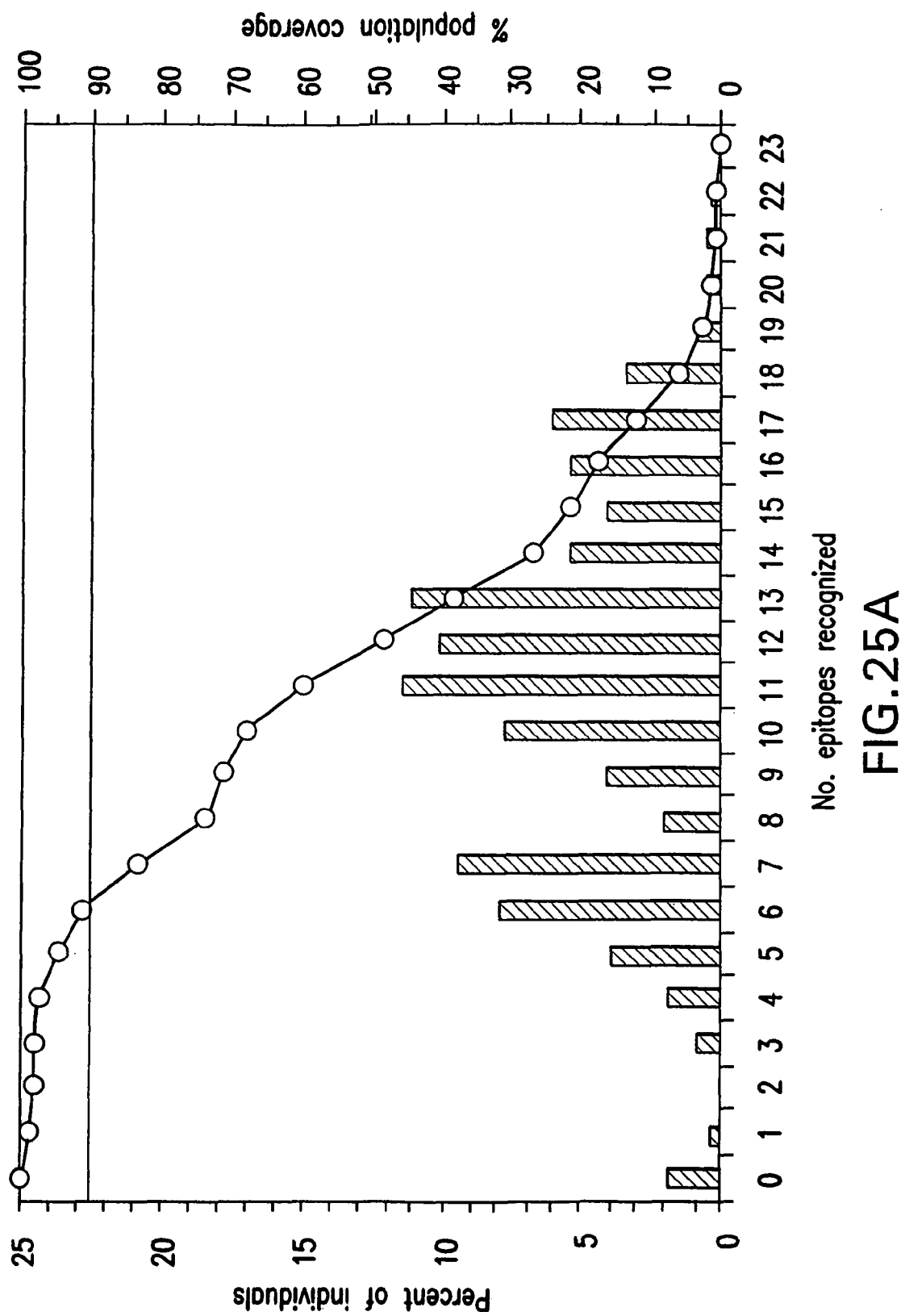
Figure 25B:
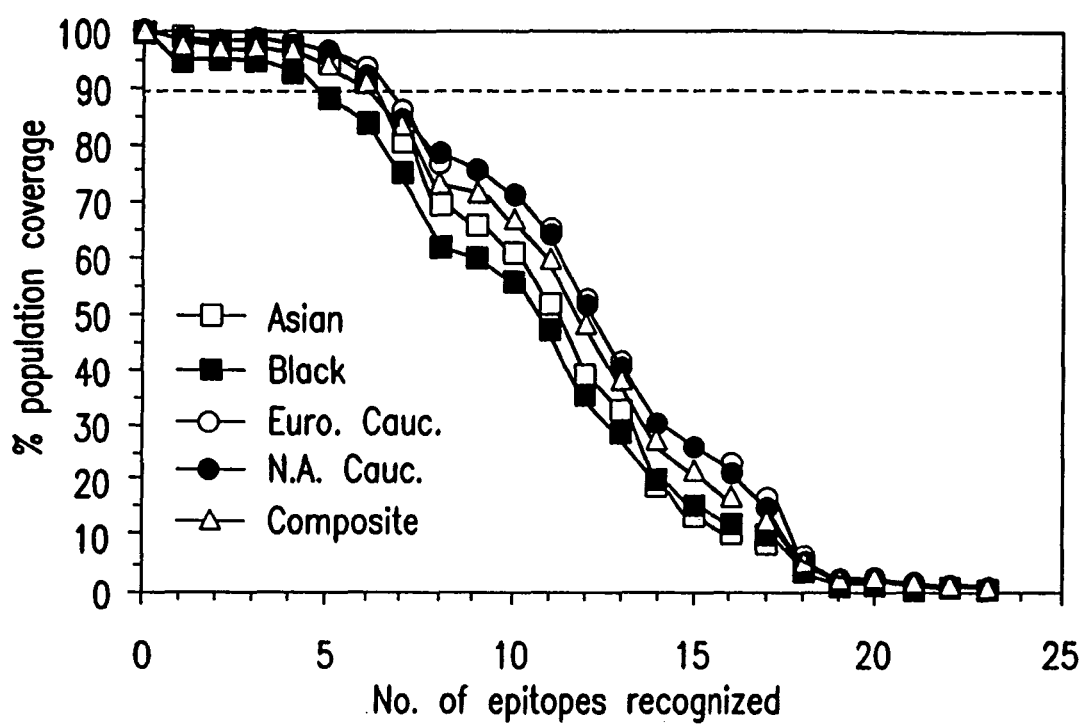

The most common HLA molecules contained within each of the five selected HLA class I supertypes and their distribution in common ethnic groups is shown in Table 6A. The calculated phenotypic frequency of individuals with HLA types capable of binding the indicated number of class I-restricted epitopes and the cumulative frequency of individuals predicted to be genetically capable of responding immunologically to the selected epitopes is shown in FIGS. 25A-25B. An average of 11.1 epitope-HLA combinations could be recognized in an idealized composite population with average HLA frequencies (FIG. 25A). Analyses of projected population coverage in the major ethnic groups demonstrated no appreciable ethnic bias (FIG. 25B).

D. Selection of HTL Epitopes

HLA-DR types can be grouped into two major supertypes based on epitope-peptide binding, defined as the HLA-DR-1,4,7 and -DR3 supertypes (Wilson, C. C. et al., *J. Virol.* 75:4195-4207 (2001); Doolan, D. L. et al., *J. Immunol.* 165: 1123-1137 (2000); Southwood, S. et al., *J. Immunol.* 160: 3363-3373 (1998)). A set of HBV-derived, HLA-DR supertype epitopes was identified using a process similar to that used to identify the CTL epitopes and 16 were selected for further study based on binding characteristics (Table 11).

TABLE 11

HBV Vaccine HTL Epitopes

| HLA Supertype | Epitope | Sequence | (SEQ ID NO:) | Conservation (%)[1] | HLA-DR binding capacity ($IC_{50}$ nM) | | | | |
|---|---|---|---|---|---|---|---|---|---|
| | | | | | DRB1 *0101 | DRB1 *1501 | DRB1 *0301 | DRB1 *0401 | DRB1 *0405 |
| DR | pol 412 | LQSLTNLLSSNLSWL | (55) | 90 | 2.0 | 21 | — | 10.0 | 47 |
| | pol 664 | KQAFTFSPTYKAFLC | (56) | 60 | 10 | 41 | — | 88 | 181 |
| | env 180 | AGFFLLTRILTIPQS | (57) | 80 | 1 | 217 | — | 9 | 258 |
| | pol 774 | GTSFVYVPSALNPAD | (58) | 80 | 15 | 748 | — | 119 | 94 |
| | core 120 | VSFGVWIRTPPAYRPPNAPI | (59) | 90 | 27 | 43 | — | 58 | 220 |
| | pol 145 | RHYLHTLWKAGILYK | (60) | 100 | 17 | 4.0 | — | 2271 | 1499 |
| | env 339 | LVPFVQWFVGLSPTV | (61) | 95 | 408 | 14 | — | 315 | 28 |
| | pol 501 | LHLYSHPIILGFRKI | (62) | 80 | 248 | 558 | — | 77 | 244 |
| | pol 523 | PFLLAQFTSAICSVV | (63) | 95 | 27 | 359 | — | 560 | 246 |
| | pol 618 | KQCFRKLPVNRPIDW | (64) | 45 | 3.0 | 4370 | — | 40 | 34 |
| | pol 767 | AANWILRGTSFVYVP | (65) | 70 | 55 | 386 | — | 966 | 1634 |
| | core 50 | PHHTALRQAILCWGELMTLA | (66) | 90 | 810 | 8.0 | — | 326 | — |
| DR3 | pol 694 | LCQVFADATPTGWGL | (67) | 95 | 7470 | 5009 | 67 | 490 | 1203 |
| | pol 385 | ESRLVVDFSQFSRGN | (68) | 45 | 7372 | 1368 | 36 | 208 | 251 |
| | pol 96 | VGPLTVNEKRRLKLI | (69) | 60 | 8415 | 4153 | 43 | 3916 | 1908 |
| | pol 420 | SSNLSWLSLDVSAAF | (70) | 85 | 38 | 3089 | 62 | 168 | 17 |

| HLA Supertype | Epitope | HLA-DR binding capacity ($IC_{50}$ nM) | | | | | | | | # DR bound[2] |
|---|---|---|---|---|---|---|---|---|---|---|
| | | DRB1 *1101 | DRB1 *1201 | DRB1 *1302 | DRB1 *0701 | DRB1 *0802 | DRB1 *0901 | DRB5 0101 | DRB3 *0101 | DRB4 *0101 | |
| DR | pol 412 | 303 | 397 | 143 | 173 | 598 | 791 | 1067 | 1837 | 4179 | 10 |
| | pol 664 | 82 | — | 190 | 90 | 416 | 142 | 144 | 4848 | 322 | 11 |
| | env 180 | 6 | 4229 | 9 | 8 | 189 | 56 | 1158 | 4374 | 696 | 10 |
| | pol 774 | 443 | — | — | 94 | 818 | 220 | 400 | — | — | 9 |
| | core 120 | 11 | 817 | 565 | 78 | 76 | 1773 | 7 | 6454 | 395 | 8 |
| | pol 145 | 42 | 149 | 766 | 61 | 36 | 133 | 35 | — | 782 | 10 |
| | env 339 | 54 | 452 | 2330 | 2744 | 60 | 31 | 1516 | 1661 | 22 | 9 |
| | pol 501 | 492 | 9462 | — | — | 800 | 1551 | 560 | — | 102 | 8 |
| | pol 523 | 1749 | — | 59 | 328 | 940 | 1373 | 4764 | — | 1347 | 7 |
| | pol 618 | 1617 | — | 821 | 62 | 872 | 5175 | 1246 | — | 3060 | 6 |
| | pol 767 | 1520 | 802 | 143 | 44 | 214 | 299 | 3276 | — | 6553 | 8 |
| | core 50 | 458 | — | — | 676 | 210 | 952 | 124 | 575 | 48 | 7 |
| DR3 | pol 694 | — | — | 2022 | — | — | — | — | 1808 | 1044 | 2 |
| | pol 385 | — | — | 946 | — | — | — | — | 2525 | 8711 | 3 |
| | pol 96 | 6666 | — | 4461 | — | 5354 | — | 4330 | — | 8121 | 1 |
| | pol 420 | 4923 | 1859 | 36 | 5063 | 1065 | 7126 | — | 5 | 7 | 4 |

[1] Sequence identity in 20 strains of HBV including adr, adw, ayr, and ayw isolates.
[2] Number of DR alleles bound with IC50 ≦1000 nM.

The immunogenicity of the vaccine HTL epitopes was evaluated in both HBV patients and mice (Table 12). distribution in common ethnic groups. The calculated phenotypic frequency of individuals with HLA types capable of

TABLE 12

Immunogenicity of HBV Vaccine HTL Epitopes

| HLA Supertype | Alt pep | overlaps with | Ag | Epitope | Sequence | Core Freq (X/20) | SEQ ID NO: | Immunogenicity HBV patients[1] | H2$^{bxd}$ mice[2] |
|---|---|---|---|---|---|---|---|---|---|
| DR | 1186.13 | | HBV pol | 412 | LQSLTNLLSSNLSWL | 18 | 55 | + | + |
| | | | HBV pol | 664 | KQAFTFSPTYKAFLC | 19 | 56 | + | + |
| | 830.01 | 1280.08 | HBV env | 180 | AGFFLLTRILTIPQS | 16 | 57 | + | + |
| | | | HBV pol | 774 | GTSFVYVPSALNPAD | 18 | 58 | + | + |
| | 1186.25 | | HBV core | 120 | VSFGVWIRTPPAYRPPNAPI | | 59 | + | + |
| | | | HBV pol | 145 | RHYLHTLWKAGILYK | 20 | 60 | + | + |
| | | | HBV env | 339 | LVPFVQWFVGLSPTV | 19 | 61 | + | − |
| | | | HBV pol | 501 | LHLYSHPIILGFRKI | 16 | 62 | + | + |
| | 1186.19 | 1186.26 | HBV pol | 523 | PFLLAQFTSAICSVV | 19 | 63 | + | + |
| | | | HBV pol | 618 | KQCFRKLPVNRPIDW | 16 | 64 | + | − |
| | | | HBV pol | 767 | AANWILRGTSFVYVP | 16 | 65 | + | − |
| | F039.01 | | HBV core | 50 | PHHTALRQAILCWGELMTLA | | 66 | + | − |
| DR3 | 35.0100 | | HBV pol | 694 | LCQVFADATPTGWGL | 19 | 67 | + | + |
| | | | HBV pol | 385 | ESRLVVDFSQFSRGN | 20 | 68 | + | + |
| | | | HBV pol | 96 | VGPLTVNEKRRLKLI | | 69 | − | + |
| | | 1186.18 | HBV pol | 420 | SSNLSWLSLDVSAAF | 20 | 70 | − | + |

[1]Recall CTL responses in patients with chronic or active HBV infection
[2]HTL responses induced in H2$^{bxd}$ mice after immunization with a peptide/CFA emulsion.

With the exception of two HLA-DR3 epitopes, all epitopes are recognized in HBV-infected humans. The immunogenicity of the HTL epitopes was also characterized using H2$^{bxd}$ mice. Epitope-peptide binding preferences are similar for HLA-DR1 and IA$^b$ allowing for comparison testing (Wall, K. A. et al., J. Immunol. 152:4526-4536 (1994)) in non-transgenic mice. Twelve of the HTL epitopes were immunogenic in these mice, as judged by fresh ELISPOT assays performed 11-14 days after immunization with 25 µg of purified, synthetic peptides (Table 12).

In conclusion, these data identify a set of HTL epitopes suitable for inclusion in an HBV vaccine construct.

Projected Population Coverage at the Level of HTL Epitopes

Figure 26A:
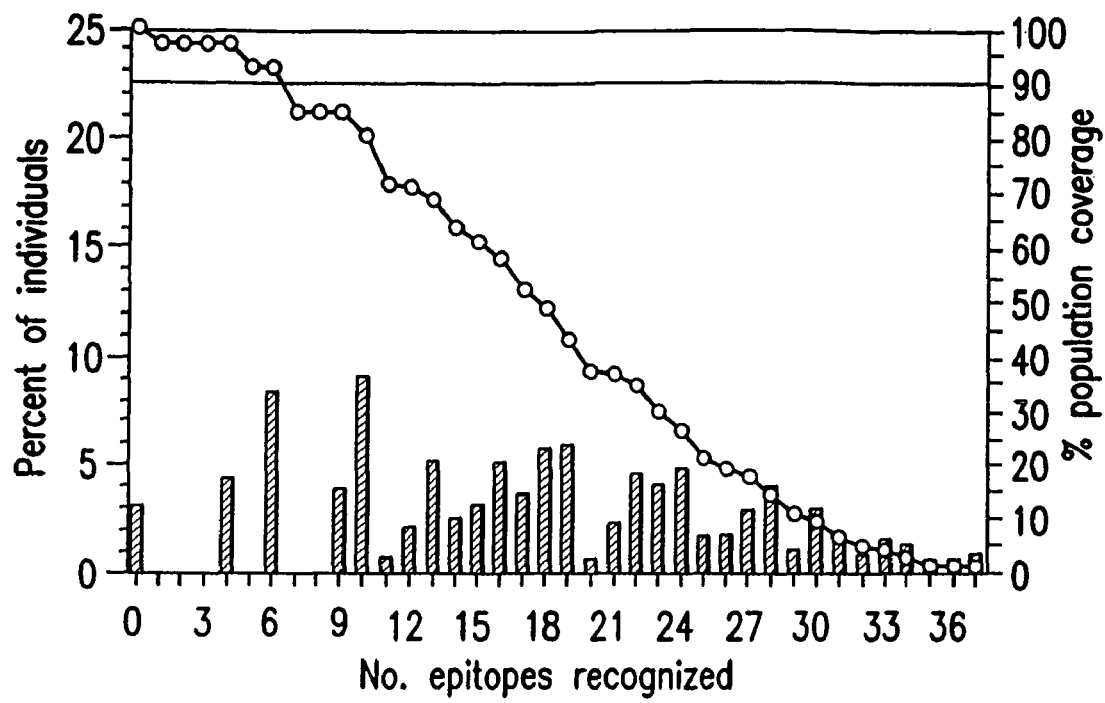
Figure 26B:
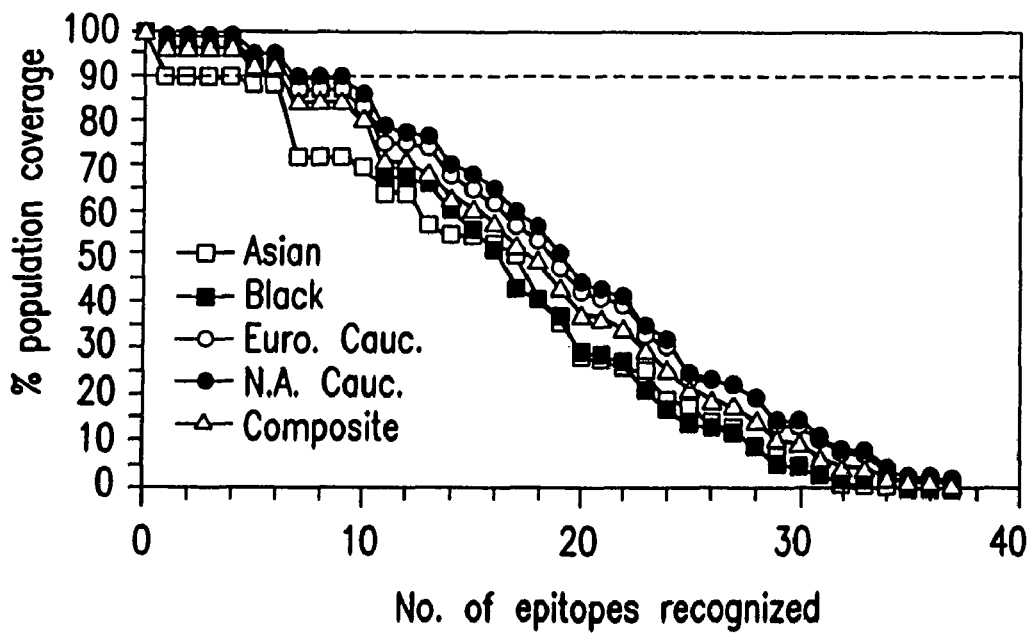
Figure 27A:
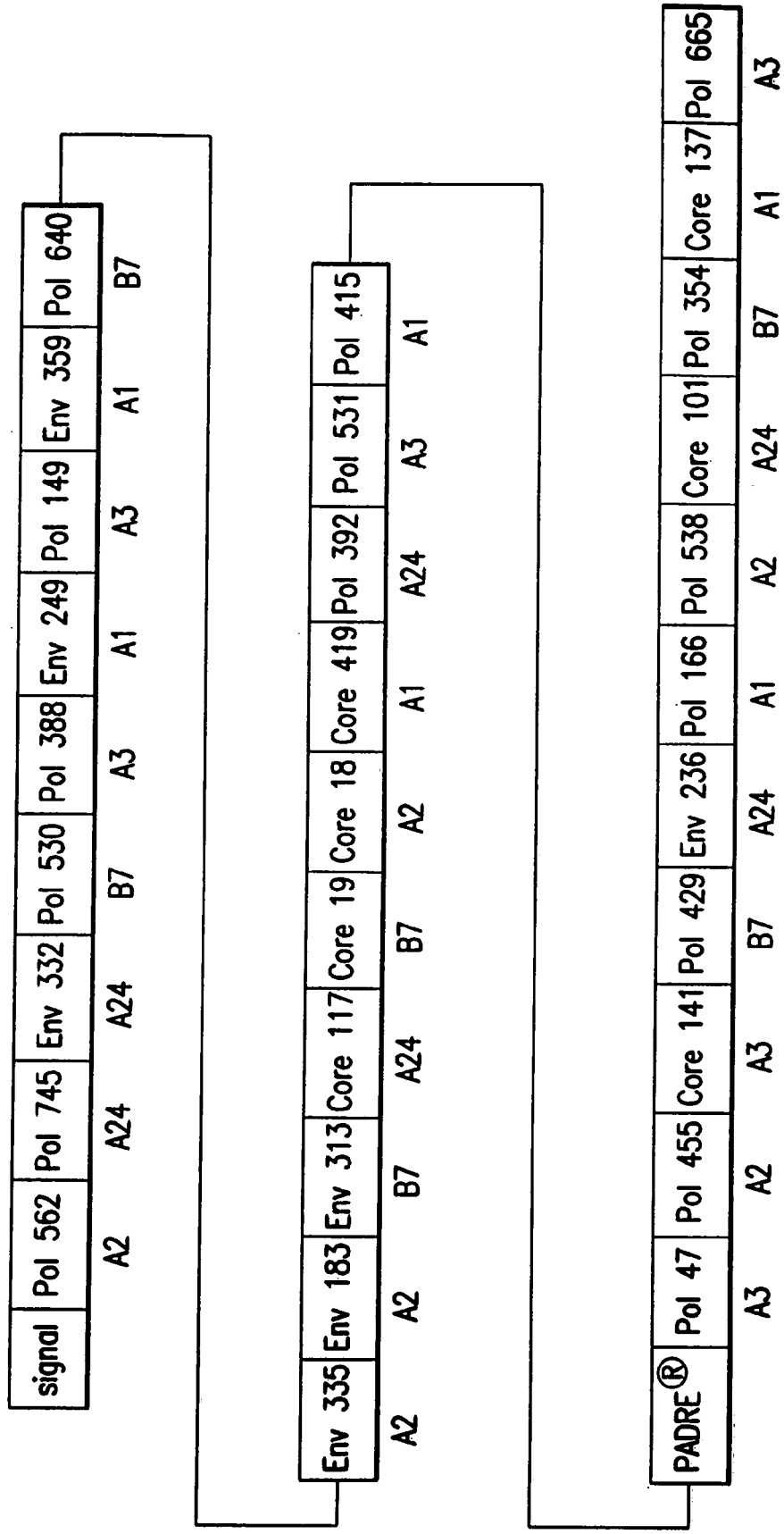
Figure 27B:
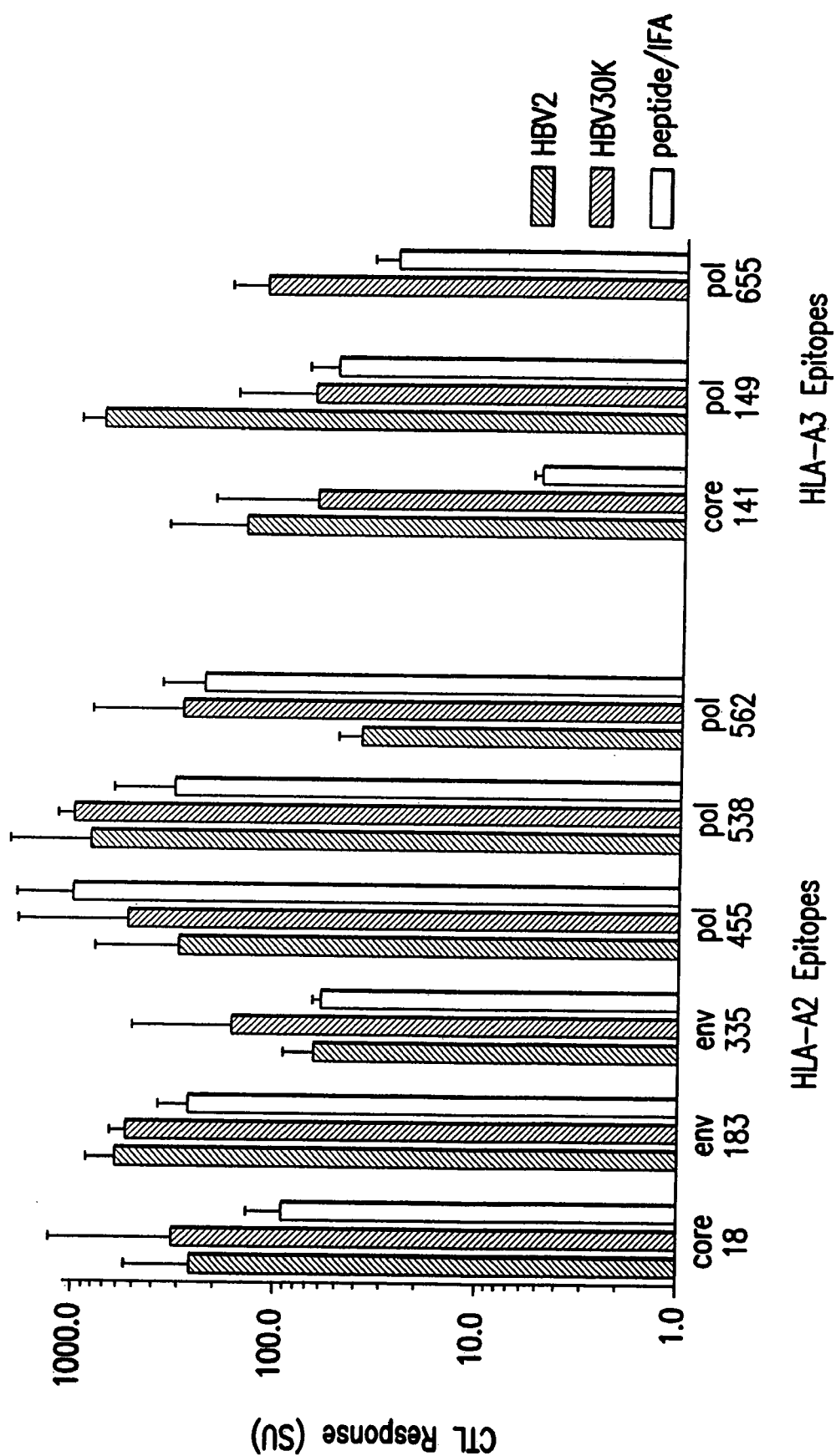

The selected HTL epitopes were derived from the core, pol and env antigens, thus offering the opportunity of generating multi-specific responses in immunized individuals. These epitopes also provide a high level of predicted population coverage across the most common ethnic groups. Table 6B summarizes the HLA types included in the analysis and their binding the indicated number of class II-restricted epitopes and the cumulative frequency of individuals predicted to be genetically capable of responding immunologically to the selected epitopes is shown in FIGS. 26A-26B. We predict that an average of 17.2 epitope-HLA combinations could be recognized in an idealized population composed of averaging HLA frequencies observed in major ethnic groups (FIG. 26A). The average number of epitope-combinations potentially recognized is higher than 16 (the total number of epitopes) because the heterozygosity and of the highly degenerate binding capacity of the epitopes. Analysis of the major ethnic groups demonstrated very broad population coverage (FIG. 26B).

3. Minigene Construct Design

Background

The focus of our research is the development of vaccine constructs composed of multiple epitopes. Studies from a number of different laboratories demonstrated that multi-epitope constructs can be configured by stringing epitopes one after the other in a "string of beads" manner. However, the immunogenicity of individual CTL epitopes in constructs of this type is often highly variable. Variation can be attributed to the differential efficiency of the cellular processing that generates epitopes. We found that the use of appropriate amino acid spacers to ensure efficient proteosomal cleavage results in balanced epitope processing and immunogenicity. (Velders, M. P. et al., *J. Immunol.* 166:5366-5373 (2001); Livingston, B. D. et al., *Vaccine.* 19:4652-4660 (2001)).

The possibility of creating artificial epitopes, referred to as "junctional epitopes," has been considered. Junctional epitopes may dominate or redirect responses in an inappropriate manner and/or may be homologous to human (self) sequences and thereby induce anti-self responses. A computer program has been designed that, for each epitope pair, selects the spacer composition that optimizes proteosomal cleavage and minimizes the occurrence of epitope motifs through the addition of additional amino acids as spacers. Thus, our epigene construct design software evaluates different epitope arrangements and selects those with optimal predicted proteosomal cleavage and minimal occurrence rate of junctional motifs.

Optimization of HLA-DR binding epitopes for proteosomal cleavage is not relevant, although avoiding junctional epitopes remains a primary design consideration. Since the motifs recognized by HLA class II molecules are more broadly defined, we designed a strategy based on the use of a universal spacer consisting of GPGPG (SEQ ID NO:2); (Livingston et al. *J. Immunol.* 168:5499-5509 (2002)). This spacer has the capacity of disrupting binding to most, if not all, of the most common HLA-DR types since it is poorly compatible with the majority of human and murine class II binding motifs (Livingston, B. et al., *J. Immunol.* 168:5499-5506 (2002)).

The N-terminus of the epigene CTL constructs includes the sequence MGMQVQIQSLFLLLLWVPGSRG (e.g., amino acids 1-22 of SEQ ID NO:72). This is a consensus sequence based on the Ig kappa secretory signal, and included to assist in MHC Class I targeting of the polypeptide product.

Another important element of the vaccine design strategy is the inclusion of a universal HTL epitope (Alexander, J. et al., *Immunity* 1:751-761 (1994)). This non-natural epitope was designed to bind to the most common HLA molecules with high affinity and for optimal immunogenicity by maximizing TCR contact residues. This HTL epitope can induce HTL responses to support the induction and augmentation of CTL responses (Alexander, J. et al., *Immunity* 1:751-761 (1994); Alexander, J. et al., *Immunol. Res.* 18:79-92 (1998)). Utilization of a non-HBV-derived HTL epitope might offer unique advantages in terms of support for CTL induction in the chronic setting because HBV-specific HTL responses may, in part, be impaired by the tolerance associated with chronic infection. In fact, it has been demonstrated that this HTL epitope allows the immune system to overcome HBV-specific T cell tolerance in transgenic mice expressing HBV antigens (Livingston, B. D. et al., *Hum. Immunol.* 60:1013-1017 (1999); Livingston, B. D. et al., *J. Immunol.* 162:3088-3095 (1999); Alexander, J. et al., *Immunol. Res.* 18:79-92 (1998); Sette, A. D. et al., *J. Immunol.* 166:1389-1397 (2001)). This HTL epitope is also included in HTL vaccine constructs because it enhances responses induced by other HTL epitopes. This "help for the helpers" concept is consistent with recently published observation in the CD40 system, which suggests that dendritic cell licensing, defined as HTL-induced upregulation of accessory molecules on dendritic cells, can also apply to HTL responses (Gerloni, M. S. et al., *Proc. Natl. Acad. Sci. USA.* 97:13269-13274 (2000); van Mierlo, G. J. et al., *Proc. Natl. Acad. Sci. USA.* 99:5561-5566 (2002)).

B. Design of a Minigene Construct Encoding HBV-Derived CTL Epitopes

A first prototype vaccine construct, HBV1, included 17 HLA-A2, -A3 and -B7 epitopes and lacked amino acid spacers. This construct was modified (HBV2) to incorporate appropriate spacers and increase the immunogenicity of a number of the component epitopes. HBV2 induced CTL responses to a wide spectrum of epitopes that were in general comparable to those induced by immunization with peptides emulsified in IFA (data not shown). This type of control allows one to estimate the activity detectable for each particular epitope in the absence of any processing constraint, and thus allows standardization of factors such as availability and size of an epitope-specific TCR repertoire in the various strains of mice utilized for preclinical evaluations.

A number of new epigene constructs were designed to include HLA-A1 and -A24 epitopes to provide greater population coverage. Four epigene constructs incorporating 21 and 30 CTL epitopes were constructed and tested for immunogenicity, focusing on the HLA-A2 epitopes. All four constructs induced broad, potent CTL responses (data not shown). As the 30 epitope constructs should provide a greater redundancy of epitope coverage in the prospective patient population, additional studies centered on these larger epigene constructs. One particular 30 epitope construct, HBV30C, induced strong CTL responses to both the HLA-A3 and -A24 epitopes (the latter measured using $H2^{bxd}$ mice). Although two of the HLA-A2 epitopes, core 18 and env 183, were poorly immunogenic in this construct, further spacer optimization restored the immunogenicity of these epitopes. A schematic and the amino acid sequence of the CTL vaccine HBV30K are shown in FIG. 27A and Table 13. An example of a polynucleotide sequence encoding HBV30K is shown in Table 13.

The immunogenicity of HBV30K in HLA-A2 and -A11 transgenic mice is shown in FIG. 27B. As a means of comparison, the CTL activity induced following immunization with the potent HBV2 prototype construct as well as peptide/IFA is also shown. Overall, HBV30K elicited CTL responses as vigorous as HBV2. In fact, HBV30K induced CTL responses against all the component epitopes that are immunogenic in the HLA transgenic animals and typically these CTL responses were comparable to the responses induced following peptide immunization. This data lead to the selection of HBV30K as the lead CTL vaccine.

TABLE 13

HBV30K construct

| HBV30K | Polynucleotide |
|---|---|

SEQ ID NO: 71  1
↑ Start
[ATG]GGAATGCAGGTGCAAATACAGTCTCTCTTCCTTTTGCTTCTCTGGGTTCCAGGAT
CACGGGGCTTCTTGCTTAGCTTGGGCATCCACCTAAATGCTGCTGCAAAATACACATC
TTTTCCTTGGCTCCTTAATGCCGCCGCTAGGTTTTCATGGCTGAGTCTGCTAGTACCTT
TCAATGCGGCTTTCCCACATTGCCTAGCTTTTAGCTATATGAAAGCTGCTTTAGTCGTG
GACTTTTCACAGTTTAGCAGAGGAGCAATCCTGCTGCTATGTCTGATATTCCTTCTAAA
CGCAGCCAGCCACACACTCTGGAAAGCTGGTATCCTTTACAAGAAAGCCTGGATGAT
GTGGTATTGGGGACCCAGCCTCTACAAAGCATACCCTGCCCTGATGCCACTATACGCA
TGCATTGGCGCGGCAGCCTGGTTATCCCTTTTAGTACCGTTTGTCAACGCCGCAGCGG
GATTTCTATTAACCAGAATCCTGACGATTAATGCTGCCGCCATTCCGATCCCAAGTTC
CTGGGCATTCAAAGCAGCCGCGGAGTATCTGGTTTCATTTGGCGTATGGAACCTGCCA
AGCGACTTCTTTCCTTCTGTTAAGGCCGCTGCTTTCCTCCCCTCCGATTTCTTTCCATCG
GTGAAAGCCGCTGCCGACCTCCTTGATACCGCGAGCGCTCTGTACAACTCGTGGCCAA
AATTCGCAGTTCCAAACCTAAAAGCCGCCGCCAGTGCCATTTGTTCCGTGGTAAGGAG
AAAATTATCACTCGACGTGTCCGCAGCATTTTATAACGCTGCTGCAAAGTTTGTCGCA
GCATGGACATTGAAGGCTGCAGCGAAAGCAGCAAATGTATCAATACCCTGGACCCAC
AAGGGTGCAGCCGGGCTGTCTAGGTATGTGGCGAGGCTAAACGCCGCCGCCTCAACA
CTGCCTGAGACTACTGTCGTGAGACGCAAACACCCTGCCGCAATGCCCCACCTGCTGA
AAGCAGCCGCACGATGGATGTGCCTCAGAAGATTCATAATAAACGCTTCTTTCTGTGG
GTCACCCTACAAAGCCGCTTACATGGACGATGTGGTCCTCGGAGTGAATGCCCTCTGG
TTCCATATCAGCTGCCTGACATTCAAGGCAGCCGCCACCCCCGCTCGTGTGACAGGAG
GTGTCTTCAAAGCCGCGGCACTGACTTTCGGTCGGGAAACTGTATTGGAATATAAGCA
GGCCTTCACATTCTCCCCAACATACAAG[TGA]
↓ Stop
1248

| HBV30K | Polypeptide |
|---|---|

SEQ ID NO: 72  1
↑
MGMQVQ1QSLFLLLLWVPGSRGFLLSLGIHLNAAAKYTAFPWLLNAAARFSWLSLLVPFN
AAFPHCLAFSYMKAALVVDFSQFSRGAILLLCLIFLLNAAAHTLWKAGILYKKAWMMW
YWGPSLYKAYPALMPLYACIGAAAWLSLLVPFVNAAAGFLLTR1LTINAAA1P1PSSWAFK
AAAEYLVSFGVWNLPSDFFPSVKAAAFLPSDFFPSVKAAADLLDTASALYNSWPKFAVPN
LKAAASAICSVVRRKLSLDVSAAFYNAAAKFVAAWTLKAAAKAANVSIPWTHKGAAGL
SRYVARLNAAASTLPETTVVRRKHPAAMPHLLKAAARWMCLRRFIINASFCGSPYKAAY
MDDVVLGVNALWFHISCLTFKAAATPARVTGGVFKAAALTFGRETVLEYKQAFTFSPTY
K
↓
416

C. Design of a Minigene Construct Encoding HBV Derived HTL Epitopes

Figure 28A:
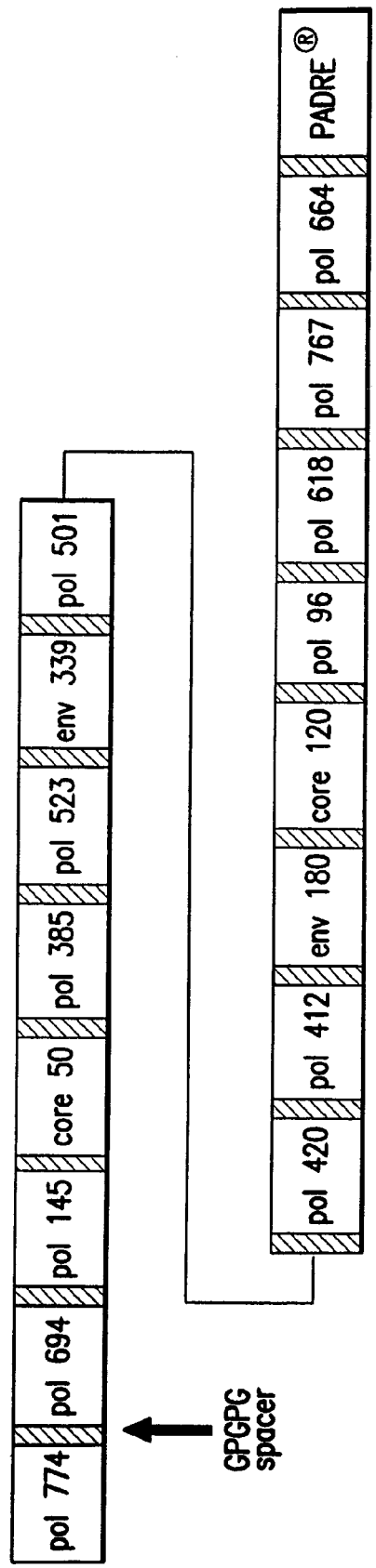
Figure 28B:
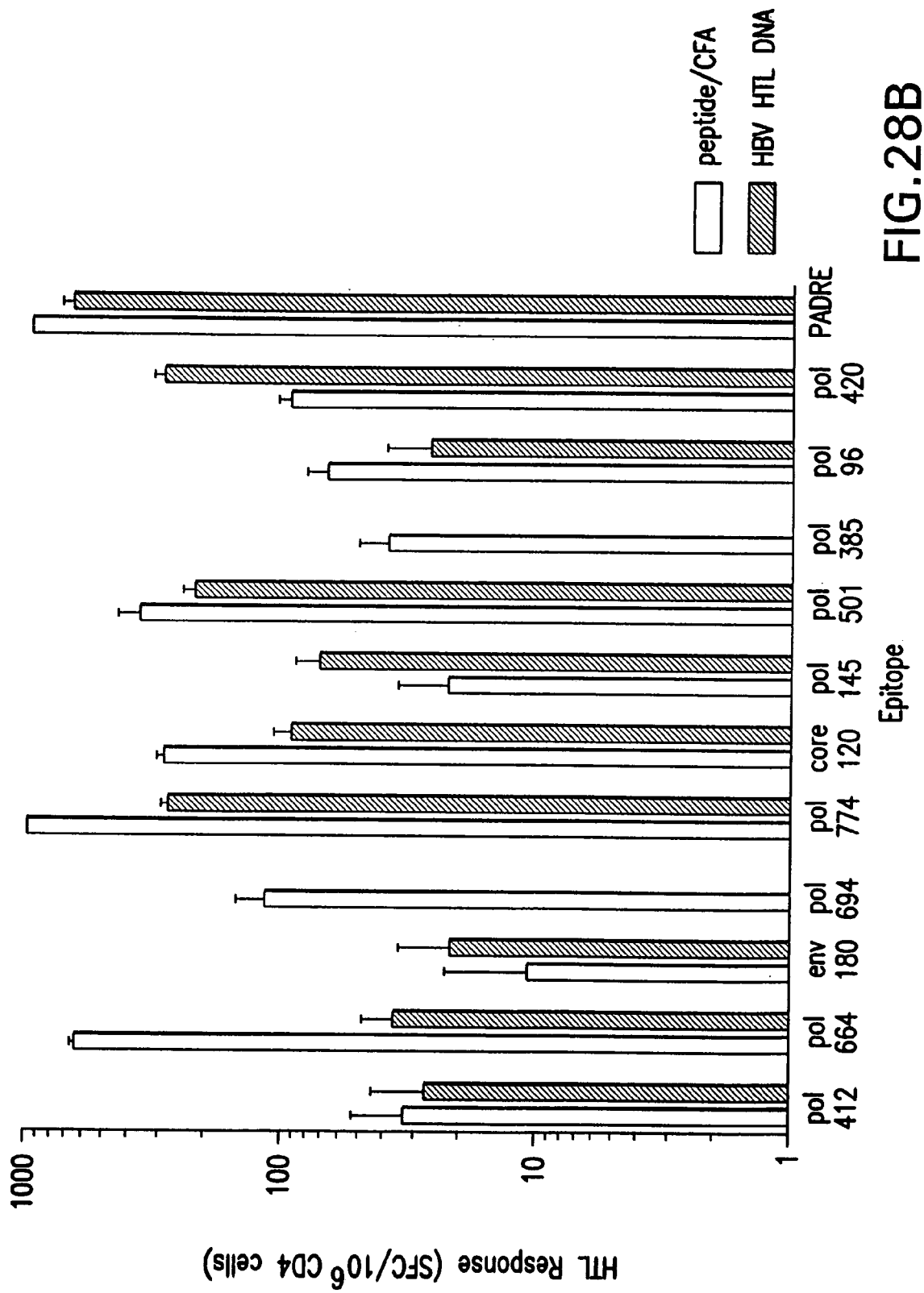
Figure 29A:
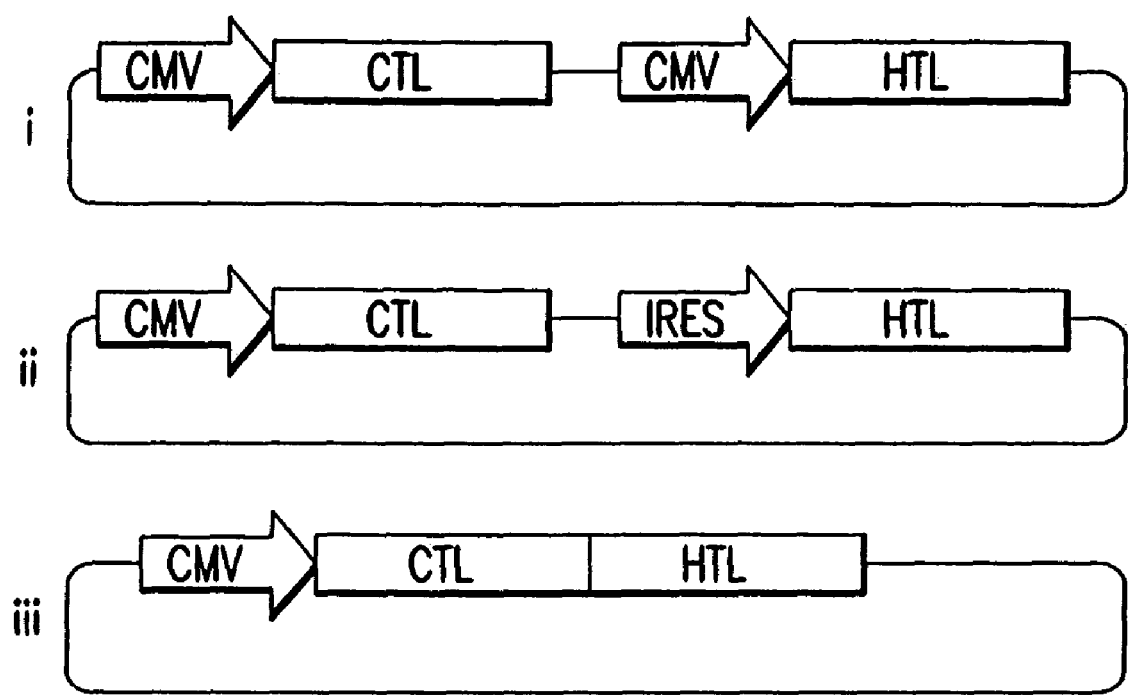
Figure 29B:
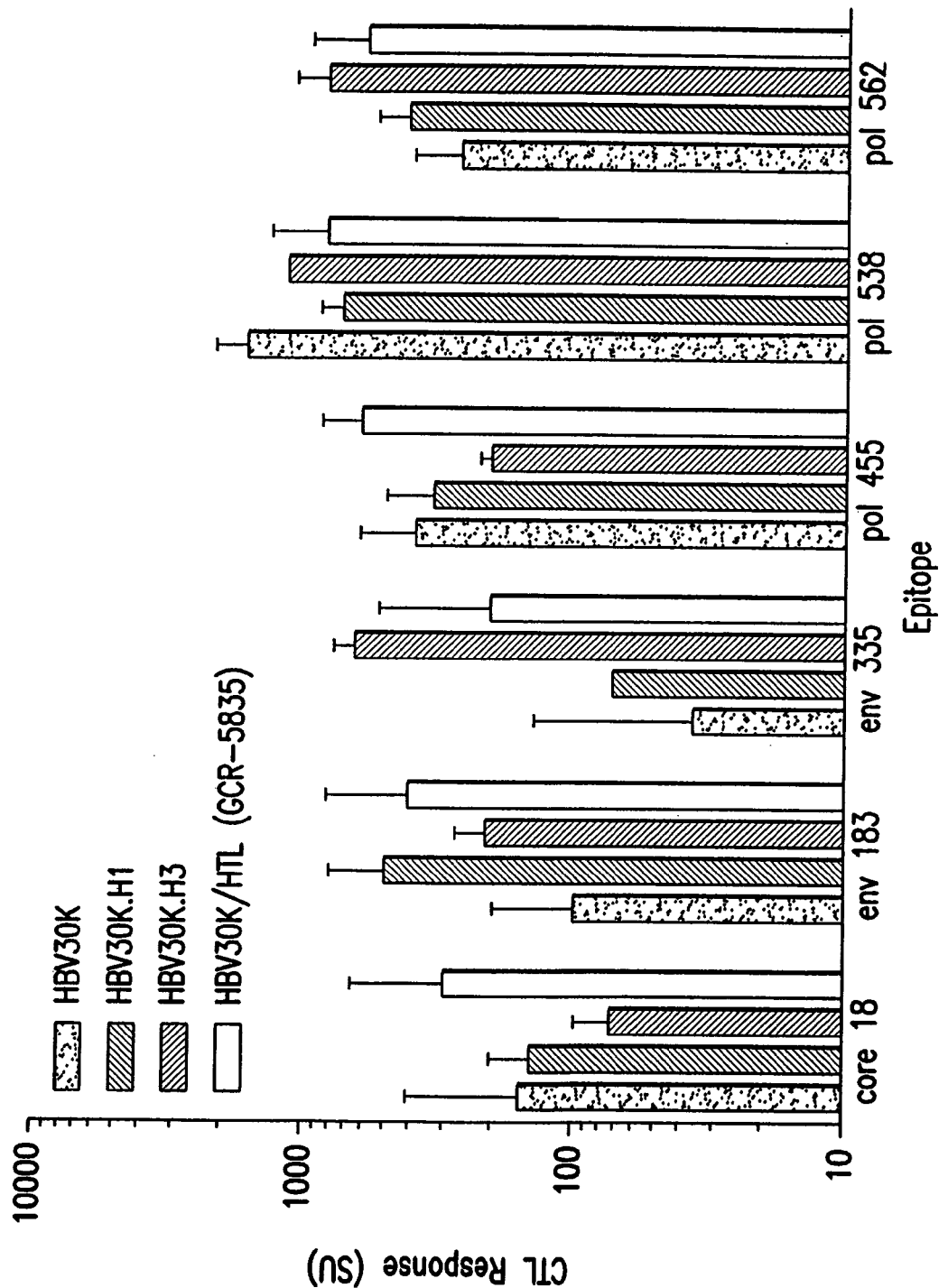
Figure 30:
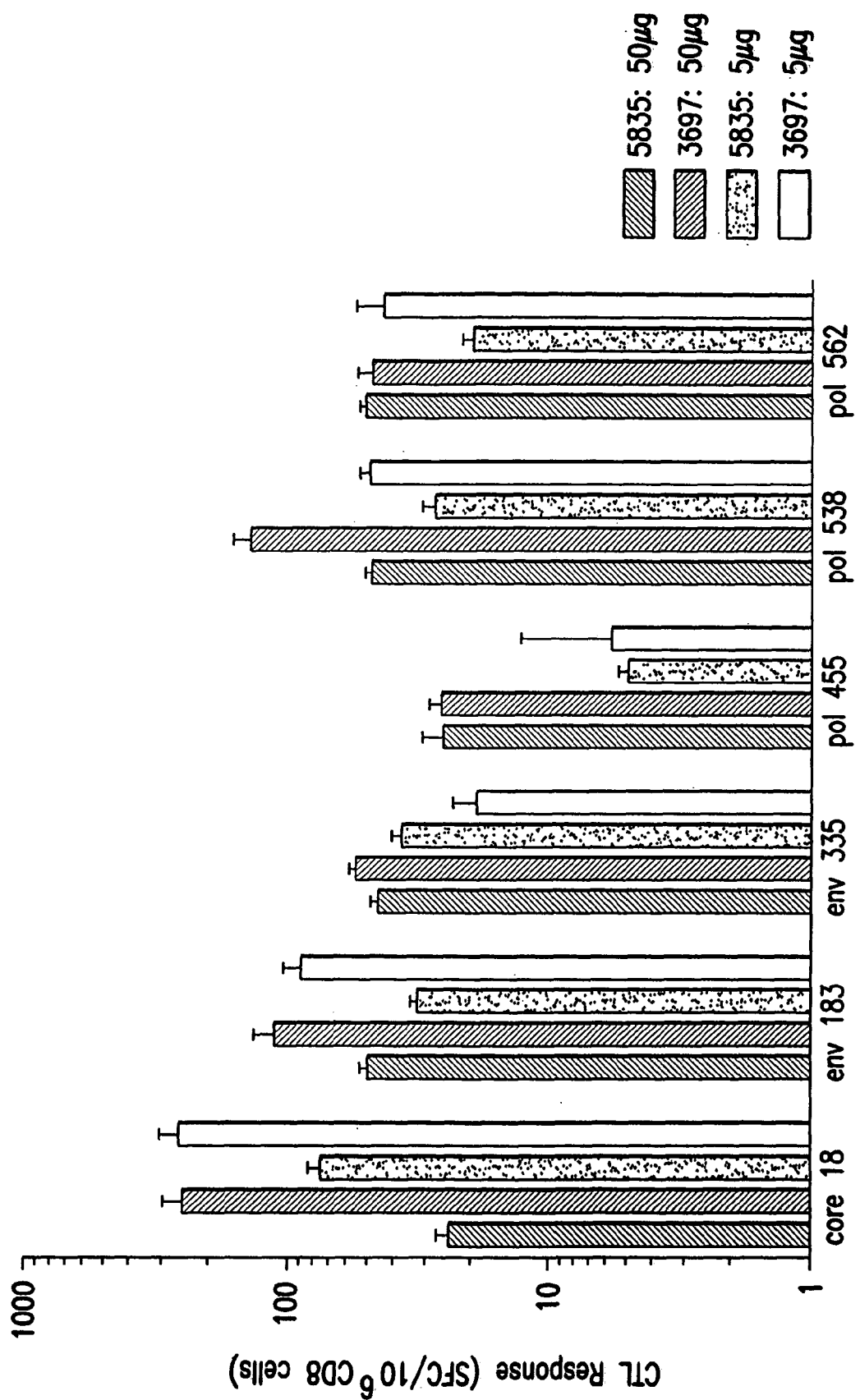

A single epigene construct encoding the 16 HTL epitopes was designed incorporating the GPGPG (SEQ ID NO:2) universal spacer. A schematic and the amino acid sequence of this HBV HTL construct are shown in FIG. 28A and Table 14. An example of a polynucleotide sequence encoding the HBV HTL construct is shown in Table 14. This construct was tested for immunogenicity in H2$^{bxd}$ mice (FIG. 28B), measuring IFN-γ production by CD4+ T-lymphocytes using an ELISPOT assay. Responses were as vigorous as those induced by a peptides emulsified in CFA for 50% of the epitopes (6/12) tested. Of the remaining six epitopes, and only two epitopes failed to induce a response following immunization with the HTL vaccine construct.

TABLE 14

HBV HTL construct

| HTL | Polynucleotide |
|---|---|

SEQ ID NO: 73  1
↑ Start
```
ATGGGAACTTCTTTTGTGTATGTCCCTTCCGCTCTGAACCCAGCAGACGGACCCGGGCCT
GGCCTGTGCCAG
GTCTTCGCCGACGCAACTCCCACAGGGTGGGGGCTGGGGCCAGGACCAGGCAGGCACTA
CCTGCATACTCTGTGGAAGGCAGGAATCCTCTATAAAGGGCCCGGCCCAGGCCCTCACC
ACACCGCCCTGAGGCAGGCCATCCTGTGCTGGGGGGAGCTCATGACCCTGGCCGGACCT
GGACCCGGGGAGAGCAGACTGGTGGTGGATTTCAGCCAATTCAGCAGAGGAAACGGAC
CCGGCCCTGGGCCTTTTCTGCTGGCTCAGTTTACATCTGCTATTTGTTCTGTGGTCGGCCC
CGGGCCCGGACTCGTGCCTTTCGTGCAGTGGTTCGTGGGACTGTCCCCTACAGTCGGGCC
CGGCCCAGGGCTGCATCTGTACTCCCACCCAATCATCCTCGGCTTCCGCAAGATTGGACC
CGGCCCAGGCTCCAGCAATCTCTCCTGGCTCTCTCTGGACGTGTCTGCCGCCTTTGGCCC
TGGACCAGGCCTGCAAAGCCTGACTAATCTGCTCAGCAGCAACCTGTCCTGGCTGGGAC
CTGGCCCAGGGGCTGGCTTCTTTCTGCTCACCCGGATTCTCACAATTCCCCAGTCCGGAC
CAGGACCAGGAGTCAGTTTCGGGGTGTGGATCAGGACCCCTCCTGCTTATAGACCACCC
AATGCTCCAATCGGCCCCGGCCCTGGCGTCGGGCCACTGACCGTGAATGAGAAGCGCCG
GCTGAAGCTGATCGGCCCTGGCCCTGGCAAGCAGTGCTTTCGCAAACTGCCCGTGAACA
GACCTATTGATTGGGGCCCCGGCCCTGGAGCAGCCAACTGGATTCTCAGGGGAACAAGC
TTCGTCTACGTGCCCGGGCCCGGACCAGGGAAGCAGGCTTTTACCTTCTCTCCCACTTAC
AAGGCCTTCCTCTGTGGGCCAGGCCCCGGCGCCAAGTTTGTGGCAGCATGGACCCTCAA
AGCCGCTGCCTGA
```
↓ Stop
1032

| HTL | Polypeptide |
|---|---|

SEQ ID NO: 74  1
↑
```
MGTSFVYVPSALNPADGPGPGLCQVFADATPTGWGLGPGPGRIIYLIITLWKAGILYKGPGP
GPHHTALRQAILCWGELMTLAGPGPGESRLVVDFSQFSRGNGPGPGPFLLAQFTSAICSVVG
PGPGLVPFVQWFVGLSPTVGPGPGLHLYSHPIILGFRKIGPGPGSSNLSWLSLDVSAAFGPGPG
LQSLTNLLSSNLSWLGPGPGAGFFLLTRILTIPQSGPGPGVSFGVWIRTPPAYRPPNAPIGPGPG
VGPLTVNEKRRLKLIGPGPGKQCFRKLPVNRPIDWGPGPGAANWILRGTSFVYVPGPGPGKQ
AFTFSPTYKAFLCGPGPGAKFVAAWTLKAAA
```
↓344

Effective Minimization of Junctional Epitope Content

After defining epigene constructs for the CTL and HTL vaccine constructs, we proceeded with a more in-depth characterization. First, we verified that the computer-based epigene construct design effort effectively minimized the presence of junctional epitopes. The junctional epitope content of the CTL and HTL components was determined using a motif scan and compared to two sets of random assortments of the same CTL and HTL epitopes. The results are shown in Table 15.

TABLE 15

Example of minimization of junctional epitopes in vaccine constructs

| Construct | Protocol | SEQ ID NO: | Junctional CTL Motifs[4] |
|---|---|---|---|
| HBV30K[1] | minimized | 1 | 1 |
| HBV30R1 | random[2] | | 84 |
| HBV30R2 | random | | 99 |
| HBV HTL[1] | GPGPG | 2 | 12 |
| HBV HTL NS1 | no spacer[3] | | 42 |
| HBV HTL NS2 | no spacer | | 37 |

[1]Vaccine CTL and HTL epigene constructs.
[2]Random arrangement of CTL epitopes optimized for processing.
[3]HTL epigene constructs without spacers.
[4]Number of junctional epitopes bearing HLA-A1, -A2, -A3, -A24 or B7 motifs.

The number of junctional epitopes present in the optimally designed CTL epitope vaccine is approximately 100-fold lower, compared to random arrangements. While the HTL component was not specifically minimized for the presence of junctional CTL epitopes, the use of the GPGPG spacer (SEQ ID NO:2), to eliminate HTL functional epitopes within the string of HBV-specific HTL epitopes, did reduce the presence of junctional CTL epitopes by approximately 4-fold. Junctional HTL epitopes were not considered in the analysis of the CTL epitope string as the presence of such epitopes in the CTL epigene construct should only serve to stimulate non-specific help much in the same way as the universal HTL epitope mentioned above (Alexander, J. et al., Immunity 1:751-761 (1994)).

BLAST searches were performed to evaluate the potential for homology of junctional regions in the HBV CTL and HTL epigene constructs. As input sequences, we considered each of the 47 sequences comprised of four C-terminal residues of an epitope, the spacer sequence itself, if present, and the four N-terminal residues of the following epitope. For the BLAST search parameters, we used the search option "Short nearly exact matches." To run the search with the least stringent criteria, we used the default settings present on the web page; expect value at 20,000 and word size set at 2. The organism field was restricted to Homo sapiens. Table 16 lists the results.

No junctional region was 100% homologous to any human sequence. The highest homology was 78% and the least was 54% (mean 63±7.4). For the sake of comparison, an identical homology search was run on a random sample of seven CTL and four HTL HBV epitopes (Table 17).

The best homology detected was 67% and the least was 30% (mean 54±13).

TABLE 16

Results of human homology search based on epigene construct junctional motifs

| Junctional Region | Source | SEQ ID NO | Sequence | % Homology | Accession No. |
|---|---|---|---|---|---|
| 1 | pol 562-NAAA-pol 745 | 75 | GIHLNAAAKYTS | — | |
| | Unknown protein for MGC:20975 | 76 | GIHLN*AA**** | 58 | AAH14187 |
| 2 | pol 745-NAAA-env 332 | 77 | PWLLNAAARFSW | — | |
| | sulfonylurea receptor 1 | 78 | PWLLNA****** | 50 | AAC36724.1 |
| 3 | env 332-NAA-pol 530 | 79 | LVPFNAAFPHC | — | |
| | KIAAI219 protein | 80 | ***F+AAF*HC | 55 | BAA86533.2 |
| 4 | pol 530-KAA-pol 388 | 81 | FSYMKAALVVD | — | |
| | Hypothetical protein | 82 | FSYMKAA**** | 63 | XP_073807.1 |
| 5 | pol 388-GA-env 249 | 83 | QFSRGAILLL | — | |
| | Hypothetical protein | 84 | QFS*GAIL** | 70 | XP_066589.1 |
| | Hypothetical protein FLJ22313 | 85 | *FSR*AILL* | 70 | NP_071768.2 |
| 6 | env 249-NAAA-pol 149 | 86 | IFLLNAAAHTLW | — | |
| | Hypothetical protein | 87 | LLNAH*LW | 58 | XP_060325.1 |
| 7 | pol 149-KA-env 359 | 88 | ILYKKAWMMW | — | |
| | Nebulin | 89 | ILYK*AW*** | 60 | AAB02622.1 |
| | Hypothetical protein FLJ14753 | 90 | *****AWMMW | 50 | AAH21093 |
| 8 | pol 149-KA-pol 640 | 91 | PSLYKAYPAL | — | |
| | Intergrase interactor 1 | 92 | *SLYK*YP+L | 70 | AAA81905.1 |
| 9 | pol 640-GAA-env 335 | 93 | YACIGAAWLSL | — | |
| | Steroid 18-hydroxylase | 94 | **C+*A*WLSL | 55 | AAB34642.1 |
| | CGI-67 protein | 95 | YA*1*AAWL+L | 73 | AAD34062.1 |
| 10 | env 335-NAAA-env 183 | 96 | VPFVNAAAFLLT | — | |
| | Hypothetical protein | 97 | *PFVNAFL | 58 | CAD38882.1 |
| | KIAA1742 protein | 98 | *PFVN*AA*LL* | 67 | BAB21833.2 |
| 11 | env 183-NAAA-env 313 | 99 | ILTINAAAIPIP | — | |
| | hRANKL2 | 100 | *LTINAIP | 58 | AAC517.62.1 |
| 12 | env313-KAAA-core 117 | 101 | SWAFKAAAEYLV | — | |
| | AP-2 beta transcription factor | 102 | ****KAAAEYL* | 58 | CAC04182.1 |
| 13 | core 117-N-core 19 | 103 | FGVWNLPSD | — | |
| | Hypothetical protein | 104 | *GVWNL*SD | 78 | CAD38975.1 |

TABLE 16-continued

Results of human homology search based on epigene construct junctional motifs

| Junctional Region | Source | SEQ ID NO | Sequence | % Homology | Accession No. |
|---|---|---|---|---|---|
| 14 | core 19-KAAA-core 18 | 105 | FPSVKAAAFLPS | — | |
| | Nascent-polypeptide-associated complex | 106 | *PS*KAAAFL** | 67 | XP_061543.1 |
| 15 | core 18-KAAA-core 419 | 107 | FPSVKAAADLLD | — | |
| | Zinc finger protein 64 | 108 | **SVKAA++LL* | 58 | XP_087479.4 |
| 16 | core 419-N-pol 392 | 109 | SALYNSWPK | — | |
| | Immunoglobulin kappa VLJ region | 110 | ***YN+WPK | 55 | AAM46537.1 |
| 17 | pol 392-KAAA-pol 531 | 111 | VPNLKAAASAIC | — | |
| | DNA poly. epsilon catalytic subunit | 112 | NLKAAAS* | 58 | AAA15448.1 |
| 18 | pol 531-K-pol 415 | 113 | VVRRKLSLD | — | |
| | Hypothetical protein | 114 | V+RRK+SLD | 78 | XP_064183.1 |
| 19 | pol 415-NAA-padre | 115 | AAFYNAAAKFV | — | |
| | Potassium voltage-gated channel | 116 | *AFYN*A+KF* | 64 | AAH27932.1 |
| 20 | padre-KAA-pol 47 | 117 | KAAAKAANVSI | — | |
| | Laminin beta precursor | 118 | KAA*KAAN+** | 64 | AC005048.1 |
| 21 | pol 47-GAA-pol 455 | 119 | WTHKGAAGLSR | — | |
| | Hypothetical protein | 120 | WTHKG+*GL+R | 73 | XP_117843.1 |
| 22 | pol 455-NAAA-core 141 | 121 | VARLNAAASTLP | — | |
| | Solute carrier family 39 (zinc transporter) | 122 | VARL+AAA**** | 58 | NP_060237.1 |
| | Hypothetical protein | 123 | VA*L*AAA+TL* | 67 | XP_120525.1 |
| 23 | core 141-K-pol 429 | 124 | VVRRKHPAA | — | |
| | Hypothetical protein | 125 | VRRKHP*A* | 78 | XP_117855.1 |
| 24 | pol 429-KAAA-env 236 | 126 | PHLLKAAARWMC | — | |
| | Hypothetical protein | 127 | **LL*AA*RW*C | 58 | XP_105701.1 |
| 25 | env 236-N-pol 166 | 128 | RFIINASFC | — | |
| | Hypothetical protein | 129 | RFII+A*F* | 67 | XP_072766.5 |
| 26 | pol 166-KAA-pol 538 | 130 | GSPYKAAYMDD | — | |
| | Hypothetical protein | 131 | PYAYMD* | 54 | AAH01463 |
| 27 | pol 538-NA-core 101 | 132 | VLGVNALWFH | — | |
| | Hypothetical protein | 133 | **GV+ALWF* | 60 | XP_118305.1 |
| | Hypothetical protein | 134 | VL*+*ALWFH | 70 | XP_059358.1 |

TABLE 16-continued

Results of human homology search based on epigene construct junctional motifs

| Junctional Region | Source | SEQ ID NO | Sequence | % Homology | Accession No. |
|---|---|---|---|---|---|
| 28 | core 101-KAAA-pol 354 | 135 | CLTFKAAATPAR | — | |
| | KIAA 1853 protein | 136 | **TFKA*ATP** | 58 | BAB47482.1 |
| | Alpha 1 type XIII collagen | 137 | **T*KAAAT*AR | 67 | NP_542994.1 |
| 29 | pol 354-KAAA-core 137 | 138 | GGVFKAAALTFG | — | |
| | Unknown | 139 | *GV**AA+LTFG | 67 | AE006639.1 |
| 30 | core 137-K-pol 665 | 140 | VLEYKQAFT | — | |
| | Hypothetical protein | 141 | VL+YKQ*F* | 67 | XP_101671.1 |
| | X-linked mental retardation cand. gene | 142 | VL*YKQ*FT | 78 | CAA65075.1 |
| 31 | pol 665-GPGPG-pol 774 | 143 | PTYKGPGPGGTSF | — | |
| | sialyltransferase 1 | 144 | YKGPGPG** | 54 | CAA35111.1 |
| | N2B-Titin isoform | 145 | **YK*PGP*GT*F | 61 | CAD12455.1 |
| 32 | pol 774-GPGPG-pol 694 | 146 | NPADGPGPGLCQV | — | |
| | golgi antigen | 147 | NPAD*PGPG**** | 61 | AAC06338.1 |
| 33 | pol 694-GPGPG-pol 145 | 148 | GWGLGPGPGRHYL | — | |
| | L-myc-1 proto-oncogene protein | 149 | *WGLGPG*G**** | 54 | AAA59879.1 |
| 34 | pol 145-GPGPG-core 50 | 150 | ILYKGPGPGPHHT | — | |
| | sialyltransferase 1 | 151 | YKGPGPG** | 54 | CAA35111.1 |
| 35 | core 50-GPGPG-pol 385 | 152 | MTLAGPGPGESRL | — | |
| | Hypothetical protein | 153 | **LAGPGPG*SR* | 69 | XP_069591.1 |
| | Mitogen-activated protein kinase | 154 | ****GPG*GESRL | 61 | XP_027237.1 |
| 36 | pol 385-GPGPG-pol 523 | 155 | SRGNGPGPGPFLL | — | |
| | protein kinase C mu | 156 | **G+GPGP*PFL* | 61 | CAA53384.1 |
| | CD1-alpha-3 antigen | 157 | SRGPGPGLL | 69 | AAA51935.1 |
| 37 | pol 523-GPGPG-env 339 | 158 | CSVVGPGPGLVPF | — | |
| | Inducible nitric oxide synthase | 159 | C*++GPG*G+VPF | 61 | AAL02120.1 |
| 38 | env 339-GPGPG-pol 501 | 160 | SPTVGPGPGLHLY | — | |
| | Atrophin-1 | 161 | SPTVGPGP***** | 61 | S50832 |
| 39 | pol 501-GPGPG-pol 420 | 162 | FRKIGPGPGSSNL | — | |
| | Hypothetical protein | 163 | *RKI*PGPG**** | 54 | XP_069589.1 |
| | Hypothetical protein | 164 | *RKI**G*GSSN* | 61 | XP_169769.1 |
| 40 | pol 420-GPGPG-pol 412 | 165 | SAAFGPGPGLQSL | — | |
| | Epsin 2b protein | 166 | S*+FGPGPG++S+ | 61 | AAC78609.1 |

TABLE 16-continued

Results of human homology search based on epigene construct junctional motifs

| Junctional Region | Source | SEQ ID NO | Sequence | % Homology | Accession No. |
|---|---|---|---|---|---|
| 41 | pol 412-GPGPG-env 180 | 167 | LSWLGPGPGAGFF | — | |
| | Hypothetical protein | 168 | LSWLGPG*G**** | 61 | XP_097563.1 |
| | Unnamed protein product | 169 | *LGPGPGFF | 61 | BAC05301.1 |
| 42 | env 180 GPGPG-core 120 | 170 | IPQSGPGPGVSFG | — | |
| | Transmembrane protein | 171 | PQ+GPGPGV | 61 | AAC64943.1 |
| 43 | core 120-GPGPG-pol 96 | 172 | NAPIGPGPGVGPL | — | |
| | Unnamed protein product | 173 | ****GPGPG*GPL | 61 | BAC05043.1 |
| | Neuregulin 2 isoform 4 | 174 | *AP*GPGPG*GP* | 69 | AAF28851.1 |
| 44 | pol 96-GPGPG-pol 618 | 175 | LKLIGPGPGKQCF | — | |
| | Unknown protein | 176 | LKL*GPGPG**** | 61 | AF318376.1 |
| 45 | pol 618-GPGPG-pol 767 | 177 | PIDWGPGPGAANW | — | |
| | Hypothetical protein | 178 | DWGPGPG** | 54 | XP_066062.1 |
| 46 | pol 767-GPGPG-pol 664 | 179 | VYVPGPGPGKQAF | — | |
| | TAF4 RNA polymerase II | 180 | ***PGPGPGK*A* | 61 | XP_036470.2 |
| 47 | pol 664-GPGPG-padre | 181 | AFLCGPGPGAKFV | — | |
| | Polycystic kidney disease 1 protein | 182 | **LCGP*PGA*** | 54 | AAC37576.1 |

1. Spacer groups with the 4 adjacent residues from neighboring epitopes were utilizied as query sequences.
2. BLAST search parameters: Expect 20000, Word size 2, Matrix PAM30, No. of alignments 250
3. Resultant sequence matches with the lowest E value are presented first. No sequence identified had an E value <1.
4. If additional sequences were identified with greater homology, they are also presented.
5. Asterisks (*) denote non-matching residues; plus signs (+) denote residues of similar chemical composition.

TABLE 17

Results of human immunology search using random epitope order

| Junctional Region | Source | SEQ ID NO: | Sequence | % Homology | Accession No. |
|---|---|---|---|---|---|
| 4 | pol 530 | 183 | FPHCLAFSYM | — | |
| | Endothelin receptorB delta 3 | 184 | HCLAFS | 60 | AF114165.1 |
| 8 | pol 149 | 185 | WMMWYWGPSLY | — | |
| | Hypothetical protein FLJ12389 | 186 | WMMW*W***** | 45 | NP_076417.1 |
| 11 | env 183 | 187 | FLLTRILTI | — | |
| | Hypothetical protein DKFZ | 188 | *LLTR+LT* | 67 | AAH30825.1 |
| 13 | core 117 | 189 | EYLVSFGVW | — | |
| | Glucose 6-phosphate translocase | 190 | *YLV*FGV* | 67 | CAA75608.1 |
| 15 | core 18 | 191 | FLPSDFFPSV | — | |
| | T-cell activation NFKB-like protein | 192 | FLP*DF+P** | 60 | NP_116110.2 |

TABLE 17-continued Results of human immunology search using random epitope order

| Junctional Region | Source | SEQ ID NO: Sequence | % Homology | Accession No. |
|---|---|---|---|---|
| 18 | pol 531 | 193 SAICSVVRR | — | |
| | Membrane-spanning 4-domains (MS4A8B) protein | 194 SAICS*V** | 67 | AF237905.1 |
| 24 | pol 429 | 195 HPAAMPHLL | — | |
| | Hypothetical protein | 196 H*AAMPH** | 67 | XP_120541.1 |
| 35 | core 50 | 197 PHHTALRQAILCWGELMTLA | — | |
| | Cysteine dioxygenase | 198 *******ILCWGE*** | 30 | BAA12873.1 |
| 36 | pol 385 | 199 ESRLVVDFSQFSRGN | — | |
| | B/K protein | 200 ****VVDF*+FSR** | 47 | NP_057608.1 |
| 38 | env 339 | 201 LVPFVQWFVGLSPTV | — | |
| | Cytochrome B561 | 202 ***FVQW*VG*S*** | 47 | AAC50212.1 |
| 47 | pol 664 | 203 KQAFTFSPTYKAFLC | — | |
| | hypothetical protein FLJ23441 | 204 *Q*FTF*PT+A*** | 47 | AAH07800 |

1. Spacer groups with the 4 adjacent residues from neighboring epitopes were utilizied as query sequences.
2. BLAST search parameters: Expect 20000, Word size 2, Matrix PAM30, No. of alignments 250.
3. Resultant sequence matches with the lowest E value are presented first. No sequence identified (except human Hepatitis B viral capsid) had an E value <1.
4. Asterisks (*) denote non-matching residues; plus signs (+) denote residues of similar chemical composition.

In conclusion, the degree of homology of the vaccine junctional regions to human sequences was not dissimilar from other sequences, such as the HBV epitopes themselves which are regarded as non-self by the immune system and which are not associated with autoimmune manifestations.

E. Effective Optimization of Antigen Processing and Epitope Presentation

To demonstrate that optimized epigene constructs were efficient for delivery of epitopes to the immune system, human lymphoblastoid cell lines were transfected with the vaccine construct and which were then used as APC in antigenicity assays (Livingston, B. D. et al., *Vaccine.* 19:4652-4660 (2001)). These assays provide a means to determine the relative amounts of epitopes produced as a result of processing. Utilizing these assays, Livingston demonstrated that spacer optimization can enhance, by as much as a thousand fold, the yield of specific epitopes (Livingston, B. D. et al., *Vaccine.* 19:4652-4660 (2001)). Transfectants are generated with various vaccine constructs, including GCR-5835 (see below), as constructs based on whole HBV genes. These results demonstrate that the approach of processing optimization, based on specific spacer residues, is highly effective. Furthermore, since the cell lines used for transfection are of human origin, these data provide an important validation, in a human system, of the results described above obtained in HLA-transgenic mice.

4. Configuration, Formulation and Delivery of the Vaccine

Vaccine Configuration

The HTL and CTL epigene constructs were designed and optimized independently. However, co-delivery of the HTL and CTL components in a single DNA vaccine is considered optimal. Three vaccine alternatives include (1) the use of two separate CMV promoters; (2) the use of the CMV promoter in conjunction with an IRES, and (3) a construct encoding the CTL+HTL components in a single reading frame (FIG. 29A). For examples of the third alternative, see Tables 18 and 19 (e.g. GCR-5835 and GCR-3697). The immunogenicity of these different strategies was evaluated utilizing HLA-A2 transgenic mice; the results are shown in FIG. 29B. It is apparent that each of the configurations induced generally comparable CTL responses against all the HLA-A2 epitopes. Overall, the fused construct performed as well or better than the other vaccine configurations and it is currently regarded as the leading vaccine configuration due to simplicity.

To create a vaccine better suited for human use and potentially augment immunogenicity, the nucleotide sequence of GCR-5835 (Table 18) was modified to match human codon frequencies, increase mRNA stability and reduce mRNA secondary structure. The immunogenicity of the modified construct, referred to as GCR-3697 (Table 19), was compared to that of GCR-5835 in HLA-A2 transgenic mice. Animals were immunized i.m. with either 5 μg or 50 μg of the human optimized GCR-3697 or GCR-5835 and CTL responses were measured using primary IFN-γ ELISPOT assays (FIG. 30). At the 50 μg dose there was an average five-fold increase in the magnitude of CTL responses to epitopes core 18, env 183 and pol 538 in the animals immunized with GCR-3697. The HTL responses induced by the two constructs were generally equivalent (data not shown). Since the GCR-3697 vaccine construct appeared to have greater potency, with respect to CTL immunogenicity, and may possess attributes that will enhance immunogenicity in humans, its selection as the primary vaccine is warranted.

TABLE 18

Epigene fusion construct in GCR-5835 plasmid

GCR-5835     Polynucleotide

SEQ ID NO: 205

1 Start
↑ * * *
GAATTCAGGTCGCCGCCACC[ATG]GGAATGCAGGTGCAAATACAGTCTCTCTTCCTTTTGCT
TCTCTGGGTTCCAGGATCACGGGGCTTCTTGCTTAGCTTGGGCATCCACCTAAATGCTGCT
GCAAAATACACATCTTTTCCTTGGCTCCTTAATGCCGCCGCTAGGTTTTCATGGCTGAGTC
TGCTAGTACCTTTCAATGCGGCTTTCCCACATTGCCTAGCTTTTAGCTATATGAAAGCTGC
TTTAGTCGTGGACTTTTCACSGTTTAGCAGAGGAGCAATCCTGCTGCTATGTCTGATATTC
CTTCTAAACGCAGCAGCCCACACACTCTGGAAAGCTGGTATCCTTTACAAGAAAGCCTGG
ATGATGTGGTATTGGGGACCCAGCCTCTACAAAGCATACCCTGCCCTGATGCCACTATAC
GCATGCATTGGCGCGGCAGCCTGGTTATCCCTTTTAGTACCGTTTGTCAACGCCGCAGCGG
GATTTCTATTAACCAGAATCCTGACGATTAATGCTGCCGCCATTCCGATCCCAAGTTCCTG
GGCATTCAAAGCAGCCGCGGAGTATCTGGTTTCATTTGGCGTATGGAACCTGCCAAGCGA
CTTCTTTCCTTCTGTTAAGGCCGCTGCTTTCCTCCCCTCCGATTTCTTTCCATCGGTGAAAG
CCGCTGCCGACCTCCTTGATACCGCGAGCGCTCTGTACAACTCGTGGCCAAAATTCGCAGT
TCCAAACCTAAAAGCCGCCGCCAGTGCCATTTGTTCCGTGGTAAGGAGAAAATTATCACT
CGACGTGTCCGCAGCATTTTATAACGCTGCTGCAAAGTTTGTCGCAGCATGGACATTGAA
GGCTGCAGCGAAAGCAGCAAATGTATCAATACCCTGGACCCACAAGGGTGCAGCCGGGC
TGTCTAGGTATGTGGCGAGGCTAAACGCCGCCGCCTCAACACTGCCTGAGACTACTGTCG
TGAGACGCAAACACCCTGCCGCAATGCCCCACCTGCTGAAAGCAGCCGCACGATGGATGT
GCCTCAGAAGATTCATAATAAACGCTTCTTTCTGTGGGTCACCCTACAAAGCCGCTTACAT
GGACGATGTGGTCCTCGGAGTGAATGCCCTCTGGTTCCATATCAGCTGCCTGACATTCAAG
GCAGCCGCCACCCCCGCTCGTGTGACAGGAGGTGTCTTCAAAGCCGCGGCACTGACTTTC
GGTCGGGAAACTGTATTGGAATATAAGCAGGCCTTCACATTCTCCCCAACATACAAGAAC
GCAGGAACTTCTTTTGTGTATGTCCCTTCCGCTCTGAACCCAGCAGACGGACCCGGGCCTG
GCCTGTGCCAGGTCTTCGCCGACGCAACTCCCACAGGGTGGGGGCTGGGGCCAGGACCAG
GCAGGCACTACCTGCATACTCTGTGGAAGGCAGGAATCCTCTATAAAGGGCCCGGCCCAG
GCCCTCACCACACCGCCCTGAGGCAGGCCATCCTGTGCTGGGGGGAGCTCATGACCCTGG
CCGGACCTGGACCCGGGGAGAGCAGACTGGTGGTGGATTTCAGCCAATTCAGCAGAGGA
AACGGACCCGGCCCTGGGCCTTTTCTGCTGGCTCAGTTTACATCTGCTATTTGTTCTGTGGT
CGGCCCCGGGCCCGGACTCGTGCCTTTCGTGCAGTGGTTCGTGGGACTGTCCCCTACAGTC
GGGCCCGGCCCAGGGCTGCATCTGTACTCCCACCCAATCATCCTCGGCTTCCGCAAGATTG
GACCCGGCCCAGGCTCCAGCAATCTCTCCTGGCTCTCTCTGGACGGTGTCTGCCGCCTTTGG
CCCTGGACCAGGCCTGCAAAGCCTGACTAATCTGCTCAGCAGCAACCTGTCCTGGCTGGG
ACCTGGCCCAGGGGCTGGCTTCTTTCTGCTCACCCGGATTCTCACAATTCCCCAGTCCGGA
CCAGGACCAGGAGTCAGTTTCGGGGTGTGGATCAGGACCCCTCCTGCTTATAGACCACCC
AATGCTCCAATCGGCCCCGGCCCTGGCGTCGGGCCACTGACCGTGAATGAGAAGCGCCGG
CTGAAGCTGATCGGCCCTGGCCCTGGCAAGCAGTGCTTTCGCAAACTGCCCGTGAACAGA
CCTATTGATTGGGCCCGGCCCTGGAGCAGCCAACTGGATTCTCAGGGGAACAAGCTTC
GTCTACGTGCCCGGGCCCGGACCAGGGAAGCAGGCTTTTACCTTCTCTCCCACTTACAAG
GCCTTCCTCTGTGGGCCAGGCCCCGGCGCCAAGTTTGTGGCAGCATGGACCCTCAAAGCC
GCTGCCTGAGGATCC[TGA]
↓ Stop
2292

GCR-5835     Polypeptide

SEQ ID NO: 206

1
↑
MGMQVQIQSLFLLLLWVPGSRGFLLSLGIHLNAAAKYTSFPWLLNAAARFSWLSLLVPFNAA
FPHCLAFSSYMKAALVVDFSQFSRGAILLLCLIFLLNAAAHTLWKAGILYKKAWMMWYWGPS
LYKAYPALMPLYACIGAAAWLSLLVPFVNAAAGFLLTRILTINAAAIPIPSSWAFKAAAEYLVS
FGVWNLPSDFFPSVKAAAFLPSDFFPSVKAAADLLDTASALYNSWPKFAVPNLKAAASAICSV
VRRKLSLDVSAAFYNAAAKFVAAWTLKAAAKAANVSIPWTHKGAAGLSRYVARLNAAAST
LPETTVVRRKHPAAMPHLLKAAARWMCLRRFIINASFCGSPYKAAYMDDVVLGVNALWFHI
SCLTFKAAATPARVTGGVFKAAALTFGRETVLEYKQAFTFSPTYKNAGTSFVYVPSALNPAD
GPGPGLCQVFADATPTGWGLGPGPGRHYLHTLWKAGILYKGPGPGPHHTALRQAILCWGEL
MTLAGPGPGESRLVVDFSQFSRGNGPGPGPFLLAQFTSAICSVVGPGPGLVPFVQWFVGLSPT
VGPGPGLHLYSHPIILGFRKIGPGPGSSNLSWLSLDVSAAFGPGPGLQSLTNLLSSNLSWLGPGP
GAGFFLLTRILTIPQSGPGPGVSFGVWIRTPPAYRPPNAPIGPGPGVGPLTVNEKRRLKLIGPGP
GKQCFRKLPVNRPIDWGPGPGAANWILRGTSFVYVPGPGPGKQAFTFSPTYKAFLCGPGPGAK
FVAAWTLKAAAGS
↓
763

TABLE 19

| Epigene fusion construct in GCR-3697 plasmid | |
|---|---|
| GCR-3697 | Polynucleotide |
| SEQ ID NO: 207 | 1 Start<br>↑* * *<br>ATGGGCATGCAGGTGCAGATCCAGAGCCTGTTCCTGCTCCTGCTGTGGGTGCCAGGA<br>AGCAGAGGCTTTCTCCTGTCCCTGGGCATCCACCTGAACGCCGCTGCAAAGTACACC<br>AGCTTCCCCTGGCTGCTCAACGCCGCTGCCCGGTTCAGCTGGCTGTCCCTGCTCGTGC<br>CCTTCAACGCAGCCTTCCCCCACTGCCTGGCCTTCAGCTACATGAAAGCAGCCCTGG<br>TGGTCGACTTCTCCCAGTTCAGCCGGGGAGCCATCCTGCTCCTGTGCCTGATCTTTC<br>GCTCAACGCCGCTGCCCACACCCTGTGGAAGGCTGGCATCCTGTACAAGAAAGCCTG<br>GATGATGTGGTACTGGGGACCCAGCCTGTACAAGGCATATCCAGCCCTGATGCCCCT<br>GTACGCCTGCATCGGAGCTGCCGCATGGCTGAGCCTCCTGGTGCCCTTCGTGAACGC<br>CGCTGCCGGGTTCCTGCTGACAAGAATCCTGACCATCAACGCCGCAGCCATTCCTAT<br>CCCCTCCAGCTGGGCCTTCAAGGCAGCCGCCGAGTACCTGGTGAGCTTCGGAGTCTG<br>GAACCTGCCCAGCGACTTCTTTCCCAGCGTGAAAGCCGCAGCCTTCCTGCCCTCCGA<br>CTTCTTTCCCAGCGGTGAAGGCCGCAGCCGATCTCCTGGACACCGCTAGCGCCCTGTA<br>CAACAGCTGGCCCAAGTTCGCCGTGCCCAACCTGAAGGCCGCAGCCAGCGCCATCTG<br>CAGCGTGGTCAGACGGAAGCTGTCCCTCGATGTGAGCGCCGCTTTCTACAACGCCGC<br>CGCAAAGTTCGTGGCCGCCTGGACCCTGAAAGCCGCTGCCAAGGCAGCCAACGTGA<br>GCATCCCCTGGACCCACAAAGGAGCCGCAGGACTGAGCCGGTATGTGGCCAGACTG<br>AACGCCGCTGCCAGCACCCTGCCCGAGACCACAGTGGTCAGACGGAAGCACCCCGC<br>CGCCATGCCCCACCTGCTGAAGGCCGCAGCCCGGTGGATGTGCCTCAGACGGTTCAT<br>CATCAACGCTTCCTTCTGTGGCAGCCCCTACAAGGCCGCCTACATGGATGACGTGGT<br>CCTGGGAGTGAACGCCCTCTGGTTCCACATCAGCTGCCTGACCTTCAAAGCCGCTGC<br>CACACCCGCAAGAGTGACCGGAGGCGTGTTCAAGGCTGCAGCCCTGACCTTCGGCC<br>GGGAGACCGTGCTGGAGTACAAGCAGGCCTTCACCTTCAGCCCCACCTACAAGAAC<br>GCCGGCACCAGCTTTGTGTACGTCCCAAGCGCCCTGAATCCCGCAGACGGCCCCGGC<br>CCCGGACTGTGCCAGGTGTTCGCCGATGCCACACCAACCGGATGGGGCCTGGGCCCT<br>GGACCCGGCAGACACTACCTGCATACCCTGTGGAAGGCAGGAATCCTGTACAAAGG<br>CCCCGGCCCTGGACCCCATCACACCGCTCTGCGGCAGGCCATCCTGTGCTGGGGCGA<br>GCTCATGACTCTGGCAGGACCCGGCCCCGGCGAATCCAGGCTGGTGGTGGACTTTAG<br>CCAGTTCTCCAGAGGCAACGGACCCGGCCCAGGACCCTTCCTGCTCGCCCAGTTCAC<br>CAGCGCCATCTGCAGCGTGGTCGGACCTGGCCCAGGACTGGTGCCCTTCGTGCAGTG<br>GTTCGTCGGCCTCAGCCCCACCGTCGGACCTGGCCCCGGCCTGCACCTCTACAGCCA<br>CCCTATCATTCTGGGCTTCAGAAAGATCGGACCAGGCCCCGGCTCCAGCAACCTGTC<br>CTGGCTCCAGCCTGGACGTCAGCGCAGCCTTCGGACCCGGCCCTGGCCTGCAGAGCCT<br>GACCAACCTGCTCAGCAGCAACCTCAGCTGGCTGGGCCCAGGACCCGGCGCAGGCT<br>TCTTTCTGCTCACCAGAATCCTGACCATCCCTCAGAGCGGCCCCGGACCAGGCGTGA<br>GCTTCGGCGTGTGGATTCGGACTCCTCCCGCCTACAGACCCCCAAATGCCCCCATCG<br>GCCCAGGACCCGGCGTCGGACCTCTGACTGTGAACGAGAAGCGGAGACTGAAGCTG<br>ATCGGCCCCGGACCAGGCAAACAGTGCTTCAGGAAGCTCCCTGTGAACAGACCTATC<br>GACTGGGGCCCCGGACCCGGCGCAGCCAACTGGATTCTGAGAGGCACCAGCTTCGT<br>GTACGTCCCTGGACCCGGCCCTGGCAAGCAAGCCTTCACCTTCAGCCCCACCTACAA<br>GGCATTCCTGTGCGGATAG<br>↓ Stop<br>2232 |
| GCR-3697 | Polypeptide |
| SEQ ID NO: 208 | 1<br>↑<br>MGMQVQIQSLFLLLLWVPGSRGFLLSLGIHLNAAAKYTSFPWLLNAAARFSWLSLLVPF<br>NAAFPHCLAFSYMKAALVVDFSQFSRGAILLLCLIFLLNAAAHTLWKAGILYKKAWMM<br>WYWGPSLYKAYPALMPLYACIGAAAWLSLLVPFVNAAAGFLLTRILTINAAAIPIPSSWA<br>FKAAAEYLVSFGVWNLPSDFFPSVKAAAFLPSDFFPSVKAAADLLDTASALYNSWPKFA<br>VPNLKAAASAICSVVRRKLSLDVSAAFYNAAAKFVAAWTLKAAAKAANVSIPWTHKG<br>AAGLSRYVARLNAAASTLPETTVVRRKHPAAMPHLLKAAARWMCLRRFIINASFCGSPY<br>KAAYMDDVVLGVNALWFHISCLTFKAAATPARVTGGVFKAAALTFGRETVLEYKQAFT<br>FSPTYKNAGTSFVYVPSALNPADGPGPGLCQVFADATPTGWGLGPGPGRHYLHTLWKA<br>GILYKGPGPGPHHTALRQAILCWGELMTLAGPGPGESRLVVDFSQFSRGNGPGPGPFLLA<br>QFTSAICSVVGPGPGLVPFVQWFVGLSPTVGPGPGLHLYSHPIILGFRKIGPGPGSSNLSW<br>LSLDVSAAFGPGPGLQSLTNLLSSNLSWLGPGPGAGFFLLTRILTIPQSGPGPGVSFGVWI<br>RTPPAYRPPNAPIGPGPGVGPLTVNEKRRLKLIGPGPGKQCFRKLPVNRPIDWGPGPGAA<br>NWILRGTSFVYVPGPGPGKQAFTFSPTYKAFLCG<br>↓<br>744 |

Vaccine Formulation

Naked-DNA vaccines have not proved optimal for delivering vaccine immunogens in humans (Wang, et al., *Science* 282:476 (1998)). We therefore selected an alternative formulation based on the use of a polymer surfactant, polyvinylpyrrolidone (PVP). This is a non-condensing delivery system designed to increase the tissue distribution of the DNA, to protect DNA from degradation and to increase uptake by cells. PVP is a commonly used pharmaceutical formulation excipient that is nontoxic and approved for human clinical use. The properties and mechanisms of action for PVP appear to be very similar to the nonionic block copolymer, CRL1005. Safety, toxicity and biodistribution/clearance tests were completed to support use for a HIV-1 vaccine program. The data not only support the safety of the formulation, but also cellular uptake of DNA appears to be increased by more than a log, based on comparison to naked DNA. Thus, the use of this delivery system can be supported by available data.

We evaluated the effects of the PVP on the immunogenicity of the CTL and HTL epitopes using an HIV-1 vaccine and several of the HBV vaccine constructs. Data obtained using an HIV-1 epitope encoding epigene construct demonstrated that PVP increased the immunogenicity of epitopes that were only poorly immunogenic when delivered in a naked-DNA vaccine can enhance cellular uptake of DNA, relative to larger clinically tested constructs.

TABLE 20

Comparison of route of DNA delivery for induction of CTL responses
Comparison of route of DNA delivery for indcution of CTL responses

| | Immunogenicity (SU)[1] | | |
|---|---|---|---|
| Delivery | HBV core 18 | HIV pol 476 | HBV pol 455 |
| IM | 1342.9 (1.8) | 1133.3 (1.3) | 879.5 (2.1) |
| ID | 740.1 (1.5) | 0 | 0 |
| Biojector | 44.7 (3.9) | 103.2 (1.4) | 44.8 (3.1) |

| | Immunogenicity (SFC/$10^6$ CD8 cells)[2] | | | | | |
|---|---|---|---|---|---|---|
| Delivery | HBV core 18 | HIV pol 476 | HBV pol 455 | HIV env 120 | HBV pol 551 | HBV env 335 |
| IM | 285.0 (17.4) | 147.5 (19.8) | 155.0 (15.0) | 60.0 (15.6) | 485.0 (24.9) | 68.3 (8.2) |
| Gene Gun | 287.5 (23.8) | 146.7 (24.2) | 25.8 (7.5) | 0.8 (5.5) | 35.5 (7.6) | 35.8 (16.2) |

Figure 31:
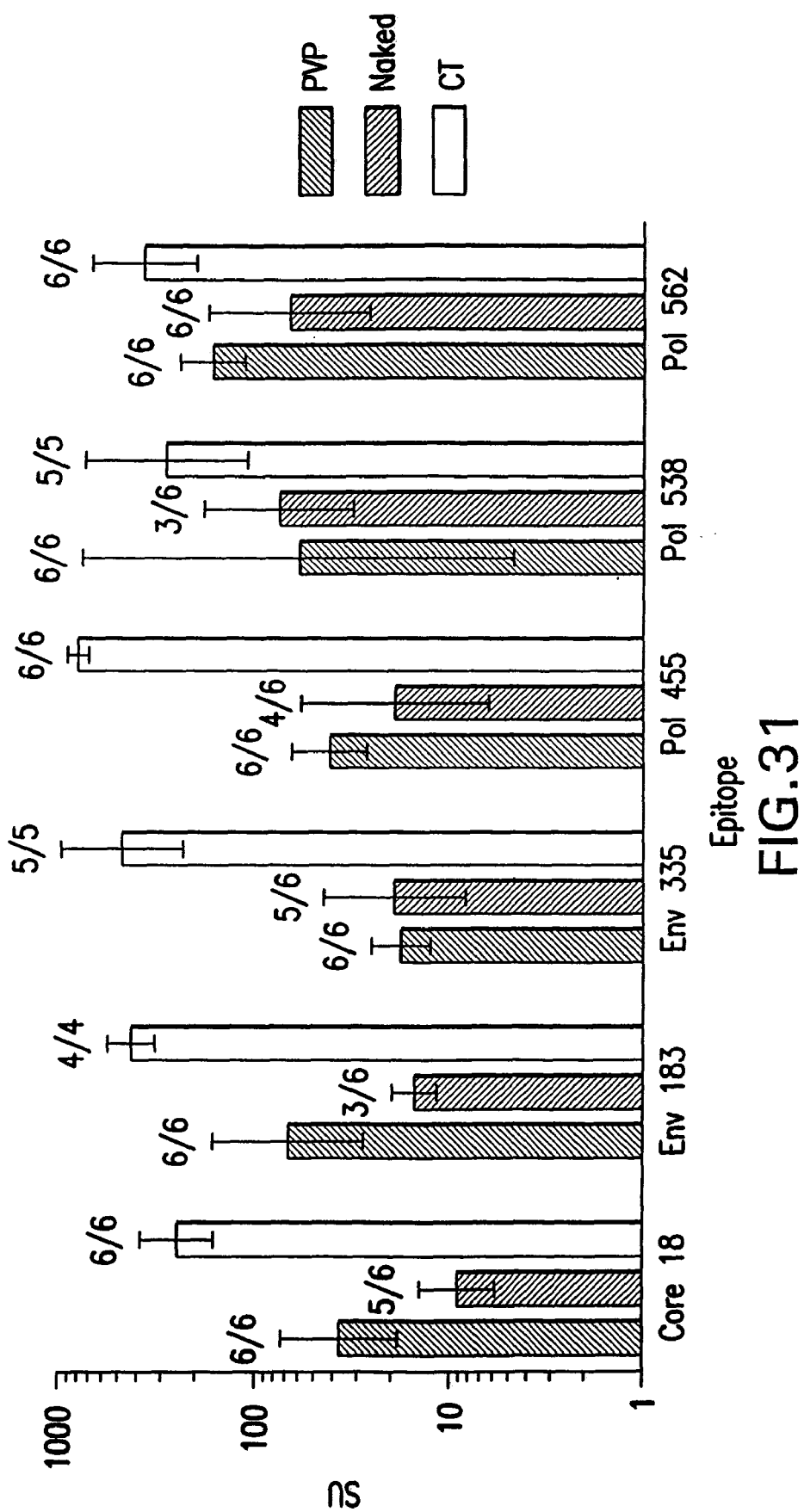

[1] Immunogenicity of pMin1 in HLA-A2 using different routes of delivery. CTL responses were measured using an in situ ELISA assay (McKinney, D. M. et al., J. Immunol. Methods. 237: 105-117 (2000)).
[2] Immunogenicity of pMin1 in HLA-A2 using needle IM or Gene Gun immunization CTL responses were measured using a primary IFN-γ ELISPOT vaccine (data not shown). The immunogenicity of GCR-5835 was evaluated in the context of three different formulations, PVP, naked DNA, and cardiotoxin (CT) pre-priming. CT pretreatment is an experimental approach commonly utilized in laboratory animals to enhance effectiveness of naked DNA injections. CT destroys muscle fibers which then take up DNA as they regenerate (Davis, H. L. et al., Mol. Genet. 2:1847-1851 (1993)). The results are shown in FIG. 31. While CT pretreatment was the most effective at priming high magnitude responses, this approach is not clinically applicable. The PVP-formulated DNA increased the magnitude of responses for two of the six epitopes measured when compared to naked DNA, while the frequency of positive responses was higher for five of six epitopes. This data establishes that the PVP formulation increases the potency of the vaccine as compared to a naked DNA delivery.

Vaccine Route of Administration and Delivery

A PVP-formulated DNA plasmid vaccine can be delivered intramuscularly (i.m.). The i.m. route of administration is commonly used for DNA vaccines. In preliminary experiments, we utilized an HBV prototype epigene construct, pMin1, to evaluate various DNA delivery routes (Table 20). In these experiments, i.m. needle delivery was compared with needleless delivery of PVP-formulated DNA via Biojector and ballistic delivery of gold particle/DNA via PowderJect. Overall, the i.m. needle delivery performed as well or better than the other delivery methods tested although other delivery methods may be used.

Improvements to the Naked-DNA Vaccine Technology

Naked DNA vaccines have proven to be relatively poor immunogens in non-human primates and humans but studies completed thus far were based on the delivery of intact genes encoding full-length proteins, or epitopes without spacer optimizations. Despite its relatively modest human immunogenicity, naked DNA immunization does appear to be remarkably effective in "priming" CTL responses (Ramshaw, J. A. and Ramsay, A. J., Immunol. Today 21:163-165 (2000)).

Epigene construct design and addition of PVP are utilized to increase DNA uptake. Epigene constructs may include a small plasmid DNA backbone and a small vaccine insert that The heterologous prime-boost regimen, using a DNA vaccine first and either proteins or viral vectors to boost responses, is currently considered to be the most immunogenic for genetic vaccines (Ramshaw, J. A. and Ramsay, A. J., Immunol. Today 21:163-165 (2000)). Heterologous prime: boost approaches can be utilized as a component of HBV vaccine delivery.

5. Potency and Characterization of the Vaccine

A. Relevant Levels of Immunogenicity are Obtained in HLA-Transgenic Mice

Figure 32A:
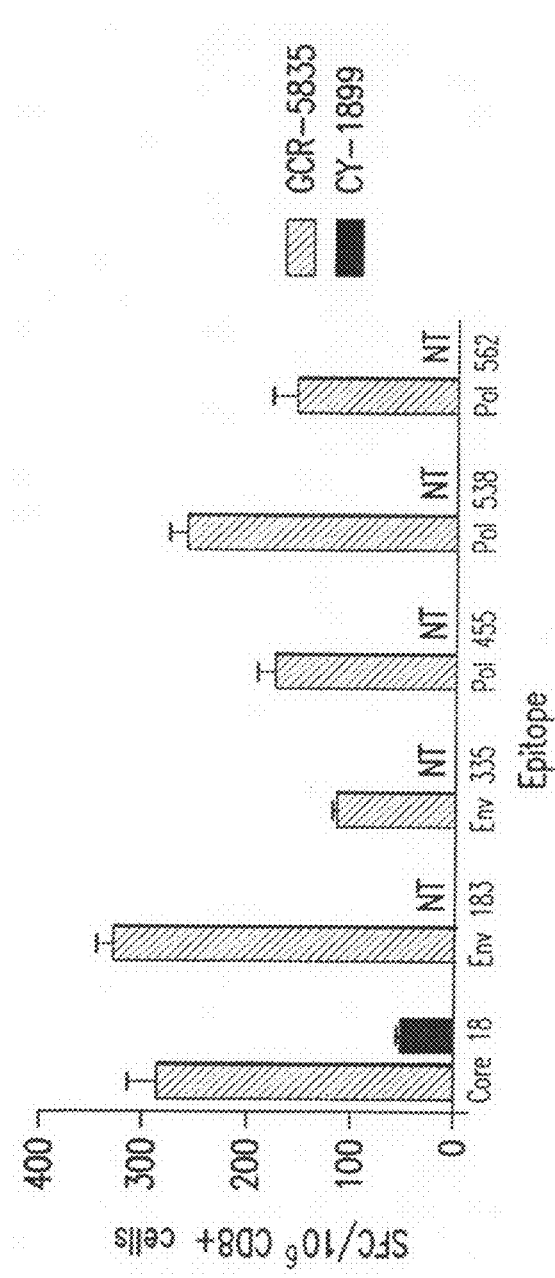
Figure 32B:
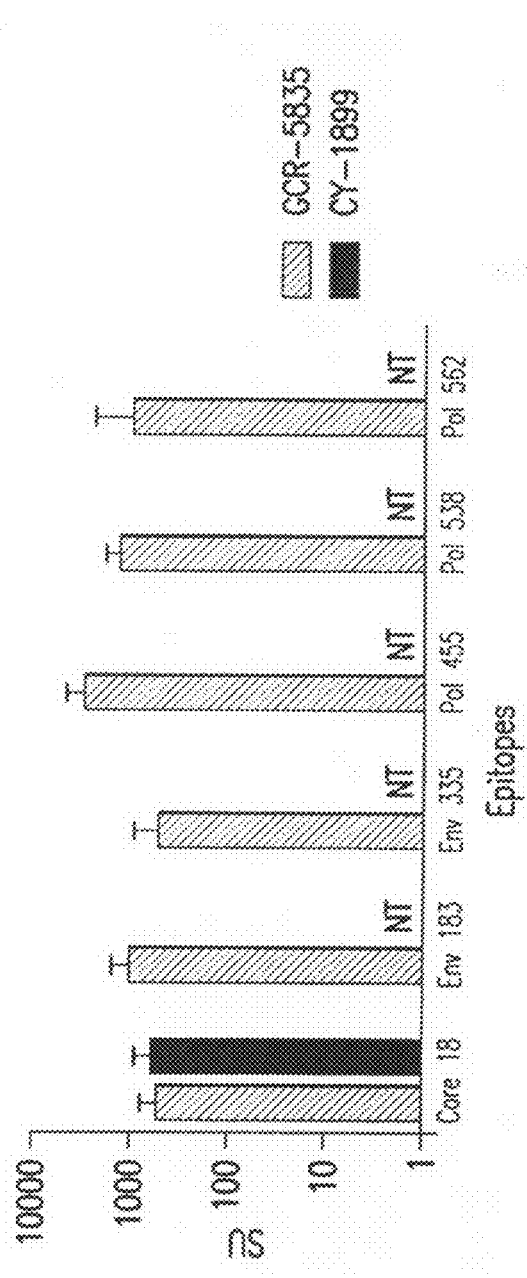

The magnitude of responses obtained using the GCR-5835 vaccine was evaluated in HLA-A2-transgenic mice and compared to responses induced following immunization with the experimental lipopeptide vaccine CY-1899. The lipopeptide vaccine was selected for this evaluation because the core 18 epitope is present in both vaccine constructs and CY-1899 is known to elicit a potent CTL response in healthy humans (Livingston, B. D. et al., J. Immunol. 159:1383-1392 (1997)). Responses induced in the mice are shown in FIG. 32. Splenocytes from mice immunized with the GCR-5835 construct produced IFN-γ responses to all six HLA-A2-restricted epitopes encoded in the construct; measured using an ELISPOT assay (FIG. 32A). A response to the core 18 epitope in CY-1899 was also observed, but the magnitude was considerably lower than the core 18 epitope response induced using the GCR-5835 vaccine construct. However, after a 6 day restimulation with peptide, the core 18 responses induced by these two different format vaccines were very similar (FIG. 32B).

The magnitude of responses obtained for the other A2-restricted epitopes was found to be comparable to those known to mediate clearance of HBV infection. We observed primary ELISPOT responses ranging from approximately 100 SFC/$10^6$ CD8+ cells (env 335) to greater than 300 SFC/$10^6$ CD8+ cells (env 183), well within the range of other responses detected in acute infections as detailed in Section 1A.

B. Quality of Responses

Clearance of HBV is mediated by a complex series of molecular events, including indirect, lymphokines-mediated effects, as well as direct lysis of infected cells, especially the ones harboring integrated virus. IFN-γ production was measured in all experiments described thus far, which is relevant since this lymphokine is involved in clearance of HBV infection (Chisari, F. V. and Ferrari, C. *Annu. Rev. Immunol.* 13:29-60 (1995); Guidotti, L. G. et al., *Immunity.* 4:25-36 (1996)). DNA immunization has been shown to induce CTL capable of lytic activity (Ishioka, G. Y. et al., *J. Immunol.* 162:3915-3925 (1999)). HLA-transgenic mice can be also be immunized with GCR-5835 and/or GCR-3697.

Figure 33A:
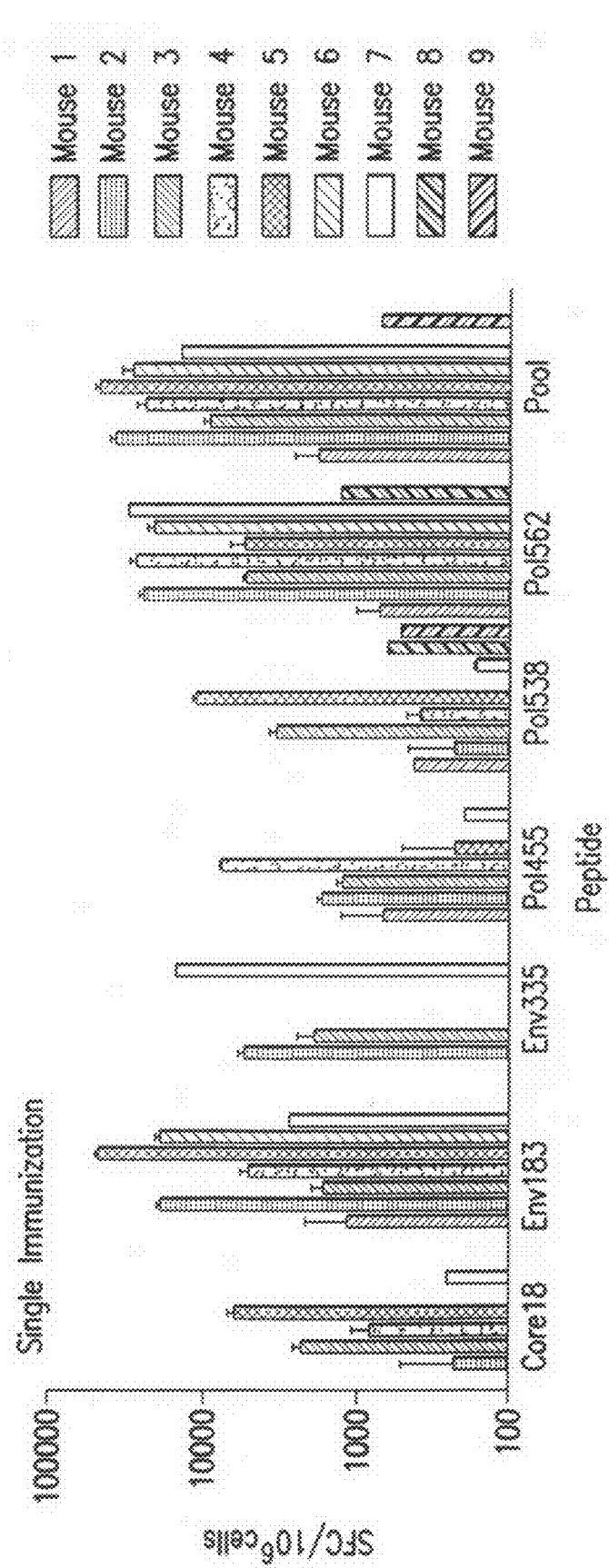
Figure 33B:
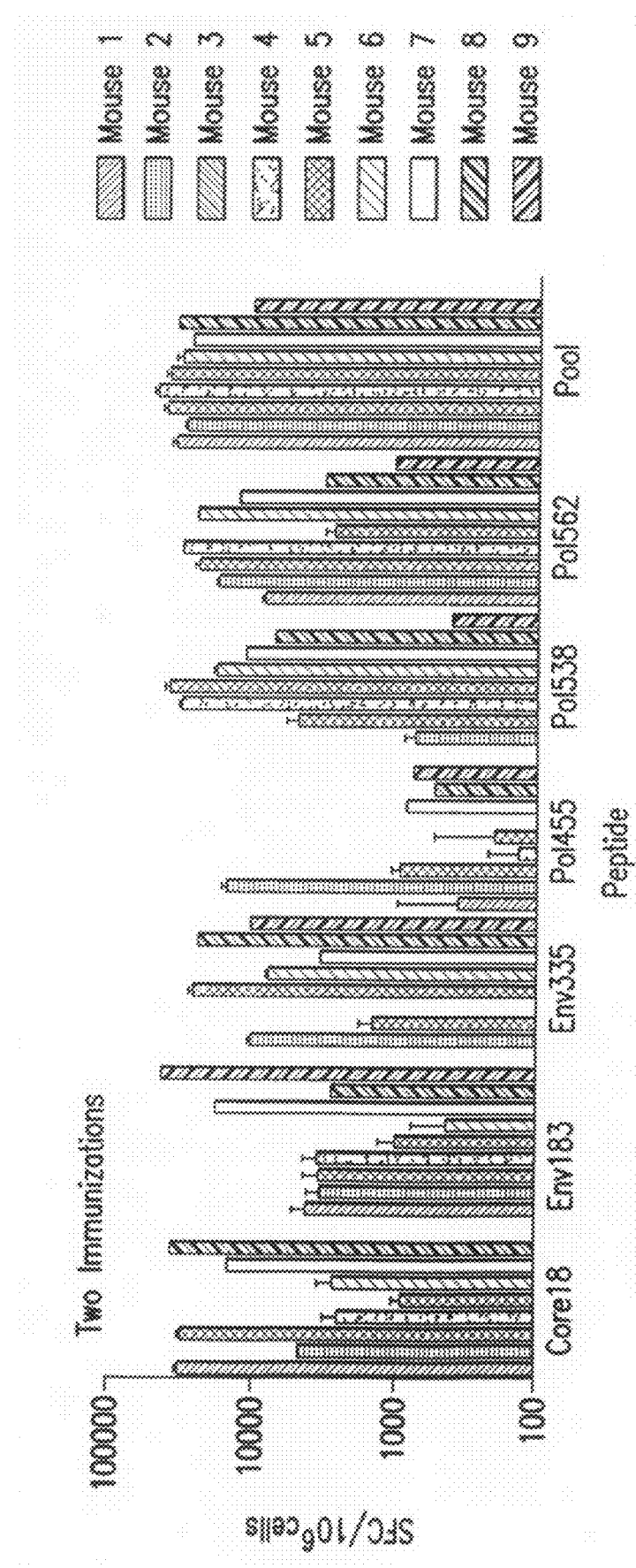

The immunological assay results presented were generally derived using pooled preparations of splenocytes from 3-6 mice. Additional experiments were performed to determine if responses against multiple epitopes were induced in individual animals. HLA-A2 transgenic mice were immunized either once or twice, at a one week interval, with GCR-5835 formulated in PVP. Splenocytes from individual animals were harvested separately and restimulated with a pool of the six HLA-A2 epitope peptides encoded in the vaccine. IFN-γ secretion was then measured in response to individual peptides using an ELISPOT assay. After a single immunization, all the mice responded to at least one epitope, average response rate was 4.2±2.0 epitope/mouse (FIG. 33A). After a second immunization, the average number of epitopes recognized was increased to 5.6±0.5 (FIG. 33B). These data have particular relevance in light of recent data on immunodominance (Rodriguez, F. et al., *J. Virol.* 76:4251-4259 (2002)), and indicates that immunogen optimization and repeated immunizations may be used to counterbalance the narrowness of responses resulting from immunodominance (Chen, M. et al., *J. Virol.* 74:7587-7599 (2000); Yewdell, J. W. et al., *Annu. Rev. Immunol.* 17:51-88 (1999)).

6. Summary and Conclusions

Multi-epitope CTL/HTL epigene constructs are effective for immunotherapy of chronic HBV infection and can be used in the treatment of anti-viral-treated, chronically-infected individuals.

Processes used for identifying CTL and HTL epitopes suitable for use in the design of vaccines are described above. The projected population coverage and immune response redundancy afforded by these epitope sets in different ethnic backgrounds is consistent with the breadth and multi-specificity of responses naturally associated with resolution of HBV infection. The vaccine design methods utilized to assemble the multi-epitope constructs entailed the optimization of proteosomal cleavage (CTL epitopes), and the minimization of junctional motifs (HTL epitopes).

Specific vaccine constructs were produced that induced potent CTL responses in HLA-transgenic mice against most or all of the epitopes evaluated. The vaccine construct induces levels of HBV epitope-specific CTL in transgenic mice that are similar, in magnitude, to the responses induced using the CY-1899 vaccine, which is known to be immunogenic in humans, and that are similar to the levels of CTL responses observed in humans during resolution of HBV infection.

In addition, we showed how different vaccine configurations are effective for simultaneous delivery of CTL and HTL epitopes. Epigene constructs may contain HTL and CTL epitopes that are co-linearly synthesized from a single genetic insert and as such, the vaccine is readily manufactured and stable.

A PVP-based DNA formulation is associated with increased activity, as compared to naked DNA. Similarly, i.m. delivery appears to be, in the system investigated, the most practical and is associated with activity at least as good as other delivery methods (Biojector or gene gun). A combination of priming with an optimized epigene construct formulated in PVP, followed by boosting with a viral vector can also be used.

TABLE 21

Codon Usage Table for Human Genes
(*Homo sapiens*)

| Amino Acid | Codon | Number | Frequency |
|---|---|---|---|
| Phe | UUU | 326146 | 0.4525 |
| Phe | UUC | 394680 | 0.5475 |
| Total | | 720826 | |
| Leu | UUA | 139249 | 0.0728 |
| Leu | UUG | 242151 | 0.1266 |
| Leu | CUU | 246206 | 0.1287 |
| Leu | CUC | 374262 | 0.1956 |
| Leu | CUA | 133980 | 0.0700 |
| Leu | CUG | 777077 | 0.4062 |
| Total | | 1912925 | |
| Ile | AUU | 303721 | 0.3554 |
| Ile | AUC | 414483 | 0.4850 |
| Ile | AUA | 136399 | 0.1596 |
| Total | | 854603 | |
| Met | AUG | 430946 | 1.0000 |
| Total | | 430946 | |
| Val | GUU | 210423 | 0.1773 |
| Val | GUC | 282445 | 0.2380 |
| Val | GUA | 134991 | 0.1137 |
| Val | GUG | 559044 | 0.4710 |
| Total | | 1186903 | |
| Ser | UCU | 282407 | 0.1840 |
| Ser | UCC | 336349 | 0.2191 |
| Ser | UCA | 225963 | 0.1472 |
| Ser | UCG | 86761 | 0.0565 |
| Ser | AGU | 230047 | 0.1499 |
| Ser | AGC | 373362 | 0.2433 |
| Total | | 1534889 | |
| Pro | CCU | 333705 | 0.2834 |
| Pro | CCC | 386462 | 0.3281 |
| Pro | CCA | 322220 | 0.2736 |
| Pro | CCG | 135317 | 0.1149 |
| Total | | 1177704 | |
| Thr | ACU | 247913 | 0.2419 |
| Thr | ACC | 371420 | 0.3624 |
| Thr | ACA | 285655 | 0.2787 |
| Thr | ACG | 120022 | 0.1171 |
| Total | | 1025010 | |
| Ala | GCU | 360146 | 0.2637 |
| Ala | GCC | 551452 | 0.4037 |
| Ala | GCA | 308034 | 0.2255 |
| Ala | GCG | 146233 | 0.1071 |
| Total | | 1365865 | |

TABLE 21-continued

Codon Usage Table for Human Genes
(*Homo sapiens*)

| Amino Acid | Codon | Number | Frequency |
|---|---|---|---|
| Tyr | UAU | 232240 | 0.4347 |
| Tyr | UAC | 301978 | 0.5653 |
| Total | | 534218 | |
| His | CAU | 201389 | 0.4113 |
| His | CAC | 288200 | 0.5887 |
| Total | | 489589 | |
| Gln | CAA | 227742 | 0.2541 |
| Gln | CAG | 668391 | 0.7459 |
| Total | | 896133 | |
| Asn | AAU | 322271 | 0.4614 |
| Asn | AAC | 376210 | 0.5386 |
| Total | | 698481 | |
| Lys | AAA | 462660 | 0.4212 |
| Lys | AAG | 635755 | 0.5788 |
| Total | | 1098415 | |
| Asp | GAU | 430744 | 0.4613 |
| Asp | GAC | 502940 | 0.5387 |
| Total | | 933684 | |
| Glu | GAA | 561277 | 0.4161 |
| Glu | GAG | 787712 | 0.5839 |
| Total | | 1348989 | |
| Cys | UGU | 190962 | 0.4468 |
| Cys | UGC | 236400 | 0.5532 |
| Total | | 427362 | |
| Trp | UGG | 248083 | 1.0000 |
| Total | | 248083 | |
| Arg | CGU | 90899 | 0.0830 |
| Arg | CGC | 210931 | 0.1927 |
| Arg | CGA | 122555 | 0.1120 |
| Arg | CGG | 228970 | 0.2092 |
| Arg | AGA | 221221 | 0.2021 |
| Arg | AGG | 220119 | 0.2011 |
| Total | | 1094695 | |
| Gly | GGU | 209450 | 0.1632 |
| Gly | GGC | 441320 | 0.3438 |
| Gly | GGA | 315726 | 0.2459 |
| Gly | GGG | 317263 | 0.2471 |
| Total | | 1283759 | |
| Stop | UAA | 13963 | |
| Stop | UAG | 10631 | |
| Stop | UGA | 24607 | |

TABLE 22

Codon Usage Table for Mouse Genes
(*Mus musculus*)

| Amino Acid | Codon | Number | Frequency |
|---|---|---|---|
| Phe | UUU | 150467 | 0.4321 |
| Phe | UUC | 197795 | 0.5679 |
| Total | | 348262 | |
| Leu | UUA | 55635 | 0.0625 |
| Leu | UUG | 116210 | 0.1306 |
| Leu | CUU | 114699 | 0.1289 |
| Leu | CUC | 179248 | 0.2015 |
| Leu | CUA | 69237 | 0.0778 |
| Leu | CUG | 354743 | 0.3987 |
| Total | | 889772 | |
| Ile | AUU | 137513 | 0.3367 |
| Ile | AUC | 208533 | 0.5106 |
| Ile | AUA | 62349 | 0.1527 |
| Total | | 408395 | |
| Met | AUG | 204546 | 1.0000 |
| Total | | 204546 | |
| Val | GUU | 93754 | 0.1673 |
| Val | GUC | 140762 | 0.2513 |
| Val | GUA | 64417 | 0.1150 |
| Val | GUG | 261308 | 0.4664 |
| Total | | 560241 | |
| Ser | UCU | 139576 | 0.1936 |
| Ser | UCC | 160313 | 0.2224 |
| Ser | UCA | 100524 | 0.1394 |
| Ser | UCG | 38632 | 0.0536 |
| Ser | AGU | 108413 | 0.1504 |
| Ser | AGC | 173518 | 0.2407 |
| Total | | 720976 | |
| Pro | CCU | 162613 | 0.3036 |
| Pro | CCC | 164796 | 0.3077 |
| Pro | CCA | 151091 | 0.2821 |
| Pro | CCG | 57032 | 0.1065 |
| Total | | 535532 | |
| Thr | ACU | 119832 | 0.2472 |
| Thr | ACC | 172415 | 0.3556 |
| Thr | ACA | 140420 | 0.2896 |
| Thr | ACG | 52142 | 0.1076 |
| Total | | 484809 | |
| Ala | GCU | 178593 | 0.2905 |
| Ala | GCC | 236018 | 0.3839 |
| Ala | GCA | 139697 | 0.2272 |
| Ala | GCG | 60444 | 0.0983 |
| Total | | 614752 | |
| Tyr | UAU | 108556 | 0.4219 |
| Tyr | UAC | 148772 | 0.5781 |
| Total | | 257328 | |

TABLE 22-continued

Codon Usage Table for Mouse Genes
(Mus musculus)

| Amino Acid | Codon | Number | Frequency |
|---|---|---|---|
| His | CAU | 88786 | 0.3973 |
| His | CAC | 134705 | 0.6027 |
| Total | | 223491 | |
| Gln | CAA | 101783 | 0.2520 |
| Gln | CAG | 302064 | 0.7480 |
| Total | | 403847 | |
| Asn | AAU | 138868 | 0.4254 |
| Asn | AAC | 187541 | 0.5746 |
| Total | | 326409 | |
| Lys | AAA | 188707 | 0.3839 |
| Lys | AAG | 302799 | 0.6161 |
| Total | | 491506 | |
| Asp | GAU | 189372 | 0.4414 |
| Asp | GAC | 239670 | 0.5586 |
| Total | | 429042 | |
| Glu | GAA | 235842 | 0.4015 |
| Glu | GAG | 351582 | 0.5985 |
| Total | | 587424 | |
| Cys | UGU | 97385 | 0.4716 |
| Cys | UGC | 109130 | 0.5284 |
| Total | | 206515 | |
| Trp | UGG | 112588 | 1.0000 |
| Total | | 112588 | |
| Arg | CGU | 41703 | 0.0863 |
| Arg | CGC | 86351 | 0.1787 |
| Arg | CGA | 58928 | 0.1220 |
| Arg | CGG | 92277 | 0.1910 |
| Arg | AGA | 101029 | 0.2091 |
| Arg | AGG | 102859 | 0.2129 |
| Total | | 483147 | |
| Gly | GGU | 103673 | 0.1750 |
| Gly | GGC | 198604 | 0.3352 |
| Gly | GGA | 151497 | 0.2557 |
| Gly | GGG | 138700 | 0.2341 |
| Total | | 592474 | |
| Stop | UAA | 5499 | |
| Stop | UAG | 14661 | |
| Stop | UGA | 10356 | |

Example 18

Proteasomal Processing of a Hepatitis B Virus Polyepitope Gene Product In Vitro

Introduction

A CTL epitope-based approach to the design of a vaccine against chronic hepatitis B virus (HBV) was taken. A synthetic gene encoding a series of 16 epitopes was made where the epitopes are separated by amino acid spacers designed to enhance proteolytic processing. In vitro translation as well as transient expression of this HBV polyepitope minigene in a human cell line results in rapid degradation of the polyprotein, as expected for a gene product that is labile to proteasome activity. This HBV polyepitope (AOSIb) was fused directly to a fluorescent protein for ease of detection. Addition of proteasome-specific inhibitors to transfected cultures showed a marked increase in the amount of fusion protein present in cells, as judged by FACS analysis, fluorescence microscopy and Western blot. The ability of proteasome inhibitors to block processing of the polyepitope gene product, combined with in vivo immunogenicity to the pathogen-specific epitopes in the DNA plasmid show that the amino acid spacers were efficacious in assuring class I processing. A subsequent HBV polyepitope construct (AOSIb.2) was made that incorporates several amino acid additions expected to improve proteasomal processing. The results show that the spacer sequences used in this HBV polyepitope plasmid can promote proteasome processing of the expressed polypeptide and efficient CTL epitope presentation.

2. Experimental Approach

DNA expression cassettes were designed where HBV polyepitope strings were fused to a fluorescent marker to facilitate protein detection and quantitation in vitro. Spacers of varying composition were added to one construct to evaluate potential improvements in intracellular epitope processing. Proteasome inhibitors were added to plasmid-transfected cells to prevent proteasome degradation of cytosolic proteins. The presence of fusion proteins was monitored by fluorescent marker detection via FACS, fluorescence microscopy or Western blots. The amount of fluorescence trapped in the cells was quantified to look for changes in polyprotein processing. The effect on in vivo immunogenicity in HLA-A2 transgenic mice was also measured for both plasmids to determine if the amino acid spacers had beneficial effects.

3. Composition of HBV Polyepitope Constructs

HBV AOSIb and HBV AOSIb2 carry virus specific epitopes that are optimized. The constructs encode HLA-A2, HLA-A3 and HLA-B7 supertype epitopes, 16 epitopes total. The HBV AOSIb2 construct has additional amino acids added to enhance proteasomal processing while the HBV AOSIb has no added residues. A schematic and the amino acid sequence of the CTL constructs HBV AOSIb and HBV AOSIb2 are shown in FIG. 34 and Tables 23-24. An example of a polynucleotide sequence encoding HBV AOSIb and HBV AOSIb2 is shown in Tables 23-24.

TABLE 23

Epigene encoded by HBV AOSIb construct

HBV AOSIb    Polynucleotide

SEQ ID NO: 209    1 Start
↑
[ATG]GGAATGCAGGTGCAGATCCAGAGCCTGTTTCTGCTCCTCCTGTGGGTGCCC
GGGTCCAGAGGACACACCCTGTGGAAGGCCGGAATCCTGTATAAGGCCAAGTT
CGTGGCTGCCTGGACCCTGAAGGCTGCCGCTTTCCTGCCTAGCGATTTCTTTCCT
AGCGTGTTCCTGCTGTCCCTGGGAATCCACCTGTATATGGATGACGTGGTGCTG
GGAGTGGGACTGTCCAGGTACGTGGCTAGGCGTGTTCCTGCTGACCAGAATCCTG
ACCATATCCACCCTGCCA
GAGACCACCGTGGTGAGGAGGCAGGCCTTCACCTTTAGCCCTACCTATAAGTG
GCTGAGCCTGCTGGTGCCC
TTTGTGATCCCTATCCCTAGCTCCTGGGCTTTCACCCCAGCCAGGGTGACCGGA
GGAGTGTTTAAGGTGGGA
AACTTCACCGGCCTGTATCTGCCCAGCGATTTCTTTCCTAGCGTGACCCTGTGG
AAGGCCGGGATCCTGTAC
AAGAATGTGTCCATCCCTTGGACCCACAAGCTGGTGGTGGACTTTTCCCAGTTC
AGCAGATCCGCTATCTGC
TCCGTGGTGAGGAGAGCTCTGATGCCACTGTATGCCTGTATC[TGA]
↓ Stop
618

AOSIb    Polypeptide

SEQ ID NO: 210    1
↑
MGMQVQIQSLFLLLLWVPGSRGHTLWKAGILYKAKFVAAWTLKAAAFLPSDFFPS
VFLLSLGIHLYMDDVVLGVGLSRYVARLFLLTRILTISTLPETTVVRRQAFTFSPTYK
WLSLLVPFVIPIPSSWAFTPARVTGGVFKVGNFTGLYLPSDFFPSVTLWKAGILYKN
VSIPWTHKLVVDFSQFSRSAICSVVRRALMPLYACI
↓
206

TABLE 24

Epigene encoded by HBV AOSIb2 construct

HBV AOSIb2    Polynucleotide

SEQ ID NO: 211    1 Start
↑
[ATG]GGAATGCAGGTGCAGATCCAGAGCCTGTTTCTGCTCCTCCTGTGGGTGCCC
GGGTCCAGAGGACACACCCTGTGGAAGGCCGGAATCCTGTATAAGGCCAAGTT
CGTGGCTGCCTGGACCCTGAAGGCTGCCGCTTTCCTGCCTAGCGATTTCTTTCCT
AGCGTGAACTTCCTGCTGTCCCTGGGAATCCACCTGTATATGGATGACGTGGTG
CTGGGAGTGGGACTGTCCAGGTACGTGGCTAGGCTGTTCCTGCTGACCAGAATC
CTGACCATCTCCACCCTGCCAGAGACCACCGTGGTGAGGAGGCAGGCCTTCAC
CTTTAGCCCTACCTATAAGGGAGCCGCTGCCTGGCTGAGCCTGCTGGTGCCCTT
TGTGAATATCCCTATCCCTAGCTCCTGGGCTTTCAAGACCCCAGCCAGGGTGAC
CGGAGGAGTGTTTAAGGTGGGAAACTTCACCGGCCTGTATAACCTGCCCAGCG
ATTTCTTTCCTAGCGTGAAGACCCTGTGGAAGGCCGGAATCCTGTACAAGAATG
TGTCCATCCCTTGGACCCACAAGGGAGCCGCTCTGGTGGTGGACTTTTCCCAGT
TCAGCAGAAATTCCGCTATCTGCTCCGTGGTGAGGAGAGCTCTGATGCCACTGT
ATGCCTGTATC[TGA]
↓ Stop
657

HBV AOSIb2    Polypeptide

SEQ ID NO: 212    1
↑
MGMQVQIQSLFLLLLWVPGSRGHTLWKAGILYKAKFVAAWTLKAAAFLPSDFFPS
VNFLLSLGIHLYMDDVVLGVGLSRYVARLFLLTRILTISTLPETTVVRRQAFTFSPTY
KGAAAWLSLLVPFVNIPIPSSWAFKTPARVTGGVFKVGNFTGLYNLPSDFFPSVKTL
WKAGILYKNVSIPWTHKGAALVVDFSQFSRNSAICSVVRRALMPLYACI
↓
219

4. In Vitro Protein Expression and Detection Method

Transient transfection of human 293 cell lines was carried out with plasmids encoding the fluorescent-conjugated polyepitopes HBV AOSIb or HBV AOSIb.2, or the fluorescence reporter plasmid with no epitopes. 5 µM of the irreversible proteasome inhibitor MG132 was added 24 hours post-transfection. Fluorescence was detected in live cells by either flow cytometry (FACS) or fluorescence microscopy within 24 hours of the addition of the proteasome inhibitor. The increase in the number of fluorescent cells transfected with plasmid HBV AOSIb in the presence or absence of proteasome inhibitor was measured as shown in FIG. 35A, as a function of incubation time with the inhibitor. FIG. 38 shows the comparison in number of fluorescent cells detected (by FACS) after 24 hour incubation with inhibitor for cells transfected with the three different plasmids. The more profound effect was noted for the spacer-optimized plasmid HBV AOSIb.2. The number of cells expressing the various fluorescent fusion proteins was also measured by fluorescence microscopy of live cells as shown in FIG. 39. Western blot detection was performed by preparing whole cell lysates from transfected cells, separating proteins by gel electrophoresis, transferring to blotting membranes, and detecting proteins with an antibody against the fusion partner protein. The increase in amount of proteins detectable upon addition of the proteasome inhibitors lactacystin (25 µM) or MG132 (5 µM) was then determined. The results are shown in FIG. 36.

5. Mouse Immunogenicity Assay Method

Transgenic HLA-A2 mice were injected i.m. with 100 ug of a plasmid encoding HBV AOSIb or HBV AOSIb2 polyepitopes. Mice were sacrificed 14 days later and their spleens were homogenized to collect T lymphocytes and APCs. Cells were stimulated in culture with peptides corresponding to the various HBV epitopes. The secretion of IFN-γ was measured by a modified ELISA method (to detect secretory units). The results are summarized in Table 25.

TABLE 25

HLA-A2 Tg mice immunogenicity for plasmids AOSIb and AOSIb.2

| Epitope | HBV AOSIb (100 ug dose) | | HBV AOSIb2 (100 ug dose) | |
| --- | --- | --- | --- | --- |
| | magnitude | frequency | magnitude | frequency |
| core 18 | 102.7 (1.8) | 6/6 | 480.6 (1.4) | 6/6 |
| pol 562 | — | 0/6 | 260.2 (2.1) | 6/6 |
| pol 538 | 2643.8 (1.3) | 6/6 | 2332.3 (1.4) | 6/6 |
| pol 455 | 2234.6 (1.3) | 6/6 | 334.3 (1.3) | 6/6 |
| env 183 | 877.5 (1.3) | 6/6 | 962.8 (1.3) | 6/6 |
| env 335 | 6.1 | 1/6 | 44.9 (1.6) | 6/6 |
| pol 642 | 1859.8 (1.6) | 6/6 | 1819.0 (1.6) | 6/6 |

6. Summary of Results

The HBV DNA constructs carry virus specific epitopes in optimized cassettes able to elicit CTL responses, and additional amino acids were introduced between the epitopes of one construct to potentially enhance proteasomal processing and thereby class I presentation of antigen.

Both HBV-fluorescent protein fusions were more labile than the fluorescent protein alone, suggesting the HBV polyepitopes are readily degraded and drive the degradation of the whole fusion product. Proteasome inhibitors allow the detection of greater amounts of fluorescent fusion products but have no effect on the fusion partner if expressed alone, indicating that this is indeed a cytosomal proteasome activity enhanced by the polyepitopes. The effect of proteasome inhibitor is more pronounced for the spacer-optimized HBV AOSIb2 product than for the HBV AOSIb fusion protein indicating that the processing sites added to the HBV AOSIb2 molecule had the desired effect of increasing its processivity. Studies in HLA-A2 transgenic mice showed an improvement in immunogenicity of several epitopes for the "optimized" HBV AOSIb2 plasmid compared to HBV AOSIb.

Example 19

Epitope-Specific T Cell Responses Measured in HLA Transgenic Mice Immunized with GCR-3697

Epitope-specific T cell responses were measured in HLA transgenic mice immunized with GCR-3697 using splenic lymphocytes obtained 11-14 days following immunization (FIG. 37). Groups of 6-9 HLA-transgenic mice were immunized bilaterally with 100 µg of DNA in the tibialis anterior muscle. DNA was delivered in either PBS or PVP formulations; in the case of PBS formulations the injection site was pre-treated by cardiotoxin injection. Mice immunized with PVP based formulations were immunized twice with 100 µg of DNA in a four day period.

CTL responses were measured using an in situ ELISA assay based on the production of IFN-γ. Assays were conducted by culturing splenocytes ($2.5 \times 10^7$) with peptide (1 µg/ml) and irradiated lipopolysaccharide (LPS)-activated splenocytes ($10^7$) in RPMI medium for 6 days at 37° C. in 5% $CO_2$. After the 6-day stimulation, serially diluted splenocytes were cultured for 20 hours, with and without peptide (1 µg/ml), and $10^5$ HLA-matched Jurkat target cells. Assays were performed on ELISA plates (Costar, Corning, N.Y.) pre-coated with rat monoclonal antibody specific for murine IFN-γ (Clone RA-6A2, BD Biosciences/Pharmingen). The following day, the cells were removed by washing the plates with PBS with 0.05% Tween-20 and the amount of IFN-γ secreted was measured using a sandwich format ELISA. A biotinylated rat monoclonal antibody (clone XMG1.2, BD Biosciences/Pharmingen) was used to detect captured IFN-γ. Horseradish peroxidase-coupled strepavidin (Zymed) and 3,3',5,5' tetramethylbenzidine and $H_2O_2$ (ImmunoPure TMB Substrate Kit, Pierce) were used according to the manufacturer's directions for color development. The absorbance was read at 450 nm on a Labsystems Multiskan RC ELISA plate reader. In situ ELISA data was converted to secretory units (SU) for evaluation (McKinney et al 2000).

Overall, GCR-3697 induced CTL responses to multiple epitopes restricted by a variety of HLA-supertypes. The magnitude and the breadth of the responses induced are consistent with the nature of the immune responses generally considered to of therapeutic value.

The entire disclosure of each document cited (including patents, patent applications, journal articles, abstracts, laboratory manuals, books, entries in sequence databases, or other disclosures) in the Background, Definitions, Detailed Description, and Examples is hereby incorporated herein by reference.

Those skilled in the art will know, or be able to ascertain using no more than routine experimentation, many equivalents to the specific embodiments of the invention described herein. These equivalents are intended to be encompassed by the following claims.

What is claimed is:

1. An isolated polypeptide encoded by a polynucleotide selected from the group consisting of: SEQ ID NO:205 and SEQ ID NO:207.

2. An isolated polypeptide selected from the group consisting of SEQ ID NO:206 and SEQ ID NO:208.

3. A composition comprising the polypeptide of claim 1.

4. A method of inducing an immune response against hepatitis B virus (HBV) in an individual in need thereof, comprising administering the polypeptide of claim 1 to said individual.

5. A composition comprising the polypeptide of claim 2.

6. A method of inducing an immune response against hepatitis B virus (HBV) in an individual in need thereof, comprising administering the polypeptide of claim 2 to said individual.

* * * * *

SEQUENCE LISTING

<160> NUMBER OF SEQ ID NOS: 479

<210> SEQ ID NO 1
<211> LENGTH: 13
<212> TYPE: PRT
<213> ORGANISM: Unknown
<220> FEATURE:
<223> OTHER INFORMATION: PADRE peptide, HLA Class II supermotif
      example
<220> FEATURE:
<221> NAME/KEY: MISC_FEATURE
<222> LOCATION: (1)..(1)
<223> OTHER INFORMATION: May be D- or L-Alanine
<220> FEATURE:
<221> NAME/KEY: MISC_FEATURE
<222> LOCATION: (3)..(3)
<223> OTHER INFORMATION: Xaa may be cyclohexylalanine, Phenylalanine
      or Tyrosine
<220> FEATURE:
<221> NAME/KEY: MISC_FEATURE
<222> LOCATION: (13)..(13)
<223> OTHER INFORMATION: May be D- or L-Alanine

<400> SEQUENCE: 1

Ala Lys Xaa Val Ala Ala Trp Thr Leu Lys Ala Ala Ala
1               5                   10

<210> SEQ ID NO 2
<211> LENGTH: 5
<212> TYPE: PRT
<213> ORGANISM: Unknown
<220> FEATURE:
<223> OTHER INFORMATION: Spacer peptide

<400> SEQUENCE: 2

Gly Pro Gly Pro Gly
1               5

<210> SEQ ID NO 3
<211> LENGTH: 22
<212> TYPE: PRT
<213> ORGANISM: Unknown
<220> FEATURE:
<223> OTHER INFORMATION: CTL multi-epitope construct

<400> SEQUENCE: 3

Thr Leu Lys Ala Ala Ala Phe Leu Pro Ser Asp Phe Phe Pro Ser Val
1               5                   10                  15

Phe Leu Leu Ser Leu Gly
            20

<210> SEQ ID NO 4
<211> LENGTH: 22
<212> TYPE: PRT
<213> ORGANISM: Unknown
<220> FEATURE:
<223> OTHER INFORMATION: CTL multi-epitope construct

<400> SEQUENCE: 4

Thr Leu Lys Ala Ala Ala Phe Leu Pro Ser Asp Phe Phe Pro Ser Val
1               5                   10                  15

Lys Leu Thr Pro Leu Cys
            20

<210> SEQ ID NO 5
<211> LENGTH: 15

```
<212> TYPE: PRT
<213> ORGANISM: Unknown
<220> FEATURE:
<223> OTHER INFORMATION: CTL multi-epitope construct

<400> SEQUENCE: 5

Ile Leu Gly Gly Trp Val Asp Leu Met Gly Tyr Ile Pro Leu Val
1               5                   10                  15

<210> SEQ ID NO 6
<211> LENGTH: 20
<212> TYPE: PRT
<213> ORGANISM: Unknown
<220> FEATURE:
<223> OTHER INFORMATION: CTL multi-epitope construct

<400> SEQUENCE: 6

Val Pro Gly Ser Arg Gly Asp Leu Met Gly Tyr Ile Pro Leu Val Ala
1               5                   10                  15

Lys Phe Val Ala
            20

<210> SEQ ID NO 7
<211> LENGTH: 9
<212> TYPE: PRT
<213> ORGANISM: Unknown
<220> FEATURE:
<223> OTHER INFORMATION: Artificial Peptide

<400> SEQUENCE: 7

Val Leu Ala Glu Ala Met Ser Gln Val
1               5

<210> SEQ ID NO 8
<211> LENGTH: 9
<212> TYPE: PRT
<213> ORGANISM: Unknown
<220> FEATURE:
<223> OTHER INFORMATION: Artificial Peptide

<400> SEQUENCE: 8

Ile Leu Lys Glu Pro Val His Gly Val
1               5

<210> SEQ ID NO 9
<211> LENGTH: 10
<212> TYPE: PRT
<213> ORGANISM: Hepatitis B Virus

<400> SEQUENCE: 9

Phe Leu Pro Ser Asp Phe Phe Pro Ser Val
1               5                   10

<210> SEQ ID NO 10
<211> LENGTH: 9
<212> TYPE: PRT
<213> ORGANISM: Hepatitis B Virus

<400> SEQUENCE: 10

Phe Leu Leu Thr Arg Ile Leu Thr Ile
1               5

<210> SEQ ID NO 11
<211> LENGTH: 9
<212> TYPE: PRT
<213> ORGANISM: Hepatitis B Virus
```

```
<400> SEQUENCE: 11

Trp Leu Ser Leu Leu Val Pro Phe Val
1               5

<210> SEQ ID NO 12
<211> LENGTH: 10
<212> TYPE: PRT
<213> ORGANISM: Hepatitis B Virus

<400> SEQUENCE: 12

Leu Leu Val Pro Phe Val Gln Trp Phe Val
1               5                   10

<210> SEQ ID NO 13
<211> LENGTH: 10
<212> TYPE: PRT
<213> ORGANISM: Hepatitis B Virus

<400> SEQUENCE: 13

Leu Leu Pro Ile Phe Phe Cys Leu Trp Val
1               5                   10

<210> SEQ ID NO 14
<211> LENGTH: 9
<212> TYPE: PRT
<213> ORGANISM: Hepatitis B Virus

<400> SEQUENCE: 14

Gly Leu Ser Arg Tyr Val Ala Arg Leu
1               5

<210> SEQ ID NO 15
<211> LENGTH: 9
<212> TYPE: PRT
<213> ORGANISM: Hepatitis B Virus

<400> SEQUENCE: 15

Tyr Met Asp Asp Val Val Leu Gly Val
1               5

<210> SEQ ID NO 16
<211> LENGTH: 10
<212> TYPE: PRT
<213> ORGANISM: Hepatitis B Virus

<400> SEQUENCE: 16

Ile Leu Arg Gly Thr Ser Phe Val Tyr Val
1               5                   10

<210> SEQ ID NO 17
<211> LENGTH: 9
<212> TYPE: PRT
<213> ORGANISM: Hepatitis B Virus

<400> SEQUENCE: 17

Phe Leu Leu Ser Leu Gly Ile His Leu
1               5

<210> SEQ ID NO 18
<211> LENGTH: 9
<212> TYPE: PRT
<213> ORGANISM: Hepatitis B Virus

<400> SEQUENCE: 18
```

```
Ala Leu Met Pro Leu Tyr Ala Cys Ile
1               5

<210> SEQ ID NO 19
<211> LENGTH: 10
<212> TYPE: PRT
<213> ORGANISM: Hepatitis B Virus

<400> SEQUENCE: 19

Gly Leu Ser Pro Thr Val Trp Leu Ser Val
1               5                   10

<210> SEQ ID NO 20
<211> LENGTH: 11
<212> TYPE: PRT
<213> ORGANISM: Hepatitis B Virus

<400> SEQUENCE: 20

Ser Thr Leu Pro Glu Thr Thr Val Val Arg Arg
1               5                   10

<210> SEQ ID NO 21
<211> LENGTH: 11
<212> TYPE: PRT
<213> ORGANISM: Hepatitis B Virus

<400> SEQUENCE: 21

His Thr Leu Trp Lys Ala Gly Ile Leu Tyr Lys
1               5                   10

<210> SEQ ID NO 22
<211> LENGTH: 10
<212> TYPE: PRT
<213> ORGANISM: Hepatitis B Virus

<400> SEQUENCE: 22

Thr Leu Trp Lys Ala Gly Ile Leu Tyr Lys
1               5                   10

<210> SEQ ID NO 23
<211> LENGTH: 10
<212> TYPE: PRT
<213> ORGANISM: Hepatitis B Virus

<400> SEQUENCE: 23

Leu Val Val Asp Phe Ser Gln Phe Ser Arg
1               5                   10

<210> SEQ ID NO 24
<211> LENGTH: 9
<212> TYPE: PRT
<213> ORGANISM: Hepatitis B Virus

<400> SEQUENCE: 24

Asn Val Ser Ile Pro Trp Thr His Lys
1               5

<210> SEQ ID NO 25
<211> LENGTH: 9
<212> TYPE: PRT
<213> ORGANISM: Hepatitis B Virus

<400> SEQUENCE: 25

Ser Ala Ile Cys Ser Val Val Arg Arg
```

```
<210> SEQ ID NO 26
<211> LENGTH: 9
<212> TYPE: PRT
<213> ORGANISM: Hepatitis B Virus

<400> SEQUENCE: 26

Lys Val Gly Asn Phe Thr Gly Leu Tyr
1               5

<210> SEQ ID NO 27
<211> LENGTH: 10
<212> TYPE: PRT
<213> ORGANISM: Hepatitis B Virus

<400> SEQUENCE: 27

Gln Ala Phe Thr Phe Ser Pro Thr Tyr Lys
1               5                   10

<210> SEQ ID NO 28
<211> LENGTH: 9
<212> TYPE: PRT
<213> ORGANISM: Hepatitis B Virus

<400> SEQUENCE: 28

Leu Pro Ser Asp Phe Phe Pro Ser Val
1               5

<210> SEQ ID NO 29
<211> LENGTH: 9
<212> TYPE: PRT
<213> ORGANISM: Hepatitis B Virus

<400> SEQUENCE: 29

Ile Pro Ile Pro Ser Ser Trp Ala Phe
1               5

<210> SEQ ID NO 30
<211> LENGTH: 10
<212> TYPE: PRT
<213> ORGANISM: Hepatitis B Virus

<400> SEQUENCE: 30

Thr Pro Ala Arg Val Thr Gly Gly Val Phe
1               5                   10

<210> SEQ ID NO 31
<211> LENGTH: 9
<212> TYPE: PRT
<213> ORGANISM: Hepatitis B Virus

<400> SEQUENCE: 31

His Pro Ala Ala Met Pro His Leu Leu
1               5

<210> SEQ ID NO 32
<211> LENGTH: 9
<212> TYPE: PRT
<213> ORGANISM: Hepatitis B Virus

<400> SEQUENCE: 32

Tyr Pro Ala Leu Met Pro Leu Tyr Ala
1               5
```

```
<210> SEQ ID NO 33
<211> LENGTH: 9
<212> TYPE: PRT
<213> ORGANISM: Hepatitis B Virus

<400> SEQUENCE: 33

Phe Pro His Cys Leu Ala Phe Ser Tyr
1               5

<210> SEQ ID NO 34
<211> LENGTH: 10
<212> TYPE: PRT
<213> ORGANISM: Hepatitis B Virus

<400> SEQUENCE: 34

Phe Pro His Cys Leu Ala Phe Ser Tyr Met
1               5                   10

<210> SEQ ID NO 35
<211> LENGTH: 7
<212> TYPE: PRT
<213> ORGANISM: Hepatitis B Virus

<400> SEQUENCE: 35

Tyr Pro Ala Leu Met Leu Tyr
1               5

<210> SEQ ID NO 36
<211> LENGTH: 11
<212> TYPE: PRT
<213> ORGANISM: Hepatitis B Virus

<400> SEQUENCE: 36

Tyr Pro Ala Leu Met Pro Leu Tyr Ala Cys Ile
1               5                   10

<210> SEQ ID NO 37
<211> LENGTH: 11
<212> TYPE: PRT
<213> ORGANISM: Hepatitis B Virus

<400> SEQUENCE: 37

Trp Met Met Trp Tyr Trp Gly Pro Ser Leu Tyr
1               5                   10

<210> SEQ ID NO 38
<211> LENGTH: 10
<212> TYPE: PRT
<213> ORGANISM: Hepatitis B Virus

<400> SEQUENCE: 38

Asp Leu Leu Asp Thr Ala Ser Ala Leu Tyr
1               5                   10

<210> SEQ ID NO 39
<211> LENGTH: 11
<212> TYPE: PRT
<213> ORGANISM: Hepatitis B Virus

<400> SEQUENCE: 39

Leu Thr Phe Gly Arg Glu Thr Val Leu Glu Tyr
1               5                   10

<210> SEQ ID NO 40
```

```
<211> LENGTH: 10
<212> TYPE: PRT
<213> ORGANISM: Hepatitis B Virus

<400> SEQUENCE: 40

His Thr Leu Trp Lys Ala Gly Ile Leu Tyr
1               5                   10

<210> SEQ ID NO 41
<211> LENGTH: 8
<212> TYPE: PRT
<213> ORGANISM: Hepatitis B Virus

<400> SEQUENCE: 41

Ala Ser Phe Cys Gly Ser Pro Tyr
1               5

<210> SEQ ID NO 42
<211> LENGTH: 10
<212> TYPE: PRT
<213> ORGANISM: Hepatitis B Virus

<400> SEQUENCE: 42

Leu Ser Leu Asp Val Ser Ala Ala Phe Tyr
1               5                   10

<210> SEQ ID NO 43
<211> LENGTH: 8
<212> TYPE: PRT
<213> ORGANISM: Hepatitis B Virus

<400> SEQUENCE: 43

Tyr Ser Leu Asn Phe Met Gly Tyr
1               5

<210> SEQ ID NO 44
<211> LENGTH: 10
<212> TYPE: PRT
<213> ORGANISM: Hepatitis B Virus

<400> SEQUENCE: 44

Ile Leu Leu Leu Cys Leu Ile Phe Leu Leu
1               5                   10

<210> SEQ ID NO 45
<211> LENGTH: 10
<212> TYPE: PRT
<213> ORGANISM: Hepatitis B Virus

<400> SEQUENCE: 45

Arg Trp Met Cys Leu Arg Arg Phe Ile Ile
1               5                   10

<210> SEQ ID NO 46
<211> LENGTH: 10
<212> TYPE: PRT
<213> ORGANISM: Hepatitis B Virus

<400> SEQUENCE: 46

Ser Trp Pro Lys Phe Ala Val Pro Asn Leu
1               5                   10

<210> SEQ ID NO 47
<211> LENGTH: 11
<212> TYPE: PRT
```

<213> ORGANISM: Hepatitis B Virus

<400> SEQUENCE: 47

Arg Phe Ser Trp Leu Ser Leu Leu Val Pro Phe
1               5                   10

<210> SEQ ID NO 48
<211> LENGTH: 10
<212> TYPE: PRT
<213> ORGANISM: Hepatitis B Virus

<400> SEQUENCE: 48

Leu Trp Phe His Ile Ser Cys Leu Thr Phe
1               5                   10

<210> SEQ ID NO 49
<211> LENGTH: 9
<212> TYPE: PRT
<213> ORGANISM: Hepatitis B Virus

<400> SEQUENCE: 49

Glu Tyr Leu Val Ser Phe Gly Val Trp
1               5

<210> SEQ ID NO 50
<211> LENGTH: 9
<212> TYPE: PRT
<213> ORGANISM: Hepatitis B Virus

<400> SEQUENCE: 50

Ser Phe Cys Gly Ser Pro Tyr Ser Trp
1               5

<210> SEQ ID NO 51
<211> LENGTH: 8
<212> TYPE: PRT
<213> ORGANISM: Hepatitis B Virus

<400> SEQUENCE: 51

Ala Phe Pro His Cys Leu Ala Phe
1               5

<210> SEQ ID NO 52
<211> LENGTH: 9
<212> TYPE: PRT
<213> ORGANISM: Hepatitis B Virus

<400> SEQUENCE: 52

Gly Tyr Pro Ala Leu Met Pro Leu Tyr
1               5

<210> SEQ ID NO 53
<211> LENGTH: 9
<212> TYPE: PRT
<213> ORGANISM: Hepatitis B Virus

<400> SEQUENCE: 53

Lys Tyr Thr Ser Phe Pro Trp Leu Leu
1               5

<210> SEQ ID NO 54
<211> LENGTH: 9
<212> TYPE: PRT
<213> ORGANISM: Hepatitis B Virus -continued

```
<400> SEQUENCE: 54

Ser Tyr Ile Pro Ser Ala Glu Lys Ile
1               5

<210> SEQ ID NO 55
<211> LENGTH: 15
<212> TYPE: PRT
<213> ORGANISM: Hepatitis B Virus

<400> SEQUENCE: 55

Leu Gln Ser Leu Thr Asn Leu Leu Ser Ser Asn Leu Ser Trp Leu
1               5                   10                  15

<210> SEQ ID NO 56
<211> LENGTH: 15
<212> TYPE: PRT
<213> ORGANISM: Hepatitis B Virus

<400> SEQUENCE: 56

Lys Gln Ala Phe Thr Phe Ser Pro Thr Tyr Lys Ala Phe Leu Cys
1               5                   10                  15

<210> SEQ ID NO 57
<211> LENGTH: 15
<212> TYPE: PRT
<213> ORGANISM: Hepatitis B Virus

<400> SEQUENCE: 57

Ala Gly Phe Phe Leu Leu Thr Arg Ile Leu Thr Ile Pro Gln Ser
1               5                   10                  15

<210> SEQ ID NO 58
<211> LENGTH: 15
<212> TYPE: PRT
<213> ORGANISM: Hepatitis B Virus

<400> SEQUENCE: 58

Gly Thr Ser Phe Val Tyr Val Pro Ser Ala Leu Asn Pro Ala Asp
1               5                   10                  15

<210> SEQ ID NO 59
<211> LENGTH: 20
<212> TYPE: PRT
<213> ORGANISM: Hepatitis B Virus

<400> SEQUENCE: 59

Val Ser Phe Gly Val Trp Ile Arg Thr Pro Pro Ala Tyr Arg Pro Pro
1               5                   10                  15

Asn Ala Pro Ile
            20

<210> SEQ ID NO 60
<211> LENGTH: 15
<212> TYPE: PRT
<213> ORGANISM: Hepatitis B Virus

<400> SEQUENCE: 60

Arg His Tyr Leu His Thr Leu Trp Lys Ala Gly Ile Leu Tyr Lys
1               5                   10                  15

<210> SEQ ID NO 61
<211> LENGTH: 15
<212> TYPE: PRT
<213> ORGANISM: Hepatitis B Virus
```

```
<400> SEQUENCE: 61

Leu Val Pro Phe Val Gln Trp Phe Val Gly Leu Ser Pro Thr Val
1               5                   10                  15

<210> SEQ ID NO 62
<211> LENGTH: 15
<212> TYPE: PRT
<213> ORGANISM: Hepatitis B Virus

<400> SEQUENCE: 62

Leu His Leu Tyr Ser His Pro Ile Ile Leu Gly Phe Arg Lys Ile
1               5                   10                  15

<210> SEQ ID NO 63
<211> LENGTH: 15
<212> TYPE: PRT
<213> ORGANISM: Hepatitis B Virus

<400> SEQUENCE: 63

Pro Phe Leu Leu Ala Gln Phe Thr Ser Ala Ile Cys Ser Val Val
1               5                   10                  15

<210> SEQ ID NO 64
<211> LENGTH: 15
<212> TYPE: PRT
<213> ORGANISM: Hepatitis B Virus

<400> SEQUENCE: 64

Lys Gln Cys Phe Arg Lys Leu Pro Val Asn Arg Pro Ile Asp Trp
1               5                   10                  15

<210> SEQ ID NO 65
<211> LENGTH: 15
<212> TYPE: PRT
<213> ORGANISM: Hepatitis B Virus

<400> SEQUENCE: 65

Ala Ala Asn Trp Ile Leu Arg Gly Thr Ser Phe Val Tyr Val Pro
1               5                   10                  15

<210> SEQ ID NO 66
<211> LENGTH: 20
<212> TYPE: PRT
<213> ORGANISM: Hepatitis B Virus

<400> SEQUENCE: 66

Pro His His Thr Ala Leu Arg Gln Ala Ile Leu Cys Trp Gly Glu Leu
1               5                   10                  15

Met Thr Leu Ala
            20

<210> SEQ ID NO 67
<211> LENGTH: 15
<212> TYPE: PRT
<213> ORGANISM: Hepatitis B Virus

<400> SEQUENCE: 67

Leu Cys Gln Val Phe Ala Asp Ala Thr Pro Thr Gly Trp Gly Leu
1               5                   10                  15

<210> SEQ ID NO 68
<211> LENGTH: 15
<212> TYPE: PRT
```

<213> ORGANISM: Hepatitis B Virus

<400> SEQUENCE: 68

Glu Ser Arg Leu Val Val Asp Phe Ser Gln Phe Ser Arg Gly Asn
1               5                   10                  15

<210> SEQ ID NO 69
<211> LENGTH: 15
<212> TYPE: PRT
<213> ORGANISM: Hepatitis B Virus

<400> SEQUENCE: 69

Val Gly Pro Leu Thr Val Asn Glu Lys Arg Arg Leu Lys Leu Ile
1               5                   10                  15

<210> SEQ ID NO 70
<211> LENGTH: 15
<212> TYPE: PRT
<213> ORGANISM: Hepatitis B Virus

<400> SEQUENCE: 70

Ser Ser Asn Leu Ser Trp Leu Ser Leu Asp Val Ser Ala Ala Phe
1               5                   10                  15

<210> SEQ ID NO 71
<211> LENGTH: 1251
<212> TYPE: DNA
<213> ORGANISM: Hepatitis B Virus

<400> SEQUENCE: 71

| | |
|---|---|
| atgggaatgc aggtgcaaat acagtctctc ttccttttgc ttctctgggt tccaggatca | 60 |
| cggggcttct tgcttagctt gggcatccac ctaaatgctg ctgcaaaata cacatctttt | 120 |
| ccttggctcc ttaatgccgc cgctaggttt tcatggctga gtctgctagt acctttcaat | 180 |
| gcggctttcc cacattgcct agcttttagc tatatgaaag ctgctttagt cgtggacttt | 240 |
| tcacagttta gcagaggagc aatcctgctg ctatgtctga tattccttct aaacgcagca | 300 |
| gcccacacac tctggaaagc tggtatcctt acaagaaag cctggatgat gtggtattgg | 360 |
| ggacccagcc tctacaaagc ataccctgcc ctgatgccac tatacgcatg cattggcgcg | 420 |
| gcagcctggt tatccttttt agtaccgttt gtcaacgccg cagcgggatt tctattaacc | 480 |
| agaatcctga cgattaatgc tgccgccatt ccgatcccaa gttcctgggc attcaaagca | 540 |
| gccgcggagt atctggtttc atttggcgta tggaacctgc caagcgactt ctttccttct | 600 |
| gttaaggccg ctgctttcct cccctccgat ttctttccat cggtgaaagc cgctgccgac | 660 |
| ctccttgata ccgcgagcgc tctgtacaac tcgtggccaa aattcgcagt tccaaaccta | 720 |
| aaagccgccg ccagtgccat tgttccgtg gtaaggagaa aattatcact cgacgtgtcc | 780 |
| gcagcatttt ataacgctgc tgcaaagttt gtcgcagcat ggacattgaa ggctgcagcg | 840 |
| aaagcagcaa atgtatcaat accctggacc cacaagggtg cagccgggct gtctaggtat | 900 |
| gtggcgaggc taaacgccgc cgcctcaaca ctgcctgaga ctactgtcgt gagacgcaaa | 960 |
| cacccctgccg caatgcccca cctgctgaaa gcagccgcac gatggatgtg cctcagaaga | 1020 |
| ttcataataa acgcttcttt ctgtgggtca cctacaaag ccgcttacat ggacgatgtg | 1080 |
| gtcctcggag tgaatgccct ctggttccat atcagctgcc tgacattcaa ggcagccgcc | 1140 |
| accccgctc gtgtgacagg aggtgtcttc aaagccgcgg cactgacttt cggtcgggaa | 1200 |
| actgtattgg aatataagca ggccttcaca ttctcccca catacaagtg a | 1251 |

-continued

<210> SEQ ID NO 72
<211> LENGTH: 416
<212> TYPE: PRT
<213> ORGANISM: Hepatitis B Virus

<400> SEQUENCE: 72

```
Met Gly Met Gln Val Gln Ile Gln Ser Leu Phe Leu Leu Leu Leu Trp
1               5                   10                  15

Val Pro Gly Ser Arg Gly Phe Leu Leu Ser Leu Gly Ile His Leu Asn
            20                  25                  30

Ala Ala Ala Lys Tyr Thr Ser Phe Pro Trp Leu Leu Asn Ala Ala Ala
        35                  40                  45

Arg Phe Ser Trp Leu Ser Leu Leu Val Pro Phe Asn Ala Ala Phe Pro
    50                  55                  60

His Cys Leu Ala Phe Ser Tyr Met Lys Ala Ala Leu Val Val Asp Phe
65                  70                  75                  80

Ser Gln Phe Ser Arg Gly Ala Ile Leu Leu Leu Cys Leu Ile Phe Leu
                85                  90                  95

Leu Asn Ala Ala Ala His Thr Leu Trp Lys Ala Gly Ile Leu Tyr Lys
            100                 105                 110

Lys Ala Trp Met Met Trp Tyr Trp Gly Pro Ser Leu Tyr Lys Ala Tyr
        115                 120                 125

Pro Ala Leu Met Pro Leu Tyr Ala Cys Ile Gly Ala Ala Ala Trp Leu
    130                 135                 140

Ser Leu Leu Val Pro Phe Val Asn Ala Ala Ala Gly Phe Leu Leu Thr
145                 150                 155                 160

Arg Ile Leu Thr Ile Asn Ala Ala Ala Ile Pro Ile Pro Ser Ser Trp
                165                 170                 175

Ala Phe Lys Ala Ala Ala Glu Tyr Leu Val Ser Phe Gly Val Trp Asn
            180                 185                 190

Leu Pro Ser Asp Phe Phe Pro Ser Val Lys Ala Ala Ala Phe Leu Pro
        195                 200                 205

Ser Asp Phe Phe Pro Ser Val Lys Ala Ala Ala Asp Leu Leu Asp Thr
    210                 215                 220

Ala Ser Ala Leu Tyr Asn Ser Trp Pro Lys Phe Ala Val Pro Asn Leu
225                 230                 235                 240

Lys Ala Ala Ala Ser Ala Ile Cys Ser Val Val Arg Arg Lys Leu Ser
                245                 250                 255

Leu Asp Val Ser Ala Ala Phe Tyr Asn Ala Ala Ala Lys Phe Val Ala
            260                 265                 270

Ala Trp Thr Leu Lys Ala Ala Ala Lys Ala Ala Asn Val Ser Ile Pro
        275                 280                 285

Trp Thr His Lys Gly Ala Ala Gly Leu Ser Arg Tyr Val Ala Arg Leu
    290                 295                 300

Asn Ala Ala Ala Ser Thr Leu Pro Glu Thr Thr Val Val Arg Arg Lys
305                 310                 315                 320

His Pro Ala Ala Met Pro His Leu Leu Lys Ala Ala Ala Arg Trp Met
                325                 330                 335

Cys Leu Arg Arg Phe Ile Ile Asn Ala Ser Phe Cys Gly Ser Pro Tyr
            340                 345                 350

Lys Ala Ala Tyr Met Asp Asp Val Val Leu Gly Val Asn Ala Leu Trp
        355                 360                 365

Phe His Ile Ser Cys Leu Thr Phe Lys Ala Ala Ala Thr Pro Ala Arg
    370                 375                 380
```

```
Val Thr Gly Gly Val Phe Lys Ala Ala Ala Leu Thr Phe Gly Arg Glu
385                 390                 395                 400

Thr Val Leu Glu Tyr Lys Gln Ala Phe Thr Phe Ser Pro Thr Tyr Lys
            405                 410                 415

<210> SEQ ID NO 73
<211> LENGTH: 1035
<212> TYPE: DNA
<213> ORGANISM: Hepatitis B virus

<400> SEQUENCE: 73
atgggaactt cttttgtgta tgtcccttcc gctctgaacc cagcagacgg acccgggcct      60
ggcctgtgcc aggtcttcgc cgacgcaact cccacagggt gggggctggg gccaggacca     120
ggcaggcact acctgcatac tctgtggaag gcaggaatcc tctataaagg gcccggccca     180
ggccctcacc acaccgccct gaggcaggcc atcctgtgct gggggagct catgaccctg      240 gccggacctg gacccgggga gagcagactg gtggtggatt tcagccaatt cagcagagga     300
aacggacccg ccctgggcc ttttctgctg gctcagttta catctgctat ttgttctgtg      360
gtcggccccg ggcccggact cgtgcctttc gtgcagtggt cgtgggact gtcccctaca      420 gtcgggcccg gccagggct gcatctgtac tcccacccaa tcatcctcgg cttccgcaag      480
attggacccg gccaggctc cagcaatctc tcctggctct ctctggacgt gtctgccgcc      540
tttggccctg gaccaggcct gcaaagcctg actaatctgc tcagcagcaa cctgtcctgg      600 ctgggaccctg gcccaggggc tggcttcttt ctgctcaccc ggattctcac aattccccag      660
tccggaccag gaccaggagt cagtttcggg gtgtggatca ggaccctcc tgcttataga      720 ccacccaatg ctccaatcgg ccccggccct ggcgtcgggc cactgaccgt gaatgagaag      780
cgccggctga gctgatcgg ccctggccct ggcaagcagt gctttcgcaa actgcccgtg      840
aacagaccta ttgattgggg ccccggccct ggagcagcca actggattct caggggaaca      900
agcttcgtct acgtgcccgg gccggacca gggaagcagg ctttttacctt ctctcccact      960 tacaaggcct cctctgtgtg gccaggcccc ggcgccaagt tgtgtggcagc atggaccctc     1020 aaagccgctg cctga                                                       1035

<210> SEQ ID NO 74
<211> LENGTH: 344
<212> TYPE: PRT
<213> ORGANISM: Hepatitis B virus

<400> SEQUENCE: 74

Met Gly Thr Ser Phe Val Tyr Val Pro Ser Ala Leu Asn Pro Ala Asp
1               5                   10                  15

Gly Pro Gly Pro Gly Leu Cys Gln Val Phe Ala Asp Ala Thr Pro Thr
            20                  25                  30

Gly Trp Gly Leu Gly Pro Gly Pro Gly Arg His Tyr Leu His Thr Leu
        35                  40                  45

Trp Lys Ala Gly Ile Leu Tyr Lys Gly Pro Gly Pro Gly Pro His His
    50                  55                  60

Thr Ala Leu Arg Gln Ala Ile Leu Cys Trp Gly Glu Leu Met Thr Leu
65                  70                  75                  80

Ala Gly Pro Gly Pro Gly Glu Ser Arg Leu Val Val Asp Phe Ser Gln
                85                  90                  95

Phe Ser Arg Gly Asn Gly Pro Gly Pro Gly Pro Phe Leu Leu Ala Gln
            100                 105                 110
```

```
Phe Thr Ser Ala Ile Cys Ser Val Gly Pro Gly Pro Gly Leu Val
        115                 120                 125

Pro Phe Val Gln Trp Phe Val Gly Leu Ser Pro Thr Val Gly Pro Gly
    130                 135                 140

Pro Gly Leu His Leu Tyr Ser His Pro Ile Ile Leu Gly Phe Arg Lys
145                 150                 155                 160

Ile Gly Pro Gly Pro Gly Ser Ser Asn Leu Ser Trp Leu Ser Leu Asp
                165                 170                 175

Val Ser Ala Ala Phe Gly Pro Gly Pro Gly Leu Gln Ser Leu Thr Asn
            180                 185                 190

Leu Leu Ser Ser Asn Leu Ser Trp Leu Gly Pro Gly Pro Gly Ala Gly
        195                 200                 205

Phe Phe Leu Leu Thr Arg Ile Leu Thr Ile Pro Gln Ser Gly Pro Gly
        210                 215                 220

Pro Gly Val Ser Phe Gly Val Trp Ile Arg Thr Pro Pro Ala Tyr Arg
225                 230                 235                 240

Pro Pro Asn Ala Pro Ile Gly Pro Gly Pro Gly Val Gly Pro Leu Thr
                245                 250                 255

Val Asn Glu Lys Arg Arg Leu Lys Leu Ile Gly Pro Gly Pro Gly Lys
            260                 265                 270

Gln Cys Phe Arg Lys Leu Pro Val Asn Arg Pro Ile Asp Trp Gly Pro
        275                 280                 285

Gly Pro Gly Ala Ala Asn Trp Ile Leu Arg Gly Thr Ser Phe Val Tyr
    290                 295                 300

Val Pro Gly Pro Gly Pro Gly Lys Gln Ala Phe Thr Phe Ser Pro Thr
305                 310                 315                 320

Tyr Lys Ala Phe Leu Cys Gly Pro Gly Pro Gly Ala Lys Phe Val Ala
                325                 330                 335

Ala Trp Thr Leu Lys Ala Ala Ala
            340

<210> SEQ ID NO 75
<211> LENGTH: 12
<212> TYPE: PRT
<213> ORGANISM: Hepatitis B virus

<400> SEQUENCE: 75

Gly Ile His Leu Asn Ala Ala Ala Lys Tyr Thr Ser
1               5                   10

<210> SEQ ID NO 76
<211> LENGTH: 12
<212> TYPE: PRT
<213> ORGANISM: Homo sapiens

<400> SEQUENCE: 76

Gly Ile His Leu Asn Met Ala Ala Gly Ser Gly Val
1               5                   10

<210> SEQ ID NO 77
<211> LENGTH: 12
<212> TYPE: PRT
<213> ORGANISM: Hepatitis B virus

<400> SEQUENCE: 77

Pro Trp Leu Leu Asn Ala Ala Ala Arg Phe Ser Trp
1               5                   10
```

```
<210> SEQ ID NO 78
<211> LENGTH: 12
<212> TYPE: PRT
<213> ORGANISM: Homo sapiens

<400> SEQUENCE: 78

Pro Trp Leu Leu Asn Ala Thr Val Glu Glu Asn Ile
1               5                   10

<210> SEQ ID NO 79
<211> LENGTH: 11
<212> TYPE: PRT
<213> ORGANISM: Hepatitis B virus

<400> SEQUENCE: 79

Leu Val Pro Phe Asn Ala Ala Phe Pro His Cys
1               5                   10

<210> SEQ ID NO 80
<211> LENGTH: 11
<212> TYPE: PRT
<213> ORGANISM: Homo sapiens

<400> SEQUENCE: 80

Ser Trp Leu Phe Asp Ala Ala Phe Val His Cys
1               5                   10

<210> SEQ ID NO 81
<211> LENGTH: 11
<212> TYPE: PRT
<213> ORGANISM: Hepatitis B virus

<400> SEQUENCE: 81

Phe Ser Tyr Met Lys Ala Ala Leu Val Val Asp
1               5                   10

<210> SEQ ID NO 82
<211> LENGTH: 11
<212> TYPE: PRT
<213> ORGANISM: Homo sapiens

<400> SEQUENCE: 82

Phe Ser Tyr Met Lys Ala Ala Met Thr Pro Ala
1               5                   10

<210> SEQ ID NO 83
<211> LENGTH: 10
<212> TYPE: PRT
<213> ORGANISM: Hepatitis B virus

<400> SEQUENCE: 83

Gln Phe Ser Arg Gly Ala Ile Leu Leu Leu
1               5                   10

<210> SEQ ID NO 84
<211> LENGTH: 10
<212> TYPE: PRT
<213> ORGANISM: Homo sapiens

<400> SEQUENCE: 84

Gln Phe Ser Ser Gly Ala Ile Leu Arg Val
1               5                   10

<210> SEQ ID NO 85
```

```
<211> LENGTH: 10
<212> TYPE: PRT
<213> ORGANISM: Homo sapiens

<400> SEQUENCE: 85

Thr Phe Ser Arg Ala Ala Ile Leu Leu Ser
1               5                   10

<210> SEQ ID NO 86
<211> LENGTH: 12
<212> TYPE: PRT
<213> ORGANISM: Hepatitis B virus

<400> SEQUENCE: 86

Ile Phe Leu Leu Asn Ala Ala Ala His Thr Leu Trp
1               5                   10

<210> SEQ ID NO 87
<211> LENGTH: 12
<212> TYPE: PRT
<213> ORGANISM: Homo sapiens

<400> SEQUENCE: 87

Ile Thr Leu Leu Asn Ala Arg Asn His Lys Leu Trp
1               5                   10

<210> SEQ ID NO 88
<211> LENGTH: 10
<212> TYPE: PRT
<213> ORGANISM: Hepatitis B virus

<400> SEQUENCE: 88

Ile Leu Tyr Lys Lys Ala Trp Met Met Trp
1               5                   10

<210> SEQ ID NO 89
<211> LENGTH: 10
<212> TYPE: PRT
<213> ORGANISM: Homo sapiens

<400> SEQUENCE: 89

Ile Leu Tyr Lys Gly Ala Trp Glu Gly Thr
1               5                   10

<210> SEQ ID NO 90
<211> LENGTH: 10
<212> TYPE: PRT
<213> ORGANISM: Homo sapiens

<400> SEQUENCE: 90

Gly Phe Gly Ser Gln Ala Trp Met Met Trp
1               5                   10

<210> SEQ ID NO 91
<211> LENGTH: 10
<212> TYPE: PRT
<213> ORGANISM: Hepatitis B virus

<400> SEQUENCE: 91

Pro Ser Leu Tyr Lys Ala Tyr Pro Ala Leu
1               5                   10

<210> SEQ ID NO 92
<211> LENGTH: 10
<212> TYPE: PRT
```

-continued

<213> ORGANISM: Homo sapiens

<400> SEQUENCE: 92

Gly Ser Leu Tyr Lys Arg Tyr Pro Ser Leu
1               5                   10

<210> SEQ ID NO 93
<211> LENGTH: 11
<212> TYPE: PRT
<213> ORGANISM: Hepatitis B virus

<400> SEQUENCE: 93

Tyr Ala Cys Ile Gly Ala Ala Trp Leu Ser Leu
1               5                   10

<210> SEQ ID NO 94
<211> LENGTH: 11
<212> TYPE: PRT
<213> ORGANISM: Homo sapiens

<400> SEQUENCE: 94

Glu Val Cys Val Ala Ala Pro Trp Leu Ser Leu
1               5                   10

<210> SEQ ID NO 95
<211> LENGTH: 11
<212> TYPE: PRT
<213> ORGANISM: Homo sapiens

<400> SEQUENCE: 95

Tyr Ala Asp Ile Glu Ala Ala Trp Leu Ala Leu
1               5                   10

<210> SEQ ID NO 96
<211> LENGTH: 12
<212> TYPE: PRT
<213> ORGANISM: Hepatitis B virus

<400> SEQUENCE: 96

Val Pro Phe Val Asn Ala Ala Ala Phe Leu Leu Thr
1               5                   10

<210> SEQ ID NO 97
<211> LENGTH: 12
<212> TYPE: PRT
<213> ORGANISM: Homo sapiens

<400> SEQUENCE: 97

Ile Pro Phe Val Asn Ala Gly Thr Phe Leu Lys Asn
1               5                   10

<210> SEQ ID NO 98
<211> LENGTH: 12
<212> TYPE: PRT
<213> ORGANISM: Homo sapiens

<400> SEQUENCE: 98

Phe Pro Phe Val Asn Leu Ala Ala Leu Leu Leu Leu
1               5                   10

<210> SEQ ID NO 99
<211> LENGTH: 12
<212> TYPE: PRT
<213> ORGANISM: Hepatitis B virus

```
<400> SEQUENCE: 99

Ile Leu Thr Ile Asn Ala Ala Ala Ile Pro Ile Pro
1               5                   10

<210> SEQ ID NO 100
<211> LENGTH: 12
<212> TYPE: PRT
<213> ORGANISM: Homo sapiens

<400> SEQUENCE: 100

His Leu Thr Ile Asn Ala Thr Asp Ile Pro Ser Gly
1               5                   10

<210> SEQ ID NO 101
<211> LENGTH: 12
<212> TYPE: PRT
<213> ORGANISM: Hepatitis B virus

<400> SEQUENCE: 101

Ser Trp Ala Phe Lys Ala Ala Ala Glu Tyr Leu Val
1               5                   10

<210> SEQ ID NO 102
<211> LENGTH: 12
<212> TYPE: PRT
<213> ORGANISM: Homo sapiens

<400> SEQUENCE: 102

Glu Phe Pro Ala Lys Ala Ala Ala Glu Tyr Leu Cys
1               5                   10

<210> SEQ ID NO 103
<211> LENGTH: 9
<212> TYPE: PRT
<213> ORGANISM: Hepatitis B virus

<400> SEQUENCE: 103

Phe Gly Val Trp Asn Leu Pro Ser Asp
1               5

<210> SEQ ID NO 104
<211> LENGTH: 9
<212> TYPE: PRT
<213> ORGANISM: Homo sapiens

<400> SEQUENCE: 104

Asn Gly Val Trp Asn Leu Ser Ser Asp
1               5

<210> SEQ ID NO 105
<211> LENGTH: 12
<212> TYPE: PRT
<213> ORGANISM: Hepatitis B virus

<400> SEQUENCE: 105

Phe Pro Ser Val Lys Ala Ala Ala Phe Leu Pro Ser
1               5                   10

<210> SEQ ID NO 106
<211> LENGTH: 12
<212> TYPE: PRT
<213> ORGANISM: Homo sapiens

<400> SEQUENCE: 106
```

Gly Pro Ser Thr Lys Ala Ala Ala Phe Leu Gln Arg
1               5                   10

<210> SEQ ID NO 107
<211> LENGTH: 12
<212> TYPE: PRT
<213> ORGANISM: Hepatitis B virus

<400> SEQUENCE: 107

Phe Pro Ser Val Lys Ala Ala Ala Asp Leu Leu Asp
1               5                   10

<210> SEQ ID NO 108
<211> LENGTH: 12
<212> TYPE: PRT
<213> ORGANISM: Homo sapiens

<400> SEQUENCE: 108

Asp Val Ser Val Lys Ala Ala Ser Glu Leu Leu Met
1               5                   10

<210> SEQ ID NO 109
<211> LENGTH: 9
<212> TYPE: PRT
<213> ORGANISM: Hepatitis B virus

<400> SEQUENCE: 109

Ser Ala Leu Tyr Asn Ser Trp Pro Lys
1               5

<210> SEQ ID NO 110
<211> LENGTH: 9
<212> TYPE: PRT
<213> ORGANISM: Homo sapiens

<400> SEQUENCE: 110

Cys Gln Gln Tyr Asn Asn Trp Pro Lys
1               5

<210> SEQ ID NO 111
<211> LENGTH: 12
<212> TYPE: PRT
<213> ORGANISM: Hepatitis B virus

<400> SEQUENCE: 111

Val Pro Asn Leu Lys Ala Ala Ala Ser Ala Ile Cys
1               5                   10

<210> SEQ ID NO 112
<211> LENGTH: 12
<212> TYPE: PRT
<213> ORGANISM: Homo sapiens

<400> SEQUENCE: 112

Ser His Asn Leu Lys Ala Ala Ala Ser Lys Leu Gly
1               5                   10

<210> SEQ ID NO 113
<211> LENGTH: 9
<212> TYPE: PRT
<213> ORGANISM: Hepatitis B virus

<400> SEQUENCE: 113

Val Val Arg Arg Lys Leu Ser Leu Asp
1               5

<210> SEQ ID NO 114
<211> LENGTH: 9
<212> TYPE: PRT
<213> ORGANISM: Homo sapiens

<400> SEQUENCE: 114

Val Leu Arg Arg Lys Val Ser Leu Asp
1               5

<210> SEQ ID NO 115
<211> LENGTH: 11
<212> TYPE: PRT
<213> ORGANISM: Hepatitis B virus

<400> SEQUENCE: 115

Ala Ala Phe Tyr Asn Ala Ala Ala Lys Phe Val
1               5                   10

<210> SEQ ID NO 116
<211> LENGTH: 11
<212> TYPE: PRT
<213> ORGANISM: Homo sapiens

<400> SEQUENCE: 116

Leu Ala Phe Tyr Asn Asp Ala Ser Lys Phe Asp
1               5                   10

<210> SEQ ID NO 117
<211> LENGTH: 11
<212> TYPE: PRT
<213> ORGANISM: Hepatitis B virus

<400> SEQUENCE: 117

Lys Ala Ala Ala Lys Ala Ala Asn Val Ser Ile
1               5                   10

<210> SEQ ID NO 118
<211> LENGTH: 11
<212> TYPE: PRT
<213> ORGANISM: Homo sapiens

<400> SEQUENCE: 118

Lys Ala Ala Glu Lys Ala Ala Asn Ile Leu Leu
1               5                   10

<210> SEQ ID NO 119
<211> LENGTH: 11
<212> TYPE: PRT
<213> ORGANISM: Hepatitis B virus

<400> SEQUENCE: 119

Trp Thr His Lys Gly Ala Ala Gly Leu Ser Arg
1               5                   10

<210> SEQ ID NO 120
<211> LENGTH: 11
<212> TYPE: PRT
<213> ORGANISM: Homo sapiens

<400> SEQUENCE: 120

Trp Thr His Lys Gly Ser Pro Gly Leu Thr Arg
1               5                   10

```
<210> SEQ ID NO 121
<211> LENGTH: 12
<212> TYPE: PRT
<213> ORGANISM: Hepatitis B virus

<400> SEQUENCE: 121

Val Ala Arg Leu Asn Ala Ala Ala Ser Thr Leu Pro
1               5                   10

<210> SEQ ID NO 122
<211> LENGTH: 12
<212> TYPE: PRT
<213> ORGANISM: Homo sapiens

<400> SEQUENCE: 122

Val Ala Arg Leu Ser Ala Ala Ala Val Leu Tyr Leu
1               5                   10

<210> SEQ ID NO 123
<211> LENGTH: 12
<212> TYPE: PRT
<213> ORGANISM: Homo sapiens

<400> SEQUENCE: 123

Val Ala Ala Leu Gly Ala Ala Ala Thr Thr Leu Glu
1               5                   10

<210> SEQ ID NO 124
<211> LENGTH: 9
<212> TYPE: PRT
<213> ORGANISM: Hepatitis B virus

<400> SEQUENCE: 124

Val Val Arg Arg Lys His Pro Ala Ala
1               5

<210> SEQ ID NO 125
<211> LENGTH: 9
<212> TYPE: PRT
<213> ORGANISM: Homo sapiens

<400> SEQUENCE: 125

Val Arg Arg Lys His Pro Asp Ala Asn
1               5

<210> SEQ ID NO 126
<211> LENGTH: 12
<212> TYPE: PRT
<213> ORGANISM: Hepatitis B virus

<400> SEQUENCE: 126

Pro His Leu Leu Lys Ala Ala Ala Arg Trp Met Cys
1               5                   10

<210> SEQ ID NO 127
<211> LENGTH: 12
<212> TYPE: PRT
<213> ORGANISM: Homo sapiens

<400> SEQUENCE: 127

Leu Pro Leu Leu Thr Ala Ala Thr Arg Trp Arg Cys
1               5                   10

<210> SEQ ID NO 128
<211> LENGTH: 9
```

<212> TYPE: PRT
<213> ORGANISM: Hepatitis B virus

<400> SEQUENCE: 128

Arg Phe Ile Ile Asn Ala Ser Phe Cys
1               5

<210> SEQ ID NO 129
<211> LENGTH: 9
<212> TYPE: PRT
<213> ORGANISM: Homo sapiens

<400> SEQUENCE: 129

Arg Phe Ile Ile Ser Ala Glu Phe Arg
1               5

<210> SEQ ID NO 130
<211> LENGTH: 11
<212> TYPE: PRT
<213> ORGANISM: Hepatitis B virus

<400> SEQUENCE: 130

Gly Ser Pro Tyr Lys Ala Ala Tyr Met Asp Asp
1               5                   10

<210> SEQ ID NO 131
<211> LENGTH: 11
<212> TYPE: PRT
<213> ORGANISM: Homo sapiens

<400> SEQUENCE: 131

Gln Pro Pro Tyr Asn Pro Ala Tyr Met Asp Ala
1               5                   10

<210> SEQ ID NO 132
<211> LENGTH: 10
<212> TYPE: PRT
<213> ORGANISM: Hepatitis B virus

<400> SEQUENCE: 132

Val Leu Gly Val Asn Ala Leu Trp Phe His
1               5                   10

<210> SEQ ID NO 133
<211> LENGTH: 10
<212> TYPE: PRT
<213> ORGANISM: Homo sapiens

<400> SEQUENCE: 133

Asp Pro Gly Val Ser Ala Leu Trp Phe Lys
1               5                   10

<210> SEQ ID NO 134
<211> LENGTH: 10
<212> TYPE: PRT
<213> ORGANISM: Homo sapiens

<400> SEQUENCE: 134

Val Leu Phe Ile Pro Ala Leu Trp Phe His
1               5                   10

<210> SEQ ID NO 135
<211> LENGTH: 12
<212> TYPE: PRT
<213> ORGANISM: Hepatitis B virus

```
<400> SEQUENCE: 135

Cys Leu Thr Phe Lys Ala Ala Thr Pro Ala Arg
1               5                   10

<210> SEQ ID NO 136
<211> LENGTH: 12
<212> TYPE: PRT
<213> ORGANISM: Homo sapiens

<400> SEQUENCE: 136

Arg Gly Thr Phe Lys Ala Val Ala Thr Pro Arg Pro
1               5                   10

<210> SEQ ID NO 137
<211> LENGTH: 12
<212> TYPE: PRT
<213> ORGANISM: Homo sapiens

<400> SEQUENCE: 137

Glu Arg Thr His Lys Ala Ala Ala Thr Gly Ala Arg
1               5                   10

<210> SEQ ID NO 138
<211> LENGTH: 12
<212> TYPE: PRT
<213> ORGANISM: Hepatitis B virus

<400> SEQUENCE: 138

Gly Gly Val Phe Lys Ala Ala Ala Leu Thr Phe Gly
1               5                   10

<210> SEQ ID NO 139
<211> LENGTH: 12
<212> TYPE: PRT
<213> ORGANISM: Homo sapiens

<400> SEQUENCE: 139

Ser Gly Val Leu Gly Ala Ala Ser Leu Thr Phe Gly
1               5                   10

<210> SEQ ID NO 140
<211> LENGTH: 9
<212> TYPE: PRT
<213> ORGANISM: Hepatitis B virus

<400> SEQUENCE: 140

Val Leu Glu Tyr Lys Gln Ala Phe Thr
1               5

<210> SEQ ID NO 141
<211> LENGTH: 9
<212> TYPE: PRT
<213> ORGANISM: Homo sapiens

<400> SEQUENCE: 141

Val Leu Gln Tyr Lys Gln Val Phe Leu
1               5

<210> SEQ ID NO 142
<211> LENGTH: 9
<212> TYPE: PRT
<213> ORGANISM: Homo sapiens

<400> SEQUENCE: 142
```

-continued

Val Leu Leu Tyr Lys Gln Asp Phe Thr
1               5

<210> SEQ ID NO 143
<211> LENGTH: 13
<212> TYPE: PRT
<213> ORGANISM: Hepatitis B virus

<400> SEQUENCE: 143

Pro Thr Tyr Lys Gly Pro Gly Pro Gly Thr Ser Phe
1               5                   10

<210> SEQ ID NO 144
<211> LENGTH: 13
<212> TYPE: PRT
<213> ORGANISM: Homo sapiens

<400> SEQUENCE: 144

Val Ser Tyr Lys Gly Pro Gly Pro Gly Ile Lys Phe Ser
1               5                   10

<210> SEQ ID NO 145
<211> LENGTH: 13
<212> TYPE: PRT
<213> ORGANISM: Homo sapiens

<400> SEQUENCE: 145

Tyr Pro Tyr Lys Glu Pro Gly Pro Gly Thr Pro Phe
1               5                   10

<210> SEQ ID NO 146
<211> LENGTH: 13
<212> TYPE: PRT
<213> ORGANISM: Hepatitis B virus

<400> SEQUENCE: 146

Asn Pro Ala Asp Gly Pro Gly Pro Gly Leu Cys Gln Val
1               5                   10

<210> SEQ ID NO 147
<211> LENGTH: 13
<212> TYPE: PRT
<213> ORGANISM: Homo sapiens

<400> SEQUENCE: 147

Asn Pro Ala Asp Glu Pro Gly Pro Gly Ala Pro Ala Pro
1               5                   10

<210> SEQ ID NO 148
<211> LENGTH: 13
<212> TYPE: PRT
<213> ORGANISM: Hepatitis B virus

<400> SEQUENCE: 148

Gly Trp Gly Leu Gly Pro Gly Pro Gly Arg His Tyr Leu
1               5                   10

<210> SEQ ID NO 149
<211> LENGTH: 13
<212> TYPE: PRT
<213> ORGANISM: Homo sapiens

<400> SEQUENCE: 149

Pro Trp Gly Leu Gly Pro Gly Ala Gly Asp Pro Ala Pro

```
<210> SEQ ID NO 150
<211> LENGTH: 13
<212> TYPE: PRT
<213> ORGANISM: Hepatitis B virus

<400> SEQUENCE: 150

Ile Leu Tyr Lys Gly Pro Gly Pro Gly Pro His His Thr
1               5                   10

<210> SEQ ID NO 151
<211> LENGTH: 13
<212> TYPE: PRT
<213> ORGANISM: Homo sapiens

<400> SEQUENCE: 151

Val Ser Tyr Lys Gly Pro Gly Pro Gly Ile Lys Phe Ser
1               5                   10

<210> SEQ ID NO 152
<211> LENGTH: 13
<212> TYPE: PRT
<213> ORGANISM: Hepatitis B virus

<400> SEQUENCE: 152

Met Thr Leu Ala Gly Pro Gly Pro Gly Glu Ser Arg Leu
1               5                   10

<210> SEQ ID NO 153
<211> LENGTH: 13
<212> TYPE: PRT
<213> ORGANISM: Homo sapiens

<400> SEQUENCE: 153

Gly Leu Leu Ala Gly Pro Gly Pro Gly Gly Ser Arg Val
1               5                   10

<210> SEQ ID NO 154
<211> LENGTH: 13
<212> TYPE: PRT
<213> ORGANISM: Homo sapiens

<400> SEQUENCE: 154

Glu Asp Ser Glu Gly Pro Gly Ser Gly Glu Ser Arg Leu
1               5                   10

<210> SEQ ID NO 155
<211> LENGTH: 13
<212> TYPE: PRT
<213> ORGANISM: Hepatitis B virus

<400> SEQUENCE: 155

Ser Arg Gly Asn Gly Pro Gly Pro Gly Pro Phe Leu Leu
1               5                   10

<210> SEQ ID NO 156
<211> LENGTH: 13
<212> TYPE: PRT
<213> ORGANISM: Homo sapiens

<400> SEQUENCE: 156

Val Pro Gly Ser Gly Pro Gly Pro Ala Pro Phe Leu Ala
1               5                   10
```

```
<210> SEQ ID NO 157
<211> LENGTH: 13
<212> TYPE: PRT
<213> ORGANISM: Homo sapiens

<400> SEQUENCE: 157

Ser Arg Gly Pro Ser Pro Gly Pro Gly Arg Leu Leu Leu
1               5                   10

<210> SEQ ID NO 158
<211> LENGTH: 13
<212> TYPE: PRT
<213> ORGANISM: Hepatitis B virus

<400> SEQUENCE: 158

Cys Ser Val Val Gly Pro Gly Pro Gly Leu Val Pro Phe
1               5                   10

<210> SEQ ID NO 159
<211> LENGTH: 13
<212> TYPE: PRT
<213> ORGANISM: Homo sapiens

<400> SEQUENCE: 159

Cys Ile Leu Ile Gly Pro Gly Thr Gly Ile Val Pro Phe
1               5                   10

<210> SEQ ID NO 160
<211> LENGTH: 13
<212> TYPE: PRT
<213> ORGANISM: Hepatitis B virus

<400> SEQUENCE: 160

Ser Pro Thr Val Gly Pro Gly Pro Gly Leu His Leu Tyr
1               5                   10

<210> SEQ ID NO 161
<211> LENGTH: 13
<212> TYPE: PRT
<213> ORGANISM: Homo sapiens

<400> SEQUENCE: 161

Ser Pro Thr Val Gly Pro Gly Pro Leu Pro Pro Ala Gly
1               5                   10

<210> SEQ ID NO 162
<211> LENGTH: 13
<212> TYPE: PRT
<213> ORGANISM: Hepatitis B virus

<400> SEQUENCE: 162

Phe Arg Lys Ile Gly Pro Gly Pro Gly Ser Ser Asn Leu
1               5                   10

<210> SEQ ID NO 163
<211> LENGTH: 13
<212> TYPE: PRT
<213> ORGANISM: Homo sapiens

<400> SEQUENCE: 163

Asn Arg Lys Ile Ala Pro Gly Pro Gly Gly Gln Ser Glu
1               5                   10

<210> SEQ ID NO 164
```

-continued

<211> LENGTH: 13
<212> TYPE: PRT
<213> ORGANISM: Homo sapiens

<400> SEQUENCE: 164

Gly Arg Lys Ile Glu Ser Gly Leu Gly Ser Ser Asn Gly
1               5                   10

<210> SEQ ID NO 165
<211> LENGTH: 13
<212> TYPE: PRT
<213> ORGANISM: Hepatitis B virus

<400> SEQUENCE: 165

Ser Ala Ala Phe Gly Pro Gly Pro Gly Leu Gln Ser Leu
1               5                   10

<210> SEQ ID NO 166
<211> LENGTH: 13
<212> TYPE: PRT
<213> ORGANISM: Homo sapiens

<400> SEQUENCE: 166

Ser Thr Ser Phe Gly Pro Gly Pro Gly Val Glu Ser Met
1               5                   10

<210> SEQ ID NO 167
<211> LENGTH: 13
<212> TYPE: PRT
<213> ORGANISM: Hepatitis B virus

<400> SEQUENCE: 167

Leu Ser Trp Leu Gly Pro Gly Pro Gly Ala Gly Phe Phe
1               5                   10

<210> SEQ ID NO 168
<211> LENGTH: 13
<212> TYPE: PRT
<213> ORGANISM: Homo sapiens

<400> SEQUENCE: 168

Leu Ser Trp Leu Gly Pro Gly Arg Gly Cys Gln Ile Cys
1               5                   10

<210> SEQ ID NO 169
<211> LENGTH: 13
<212> TYPE: PRT
<213> ORGANISM: Homo sapiens

<400> SEQUENCE: 169

Ser Lys Val Leu Gly Pro Gly Pro Asp Thr Gly Phe Phe
1               5                   10

<210> SEQ ID NO 170
<211> LENGTH: 13
<212> TYPE: PRT
<213> ORGANISM: Hepatitis B virus

<400> SEQUENCE: 170

Ile Pro Gln Ser Gly Pro Gly Pro Gly Val Ser Phe Gly
1               5                   10

<210> SEQ ID NO 171
<211> LENGTH: 13
<212> TYPE: PRT

<210> SEQ ID NO 171
<211> LENGTH: 13
<212> TYPE: PRT
<213> ORGANISM: Homo sapiens

<400> SEQUENCE: 171

Pro Gly Pro Gln Ala Gly Pro Gly Pro Gly Val Arg Asp
1               5                   10

<210> SEQ ID NO 172
<211> LENGTH: 13
<212> TYPE: PRT
<213> ORGANISM: Hepatitis B virus

<400> SEQUENCE: 172

Asn Ala Pro Ile Gly Pro Gly Pro Gly Val Gly Pro Leu
1               5                   10

<210> SEQ ID NO 173
<211> LENGTH: 13
<212> TYPE: PRT
<213> ORGANISM: Homo sapiens

<400> SEQUENCE: 173

Asn Arg Glu Ala Gly Pro Gly Pro Gly Pro Gly Pro Leu
1               5                   10

<210> SEQ ID NO 174
<211> LENGTH: 13
<212> TYPE: PRT
<213> ORGANISM: Homo sapiens

<400> SEQUENCE: 174

Pro Ala Pro Pro Gly Pro Gly Pro Gly Pro Gly Pro Gly
1               5                   10

<210> SEQ ID NO 175
<211> LENGTH: 13
<212> TYPE: PRT
<213> ORGANISM: Hepatitis B virus

<400> SEQUENCE: 175

Leu Lys Leu Ile Gly Pro Gly Pro Gly Lys Gln Cys Phe
1               5                   10

<210> SEQ ID NO 176
<211> LENGTH: 13
<212> TYPE: PRT
<213> ORGANISM: Homo sapiens

<400> SEQUENCE: 176

Leu Lys Leu Arg Gly Pro Gly Pro Gly Leu Ala Ala Ala
1               5                   10

<210> SEQ ID NO 177
<211> LENGTH: 13
<212> TYPE: PRT
<213> ORGANISM: Hepatitis B virus

<400> SEQUENCE: 177

Pro Ile Asp Trp Gly Pro Gly Pro Gly Ala Ala Asn Trp
1               5                   10

<210> SEQ ID NO 178
<211> LENGTH: 13
<212> TYPE: PRT
<213> ORGANISM: Homo sapiens

```
<400> SEQUENCE: 178

Cys Leu Asp Trp Gly Pro Gly Pro Gly Thr Gly Glu Gln
1               5                   10

<210> SEQ ID NO 179
<211> LENGTH: 13
<212> TYPE: PRT
<213> ORGANISM: Hepatitis B virus

<400> SEQUENCE: 179

Val Tyr Val Pro Gly Pro Gly Pro Gly Lys Gln Ala Phe
1               5                   10

<210> SEQ ID NO 180
<211> LENGTH: 13
<212> TYPE: PRT
<213> ORGANISM: Homo sapiens

<400> SEQUENCE: 180

Gly Pro Gly Pro Gly Pro Gly Pro Gly Lys Pro Ala Gly
1               5                   10

<210> SEQ ID NO 181
<211> LENGTH: 13
<212> TYPE: PRT
<213> ORGANISM: Hepatitis B virus

<400> SEQUENCE: 181

Ala Phe Leu Cys Gly Pro Gly Pro Gly Ala Lys Phe Val
1               5                   10

<210> SEQ ID NO 182
<211> LENGTH: 13
<212> TYPE: PRT
<213> ORGANISM: Homo sapiens

<400> SEQUENCE: 182

Pro Cys Leu Cys Gly Pro Ala Pro Gly Ala Ala Cys Arg
1               5                   10

<210> SEQ ID NO 183
<211> LENGTH: 10
<212> TYPE: PRT
<213> ORGANISM: Hepatitis B virus

<400> SEQUENCE: 183

Phe Pro His Cys Leu Ala Phe Ser Tyr Met
1               5                   10

<210> SEQ ID NO 184
<211> LENGTH: 10
<212> TYPE: PRT
<213> ORGANISM: Homo sapiens

<400> SEQUENCE: 184

Arg Leu His Cys Leu Ala Phe Ser Gln Arg
1               5                   10

<210> SEQ ID NO 185
<211> LENGTH: 11
<212> TYPE: PRT
<213> ORGANISM: Hepatitis B virus

<400> SEQUENCE: 185
```

```
Trp Met Met Trp Tyr Trp Gly Pro Ser Leu Tyr
1               5                   10
```

<210> SEQ ID NO 186
<211> LENGTH: 11
<212> TYPE: PRT
<213> ORGANISM: Homo sapiens

<400> SEQUENCE: 186

```
Trp Met Met Trp Asn Trp Met Val Ser Leu Leu
1               5                   10
```

<210> SEQ ID NO 187
<211> LENGTH: 9
<212> TYPE: PRT
<213> ORGANISM: Hepatitis B virus

<400> SEQUENCE: 187

```
Phe Leu Leu Thr Arg Ile Leu Thr Ile
1               5
```

<210> SEQ ID NO 188
<211> LENGTH: 9
<212> TYPE: PRT
<213> ORGANISM: Homo sapiens

<400> SEQUENCE: 188

```
Asp Leu Leu Thr Arg Val Leu Thr Trp
1               5
```

<210> SEQ ID NO 189
<211> LENGTH: 9
<212> TYPE: PRT
<213> ORGANISM: Hepatitis B virus

<400> SEQUENCE: 189

```
Glu Tyr Leu Val Ser Phe Gly Val Trp
1               5
```

<210> SEQ ID NO 190
<211> LENGTH: 9
<212> TYPE: PRT
<213> ORGANISM: Homo sapiens

<400> SEQUENCE: 190

```
Gly Tyr Leu Val Val Phe Gly Val Lys
1               5
```

<210> SEQ ID NO 191
<211> LENGTH: 10
<212> TYPE: PRT
<213> ORGANISM: Hepatitis B virus

<400> SEQUENCE: 191

```
Phe Leu Pro Ser Asp Phe Phe Pro Ser Val
1               5                   10
```

<210> SEQ ID NO 192
<211> LENGTH: 10
<212> TYPE: PRT
<213> ORGANISM: Homo sapiens

<400> SEQUENCE: 192

```
Phe Leu Pro Pro Asp Phe Tyr Pro Pro Ser
1               5                   10
```

```
<210> SEQ ID NO 193
<211> LENGTH: 9
<212> TYPE: PRT
<213> ORGANISM: Hepatitis B virus

<400> SEQUENCE: 193

Ser Ala Ile Cys Ser Val Val Arg Arg
1               5

<210> SEQ ID NO 194
<211> LENGTH: 9
<212> TYPE: PRT
<213> ORGANISM: Homo sapiens

<400> SEQUENCE: 194

Ser Ala Ile Cys Ser Ala Val Gly Val
1               5

<210> SEQ ID NO 195
<211> LENGTH: 9
<212> TYPE: PRT
<213> ORGANISM: Hepatitis B virus

<400> SEQUENCE: 195

His Pro Ala Ala Met Pro His Leu Leu
1               5

<210> SEQ ID NO 196
<211> LENGTH: 9
<212> TYPE: PRT
<213> ORGANISM: Homo sapiens

<400> SEQUENCE: 196

His Ala Ala Ala Met Pro His Ser Cys
1               5

<210> SEQ ID NO 197
<211> LENGTH: 20
<212> TYPE: PRT
<213> ORGANISM: Hepatitis B virus

<400> SEQUENCE: 197

Pro His His Thr Ala Leu Arg Gln Ala Ile Leu Cys Trp Gly Glu Leu
1               5                   10                  15

Met Thr Leu Ala
            20

<210> SEQ ID NO 198
<211> LENGTH: 20
<212> TYPE: PRT
<213> ORGANISM: Homo sapiens

<400> SEQUENCE: 198

Gln Gly Asn Gly Lys Phe Asn Leu Met Ile Leu Cys Trp Gly Glu Gly
1               5                   10                  15

His Gly Ser Ser
            20

<210> SEQ ID NO 199
<211> LENGTH: 15
<212> TYPE: PRT
<213> ORGANISM: Hepatitis B virus
```

<400> SEQUENCE: 199

Glu Ser Arg Leu Val Val Asp Phe Ser Gln Phe Ser Arg Gly Asn
1               5                   10                  15

<210> SEQ ID NO 200
<211> LENGTH: 15
<212> TYPE: PRT
<213> ORGANISM: Homo sapiens

<400> SEQUENCE: 200

Leu Leu Leu Thr Val Val Asp Phe Asp Lys Phe Ser Arg His Cys
1               5                   10                  15

<210> SEQ ID NO 201
<211> LENGTH: 15
<212> TYPE: PRT
<213> ORGANISM: Hepatitis B virus

<400> SEQUENCE: 201

Leu Val Pro Phe Val Gln Trp Phe Val Gly Leu Ser Pro Thr Val
1               5                   10                  15

<210> SEQ ID NO 202
<211> LENGTH: 15
<212> TYPE: PRT
<213> ORGANISM: Homo sapiens

<400> SEQUENCE: 202

Val Leu Tyr Phe Val Gln Trp Leu Val Gly Phe Ser Phe Phe Leu
1               5                   10                  15

<210> SEQ ID NO 203
<211> LENGTH: 15
<212> TYPE: PRT
<213> ORGANISM: Hepatitis B virus

<400> SEQUENCE: 203

Lys Gln Ala Phe Thr Phe Ser Pro Thr Tyr Lys Ala Phe Leu Cys
1               5                   10                  15

<210> SEQ ID NO 204
<211> LENGTH: 15
<212> TYPE: PRT
<213> ORGANISM: Homo sapiens

<400> SEQUENCE: 204

Thr Gln Val Phe Thr Phe Gly Pro Thr Phe Arg Ala Glu Asn Ser
1               5                   10                  15

<210> SEQ ID NO 205
<211> LENGTH: 2315
<212> TYPE: DNA
<213> ORGANISM: Hepatitis B virus

<400> SEQUENCE: 205
gaattcaggt cgccgccacc atgggaatgc aggtgcaaat acagtctctc ttcctttgc       60 ttctctgggt tccaggatca cggggcttct tgcttagctt gggcatccac ctaaatgctg     120
ctgcaaaata cacatctttt ccttggctcc ttaatgccgc cgctaggttt catggctga      180 gtctgctagt acctttcaat gcggctttcc cacattgcct agcttttagc tatatgaaag     240
ctgctttagt cgtggacttt tcacagttta gcagaggagc aatcctgctg ctatgtctga     300
tattccttct aaacgcagca gcccacacac tctggaaagc tggtatcctt acaagaaag     360

-continued

```
cctggatgat gtggtattgg ggacccagcc tctacaaagc ataccctgcc ctgatgccac      420
tatacgcatg cattggcgcg gcagcctggt tatcccttt agtaccgttt gtcaacgccg       480
cagcgggatt tctattaacc agaatcctga cgattaatgc tgccgccatt ccgatcccaa      540
gttcctgggc attcaaagca gccgcggagt atctggtttc atttggcgta tggaacctgc     600
caagcgactt ctttccttct gttaaggccg ctgctttcct ccctccgat ttctttccat      660 cggtgaaagc cgctgccgac ctccttgata ccgcgagcgc tctgtacaac tcgtggccaa     720
aattcgcagt tccaaaccta aaagccgccg ccagtgccat ttgttccgtg gtaaggagaa     780
aattatcact cgacgtgtcc gcagcatttt ataacgctgc tgcaaagttt gtcgcagcat     840
ggacattgaa ggctgcagcg aaagcagcaa atgtatcaat accctggacc acaagggtg     900 cagccgggct gtctaggtat gtggcgaggc taaacgccgc cgcctcaaca ctgcctgaga     960
ctactgtcgt gagacgcaaa cacccctgccg caatgcccca cctgctgaaa gcagccgcac    1020
gatggatgtg cctcagaaga ttcataataa acgcttcttt ctgtgggtca ccctacaaag    1080
ccgcttacat ggacgatgtg gtcctcggag tgaatgccct ctggttccat atcagctgcc    1140
tgacattcaa ggcagccgcc accccgctc gtgtgacagg aggtgtcttc aaagccgcgg     1200
cactgacttt cggtcgggaa actgtattgg aatataagca ggcttcaca ttctcccccaa    1260 catacaagaa cgcaggaact tcttttgtgt atgtcccttc cgctctgaac ccagcagacg    1320
gacccgggcc tggcctgtgc caggtcttcg ccgacgcaac tcccacaggg tgggggctgg    1380
ggccaggacc aggcaggcac tacctgcata tctctgtgga ggcaggaatc ctctataaag    1440 ggccccggccc aggccctcac cacaccgccc tgaggcaggc catcctgtgc tggggggagc   1500 tcatgacccct ggccggacct ggacccgggg agagcagact ggtggtggat ttcagccaat   1560
tcagcagagg aaacggaccc ggccctgggc cttttctgct ggctcagttt acatctgcta    1620
tttgttctgt ggtcggcccc gggcccggac tcgtgccttt cgtgcagtgg ttcgtgggac    1680
tgtcccctac agtcgggccc ggcccagggc tgcatctgta ctcccaccca atcatcctcg    1740
gcttccgcaa gattggaccc ggcccaggct ccagcaatct ctcctggctc tctctggacg    1800
tgtctgccgc ctttggccct ggaccaggcc tgcaaagcct gactaatctg ctcagcagca    1860
acctgtcctg gctgggacct ggaccagggg ctggcttctt tctgctcacc cggattctca    1920
caattcccca gtccggacca ggaccaggag tcagtttcgg ggtgtggatc aggacccctc    1980
ctgcttatag accacccaat gctccaatcg gccccggccc tggcgtcggg ccactgaccg    2040
tgaatgagaa gcgccggctg aagctgatcg gccctggccc tggcaagcag tgctttcgca    2100
aactgcccgt gaacagacct attgattggg gccccgccc tggagcagcc aactggattc    2160
tcaggggaac aagcttcgtc tacgtgcccg gccccggacc agggaagcag gcttttacct    2220
tctctcccac ttacaaggcc ttcctctgtg ggccaggccc cggcgccaag tttgtggcag    2280 catggacccct caaagccgct gcctgaggat cctga                              2315
```

<210> SEQ ID NO 206
<211> LENGTH: 763
<212> TYPE: PRT
<213> ORGANISM: Hepatitis B virus

<400> SEQUENCE: 206

Met Gly Met Gln Val Gln Ile Gln Ser Leu Phe Leu Leu Leu Leu Trp
1               5                   10                  15

Val Pro Gly Ser Arg Gly Phe Leu Leu Ser Leu Gly Ile His Leu Asn

-continued

```
                20                  25                  30
Ala Ala Ala Lys Tyr Thr Ser Phe Pro Trp Leu Leu Asn Ala Ala Ala
            35                  40                  45
Arg Phe Ser Trp Leu Ser Leu Leu Val Pro Phe Asn Ala Ala Phe Pro
    50                  55                  60
His Cys Leu Ala Phe Ser Tyr Met Lys Ala Ala Leu Val Val Asp Phe
65                  70                  75                  80
Ser Gln Phe Ser Arg Gly Ala Ile Leu Leu Cys Leu Ile Phe Leu
                85                  90                  95
Leu Asn Ala Ala Ala His Thr Leu Trp Lys Ala Gly Ile Leu Tyr Lys
            100                 105                 110
Lys Ala Trp Met Met Trp Tyr Trp Gly Pro Ser Leu Tyr Lys Ala Tyr
    115                 120                 125
Pro Ala Leu Met Pro Leu Tyr Ala Cys Ile Gly Ala Ala Trp Leu
    130                 135                 140
Ser Leu Leu Val Pro Phe Val Asn Ala Ala Gly Phe Leu Leu Thr
145                 150                 155                 160
Arg Ile Leu Thr Ile Asn Ala Ala Ile Pro Ile Pro Ser Ser Trp
            165                 170                 175
Ala Phe Lys Ala Ala Ala Glu Tyr Leu Val Ser Phe Gly Val Trp Asn
            180                 185                 190
Leu Pro Ser Asp Phe Pro Ser Val Lys Ala Ala Phe Leu Pro
    195                 200                 205
Ser Asp Phe Phe Pro Ser Val Lys Ala Ala Asp Leu Leu Asp Thr
    210                 215                 220
Ala Ser Ala Leu Tyr Asn Ser Trp Pro Lys Phe Ala Val Pro Asn Leu
225                 230                 235                 240
Lys Ala Ala Ala Ser Ala Ile Cys Ser Val Val Arg Arg Lys Leu Ser
            245                 250                 255
Leu Asp Val Ser Ala Ala Phe Tyr Asn Ala Ala Lys Phe Val Ala
            260                 265                 270
Ala Trp Thr Leu Lys Ala Ala Lys Ala Ala Asn Val Ser Ile Pro
    275                 280                 285
Trp Thr His Lys Gly Ala Ala Gly Leu Ser Arg Tyr Val Ala Arg Leu
    290                 295                 300
Asn Ala Ala Ala Ser Thr Leu Pro Glu Thr Thr Val Val Arg Arg Lys
305                 310                 315                 320
His Pro Ala Ala Met Pro His Leu Leu Lys Ala Ala Arg Trp Met
            325                 330                 335
Cys Leu Arg Arg Phe Ile Ile Asn Ala Ser Phe Cys Gly Ser Pro Tyr
            340                 345                 350
Lys Ala Ala Tyr Met Asp Asp Val Val Leu Gly Val Asn Ala Leu Trp
    355                 360                 365
Phe His Ile Ser Cys Leu Thr Phe Lys Ala Ala Thr Pro Ala Arg
    370                 375                 380
Val Thr Gly Gly Val Phe Lys Ala Ala Ala Leu Thr Phe Gly Arg Glu
385                 390                 395                 400
Thr Val Leu Glu Tyr Lys Gln Ala Phe Thr Phe Ser Pro Thr Tyr Lys
            405                 410                 415
Asn Ala Gly Thr Ser Phe Val Tyr Val Pro Ser Ala Leu Asn Pro Ala
            420                 425                 430
Asp Gly Pro Gly Pro Gly Leu Cys Gln Val Phe Ala Asp Ala Thr Pro
    435                 440                 445
```

```
Thr Gly Trp Gly Leu Gly Pro Gly Pro Gly Arg His Tyr Leu His Thr
    450                 455                 460
Leu Trp Lys Ala Gly Ile Leu Tyr Lys Gly Pro Gly Pro Gly Pro His
465                 470                 475                 480
His Thr Ala Leu Arg Gln Ala Ile Leu Cys Trp Gly Glu Leu Met Thr
                485                 490                 495
Leu Ala Gly Pro Gly Pro Gly Glu Ser Arg Leu Val Val Asp Phe Ser
            500                 505                 510
Gln Phe Ser Arg Gly Asn Gly Pro Gly Pro Gly Pro Phe Leu Leu Ala
        515                 520                 525
Gln Phe Thr Ser Ala Ile Cys Ser Val Val Gly Pro Gly Pro Gly Leu
    530                 535                 540
Val Pro Phe Val Gln Trp Phe Val Gly Leu Ser Pro Thr Val Gly Pro
545                 550                 555                 560
Gly Pro Gly Leu His Leu Tyr Ser His Pro Ile Ile Leu Gly Phe Arg
                565                 570                 575
Lys Ile Gly Pro Gly Pro Gly Ser Ser Asn Leu Ser Trp Leu Ser Leu
            580                 585                 590
Asp Val Ser Ala Ala Phe Gly Pro Gly Pro Gly Leu Gln Ser Leu Thr
        595                 600                 605
Asn Leu Leu Ser Ser Asn Leu Ser Trp Leu Gly Pro Gly Pro Gly Ala
    610                 615                 620
Gly Phe Phe Leu Leu Thr Arg Ile Leu Thr Ile Pro Gln Ser Gly Pro
625                 630                 635                 640
Gly Pro Gly Val Ser Phe Gly Val Trp Ile Arg Thr Pro Pro Ala Tyr
                645                 650                 655
Arg Pro Pro Asn Ala Pro Ile Gly Pro Gly Pro Gly Val Gly Pro Leu
            660                 665                 670
Thr Val Asn Glu Lys Arg Arg Leu Lys Leu Ile Gly Pro Gly Pro Gly
        675                 680                 685
Lys Gln Cys Phe Arg Lys Leu Pro Val Asn Arg Pro Ile Asp Trp Gly
    690                 695                 700
Pro Gly Pro Gly Ala Ala Asn Trp Ile Leu Arg Gly Thr Ser Phe Val
705                 710                 715                 720
Tyr Val Pro Gly Pro Gly Pro Gly Lys Gln Ala Phe Thr Phe Ser Pro
                725                 730                 735
Thr Tyr Lys Ala Phe Leu Cys Gly Pro Gly Pro Gly Ala Lys Phe Val
            740                 745                 750
Ala Ala Trp Thr Leu Lys Ala Ala Ala Gly Ser
        755                 760

<210> SEQ ID NO 207
<211> LENGTH: 2235
<212> TYPE: DNA
<213> ORGANISM: Hepatitis B virus

<400> SEQUENCE: 207
atgggcatgc aggtgcagat ccagagcctg ttcctgctcc tgctgtgggt gccaggaagc     60
agaggctttc tcctgtccct gggcatccac ctgaacgccg ctgcaaagta caccagcttc    120
ccctggctgc tcaacgccgc tgcccggttc agctggctgt ccctgctcgt gcccttcaac    180
gcagccttcc cccactgcct ggccttcagc tacatgaaag cagccctggt ggtcgacttc    240
tcccagttca gccggggagc catcctgctc ctgtgcctga tctttctgct caacgccgct    300
```

```
gcccacaccc tgtggaaggc tggcatcctg tacaagaaag cctggatgat gtggtactgg    360
ggacccagcc tgtacaaggc atatccagcc ctgatgcccc tgtacgcctg catcggagct    420
gccgcatggc tgagcctcct ggtgcccttc gtgaacgccg ctgccggtt cctgctgaca     480 agaatcctga ccatcaacgc cgcagccatt cctatcccct ccagctgggc cttcaaggca    540 gccgccagt acctggtgag cttcggagtc tggaacctgc cagcgactt ctttcccagc      600 gtgaaagccg cagccttcct gccctccgac ttctttccca gcgtgaaggc cgcagccgat    660
ctcctggaca ccgctagcgc cctgtacaac agctggccca gttcgccgt gcccaacctg     720 aaggccgcag ccagcgccat ctgcagcgtg gtcagacgga gctgtccct cgatgtgagc     780 gccgctttct acaacgccgc cgcaaagttc gtggccgcct ggaccctgaa agccgctgcc    840
aaggcagcca acgtgagcat ccctggacc cacaaaggag ccgcaggact gagccggtat     900
gtggccagac tgaacgccgc tgccagcacc ctgcccgaga ccacagtggt cagacggaag    960
caccccgccg ccatgcccca cctgctgaag gccgcagccc ggtggatgtg cctcagacgg   1020
ttcatcatca acgcttcctt ctgtggcagc ccctacaagg ccgcctacat ggatgacgtg   1080
gtcctgggag tgaacgccct ctggttccac atcagctgcc tgaccttcaa agccgctgcc   1140 acaccgcaa gagtgaccgg aggcgtgttc aaggctgcag ccctgacctt cggccgggag    1200
accgtgctgg agtacaagca ggccttcacc ttcagcccca cctacaagaa cgccggcacc   1260
agctttgtgt acgtcccaag cgccctgaat ccgcagacg gccccggccc cggactgtgc    1320
caggtgttcg ccgatgccac accaaccgga tggggcctgg ccctggacc cggcagacac    1380 tacctgcata ccctgtggaa ggcaggaatc ctgtacaaag gccccggccc tggaccccat   1440
cacaccgctc tgcggcaggc catcctgtgc tggggcgagc tcatgactct ggcaggaccc   1500
ggccccggcg aatccaggct ggtggtggac tttagccagt ctccagagg caacggaccc    1560 ggcccaggac ccttcctgct cgcccagttc accagcgcca tctgcagcgt ggtcggacct   1620
ggcccaggac tggtgccctt cgtgcagtgg ttcgtcggcc tcagccccac cgtcggacct   1680
ggccccggcc tgcacctcta cagccaccct atcattctgg gcttcagaaa gatcggacca   1740
ggccccggct ccagcaacct gtcctggctc agcctggacg tcagcgcagc cttcggaccc   1800
ggccctggcc tgcagagcct gaccaacctg ctcagcagca acctcagctg gctgggccca   1860
ggacccggcg caggcttctt tctgctcacc agaatcctga ccatccctca gagcggcccc   1920
ggaccaggcg tgagcttcgg cgtgtggatt cggactcctc ccgcctacag acccccaaat   1980 gccccatcg gcccaggacc cggcgtcgga cctctgactg tgaacgagaa gcggagactg    2040
aagctgatcg gccccggacc aggcaaacag tgcttcagga agctccctgt gaacagacct   2100
atcgactggg ccccggacc cggcgcagcc aactggattc tgagaggcac cagcttcgtg   2160
tacgtccctg acccggcccc tggcaagcaa gccttcacct cagccccac ctacaaggca    2220 ttcctgtgcg gatag                                                    2235
```

<210> SEQ ID NO 208
<211> LENGTH: 744
<212> TYPE: PRT
<213> ORGANISM: Hepatitis B virus

<400> SEQUENCE: 208

Met Gly Met Gln Val Gln Ile Gln Ser Leu Phe Leu Leu Leu Leu Trp
1               5                   10                  15

Val Pro Gly Ser Arg Gly Phe Leu Leu Ser Leu Gly Ile His Leu Asn
            20                  25                  30

```
Ala Ala Ala Lys Tyr Thr Ser Phe Pro Trp Leu Leu Asn Ala Ala Ala
             35                  40                  45

Arg Phe Ser Trp Leu Ser Leu Val Pro Phe Asn Ala Ala Phe Pro
 50                  55                  60

His Cys Leu Ala Phe Ser Tyr Met Lys Ala Ala Leu Val Val Asp Phe
 65                  70                  75                  80

Ser Gln Phe Ser Arg Gly Ala Ile Leu Leu Cys Leu Ile Phe Leu
                 85                  90                  95

Leu Asn Ala Ala Ala His Thr Leu Trp Lys Ala Gly Ile Leu Tyr Lys
                100                 105                 110

Lys Ala Trp Met Met Trp Tyr Trp Gly Pro Ser Leu Tyr Lys Ala Tyr
            115                 120                 125

Pro Ala Leu Met Pro Leu Tyr Ala Cys Ile Gly Ala Ala Trp Leu
            130                 135                 140

Ser Leu Leu Val Pro Phe Val Asn Ala Ala Gly Phe Leu Leu Thr
145                 150                 155                 160

Arg Ile Leu Thr Ile Asn Ala Ala Ile Pro Ile Pro Ser Ser Trp
                165                 170                 175

Ala Phe Lys Ala Ala Ala Glu Tyr Leu Val Ser Phe Gly Val Trp Asn
            180                 185                 190

Leu Pro Ser Asp Phe Phe Pro Ser Val Lys Ala Ala Phe Leu Pro
            195                 200                 205

Ser Asp Phe Phe Pro Ser Val Lys Ala Ala Asp Leu Leu Asp Thr
            210                 215                 220

Ala Ser Ala Leu Tyr Asn Ser Trp Pro Lys Phe Ala Val Pro Asn Leu
225                 230                 235                 240

Lys Ala Ala Ala Ser Ala Ile Cys Ser Val Val Arg Arg Lys Leu Ser
                245                 250                 255

Leu Asp Val Ser Ala Ala Phe Tyr Asn Ala Ala Ala Lys Phe Val Ala
                260                 265                 270

Ala Trp Thr Leu Lys Ala Ala Lys Ala Ala Asn Val Ser Ile Pro
            275                 280                 285

Trp Thr His Lys Gly Ala Ala Gly Leu Ser Arg Tyr Val Ala Arg Leu
            290                 295                 300

Asn Ala Ala Ala Ser Thr Leu Pro Glu Thr Thr Val Val Arg Arg Lys
305                 310                 315                 320

His Pro Ala Ala Met Pro His Leu Leu Lys Ala Ala Ala Arg Trp Met
                325                 330                 335

Cys Leu Arg Arg Phe Ile Ile Asn Ala Ser Phe Cys Gly Ser Pro Tyr
                340                 345                 350

Lys Ala Ala Tyr Met Asp Asp Val Val Leu Gly Val Asn Ala Leu Trp
            355                 360                 365

Phe His Ile Ser Cys Leu Thr Phe Lys Ala Ala Ala Thr Pro Ala Arg
            370                 375                 380

Val Thr Gly Gly Val Phe Lys Ala Ala Ala Leu Thr Phe Gly Arg Glu
385                 390                 395                 400

Thr Val Leu Glu Tyr Lys Gln Ala Phe Thr Phe Ser Pro Thr Tyr Lys
                405                 410                 415

Asn Ala Gly Thr Ser Phe Val Tyr Val Pro Ser Ala Leu Asn Pro Ala
                420                 425                 430

Asp Gly Pro Gly Pro Gly Leu Cys Gln Val Phe Ala Asp Ala Thr Pro
                435                 440                 445
```

```
Thr Gly Trp Gly Leu Gly Pro Gly Arg His Tyr Leu His Thr
    450                 455                 460

Leu Trp Lys Ala Gly Ile Leu Tyr Lys Gly Pro Gly Pro His
465                 470                 475             480

His Thr Ala Leu Arg Gln Ala Ile Leu Cys Trp Gly Glu Leu Met Thr
                485                 490                 495

Leu Ala Gly Pro Gly Pro Gly Glu Ser Arg Leu Val Val Asp Phe Ser
                500                 505                 510

Gln Phe Ser Arg Gly Asn Gly Pro Gly Pro Phe Leu Leu Ala
            515                 520                 525

Gln Phe Thr Ser Ala Ile Cys Ser Val Val Gly Pro Gly Leu
    530                 535                 540

Val Pro Phe Val Gln Trp Phe Val Gly Leu Ser Pro Thr Val Gly Pro
545                 550                 555                 560

Gly Pro Gly Leu His Leu Tyr Ser His Pro Ile Ile Leu Gly Phe Arg
                565                 570                 575

Lys Ile Gly Pro Gly Pro Gly Ser Ser Asn Leu Ser Trp Leu Ser Leu
                580                 585                 590

Asp Val Ser Ala Ala Phe Gly Pro Gly Pro Gly Leu Gln Ser Leu Thr
                595                 600                 605

Asn Leu Leu Ser Ser Asn Leu Ser Trp Leu Gly Pro Gly Pro Gly Ala
    610                 615                 620

Gly Phe Phe Leu Leu Thr Arg Ile Leu Thr Ile Pro Gln Ser Gly Pro
625                 630                 635                 640

Gly Pro Gly Val Ser Phe Gly Val Trp Ile Arg Thr Pro Pro Ala Tyr
                645                 650                 655

Arg Pro Pro Asn Ala Pro Ile Gly Pro Gly Pro Gly Val Gly Pro Leu
                660                 665                 670

Thr Val Asn Glu Lys Arg Arg Leu Lys Leu Ile Gly Pro Gly Pro Gly
                675                 680                 685

Lys Gln Cys Phe Arg Lys Leu Pro Val Asn Arg Pro Ile Asp Trp Gly
    690                 695                 700

Pro Gly Pro Gly Ala Ala Asn Trp Ile Leu Arg Gly Thr Ser Phe Val
705                 710                 715                 720

Tyr Val Pro Gly Pro Gly Pro Gly Lys Gln Ala Phe Thr Phe Ser Pro
                725                 730                 735

Thr Tyr Lys Ala Phe Leu Cys Gly
            740

<210> SEQ ID NO 209
<211> LENGTH: 621
<212> TYPE: DNA
<213> ORGANISM: Hepatitis B virus

<400> SEQUENCE: 209
atgggaatgc aggtgcagat ccagagcctg tttctgctcc tcctgtgggt gcccgggtcc      60
agaggacaca ccctgtggaa ggccggaatc ctgtataagg ccaagttcgt ggctgcctgg     120
accctgaagg ctgccgcttt cctgcctagc gatttctttc ctagcgtgtt cctgctgtcc     180
ctgggaatcc acctgtatat ggatgacgtg gtgctgggag tgggactgtc caggtacgtg     240
gctaggctgt tcctgctgac cagaatcctg accatctcca ccctgccaga gaccaccgtg     300
gtgaggaggc aggccttcac ctttagccct acctataagt ggctgagcct gctggtgccc     360
tttgtgatcc ctatccctag ctcctgggct ttcaccccag ccagggtgac cggaggagtg     420
```

-continued

```
tttaaggtgg gaaacttcac cggcctgtat ctgcccagcg atttcttttcc tagcgtgacc    480 ctgtggaagg ccgggatcct gtacaagaat gtgtccatcc cttggaccca caagctggtg    540
gtggactttt cccagttcag cagatccgct atctgctccg tggtgaggag agctctgatg    600
ccactgtatg cctgtatctg a                                              621
```

<210> SEQ ID NO 210
<211> LENGTH: 206
<212> TYPE: PRT
<213> ORGANISM: Hepatitis B virus

<400> SEQUENCE: 210

```
Met Gly Met Gln Val Gln Ile Gln Ser Leu Phe Leu Leu Leu Leu Trp
1               5                   10                  15

Val Pro Gly Ser Arg Gly His Thr Leu Trp Lys Ala Gly Ile Leu Tyr
            20                  25                  30

Lys Ala Lys Phe Val Ala Ala Trp Thr Leu Lys Ala Ala Ala Phe Leu
        35                  40                  45

Pro Ser Asp Phe Phe Pro Ser Val Phe Leu Leu Ser Leu Gly Ile His
    50                  55                  60

Leu Tyr Met Asp Asp Val Val Leu Gly Val Gly Leu Ser Arg Tyr Val
65                  70                  75                  80

Ala Arg Leu Phe Leu Leu Thr Arg Ile Leu Thr Ile Ser Thr Leu Pro
                85                  90                  95

Glu Thr Thr Val Val Arg Arg Gln Ala Phe Thr Phe Ser Pro Thr Tyr
            100                 105                 110

Lys Trp Leu Ser Leu Leu Val Pro Phe Val Ile Pro Ile Pro Ser Ser
        115                 120                 125

Trp Ala Phe Thr Pro Ala Arg Val Thr Gly Gly Val Phe Lys Val Gly
    130                 135                 140

Asn Phe Thr Gly Leu Tyr Leu Pro Ser Asp Phe Phe Pro Ser Val Thr
145                 150                 155                 160

Leu Trp Lys Ala Gly Ile Leu Tyr Lys Asn Val Ser Ile Pro Trp Thr
                165                 170                 175

His Lys Leu Val Val Asp Phe Ser Gln Phe Ser Arg Ser Ala Ile Cys
            180                 185                 190

Ser Val Val Arg Arg Ala Leu Met Pro Leu Tyr Ala Cys Ile
        195                 200                 205
```

<210> SEQ ID NO 211
<211> LENGTH: 660
<212> TYPE: DNA
<213> ORGANISM: Hepatitis B virus

<400> SEQUENCE: 211

```
atgggaatgc aggtgcagat ccagagcctg tttctgctcc tcctgtgggt gcccgggtcc     60
agaggacaca ccctgtggaa ggccggaatc ctgtataagg ccaagttcgt ggctgcctgg    120
accctgaagg ctgccgcttt cctgcctagc gatttctttc ctagcgtgaa cttcctgctg    180
tccctgggaa tccacctgta tatggatgac gtggtgctgg gagtgggact gtccaggtac    240
gtggctaggc tgttcctgct gaccagaatc ctgaccatct ccaccctgcc agagaccacc    300
gtggtgagga ggcaggcctt cacctttagc cctacctata agggagccgc tgcctggctg    360
agcctgctgg tgccctttgt gaatatccct atccctagct cctgggcttt caagacccca    420
gccagggtga ccggaggagt gtttaaggtg ggaaacttca ccggcctgta taacctgccc    480
```

```
agcgatttct tcctagcgt gaagaccctg tggaaggccg gaatcctgta caagaatgtg    540
tccatccctt ggacccacaa gggagccgct ctggtggtgg acttttccca gttcagcaga    600
aattccgcta tctgctccgt ggtgaggaga gctctgatgc cactgtatgc ctgtatctga    660
```

<210> SEQ ID NO 212
<211> LENGTH: 219
<212> TYPE: PRT
<213> ORGANISM: Hepatitis B virus

<400> SEQUENCE: 212

```
Met Gly Met Gln Val Gln Ile Gln Ser Leu Phe Leu Leu Leu Leu Trp
1               5                   10                  15

Val Pro Gly Ser Arg Gly His Thr Leu Trp Lys Ala Gly Ile Leu Tyr
            20                  25                  30

Lys Ala Lys Phe Val Ala Ala Trp Thr Leu Lys Ala Ala Ala Phe Leu
        35                  40                  45

Pro Ser Asp Phe Phe Pro Ser Val Asn Phe Leu Ser Leu Gly Ile
    50                  55                  60

His Leu Tyr Met Asp Asp Val Val Leu Gly Val Gly Leu Ser Arg Tyr
65                  70                  75                  80

Val Ala Arg Leu Phe Leu Leu Thr Arg Ile Leu Thr Ile Ser Thr Leu
                85                  90                  95

Pro Glu Thr Thr Val Val Arg Arg Gln Ala Phe Thr Phe Ser Pro Thr
            100                 105                 110

Tyr Lys Gly Ala Ala Ala Trp Leu Ser Leu Leu Val Pro Phe Val Asn
        115                 120                 125

Ile Pro Ile Pro Ser Ser Trp Ala Phe Lys Thr Pro Ala Arg Val Thr
    130                 135                 140

Gly Gly Val Phe Lys Val Gly Asn Phe Thr Gly Leu Tyr Asn Leu Pro
145                 150                 155                 160

Ser Asp Phe Phe Pro Ser Val Lys Thr Leu Trp Lys Ala Gly Ile Leu
                165                 170                 175

Tyr Lys Asn Val Ser Ile Pro Trp Thr His Lys Gly Ala Ala Leu Val
            180                 185                 190

Val Asp Phe Ser Gln Phe Ser Arg Asn Ser Ala Ile Cys Ser Val Val
        195                 200                 205

Arg Arg Ala Leu Met Pro Leu Tyr Ala Cys Ile
    210                 215
```

<210> SEQ ID NO 213
<211> LENGTH: 9
<212> TYPE: PRT
<213> ORGANISM: Hepatitis B virus

<400> SEQUENCE: 213

```
Thr Leu Asn Phe Pro Ile Ser Pro Ile
1               5
```

<210> SEQ ID NO 214
<211> LENGTH: 10
<212> TYPE: PRT
<213> ORGANISM: Hepatitis B virus

<400> SEQUENCE: 214

```
Ser Leu Leu Asn Ala Thr Asp Ile Ala Val
1               5                   10
```

```
<210> SEQ ID NO 215
<211> LENGTH: 10
<212> TYPE: PRT
<213> ORGANISM: Hepatitis B virus

<400> SEQUENCE: 215

Gln Met Ala Val Phe Ile His Asn Phe Lys
1               5                   10

<210> SEQ ID NO 216
<211> LENGTH: 11
<212> TYPE: PRT
<213> ORGANISM: Hepatitis B virus

<400> SEQUENCE: 216

Val Thr Val Tyr Tyr Gly Val Pro Val Trp Lys
1               5                   10

<210> SEQ ID NO 217
<211> LENGTH: 9
<212> TYPE: PRT
<213> ORGANISM: Hepatitis B virus

<400> SEQUENCE: 217

Phe Pro Val Arg Pro Gln Val Pro Leu
1               5

<210> SEQ ID NO 218
<211> LENGTH: 10
<212> TYPE: PRT
<213> ORGANISM: Hepatitis B virus

<400> SEQUENCE: 218

Tyr Pro Leu Ala Ser Leu Arg Ser Leu Phe
1               5                   10

<210> SEQ ID NO 219
<211> LENGTH: 10
<212> TYPE: PRT
<213> ORGANISM: Hepatitis B virus

<400> SEQUENCE: 219

Val Ile Tyr Gln Tyr Met Asp Asp Leu Tyr
1               5                   10

<210> SEQ ID NO 220
<211> LENGTH: 9
<212> TYPE: PRT
<213> ORGANISM: Hepatitis B virus

<400> SEQUENCE: 220

Ile Tyr Gln Glu Pro Phe Lys Asn Leu
1               5

<210> SEQ ID NO 221
<211> LENGTH: 9
<212> TYPE: PRT
<213> ORGANISM: Hepatitis B virus

<400> SEQUENCE: 221

Ile Trp Gly Cys Ser Gly Lys Leu Ile
1               5

<210> SEQ ID NO 222
<211> LENGTH: 4
```

```
<212> TYPE: PRT
<213> ORGANISM: Unknown
<220> FEATURE:
<223> OTHER INFORMATION: Peptide linker

<400> SEQUENCE: 222

Gly Ala Ala Ala
1

<210> SEQ ID NO 223
<211> LENGTH: 4
<212> TYPE: PRT
<213> ORGANISM: Unknown
<220> FEATURE:
<223> OTHER INFORMATION: Peptide linker

<400> SEQUENCE: 223

Asn Ala Ala Ala
1

<210> SEQ ID NO 224
<211> LENGTH: 4
<212> TYPE: PRT
<213> ORGANISM: Unknown
<220> FEATURE:
<223> OTHER INFORMATION: Peptide linker

<400> SEQUENCE: 224

Lys Ala Ala Ala
1

<210> SEQ ID NO 225
<211> LENGTH: 277
<212> TYPE: PRT
<213> ORGANISM: Human immunodeficiency virus

<400> SEQUENCE: 225

Met Gly Met Gln Val Gln Ile Gln Ser Leu Phe Leu Leu Leu Leu Trp
1               5                   10                  15

Val Pro Gly Ser Arg Gly Lys Leu Val Gly Lys Leu Asn Trp Ala Gly
            20                  25                  30

Ala Ala Ile Leu Lys Glu Pro Val His Gly Val Asn Ala Ala Cys Pro
        35                  40                  45

Lys Val Ser Phe Glu Pro Ile Lys Ile Pro Ile His Tyr Cys Ala Pro
    50                  55                  60

Ala Lys Ala Lys Phe Val Ala Ala Trp Thr Leu Lys Ala Ala Ala Lys
65                  70                  75                  80

Ala Phe Pro Val Arg Pro Gln Val Pro Leu Gly Ala Ala Lys Leu Thr
                85                  90                  95

Pro Leu Cys Val Thr Leu Gly Ala Ala Val Leu Ala Glu Ala Met
            100                 105                 110

Ser Gln Val Lys Val Tyr Leu Ala Trp Val Pro Ala His Lys Gly Ala
        115                 120                 125

Ala Ala Ala Ile Phe Gln Ser Ser Met Thr Lys Thr Thr Leu Phe
    130                 135                 140

Cys Ala Ser Asp Ala Lys Asn Ile Pro Tyr Asn Pro Gln Ser Gln Gly
145                 150                 155                 160

Val Val Lys His Pro Val His Ala Gly Pro Ile Ala Asn Val Thr Val
                165                 170                 175

Tyr Tyr Gly Val Pro Val Trp Lys Ala Ala Ala Gln Met Ala Val
            180                 185                 190
```

```
Phe Ile His Asn Phe Lys Asn Ala Ala Ala Tyr Pro Leu Ala Ser Leu
        195                 200                 205

Arg Ser Leu Phe Asn Leu Thr Phe Gly Trp Cys Phe Lys Leu Asn Arg
        210                 215                 220

Ile Leu Gln Gln Leu Leu Phe Ile Asn Ala Lys Ile Gln Asn Phe Arg
225                 230                 235                 240

Val Tyr Tyr Arg Lys Ala Ala Val Thr Ile Lys Ile Gly Gly Gln Leu
                245                 250                 255

Lys Lys Val Pro Leu Gln Leu Pro Pro Leu Lys Ala Met Thr Asn Asn
                260                 265                 270

Pro Pro Ile Pro Val
        275

<210> SEQ ID NO 226
<211> LENGTH: 834
<212> TYPE: DNA
<213> ORGANISM: Human immunodeficiency virus

<400> SEQUENCE: 226
atgggaatgc aggtgcagat ccagagcctg tttctgctcc tcctgtgggt gcccggatcc     60
agaggaaagc tggtgggcaa actcaactgg gccggagctg caatcctgaa ggagcccgtc    120
cacggggtga atgccgcttg ccctaaagtc agcttcgaac caattaagat ccccattcat    180
tactgtgcac ctgccaaagc taagtttgtg gccgcttgga ccctcaaggc cgctgcaaaa    240
gccttcccag tgaggcccca ggtgcctctg gcgccgcta aactcacacc actgtgcgtc    300
actctgggag ccgctgcagt gctggcagag gccatgtccc aagtgaaggt gtatctggct    360
tgggtgcccg cccacaaggg ggccgctgca gccatctttc agtctagcat gaccaagaaa    420
acaactctgt tctgtgcctc cgacgctaag aacatccctt ataatccaca gtctcagggc    480
gtggtcaagc atcccgtgca cgccggacct attgctaacg tgaccgtgta ctatggggtc    540
ccagtgtgga agaaagccgc tgcacagatg gccgtgttta ttcacaattt caaaaacgcc    600
gctgcatacc ccctcgccag cctgagatcc ctcttcaacc tgacattcgg ctggtgcttt    660
aagctgaacc ggatcctgca gcaactgctc tttatcaatg ctaaaatcca gaacttccgc    720
gtctactata ggaaggctgc agtgactatc aaaattggcg gacaactgaa gaaagtgcct    780
ctccagctgc cccctctcaa ggcaatgacc aacaatcccc ctatcccagt ctga          834

<210> SEQ ID NO 227
<211> LENGTH: 280
<212> TYPE: PRT
<213> ORGANISM: Human immunodeficiency virus

<400> SEQUENCE: 227

Met Gly Met Gln Val Gln Ile Gln Ser Leu Phe Leu Leu Leu Leu Trp
1               5                  10                  15

Val Pro Gly Ser Arg Gly Ile Pro Ile His Tyr Cys Ala Pro Ala Lys
                20                  25                  30

Ala Ala Lys Ile Gln Asn Phe Arg Val Tyr Tyr Arg Lys Ala Ala Val
            35                  40                  45

Thr Ile Lys Ile Gly Gly Gln Leu Lys Lys Ala Lys Phe Val Ala Ala
        50                  55                  60

Trp Thr Leu Lys Ala Ala Ala Lys Val Pro Leu Gln Leu Pro Pro Leu
65                  70                  75                  80

Lys Ala Ile Phe Gln Ser Ser Met Thr Lys Lys Leu Thr Pro Leu Cys
```

```
                 85                  90                  95
Val Thr Leu Gly Ala Gln Met Ala Val Phe Ile His Asn Phe Lys Gly
            100                 105                 110
Ala Lys Val Tyr Leu Ala Trp Val Pro Ala His Lys Asn Ala Ile Pro
        115                 120                 125
Tyr Asn Pro Gln Ser Gln Gly Val Val Lys Ala Ile Leu Lys Glu Pro
    130                 135                 140
Val His Gly Val Gly Ala Ala Leu Thr Phe Gly Trp Cys Phe Lys
145                 150                 155                 160
Leu Asn Ala Val Leu Ala Glu Ala Met Ser Gln Val Asn Arg Ile Leu
                165                 170                 175
Gln Gln Leu Leu Phe Ile Asn Ala Ala Ala Cys Pro Lys Val Ser Phe
            180                 185                 190
Glu Pro Ile Lys Val Thr Val Tyr Tyr Gly Val Pro Val Trp Lys Lys
        195                 200                 205
Ala Ala His Pro Val His Ala Gly Pro Ile Ala Asn Ala Ala Ala Tyr
    210                 215                 220
Pro Leu Ala Ser Leu Arg Ser Leu Phe Asn Ala Ala Ala Thr Thr Leu
225                 230                 235                 240
Phe Cys Ala Ser Asp Ala Lys Asn Lys Leu Val Gly Lys Leu Asn Trp
                245                 250                 255
Ala Asn Ala Ala Ala Phe Pro Val Arg Pro Gln Val Pro Leu Asn Met
            260                 265                 270
Thr Asn Asn Pro Pro Ile Pro Val
        275                 280

<210> SEQ ID NO 228
<211> LENGTH: 843
<212> TYPE: DNA
<213> ORGANISM: Human immunodeficiency virus

<400> SEQUENCE: 228
atggggatgc aggtgcagat ccagagcctg tttctgctcc tcctgtgggt gcccggatcc      60
agaggaatcc ccattcacta ctgcgcccct gctaaggcag ccaaaatcca gaacttcagg     120
gtgtattaca gaaaggctgc agtcaccatt aaaatcggcg acaactgaa gaaagccaag     180
tttgtggccg cttggacact caaggccgct gcaaaggtcc cactgcagct ccccctctg     240
aaggccatct tccagagctc catgactaag aaactgaccc cactgtgtgt gacactcggg     300
gcccagatgg ctgtgttcat ccataatttt aaaggcgcca aggtctacct ggcttgggtg     360
cccgcacaca gaacgccat tccttacaat ccacagtctc aaggagtggt caaagctatt     420
ctgaaggagc ccgtgcacgg ggtggcgcc gctgcactca ctttcggatg gtgcttaa      480
ctgaacgccg tgctggctga agccatgagc aggtcaatc ggatcctgca gcaactgctc     540
ttcattaacg ccgctgcatg tcctaaggtg tccttcgagc caatcaaagt gaccgtgtat     600
tacggggtcc ccgtgtggaa gaaagccgct catcctgtcc acgcaggccc aatcgccaac     660
gccgctgcat atccctcgc ctctctgcgc agcctgttta cgccgctgc aacaaccctc     720
ttttgcgcct ccgacgctaa gaataaactg gtgggaaagc tgaactggc caacgcagct     780
gcattccctg tgaggccaca ggtccccctc aatatgacta caatcccc tatcccagtg     840
tga                                                                 843

<210> SEQ ID NO 229
<211> LENGTH: 211
```

```
<212> TYPE: PRT
<213> ORGANISM: Human immunodeficiency virus

<400> SEQUENCE: 229

Met Gln Val Gln Ile Gln Ser Leu Phe Leu Leu Leu Trp Val Pro
1               5                   10                  15

Gly Ser Arg Gly Lys Leu Val Gly Lys Leu Asn Trp Ala Met Ala Ser
            20                  25                  30

Asp Phe Asn Leu Pro Pro Val Ala Ile Phe Gln Ser Ser Met Thr Lys
        35                  40                  45

Val Thr Ile Lys Ile Gly Gly Gln Leu Lys Arg Ile Leu Gln Gln Leu
    50                  55                  60

Leu Phe Ile Met Ala Val Phe Ile His Asn Phe Lys Ile Pro Tyr Asn
65                  70                  75                  80

Pro Gln Ser Gln Gly Val Val Thr Thr Leu Phe Cys Ala Ser Asp Ala
                85                  90                  95

Lys Ile Leu Lys Glu Pro Val His Gly Val Gln Met Ala Val Phe Ile
            100                 105                 110

His Asn Phe Lys Gly Ala Ala Val Phe Ile His Asn Phe Lys Arg Cys
        115                 120                 125

Pro Lys Val Ser Phe Glu Pro Ile Lys Ile Gln Asn Phe Arg Val Tyr
    130                 135                 140

Tyr Arg Leu Thr Phe Gly Trp Cys Phe Lys Leu Gln Val Pro Leu Arg
145                 150                 155                 160

Pro Met Thr Tyr Lys Met Thr Asn Asn Pro Ile Pro Val Thr Val
                165                 170                 175

Tyr Tyr Gly Val Pro Val Trp Lys Val Leu Ala Glu Ala Met Ser Gln
            180                 185                 190

Val Ile Pro Ile His Tyr Cys Ala Pro Ala Lys Leu Thr Pro Leu Cys
        195                 200                 205

Val Thr Leu
    210

<210> SEQ ID NO 230
<211> LENGTH: 633
<212> TYPE: DNA
<213> ORGANISM: Human immunodeficiency virus

<400> SEQUENCE: 230
atgcaggtgc agatccagag cctgtttctg ctcctcctgt gggtgcccgg atccagagga      60
aagctggtgg ggaagctgaa ctgggccatg gccagcgatt tcaacctgcc ccccgtggcc     120
atcttccaga gcagcatgac caaggtgacc atcaagatcg ggggcagct gaagaggatc      180 ctgcagcagc tgctgttcat catggccgtg ttcatccaca acttcaagat cccctacaac     240
ccccagagcc agggggtggt gaccacctg ttctgcgcca gcgatgccaa gatcctgaag      300
gagcccgtgc acggggtgca gatggccgtg ttcatccaca acttcaaggg cgccgccgtg     360
ttcatccaca acttcaagag ggtgccccaag gtgagcttcg agcccatcaa gatccagaac    420
ttcagggtgt actacaggct gaccttcggg tggtgcttca gctgcaggt gcccctgagg      480 cccatgacct acaagatgac caacaacccc cccatccccg tgaccgtgta ctacggggtg     540
cccgtgtgga aggtgctggc cgaggccatg agccaggtga tccccatcca ctactgcgcc    600
cccgccaagc tgaccccccct gtgcgtgacc ctg                                 633

<210> SEQ ID NO 231
```

```
<211> LENGTH: 585
<212> TYPE: PRT
<213> ORGANISM: Human immunodeficiency virus

<400> SEQUENCE: 231

Met Gly Met Gln Val Gln Ile Gln Ser Leu Phe Leu Leu Leu Leu Trp
1               5                   10                  15

Val Pro Gly Ser Arg Gly Tyr Trp Gln Ala Thr Trp Ile Pro Glu Trp
            20                  25                  30

Lys Ala Ile Phe Gln Ser Ser Met Thr Lys Val Tyr Leu Ala Trp
        35                  40                  45

Val Pro Ala His Lys Asn Ala Ala Cys Pro Lys Val Ser Phe Glu Pro
    50                  55                  60

Ile Lys His Pro Val His Ala Gly Pro Ile Ala Asn Leu Thr Phe Gly
65                  70                  75                  80

Trp Cys Phe Lys Leu Asn Lys Met Ile Gly Gly Ile Gly Gly Phe Ile
                85                  90                  95

Lys Phe Arg Asp Tyr Val Asp Arg Phe Tyr Lys Ala Ala Ala Arg Ile
            100                 105                 110

Leu Gln Gln Leu Leu Phe Ile Asn Thr Thr Leu Phe Cys Ala Ser Asp
        115                 120                 125

Ala Lys Asn Gln Met Val His Gln Ala Ile Ser Pro Arg Gly Ala Lys
    130                 135                 140

Leu Val Gly Lys Leu Asn Trp Ala Gly Ala Ala Ile Tyr Glu Thr
145                 150                 155                 160

Tyr Gly Asp Thr Trp Lys Ala Ala Gln Val Pro Leu Arg Pro Met Thr
                165                 170                 175

Tyr Lys Gly Ala Ala Ala Val Thr Val Leu Asp Val Gly Asp Ala Tyr
            180                 185                 190

Asn Ala Ala Ala Arg Tyr Leu Lys Asp Gln Gln Leu Leu Asn Thr Leu
        195                 200                 205

Asn Phe Pro Ile Ser Pro Ile Asn Met Thr Asn Asn Pro Pro Ile Pro
    210                 215                 220

Val Asn Ala Pro Tyr Asn Thr Pro Val Phe Ala Ile Lys Ala Ala Ala
225                 230                 235                 240

Val Pro Leu Gln Leu Pro Pro Leu Lys Ala Ala Ile Pro Tyr Asn Pro
                245                 250                 255

Gln Ser Gln Gly Val Val Lys Ala Leu Leu Gln Leu Thr Val Trp Gly
            260                 265                 270

Ile Gly Ala Ala Ile Leu Lys Glu Pro Val His Gly Val Asn Ala Ala
        275                 280                 285

Ala Phe Pro Ile Ser Pro Ile Glu Thr Val Lys Val Trp Lys Glu Ala
    290                 295                 300

Thr Thr Thr Leu Phe Lys Ala Ala Ala Val Thr Ile Lys Ile Gly Gly
305                 310                 315                 320

Gln Leu Lys Lys Ile Tyr Gln Glu Pro Phe Lys Asn Leu Lys Ala Ala
                325                 330                 335

Ala Val Leu Ala Glu Ala Met Ser Gln Val Asn Leu Val Gly Pro Thr
            340                 345                 350

Pro Val Asn Ile Gly Ala Ala Glu Val Asn Ile Val Thr Asp Ser
        355                 360                 365

Gln Tyr Lys Ala Ala Ile Pro Ile His Tyr Cys Ala Pro Ala Lys
    370                 375                 380

Ala Val Ile Tyr Gln Tyr Met Asp Asp Leu Tyr Lys Ala Ala Ala Gln
```

```
                385                 390                 395                 400
Met Ala Val Phe Ile His Asn Phe Lys Asn Ala Thr Tyr Gln Ile
                    405                 410                 415
Tyr Gln Glu Pro Phe Lys Pro Tyr Asn Glu Trp Thr Leu Glu Leu Lys
            420                 425                 430
Ala Lys Ile Gln Asn Phe Arg Val Tyr Tyr Arg Lys Ala Phe Pro Val
        435                 440                 445
Arg Pro Gln Val Pro Leu Gly Ala Ala Ile Trp Gly Cys Ser Gly
        450                 455                 460
Lys Leu Ile Lys Val Met Ile Val Trp Gln Val Asp Arg Asn Ala Ala
465                 470                 475                 480
Lys Ala Ala Cys Trp Trp Ala Gly Ile Lys Ala Lys Phe Val Ala Ala
                485                 490                 495
Trp Thr Leu Lys Ala Ala Ala Lys Leu Thr Pro Leu Cys Val Thr Leu
                500                 505                 510
Asn Ala Ala Met Ala Ser Asp Phe Asn Leu Pro Val Lys Ser Leu
                515                 520                 525
Leu Asn Ala Thr Asp Ile Ala Val Asn Val Thr Val Tyr Tyr Gly Val
            530                 535                 540
Pro Val Trp Lys Lys Ala Ala Ala Ile Ile Arg Ile Leu Gln Gln
545                 550                 555                 560
Leu Lys Arg Ala Met Ala Ser Asp Phe Asn Leu Asn Ala Ala Ala Tyr
                565                 570                 575
Pro Leu Ala Ser Leu Arg Ser Leu Phe
            580                 585

<210> SEQ ID NO 232
<211> LENGTH: 1758
<212> TYPE: DNA
<213> ORGANISM: Human immunodeficiency virus

<400> SEQUENCE: 232
atggggatgc aggtgcagat ccagagcctg tttctgctcc tcctgtgggt gcccggatct      60
agaggatact ggcaagctac ttggattcca gaatggaaag ctatctttca atcctcaatg     120
acgaagaagg tatacctggc atgggtccca gcacacaaga cgccgcttg cccaaaggtg     180
tcctttgaac ccattaaaca cccagtgcac gcagggccaa tagcgaattt gacattcggg     240
tggtgcttca aactaaacaa aatgatcggc ggcattggag ctttatcaa gtttagagat     300
tacgtggacc gattctataa agccgctgcc cgtatactcc agcagctact attcatcaac     360
accactctct tctgcgcttc agacgctaag aaccaaatgg tacaccaagc cataagccct     420
agaggagcca agctcgtagg gaaattaaat tgggcgggtg cagcagcaat ctacgagact     480
tacggcgata cctggaaagc agcccaggtt ccgttacgcc caatgaccta taaaggcgca     540
gcagcagtaa cagttctaga tgtaggagac gcttacaacg ctgccgcaag ataccttaaaa     600
gatcagcagt tactcaacac actaaatttc ccaattagcc cgataaacat gacaaataac     660
ccaccaattc ccgtcaatgc tccctacaac actccagtat cgcaatcaa gccgctgct     720
gtcccctgc agctccctcc tctgaaagct gcgataccttt acaacccaca gagccaaggt     780
gttgtcaaag cactgcttca gctaacagtt tggggaattg tgctgcaat tctaaaagag     840
ccagttcatg gggttaacgc cgccgccttc ccaatcagtc ctattgagac tgtgaaagta     900
tggaaagaag ccacaaccac acttttttaag gcagccgcag ttacaattaa aatagggggc     960
caacttaaga aaatatacca ggaacctttc aagaatctca agccgctgc agtgctcgcc    1020
```

```
gaggctatgt cacaggtgaa tttggtcgga ccaacacccg taaacatcgg agccgcagcc    1080
gaagtgaaca tagtcaccga ctcacagtac aaagccgctg caatacccat acattattgt    1140
gctcccgcaa aggccgtgat ctatcaatat atggacgacc tgtataaggc cgccgcgcag    1200
atggcagtct ttatccacaa ctttaaaaac gcagctactt atcagatcta ccaggaacca    1260
ttcaaaccgt acaatgagtg gaccttggaa ctaaaggcca aaattcagaa cttcagggta    1320
tattatagaa aagcatttcc agtgaggccc caggtgcctc tgggtgccgc agcaatatgg    1380
ggatgttctg gaaaactgat caaggtgatg attgtatggc aagtggacag aaatgcagct    1440
aaggcagcct gttggtgggc aggtataaaa gcaaagttcg tggcagcatg gacgcttaaa    1500
gcagccgcaa aactcactcc tctctgcgtg acacttaatg cagccatggc ctctgatttc    1560
aaccttcccc ctgtaaaatc cctgcttaat gcgacagata tcgcagtcaa cgtaacagta    1620
tattatggcg tgccagtctg gaaaaaagcc gccgcggcca taattcggat actgcagcag    1680
ctgaaaagag ctatggcgag tgacttcaac ctgaatgcgg ccgcctaccc cttggcatcg    1740
ttaaggtcac tattttga                                                  1758
```

<210> SEQ ID NO 233
<211> LENGTH: 255
<212> TYPE: PRT
<213> ORGANISM: Hepatitis C virus

<400> SEQUENCE: 233

```
Met Gly Met Gln Val Gln Ile Gln Ser Leu Phe Leu Leu Leu Leu Trp
1               5                   10                  15

Val Pro Gly Ser Arg Gly Leu Leu Phe Asn Ile Leu Gly Gly Trp Val
            20                  25                  30

Asp Leu Met Gly Tyr Ile Pro Leu Val Tyr Leu Val Ala Tyr Gln Ala
        35                  40                  45

Thr Val Ile Leu Ala Gly Tyr Gly Ala Gly Val Arg Leu Ile Val Phe
    50                  55                  60

Pro Asp Leu Gly Val His Met Trp Asn Phe Ile Ser Gly Ile Tyr Leu
65                  70                  75                  80

Leu Pro Arg Arg Gly Pro Arg Leu Tyr Leu Val Thr Arg His Ala Asp
                85                  90                  95

Val Val Leu Val Gly Gly Val Leu Ala Ala Leu Leu Phe Leu Leu Leu
            100                 105                 110

Ala Asp Ala Phe Leu Leu Leu Ala Asp Ala Arg Val Trp Met Asn Arg
        115                 120                 125

Leu Ile Ala Phe Ala Cys Thr Cys Gly Ser Ser Asp Leu Tyr Leu Ser
    130                 135                 140

Ala Phe Ser Leu His Ser Tyr Gly Val Ala Gly Ala Leu Val Ala Phe
145                 150                 155                 160

Lys Leu Pro Gly Cys Ser Phe Ser Ile Phe Lys Thr Ser Glu Arg Ser
                165                 170                 175

Gln Pro Arg Leu Ile Phe Cys His Ser Lys Lys Lys Phe Trp Ala Lys
            180                 185                 190

His Met Trp Asn Phe Ile Pro Phe Tyr Gly Lys Ala Ile Arg Met Tyr
        195                 200                 205

Val Gly Gly Val Glu His Arg Gln Leu Phe Thr Phe Ser Pro Arg Arg
    210                 215                 220

Arg Leu Gly Val Arg Ala Thr Arg Lys Val Gly Ile Tyr Leu Leu Pro
225                 230                 235                 240
```

-continued

Asn Arg Ala Lys Phe Val Ala Ala Trp Thr Leu Lys Ala Ala Ala
            245                 250                 255

<210> SEQ ID NO 234
<211> LENGTH: 747
<212> TYPE: DNA
<213> ORGANISM: Hepatitis C virus

<400> SEQUENCE: 234
gaattcgccg ccaccatgca ggtgcagatc cagagcctgt ttctgctcct cctgtgggtg      60
cccggatcca gaggactgct gttcaacatc ctggggggg gggtggatct gatggggtac     120
atcccctgg tgtacctggt ggcctaccag gccaccgtga tcctggccgg gtacggggcc     180
ggggtgaggc tgatcgtgtt ccccgatctg ggggtgcaca tgtggaactt catcagcggg     240
atctacctgc tgcccaggag aggacctaga ctgtacctgg tgactagaca cgctgatgtg     300
gtgctggtgg gaggagtgct ggctgctctg ctgtttctgc tgctggctga tgctttcctg     360
ctgctggctg atgctagagt gtggatgaac agactgatcg ctttcgcttg tacatgtgga     420
agctccgatc tgtatctgag cgctttcagc ctgcacagct acggagtggc tggagctctg     480
gtggctttta agctgcctgg atgtagcttt agcatctta agaccagcga agaagccag      540
cctagactga tcttttgtca cagcaagaag aagttttggg ctaagcacat gtggaatttt     600
atcccttct atggaaaggc tatcagaatg tatgtgggag gagtggaaca cagacagctg     660
tttacattta gccctagaag gagactggga gtgagagcta caagaaaggt gggaatctat     720
ctgctgccta atagatgaaa gcttggg                                          747

<210> SEQ ID NO 235
<211> LENGTH: 281
<212> TYPE: PRT
<213> ORGANISM: Hepatitis C virus

<400> SEQUENCE: 235

Met Gly Met Gln Val Gln Ile Gln Ser Leu Phe Leu Leu Leu Trp
1               5                  10                  15

Val Pro Gly Ser Arg Gly Asp Leu Met Gly Tyr Ile Pro Leu Val Ala
                20                  25                  30

Lys Phe Val Ala Ala Trp Thr Leu Lys Ala Ala Ala Leu Leu Phe Leu
            35                  40                  45

Leu Leu Ala Asp Ala Leu Ile Phe Cys His Ser Lys Lys Lys Gln Leu
        50                  55                  60

Phe Thr Phe Ser Pro Arg Arg Tyr Leu Val Thr Arg His Ala Asp Val
65                  70                  75                  80

Tyr Leu Leu Pro Arg Arg Gly Pro Arg Leu Cys Thr Cys Gly Ser Ser
                85                  90                  95

Asp Leu Tyr His Met Trp Asn Phe Ile Ser Gly Ile Phe Trp Ala Lys
            100                 105                 110

His Met Trp Asn Phe Ala Lys Phe Val Ala Ala Trp Thr Leu Lys Ala
        115                 120                 125

Ala Ala Ile Leu Ala Gly Tyr Gly Ala Gly Val Tyr Leu Val Ala Tyr
    130                 135                 140

Gln Ala Thr Val Gly Val Ala Gly Ala Leu Ala Phe Lys Ile Pro
145                 150                 155                 160

Phe Tyr Gly Lys Ala Ile Arg Met Tyr Val Gly Gly Val Glu His Arg
                165                 170                 175

```
Val Leu Val Gly Gly Val Leu Ala Ala Phe Leu Leu Ala Asp Ala
            180                 185                 190

Arg Val Leu Pro Gly Cys Ser Phe Ser Ile Phe Ala Lys Phe Val Ala
            195                 200                 205

Ala Trp Thr Leu Lys Ala Ala Lys Thr Ser Glu Arg Ser Gln Pro
        210                 215                 220

Arg Arg Leu Gly Val Arg Ala Thr Arg Lys Arg Leu Ile Val Phe Pro
225                 230                 235                 240

Asp Leu Gly Val Trp Met Asn Arg Leu Ile Ala Phe Ala Leu Ser Ala
                245                 250                 255

Phe Ser Leu His Ser Tyr Leu Leu Phe Asn Ile Leu Gly Gly Trp Val
            260                 265                 270

Val Gly Ile Tyr Leu Leu Pro Asn Arg
        275                 280

<210> SEQ ID NO 236
<211> LENGTH: 789
<212> TYPE: DNA
<213> ORGANISM: Hepatitis C virus

<400> SEQUENCE: 236
gaattcgccg ccaccatggg aatgcaggtg cagatccaga gcctgtttct gctcctcctg      60
tgggtgcccg atccagagg agatctgatg gatatatcc ctctggtggc taagtttgtg     120
gctgcttgga cactgaaggc tgctgctctg ctgtttctgc tgctggctga tgctctgatc     180
ttctgtcaca gcaagaagaa gcagctgttt acatttagcc aagaagata tctggtgaca     240 agacacgctg atgtgtatct gctgcctaga cgcggaccta gactgtgtac atgtggaagc     300
tccgatctgt atcacatgtg gaactttatc agcggaatct tttgggctaa gcacatgtgg     360
aatttcatcc tggctggata tggagctgga gtgtatctgg tggcttatca ggctacagtg     420
ggagtggctg gagctctggt ggcttttcaag atcccattct atggaaaggc tatcagaatg     480
tatgtgggag gagtggaaca cagagtgctg gtgggaggag tgctggctgc tttcctgctg     540
ctggctgatg ctagagtgct gccaggatgt agctttagca tcttcaagac ttccgaacgc     600
tcccagccta aagactggg agtgagagct acaaggaaga gactgatcgt gtttccagat     660
ctgggagtgt ggatgaatag actgatcgct ttcgctctga gcgctttcag cctgcacagc     720
tatctgctgt tcaacatcct gggaggatgg gtggtgggaa tctatctgct gccaaacaga     780
tgaaagctt                                                            789

<210> SEQ ID NO 237
<211> LENGTH: 107
<212> TYPE: PRT
<213> ORGANISM: Hepatitis C virus

<400> SEQUENCE: 237

Met Gly Met Gln Val Gln Ile Gln Ser Leu Phe Leu Leu Leu Leu Trp
1               5                  10                  15

Val Pro Gly Ser Arg Gly Tyr Leu Val Ala Tyr Gln Ala Thr Val Ala
            20                  25                  30

Lys Phe Val Ala Ala Trp Thr Leu Lys Ala Ala Leu Leu Phe Leu
        35                  40                  45

Leu Leu Ala Asp Ala Leu Ile Phe Cys His Ser Lys Lys Lys Tyr Leu
    50                  55                  60

Val Thr Arg His Ala Asp Val Leu Gly Phe Gly Ala Tyr Met Ser Lys
65                  70                  75                  80
```

Cys Thr Cys Gly Ser Ser Asp Leu Tyr His Met Trp Asn Phe Ile Ser
                85                  90                  95

Gly Ile Phe Trp Ala Lys His Met Trp Asn Phe
            100                 105

<210> SEQ ID NO 238
<211> LENGTH: 345
<212> TYPE: DNA
<213> ORGANISM: Hepatitis C virus

<400> SEQUENCE: 238
gaattcgccg ccaccatggg aatgcaggtg cagatccaaa gcctgtttct gctcctcctg      60
tgggtgcccg gatccagagg atacctcgtc gcctaccagg ccactgtggc taaattcgtg     120
gcagcctgga cactgaaagc tgcagctctg ctcttcctgc tcctggccga tgcactcatc     180
ttctgccatt ccaagaaaaa gtatctggtc accagacatg ctgacgtgct ggggtttggc     240
gcctacatga gcaagtgcac ctgtggcagc tccgacctgt atcacatgtg gaactttatt     300
tctggaatct tttgggccaa gcacatgtgg aatttctgaa agctt                     345

<210> SEQ ID NO 239
<211> LENGTH: 106
<212> TYPE: PRT
<213> ORGANISM: Hepatitis C virus

<400> SEQUENCE: 239

Met Gly Met Gln Val Gln Ile Gln Ser Leu Phe Leu Leu Leu Leu Trp
1               5                   10                  15

Val Pro Gly Ser Arg Gly Val Leu Val Gly Gly Val Leu Ala Ala Ala
            20                  25                  30

Lys Phe Val Ala Ala Trp Thr Leu Lys Ala Ala Ala Phe Leu Leu Leu
        35                  40                  45

Ala Asp Ala Arg Val Leu Ser Ala Phe Ser Leu His Ser Tyr Ile Leu
    50                  55                  60

Ala Gly Tyr Gly Ala Gly Val Trp Met Asn Arg Leu Ile Ala Phe Ala
65                  70                  75                  80

Ile Pro Phe Tyr Gly Lys Ala Ile Val Ala Gly Ala Leu Val Ala Phe
                85                  90                  95

Lys Val Gly Ile Tyr Leu Leu Pro Asn Arg
            100                 105

<210> SEQ ID NO 240
<211> LENGTH: 342
<212> TYPE: DNA
<213> ORGANISM: Hepatitis C virus

<400> SEQUENCE: 240
gaattcgccg ccaccatggg aatgcaggtg cagatccaaa gcctgtttct gctcctcctg      60
tgggtgcccg gatccagagg agtcctggtg ggcggcgtcc tggccgctgc taagtttgtc     120
gctgcttgga cactgaaggc agccgctttc ctgctcctgg cagacgccag ggtgctgtct     180
gccttcagcc tccactccta catcctcgca gggtatggcg caggcgtgtg gatgaatcgg     240
ctgatcgcct ttgccattcc attctatggg aaagccattg tggctggcgc cctggtggca     300
ttcaaggtcg ggatctacct cctgcctaac cgctgaaagc tt                        342

<210> SEQ ID NO 241
<211> LENGTH: 80

```
<212> TYPE: PRT
<213> ORGANISM: Hepatitis C virus

<400> SEQUENCE: 241

Met Gly Met Gln Val Gln Ile Gln Ser Leu Phe Leu Leu Leu Trp
1               5                   10                  15

Val Pro Gly Ser Arg Gly Val Leu Val Gly Gly Val Leu Ala Ala
                20                  25                  30

Lys Phe Val Ala Ala Trp Thr Leu Lys Ala Ala Ala Phe Leu Leu
            35                  40                  45

Ala Asp Ala Arg Val Leu Ser Ala Phe Ser Leu His Ser Tyr Ile Leu
50                      55                  60

Ala Gly Tyr Gly Ala Gly Val Trp Met Asn Arg Leu Ile Ala Phe Ala
65                      70                  75                  80

<210> SEQ ID NO 242
<211> LENGTH: 264
<212> TYPE: DNA
<213> ORGANISM: Hepatitis C virus

<400> SEQUENCE: 242
gaattcgccg ccaccatggg aatgcaggtg cagatccaaa gcctgttttct gctcctcctg      60 tgggtgcccg gatccagagg agtcctggtg ggcggcgtcc tggccgctgc taagtttgtc     120
gctgcttgga cactgaaggc agccgctttc ctgctcctgg cagacgccag ggtgctgtct     180
gccttcagcc tccactccta catcctcgca gggtatggcg caggcgtgtg gatgaatcgg     240
ctgatcgcct ttgcctgagg atcc                                            264

<210> SEQ ID NO 243
<211> LENGTH: 130
<212> TYPE: PRT
<213> ORGANISM: Hepatitis C virus

<400> SEQUENCE: 243

Met Gly Met Gln Val Gln Ile Gln Ser Leu Phe Leu Leu Leu Trp
1               5                   10                  15

Val Pro Gly Ser Arg Gly Asp Leu Met Gly Tyr Ile Pro Leu Val Ala
                20                  25                  30

Lys Phe Val Ala Ala Trp Thr Leu Lys Ala Ala Ala Arg Leu Gly Val
            35                  40                  45

Arg Ala Thr Arg Lys Leu Leu Phe Asn Ile Leu Gly Gly Trp Val Arg
50                      55                  60

Met Tyr Val Gly Gly Val Glu His Arg Arg Leu Ile Val Phe Pro Asp
65                      70                  75                  80

Leu Gly Val Gly Val Ala Gly Ala Leu Val Ala Phe Lys Leu Pro Gly
                85                  90                  95

Cys Ser Phe Ser Ile Phe Lys Thr Ser Glu Arg Ser Gln Pro Arg Gln
                100                 105                 110

Leu Phe Thr Phe Ser Pro Arg Arg Tyr Leu Leu Pro Arg Arg Gly Pro
            115                 120                 125

Arg Leu
    130

<210> SEQ ID NO 244
<211> LENGTH: 414
<212> TYPE: DNA
<213> ORGANISM: Hepatitis C virus
```

<400> SEQUENCE: 244

```
gaattcgccg ccaccatggg aatgcaggtg cagatccaaa gcctgtttct gctcctcctg    60
tgggtgcccg gatccagagg agacctgatg ggctacatcc ctctcgtggc caagtttgtg   120
gcagcttgga ccctgaaggc cgctgccaga ctggagtgc gcgctacacg aaactcctg    180
tttaacatcc tgggagggtg ggtgcggatg tacgtcggag cgtcgagca cagaaggctc    240
attgtctttc cagatctcgg cgtgggcgtc gcaggcgcac tcgtggcctt caaactgcca   300
gggtgcagct tcagcatttt caagacctcc gaacgctccc aacccagaca gctgttcact   360
ttctctcctc ggaggtatct gctgcccaga cgcggaccca ggctgtgaaa gctt         414
```

<210> SEQ ID NO 245
<211> LENGTH: 98
<212> TYPE: PRT
<213> ORGANISM: Hepatitis C virus

<400> SEQUENCE: 245

```
Met Gly Met Gln Val Gln Ile Gln Ser Leu Phe Leu Leu Leu Leu Trp
  1               5                  10                  15
Val Pro Gly Ser Arg Gly Leu Leu Phe Asn Ile Leu Gly Gly Trp Val
             20                  25                  30
Lys Ala Lys Phe Val Ala Ala Trp Thr Leu Lys Ala Ala Ala Leu Ala
         35                  40                  45
Asp Gly Gly Cys Ser Gly Gly Ala Tyr Arg Leu Ile Val Phe Pro Asp
     50                  55                  60
Leu Gly Val Lys Phe Trp Ala Lys His Met Trp Asn Phe Ile Gly Val
 65                  70                  75                  80
Ala Gly Ala Leu Val Ala Phe Lys Lys Gln Leu Phe Thr Phe Ser Pro
                 85                  90                  95
Arg Arg
```

<210> SEQ ID NO 246
<211> LENGTH: 318
<212> TYPE: DNA
<213> ORGANISM: Hepatitis C virus

<400> SEQUENCE: 246

```
gaattcgccg ccaccatggg aatgcaggtg cagatccaaa gcctgtttct gctcctcctg    60
tgggtgcccg gatccagagg actgctcttc aacatcctgg gcggatgggt gaaggccaag   120
ttcgtggctg cctggaccct gaaggctgcc gctctggccg acgggggatg cagcggcgga   180
gcttacaggc tcattgtctt tcccgatctc ggagtcaaat tttgggcaaa gcacatgtgg   240
aatttcatcg ggtggccgg agccctggtc gcttttaaaa agcagctctt caccttctcc   300
ccaagacggt gaggtacc                                                 318
```

<210> SEQ ID NO 247
<211> LENGTH: 107
<212> TYPE: PRT
<213> ORGANISM: Hepatitis C virus

<400> SEQUENCE: 247

```
Met Gly Met Gln Val Gln Ile Gln Ser Leu Phe Leu Leu Leu Leu Trp
  1               5                  10                  15
Val Pro Gly Ser Arg Gly Arg Leu Gly Val Arg Ala Thr Arg Lys Lys
             20                  25                  30
Ala Lys Phe Val Ala Ala Trp Thr Leu Lys Ala Ala Ala Lys Thr Ser
```

```
                35                  40                  45
Glu Arg Ser Gln Pro Arg Asn Leu Pro Gly Cys Ser Phe Ser Ile Phe
 50                  55                  60

Asn Asp Leu Met Gly Tyr Ile Pro Leu Val Lys Tyr Leu Leu Pro Arg
 65                  70                  75                  80

Arg Gly Pro Arg Leu Asn Thr Leu Cys Gly Phe Ala Asp Leu Met Gly
                 85                  90                  95

Tyr Arg Met Tyr Val Gly Gly Val Glu His Arg
            100                 105

<210> SEQ ID NO 248
<211> LENGTH: 345
<212> TYPE: DNA
<213> ORGANISM: Hepatitis C virus

<400> SEQUENCE: 248
gaattcgccg ccaccatggg aatgcaggtg cagatccaaa gcctgtttct gctcctcctg      60
tgggtgcccg gatccagagg aaggctgggc gtgagagcca cccggaagaa ggccaagttc     120
gtggctgcct ggaccctgaa ggctgccgct aaaacaagcg agcgctccca gcccaggaac     180
ctgcctggat gctctttcag catctttaat gacctcatgg ggtacattcc actggtgaag     240
tatctgctcc ccagacgggg ccctcgcctg aacactctct gtggatttgc tgatctgatg     300
gggtacagga tgtatgtcgg cggagtcgaa cacagatgag gtacc                     345

<210> SEQ ID NO 249
<211> LENGTH: 308
<212> TYPE: PRT
<213> ORGANISM: Hepatitis C virus

<400> SEQUENCE: 249

Met Gly Met Gln Val Gln Ile Gln Ser Leu Phe Leu Leu Leu Leu Trp
  1               5                  10                  15

Val Pro Gly Ser Arg Gly Val Leu Val Gly Gly Val Leu Ala Ala Ala
                 20                  25                  30

Phe Leu Leu Leu Ala Asp Ala Arg Val Leu Ser Ala Phe Ser Leu His
                 35                  40                  45

Ser Tyr Ile Leu Ala Gly Tyr Gly Ala Gly Val Trp Met Asn Arg Leu
 50                  55                  60

Ile Ala Phe Ala Gly Ala Ala Arg Leu Gly Val Arg Ala Thr Arg
 65                  70                  75                  80

Lys Lys Ala Ala Ala Lys Thr Ser Glu Arg Ser Gln Pro Arg Asn Leu
                 85                  90                  95

Pro Gly Cys Ser Phe Ser Ile Phe Asn Asp Leu Met Gly Tyr Ile Pro
                100                 105                 110

Leu Val Lys Tyr Leu Leu Pro Arg Arg Gly Pro Arg Leu Asn Thr Leu
            115                 120                 125

Cys Gly Phe Ala Asp Leu Met Gly Tyr Arg Met Tyr Val Gly Gly Val
        130                 135                 140

Glu His Arg Lys Leu Leu Phe Asn Ile Leu Gly Trp Val Lys Ala
145                 150                 155                 160

Ala Ala Leu Ala Asp Gly Gly Cys Ser Gly Gly Ala Tyr Arg Leu Ile
                165                 170                 175

Val Phe Pro Asp Leu Gly Val Lys Phe Trp Ala Lys His Met Trp Asn
            180                 185                 190

Phe Ile Gly Val Ala Gly Ala Leu Val Ala Phe Lys Lys Gln Leu Phe
```

```
              195                 200                 205
Thr Phe Ser Pro Arg Arg Asn Gly Tyr Leu Val Ala Tyr Gln Ala Thr
    210                 215                 220

Val Ala Ala Ala Leu Leu Phe Leu Leu Leu Ala Asp Ala Leu Ile Phe
225                 230                 235                 240

Cys His Ser Lys Lys Lys Tyr Leu Val Thr Arg His Ala Asp Val Leu
                245                 250                 255

Gly Phe Gly Ala Tyr Met Ser Lys Cys Thr Cys Gly Ser Ser Asp Leu
            260                 265                 270

Tyr His Met Trp Asn Phe Ile Ser Gly Ile Phe Trp Ala Lys His Met
        275                 280                 285

Trp Asn Phe Lys Ala Ala Ala Lys Phe Val Ala Ala Trp Thr Leu
    290                 295                 300

Lys Ala Ala Ala
305
```

<210> SEQ ID NO 250
<211> LENGTH: 948
<212> TYPE: DNA
<213> ORGANISM: Hepatitis C virus

<400> SEQUENCE: 250

```
gaattcgccg ccaccatggg aatgcaggtg cagatccaaa gcctgttttct gctcctcctg    60
tgggtgcccg gctccagagg agtcctggtg ggcggcgtcc tggcagccgc tttcctgctc   120
ctggcagacg ccagggtgct gtctgccttc agcctccact cctacatcct cgcagggtat   180
ggcgcaggcg tgtggatgaa tcggctgatc gcctttgccg gcgctgccgc aaggctgggc   240
gtgagagcca cccggaagaa ggctgccgct aaaacaagcg agcgctccca gcccaggaac   300
ctgcctggat gctctttcag catctttaat gacctcatgg ggtacattcc actggtgaag   360
tatctgctcc ccagacgggg ccctcgcctg aacactctct gtggatttgc tgatctgatg   420
gggtacagga tgtatgtcgg cggagtcgaa cacagaaaac tgctcttcaa catcctgggc   480
ggatgggtga aggctgccgc tctggccgac ggggatgca gcggcggagc ttacaggctc   540
attgtctttc ccgatctcgg agtcaaattt tgggcaaagc acatgtggaa tttcatcggg   600
gtggccggag ccctggtcgc ttttaaaaag cagctcttca ccttctcccc aagacggaac   660
ggatacctcg tcgcctacca ggccactgtg gctgcagctc tgctcttcct gctcctggcc   720
gatgcactca tcttctgcca ttccaagaaa aagtatctgg tcaccagaca tgctgacgtg   780
ctggggtttg gcgcctacat gagcaagtgc acctgtggca gctccgacct gtatcacatg   840
tggaacttta tttctggaat cttttgggcc aagcacatgt ggaattttaa ggccgcagca   900
gctaaattcg tggcagcctg gacactgaaa gcagctgcat gaggatcc              948
```

<210> SEQ ID NO 251
<211> LENGTH: 308
<212> TYPE: PRT
<213> ORGANISM: Hepatitis C virus

<400> SEQUENCE: 251

```
Met Gly Met Gln Val Gln Ile Gln Ser Leu Phe Leu Leu Leu Leu Trp
1               5                   10                  15

Val Pro Gly Ser Arg Gly Arg Leu Gly Val Arg Ala Thr Arg Lys Lys
            20                  25                  30

Ala Ala Ala Lys Thr Ser Glu Arg Ser Gln Pro Arg Asn Leu Pro Gly
        35                  40                  45
```

```
Cys Ser Phe Ser Ile Phe Asn Asp Leu Met Gly Tyr Ile Pro Leu Val
 50                  55                  60

Lys Tyr Leu Leu Pro Arg Arg Gly Pro Arg Leu Asn Thr Leu Cys Gly
 65                  70                  75                  80

Phe Ala Asp Leu Met Gly Tyr Arg Met Tyr Val Gly Gly Val Glu His
                 85                  90                  95

Arg Lys Leu Leu Phe Asn Ile Leu Gly Gly Trp Val Lys Ala Ala
                100                 105                 110

Leu Ala Asp Gly Gly Cys Ser Gly Gly Ala Tyr Arg Leu Ile Val Phe
                115                 120                 125

Pro Asp Leu Gly Val Lys Phe Trp Ala Lys His Met Trp Asn Phe Ile
            130                 135                 140

Gly Val Ala Gly Ala Leu Val Ala Phe Lys Lys Gln Leu Phe Thr Phe
145                 150                 155                 160

Ser Pro Arg Arg Asn Gly Tyr Leu Val Ala Tyr Gln Ala Thr Val Ala
                165                 170                 175

Ala Ala Leu Leu Phe Leu Leu Leu Ala Asp Ala Leu Ile Phe Cys His
                180                 185                 190

Ser Lys Lys Lys Tyr Leu Val Thr Arg His Ala Asp Val Leu Gly Phe
            195                 200                 205

Gly Ala Tyr Met Ser Lys Cys Thr Cys Gly Ser Ser Asp Leu Tyr His
            210                 215                 220

Met Trp Asn Phe Ile Ser Gly Ile Phe Trp Ala Lys His Met Trp Asn
225                 230                 235                 240

Phe Lys Lys Ala Ala Ala Val Leu Val Gly Gly Val Leu Ala Ala Ala
                245                 250                 255

Phe Leu Leu Leu Ala Asp Ala Arg Val Leu Ser Ala Phe Ser Leu His
                260                 265                 270

Ser Tyr Ile Leu Ala Gly Tyr Gly Ala Gly Val Trp Met Asn Arg Leu
            275                 280                 285

Ile Ala Phe Ala Asn Ala Ala Ala Lys Phe Val Ala Ala Trp Thr Leu
            290                 295                 300

Lys Ala Ala Ala
305

<210> SEQ ID NO 252
<211> LENGTH: 948
<212> TYPE: DNA
<213> ORGANISM: Hepatitis C virus

<400> SEQUENCE: 252
gaattcgccg ccaccatggg aatgcaggtg cagatccaaa gcctgtttct gctcctcctg      60
tgggtgcccg ctccagagg aaggctgggc gtgagagcca cccggaagaa ggctgccgct     120
aaaacaagcg agcgctccca gcccaggaac ctgcctggat gctctttcag catctttaat     180
gacctcatgg ggtacattcc actggtgaag tatctgctcc ccagacgggg ccctcgcctg     240
aacactctct gtggatttgc tgatctgatg gggtacagga tgtatgtcgg cggagtcgaa     300
cacagaaaac tgctcttcaa catcctgggc ggatgggtga aggctgccgc tctggccgac     360
gggggatgca gcggcggagc ttacaggctc attgtctttc ccgatctcgg agtcaaattt     420
tgggcaaagc acatgtggaa tttcatcggg gtggccggag ccctggtcgc ttttaaaaag     480
cagctcttca cctttccccc aagacggaac ggatacctcg tcgcctacca ggccactgtg     540
gctgcagctc tgctcttcct gctcctggcc gatgcactca tcttctgcca ttccaagaaa     600
```

```
aagtatctgg tcaccagaca tgctgacgtg ctggggtttg gcgcctacat gagcaagtgc      660
acctgtggca gctccgacct gtatcacatg tggaacttta tttctggaat cttttgggcc      720
aagcacatgt ggaattttaa gaaagccgct gcagtcctgg tgggcggcgt cctggcagcc      780
gctttcctgc tcctggcaga cgccagggtg ctgtctgcct tcagcctcca ctcctacatc      840
ctcgcagggt atggcgcagg cgtgtggatg aatcggctga tcgcctttgc caatgctgca      900
gctaaattcg tggcagcctg gacactgaaa gcagctgcat gaggatcc                   948
```

<210> SEQ ID NO 253
<211> LENGTH: 123
<212> TYPE: PRT
<213> ORGANISM: Unknown
<220> FEATURE:
<223> OTHER INFORMATION: AOSI.K

<400> SEQUENCE: 253

```
Met Gly Met Gln Val Gln Ile Gln Ser Leu Phe Leu Leu Leu Leu Trp
1               5                   10                  15

Val Pro Gly Ser Arg Gly His Thr Leu Trp Lys Ala Gly Ile Leu Tyr
            20                  25                  30

Lys Ala Lys Phe Val Ala Ala Trp Thr Leu Lys Ala Ala Ala Phe Leu
        35                  40                  45

Pro Ser Asp Phe Phe Pro Ser Val Lys Phe Leu Leu Ser Leu Gly Ile
    50                  55                  60

His Leu Tyr Met Asp Asp Val Val Leu Gly Val Gly Leu Ser Arg Tyr
65                  70                  75                  80

Val Ala Arg Leu Phe Leu Leu Thr Arg Ile Leu Thr Ile Ser Thr Leu
                85                  90                  95

Pro Glu Thr Thr Val Val Arg Arg Gln Ala Phe Thr Phe Ser Pro Thr
            100                 105                 110

Tyr Lys Trp Leu Ser Leu Leu Val Pro Phe Val
        115                 120
```

<210> SEQ ID NO 254
<211> LENGTH: 372
<212> TYPE: DNA
<213> ORGANISM: Unknown
<220> FEATURE:
<223> OTHER INFORMATION: AOSI.K

<400> SEQUENCE: 254

```
atgggaatgc aggtgcagat ccagagcctg tttctgctcc tcctgtgggt gcccgggtcc       60
agaggacaca ccctgtggaa ggccggaatc ctgtataagg ccaagttcgt ggctgcctgg      120
accctgaagg ctgccgcttt cctgcctagc gatttctttc ctagcgtgaa gttcctgctg      180
tccctgggaa tccacctgta tatggatgac gtggtgctgg gagtgggact gtccaggtac      240
gtggctaggc tgttcctgct gaccagaatc ctgaccatct ccaccctgcc agagaccacc      300
gtggtgagga ggcaggcctt cacctttagc cctacctata agtggctgag cctgctggtg      360 cccttttgtgt ga                                                         372
```

<210> SEQ ID NO 255
<211> LENGTH: 206
<212> TYPE: PRT
<213> ORGANISM: Hepatitis B virus

<400> SEQUENCE: 255

Met Gly Met Gln Val Gln Ile Gln Ser Leu Phe Leu Leu Leu Leu Trp
1               5                   10                  15

Val Pro Gly Ser Arg Gly His Thr Leu Trp Lys Ala Gly Ile Leu Tyr
            20                  25                  30

Lys Ala Lys Phe Val Ala Ala Trp Thr Leu Lys Ala Ala Ala Phe Leu
        35                  40                  45

Pro Ser Asp Phe Phe Pro Ser Val Phe Leu Leu Ser Leu Gly Ile His
    50                  55                  60

Leu Tyr Met Asp Asp Val Val Leu Gly Val Gly Leu Ser Arg Tyr Val
65                  70                  75                  80

Ala Arg Leu Phe Leu Leu Thr Arg Ile Leu Thr Ile Ser Thr Leu Pro
                85                  90                  95

Glu Thr Thr Val Val Arg Arg Gln Ala Phe Thr Phe Ser Pro Thr Tyr
                100                 105                 110

Lys Trp Leu Ser Leu Leu Val Pro Phe Val Ile Pro Ile Pro Ser Ser
            115                 120                 125

Trp Ala Phe Thr Pro Ala Arg Val Thr Gly Gly Val Phe Lys Val Gly
    130                 135                 140

Asn Phe Thr Gly Leu Tyr Leu Pro Ser Asp Phe Phe Pro Ser Val Thr
145                 150                 155                 160

Leu Trp Lys Ala Gly Ile Leu Tyr Lys Asn Val Ser Ile Pro Trp Thr
                165                 170                 175

His Lys Leu Val Val Asp Phe Ser Gln Phe Ser Arg Ser Ala Ile Cys
                180                 185                 190

Ser Val Val Arg Arg Ala Leu Met Pro Leu Tyr Ala Cys Ile
            195                 200                 205

<210> SEQ ID NO 256
<211> LENGTH: 621
<212> TYPE: DNA
<213> ORGANISM: Hepatitis B virus

<400> SEQUENCE: 256
atgggaatgc aggtgcagat ccagagcctg tttctgctcc tcctgtgggt gcccgggtcc      60
agaggacaca ccctgtggaa ggccggaatc ctgtataagg ccaagttcgt ggctgcctgg     120
accctgaagg ctgccgcttt cctgcctagc gatttctttc ctagcgtgtt cctgctgtcc     180
ctgggaatcc acctgtatat ggatgacgtg gtgctgggag tgggactgtc caggtacgtg     240
gctaggctgt tcctgctgac cagaatcctg accatctcca ccctgccaga gaccaccgtg     300
gtgaggaggc aggccttcac ctttagccct acctataagt ggctgagcct gctggtgccc     360
tttgtgatcc ctatccctag ctcctgggct ttcaccccag ccagggtgac cggaggagtg     420
tttaaggtgg gaaacttcac cggcctgtat ctgcccagcg atttctttcc tagcgtgacc     480
ctgtggaagg ccgggatcct gtacaagaat gtgtccatcc cttggaccca caagctggtg     540
gtggactttt cccagttcag cagatccgct atctgctccg tggtgaggag agctctgatg     600
ccactgtatg cctgtatctg a                                               621

<210> SEQ ID NO 257
<211> LENGTH: 219
<212> TYPE: PRT
<213> ORGANISM: Hepatitis B virus

<400> SEQUENCE: 257

Met Gly Met Gln Val Gln Ile Gln Ser Leu Phe Leu Leu Leu Leu Trp
1               5                   10                  15

```
Val Pro Gly Ser Arg Gly His Thr Leu Trp Lys Ala Gly Ile Leu Tyr
         20                  25                  30

Lys Ala Lys Phe Val Ala Ala Trp Thr Leu Lys Ala Ala Ala Phe Leu
     35                  40                  45

Pro Ser Asp Phe Phe Pro Ser Val Asn Phe Leu Leu Ser Leu Gly Ile
 50                  55                  60

His Leu Tyr Met Asp Asp Val Val Leu Gly Val Gly Leu Ser Arg Tyr
 65                  70                  75                  80

Val Ala Arg Leu Phe Leu Leu Thr Arg Ile Leu Thr Ile Ser Thr Leu
                 85                  90                  95

Pro Glu Thr Thr Val Val Arg Arg Gln Ala Phe Thr Phe Ser Pro Thr
                100                 105                 110

Tyr Lys Gly Ala Ala Ala Trp Leu Ser Leu Leu Val Pro Phe Val Asn
            115                 120                 125

Ile Pro Ile Pro Ser Ser Trp Ala Phe Lys Thr Pro Ala Arg Val Thr
        130                 135                 140

Gly Gly Val Phe Lys Val Gly Asn Phe Thr Gly Leu Tyr Asn Leu Pro
145                 150                 155                 160

Ser Asp Phe Phe Pro Ser Val Lys Thr Leu Trp Lys Ala Gly Ile Leu
                165                 170                 175

Tyr Lys Asn Val Ser Ile Pro Trp Thr His Lys Gly Ala Ala Leu Val
            180                 185                 190

Val Asp Phe Ser Gln Phe Ser Arg Asn Ser Ala Ile Cys Ser Val Val
        195                 200                 205

Arg Arg Ala Leu Met Pro Leu Tyr Ala Cys Ile
        210                 215

<210> SEQ ID NO 258
<211> LENGTH: 660
<212> TYPE: DNA
<213> ORGANISM: Hepatitis B virus

<400> SEQUENCE: 258
atgggaatgc aggtgcagat ccagagcctg tttctgctcc tcctgtgggt gcccgggtcc      60
agaggacaca ccctgtggaa ggccggaatc ctgtataagg ccaagttcgt ggctgcctgg     120
accctgaagg ctgccgcttt cctgcctagc gatttctttc ctagcgtgaa cttcctgctg     180
tccctgggaa tccacctgta tatggatgac gtggtgctgg gagtgggact gtccaggtac     240
gtggctaggc tgttcctgct gaccagaatc ctgaccatct ccaccctgcc agagaccacc     300
gtggtgagga ggcaggcctt caccttttagc cctacctata agggagccgc tgcctggctg     360
agcctgctgg tgccctttgt gaatatccct atccctagcc ctgggctttt caagacccca     420
gccagggtga ccggaggagt gtttaaggtg ggaaacttca ccggcctgta taacctgccc     480
agcgatttct ttcctagcgt gaagaccctg tggaaggccg gaatcctgta caagaatgtg     540
tccatccctt ggacccacaa gggagccgct ctggtggtgg acttttccca gttcagcaga     600
aattccgcta tctgctccgt ggtgaggaga gctctgatgc cactgtatgc ctgtatctga     660

<210> SEQ ID NO 259
<211> LENGTH: 168
<212> TYPE: PRT
<213> ORGANISM: Unknown
<220> FEATURE:
<223> OTHER INFORMATION: PfCTL.1

<400> SEQUENCE: 259
```

Met Gln Val Gln Ile Gln Ser Leu Phe Leu Leu Leu Trp Val Pro
1               5                   10                  15

Gly Ser Arg Gly Ile Leu Ser Val Ser Ser Phe Leu Phe Val Asn Ala
            20                  25                  30

Ala Ala Gln Thr Asn Phe Lys Ser Leu Leu Arg Asn Leu Pro Ser Glu
        35                  40                  45

Asn Glu Arg Gly Tyr Lys Ala Ala Leu Leu Ala Cys Ala Gly Leu
50                  55                  60

Ala Tyr Lys Lys Ala Ala Ala Lys Phe Val Ala Ala Trp Thr Leu
65              70                  75                  80

Lys Ala Ala Lys Ala Phe Met Lys Ala Val Cys Val Glu Val Asn
                85                  90                  95

Ala Ala Ala Ser Phe Leu Phe Val Glu Ala Leu Phe Asn Ala Thr Pro
            100                 105                 110

Tyr Ala Gly Glu Pro Ala Pro Phe Lys Ala Ala Lys Tyr Lys Leu
            115                 120                 125

Ala Thr Ser Val Leu Lys Ala Gly Val Ser Glu Asn Ile Phe Leu Lys
130                 135                 140

Asn Ala Ala Tyr Phe Ile Leu Val Asn Leu Leu Ile Lys Ala Gly
145             150                 155                 160

Leu Leu Gly Val Val Ser Thr Val
                165

<210> SEQ ID NO 260
<211> LENGTH: 513
<212> TYPE: DNA
<213> ORGANISM: Unknown
<220> FEATURE:
<223> OTHER INFORMATION: PfCTL.1

<400> SEQUENCE: 260
atgggaatgc aggtgcagat ccagagcctg tttctgctcc tcctgtgggt gcccggatcc      60
agaggaatcc tgagcgtgtc ctctttcctg tttgtcaacg ccgctgcaca gaccaatttc     120
aagagcctcc tgaggaacct ccctccgag aacgaaagag gctacaaagc cgctgcactg     180
ctcgcctgcg ctggactggc ctataagaaa gccgctgcag ccaagttcgt ggccgcttgg     240
acactgaagg ccgctgcaaa agcctttatg aaggctgtct gtgtggaggt caatgccgct     300
gcatcttttcc tgtttgtgga ggccctcttt aacgctactc cttacgcagg gaaccagcc     360
cccttcaagg ccgctgcaaa atataagctg gcaaccagcg tgctgaaggc tggcgtgtcc     420
gagaatattt ttctgaaaaa cgccgctgca tacttcatcc tggtgaatct gctcattaag     480
gccggactcc tggggtggt ctctacagtg tga                                   513

<210> SEQ ID NO 261
<211> LENGTH: 157
<212> TYPE: PRT
<213> ORGANISM: Unknown
<220> FEATURE:
<223> OTHER INFORMATION: PfCTL.2

<400> SEQUENCE: 261

Met Gln Val Gln Ile Gln Ser Leu Phe Leu Leu Leu Trp Val Pro
1               5                   10                  15

Gly Ser Arg Gly Phe Val Glu Ala Leu Phe Gln Glu Tyr Asn Ala Ala
            20                  25                  30

Ala Lys Tyr Leu Val Ile Val Phe Leu Ile Asn Ala Leu Ala Cys Ala

```
                35                  40                  45
Gly Leu Ala Tyr Lys Lys Phe Tyr Phe Ile Leu Val Asn Leu Leu Lys
 50                  55                  60

Ala Ala Leu Phe Phe Ile Ile Phe Asn Lys Asn Ala Ala Ala Lys Phe
 65                  70                  75                  80

Val Ala Ala Trp Thr Leu Lys Ala Ala Ala Lys Phe Ile Leu Val Asn
                 85                  90                  95

Leu Leu Ile Phe His Asn Phe Gln Asp Glu Asn Ile Gly Ile Tyr
                100                 105                 110

Lys Leu Pro Tyr Gly Arg Thr Asn Leu Lys Ala Ala Val Leu Leu
            115                 120                 125

Gly Gly Val Gly Leu Val Leu Asn Phe Leu Ile Phe Phe Asp Leu Phe
130                 135                 140

Leu Val Lys Ala Val Leu Ala Gly Leu Leu Gly Val Val
145                 150                 155

<210> SEQ ID NO 262
<211> LENGTH: 480
<212> TYPE: DNA
<213> ORGANISM: Unknown
<220> FEATURE:
<223> OTHER INFORMATION: PfCTL.2

<400> SEQUENCE: 262
atgggaatgc aggtgcagat ccagagcctg tttctgctcc tcctgtgggt gcccggatcc    60
agaggattcg tggaggccct gtttcaggaa tacaacgccg ctgcaaagta tctcgtcatc   120
gtgttcctga tcaatgctct ggcatgcgcc ggcctcgctt acaaaaagtt ttacttcatt   180
ctggtcaacc tgctcaaggc cgctctgttc tttatcattt tcaataaaaa cgccgcagct   240
aagtttgtgg ccgcatggac cctgaaggcc gctgcaaaat catcctcgt gaatctgctc    300
attttcaca acttccaaga cgaggaaaat atcggaattt ataagctgcc ctacggagg    360
acaaacctga agccgctgc agtcctgctc ggcggagtgg ggctggtgct caattttctg   420
atcttctttg atctgttcct ggtgaaggcc gtcctggccg cctgctcgg agtcgtgtga   480

<210> SEQ ID NO 263
<211> LENGTH: 169
<212> TYPE: PRT
<213> ORGANISM: Unknown
<220> FEATURE:
<223> OTHER INFORMATION: PfCTL.3

<400> SEQUENCE: 263

Met Gln Val Gln Ile Gln Ser Leu Phe Leu Leu Leu Trp Val Pro
  1               5                  10                  15

Gly Ser Arg Gly Val Phe Leu Ile Phe Phe Asp Leu Phe Leu Asn Ala
             20                  25                  30

Ala Ala Pro Ser Asp Gly Lys Cys Asn Leu Tyr Lys Ala Ala Val
             35                  40                  45

Thr Cys Gly Asn Gly Ile Gln Val Arg Lys Leu Phe His Ile Phe Asp
 50                  55                  60

Gly Asp Asn Glu Ile Lys Ala His Val Leu Ser His Asn Ser Tyr Glu
 65                  70                  75                  80

Lys Asn Tyr Tyr Gly Lys Gln Glu Asn Trp Tyr Ser Leu Lys Lys Ile
                 85                  90                  95

Leu Ser Val Phe Phe Leu Ala Asn Ala Ala Ala Lys Phe Ile Lys Ser
                100                 105                 110
```

Leu Phe His Ile Phe Lys Ala Ala Ala Leu Tyr Ile Ser Phe Tyr Phe
            115                 120                 125

Ile Lys Ala Lys Phe Val Ala Ala Trp Thr Leu Lys Ala Ala Ala Lys
        130                 135                 140

Ala Ala Ala Tyr Tyr Ile Pro His Gln Ser Ser Leu Lys Ala Ala Ala
145                 150                 155                 160

Gly Leu Ile Met Val Leu Ser Phe Leu
                165

<210> SEQ ID NO 264
<211> LENGTH: 516
<212> TYPE: DNA
<213> ORGANISM: Unknown
<220> FEATURE:
<223> OTHER INFORMATION: PfCTL.3

<400> SEQUENCE: 264
atgggaatgc aggtgcagat ccagagcctg tttctgctcc tcctgtgggt gcccggatcc      60
agaggagtgt ccctgatctt cttttgacctg ttcctgaacg ccgctgcacc cagcgatggc     120
aagtgcaatc tctacaaggc cgctgcagtg acctgtggaa acgggattca ggtcaggaaa     180
ctctttcaca tcttcgacgg cgataacgag atcaaggccc atgtgctgtc ccacaattct     240
tatgaaaaaa actactatgg aaagcaagag aattggtaca gcctgaagaa aattctgtcc     300
gtgttctttc tcgccaacgc cgctgcaaag tttatcaagt ctctgttcca tattttcaag     360
gccgctgcac tctacatcag cttctatttt attaaagcca aatttgtggc cgcttggaca     420
ctgaaggccg ctgcaaaagc cgctgcatac tatatccctc accagagctc cctgaaggcc     480
gctgcagggc tgatcatggt gctctctttc ctgtga                              516

<210> SEQ ID NO 265
<211> LENGTH: 456
<212> TYPE: PRT
<213> ORGANISM: Unknown
<220> FEATURE:
<223> OTHER INFORMATION: PfCTL/HTL/(N)

<400> SEQUENCE: 265

Met Gln Val Gln Ile Gln Ser Leu Phe Leu Leu Leu Trp Val Pro
1               5                   10                  15

Gly Ser Arg Gly Ser Ser Val Phe Asn Val Val Asn Ser Ser Ile Gly
            20                  25                  30

Leu Ile Met Val Leu Ser Phe Leu Gly Pro Gly Pro Gly Leu Tyr Ile
        35                  40                  45

Ser Phe Tyr Phe Ile Leu Val Asn Leu Leu Ile Phe His Ile Asn Gly
    50                  55                  60

Lys Ile Ile Lys Asn Ser Glu Gly Pro Gly Pro Gly Pro Asp Ser Ile
65                  70                  75                  80

Gln Asp Ser Leu Lys Glu Ser Arg Lys Leu Ser Gly Pro Gly Pro Gly
                85                  90                  95

Val Leu Ala Gly Leu Leu Gly Val Val Ser Thr Val Leu Leu Gly Gly
            100                 105                 110

Val Gly Leu Val Leu Gly Pro Gly Pro Gly Leu Pro Ser Glu Asn Glu
        115                 120                 125

Arg Gly Tyr Tyr Ile Pro His Gln Ser Ser Leu Gly Pro Gly Pro Gly
    130                 135                 140

Gln Thr Asn Phe Lys Ser Leu Leu Arg Asn Leu Gly Val Ser Glu Asn

-continued

```
            145                 150                 155                 160
Ile Phe Leu Lys Gly Pro Gly Pro Gly Phe Gln Asp Glu Glu Asn Ile
                165                 170                 175
Gly Ile Tyr Gly Pro Gly Pro Gly Lys Tyr Leu Val Ile Val Phe Leu
                180                 185                 190
Ile Phe Phe Asp Leu Phe Leu Val Gly Pro Gly Pro Gly Lys Phe Ile
                195                 200                 205
Lys Ser Leu Phe His Ile Phe Asp Gly Asp Asn Glu Ile Gly Pro Gly
                210                 215                 220
Pro Gly Lys Ser Lys Tyr Lys Leu Ala Thr Ser Val Leu Ala Gly Leu
225                 230                 235                 240
Leu Gly Pro Gly Pro Gly Leu Pro Tyr Gly Lys Thr Asn Leu Gly Pro
                245                 250                 255
Gly Pro Gly Arg His Asn Trp Val Asn His Ala Val Pro Leu Ala Met
                260                 265                 270
Lys Leu Ile Gly Pro Gly Pro Gly Met Arg Lys Leu Ala Ile Leu Ser
                275                 280                 285
Val Ser Ser Phe Leu Phe Val Glu Ala Leu Phe Gln Glu Tyr Gly Pro
                290                 295                 300
Gly Pro Gly Val Thr Cys Gly Asn Gly Ile Gln Val Arg Gly Pro Gly
305                 310                 315                 320
Pro Gly Met Asn Tyr Tyr Gly Lys Gln Glu Asn Trp Tyr Ser Leu Lys
                325                 330                 335
Lys Gly Pro Gly Pro Gly Pro Ser Asp Gly Lys Cys Asn Leu Tyr Ala
                340                 345                 350
Asp Ser Ala Trp Glu Asn Val Lys Asn Val Ile Gly Pro Phe Met Lys
                355                 360                 365
Ala Val Cys Val Glu Val Gly Pro Gly Pro Gly Lys Ile Leu Ser Val
                370                 375                 380
Phe Phe Leu Ala Leu Phe Ile Ile Phe Asn Lys Gly Pro Gly Pro
385                 390                 395                 400
Gly His Val Leu Ser His Asn Ser Tyr Glu Lys Gly Pro Gly Pro Gly
                405                 410                 415
Lys Tyr Lys Ile Ala Gly Gly Ile Ala Gly Gly Leu Ala Leu Leu Ala
                420                 425                 430
Cys Ala Gly Leu Ala Tyr Lys Phe Val Val Pro Gly Ala Ala Thr Pro
                435                 440                 445
Tyr Ala Gly Glu Pro Ala Pro Phe
                450                 455

<210> SEQ ID NO 266
<211> LENGTH: 1385
<212> TYPE: DNA
<213> ORGANISM: Unknown
<220> FEATURE:
<223> OTHER INFORMATION: PfCTL/HTL/(N)

<400> SEQUENCE: 266
atgggaatgc aggtgcagat ccagagcctg tttctgctcc tcctgtgggt gcccggatcc      60
agaggaagta gtgtgttcaa tgttgtgaac tcatcaattg gtctgatcat ggtgctgagc     120
tttctcgggc agggccagg attatatatt tctttctact tcatccttgt caacctgtta     180
atattccaca ttaacggcaa aataataaag aacagtgaag gcctgggcc tgggcctgac     240 tcgatccagg attctctaaa agaatcgagg aagctctccg gaccaggccc tggtgtactc     300
```

```
gccgggttgc tgggagtagt tagcacagtg ctgttaggag gcgtcggcct cgtcttagga     360
cctggaccag gtctgccgtc cgaaaacgaa agaggatact acatacctca ccagagcagc     420
ctcggcccag gccccggaca aaccaatttc aaatccctct tgcgaaatct aggagtgagc     480
gagaacatat ttcttaaagg acccggtccc ggctttcagg acgaggagaa tataggtatt     540
tacggtccag gacctggaaa atacctagta atcgtattcc taatttttt tgacctattt      600 ctggtgggcc caggtcccgg aaagttcatt aaatcactct tccacatttt tgacggagat     660
aacgagatag gacccggtcc cgggaaatca agtacaaac tagccacttc agtgctggcc      720
ggccttctag ggccgggccc agggctcccc tatggaaaga caaatcttgg ccccggtcca     780
ggacggcaca actgggtgaa tcatgcggtt ccattggcca tgaaactaat cgggcccggt     840
ccaggcatgc gcaaacttgc aattctaagc gtaagttcat ttctgttcgt agaggcactg     900
tttcaagaat atggcccagg acctggcgtc acatgtggga atgggatcca ggtgagagga     960
ccgggacctg gtatgaacta ttacggtaaa caggaaaatt ggtactccct gaaaaagggt    1020
ccaggccccg gcccctcaga tggtaagtgc aacctgtatg ctgactcagc atgggagaac    1080 gtaaaaatg taataggccc attcatgaag gcagtttgtg tcgaagtcgg accaggccca    1140
ggaaaaatac tttctgtctt cttcctagct ctcttcttca tcatcttcaa caagggacca    1200
gggccaggtc acgtgttatc ccataactct tatgaaaaag gccaggacc tgggaaatac     1260 aaaatcgcag gagggatcgc cggcgggcta gcgctccttg cctgcgcagg cttggcttac    1320
aaattcgttg taccaggagc tgcaacaccc tatgcaggag aacctgcccc attttgaaga    1380
tctgc                                                                1385

<210> SEQ ID NO 267
<211> LENGTH: 419
<212> TYPE: PRT
<213> ORGANISM: Unknown
<220> FEATURE:
<223> OTHER INFORMATION: Pf33

<400> SEQUENCE: 267

Met Gly Met Gln Val Gln Ile Gln Ser Leu Phe Leu Leu Leu Leu Trp
1               5                   10                  15

Val Pro Gly Ser Arg Gly Phe Met Lys Ala Val Cys Val Glu Val Asn
            20                  25                  30

Val Thr Cys Gly Asn Gly Ile Gln Val Arg Lys Gly Leu Ile Met Val
        35                  40                  45

Leu Ser Phe Leu Asn Ala Ala Leu Phe His Ile Phe Asp Gly Asp Asn
    50                  55                  60

Glu Ile Lys Ala Ala Leu Leu Ala Cys Ala Gly Leu Ala Tyr Lys Lys
65                  70                  75                  80

Ser Phe Leu Phe Val Glu Ala Leu Phe Asn Ala Ala Pro Ser Asp Gly
                85                  90                  95

Lys Cys Asn Leu Tyr Lys Ala Ala Gln Thr Asn Phe Lys Ser Leu Leu
            100                 105                 110

Arg Asn Leu Pro Ser Glu Asn Glu Arg Gly Tyr Lys Ala Ala Gly Val
        115                 120                 125

Ser Glu Asn Ile Phe Leu Lys Asn Ala Ala Tyr Phe Ile Leu Val
    130                 135                 140

Asn Leu Leu Ile Lys Ala Ala Ala Ile Leu Ser Val Ser Ser Phe Leu
145                 150                 155                 160

Phe Val Asn Thr Pro Tyr Ala Gly Glu Pro Ala Pro Phe Lys Ala Ala
```

165                 170                 175
Ala Lys Tyr Lys Leu Ala Thr Ser Val Leu Lys Ala Ala Val Phe Leu
            180                 185                 190

Ile Phe Phe Asp Leu Phe Leu Asn Tyr Tyr Ile Pro His Gln Ser Ser
        195                 200                 205

Leu Lys Ala Ala Gly Leu Leu Gly Asn Val Ser Thr Val Gly Ala Val
    210                 215                 220

Leu Leu Gly Gly Val Gly Leu Val Leu Asn Leu Ala Cys Ala Gly Leu
225                 230                 235                 240

Ala Tyr Lys Lys Ala Lys Phe Ile Lys Ser Leu Phe His Ile Phe Lys
                245                 250                 255

Ala Ala Phe Tyr Phe Ile Leu Val Asn Leu Leu Lys Ala Phe Leu Ile
            260                 265                 270

Phe Phe Asp Leu Phe Leu Val Lys Ala Leu Phe Phe Ile Ile Phe Asn
        275                 280                 285

Lys Asn Tyr Tyr Gly Lys Gln Glu Asn Trp Tyr Ser Leu Lys Phe Val
    290                 295                 300

Glu Ala Leu Phe Gln Glu Tyr Asn Ala Ala Lys Phe Val Ala Ala
305                 310                 315                 320

Trp Thr Leu Lys Ala Ala Ala Lys Ile Leu Ser Val Phe Phe Leu Ala
                325                 330                 335

Asn Ala Val Leu Ala Gly Leu Gly Asn Val Asn Phe Gln Asp Glu
            340                 345                 350

Glu Asn Ile Gly Ile Tyr Lys Ala Ala Ala Leu Tyr Ile Ser Phe Tyr
        355                 360                 365

Phe Ile Lys Ala Phe Ile Leu Val Asn Leu Ile Phe His Asn Ala
    370                 375                 380

Ala Leu Pro Tyr Gly Arg Thr Asn Leu Lys Ala Ala His Val Leu Ser
385                 390                 395                 400

His Asn Ser Tyr Glu Lys Asn Ala Ala Ala Lys Tyr Leu Val Ile Val
                405                 410                 415

Phe Leu Ile

<210> SEQ ID NO 268
<211> LENGTH: 1269
<212> TYPE: DNA
<213> ORGANISM: Unknown
<220> FEATURE:
<223> OTHER INFORMATION: Pf33

<400> SEQUENCE: 268
gccgccacca tgggaatgca ggtgcagatc cagagcctgt tctgctcct cctgtgggtg      60 cccggatcca gaggatttat gaaagctgtc tgtgtagagg tgaatgtaac atgcggtaac     120
ggaattcagg tgagaaaggg actcatcatg gtactcagct ttctgaacgc agccctgttc     180
cacatctttg acggagacaa tgaaatcaaa gccgcattgc tcgcctgtgc cggactagcc     240
tataaaaaga gtttccttt cgttgaagca ctatttaacg cagcacccag tgacggtaaa     300
tgcaacctat ataaagcagc tcagactaat ttcaaaagcc tgttaagaaa tctgccctca     360
gagaatgaaa ggggttacaa agccgccggc gtgtccgaga atattttcct gaagaacgcc     420
gctgcttatt ttatactcgt gaatctactc ataaaggcag ccgcaatcct ttcagtgtcc     480
agctttctgt tgttaacac accatatgcg ggcgagccgg ctcctttcaa ggctgcagca     540
aaatacaagc ttgccacatc agtattgaaa gcagctgtgt ttttgatatt ctttgatctt     600

-continued

```
tttttaaact actacatacc tcatcagtct agtcttaaag cagccgggct actgggaac    660 gtctctactg tggggccgt cttacttgga ggagttggcc tcgtgttgaa cctcgcgtgc    720
gcaggtctgg cctacaaaaa agcgaaattc atcaagtctc tgttccacat ttttaaagcc    780
gcattctatt tcatactagt gaaccttctc aaagctttcc tgatcttctt cgatctattc    840
ctcgtaaaag cgctattctt cattatcttt aacaaaaatt attacggcaa gcaagaaaat    900
tggtactcac tcaagtttgt agaagctctg ttccaggaat acaacgccgc tgctaaattc    960
gttgcagctt ggaccctgaa agcagctgca aagatcctat cggtcttctt tctcgctaat   1020
gccgtattag caggacttct aggcaacgtg aactttcaag acgaagagaa ataggcatc    1080 tacaaagccg cagcactgta catttcattc tacttcatca aggccttcat actggtcaac   1140
cttctgatat ttcataatgc agcactgcca tatgggagaa ccaacttgaa agcggcccac   1200
gtgttgagcc acaactccta cgagaagaac gccgccgcga atatctcgt cattgtcttc    1260 ctgatttga                                                           1269
```

<210> SEQ ID NO 269
<211> LENGTH: 180
<212> TYPE: PRT
<213> ORGANISM: Unknown
<220> FEATURE:
<223> OTHER INFORMATION: TB.1

<400> SEQUENCE: 269

```
Met Gln Val Gln Ile Gln Ser Leu Phe Leu Leu Leu Leu Trp Val Pro
1               5                   10                  15

Gly Ser Arg Gly Arg Met Ser Arg Val Thr Thr Phe Thr Val Lys Ala
            20                  25                  30

Leu Val Leu Leu Met Leu Pro Val Val Asn Leu Met Ile Gly Thr Ala
        35                  40                  45

Ala Ala Val Val Lys Ala Leu Val Leu Leu Met Leu Pro Val Gly Ala
    50                  55                  60

Gly Leu Met Thr Ala Val Tyr Leu Val Gly Ala Ala Met Ala Leu
65                  70                  75                  80

Leu Arg Leu Pro Val Lys Arg Met Phe Ala Ala Asn Leu Gly Val Asn
                85                  90                  95

Ser Leu Tyr Phe Gly Gly Ile Cys Val Gly Arg Leu Pro Leu Val Leu
            100                 105                 110

Pro Ala Val Asn Ala Ala Ala Lys Phe Val Ala Ala Trp Thr Leu
        115                 120                 125

Lys Ala Ala Lys Ala Ala Ala Arg Leu Met Ile Gly Thr Ala Ala
    130                 135                 140

Ala Gly Phe Val Val Ala Leu Ile Pro Leu Val Asn Ala Met Thr Tyr
145                 150                 155                 160

Ala Ala Pro Leu Phe Val Gly Ala Ala Ala Met Ala Leu Leu Arg
                165                 170                 175

Leu Pro Leu Val
            180
```

<210> SEQ ID NO 270
<211> LENGTH: 543
<212> TYPE: DNA
<213> ORGANISM: Unknown
<220> FEATURE:
<223> OTHER INFORMATION: TB.1

<400> SEQUENCE: 270

-continued

```
atgcaggtgc agatccagag cctgtttctg ctcctcctgt gggtgcccgg atccagagga      60
aggatgagca gagtgaccac attcactgtc aaggccctgg tgctcctgat gctccccgtc     120
gtgaacctga tgatcggcac cgctgcagcc gtcgtgaaag ctctcgtcct gctcatgctc     180
cctgtgggag cagggctgat gacagccgtg tacctggtcg gcgctgcagc catggccctc     240
ctgcggctgc cagtgaagcg catgtttgct gcaaatctgg gagtcaactc cctctatttc     300
gggggcattt gcgtgggaag gctgccgctc gtgctgcctg ctgtgaatgc agccgctgcc     360
aaatttgtcg ccgcttggac tctgaaggca gccgctaagg ccgctgcaag actgatgatc     420
gggaccgccg ctgccggctt cgtggtcgcc ctgattcccc tggtgaacgc catgacatac     480
gcagctcctc tgtttgtggg agccgctgca gccatggctc tcctgcggct gccactggtg     540
tga                                                                   543
```

<210> SEQ ID NO 271
<211> LENGTH: 148
<212> TYPE: PRT
<213> ORGANISM: Unknown
<220> FEATURE:
<223> OTHER INFORMATION: BCL A2 #90

<400> SEQUENCE: 271

```
Met Gln Val Gln Ile Gln Ser Leu Phe Leu Leu Leu Leu Trp Val Pro
1               5                   10                  15

Gly Ser Arg Gly Ile Met Ile Gly His Leu Val Gly Val Asn Arg Leu
            20                  25                  30

Leu Gln Glu Thr Glu Leu Val Asn Ala Lys Val Ala Glu Ile Val His
        35                  40                  45

Phe Leu Asn Ala Lys Val Phe Gly Ser Leu Ala Phe Val Asn Ala Tyr
    50                  55                  60

Leu Ser Gly Ala Asn Leu Asn Val Gly Ala Ala Tyr Leu Gln Leu Val
65                  70                  75                  80

Phe Gly Ile Glu Val Asn Ala Ala Ala Lys Phe Val Ala Ala Trp Thr
                85                  90                  95

Leu Lys Ala Ala Ala Lys Ala Ala Ala Val Val Leu Gly Val Val Phe
            100                 105                 110

Gly Ile Asn Ser Met Pro Pro Gly Thr Arg Val Asn Ala Ala Ala
            115                 120                 125

Ala Thr Val Gly Ile Met Ile Gly Val Asn Ala Lys Leu Cys Pro Val
    130                 135                 140

Gln Leu Trp Val
145
```

<210> SEQ ID NO 272
<211> LENGTH: 447
<212> TYPE: DNA
<213> ORGANISM: Unknown
<220> FEATURE:
<223> OTHER INFORMATION: BCL A2 #90

<400> SEQUENCE: 272

```
atgcaggtgc agatccagag cctgtttctg ctcctcctgt gggtgcccgg gtccagagga      60
attatgatcg gccatctggt gggcgtcaac agactgctgc aggaaaccga gctggtgaat     120
gccaaggtgg ccgaaattgt gcactttctc aacgcaaagg tgtttggttc cctggctttt     180
gtcaatgcct atctgagcgg cgctaacctc aacgtcggag ccgcctacct ccagctggtc     240
```

-continued

```
ttcggcatcg aggtcaacgc tgctgcaaaa ttcgtggcag cttggaccct caaggctgca    300
gcaaaggctg ccgccgtcgt gctcggagtg gtgttcggga tcaactctat gccacctccc    360
gggactaggg tcaatgctgc cgccgcaaca gtgggaatca tgattggggt gaatgccaaa    420
ctgtgcccag tgcaactgtg ggtgtga                                        447
```

<210> SEQ ID NO 273
<211> LENGTH: 144
<212> TYPE: PRT
<213> ORGANISM: Unknown
<220> FEATURE:
<223> OTHER INFORMATION: BCL A2 #88

<400> SEQUENCE: 273

```
Met Gln Val Gln Ile Gln Ser Leu Phe Leu Leu Leu Leu Trp Val Pro
1               5                   10                  15

Gly Ser Arg Gly Val Val Leu Gly Val Val Phe Gly Ile Asn Ala Ala
            20                  25                  30

Ala Ala Lys Phe Val Ala Ala Trp Thr Leu Lys Ala Ala Ala Lys Val
        35                  40                  45

Ala Glu Ile Val His Phe Leu Asn Ala Tyr Leu Ser Gly Ala Asn Leu
    50                  55                  60

Asn Val Gly Ala Ala Tyr Leu Gln Leu Val Phe Gly Ile Glu Val Asn
65                  70                  75                  80

Ile Met Ile Gly His Leu Val Gly Val Asn Arg Leu Leu Gln Glu Thr
                85                  90                  95

Glu Leu Val Asn Ala Lys Val Phe Gly Ser Leu Ala Phe Val Asn Ala
            100                 105                 110

Lys Leu Cys Pro Val Gln Leu Trp Val Asn Ala Ala Ala Thr Val
        115                 120                 125

Gly Ile Met Ile Gly Val Asn Ser Met Pro Pro Gly Thr Arg Val
    130                 135                 140
```

<210> SEQ ID NO 274
<211> LENGTH: 435
<212> TYPE: DNA
<213> ORGANISM: Unknown
<220> FEATURE:
<223> OTHER INFORMATION: BCL A2 #88

<400> SEQUENCE: 274

```
atgcaggtgc agatccagag cctgtttctg ctcctcctgt gggtgcccgg gtccagagga     60
gtcgtgctgg gagtcgtctt cggcattaat gccgccgctg caaagttcgt ggctgcctgg    120
accctgaagg ccgcagctaa gtggcagaga tcgtgcact ttctgaacgc ctacctgagc    180
ggagcaaatc tgaacgtcgg cgctgcctat ctgcagctcg tgtttggaat tgaagtgaac    240
atcatgattg acatctggt gggcgtgaac aggctgctcc aggaaactga gctggtcaac    300
gctaaagtgt tcgggtctct cgcctttgtg aacgctaagc tctgccccgt ccaactctgg    360
gtcaatgccg cagccgctac agtggggatc atgatcggcg tgaactccat gcctccacca    420
gggaccagag tgtga                                                      435
```

<210> SEQ ID NO 275
<211> LENGTH: 147
<212> TYPE: PRT
<213> ORGANISM: Unknown
<220> FEATURE:
<223> OTHER INFORMATION: BCL A2 #63

```
<400> SEQUENCE: 275

Met Gln Val Gln Ile Gln Ser Leu Phe Leu Leu Leu Leu Trp Val Pro
1               5                   10                  15

Gly Ser Arg Gly Lys Leu Cys Pro Val Gln Leu Trp Val Asn Ala Ala
            20                  25                  30

Ala Ala Thr Val Gly Ile Met Ile Gly Val Asn Ile Met Ile Gly His
        35                  40                  45

Leu Val Gly Val Asn Arg Leu Leu Gln Glu Thr Glu Leu Val Asn Ala
    50                  55                  60

Lys Val Ala Glu Ile Val His Phe Leu Asn Ala Lys Val Phe Gly Ser
65                  70                  75                  80

Leu Ala Phe Val Asn Ala Tyr Leu Ser Gly Ala Asn Leu Asn Val Gly
                85                  90                  95

Ala Ala Tyr Leu Gln Leu Val Phe Gly Ile Glu Val Asn Ala Ala Ala
            100                 105                 110

Lys Phe Val Ala Ala Trp Thr Leu Lys Ala Ala Lys Ala Ala Ala
            115                 120                 125

Val Val Leu Gly Val Val Phe Gly Ile Asn Ser Met Pro Pro Pro Gly
130                 135                 140

Thr Arg Val
145

<210> SEQ ID NO 276
<211> LENGTH: 450
<212> TYPE: DNA
<213> ORGANISM: Unknown
<220> FEATURE:
<223> OTHER INFORMATION: BCL A2 #63

<400> SEQUENCE: 276
atgcaggtgc agatccagag cctgtttctg ctcctcctgt gggtgcccgg gtccagagga    60
aagctctgcc ccgtgcaact gtgggtcaac gccgccgccg caaccgtcgg cattatgatc   120
ggggtgaaca tcatgatcgg acacctggtc ggcgtgaaca ggctgctgca ggagacagaa   180
ctggtcaatg ccaaggtggc tgaaattgtc catttcctga atgccaaagt gttcggctct   240
ctcgctttcg tgaacgctta tctgagcgga gctaacctca acgtgggggc cgcataccta   300
cagctcgtct ttgggattga ggtgaatgcc gcagctaaat ttgtcgctgc ctggaccctg   360
aaggcagcag ccaaggctgc cgcagtggtg ctgggagtgg tgtttggaat caattccatg   420
cctccaccag gcactagagt gtgaggatcc                                    450

<210> SEQ ID NO 277
<211> LENGTH: 183
<212> TYPE: PRT
<213> ORGANISM: Unknown
<220> FEATURE:
<223> OTHER INFORMATION: Prostate 1

<400> SEQUENCE: 277

Leu Thr Phe Phe Trp Leu Asp Arg Ser Val Lys Ala Ala Ala Val Leu
1               5                   10                  15

Val His Pro Gln Trp Val Leu Thr Val Lys Ala Ala Ala Leu Leu Gln
            20                  25                  30

Glu Arg Gly Val Ala Tyr Ile Lys Ala Ala Leu Leu Leu Ser Ile Ala
        35                  40                  45

Leu Ser Val Asn Pro Leu Val Cys Asn Gly Val Leu Gln Gly Val Lys
    50                  55                  60
```

Ala Ala Ile Met Tyr Ser Ala His Asp Thr Thr Val Lys Ala Ala
65                  70                  75                  80

Phe Leu Thr Pro Lys Lys Leu Gln Cys Val Asn Ala Met Met Asn Asp
                85                  90                  95

Gln Leu Met Phe Leu Asn Ala Gly Leu Pro Ser Ile Pro Val His Pro
            100                 105                 110

Val Lys Ala Ala Ala Leu Gly Thr Thr Cys Tyr Val Gly Ala Ala Ile
        115                 120                 125

Leu Leu Trp Gln Pro Ile Pro Val Asn Phe Leu Arg Pro Arg Ser Leu
    130                 135                 140

Gln Cys Val Lys Ala Phe Leu Thr Leu Ser Val Thr Trp Ile Gly Val
145                 150                 155                 160

Asn Ala Leu Leu Tyr Ser Leu Val His Asn Leu Gly Ala Ala Thr Leu
                165                 170                 175

Met Ser Ala Met Thr Asn Leu
            180

<210> SEQ ID NO 278
<211> LENGTH: 648
<212> TYPE: DNA
<213> ORGANISM: Unknown
<220> FEATURE:
<223> OTHER INFORMATION: Prostate 1

<400> SEQUENCE: 278
atgcaggtgc agatccagag cctgtttctg ctcctcctgt gggtgcccgg gtccagagga      60
ttgacatttt tttggctgga tagatcggtt aaggctgcag ccgtgcttgt tcatccccag     120
tgggtcttga ccgtaaaggc tgccgcgctg ctacaagaaa gaggggtcgc atacatcaaa     180
gctgctctcc tcttgagtat tgcgctaagt gtaaacccgc tagtttgtaa tggggtgtta     240
caaggtgtga aagcggcgat tatgtacagt gcccacgaca ctaccgtaaa agcagccgct     300
ttcctgaccc caaaaaaact ccaatgcgtg aacgcaatga tgaatgatca gctgatgttt     360
ttaaacgctg gcttaccttc tataccggtt catccagtca aggccgcggc attgggtacg     420
acgtgttatg ttggagcagc gatacttctt tggcagccca taccagtaaa ttttttaaga     480
cctagatcct tacaatgcgt caaagcattc cttacactct cagtaacttg gatcggagtc     540
aatgctctgc tatatagcct cgtacacaac ttgggcgcgg ccacacttat gagtgcaatg     600
acgaatttag ctaagttcgt ggcggcctgg actctaaagg ccgcagca                 648

<210> SEQ ID NO 279
<211> LENGTH: 322
<212> TYPE: PRT
<213> ORGANISM: Human immunodeficiency virus

<400> SEQUENCE: 279

Met Glu Lys Val Tyr Leu Ala Trp Val Pro Ala His Lys Gly Ile Gly
1               5                   10                  15

Gly Gly Pro Gly Pro Gly Gln Lys Gln Ile Thr Lys Ile Gln Asn Phe
            20                  25                  30

Arg Val Tyr Tyr Arg Gly Pro Gly Pro Gly Trp Glu Phe Val Asn Thr
        35                  40                  45

Pro Pro Leu Val Lys Leu Trp Tyr Gln Gly Pro Gly Pro Gly Tyr Arg
    50                  55                  60

Lys Ile Leu Arg Gln Arg Lys Ile Asp Arg Leu Ile Asp Gly Pro Gly
65                  70                  75                  80

```
Pro Gly Gln His Leu Leu Gln Leu Thr Val Trp Gly Ile Lys Gln Leu
                85                  90                  95
Gln Gly Pro Gly Pro Gly Gly Glu Ile Tyr Lys Arg Trp Ile Ile Leu
            100                 105                 110
Gly Leu Asn Lys Ile Val Arg Met Tyr Gly Pro Gly Pro Gly Gln Gly
        115                 120                 125
Gln Met Val His Gln Ala Ile Ser Pro Arg Thr Leu Asn Gly Pro Gly
    130                 135                 140
Pro Gly Ile Lys Gln Phe Ile Asn Met Trp Gln Glu Val Gly Lys Ala
145                 150                 155                 160
Met Tyr Gly Pro Gly Pro Gly Trp Ala Gly Ile Lys Gln Glu Phe Gly
                165                 170                 175
Ile Pro Tyr Asn Pro Gln Gly Pro Gly Lys Thr Ala Val Gln
            180                 185                 190
Met Ala Val Phe Ile His Asn Phe Lys Arg Gly Pro Gly Pro Gly Ser
        195                 200                 205
Pro Ala Ile Phe Gln Ser Ser Met Thr Lys Ile Leu Glu Pro Gly Pro
    210                 215                 220
Gly Pro Gly Glu Val Asn Ile Val Thr Asp Ser Gln Tyr Ala Leu Gly
225                 230                 235                 240
Ile Ile Gly Pro Gly Pro Gly His Ser Asn Trp Arg Ala Met Ala Ser
                245                 250                 255
Asp Phe Asn Leu Pro Pro Gly Pro Gly Pro Gly Ala Glu Thr Phe Tyr
            260                 265                 270
Val Asp Gly Ala Ala Asn Arg Glu Thr Lys Gly Pro Gly Pro Gly Gly
        275                 280                 285
Ala Val Val Ile Gln Asp Asn Ser Asp Ile Lys Val Val Pro Gly Pro
    290                 295                 300
Gly Pro Gly Phe Arg Lys Tyr Thr Ala Phe Thr Ile Pro Ser Ile Asn
305                 310                 315                 320
Asn Glu

<210> SEQ ID NO 280
<211> LENGTH: 969
<212> TYPE: DNA
<213> ORGANISM: Human immunodeficiency virus

<400> SEQUENCE: 280
atggagaagg tgtacctggc ctgggttcca gcccacaaag gcatcggggg agggcccgga    60
cctgggcaga aacagatcac caagatccag aacttccggg tatactaccg gggacctggt   120
ccaggttggg agtttgtgaa cacaccaccc ttagtaaagc tctggtacca gggccccggt   180
cccggatacc gtaaaatcct gaggcaaaga aagatagatc gcctcattga tgggcccggc   240
ccaggccagc accttctgca gcttacagtg tggggaatta aacagctgca ggggccgggc   300
cccggggggg aaatttataa aaggtggatc attctgggtc tgaacaagat cgtccgcatg   360
tatggccctg gacccggaca ggggcagatg gtccaccaag caatcagccc tcgaaccttg   420
aatggaccgg gcccaggaat caagcaattc attaacatgt ggcaagaagt tggtaaggct   480
atgtacggtc ccggccctgg atgggcaggg ataaaacagg agtttggaat cccttacaat   540
ccccagggtc ctgggccagg taaaacggca gtgcagatgg ccgtgttcat tcataatttt   600 aagcgggggcc ctggacctgg cagcccagct atatttcaaa gttcgatgac caaaatcttg   660
gagcccggcc agggccgggc cgaagtgaac attgtcacag attctcagta tgccctcggc   720
```

```
atcatagggc cggaccagg gcattccaat tggcgcgcca tggcgtctga ctttaatcta    780
cctcctgggc caggccctgg cgcggaaact ttctatgtgg acggcgctgc aaacagggag    840
actaagggac ccggacccgg cggcgctgta gtcattcagg acaactcaga catcaaggtg    900
gttcccggtc caggccccgg gttcagaaag tataccgcct tcactattcc gtccatcaac    960
aatgagtga                                                             969
```

```
<210> SEQ ID NO 281
<211> LENGTH: 340
<212> TYPE: PRT
<213> ORGANISM: Human immunodeficiency virus

<400> SEQUENCE: 281

Met Glu Lys Val Tyr Leu Ala Trp Val Pro Ala His Lys Gly Ile Gly
1               5                   10                  15

Gly Gly Pro Gly Pro Gly Gln Lys Gln Ile Thr Lys Ile Gln Asn Phe
            20                  25                  30

Arg Val Tyr Tyr Arg Gly Pro Gly Pro Gly Trp Glu Phe Val Asn Thr
        35                  40                  45

Pro Pro Leu Val Lys Leu Trp Tyr Gln Gly Pro Gly Pro Gly Tyr Arg
    50                  55                  60

Lys Ile Leu Arg Gln Arg Lys Ile Asp Arg Leu Ile Asp Gly Pro Gly
65                  70                  75                  80

Pro Gly Gln His Leu Leu Gln Leu Thr Val Trp Gly Ile Lys Gln Leu
                85                  90                  95

Gln Gly Pro Gly Pro Gly Gly Glu Ile Tyr Lys Arg Trp Ile Ile Leu
            100                 105                 110

Gly Leu Asn Lys Ile Val Arg Met Tyr Gly Pro Gly Pro Gly Gln Gly
        115                 120                 125

Gln Met Val His Gln Ala Ile Ser Pro Arg Thr Leu Asn Gly Pro Gly
    130                 135                 140

Pro Gly Ile Lys Gln Phe Ile Asn Met Trp Gln Glu Val Gly Lys Ala
145                 150                 155                 160

Met Tyr Gly Pro Gly Pro Gly Trp Ala Gly Ile Lys Gln Glu Phe Gly
                165                 170                 175

Ile Pro Tyr Asn Pro Gln Gly Pro Gly Pro Gly Lys Thr Ala Val Gln
            180                 185                 190

Met Ala Val Phe Ile His Asn Phe Lys Arg Gly Pro Gly Pro Gly Ser
        195                 200                 205

Pro Ala Ile Phe Gln Ser Ser Met Thr Lys Ile Leu Glu Pro Gly Pro
    210                 215                 220

Gly Pro Gly Glu Val Asn Ile Val Thr Asp Ser Gln Tyr Ala Leu Gly
225                 230                 235                 240

Ile Ile Gly Pro Gly Pro Gly His Ser Asn Trp Arg Ala Met Ala Ser
                245                 250                 255

Asp Phe Asn Leu Pro Pro Gly Pro Gly Pro Gly Ala Glu Thr Phe Tyr
            260                 265                 270

Val Asp Gly Ala Ala Asn Arg Glu Thr Lys Gly Pro Gly Pro Gly Gly
        275                 280                 285

Ala Val Val Ile Gln Asp Asn Ser Asp Ile Lys Val Val Pro Gly Pro
    290                 295                 300

Gly Pro Gly Phe Arg Lys Tyr Thr Ala Phe Thr Ile Pro Ser Ile Asn
305                 310                 315                 320
```

-continued

```
Asn Glu Gly Pro Gly Pro Gly Ala Lys Phe Val Ala Ala Trp Thr Leu
            325                 330                 335

Lys Ala Ala Ala
        340

<210> SEQ ID NO 282
<211> LENGTH: 1023
<212> TYPE: DNA
<213> ORGANISM: Human immunodeficiency virus

<400> SEQUENCE: 282
atggagaagg tgtacctggc ctgggttcca gcccacaaag gcatcggggg agggcccgga        60
cctgggcaga acagatcac caagatccag aacttccggg tatactaccg gggacctggt       120
ccaggttggg agtttgtgaa cacaccaccc ttagtaaagc tctggtacca gggccccggt       180
cccggatacc gtaaaatcct gaggcaaaga aagatagatc gcctcattga tggcccgggc       240
ccaggccagc accttctgca gcttacagtg tggggaatta acagctgca ggggccgggc        300 cccgggggg aaatttataa aggtggatc attctgggtc tgaacaagat cgtccgcatg         360
tatggccctg acccggaca ggggcagatg gtccaccaag caatcagccc tcgaaccttg        420
aatggaccgg cccaggaat caagcaattc attaacatgt ggcaagaagt tggtaaggct        480
atgtacggtc ccggccctgg atgggcaggg ataaaacagg agtttggaat cccttacaat       540
ccccagggtc ctgggccagg taaaacggca gtgcagatgg ccgtgttcat tcataatttt       600
aagcggggcc ctggacctgg cagcccagct atatttcaaa gttcgatgac caaaatcttg       660
gagcccggcc cagggccggg cgaagtgaac attgtcacag attctcagta tgccctcggc       720
atcatagggc ccggaccagg gcattccaat tggcgcgcca tggcgtctga ctttaatcta       780
cctcctgggc caggccctgg cgcggaaact ttctatgtgg acggcgctgc aaacagggag       840
actaagggac ccggacccgg cggcgctgta gtcattcagg acaactcaga catcaaggtg       900
gttcccggtc caggccccgg gttcagaaag tataccgcct tcactattcc gtccatcaac       960
aatgagggcc ccggcccagg tgccaagttc gtggctgcct ggaccctgaa ggctgccgct      1020
tga                                                                    1023

<210> SEQ ID NO 283
<211> LENGTH: 75
<212> TYPE: PRT
<213> ORGANISM: Human immunodeficiency virus

<400> SEQUENCE: 283

Glu Lys Val Tyr Leu Ala Trp Val Pro Ala His Lys Gly Ile Gly Gly
1               5                  10                  15

Pro Gly Pro Gly Gln Gly Gln Met Val His Gln Ala Ile Ser Pro Arg
            20                 25                  30

Thr Leu Asn Gly Pro Gly Pro Gly Ser Pro Ala Ile Phe Gln Ser Ser
        35                 40                  45

Met Thr Lys Ile Leu Glu Pro Gly Pro Gly Pro Gly Phe Arg Lys Tyr
    50                  55                  60

Thr Ala Phe Thr Ile Pro Ser Ile Asn Asn Glu
65                  70                  75

<210> SEQ ID NO 284
<211> LENGTH: 228
<212> TYPE: DNA
<213> ORGANISM: Human immunodeficiency virus
```

-continued

```
<400> SEQUENCE: 284
gagaaggtgt acctggcctg ggtgcctgcc cacaagggaa tcggaggacc tggccctgga      60
cagggacaga tggtgcacca ggccatcagc cctaggaccc tgaacggacc tggacctgga     120
agccctgcca tcttccagag cagcatgacc aagatcctgg agcccggacc tggacctgga     180
ttcaggaagt acaccgcctt caccatcccc agcatcaaca acgagtga                 228

<210> SEQ ID NO 285
<211> LENGTH: 276
<212> TYPE: PRT
<213> ORGANISM: Unknown
<220> FEATURE:
<223> OTHER INFORMATION: PfHTL

<400> SEQUENCE: 285

Met Gln Val Gln Ile Gln Ser Leu Phe Leu Leu Leu Trp Val Pro
1               5                   10                  15

Gly Ser Arg Gly Arg His Asn Trp Val Asn His Ala Val Pro Leu Ala
            20                  25                  30

Met Lys Leu Ile Gly Pro Gly Pro Gly Lys Cys Asn Leu Tyr Ala Asp
        35                  40                  45

Ser Ala Trp Glu Asn Val Lys Asn Gly Pro Gly Pro Gly Lys Ser Lys
    50                  55                  60

Tyr Lys Leu Ala Thr Ser Val Leu Ala Gly Leu Gly Pro Gly Pro
65                  70                  75                  80

Gly Gln Thr Asn Phe Lys Ser Leu Leu Arg Asn Leu Gly Val Ser Glu
                85                  90                  95

Gly Pro Gly Pro Gly Ser Ser Val Phe Asn Val Val Asn Ser Ser Ile
            100                 105                 110

Gly Leu Ile Met Gly Pro Gly Pro Gly Val Lys Asn Val Ile Gly Pro
        115                 120                 125

Phe Met Lys Ala Val Cys Val Glu Gly Pro Gly Pro Gly Met Asn Tyr
    130                 135                 140

Tyr Gly Lys Gln Glu Asn Trp Tyr Ser Leu Lys Lys Gly Pro Gly Pro
145                 150                 155                 160

Gly Gly Leu Ala Tyr Lys Phe Val Val Pro Gly Ala Ala Thr Pro Tyr
                165                 170                 175

Gly Pro Gly Pro Gly Pro Asp Ser Ile Gln Asp Ser Leu Lys Glu Ser
            180                 185                 190

Arg Lys Leu Asn Gly Pro Gly Pro Gly Leu Leu Ile Phe His Ile Asn
        195                 200                 205

Gly Lys Ile Ile Lys Asn Ser Glu Gly Pro Gly Pro Gly Ala Gly Leu
    210                 215                 220

Leu Gly Asn Val Ser Thr Val Leu Leu Gly Gly Val Gly Pro Gly Pro
225                 230                 235                 240

Gly Lys Tyr Lys Ile Ala Gly Gly Ile Ala Gly Gly Leu Ala Leu Leu
                245                 250                 255

Gly Pro Gly Pro Gly Met Arg Lys Leu Ala Ile Leu Ser Val Ser Ser
            260                 265                 270

Phe Leu Phe Val
        275

<210> SEQ ID NO 286
<211> LENGTH: 837
<212> TYPE: DNA
<213> ORGANISM: Unknown
```

<220> FEATURE:
<223> OTHER INFORMATION: PfHTL

<400> SEQUENCE: 286

| | | | | | |
|---|---|---|---|---|---|
| atgggaatgc | aggtgcagat | ccagagcctg | tttctgctcc | tcctgtgggt | gcccggatcc | 60 |
| agaggaaggc | acaactgggt | gaatcatgct | gtgccctgg | ctatgaagct | gatcggccct | 120 |
| ggaccaggga | atgcaacct | ctacgcagac | agcgcctggg | agaacgtcaa | gaatggcccc | 180 |
| ggacctggga | atccaagta | taagctcgct | acctctgtgc | tggcaggcct | gctcggacca | 240 |
| ggccccggac | agacaaattt | caaaagcctg | ctcagaaacc | tgggagtgtc | cgaggggcct | 300 |
| ggcccaggat | ctagcgtctt | taatgtggtc | aactcctcta | ttgggctcat | catgggaccc | 360 |
| ggacctgggg | tgaaaaatgt | cattggccca | ttcatgaagg | ccgtgtgtgt | cgaaggaccc | 420 |
| gggcctggca | tgaactacta | tggaaagcaa | gaaaattggt | acagcctgaa | gaaaggccct | 480 |
| gggccaggcg | gactggctta | caagtttgtg | gtcccagggg | cagccactcc | ctatgggcct | 540 |
| gggccaggcc | ccgattccat | ccaggactct | ctcaaagaga | gccggaaact | gaacggaccc | 600 |
| gggcctggac | tgctcatttt | ccacatcaat | ggcaaaatta | tcaagaacag | cgagggacct | 660 |
| gggccaggcg | ccggactgct | ggggaacgtg | tccaccgtcc | tgctcggcgg | agtggggccc | 720 |
| ggccctggga | agtacaagat | cgctggaggg | atcgcaggcg | gactggccct | cctgggccca | 780 |
| ggaccaggga | tgcgcaaact | ggctattctc | tctgtctcca | gctttctgtt | tgtgtga | 837 |

<210> SEQ ID NO 287
<211> LENGTH: 9
<212> TYPE: PRT
<213> ORGANISM: Human immunodeficiency virus

<400> SEQUENCE: 287

Val Leu Ala Glu Ala Met Ser Gln Val
1               5

<210> SEQ ID NO 288
<211> LENGTH: 9
<212> TYPE: PRT
<213> ORGANISM: Human immunodeficiency virus

<400> SEQUENCE: 288

Met Thr Asn Asn Pro Pro Ile Pro Val
1               5

<210> SEQ ID NO 289
<211> LENGTH: 10
<212> TYPE: PRT
<213> ORGANISM: Human immunodeficiency virus

<400> SEQUENCE: 289

Met Ala Ser Asp Phe Asn Leu Pro Pro Val
1               5                   10

<210> SEQ ID NO 290
<211> LENGTH: 9
<212> TYPE: PRT
<213> ORGANISM: Human immunodeficiency virus

<400> SEQUENCE: 290

Lys Leu Val Gly Lys Leu Asn Trp Ala
1               5

<210> SEQ ID NO 291

```
<211> LENGTH: 9
<212> TYPE: PRT
<213> ORGANISM: Human immunodeficiency virus

<400> SEQUENCE: 291

Leu Val Gly Pro Thr Pro Val Asn Ile
1               5

<210> SEQ ID NO 292
<211> LENGTH: 9
<212> TYPE: PRT
<213> ORGANISM: Human immunodeficiency virus

<400> SEQUENCE: 292

Ile Leu Lys Glu Pro Val His Gly Val
1               5

<210> SEQ ID NO 293
<211> LENGTH: 9
<212> TYPE: PRT
<213> ORGANISM: Human immunodeficiency virus

<400> SEQUENCE: 293

Lys Ala Ala Cys Trp Trp Ala Gly Ile
1               5

<210> SEQ ID NO 294
<211> LENGTH: 10
<212> TYPE: PRT
<213> ORGANISM: Human immunodeficiency virus

<400> SEQUENCE: 294

Lys Met Ile Gly Gly Ile Gly Gly Phe Ile
1               5                   10

<210> SEQ ID NO 295
<211> LENGTH: 9
<212> TYPE: PRT
<213> ORGANISM: Human immunodeficiency virus

<400> SEQUENCE: 295

Arg Ala Met Ala Ser Asp Phe Asn Leu
1               5

<210> SEQ ID NO 296
<211> LENGTH: 9
<212> TYPE: PRT
<213> ORGANISM: Human immunodeficiency virus

<400> SEQUENCE: 296

Thr Leu Asn Phe Pro Ile Ser Pro Ile
1               5

<210> SEQ ID NO 297
<211> LENGTH: 9
<212> TYPE: PRT
<213> ORGANISM: Human immunodeficiency virus

<400> SEQUENCE: 297

Lys Leu Thr Pro Leu Cys Val Thr Leu
1               5

<210> SEQ ID NO 298
<211> LENGTH: 9
<212> TYPE: PRT
```

<213> ORGANISM: Human immunodeficiency virus

<400> SEQUENCE: 298

Leu Leu Gln Leu Thr Val Trp Gly Ile
1               5

<210> SEQ ID NO 299
<211> LENGTH: 10
<212> TYPE: PRT
<213> ORGANISM: Human immunodeficiency virus

<400> SEQUENCE: 299

Ser Leu Leu Asn Ala Thr Asp Ile Ala Val
1 5 10

<210> SEQ ID NO 300
<211> LENGTH: 9
<212> TYPE: PRT
<213> ORGANISM: Human immunodeficiency virus

<400> SEQUENCE: 300

Leu Thr Phe Gly Trp Cys Phe Lys Leu
1 5

<210> SEQ ID NO 301
<211> LENGTH: 9
<212> TYPE: PRT
<213> ORGANISM: Human immunodeficiency virus

<400> SEQUENCE: 301

Ala Ile Ile Arg Ile Leu Gln Gln Leu
1 5

<210> SEQ ID NO 302
<211> LENGTH: 9
<212> TYPE: PRT
<213> ORGANISM: Human immunodeficiency virus

<400> SEQUENCE: 302

Arg Ile Leu Gln Gln Leu Leu Phe Ile
1 5

<210> SEQ ID NO 303
<211> LENGTH: 10
<212> TYPE: PRT
<213> ORGANISM: Human immunodeficiency virus

<400> SEQUENCE: 303

Gln Met Ala Val Phe Ile His Asn Phe Lys
1 5 10

<210> SEQ ID NO 304
<211> LENGTH: 11
<212> TYPE: PRT
<213> ORGANISM: Human immunodeficiency virus

<400> SEQUENCE: 304

Lys Val Tyr Leu Ala Trp Val Pro Ala His Lys
1 5 10

<210> SEQ ID NO 305
<211> LENGTH: 10
<212> TYPE: PRT
<213> ORGANISM: Human immunodeficiency virus

```
<400> SEQUENCE: 305

Lys Ile Gln Asn Phe Arg Val Tyr Tyr Arg
1               5                   10

<210> SEQ ID NO 306
<211> LENGTH: 9
<212> TYPE: PRT
<213> ORGANISM: Human immunodeficiency virus

<400> SEQUENCE: 306

Ala Ile Phe Gln Ser Ser Met Thr Lys
1               5

<210> SEQ ID NO 307
<211> LENGTH: 10
<212> TYPE: PRT
<213> ORGANISM: Human immunodeficiency virus

<400> SEQUENCE: 307

Val Thr Ile Lys Ile Gly Gly Gln Leu Lys
1               5                   10

<210> SEQ ID NO 308
<211> LENGTH: 10
<212> TYPE: PRT
<213> ORGANISM: Human immunodeficiency virus

<400> SEQUENCE: 308

Thr Thr Leu Phe Cys Ala Ser Asp Ala Lys
1               5                   10

<210> SEQ ID NO 309
<211> LENGTH: 11
<212> TYPE: PRT
<213> ORGANISM: Human immunodeficiency virus

<400> SEQUENCE: 309

Val Thr Val Tyr Tyr Gly Val Pro Val Trp Lys
1               5                   10

<210> SEQ ID NO 310
<211> LENGTH: 10
<212> TYPE: PRT
<213> ORGANISM: Human immunodeficiency virus

<400> SEQUENCE: 310

Gln Val Pro Leu Arg Pro Met Thr Tyr Lys
1               5                   10

<210> SEQ ID NO 311
<211> LENGTH: 9
<212> TYPE: PRT
<213> ORGANISM: Human immunodeficiency virus

<400> SEQUENCE: 311

Val Met Ile Val Trp Gln Val Asp Arg
1               5

<210> SEQ ID NO 312
<211> LENGTH: 10
<212> TYPE: PRT
<213> ORGANISM: Human immunodeficiency virus

<400> SEQUENCE: 312
```

Gln Met Val His Gln Ala Ile Ser Pro Arg
1               5                   10

<210> SEQ ID NO 313
<211> LENGTH: 10
<212> TYPE: PRT
<213> ORGANISM: Human immunodeficiency virus

<400> SEQUENCE: 313

Tyr Pro Leu Ala Ser Leu Arg Ser Leu Phe
1               5                   10

<210> SEQ ID NO 314
<211> LENGTH: 9
<212> TYPE: PRT
<213> ORGANISM: Human immunodeficiency virus

<400> SEQUENCE: 314

His Pro Val His Ala Gly Pro Ile Ala
1               5

<210> SEQ ID NO 315
<211> LENGTH: 9
<212> TYPE: PRT
<213> ORGANISM: Human immunodeficiency virus

<400> SEQUENCE: 315

Phe Pro Ile Ser Pro Ile Glu Thr Val
1               5

<210> SEQ ID NO 316
<211> LENGTH: 11
<212> TYPE: PRT
<213> ORGANISM: Human immunodeficiency virus

<400> SEQUENCE: 316

Ile Pro Tyr Asn Pro Gln Ser Gln Gly Val Val
1               5                   10

<210> SEQ ID NO 317
<211> LENGTH: 9
<212> TYPE: PRT
<213> ORGANISM: Human immunodeficiency virus

<400> SEQUENCE: 317

Ile Pro Ile His Tyr Cys Ala Pro Ala
1               5

<210> SEQ ID NO 318
<211> LENGTH: 9
<212> TYPE: PRT
<213> ORGANISM: Human immunodeficiency virus

<400> SEQUENCE: 318

Cys Pro Lys Val Ser Phe Glu Pro Ile
1               5

<210> SEQ ID NO 319
<211> LENGTH: 9
<212> TYPE: PRT
<213> ORGANISM: Human immunodeficiency virus

<400> SEQUENCE: 319

Phe Pro Val Arg Pro Gln Val Pro Leu
1               5

```
<210> SEQ ID NO 320
<211> LENGTH: 8
<212> TYPE: PRT
<213> ORGANISM: Human immunodeficiency virus

<400> SEQUENCE: 320

Val Pro Leu Gln Leu Pro Pro Leu
1               5

<210> SEQ ID NO 321
<211> LENGTH: 10
<212> TYPE: PRT
<213> ORGANISM: Human immunodeficiency virus

<400> SEQUENCE: 321

Glu Val Asn Ile Val Thr Asp Ser Gln Tyr
1               5                   10

<210> SEQ ID NO 322
<211> LENGTH: 9
<212> TYPE: PRT
<213> ORGANISM: Human immunodeficiency virus

<400> SEQUENCE: 322

Phe Arg Asp Tyr Val Asp Arg Phe Tyr
1               5

<210> SEQ ID NO 323
<211> LENGTH: 10
<212> TYPE: PRT
<213> ORGANISM: Human immunodeficiency virus

<400> SEQUENCE: 323

Val Ile Tyr Gln Tyr Met Asp Asp Leu Tyr
1               5                   10

<210> SEQ ID NO 324
<211> LENGTH: 10
<212> TYPE: PRT
<213> ORGANISM: Human immunodeficiency virus

<400> SEQUENCE: 324

Val Thr Val Leu Asp Val Gly Asp Ala Tyr
1               5                   10

<210> SEQ ID NO 325
<211> LENGTH: 9
<212> TYPE: PRT
<213> ORGANISM: Human immunodeficiency virus

<400> SEQUENCE: 325

Ile Tyr Gln Glu Pro Phe Lys Asn Leu
1               5

<210> SEQ ID NO 326
<211> LENGTH: 9
<212> TYPE: PRT
<213> ORGANISM: Human immunodeficiency virus

<400> SEQUENCE: 326

Pro Tyr Asn Thr Pro Val Phe Ala Ile
1               5
```

```
<210> SEQ ID NO 327
<211> LENGTH: 9
<212> TYPE: PRT
<213> ORGANISM: Human immunodeficiency virus

<400> SEQUENCE: 327

Thr Tyr Gln Ile Tyr Gln Glu Pro Phe
1               5

<210> SEQ ID NO 328
<211> LENGTH: 10
<212> TYPE: PRT
<213> ORGANISM: Human immunodeficiency virus

<400> SEQUENCE: 328

Tyr Trp Gln Ala Thr Trp Ile Pro Glu Trp
1               5                   10

<210> SEQ ID NO 329
<211> LENGTH: 9
<212> TYPE: PRT
<213> ORGANISM: Human immunodeficiency virus

<400> SEQUENCE: 329

Ile Trp Gly Cys Ser Gly Lys Leu Ile
1               5

<210> SEQ ID NO 330
<211> LENGTH: 9
<212> TYPE: PRT
<213> ORGANISM: Human immunodeficiency virus

<400> SEQUENCE: 330

Arg Tyr Leu Lys Asp Gln Gln Leu Leu
1               5

<210> SEQ ID NO 331
<211> LENGTH: 10
<212> TYPE: PRT
<213> ORGANISM: Human immunodeficiency virus

<400> SEQUENCE: 331

Val Trp Lys Glu Ala Thr Thr Thr Leu Phe
1               5                   10

<210> SEQ ID NO 332
<211> LENGTH: 9
<212> TYPE: PRT
<213> ORGANISM: Human immunodeficiency virus

<400> SEQUENCE: 332

Ile Tyr Glu Thr Tyr Gly Asp Thr Trp
1               5

<210> SEQ ID NO 333
<211> LENGTH: 9
<212> TYPE: PRT
<213> ORGANISM: Human immunodeficiency virus

<400> SEQUENCE: 333

Pro Tyr Asn Glu Trp Thr Leu Glu Leu
1               5

<210> SEQ ID NO 334
<211> LENGTH: 15
```

```
<212> TYPE: PRT
<213> ORGANISM: Human immunodeficiency virus

<400> SEQUENCE: 334

Lys Arg Trp Ile Ile Leu Gly Leu Asn Lys Ile Val Arg Met Tyr
1               5                   10                  15

<210> SEQ ID NO 335
<211> LENGTH: 15
<212> TYPE: PRT
<213> ORGANISM: Human immunodeficiency virus

<400> SEQUENCE: 335

Trp Glu Phe Val Asn Thr Pro Pro Leu Val Lys Leu Trp Tyr Gln
1               5                   10                  15

<210> SEQ ID NO 336
<211> LENGTH: 15
<212> TYPE: PRT
<213> ORGANISM: Human immunodeficiency virus

<400> SEQUENCE: 336

Gln Lys Gln Ile Thr Lys Ile Gln Asn Phe Arg Val Tyr Tyr Arg
1               5                   10                  15

<210> SEQ ID NO 337
<211> LENGTH: 15
<212> TYPE: PRT
<213> ORGANISM: Human immunodeficiency virus

<400> SEQUENCE: 337

Lys Val Tyr Leu Ala Trp Val Pro Ala His Lys Gly Ile Gly Gly
1               5                   10                  15

<210> SEQ ID NO 338
<211> LENGTH: 15
<212> TYPE: PRT
<213> ORGANISM: Human immunodeficiency virus

<400> SEQUENCE: 338

Gly Glu Ile Tyr Lys Arg Trp Ile Ile Leu Gly Leu Asn Lys Ile
1               5                   10                  15

<210> SEQ ID NO 339
<211> LENGTH: 15
<212> TYPE: PRT
<213> ORGANISM: Human immunodeficiency virus

<400> SEQUENCE: 339

Glu Lys Val Tyr Leu Ala Trp Val Pro Ala His Lys Gly Ile Gly
1               5                   10                  15

<210> SEQ ID NO 340
<211> LENGTH: 15
<212> TYPE: PRT
<213> ORGANISM: Human immunodeficiency virus

<400> SEQUENCE: 340

Gln His Leu Leu Gln Leu Thr Val Trp Gly Ile Lys Gln Leu Gln
1               5                   10                  15

<210> SEQ ID NO 341
<211> LENGTH: 15
<212> TYPE: PRT
<213> ORGANISM: Human immunodeficiency virus
```

<400> SEQUENCE: 341

Gln Gly Gln Met Val His Gln Ala Ile Ser Pro Arg Thr Leu Asn
1               5                   10                  15

<210> SEQ ID NO 342
<211> LENGTH: 15
<212> TYPE: PRT
<213> ORGANISM: Human immunodeficiency virus

<400> SEQUENCE: 342

Ser Pro Ala Ile Phe Gln Ser Ser Met Thr Lys Ile Leu Glu Pro
1               5                   10                  15

<210> SEQ ID NO 343
<211> LENGTH: 16
<212> TYPE: PRT
<213> ORGANISM: Human immunodeficiency virus

<400> SEQUENCE: 343

Ile Lys Gln Phe Ile Asn Met Trp Gln Glu Val Gly Lys Ala Met Tyr
1               5                   10                  15

<210> SEQ ID NO 344
<211> LENGTH: 15
<212> TYPE: PRT
<213> ORGANISM: Human immunodeficiency virus

<400> SEQUENCE: 344

Phe Arg Lys Tyr Thr Ala Phe Thr Ile Pro Ser Ile Asn Asn Glu
1               5                   10                  15

<210> SEQ ID NO 345
<211> LENGTH: 15
<212> TYPE: PRT
<213> ORGANISM: Human immunodeficiency virus

<400> SEQUENCE: 345

His Ser Asn Trp Arg Ala Met Ala Ser Asp Phe Asn Leu Pro Pro
1               5                   10                  15

<210> SEQ ID NO 346
<211> LENGTH: 15
<212> TYPE: PRT
<213> ORGANISM: Human immunodeficiency virus

<400> SEQUENCE: 346

Lys Thr Ala Val Gln Met Ala Val Phe Ile His Asn Phe Lys Arg
1               5                   10                  15

<210> SEQ ID NO 347
<211> LENGTH: 15
<212> TYPE: PRT
<213> ORGANISM: Human immunodeficiency virus

<400> SEQUENCE: 347

Tyr Arg Lys Ile Leu Arg Gln Arg Lys Ile Asp Arg Leu Ile Asp
1               5                   10                  15

<210> SEQ ID NO 348
<211> LENGTH: 15
<212> TYPE: PRT
<213> ORGANISM: Human immunodeficiency virus

<400> SEQUENCE: 348

```
Trp Ala Gly Ile Lys Gln Glu Phe Gly Ile Pro Tyr Asn Pro Gln
1               5                   10                  15

<210> SEQ ID NO 349
<211> LENGTH: 15
<212> TYPE: PRT
<213> ORGANISM: Human immunodeficiency virus

<400> SEQUENCE: 349

Glu Val Asn Ile Val Thr Asp Ser Gln Tyr Ala Leu Gly Ile Ile
1               5                   10                  15

<210> SEQ ID NO 350
<211> LENGTH: 15
<212> TYPE: PRT
<213> ORGANISM: Human immunodeficiency virus

<400> SEQUENCE: 350

Ala Glu Thr Phe Tyr Val Asp Gly Ala Ala Asn Arg Glu Thr Lys
1               5                   10                  15

<210> SEQ ID NO 351
<211> LENGTH: 15
<212> TYPE: PRT
<213> ORGANISM: Human immunodeficiency virus

<400> SEQUENCE: 351

Gly Ala Val Val Ile Gln Asp Asn Ser Asp Ile Lys Val Val Pro
1               5                   10                  15

<210> SEQ ID NO 352
<211> LENGTH: 10
<212> TYPE: PRT
<213> ORGANISM: Hepatitis C virus

<400> SEQUENCE: 352

Leu Leu Phe Asn Ile Leu Gly Gly Trp Val
1               5                   10

<210> SEQ ID NO 353
<211> LENGTH: 9
<212> TYPE: PRT
<213> ORGANISM: Hepatitis C virus

<400> SEQUENCE: 353

Phe Leu Leu Leu Ala Asp Ala Arg Val
1               5

<210> SEQ ID NO 354
<211> LENGTH: 9
<212> TYPE: PRT
<213> ORGANISM: Hepatitis C virus

<400> SEQUENCE: 354

Tyr Leu Val Ala Tyr Gln Ala Thr Val
1               5

<210> SEQ ID NO 355
<211> LENGTH: 10
<212> TYPE: PRT
<213> ORGANISM: Hepatitis C virus

<400> SEQUENCE: 355

Arg Leu Ile Val Phe Pro Asp Leu Gly Val
```

```
                1               5                   10
```

<210> SEQ ID NO 356
<211> LENGTH: 9
<212> TYPE: PRT
<213> ORGANISM: Hepatitis C virus

<400> SEQUENCE: 356

Asp Leu Met Gly Tyr Ile Pro Leu Val
1               5

<210> SEQ ID NO 357
<211> LENGTH: 9
<212> TYPE: PRT
<213> ORGANISM: Hepatitis C virus

<400> SEQUENCE: 357

Trp Met Asn Arg Leu Ile Ala Phe Ala
1               5

<210> SEQ ID NO 358
<211> LENGTH: 9
<212> TYPE: PRT
<213> ORGANISM: Hepatitis C virus

<400> SEQUENCE: 358

Val Leu Val Gly Gly Val Leu Ala Ala
1               5

<210> SEQ ID NO 359
<211> LENGTH: 9
<212> TYPE: PRT
<213> ORGANISM: Hepatitis C virus

<400> SEQUENCE: 359

His Met Trp Asn Phe Ile Ser Gly Ile
1               5

<210> SEQ ID NO 360
<211> LENGTH: 9
<212> TYPE: PRT
<213> ORGANISM: Hepatitis C virus

<400> SEQUENCE: 360

Ile Leu Ala Gly Tyr Gly Ala Gly Val
1               5

<210> SEQ ID NO 361
<211> LENGTH: 10
<212> TYPE: PRT
<213> ORGANISM: Hepatitis C virus

<400> SEQUENCE: 361

Tyr Leu Leu Pro Arg Arg Gly Pro Arg Leu
1               5                   10

<210> SEQ ID NO 362
<211> LENGTH: 9
<212> TYPE: PRT
<213> ORGANISM: Hepatitis C virus

<400> SEQUENCE: 362

Leu Leu Phe Leu Leu Leu Ala Asp Ala
1               5

```
<210> SEQ ID NO 363
<211> LENGTH: 9
<212> TYPE: PRT
<213> ORGANISM: Hepatitis C virus

<400> SEQUENCE: 363

Tyr Leu Val Thr Arg His Ala Asp Val
1               5

<210> SEQ ID NO 364
<211> LENGTH: 9
<212> TYPE: PRT
<213> ORGANISM: Hepatitis C virus

<400> SEQUENCE: 364

Lys Thr Ser Glu Arg Ser Gln Pro Arg
1               5

<210> SEQ ID NO 365
<211> LENGTH: 9
<212> TYPE: PRT
<213> ORGANISM: Hepatitis C virus

<400> SEQUENCE: 365

Arg Leu Gly Val Arg Ala Thr Arg Lys
1               5

<210> SEQ ID NO 366
<211> LENGTH: 9
<212> TYPE: PRT
<213> ORGANISM: Hepatitis C virus

<400> SEQUENCE: 366

Gln Leu Phe Thr Phe Ser Pro Arg Arg
1               5

<210> SEQ ID NO 367
<211> LENGTH: 10
<212> TYPE: PRT
<213> ORGANISM: Hepatitis C virus

<400> SEQUENCE: 367

Arg Met Tyr Val Gly Gly Val Glu His Arg
1               5                   10

<210> SEQ ID NO 368
<211> LENGTH: 9
<212> TYPE: PRT
<213> ORGANISM: Hepatitis C virus

<400> SEQUENCE: 368

Leu Ile Phe Cys His Ser Lys Lys Lys
1               5

<210> SEQ ID NO 369
<211> LENGTH: 10
<212> TYPE: PRT
<213> ORGANISM: Hepatitis C virus

<400> SEQUENCE: 369

Gly Val Ala Gly Ala Leu Val Ala Phe Lys
1               5                   10

<210> SEQ ID NO 370
```

-continued

<211> LENGTH: 9
<212> TYPE: PRT
<213> ORGANISM: Hepatitis C virus

<400> SEQUENCE: 370

Val Ala Gly Ala Leu Val Ala Phe Lys
1 5

<210> SEQ ID NO 371
<211> LENGTH: 9
<212> TYPE: PRT
<213> ORGANISM: Hepatitis C virus

<400> SEQUENCE: 371

Leu Gly Phe Gly Ala Tyr Met Ser Lys
1 5

<210> SEQ ID NO 372
<211> LENGTH: 9
<212> TYPE: PRT
<213> ORGANISM: Hepatitis C virus

<400> SEQUENCE: 372

Leu Pro Gly Cys Ser Phe Ser Ile Phe
1 5

<210> SEQ ID NO 373
<211> LENGTH: 9
<212> TYPE: PRT
<213> ORGANISM: Hepatitis C virus

<400> SEQUENCE: 373

Leu Ser Ala Phe Ser Leu His Ser Tyr
1 5

<210> SEQ ID NO 374
<211> LENGTH: 9
<212> TYPE: PRT
<213> ORGANISM: Hepatitis C virus

<400> SEQUENCE: 374

Cys Thr Cys Gly Ser Ser Asp Leu Tyr
1 5

<210> SEQ ID NO 375
<211> LENGTH: 9
<212> TYPE: PRT
<213> ORGANISM: Hepatitis C virus

<400> SEQUENCE: 375

Leu Thr Asp Pro Ser His Ile Thr Ala
1 5

<210> SEQ ID NO 376
<211> LENGTH: 11
<212> TYPE: PRT
<213> ORGANISM: Hepatitis C virus

<400> SEQUENCE: 376

Leu Thr Cys Gly Phe Ala Asp Leu Met Gly Tyr
1 5 10

<210> SEQ ID NO 377
<211> LENGTH: 11
<212> TYPE: PRT

<213> ORGANISM: Hepatitis C virus

<400> SEQUENCE: 377

Leu Ala Asp Gly Gly Cys Ser Gly Gly Ala Tyr
1               5 10

<210> SEQ ID NO 378
<211> LENGTH: 9
<212> TYPE: PRT
<213> ORGANISM: Hepatitis C virus

<400> SEQUENCE: 378

Phe Trp Ala Lys His Met Trp Asn Phe
1 5

<210> SEQ ID NO 379
<211> LENGTH: 9
<212> TYPE: PRT
<213> ORGANISM: Hepatitis C virus

<400> SEQUENCE: 379

Arg Met Ile Leu Met Thr His Phe Phe
1 5

<210> SEQ ID NO 380
<211> LENGTH: 8
<212> TYPE: PRT
<213> ORGANISM: Hepatitis C virus

<400> SEQUENCE: 380

Val Met Gly Ser Ser Tyr Gly Phe
1 5

<210> SEQ ID NO 381
<211> LENGTH: 10
<212> TYPE: PRT
<213> ORGANISM: Hepatitis C virus

<400> SEQUENCE: 381

Phe Trp Ala Lys His Met Trp Asn Phe Ile
1 5 10

<210> SEQ ID NO 382
<211> LENGTH: 9
<212> TYPE: PRT
<213> ORGANISM: Plasmodium falciparum

<400> SEQUENCE: 382

Phe Met Lys Ala Val Cys Val Glu Val
1 5

<210> SEQ ID NO 383
<211> LENGTH: 9
<212> TYPE: PRT
<213> ORGANISM: Plasmodium falciparum

<400> SEQUENCE: 383

Gly Leu Leu Gly Val Val Ser Thr Val
1 5

<210> SEQ ID NO 384
<211> LENGTH: 10
<212> TYPE: PRT
<213> ORGANISM: Plasmodium falciparum -continued

<400> SEQUENCE: 384

Ile Leu Ser Val Ser Ser Phe Leu Phe Val
1               5                   10

<210> SEQ ID NO 385
<211> LENGTH: 9
<212> TYPE: PRT
<213> ORGANISM: Plasmodium falciparum

<400> SEQUENCE: 385

Gln Thr Asn Phe Lys Ser Leu Leu Arg
1               5

<210> SEQ ID NO 386
<211> LENGTH: 9
<212> TYPE: PRT
<213> ORGANISM: Plasmodium falciparum

<400> SEQUENCE: 386

Gly Val Ser Glu Asn Ile Phe Leu Lys
1               5

<210> SEQ ID NO 387
<211> LENGTH: 10
<212> TYPE: PRT
<213> ORGANISM: Plasmodium falciparum

<400> SEQUENCE: 387

Leu Leu Ala Cys Ala Gly Leu Ala Tyr Lys
1               5                   10

<210> SEQ ID NO 388
<211> LENGTH: 10
<212> TYPE: PRT
<213> ORGANISM: Plasmodium falciparum

<400> SEQUENCE: 388

Thr Pro Tyr Ala Gly Glu Pro Ala Pro Phe
1               5                   10

<210> SEQ ID NO 389
<211> LENGTH: 9
<212> TYPE: PRT
<213> ORGANISM: Plasmodium falciparum

<400> SEQUENCE: 389

Leu Pro Ser Glu Asn Glu Arg Gly Tyr
1               5

<210> SEQ ID NO 390
<211> LENGTH: 9
<212> TYPE: PRT
<213> ORGANISM: Plasmodium falciparum

<400> SEQUENCE: 390

Lys Tyr Lys Leu Ala Thr Ser Val Leu
1               5

<210> SEQ ID NO 391
<211> LENGTH: 9
<212> TYPE: PRT
<213> ORGANISM: Plasmodium falciparum

<400> SEQUENCE: 391

```
Ser Phe Leu Phe Val Glu Ala Leu Phe
1               5

<210> SEQ ID NO 392
<211> LENGTH: 9
<212> TYPE: PRT
<213> ORGANISM: Plasmodium falciparum

<400> SEQUENCE: 392

Tyr Phe Ile Leu Val Asn Leu Leu Ile
1               5

<210> SEQ ID NO 393
<211> LENGTH: 10
<212> TYPE: PRT
<213> ORGANISM: Plasmodium falciparum

<400> SEQUENCE: 393

Phe Leu Ile Phe Phe Asp Leu Phe Leu Val
1               5                   10

<210> SEQ ID NO 394
<211> LENGTH: 9
<212> TYPE: PRT
<213> ORGANISM: Plasmodium falciparum

<400> SEQUENCE: 394

Val Leu Ala Gly Leu Leu Gly Val Val
1               5

<210> SEQ ID NO 395
<211> LENGTH: 10
<212> TYPE: PRT
<213> ORGANISM: Plasmodium falciparum

<400> SEQUENCE: 395

Val Leu Leu Gly Gly Val Gly Leu Val Leu
1               5                   10

<210> SEQ ID NO 396
<211> LENGTH: 9
<212> TYPE: PRT
<213> ORGANISM: Plasmodium falciparum

<400> SEQUENCE: 396

Leu Ala Cys Ala Gly Leu Ala Tyr Lys
1               5

<210> SEQ ID NO 397
<211> LENGTH: 9
<212> TYPE: PRT
<213> ORGANISM: Plasmodium falciparum

<400> SEQUENCE: 397

Ala Leu Phe Phe Ile Ile Phe Asn Lys
1               5

<210> SEQ ID NO 398
<211> LENGTH: 10
<212> TYPE: PRT
<213> ORGANISM: Plasmodium falciparum

<400> SEQUENCE: 398

Phe Ile Leu Val Asn Leu Leu Ile Phe His
1               5                   10
```

<210> SEQ ID NO 399
<211> LENGTH: 8
<212> TYPE: PRT
<213> ORGANISM: Plasmodium falciparum

<400> SEQUENCE: 399

Leu Pro Tyr Gly Arg Thr Asn Leu
1               5

<210> SEQ ID NO 400
<211> LENGTH: 9
<212> TYPE: PRT
<213> ORGANISM: Plasmodium falciparum

<400> SEQUENCE: 400

Phe Val Glu Ala Leu Phe Gln Glu Tyr
1               5

<210> SEQ ID NO 401
<211> LENGTH: 10
<212> TYPE: PRT
<213> ORGANISM: Plasmodium falciparum

<400> SEQUENCE: 401

Phe Gln Asp Glu Glu Asn Ile Gly Ile Tyr
1               5                   10

<210> SEQ ID NO 402
<211> LENGTH: 9
<212> TYPE: PRT
<213> ORGANISM: Plasmodium falciparum

<400> SEQUENCE: 402

Phe Tyr Phe Ile Leu Val Asn Leu Leu
1               5

<210> SEQ ID NO 403
<211> LENGTH: 9
<212> TYPE: PRT
<213> ORGANISM: Plasmodium falciparum

<400> SEQUENCE: 403

Lys Tyr Leu Val Ile Val Phe Leu Ile
1               5

<210> SEQ ID NO 404
<211> LENGTH: 9
<212> TYPE: PRT
<213> ORGANISM: Plasmodium falciparum

<400> SEQUENCE: 404

Gly Leu Ile Met Val Leu Ser Phe Leu
1               5

<210> SEQ ID NO 405
<211> LENGTH: 9
<212> TYPE: PRT
<213> ORGANISM: Plasmodium falciparum

<400> SEQUENCE: 405

Lys Ile Leu Ser Val Phe Phe Leu Ala
1               5

```
<210> SEQ ID NO 406
<211> LENGTH: 10
<212> TYPE: PRT
<213> ORGANISM: Plasmodium falciparum

<400> SEQUENCE: 406

Val Thr Cys Gly Asn Gly Ile Gln Val Arg
1               5                   10

<210> SEQ ID NO 407
<211> LENGTH: 10
<212> TYPE: PRT
<213> ORGANISM: Plasmodium falciparum

<400> SEQUENCE: 407

His Val Leu Ser His Asn Ser Tyr Glu Lys
1               5                   10

<210> SEQ ID NO 408
<211> LENGTH: 9
<212> TYPE: PRT
<213> ORGANISM: Plasmodium falciparum

<400> SEQUENCE: 408

Pro Ser Asp Gly Lys Cys Asn Leu Tyr
1               5

<210> SEQ ID NO 409
<211> LENGTH: 9
<212> TYPE: PRT
<213> ORGANISM: Plasmodium falciparum

<400> SEQUENCE: 409

Tyr Tyr Ile Pro His Gln Ser Ser Leu
1               5

<210> SEQ ID NO 410
<211> LENGTH: 10
<212> TYPE: PRT
<213> ORGANISM: Plasmodium falciparum

<400> SEQUENCE: 410

Lys Phe Ile Lys Ser Leu Phe His Ile Phe
1               5                   10

<210> SEQ ID NO 411
<211> LENGTH: 10
<212> TYPE: PRT
<213> ORGANISM: Plasmodium falciparum

<400> SEQUENCE: 411

Val Phe Leu Ile Phe Phe Asp Leu Phe Leu
1               5                   10

<210> SEQ ID NO 412
<211> LENGTH: 11
<212> TYPE: PRT
<213> ORGANISM: Plasmodium falciparum

<400> SEQUENCE: 412

Leu Phe His Ile Phe Asp Gly Asp Asn Glu Ile
1               5                   10

<210> SEQ ID NO 413
<211> LENGTH: 11
```

```
<212> TYPE: PRT
<213> ORGANISM: Plasmodium falciparum

<400> SEQUENCE: 413

Tyr Tyr Gly Lys Gln Glu Asn Trp Tyr Ser Leu
1               5                   10

<210> SEQ ID NO 414
<211> LENGTH: 8
<212> TYPE: PRT
<213> ORGANISM: Plasmodium falciparum

<400> SEQUENCE: 414

Leu Tyr Ile Ser Phe Tyr Phe Ile
1               5

<210> SEQ ID NO 415
<211> LENGTH: 15
<212> TYPE: PRT
<213> ORGANISM: Plasmodium falciparum

<400> SEQUENCE: 415

Met Arg Lys Leu Ala Ile Leu Ser Val Ser Ser Phe Leu Phe Val
1               5                   10                  15

<210> SEQ ID NO 416
<211> LENGTH: 15
<212> TYPE: PRT
<213> ORGANISM: Plasmodium falciparum

<400> SEQUENCE: 416

Met Asn Tyr Tyr Gly Lys Gln Glu Asn Trp Tyr Ser Leu Lys Lys
1               5                   10                  15

<210> SEQ ID NO 417
<211> LENGTH: 15
<212> TYPE: PRT
<213> ORGANISM: Plasmodium falciparum

<400> SEQUENCE: 417

Ser Ser Val Phe Asn Val Val Asn Ser Ser Ile Gly Leu Ile Met
1               5                   10                  15

<210> SEQ ID NO 418
<211> LENGTH: 16
<212> TYPE: PRT
<213> ORGANISM: Plasmodium falciparum

<400> SEQUENCE: 418

Arg His Asn Trp Val Asn His Ala Val Pro Leu Ala Met Lys Leu Ile
1               5                   10                  15

<210> SEQ ID NO 419
<211> LENGTH: 15
<212> TYPE: PRT
<213> ORGANISM: Plasmodium falciparum

<400> SEQUENCE: 419

Pro Asp Ser Ile Gln Asp Ser Leu Lys Glu Ser Arg Lys Leu Asn
1               5                   10                  15

<210> SEQ ID NO 420
<211> LENGTH: 15
<212> TYPE: PRT
<213> ORGANISM: Plasmodium falciparum
```

<400> SEQUENCE: 420

Lys Cys Asn Leu Tyr Ala Asp Ser Ala Trp Glu Asn Val Lys Asn
1               5                   10                  15

<210> SEQ ID NO 421
<211> LENGTH: 15
<212> TYPE: PRT
<213> ORGANISM: Plasmodium falciparum

<400> SEQUENCE: 421

Val Lys Asn Val Ile Gly Pro Phe Met Lys Ala Val Cys Val Glu
1               5                   10                  15

<210> SEQ ID NO 422
<211> LENGTH: 15
<212> TYPE: PRT
<213> ORGANISM: Plasmodium falciparum

<400> SEQUENCE: 422

Lys Tyr Lys Ile Ala Gly Gly Ile Ala Gly Gly Leu Ala Leu Leu
1               5                   10                  15

<210> SEQ ID NO 423
<211> LENGTH: 15
<212> TYPE: PRT
<213> ORGANISM: Plasmodium falciparum

<400> SEQUENCE: 423

Gly Leu Ala Tyr Lys Phe Val Val Pro Gly Ala Ala Thr Pro Tyr
1               5                   10                  15

<210> SEQ ID NO 424
<211> LENGTH: 15
<212> TYPE: PRT
<213> ORGANISM: Plasmodium falciparum

<400> SEQUENCE: 424

Lys Ser Lys Tyr Lys Leu Ala Thr Ser Val Leu Ala Gly Leu Leu
1               5                   10                  15

<210> SEQ ID NO 425
<211> LENGTH: 15
<212> TYPE: PRT
<213> ORGANISM: Plasmodium falciparum

<400> SEQUENCE: 425

Ala Gly Leu Leu Gly Asn Val Ser Thr Val Leu Leu Gly Gly Val
1               5                   10                  15

<210> SEQ ID NO 426
<211> LENGTH: 15
<212> TYPE: PRT
<213> ORGANISM: Plasmodium falciparum

<400> SEQUENCE: 426

Leu Leu Ile Phe His Ile Asn Gly Lys Ile Ile Lys Asn Ser Glu
1               5                   10                  15

<210> SEQ ID NO 427
<211> LENGTH: 15
<212> TYPE: PRT
<213> ORGANISM: Plasmodium falciparum

<400> SEQUENCE: 427

-continued

Gln Thr Asn Phe Lys Ser Leu Leu Arg Asn Leu Gly Val Ser Glu
1               5                   10                  15

<210> SEQ ID NO 428
<211> LENGTH: 10
<212> TYPE: PRT
<213> ORGANISM: Unknown
<220> FEATURE:
<223> OTHER INFORMATION: TB

<400> SEQUENCE: 428

Arg Met Ser Arg Val Thr Thr Phe Thr Val
1               5                   10

<210> SEQ ID NO 429
<211> LENGTH: 10
<212> TYPE: PRT
<213> ORGANISM: Unknown
<220> FEATURE:
<223> OTHER INFORMATION: TB

<400> SEQUENCE: 429

Ala Leu Val Leu Leu Met Leu Pro Val Val
1               5                   10

<210> SEQ ID NO 430
<211> LENGTH: 10
<212> TYPE: PRT
<213> ORGANISM: Unknown
<220> FEATURE:
<223> OTHER INFORMATION: TB

<400> SEQUENCE: 430

Leu Met Ile Gly Thr Ala Ala Ala Val Val
1               5                   10

<210> SEQ ID NO 431
<211> LENGTH: 9
<212> TYPE: PRT
<213> ORGANISM: Unknown
<220> FEATURE:
<223> OTHER INFORMATION: TB

<400> SEQUENCE: 431

Ala Leu Val Leu Leu Met Leu Pro Val
1               5

<210> SEQ ID NO 432
<211> LENGTH: 9
<212> TYPE: PRT
<213> ORGANISM: Unknown
<220> FEATURE:
<223> OTHER INFORMATION: TB

<400> SEQUENCE: 432

Gly Leu Met Thr Ala Val Tyr Leu Val
1               5

<210> SEQ ID NO 433
<211> LENGTH: 8
<212> TYPE: PRT
<213> ORGANISM: Unknown
<220> FEATURE:
<223> OTHER INFORMATION: TB

<400> SEQUENCE: 433

Met Ala Leu Leu Arg Leu Pro Val
1               5

<210> SEQ ID NO 434
<211> LENGTH: 9
<212> TYPE: PRT
<213> ORGANISM: Unknown
<220> FEATURE:
<223> OTHER INFORMATION: TB

<400> SEQUENCE: 434

Arg Met Phe Ala Ala Asn Leu Gly Val
1               5

<210> SEQ ID NO 435
<211> LENGTH: 9
<212> TYPE: PRT
<213> ORGANISM: Unknown
<220> FEATURE:
<223> OTHER INFORMATION: TB

<400> SEQUENCE: 435

Ser Leu Tyr Phe Gly Gly Ile Cys Val
1               5

<210> SEQ ID NO 436
<211> LENGTH: 9
<212> TYPE: PRT
<213> ORGANISM: Unknown
<220> FEATURE:
<223> OTHER INFORMATION: TB

<400> SEQUENCE: 436

Arg Leu Pro Leu Val Leu Pro Ala Val
1               5

<210> SEQ ID NO 437
<211> LENGTH: 9
<212> TYPE: PRT
<213> ORGANISM: Unknown
<220> FEATURE:
<223> OTHER INFORMATION: TB

<400> SEQUENCE: 437

Arg Leu Met Ile Gly Thr Ala Ala Ala
1               5

<210> SEQ ID NO 438
<211> LENGTH: 9
<212> TYPE: PRT
<213> ORGANISM: Unknown
<220> FEATURE:
<223> OTHER INFORMATION: TB

<400> SEQUENCE: 438

Phe Val Val Ala Leu Ile Pro Leu Val
1               5

<210> SEQ ID NO 439
<211> LENGTH: 9
<212> TYPE: PRT
<213> ORGANISM: Unknown
<220> FEATURE:
<223> OTHER INFORMATION: TB

<400> SEQUENCE: 439

Met Thr Tyr Ala Ala Pro Leu Phe Val

-continued

```
1               5

<210> SEQ ID NO 440
<211> LENGTH: 10
<212> TYPE: PRT
<213> ORGANISM: Unknown
<220> FEATURE:
<223> OTHER INFORMATION: TB

<400> SEQUENCE: 440

Ala Met Ala Leu Leu Arg Leu Pro Leu Val
1               5                   10

<210> SEQ ID NO 441
<211> LENGTH: 9
<212> TYPE: PRT
<213> ORGANISM: Unknown
<220> FEATURE:
<223> OTHER INFORMATION: p53 139

<400> SEQUENCE: 441

Lys Leu Cys Pro Val Gln Leu Trp Val
1               5

<210> SEQ ID NO 442
<211> LENGTH: 9
<212> TYPE: PRT
<213> ORGANISM: Unknown
<220> FEATURE:
<223> OTHER INFORMATION: CEA 687

<400> SEQUENCE: 442

Ala Thr Val Gly Ile Met Ile Gly Val
1               5

<210> SEQ ID NO 443
<211> LENGTH: 9
<212> TYPE: PRT
<213> ORGANISM: Unknown
<220> FEATURE:
<223> OTHER INFORMATION: CEA 691

<400> SEQUENCE: 443

Ile Met Ile Gly His Leu Val Gly Val
1               5

<210> SEQ ID NO 444
<211> LENGTH: 9
<212> TYPE: PRT
<213> ORGANISM: Unknown
<220> FEATURE:
<223> OTHER INFORMATION: Her2/neu 689

<400> SEQUENCE: 444

Arg Leu Leu Gln Glu Thr Glu Leu Val
1               5

<210> SEQ ID NO 445
<211> LENGTH: 9
<212> TYPE: PRT
<213> ORGANISM: Unknown
<220> FEATURE:
<223> OTHER INFORMATION: MAGE3 112

<400> SEQUENCE: 445

Lys Val Ala Glu Ile Val His Phe Leu
1               5
```

<210> SEQ ID NO 446
<211> LENGTH: 9
<212> TYPE: PRT
<213> ORGANISM: Unknown
<220> FEATURE:
<223> OTHER INFORMATION: Her2/neu 665

<400> SEQUENCE: 446

Val Val Leu Gly Val Val Phe Gly Ile
1               5

<210> SEQ ID NO 447
<211> LENGTH: 9
<212> TYPE: PRT
<213> ORGANISM: Unknown
<220> FEATURE:
<223> OTHER INFORMATION: p53 149

<400> SEQUENCE: 447

Ser Met Pro Pro Pro Gly Thr Arg Val
1               5

<210> SEQ ID NO 448
<211> LENGTH: 10
<212> TYPE: PRT
<213> ORGANISM: Unknown
<220> FEATURE:
<223> OTHER INFORMATION: PAP.21.T2

<400> SEQUENCE: 448

Leu Thr Phe Phe Trp Leu Asp Arg Ser Val
1               5                   10

<210> SEQ ID NO 449
<211> LENGTH: 9
<212> TYPE: PRT
<213> ORGANISM: Unknown
<220> FEATURE:
<223> OTHER INFORMATION: PAP.112

<400> SEQUENCE: 449

Thr Leu Met Ser Ala Met Thr Asn Leu
1               5

<210> SEQ ID NO 450
<211> LENGTH: 10
<212> TYPE: PRT
<213> ORGANISM: Unknown
<220> FEATURE:
<223> OTHER INFORMATION: PAP.284

<400> SEQUENCE: 450

Ile Met Tyr Ser Ala His Asp Thr Thr Val
1               5                   10

<210> SEQ ID NO 451
<211> LENGTH: 10
<212> TYPE: PRT
<213> ORGANISM: Unknown
<220> FEATURE:
<223> OTHER INFORMATION: PSM.288.V10

<400> SEQUENCE: 451

Gly Leu Pro Ser Ile Pro Val His Pro Val
1               5                   10

```
<210> SEQ ID NO 452
<211> LENGTH: 10
<212> TYPE: PRT
<213> ORGANISM: Unknown
<220> FEATURE:
<223> OTHER INFORMATION: PSM.441

<400> SEQUENCE: 452

Leu Leu Gln Glu Arg Gly Val Ala Tyr Ile
1               5                   10

<210> SEQ ID NO 453
<211> LENGTH: 9
<212> TYPE: PRT
<213> ORGANISM: Unknown
<220> FEATURE:
<223> OTHER INFORMATION: PSM.469L2

<400> SEQUENCE: 453

Leu Leu Tyr Ser Leu Val His Asn Leu
1               5

<210> SEQ ID NO 454
<211> LENGTH: 9
<212> TYPE: PRT
<213> ORGANISM: Unknown
<220> FEATURE:
<223> OTHER INFORMATION: PSM.663

<400> SEQUENCE: 454

Met Met Asn Asp Gln Leu Met Phe Leu
1               5

<210> SEQ ID NO 455
<211> LENGTH: 11
<212> TYPE: PRT
<213> ORGANISM: Unknown
<220> FEATURE:
<223> OTHER INFORMATION: PSA.3.V11

<400> SEQUENCE: 455

Phe Leu Thr Leu Ser Val Thr Trp Ile Gly Val
1               5                   10

<210> SEQ ID NO 456
<211> LENGTH: 8
<212> TYPE: PRT
<213> ORGANISM: Unknown
<220> FEATURE:
<223> OTHER INFORMATION: PSA.143.V8

<400> SEQUENCE: 456

Ala Leu Gly Thr Thr Cys Tyr Val
1               5

<210> SEQ ID NO 457
<211> LENGTH: 10
<212> TYPE: PRT
<213> ORGANISM: Unknown
<220> FEATURE:
<223> OTHER INFORMATION: PSA.161

<400> SEQUENCE: 457

Phe Leu Thr Pro Lys Lys Leu Gln Cys Val
1               5                   10
```

```
<210> SEQ ID NO 458
<211> LENGTH: 9
<212> TYPE: PRT
<213> ORGANISM: Unknown
<220> FEATURE:
<223> OTHER INFORMATION: HuK2.4.L2

<400> SEQUENCE: 458

Leu Leu Leu Ser Ile Ala Leu Ser Val
1               5

<210> SEQ ID NO 459
<211> LENGTH: 11
<212> TYPE: PRT
<213> ORGANISM: Unknown
<220> FEATURE:
<223> OTHER INFORMATION: HuK2.53.V11

<400> SEQUENCE: 459

Val Leu Val His Pro Gln Trp Val Leu Thr Val
1               5                   10

<210> SEQ ID NO 460
<211> LENGTH: 10
<212> TYPE: PRT
<213> ORGANISM: Unknown
<220> FEATURE:
<223> OTHER INFORMATION: HuK2.165

<400> SEQUENCE: 460

Phe Leu Arg Pro Arg Ser Leu Gln Cys Val
1               5                   10

<210> SEQ ID NO 461
<211> LENGTH: 11
<212> TYPE: PRT
<213> ORGANISM: Unknown
<220> FEATURE:
<223> OTHER INFORMATION: HuK2.216.V11

<400> SEQUENCE: 461

Pro Leu Val Cys Asn Gly Val Leu Gln Gly Val
1               5                   10

<210> SEQ ID NO 462
<211> LENGTH: 219
<212> TYPE: PRT
<213> ORGANISM: Hepatitis B virus

<400> SEQUENCE: 462

Met Gly Met Gln Val Gln Ile Gln Ser Leu Phe Leu Leu Leu Leu Trp
1               5                   10                  15

Val Pro Gly Ser Arg Gly His Thr Leu Trp Lys Ala Gly Ile Leu Tyr
            20                  25                  30

Lys Ala Lys Phe Val Ala Ala Trp Thr Leu Lys Ala Ala Ala Phe Leu
        35                  40                  45

Pro Ser Asp Phe Phe Pro Ser Val Asn Phe Leu Leu Ser Leu Gly Ile
    50                  55                  60

His Leu Tyr Met Asp Asp Val Val Leu Gly Val Gly Leu Ser Arg Tyr
65                  70                  75                  80

Val Ala Arg Leu Phe Leu Leu Thr Arg Ile Leu Thr Ile Ser Thr Leu
                85                  90                  95

Pro Glu Thr Thr Val Val Arg Arg Gln Ala Phe Thr Phe Ser Pro Thr
            100                 105                 110
```

```
Tyr Lys Gly Ala Ala Ala Trp Leu Ser Leu Leu Val Pro Phe Val Asn
            115                 120                 125

Ile Pro Ile Pro Ser Ser Trp Ala Phe Lys Thr Pro Ala Arg Val Thr
        130                 135                 140

Gly Gly Val Phe Lys Val Gly Asn Phe Thr Gly Leu Tyr Asn Leu Pro
145                 150                 155                 160

Ser Asp Phe Phe Pro Ser Val Lys Thr Leu Trp Lys Ala Gly Ile Leu
                165                 170                 175

Tyr Lys Asn Val Ser Ile Pro Trp Thr His Lys Gly Ala Ala Leu Val
            180                 185                 190

Val Asp Phe Ser Gln Phe Ser Arg Asn Ser Ala Ile Cys Ser Val Val
        195                 200                 205

Arg Arg Ala Leu Met Pro Leu Tyr Ala Cys Ile
    210                 215
```

<210> SEQ ID NO 463
<211> LENGTH: 660
<212> TYPE: DNA
<213> ORGANISM: Hepatitis B virus

<400> SEQUENCE: 463

```
atgggaatgc aggtgcagat ccagagcctg tttctgctcc tcctgtgggt gcccgggtcc    60
agaggacaca ccctgtggaa ggccggaatc ctgtataagg ccaagttcgt ggctgcctgg   120
accctgaagg ctgccgcttt cctgcctagc gatttctttc ctagcgtgaa cttcctgctg   180
tccctgggaa tccacctgta tatggatgac gtggtgctgg agtgggact gtccaggtac   240
gtggctaggc tgttcctgct gaccagaatc ctgaccatct ccaccctgcc agagaccacc   300
gtggtgagga ggcaggcctt cacctttagc cctacctata agggagccgc tgcctggctg   360
agcctgctgg tgccctttgt gaatatccct atccctagct cctgggcttt caagacccca   420
gccagggtga ccggaggagt gtttaaggtg gaaacttca ccggcctgta taacctgccc   480
agcgatttct ttcctagcgt gaagaccctg tggaaggccg gaatcctgta caagaatgtg   540
tccatcccctt ggacccacaa gggagccgct ctggtggtgg acttttccca gttcagcaga   600
aattccgcta tctgctccgt ggtgaggaga gctctgatgc cactgtatgc ctgtatctga   660
```

<210> SEQ ID NO 464
<211> LENGTH: 333
<212> TYPE: PRT
<213> ORGANISM: Hepatitis B virus

<400> SEQUENCE: 464

```
Met Gly Met Gln Val Gln Ile Gln Ser Leu Phe Leu Leu Leu Leu Trp
1               5                   10                  15

Val Pro Gly Ser Arg Gly His Thr Leu Trp Lys Ala Gly Ile Leu Tyr
            20                  25                  30

Lys Ala Lys Phe Val Ala Ala Trp Thr Leu Lys Ala Ala Ala Phe Leu
        35                  40                  45

Pro Ser Asp Phe Phe Pro Ser Val Asn Phe Leu Leu Ser Leu Gly Ile
    50                  55                  60

His Leu Tyr Met Asp Asp Val Val Leu Gly Val Gly Leu Ser Arg Tyr
65                  70                  75                  80

Val Ala Arg Leu Phe Leu Leu Thr Arg Ile Leu Thr Ile Ser Thr Leu
                85                  90                  95

Pro Glu Thr Thr Val Val Arg Arg Gln Ala Phe Thr Phe Ser Pro Thr
```

```
                100                 105                 110
Tyr Lys Gly Ala Ala Ala Trp Leu Ser Leu Leu Val Pro Phe Val Asn
            115                 120                 125
Ile Pro Ile Pro Ser Ser Trp Ala Phe Lys Thr Pro Ala Arg Val Thr
130                 135                 140
Gly Gly Val Phe Lys Val Gly Asn Phe Thr Gly Leu Tyr Asn Leu Pro
145                 150                 155                 160
Ser Asp Phe Phe Pro Ser Val Lys Thr Leu Trp Lys Ala Gly Ile Leu
                165                 170                 175
Tyr Lys Asn Val Ser Ile Pro Trp Thr His Lys Gly Ala Ala Leu Val
            180                 185                 190
Val Asp Phe Ser Gln Phe Ser Arg Asn Ser Ala Ile Cys Ser Val Val
            195                 200                 205
Arg Arg Lys Ala Trp Met Met Trp Tyr Trp Gly Pro Ser Leu Tyr Lys
210                 215                 220
Lys Tyr Thr Ser Phe Pro Trp Leu Leu Asn Ala His Pro Ala Ala Met
225                 230                 235                 240
Pro His Leu Leu Lys Ala Ala Ala Asp Leu Leu Asp Thr Ala Ser Ala
                245                 250                 255
Leu Tyr Asn Ala Ala Ala Arg Phe Ser Trp Leu Ser Leu Leu Val Pro
                260                 265                 270
Phe Asn Ala Ala Ser Trp Pro Lys Phe Ala Val Pro Asn Leu Lys Leu
            275                 280                 285
Thr Phe Gly Arg Glu Thr Val Leu Glu Tyr Lys Ala Leu Ser Leu Asp
            290                 295                 300
Val Ser Ala Ala Phe Tyr Gly Ala Ala Glu Tyr Leu Val Ser Phe Gly
305                 310                 315                 320
Val Trp Gly Ala Ala Leu Met Pro Leu Tyr Ala Cys Ile
                325                 330

<210> SEQ ID NO 465
<211> LENGTH: 1002
<212> TYPE: DNA
<213> ORGANISM: Hepatitis B virus

<400> SEQUENCE: 465
atgggaatgc aggtgcagat ccagagcctg tttctgctcc tcctgtgggt gcccgggtcc      60
agaggacaca ccctgtggaa ggccggaatc ctgtataagg ccaagttcgt ggctgcctgg     120
accctgaagg ctgccgcttt cctgcctagc gatttctttc ctagcgtgaa cttcctgctg     180
tccctgggaa tccacctgta tatggatgac gtggtgctgg agtgggact gtccaggtac     240 gtggctaggc tgttcctgct gaccagaatc ctgaccatct ccaccctgcc agagaccacc     300
gtggtgagga ggcaggcctt cacctttagc cctacctata agggagccgc tgcctggctg     360
agcctgctgg tgcccttgt gaatatccct atccctagct cctgggcttt caagacccca     420
gccagggtga ccggaggagt gtttaaggtg ggaaacttca ccggcctgta taacctgccc     480
agcgatttct ttcctagcgt gaagaccctg tggaaggccg gaatcctgta caagaatgtg     540
tccatccctt ggacccacaa gggagccgct ctggtggtgg acttttccca gttcagcaga     600
aatagcgcca tctgttcggt cgtgagaagg aaagcctgga tgatgtggta ctggggtcct     660
agtctgtata agaagtacac ctcattccca tggctcttga atgcccatcc cgctgcaatg     720
ccacacctgc ttaagctgc ggcggatctg ctggacacag cctcagcttt atataatgct     780
gcagcaagat tctcctggtt gtctctctta gtgcccttca acgcagcttc ctggccaaaa     840
```

```
tttgccgttc cgaacctgaa gctcactttt ggaagagaga cagtacttga atacaaagca    900
ctaagccttg acgtgtcagc agccttctac ggagcagcag aatatctagt atcttttggg    960
gtctggggcg cagccctcat gcctctatac gcctgcattt ga                      1002
```

<210> SEQ ID NO 466
<211> LENGTH: 333
<212> TYPE: PRT
<213> ORGANISM: Hepatitis B virus

<400> SEQUENCE: 466

```
Met Gly Met Gln Val Gln Ile Gln Ser Leu Phe Leu Leu Leu Leu Trp
1               5                   10                  15

Val Pro Gly Ser Arg Gly His Thr Leu Trp Lys Ala Gly Ile Leu Tyr
            20                  25                  30

Lys Ala Lys Phe Val Ala Ala Trp Thr Leu Lys Ala Ala Ala Phe Leu
        35                  40                  45

Pro Ser Asp Phe Phe Pro Ser Val Asn Phe Leu Leu Ser Leu Gly Ile
    50                  55                  60

His Leu Tyr Met Asp Asp Val Val Leu Gly Val Gly Leu Ser Arg Tyr
65                  70                  75                  80

Val Ala Arg Leu Phe Leu Leu Thr Arg Ile Leu Thr Ile Ser Thr Leu
                85                  90                  95

Pro Glu Thr Thr Val Val Arg Arg Gln Ala Phe Thr Phe Ser Pro Thr
            100                 105                 110

Tyr Lys Gly Ala Ala Ala Trp Leu Ser Leu Leu Val Pro Phe Val Asn
        115                 120                 125

Ile Pro Ile Pro Ser Ser Trp Ala Phe Lys Thr Pro Ala Arg Val Thr
    130                 135                 140

Gly Gly Val Phe Lys Val Gly Asn Phe Thr Gly Leu Tyr Asn Leu Pro
145                 150                 155                 160

Ser Asp Phe Phe Pro Ser Val Lys Thr Leu Trp Lys Ala Gly Ile Leu
                165                 170                 175

Tyr Lys Asn Val Ser Ile Pro Trp Thr His Lys Gly Ala Ala Leu Val
            180                 185                 190

Val Asp Phe Ser Gln Phe Ser Arg Asn Ser Ala Ile Cys Ser Val Val
        195                 200                 205

Arg Arg Lys Glu Tyr Leu Val Ser Phe Gly Val Trp Gly Leu Ser Leu
    210                 215                 220

Asp Val Ser Ala Ala Phe Tyr Asn Ala Ala Lys Tyr Thr Ser Phe
225                 230                 235                 240

Pro Trp Leu Leu Asn Ala His Pro Ala Ala Met Pro His Leu Leu Lys
                245                 250                 255

Ala Ala Ala Asp Leu Leu Asp Thr Ala Ser Ala Leu Tyr Asn Ser Trp
            260                 265                 270

Pro Lys Phe Ala Val Pro Asn Leu Lys Leu Thr Phe Gly Arg Glu Thr
        275                 280                 285

Val Leu Glu Tyr Lys Ala Ala Trp Met Met Trp Tyr Trp Gly Pro Ser
    290                 295                 300

Leu Tyr Lys Ala Ala Arg Phe Ser Trp Leu Ser Leu Leu Val Pro
305                 310                 315                 320

Phe Gly Ala Ala Ala Leu Met Pro Leu Tyr Ala Cys Ile
                325                 330
```

<210> SEQ ID NO 467
<211> LENGTH: 1002
<212> TYPE: DNA
<213> ORGANISM: Hepatitis B virus

<400> SEQUENCE: 467

```
atgggaatgc aggtgcagat ccagagcctg tttctgctcc tcctgtgggt gcccgggtcc      60
agaggacaca ccctgtggaa ggccggaatc ctgtataagg ccaagttcgt ggctgcctgg     120
accctgaagg ctgccgcttt cctgcctagc gatttctttc tagcgtgaa cttcctgctg      180
tccctgggaa tccacctgta tatggatgac gtggtgctgg gagtgggact gtccaggtac     240
gtggctaggc tgttcctgct gaccagaatc ctgaccatct ccaccctgcc agagaccacc     300
gtggtgagga ggcaggcctt cacctttagc cctacctata agggagccgc tgcctggctg     360
agcctgctgg tgccctttgt gaatatccct atccctagct cctgggcttt caagaccca      420
gccagggtga ccggaggagt gtttaaggtg ggaaacttca ccggcctgta taacctgccc     480
agcgatttct ttcctagcgt gaagaccctg tggaaggccg gaatcctgta caagaatgtg     540
tccatccctt ggacccacaa gggagccgct ctggtggtgg actttttccca gttcagcaga     600
aattcagcaa tttgttcggt ggtgagaaga aaggaatatc ttgtttcatt tggcgtctgg     660
gggctgtcac tggatgtaag tgcggcattt acaatgccg ccgcaaaata tacaagcttc      720
ccatggctcc taaacgcaca cccagctgca atgccgcatc tactgaaagc agccgctgac     780
ctcttagaca ctgcctccgc tctgtacaac tcttggccca gtttgccgt gcctaatctc      840
aagttgacct tcggtagaga gacagtctta gaatacaaag cggcctggat gatgtggtac     900
tggggaccct ctctgtataa agccgctgca aggttctcct ggcttagcct tctcgtacca     960
ttcggagcag ctgccctaat gcctttgtac gcatgcatct ga                      1002
```

<210> SEQ ID NO 468
<211> LENGTH: 295
<212> TYPE: PRT
<213> ORGANISM: Hepatitis B virus

<400> SEQUENCE: 468

```
Met Gly Met Gln Val Gln Ile Gln Ser Leu Phe Leu Leu Leu Leu Trp
1               5                   10                  15

Val Pro Gly Ser Arg Gly Ser Trp Pro Lys Phe Ala Val Pro Asn Leu
            20                  25                  30

Lys Ala Ala Ala Ala Lys Phe Val Ala Trp Thr Leu Lys Ala Ala
        35                  40                  45

Ala Lys Ser Thr Leu Pro Glu Thr Thr Val Val Arg Arg Lys His Pro
    50                  55                  60

Ala Ala Met Pro His Leu Leu Lys Ala Ala His Thr Leu Trp Lys
65                  70                  75                  80

Ala Gly Ile Leu Tyr Lys Lys Ala Phe Leu Leu Thr Arg Ile Leu Thr
                85                  90                  95

Ile Gly Ala Leu Ser Leu Asp Val Ser Ala Ala Phe Tyr Asn Ala Ala
            100                 105                 110

Ala Lys Tyr Thr Ser Phe Pro Trp Leu Leu Asn Ala Ala Ala Arg Phe
        115                 120                 125

Ser Trp Leu Ser Leu Leu Val Pro Phe Asn Ala Ala Thr Pro Ala Arg
    130                 135                 140

Val Thr Gly Gly Val Phe Lys Ala Ala Glu Tyr Leu Val Ser Phe Gly
145                 150                 155                 160
```

```
Val Trp Gly Ala Ala Ala Tyr Met Asp Asp Val Val Leu Gly Val Asn
            165                 170                 175

Asp Leu Leu Asp Thr Ala Ser Ala Leu Tyr Asn Ala Ala Phe Pro
            180                 185                 190

His Cys Leu Ala Phe Ser Tyr Met Lys Ala Ala Ala Trp Met Met Trp
            195                 200                 205

Tyr Trp Gly Pro Ser Leu Tyr Lys Ala Ala Ser Ala Ile Cys Ser Val
        210                 215                 220

Val Arg Arg Lys Asn Phe Leu Leu Ser Leu Gly Ile His Leu Asn Ile
225                 230                 235                 240

Pro Ile Pro Ser Ser Trp Ala Phe Lys Ala Ala Trp Leu Ser Leu Leu
                245                 250                 255

Val Pro Phe Val Asn Ala Phe Leu Pro Ser Asp Phe Phe Pro Ser Val
            260                 265                 270

Lys Leu Thr Phe Gly Arg Glu Thr Val Leu Glu Tyr Lys Gln Ala Phe
            275                 280                 285

Thr Phe Ser Pro Thr Tyr Lys
            290                 295
```

```
<210> SEQ ID NO 469
<211> LENGTH: 888
<212> TYPE: DNA
<213> ORGANISM: Hepatitis B virus

<400> SEQUENCE: 469
atgggaatgc aggtgcagat ccagagcctg tttctgctcc tcctgtgggt gcccgggtcc    60
agaggatctt ggcctaaatt cgcagtgcca aaccttaaag ccgcggctgc taagttcgta   120
gctgcctgga cactaaaggc cgccgctaag agcacactgc agagaccacc gtggtccgg   180 cgaaagcatc agccgcaat gccccacttg ctcaaagcag ccgcccacac tctttggaag   240
gctgggatat tgtacaagaa agccttcctt ctgaccagga tattaactat cggagctctg   300
tcactcgacg tttctgctgc cttctacaac gcggcggcaa atacactag cttttccatgg   360 ctactcaacg cagccgccag attttcttgg ctatcactac tggtgccatt taatgcagca   420
acacctgcta gagtgactgg cggcgtcttt aaagcagccg agtacttggt gagctttggc   480
gtctggggtg cagcggcata tatggatgat gtagtgttag gggtgaacga cctcctggac   540
acagccagtg cgctgtacaa tgcagctgca ttcccgcatt gcctagcctt cagttatatg   600
aaagcagcag cctggatgat gtggtactgg ggaccgtccc tttataaagc agcttcagca   660
atctgttccg ttgtgaggag aaaaaacttt ttactctccc tcggtattca cctgaacatt   720
cccatccctt cctcatgggc attcaaagcc gcttggctga tctactcgt acctttcgtt   780 aatgcatttc tgcccagcga cttttccc tcggtaaaac tgacattcgg acgcgaaaca   840
gtccttgaat ataagcaggc cttcacgttc tcaccaacct ataaatga               888
```

```
<210> SEQ ID NO 470
<211> LENGTH: 296
<212> TYPE: PRT
<213> ORGANISM: Hepatitis B virus

<400> SEQUENCE: 470

Met Gly Met Gln Val Gln Ile Gln Ser Leu Phe Leu Leu Leu Leu Trp
1               5                   10                  15

Val Pro Gly Ser Arg Gly Tyr Met Asp Asp Val Val Leu Gly Val Asn
            20                  25                  30
```

```
Ala Ala Ala Glu Tyr Leu Val Ser Phe Gly Val Trp Asn Asp Leu Leu
            35                  40                  45
Asp Thr Ala Ser Ala Leu Tyr Gly Ala Ala His Thr Leu Trp Lys Ala
    50                  55                  60
Gly Ile Leu Tyr Lys Lys Ala Phe Leu Pro Ser Asp Phe Phe Pro Ser
65                  70                  75                  80
Val Lys Ala Phe Pro His Cys Leu Ala Phe Ser Tyr Met Lys Ala Ala
                85                  90                  95
Arg Phe Ser Trp Leu Ser Leu Leu Val Pro Phe Asn Ala Ala Ser Trp
            100                 105                 110
Pro Lys Phe Ala Val Pro Asn Leu Lys Ala Ala Ala Gln Ala Phe Thr
        115                 120                 125
Phe Ser Pro Thr Tyr Lys Asn Ala Ala Ala Ser Ala Ile Cys Ser Val
    130                 135                 140
Val Arg Arg Lys Ala Phe Leu Leu Thr Arg Ile Leu Thr Ile Asn Ile
145                 150                 155                 160
Pro Ile Pro Ser Ser Trp Ala Phe Lys Ala Ala Trp Met Met Trp Tyr
                165                 170                 175
Trp Gly Pro Ser Leu Tyr Lys Ala Ala Thr Pro Ala Arg Val Thr
            180                 185                 190
Gly Gly Val Phe Lys Ala Ala Asn Phe Leu Leu Ser Leu Gly Ile His
        195                 200                 205
Leu Asn Leu Thr Phe Gly Arg Glu Thr Val Leu Glu Tyr Lys His Pro
    210                 215                 220
Ala Ala Met Pro His Leu Leu Lys Ala Ala Ser Thr Leu Pro Glu Thr
225                 230                 235                 240
Thr Val Val Arg Arg Lys Trp Leu Ser Leu Leu Val Pro Phe Val Asn
                245                 250                 255
Ala Ala Ala Ala Lys Phe Val Ala Ala Trp Thr Leu Lys Ala Ala Ala
            260                 265                 270
Lys Leu Ser Leu Asp Val Ser Ala Ala Phe Tyr Asn Ala Ala Ala Lys
        275                 280                 285
Tyr Thr Ser Phe Pro Trp Leu Leu
    290                 295

<210> SEQ ID NO 471
<211> LENGTH: 891
<212> TYPE: DNA
<213> ORGANISM: Hepatitis B virus

<400> SEQUENCE: 471
atgggaatgc aggtgcagat ccagagcctg tttctgctcc tcctgtgggt gcccgggtcc      60
agaggataca tggatgacgt tgtgttaggc gttaatgcag ccgcagaata tctcgtgtca     120
ttcggcgtct ggaacgacct gttggacact gcatctgctc tgtacggtgc agcccatacc     180
ctgtggaagg ccggaatcct ctacaaaaag gcattcctac tagcgacttt ttttccttca     240
gtgaaagcct tcccacattg cctagcattc tcgtatatga aagcggctag gttctcatgg     300
cttagtcttc tagtaccttt caatgccgcc tcctggccca aattcgccgt accaaatcta     360
aaagcggccg cgcaggcctt tacattctct ccgacttata aaaatgcagc agcctccgct     420
atttgtagcg tcgtgcgccg aaaggccttc ctgctaaccc ggattttgac gataaacatc     480
cccatccctt ctagctgggc tttcaaagca gcatggatga tgtggtactg ggtcccagc      540
ttatacaaag ctgcggcaac cccagcaaga gtgacagggg gcgtgtttaa ggccgccaac     600
```

-continued

```
ttcctcctga gtctcggaat acacctgaac ttaacctttg ggagagagac agtactggag    660
tataaacacc cagcagctat gccgcaccta ctcaaagccg cttcaacact cccagaaaca    720
actgtagtga ggagaaaatg gctctccctg cttgtcccat tgtcaacgc cgccgccgct     780 aagtttgtgg ccgcttggac acttaaggct gcagcaaagt tgtcacttga tgttagtgca    840
gcgttctata acgcagctgc aaaatacact tcctttccct ggctgctgtg a             891
```

```
<210> SEQ ID NO 472
<211> LENGTH: 403
<212> TYPE: PRT
<213> ORGANISM: Hepatitis B virus

<400> SEQUENCE: 472
```

```
Met Gly Met Gln Val Gln Ile Gln Ser Leu Phe Leu Leu Leu Leu Trp
1               5                   10                  15

Val Pro Gly Ser Arg Gly Phe Leu Leu Thr Arg Ile Leu Thr Ile Asn
            20                  25                  30

Ala Ala Ala Ser Trp Pro Lys Phe Ala Val Pro Asn Leu Lys Ala Ala
        35                  40                  45

Ala His Thr Leu Trp Lys Ala Gly Ile Leu Tyr Lys Lys Ala Asp Leu
    50                  55                  60

Leu Asp Thr Ala Ser Ala Leu Tyr Asn Gln Ala Phe Thr Phe Ser Pro
65                  70                  75                  80

Thr Tyr Lys Gly Ala Ala Ala Asn Val Ser Ile Pro Trp Thr His Lys
                85                  90                  95

Gly Ala Ala Ala Phe Leu Leu Ser Leu Gly Ile His Leu Asn Ile Pro
            100                 105                 110

Ile Pro Ser Ser Trp Ala Phe Lys Ala Ala Ala Leu Trp Phe His Ile
        115                 120                 125

Ser Cys Leu Thr Phe Lys Ala Ala Ala Ile Leu Leu Leu Cys Leu Ile
    130                 135                 140

Phe Leu Leu Asn Ala Ala Ala Tyr Pro Ala Leu Met Pro Leu Tyr Ala
145                 150                 155                 160

Cys Ile Asn Ala His Pro Ala Ala Met Pro His Leu Leu Lys Ala Ala
                165                 170                 175

Ala Ser Phe Cys Gly Ser Pro Tyr Lys Ala Ala Gly Leu Ser Arg Tyr
            180                 185                 190

Val Ala Arg Leu Asn Lys Tyr Thr Ser Phe Pro Trp Leu Leu Asn Phe
        195                 200                 205

Leu Pro Ser Asp Phe Phe Pro Ser Val Lys Ala Phe Pro His Cys Leu
    210                 215                 220

Ala Phe Ser Tyr Met Lys Ala Glu Tyr Leu Val Ser Phe Gly Val Trp
225                 230                 235                 240

Asn Ala Ala Leu Thr Phe Gly Arg Glu Thr Val Leu Glu Tyr Lys Ala
                245                 250                 255

Ala Ala Leu Pro Ser Asp Phe Pro Ser Val Lys Ala Tyr Met Asp
            260                 265                 270

Asp Val Val Leu Gly Val Asn Leu Val Asp Phe Ser Gln Phe Ser
        275                 280                 285

Arg Asn Ala Ala Ala Arg Trp Met Cys Leu Arg Phe Ile Ile Asn
    290                 295                 300

Ala Ala Arg Phe Ser Trp Leu Ser Leu Leu Val Pro Phe Asn Ala Ala
305                 310                 315                 320

Thr Pro Ala Arg Val Thr Gly Gly Val Phe Lys Ala Ala Trp Leu Ser
```

Leu Leu Val Pro Phe Val Asn Ser Ala Ile Cys Ser Val Val Arg Arg
            340                 345                 350

Lys Ala Lys Phe Val Ala Ala Trp Thr Leu Lys Ala Ala Ala Lys Trp
        355                 360                 365

Met Met Trp Tyr Trp Gly Pro Ser Leu Tyr Lys Ala Ala Ser Thr Leu
    370                 375                 380

Pro Glu Thr Thr Val Val Arg Arg Lys Leu Ser Leu Asp Val Ser Ala
385                 390                 395                 400

Ala Phe Tyr

<210> SEQ ID NO 473
<211> LENGTH: 1215
<212> TYPE: DNA
<213> ORGANISM: Hepatitis B virus

<400> SEQUENCE: 473
atgggaatgc aggtccagat acagagcttg ttcctcctcc tgctttgggt ccccggatca      60
aggggttttcc tcctaacccg catcctgaca attaacgccg cagcctcctg gccaaaattt    120
gccgtgccaa atctcaaggc agctgcacac acactatgga aagcagggat actgtacaag    180
aaagccgatc tgctagacac agcgtctgcg ttgtacaacc aggcttttac tttctctcct    240
acatataaag gcgcagctgc aaacgtgagt atcccttgga cgcacaaagg agccgctgcc    300
aacttcttac tgtccctggg catccatcta aatatcccta ttccttcatc ctgggcattt    360
aaagcagccg ccttatggtt ccacataagt tgtctgacct caaagccgc agcaatcctg      420
ctcctttgcc tcattttctt actaaacgcc gctgcctatc cagctcttat gccattgtac    480
gcatgtatca acgccaccc cgcagcaatg ccccacctcc ttaaagctgc cgccagtttc      540
tgcggttctc cttataaagc agcagggctg tccagatacg tagctaggct aaacaagtat    600
accagcttcc cctggttact taatttcctg ccgtcagatt tctttccatc agttaaggcc    660
ttccctcatt gtctggcctt tagctacatg aaggctgaat atttggtatc cttcggcgtg    720
tggaatgcgg cactgacatt tggaagggag acagtgctcg agtacaaagc cgccgcacta    780
ccctcggact tcttcccatc ggtcaaagct tacatggacg atgtagtcct cggcgttaac    840
ttagtagtgg actttctca attttccaga aacgcagcgg ccagatggat gtgccttcgg    900
cgttttataa taaacgccgc tcgattcagc tggctatcac tcctagttcc atttaatgca    960
gctacacccg cacgggtgac aggtggagtt ttcaaggcag cgtggctttc actgcttgtg   1020
ccatttgtga actcagctat tgctcagta gtgagaagga aggcaaaatt cgtcgctgcc    1080
tggactctca aagctgccgc aaagtggatg atgtggtatt ggggaccgag cttgtacaaa   1140
gcggcctcta ctctgccaga aactaccgta gtgagaagaa aactgagcct ggacgtcagc   1200
gcggcattct actga                                                    1215

<210> SEQ ID NO 474
<211> LENGTH: 403
<212> TYPE: PRT
<213> ORGANISM: Hepatitis B virus

<400> SEQUENCE: 474

Met Gly Met Gln Val Gln Ile Gln Ser Leu Phe Leu Leu Leu Leu Trp
1               5                   10                  15

Val Pro Gly Ser Arg Gly Phe Leu Leu Ser Leu Gly Ile His Leu Asn
            20                  25                  30

Ala Ala Ala Lys Tyr Thr Ser Phe Pro Trp Leu Leu Asn Ala Ala Ala
                35                  40                  45

Arg Phe Ser Trp Leu Ser Leu Leu Val Pro Phe Asn Ala Ala Phe Pro
     50                  55                  60

His Cys Leu Ala Phe Ser Tyr Met Lys Ala Ala Leu Val Val Asp Phe
 65                  70                  75                  80

Ser Gln Phe Ser Arg Gly Ala Ile Leu Leu Cys Leu Ile Phe Leu
                 85                  90                  95

Leu Asn Ala Ala Ala His Thr Leu Trp Lys Ala Gly Ile Leu Tyr Lys
                100                 105                 110

Lys Ala Trp Met Met Trp Tyr Trp Gly Pro Ser Leu Tyr Lys Ala Tyr
                115                 120                 125

Pro Ala Leu Met Pro Leu Tyr Ala Cys Ile Gly Ala Ala Trp Leu
                130                 135                 140

Ser Leu Leu Val Pro Phe Val Asn Phe Leu Leu Thr Arg Ile Leu Thr
145                 150                 155                 160

Ile Asn Ile Pro Ile Pro Ser Ser Trp Ala Phe Lys Ala Ala Glu
                165                 170                 175

Tyr Leu Val Ser Phe Gly Val Trp Asn Leu Pro Ser Asp Phe Phe Pro
                180                 185                 190

Ser Val Lys Phe Leu Pro Ser Asp Phe Pro Ser Val Lys Asp Leu
                195                 200                 205

Leu Asp Thr Ala Ser Ala Leu Tyr Asn Ser Trp Pro Lys Phe Ala Val
    210                 215                 220

Pro Asn Leu Lys Ala Ala Ala Ser Ala Ile Cys Ser Val Val Arg Arg
225                 230                 235                 240

Lys Leu Ser Leu Asp Val Ser Ala Ala Phe Tyr Asn Ala Ala Lys
                245                 250                 255

Phe Val Ala Ala Trp Thr Leu Lys Ala Ala Ala Lys Ala Ala Asn Val
                260                 265                 270

Ser Ile Pro Trp Thr His Lys Gly Ala Ala Gly Leu Ser Arg Tyr Val
                275                 280                 285

Ala Arg Leu Asn Ala Ala Ser Thr Leu Pro Glu Thr Thr Val Val
                290                 295                 300

Arg Arg Lys His Pro Ala Ala Met Pro His Leu Leu Lys Ala Ala Ala
305                 310                 315                 320

Arg Trp Met Cys Leu Arg Arg Phe Ile Ile Asn Ala Ser Phe Cys Gly
                325                 330                 335

Ser Pro Tyr Lys Ala Ala Tyr Met Asp Asp Val Val Leu Gly Val Asn
                340                 345                 350

Ala Leu Trp Phe His Ile Ser Cys Leu Thr Phe Lys Ala Ala Ala Thr
                355                 360                 365

Pro Ala Arg Val Thr Gly Gly Val Phe Lys Ala Ala Leu Thr Phe
                370                 375                 380

Gly Arg Glu Thr Val Leu Glu Tyr Lys Gln Ala Phe Thr Phe Ser Pro
385                 390                 395                 400

Thr Tyr Lys

<210> SEQ ID NO 475
<211> LENGTH: 1212
<212> TYPE: DNA
<213> ORGANISM: Hepatitis B virus

<400> SEQUENCE: 475

-continued

```
atgggaatgc aggtgcaaat acagtctctc ttccttttgc ttctctgggt tccaggatca    60
cggggcttct tgcttagctt gggcatccac ctaaatgctg ctgcaaaata cacatctttt   120
ccttggctcc ttaatgccgc cgctaggttt tcatggctga gtctgctagt acctttcaat   180
gcggctttcc cacattgcct agcttttagc tatatgaaag ctgctttagt cgtggacttt   240
tcacagttta gcagaggagc aatcctgctg ctatgtctga tattccttct aaacgcagca   300
gcccacacac tctggaaagc tggtatcctt tacaagaaag cctggatgat gtggtattgg   360
ggacccagcc tctacaaagc ataccctgcc ctgatgccac tatacgcatg cattggcgcg   420
gcagcctggt tatcccttt agtaccgttt gtcaactttc tattaaccag aatcctgacg   480
attaatattc cgatcccaag ttcctgggca ttcaaagcag ccgcggagta tctggtttca   540
tttggcgtat ggaacctgcc aagcgacttc tttccttctg ttaagttcct ccctccgat   600
ttctttccat cggtgaaaga cctccttgat accgcgagcg ctctgtacaa ctcgtggcca   660
aaattcgcag ttccaaacct aaagccgcc gccagtgcca tttgttccgt ggtaaggaga   720
aaattatcac tcgacgtgtc cgcagcattt tataacgctg ctgcaaagtt tgtcgcagca   780
tggacattga aggctgcagc gaaagcagca atgtatcaa taccctggac ccacaagggt   840
gcagccgggc tgtctaggta tgtggcgagg ctaaacgccg ccgcctcaac actgcctgag   900
actactgtcg tgagacgcaa acaccctgcc gcaatgcccc acctgctgaa agcagccgca   960
cgatggatgt gcctcagaag attcataata acgcttctt tctgtgggtc accctacaaa  1020
gccgcttaca tggacgatgt ggtcctcgga gtgaatgccc tctggttcca tatcagctgc  1080
ctgacattca aggcagccgc caccccgct cgtgtgacag aggtgtgtct caaagccgcg  1140
gcactgactt tcggtcggga aactgtattg aatataagc aggccttcac attctcccca  1200
acatacaagt ga                                                      1212
```

<210> SEQ ID NO 476
<211> LENGTH: 410
<212> TYPE: PRT
<213> ORGANISM: Hepatitis B virus

<400> SEQUENCE: 476

```
Met Gln Val Gln Ile Gln Ser Leu Phe Leu Leu Leu Leu Trp Val Pro
1               5                   10                  15

Gly Ser Arg Gly Phe Leu Leu Ser Leu Gly Ile His Leu Asn Ala Ala
            20                  25                  30

Ala Lys Tyr Thr Ser Phe Pro Trp Leu Leu Asn Ala Ala Ala Arg Phe
        35                  40                  45

Ser Trp Leu Ser Leu Leu Val Pro Phe Asn Ala Ala Phe Pro His Cys
    50                  55                  60

Leu Ala Phe Ser Tyr Met Lys Ala Ala Leu Val Val Asp Phe Ser Gln
65                  70                  75                  80

Phe Ser Arg Gly Ala Ile Leu Leu Cys Leu Ile Phe Leu Leu Asn
                85                  90                  95

Ala Ala Ala His Thr Leu Trp Lys Ala Gly Ile Leu Tyr Lys Lys Ala
            100                 105                 110

Trp Met Met Trp Tyr Trp Gly Pro Ser Leu Tyr Lys Ala Tyr Pro Ala
        115                 120                 125

Leu Met Pro Leu Tyr Ala Cys Ile Gly Ala Ala Ala Trp Leu Ser Leu
    130                 135                 140

Leu Val Pro Phe Val Asn Phe Leu Leu Thr Arg Ile Leu Thr Ile Asn
```

```
            145                 150                 155                 160
        Ala Ala Ala Ile Pro Ile Pro Ser Ser Trp Ala Phe Lys Ala Ala Ala
                        165                 170                 175

Glu Tyr Leu Val Ser Phe Gly Val Trp Asn Leu Pro Ser Asp Phe Phe
                    180                 185                 190

Pro Ser Val Lys Ala Ala Ala Phe Leu Pro Ser Asp Phe Phe Pro Ser
                195                 200                 205

Val Lys Ala Ala Ala Asp Leu Leu Asp Thr Ala Ser Ala Leu Tyr Asn
                    210                 215                 220

Ser Trp Pro Lys Phe Ala Val Pro Asn Leu Lys Ala Ala Ala Ser Ala
        225                 230                 235                 240

Ile Cys Ser Val Val Arg Arg Lys Leu Ser Leu Asp Val Ser Ala Ala
                        245                 250                 255

Phe Tyr Asn Ala Ala Ala Lys Phe Val Ala Ala Trp Thr Leu Lys Ala
                    260                 265                 270

Ala Ala Lys Ala Ala Asn Val Ser Ile Pro Trp Thr His Lys Gly Ala
                    275                 280                 285

Ala Gly Leu Ser Arg Tyr Val Ala Arg Leu Asn Ala Ala Ala Ser Thr
                    290                 295                 300

Leu Pro Glu Thr Thr Val Val Arg Arg Lys His Pro Ala Ala Met Pro
        305                 310                 315                 320

His Leu Leu Lys Ala Ala Ala Arg Trp Met Cys Leu Arg Arg Phe Ile
                        325                 330                 335

Ile Asn Ala Ser Phe Cys Gly Ser Pro Tyr Lys Ala Ala Tyr Met Asp
                    340                 345                 350

Asp Val Val Leu Gly Val Asn Ala Leu Trp Phe His Ile Ser Cys Leu
                    355                 360                 365

Thr Phe Lys Ala Ala Ala Thr Pro Ala Arg Val Thr Gly Gly Val Phe
                370                 375                 380

Lys Ala Ala Ala Leu Thr Phe Gly Arg Glu Thr Val Leu Glu Tyr Lys
        385                 390                 395                 400

Gln Ala Phe Thr Phe Ser Pro Thr Tyr Lys
                        405                 410

<210> SEQ ID NO 477
<211> LENGTH: 1239
<212> TYPE: DNA
<213> ORGANISM: Hepatitis B virus

<400> SEQUENCE: 477
atgggaatgc aggtgcaaat acagtctctc ttccttttgc ttctctgggt tccaggatca      60
cggggcttct tgcttagctt gggcatccac ctaaatgctg ctgcaaaata cacatctttt     120
ccttggctcc ttaatgccgc cgctaggttt tcatggctga gtctgctagt acctttcaat     180
gcggctttcc cacattgcct agcttttagc tatatgaaag ctgctttagt cgtggacttt     240
tcacagttta gcagaggagc aatcctgctg ctatgtctga tattccttct aaacgcagca     300
gcccacacac tctggaaagc tggtatcctt acaagaaag cctggatgat gtggtattgg     360
ggacccagcc tctacaaagc ataccctgcc ctgatgccac tatacgcatg cattggcgcg     420
gcagcctggt tatccttttt agtaccgttt gtcaactttc tattaaccag aatcctgacg     480
attaatgctg ccgccattcc gatcccaagt cctgggcat tcaaagcagc cgcggagtat     540
ctggtttcat ttggcgtatg gaacctgcca agcgacttct ttccttctgt taaggccgct     600
gctttcctcc cctccgattt cttccatcg gtgaaagccg ctgccgacct ccttgatacc     660
```

-continued

```
gcgagcgctc tgtacaactc gtggccaaaa ttcgcagttc caaacctaaa agccgccgcc    720
agtgccattt gttccgtggt aaggagaaaa ttatcactcg acgtgtccgc agcattttat    780
aacgctgctg caaagtttgt cgcagcatgg acattgaagg ctgcagcgaa agcagcaaat    840
gtatcaatac cctggaccca caagggtgca gccgggctgt ctaggtatgt ggcgaggcta    900
aacgccgccg cctcaacact gcctgagact actgtcgtga cacgcaaaca ccctgccgca    960
atgccccacc tgctgaaagc agccgcacga tggatgtgcc tcagaagatt cataataaac   1020
gcttctttct gtgggtcacc ctacaaagcc gcttacatgg acgatgtggt cctcggagtg   1080
aatgccctct ggttccatat cagctgcctg acattcaagg cagccgccac ccccgctcgt   1140
gtgacaggag gtgtcttcaa agccgcggca ctgactttcg gtcgggaaac tgtattggaa   1200
tataagcagg ccttcacatt ctccccaaca tacaagtga                          1239
```

<210> SEQ ID NO 478
<211> LENGTH: 344
<212> TYPE: PRT
<213> ORGANISM: Hepatitis B virus

<400> SEQUENCE: 478

```
Met Gly Thr Ser Phe Val Tyr Val Pro Ser Ala Leu Asn Pro Ala Asp
1               5                   10                  15

Gly Pro Gly Pro Gly Leu Cys Gln Val Phe Ala Asp Ala Thr Pro Thr
                20                  25                  30

Gly Trp Gly Leu Gly Pro Gly Pro Gly Arg His Tyr Leu His Thr Leu
            35                  40                  45

Trp Lys Ala Gly Ile Leu Tyr Lys Gly Pro Gly Pro Gly Pro His His
        50                  55                  60

Thr Ala Leu Arg Gln Ala Ile Leu Cys Trp Gly Glu Leu Met Thr Leu
65                  70                  75                  80

Ala Gly Pro Gly Pro Gly Glu Ser Arg Leu Val Val Asp Phe Ser Gln
                85                  90                  95

Phe Ser Arg Gly Asn Gly Pro Gly Pro Gly Pro Phe Leu Leu Ala Gln
                100                 105                 110

Phe Thr Ser Ala Ile Cys Ser Val Val Gly Pro Gly Pro Gly Leu Val
            115                 120                 125

Pro Phe Val Gln Trp Phe Val Gly Leu Ser Pro Thr Val Gly Pro Gly
        130                 135                 140

Pro Gly Leu His Leu Tyr Ser His Pro Ile Ile Leu Gly Phe Arg Lys
145                 150                 155                 160

Ile Gly Pro Gly Pro Gly Ser Ser Asn Leu Ser Trp Leu Ser Leu Asp
                165                 170                 175

Val Ser Ala Ala Phe Gly Pro Gly Pro Gly Leu Gln Ser Leu Thr Asn
                180                 185                 190

Leu Leu Ser Ser Asn Leu Ser Trp Leu Gly Pro Gly Pro Gly Ala Gly
            195                 200                 205

Phe Phe Leu Leu Thr Arg Ile Leu Thr Ile Pro Gln Ser Gly Pro Gly
        210                 215                 220

Pro Gly Val Ser Phe Gly Val Trp Ile Arg Thr Pro Pro Ala Tyr Arg
225                 230                 235                 240

Pro Pro Asn Ala Pro Ile Gly Pro Gly Pro Gly Val Gly Pro Leu Thr
                245                 250                 255

Val Asn Glu Lys Arg Arg Leu Lys Leu Ile Gly Pro Gly Pro Gly Lys
                260                 265                 270
```

```
Gln Cys Phe Arg Lys Leu Pro Val Asn Arg Pro Ile Asp Trp Gly Pro
        275                 280                 285

Gly Pro Gly Ala Ala Asn Trp Ile Leu Arg Gly Thr Ser Phe Val Tyr
        290                 295                 300

Val Pro Gly Pro Gly Pro Lys Gln Ala Phe Thr Phe Ser Pro Thr
305                 310                 315                 320

Tyr Lys Ala Phe Leu Cys Gly Pro Gly Pro Gly Ala Lys Phe Val Ala
                325                 330                 335

Ala Trp Thr Leu Lys Ala Ala Ala
                340
```

<210> SEQ ID NO 479
<211> LENGTH: 1035
<212> TYPE: DNA
<213> ORGANISM: Hepatitis B virus

<400> SEQUENCE: 479

```
atgggaactt cttttgtgta tgtcccttcc gctctgaacc cagcagacgg acccgggcct    60
ggcctgtgcc aggtcttcgc cgacgcaact cccacagggt ggggctggg gccaggacca   120
ggcaggcact acctgcatac tctgtggaag gcaggaatcc tctataaagg gcccggccca   180
ggccctcacc acaccgccct gaggcaggcc atcctgtgct gggggagct catgaccctg   240
gccggacctg gacccgggga gagcagactg gtggtggatt tcagccaatt cagcagagga   300
aacggacccg gccctgggcc ttttctgctg gctcagttta catctgctat ttgttctgtg   360
gtcggccccg ggcccggact cgtgcctttc gtgcagtggt cgtgggact gtcccctaca   420
gtcgggcccg gccagggct gcatctgtac tcccacccaa tcatcctcgg cttccgcaag   480
attggacccg gccaggctc cagcaatctc tcctggctct ctctggacgt gtctgccgcc   540
tttggccctg gaccaggcct gcaaagcctg actaatctgc tcagcagcaa cctgtcctgg   600
ctgggacctg gcccagggc tggcttcttt ctgctcaccc ggattctcac aattccccag   660
tccggaccag gaccaggagt cagtttcggg gtgtggatca ggacccctcc tgcttataga   720
ccacccaatg ctccaatcgg ccccggccct ggcgtcgggc cactgaccgt gaatgagaag   780
cgccggctga agctgatcgg ccctggccct ggcaagcagt gctttcgcaa actgcccgtg   840
aacagaccta ttgattgggg ccccggccct ggagcagcca actggattct caggggaaca   900
agcttcgtct acgtgcccgg gcccggacca gggaagcagg cttttacctt ctctcccact   960
tacaaggcct tcctctgtgg gccaggcccc ggcgccaagt ttgtggcagc atggaccctc  1020
aaagccgctg cctga                                                   1035
```